United States Patent
Benton et al.

(12) 
(10) Patent No.: US 6,187,541 B1
(45) Date of Patent: Feb. 13, 2001

(54) **METHODS OF SCREENING FOR COMPOUNDS ACTIVE ON *STAPHYLOCOCCUS AUREUS* TARGET GENES**

(75) Inventors: Bret Benton, Burlingame; Ving J. Lee, Los Altos; Francois Malouin, Los Gatos; Patrick K. Martin, Sunnyvale; Molly B. Schmid, Menlo Park; Dongxu Sun, Cupertino, all of CA (US)

(73) Assignee: Microcide Pharmaceuticals, Inc., Mountain View, CA (US)

( * ) Notice: Under 35 U.S.C. 154(b), the term of this patent shall be extended for 0 days.

(21) Appl. No.: 09/265,315

(22) Filed: Mar. 9, 1999

Related U.S. Application Data

(62) Division of application No. 08/714,918, filed on Sep. 13, 1996, now Pat. No. 6,037,123.
(60) Provisional application No. 60/003,798, filed on Sep. 15, 1995, now abandoned, and provisional application No. 60/009,102, filed on Dec. 22, 1995, now abandoned.

(51) Int. Cl.[7] .................................................. C12Q 1/68
(52) U.S. Cl. .................. 435/6; 435/69.1; 514/2; 514/44
(58) Field of Search .................... 435/6, 69.1; 514/2, 514/44; 436/501, 63, 64

(56) References Cited

U.S. PATENT DOCUMENTS

| | | | |
|---|---|---|---|
| 5,246,838 | 9/1993 | Van Dijl et al. | 435/69.1 |
| 5,306,619 | 4/1994 | Edwards et al. | 435/6 |
| 5,464,750 | 11/1995 | Sanders et al. | 435/7.21 |

FOREIGN PATENT DOCUMENTS

| | | |
|---|---|---|
| 0 786 519 A2 | 7/1997 | (EP) . |
| 96/23075 | 8/1996 | (WO) . |
| 97/11690 | 4/1997 | (WO) . |

OTHER PUBLICATIONS

Abdelnour et al., "The Accessory Gene Regulator (agr) Controls *Staphylococcus aureus* Virulence in a Murine Arthritis Model," *Infection and Immunity* 61:3879–3885 (1993).

Alber, "Mutational Effects of Protein Stability," *Ann. Rev. Biochem.* 58:765–798 (1989).

Allibert et al., "Complementation of Nitrogen–Regulatory (ntr–like) Mutations in *Rhodobacter capsulatus* by an *Escherichia coli* Gene: Cloning and Sequencing of the Gene and Characterization of the Gene Product," *Journal of Bacteriology* 169:260–271 (1987).

Altschul et al., "Basic Local Alignment Search Tool," *J. Mol. Biol.* 215:403–410 (1990).

Anderson and Roth, "Tandem Genetic Duplications in Phage and Bacteria," *Ann. Rev. Biochem.* 31:473–505 (1977).

(List continued on next page.)

*Primary Examiner*—Ardin H. Marschel
(74) *Attorney, Agent, or Firm*—Lyon & Lyon LLP

(57) ABSTRACT

This disclosure describes isolated or purified deoxyribonucleotide (DNA) sequences, useful for the development of antibacterial agents, which contain the coding sequences of bacterial pathogenesis genes or essential genes, which are expressed in vivo. It further describes isolated or purified DNA sequences which are portions of such bacterial genes, which are useful as probes to identify the presence of the corresponding gene or the presence of a bacteria containing that gene. Also described are hypersensitive mutant cells containing a mutant gene corresponding to any of the identified sequences and methods of screening for antibacterial agents using such hypersensitive cells. In addition it describes methods of treating bacterial infections by administering an antibacterial agent active against one of the identified targets, as well as pharmaceutical compositions effective in such treatments.

66 Claims, 30 Drawing Sheets

| Relevant Genotype | Phenotype |
|---|---|
| ts/hypersens | No growth at high temperature |
| dom | No growth (not viable) |
| ts/hypersens   dom | No growth (not viable) |
| ts/hypersens   dom  + | Growth at high temperature<br>No growth at low temperature |

OTHER PUBLICATIONS

Arvidson et al., "Ch. 30—The Role of the δ–Lysin Gene (hld) in the agr–Dependent Regulation of Exoprotein Synthesis in *Staphylococcus aureus*," *Molecular Biology of the Staphylococci*, R.P. Novick, ed., VCH, New York, New York, pp. 419–431 (1990).

Bannatyne et al., "Comparison of the Efficacy of Cilofungin, Fluconazole and Amphotericin B in the Treatment of Systemic *Candida albicans* Infection in the Neutropenic Mouse," *Infection* 20:168–171 (1992).

Berger–Bachi et al., "FemA, a host–mediated factor essential for methicillin resistance in *Staphylococcus auerus*: Molecular cloning and characterization," *Mol. Gen. Genet.* 219:263–269 (1989).

Bergeron, "A Review of Models for the Therapy of Experimental Infections," *Scand. J. Infect Dis. Suppl.* 14:189–206 (1978).

Boden and Flock, "Cloning and characterization of a gene for a 19 kDa fibrinogen–binding protein from *Staphylococcus aureus*," *Molecular Microbiology* 12:599–606 (1994).

Bower et al., "Cloning and characterization of the *Bacillus subtilis* birA Gene Encoding a Repressor of the Biotin Operon," *Journal of Bacteriology* 9:2572–2575 (1995).

Branlant et al., "Nucleotide sequence determination of the DNA region coding for *Bacillus stearothermophilus* glyceraldehyde–3–phosphate dehydrogenase and of the flanking DNA regions required for its expression in *Escherichia coli*," *Gene* 75:145–155 (1989).

Davis, "Activity of Gentamicin, Tobramycin, Polymyxin B, and Colistimethate in Mouse Protection Tests with *Pseudomonas aeruginosa*," *Antimicrobial Agents and Chemotherapy* 8:50–53 (1975).

Day et al., "A simple method for the study in vivo of bacterial growth and accompanying host response," *Journal of Infection* 2:39–51 (1980).

Falkow et al., "The Interaction of Bacteria with Mammalian Cells," *Ann. Rev. Cell. Biol.* 8:333–363 (1992).

Ferrero et al., "Cloning and primary structure of *Staphylococcus aureus* DNA topoisomerase IV: a primary target of fluoroquinolones," *Molecular Microbiology* 13:641–653 (1994).

Fingl and Woodbury, "Chapter 1—General Principles," in *The Pharmacological Basis of Therapeutics* 5th edition, Goodman and Gilman editors, MacMillan Publishing Co., Inc., New York, pp. 1–46, (1975).

Gordee et al., "In Vitro and In Vivo Anti–Candida Activity and Toxicology of LY121019," *J. Antibiotics* 37:1054–1065 (1984).

Hamill et al., "Phagocytosis of *Staphylococcus aureus* by Cultured Bovine Aortic Endothelial Cells: Model for Post-adherence Events in Endovascular Infections," *Infection and Immunity* 54:833–836 (1986).

Hecht et al., "Mutations in λ repressor's amino–terminal domain: Implications for protein stability and DNA binding," *Proc. Natl. Acad. Sci. USA* 80:2676–2680 (1983).

Hershey and Taylor, "Nucleotide sequence and deduced amino acid sequence of *Escherichia coli* adenine phosphoribosyl–transferase and comparison with other analogous enzymes," *Gene* 43:287–293 (1986).

Hong and Ames, "Localized Mutagenesis of Any Specific Small Region of the Bacterial Chromosome," *Proc. Natl. Acad. Sci. USA* 68:3158–3162 (1971).

Horinouchi and Weisblum, "Nucleotide Sequence and Functional Map of pE194, a Plasmid That Specifies Inducible Resistance to Macrolide, Lincosamide, and Streptogramin Type B Antibiotics," *J. Bacteriology* 150:804–814 (1982).

Hoshino et al., "Nucleotide sequence of *Bacillus subtilis* dnaB: A gene essential for DNA replication initiation and membrane attachment," *Proc. Natl. Acad. Sci. USA* 84:653–657 (1987).

Imamoto and Nakamura, "*Escherichia coli* proteins involved in regulation of transcription termination function, structure, and expression of the nusA and nusB Genes," *Advances in Biophysics* 21:175–192 (1986).

Iordanescu and Bargonetti, "*Staphylococcus aureus* Chromosomal Mutations That Decrease Efficiency of Rep Utilization in Replication of pT181 and Related Plasmids," *Journal of Bacteriology* 171:4501–4503 (1989).

Ishino et al., Nucleotide sequence of the lig gene and primary structure of DNA ligase of *Escherichia coli*, *Mol. Gen. Genet.* 204:1–7 (1986).

Jackman et al., "Characterization of a nitrogen–fixation (nif) gene cluster from *Anabaena azollae* 1a shows that closely related cyanobacteria have highly variable but structured intergenic regions," *Microbiology* 141 (Part 9):2235–2244 (1995).

Jin and Benedik, "Sequences of the *Serratia marcescens* rplS and trmD genes," *Gene* 1:147–148 (1994).

Joshi and Singh, "Studies in potential organofluorine oral hypoglycemic agents," *J. Prakt. Chem.* 313(1):169–173 (1971).

Kamogashira and Takegata, "A Screening Method for Cell Wall Inhibitors Using a D–Cycloserine Hypersensitive Mutant," *J. Antibiotics* 41:803–806 (1988).

Kelly et al., "Surface Characteristics of *Pseudomonas aeruginosa* Grown in a Chamber Implant Model in Mice and Rats," *Infection and Immunity* 57:344–350 (1989).

Kontinen and Tokuda, "Overexpression of phosphatidylglycerophosphate synthase restores protein translocation in a secG deletion mutant of *Escherichia coli* at low temperture," *FEBS Letters* 364:157–160 (1995).

Lancy et al., "Nucleotide Sequences of dnaE, the Gene for the Polymerase Subunit of DNA Polymerase III in *Salmonella typhimurium*, and a Variant That Facilitates Growth in the Absence of Another Polymerase Subunit," *Journal of Bacteriology* 171:5581–5586 (1989).

Lazarevic and Karamata, "The tagGH operon of *Bacillus subtilis* 168 encodes a two–component ABC transporter involved in the metabolism of two wall teichoic acids," *Molecular Microbiology* 16:345–355 (1995).

Lee et al., "Cloning of the Gene and Amino Acid Sequence for Glucose 6–Phosphate Dehydrogenase from *Leuconostoc mesenteroides*," *J. Biol. Chem.* 266:13028–13034 (1991).

Lundberg et al., "Nucleotide sequence of the structural gene for dUTPase of *Escherichia coli* K–12," *EMBO J.* 2:967–971 (1983).

Malouin et al., "Outer Membrane and Porin Characteristics of *Serratia marcescens* Grown In Vitro and in Rat Intraperitoneal Diffusion Chambers," *Infection and Immunity* 58:1247–1253 (1990).

Margerrison et al., "Nucleotide Sequence of the *Staphylococcus aureus* gyrB–gyrA Locus Encoding the DNA Gyrase A and B Proteins," *Journal of Bacteriology* 174:1596–1603 (1992).

Mauel et al., "Genes concerned with synthesis of poly(glycerol phosphate), the essential teichoic acid in *Bacillus subtilis* strain 168, are organized in two divergent transcription units," *J. Gen. Microbiology* 137:929–941 (1991).

Metzger et al., "Characerization of the macromolecular synthesis (MMS) operon from *Listeria monocytogenes*," *Gene* 151:161–166 (1994).

Miyao et al., "Sequence of the *Bacillus subtilis* homolog of the *Escherichia coli* cell–division gene murG," *Gene* 118:147–148 (1992).

Mohan et al., "Molecular Cloning and Characterization of comC, a Late Competence Gene of *Bacillus subtilis*," *Journal of Bacteriology* 171:6043–6051 (1989).

Morohoshi et al., "*Bacillus subtilis alkA* Gene Encoding Inducible 3–Methyladenine DNA Glycosylase is Adjacent to the ada Operon," *Journal of Bacteriology* 175:6010–6017 (1993).

Murray, "Can Antibiotic Resistance by Controlled?" *New Engl. J. Med.* 330:1229–1230 (1994).

Na et al., "Isolation and Characterization of SUA5, a Novel Gene Required for Normal Growth in *Saccharomyces cerevisiae*," *Genetics* 131:791–801 (1992).

Normark et al., "*Escherichia coli* K–12 Mutants Hyperproducing Chromosomal Beta–Lactamase by Gene Repetitions," *J. Bacteriology* 132:912–922 (1977).

Numata et al., "Isolation of an Aminoglycoside Hypersensitive Mutant and its Application in Screening," *J. Antibiotics* 39:994–1000 (1986).

Ogawa et al., "Bacterial Adherence to Human Endothelial Cells In Vitro," *Infection and Immunity* 50:218–224 (1985).

Ohta et al., "Molecular Cloning of Two New Heat Shock Genes Related to the hsp70 Genes in *Staphylococcus aureus*," *Journal of Bacteriology* 176:4779–4783 (1994).

Pachamia et al., "Studies on 2,5–Disubstituted–1,3,4–oxadiazoles. Part II. Preparation and Antimicrobial Activity of 2-Arylsulphonamido/α–carbamylarylmethylamino–5–(4–pyridyl)–1,3,4–oxadiazoles," *J. Indian Chem. Soc.* 65(5):357–361 (1988).

Pattee, "Ch. 11—Genetic and Physical Mapping of the Chromosome of *Staphylococcus aureus* NCTC 8325," in *The Bacterial Chromosome*, edited by Drlica and Riley, American Society for Microbiology, Washington, D.C., pp. 163–169 (1990).

Pattee, "*Staphylococcus aureus*," in *Genetic Maps: Locus Maps of Complex Genomes*, 5th edition, edited by Stephen J. O'Brien, Cold Spring Harbor Laboratory Press, 2.22–2.27 (1990).

Pel et al., "Sequence comparison of new prokaryotic and mitochondrial members of the polypeptide chain release factor family predicts of five–domain model for release factor structure," *Nucleic Acids Research* 20:4423–4428 (1992).

Pearson and Lipman, "Improved tools for biological sequence comparison," *Proc. Natl. Acad. Sci. USA* 85:2444–2448 (1988).

Reich et al., "The RNA Component of the *Bacillus subtilis* RNase P: Sequence, Activity, and Partial Secondary Structure," *J. Biol. Chem.* 261:7888–7893 (1986).

Rouch et al., "Trimethoprim resistance transposon Tn4003 from *Staphylococcus aureus* encodes genes for a dihydrofolate reductase and thymidylate synthetase flanked by three copies of IS247," *Molecular Microbiology* 3:161–175 (1989).

Sanger et al., "DNA sequencing with chain–terminating inhibitors," *Proc. Natl. Acad. Sci. USA* 74:5463–5467 (1977).

Santoro and Levison, "Rat Model of Experimental Endocarditis," *Infection and Immunity* 19:915–918 (1978).

Schmid et al., "Genetic Analysis of Temperature–Sensitive Lethal Mutants of *Salmonella typhimurium*," *Genetics* 123:625–633 (1989).

Spagnolo et al., "Chronic Staphylococcal Osteomyelitis: a New Experimental Rat Model," *Infection and Immunity* 61:5225–5230 (1993).

Stark and Wahl, "Gene Amplification," *Ann. Rev. Biochem.* 53:447–491 (1984).

Tokunaga et al., "Isolation and Characterization of an *Escherichia coli* Clone Overproducing Proplipoprotein Signal Peptidase," *J. Biol. Chem.* 258:12102–12105 (1983).

Vann and Proctor, "Cytotoxic effects of ingested *Staphylococcus aureus* on bovine endothelial cells: Role of *S. aureus* α–hemolysin," *Microbial Pathogenesis* 4:443–453 (1988).

Vogelman et al., "In Vivo Postantibiotic Effect in a Thigh Infection in Neutropenic Mice," *Journal of Infectious Diseases* 157:287–298 (1988).

Yanisch–Perron, "Improved M13 phage cloning vectors and host strains: nucleotide sequences of the M13mp18 and pUC19 vectors," *Gene* 33:103–119 (1985).

FIG. 2

| | | Gyrase inhibitors | | | | DNA/RNA metabolism | | | | Protein metabolism | | | Cell wall inhibitors | | |
|---|---|---|---|---|---|---|---|---|---|---|---|---|---|---|---|
| | | Nov | Cou | Cipro | Nor | MitoC | φHg | NQO | Rif | Gen | Strep | Phen | Ceto | Amp | Fosfo |
| 5155 | dnaE | - | - | - | - | - | - | - | - | - | - | - | - | - | 4 |
| 7393 | gyrA216 | - | 4 | - | - | - | - | - | - | - | - | - | - | - | - |
| 7392 | gyrA215 | - | 4 | - | ≥4 | - | - | - | - | - | - | - | - | - | - |
| 7533 | gyrA212 | - | - | 8 | ≥8 | - | - | - | - | - | - | ND | ND | ND | - |
| 7784 | parC | - | - | - | - | - | - | - | - | - | - | - | - | - | - |
| 5026 | clm? | - | 4 | - | - | - | 4 | - | - | - | - | - | - | - | +8 |
| 5206 | parE | - | - | - | - | - | 4 | - | - | - | - | 4 | - | - | - |
| 8041 | parE | - | - | - | - | - | 4 | - | ND | - | ND | 4 | ND | ND | - |
| 5174 | parF | ≥4 | 16 | - | +4 | - | 16 | - | - | - | - | - | - | - | - |
| 5178 | parF | ≥2 | ≥64 | - | - | 8 | 32 | 4 | - | 8 | 8 | 8 | - | - | - |
| 7818 | parF | ≥2 | 4-16 | - | - | - | - | - | - | 4-8 | 4 | - | - | - | - |
| 7109 | clm? | - | - | - | - | - | 4 | - | - | - | - | - | - | - | - |
| 5045 | murB | - | - | - | - | - | 16 | - | - | - | - | - | - | - | - |
| 7583 | Round | - | - | - | - | - | 4 | - | - | - | - | - | - | - | - |
| 7587 | dapA | - | - | - | - | - | 32 | - | - | - | - | 32 | - | - | - |
| 5119 | murCEFG | ≥32 | ≥64 | 8 | - | 64 | 64 | 8 | - | 4 | - | 32 | - | 2-4 | - |
| 5091 | Thy inc⁻ | ≥64 | ≥64 | - | - | 8 | 4 | 4 | - | 4 | - | 8 | ≥8 | 32 | - |
| 7585 | Odd | - | - | - | - | - | - | - | - | - | - | - | 4 | 8 | - |
| 5208 | ftsH | - | - | - | - | - | - | - | - | - | 4 | - | - | - | - |
| 7141 | Filam | - | - | - | - | - | - | - | - | - | - | - | - | - | - |
| 5052 | Filam | - | - | - | - | - | - | - | - | - | - | - | - | - | - |
| 5051 | Filam | - | - | - | - | 16 | - | 64 | - | 8 | - | - | - | - | +4 |
| 5041 | UV⁻ | - | - | - | - | - | 16 | 4 | 4 | - | - | - | - | - | +32 |
| 5066 | UV⁻ | - | 4 | - | +4 | 4 | - | 32 | 4 | - | - | - | - | - | +8 |
| 5258 | clm? | - | - | - | - | 4 | 16 | 16 | 4 | 8 | - | 4 | - | - | 4 |

"-" INDICATES THAT THERE WAS NO SIGNIFICANT DIFFERENCE WITH THE WILD TYPE PARENT STRAIN. "ND": NOT DETERMINED.

FIG. 9.
Hit criteria: compd that inhibits mutant by ≥ 50%, and % inh. on mutant is higher than on WT by ≥ 30%
# of compounds tested: 480 for NT99; 240 for NT340
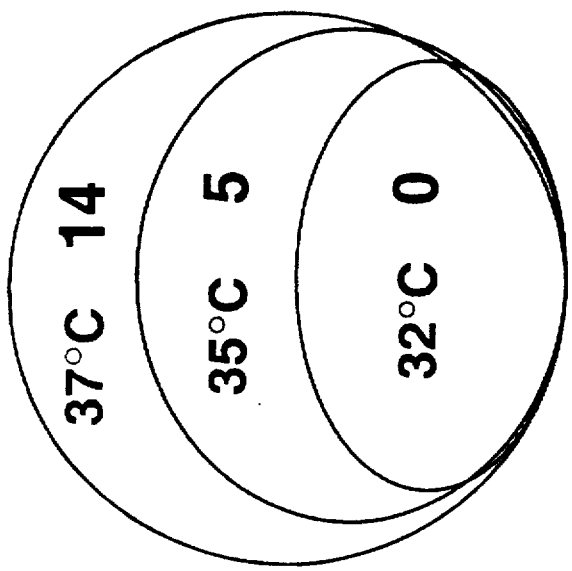
NT99
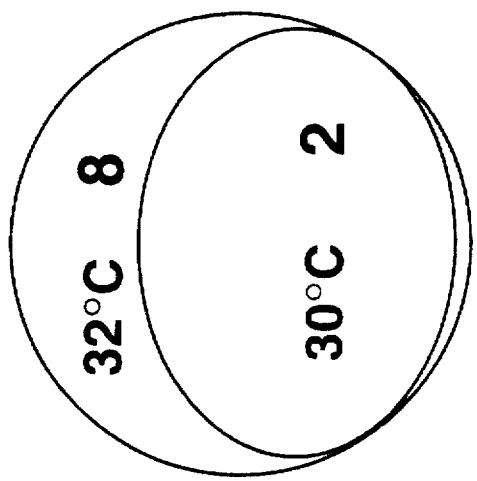
NT340

| NT | 20-0157 | 10-0167 | 50-0116 | 20-0204 | 20-0860 | 20-0123 | 10-0287 | 20-0045 | 10-0373 | 10-0752 | 20-0197 | 30-0014 | 20-0348 | 10-0797 | 00-3775 | 00-9370 | 00-2002 | 00-0167 |
|---|---|---|---|---|---|---|---|---|---|---|---|---|---|---|---|---|---|---|
| 2 | | | | | | | | | | | | | | | | 4 | 8 | 4 |
| 3 | | | | | | | | | | | | | | | | | 8 | |
| 4 | | | | | | | | | | | | | | | | 4-8 | | |
| 5 | | | | | | | | | | | | | | | | | | |
| 6 | | | | | | | | | | | | | | | | | | |
| 8 | | | | | | | | | | | | | | | | | | |
| 10 | | | | | | | | | | | | | | | | ND | ND | ND |
| 12 | | | | | | | | | | | | | | | | ≥4 | 4 | 4 |
| 14 | | | | | | | | | | | | | | | | | 16 | |
| 15 | | | | | | | | | | | | | | | | | | |
| 16 | | | | | | | | | | 16 | | | | ≥8 | | 4 | | 4 |
| 18 | | | | | | | | | | | | | | | | | 8 | 8 |
| 16 | | | | | | | | | ≥8 | | | | | | | | | |
| 22 | | | | | | | | | | | ≥4 | | | | | | | 4 |
| 23 | | | | | | | | | | | | | | | | | 4 | |
| 27 | | | | | | | | | | | | 4 | 4 | | | | | 8 |
| 28 | | | | | | | | | | | | | | 4-8 | 16-32 | 4 | 4 | 4 |
| 29 | | | | | | | | 8 | | ≥2 | | 4 | 8 | ≥2 | | 4-8 | 4-8 | 8 |
| 33 | | | | | | | | | | | | | | | | 8 | 8 | 4 |
| 36 | | | | | | 8 | | | | | 8 | 4 | 64 | 8 | 4 | | 4 | 8 |
| 42 | | | | | | | | | | | | 32 | | | | | 8 | 8 |
| 47 | | | | | | | | | | | | | | | | 8 | | |
| 50 | | | | | | | | | | | | | | | | | | |
| 51 | | | | | | | | | | | | | | 8-32 | | | | |
| 52 | | | | | | | | | | | | | | | | | 8 | 8 |

FIG. 12b.

*ND: NO DATA AVAILABLE: BLANK BOXES SHOW NO SIGNIFICANT DIFFERENCE IN MIC FROM THE WILD-TYPE STRAIN (SIGNIFICANCE LEVEL >+/- 2 FOLD).

NT 3

NT 5

NT 6

NT 8

NT 12

NT14

NT15

NT16

NT17

NT18

NT19

NT23

NT27

NT28

NT29

NT31

NT33a

NT33b

NT36

NT37

NT41/64

NT42

NT47

NT51

NT52

NT53

NT54

NT55

NT57

NT68

NT78

NT81

NT86

NT89

NT94

NT96

NT99

NT102

NT114

NT124

NT125

NT144

NT152

NT156

NT160

NT166

NT199

NT201

NT304

NT310

NT312

NT318

NT321

NT325

NT333

NT346

NT348

NT359

NT371

NT379

NT380

NT401

NT423

NT432

NT435

NT437

NT438

NT462

NT482

NT486

METHODS OF SCREENING FOR COMPOUNDS ACTIVE ON *STAPHYLOCOCCUS AUREUS* TARGET GENES

This is a divisional of co-pending application Ser. No. 08/714,918 filed Sep. 13, 1996, now U.S. Pat. No. 6,037, 123.

RELATED APPLICATIONS

This application claims priority to Martin et al., *STAPHYLOCOCCUS AUREUS ANTIBACTERIAL TARGET GENES*, United States Provisional Application No. 60/003, 798, filed Sep. 15, 1995, now abandoned, and to Benton et al., *STAPHYLOCOCCUS AUREUS ANTIBACTERIAL TARGET GENES*, U.S. Provisional Application No. 60/009,102, filed Dec. 22, 1995, now abandoned, which are incorporated herein by reference including drawings.

BACKGROUND

This invention relates to the field of antibacterial treatments and to targets for antibacterial agents. In particular, it relates to genes essential for survival of a bacterial strain in vitro or in vivo.

The following background information is not admitted to be prior art to the pending claims, but is provided only to aid the understanding of the reader.

Despite the development of numerous antibacterial agents, bacterial infections continue as a major, and currently increasing, medical problem. Prior to the 1980s, bacterial infections in developed countries could be readily treated with available antibiotics. However, during the 1980s and 1990s, antibiotic resistant bacterial strains emerged and have become a major therapeutic problem. There are, in fact, strains resistant to essentially all of the commonly used antibacterial agents, which have been observed in the clinical setting, notably including strains of *Staphylococcus aureus*. The consequences of the increase in resistant strains include higher morbidity and mortality, longer patient hospitalization, and an increase in treatment costs. (B. Murray, 1994, *New Engl. J. Med.* 330:1229–1230.) Therefore, there is a pressing need for the development of new antibacterial agents which are not significantly affected by the existing bacterial resistance mechanisms.

Such development of new antibacterial agents can proceed by a variety of methods, but generally fall into at least two categories. The first is the traditional approach of screening for antibacterial agents without concern for the specific target.

The second approach involves the identification of new targets, and the subsequent screening of compounds to find antibacterial agents affecting those targets. Such screening can involve any of a variety of methods, including screening for inhibitors of the expression of a gene, or of the product of a gene, or of a pathway requiring that product. However, generally the actual target is a protein, the inhibition of which prevents the growth or pathogenesis of the bacterium. Such protein targets can be identified by identifying genes encoding proteins essential for bacterial growth.

SUMMARY

Each pathogenic bacterial species expresses a number of different genes which are essential for growth of the bacteria in vitro or in vivo in an infection, and which are useful targets for antibacterial agents. This invention provides an approach to the identification of those genes, and the use of those genes, and bacterial strains expressing mutant forms of those genes, in the identification, characterization, and evaluation of targets of antibacterial agents. It further provides the use of those genes and mutant strains in screening for antibacterial agents active against the genes, including against the corresponding products and pathways. Such active compounds can be developed into antibacterial agents. Thus, this invention also provides methods of treating bacterial infections in mammals by administering an antibacterial agent active against such a gene, and the pharmaceutical compositions effective for such treatment.

For the *Staphylococcus aureus* essential genes identified in this invention, the essential nature of the genes was determined by the isolation of growth conditional mutants of *Staphylococcus aureus*, in this case temperature sensitive mutants (ts mutants). Each gene was then identified by isolating recombinant bacteria derived from the growth conditional mutant strains, which would grow under non-permissive conditions but which were not revertants. These recombinant bacteria contained DNA inserts derived from the normal (i.e., wild-type) *S. aureus* chromosome which encoded non-mutant products which replaced the function of the products of the mutated genes. The fact that a clone having such a recombinant insert can complement the mutant gene product under non-permissive conditions implies that the insert contains essentially a complete gene, since it produces functional product.

The Staphylococcal genes described herein have either been completely sequenced or have been partially sequenced in a manner which essentially provides the complete gene by uniquely identifying the coding sequence in question, and providing sufficient guidance to obtain the complete sequence and equivalent clones. For example, in some cases, sequences have been provided which can be used to construct PCR primers for amplification of the gene from a genomic sequence or from a cloning vector, e.g., a plasmid. The primers can be transcribed from DNA templates, or preferably synthesized by standard techniques. The PCR process using such primers provides specific amplification of the corresponding gene. Therefore, the complete gene sequence is obtainable by using the sequences provided.

In a first aspect, this invention provides a method of treating a bacterial infection in a mammal by administering a compound which is active against a bacterial gene selected from the group of genes corresponding to SEQ ID NO. 1–105. Each of these genes has been identified as an essential gene by the isolation of growth conditional mutant strains, and the complementation in recombinant strains of each of the mutated genes under non-permissive conditions, by expression from artificially-inserted DNA sequences carrying genes identified by the specified sequences of SEQ ID NO. 1–105. In particular embodiments of this method, the infection involves a bacterial strain expressing a gene corresponding to one of the specified sequences, or a homologous gene. Such homologous genes provide equivalent biological function in other bacterial species. Also in a preferred embodiment, the compound has a structure described by the general structure below:

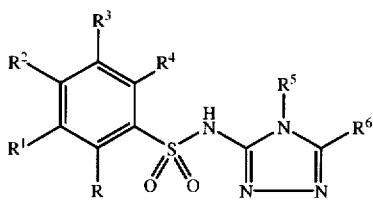

in which

R, R¹, R², and R³ are independently H, alkyl (C₁–C₅), or halogen;

R⁴ is H, alkyl (C₁–C₅) halogen, SH, or S-alkyl (C₁–C₃);

R⁵ is H, alkyl (C¹–C⁵), or aryl (C₆–C₁₀);

R⁶ is CH2NH2, alkyl (C1–C4), 2-pyridyl, 3-pyridyl, 4-pyridyl, 2-furyl, 3-furyl, 2-thienyl, 3-thienyl, or aryl (C₆–C₁₀);

or

R⁵ and R⁶ together are —C(R⁷)=C(R⁸)—C(R⁹)=C(R¹⁰)—, —N=C(R⁸)—C(R⁹)=C(R¹⁰)—, —C(R⁷)=N—C(R⁹)=C (R¹⁰)—, —C(R⁷)=C(R⁸)—N=C (R¹⁰)—, or —C(R⁷)=C(R⁸)—C(R⁹)=N—;

in which R⁷, R⁸, R⁹, and R¹⁰ are independently H, alkyl (C₁–C₅), halogen, fluoroalkyl (C₁–C5);

or

R⁷ and R⁸ together are —CH=CH—CH=CH—.

The term "alkyl" refers to a branched or unbranched aliphatic hydrocarbon group, e.g., methyl, ethyl, n-propyl, iso-propyl, and tert-butyl. Preferably the group includes from 1 to 5 carbon atoms and is unsubstituted, but alternativly may optionally be substituted with functional groups which are commonly attached to such chains, e.g., hydroxyl, fluoro, chloro, aryl, nitro, amino, amido, and the like.

The term "halogen" refers to a substituent which is fluorine, chlorine, bromine, or iodine. Preferably the substituent is fluorine.

The term "pyridyl" refers to a group from pyridine, generally having the formula C₅H₄N, forming a heterocyclic ring, which may optionally be substituted with groups commonly attached to such rings.

The term furyl refers to a heterocyclic group, having the formula C₄H₃O, which may be either the alpha or beta isomer. The ring may optionally be substituted with groups commonly attached to such rings.

The term "thienyl refers to a group from thiophen, generally having a formula C₄H₃S The term "aryl" refers to an aromatic hydrocarbon group which includes a ring structure in which the electrons are delocalized. Commonly, aryl groups contain a derivative of the benzene ring. The ring may optionally be substitued with groups commonly attached to aromatic rings, e.g., OH, CH₃, and the like.

The term "fluoroalkyl" refers to an alkyl group, as described above, which one or more hydrogens are substituted with fluorine.

"Treating", in this context, refers to administering a pharmaceutical composition for prophylactic and/or therapeutic purposes. The term "prophylactic treatment" refers to treating a patient who is not yet infected, but who is susceptible to, or otherwise at risk, of a particular infection. The term "therapeutic treatment" refers to administering treatment to a patient already suffering from an infection The term "bacterial infection" refers to the invasion of the host mammal by pathogenic bacteria. This includes the excessive growth of bacteria which are normally present in or on the body of a mammal. More generally, a bacterial infection can be any situation in which the presence of a bacterial population(s) is damaging to a host mammal. Thus, a mammal is "suffering" from a bacterial infection when excessive numbers of a bacterial population are present in or on a mammal's body, or when the effects of the presence of a bacterial population(s) is damaging the cells or other tissue of a mammal.

In the context of this disclosure, "bacterial gene" should be understood to refer to a unit of bacterial heredity as found in the chromosome of each bacterium. Each gene is composed of a linear chain of deoxyribonucleotides which can be referred to by the sequence of nucleotides forming the chain. Thus, "sequence" is used to indicate both the ordered listing of the nucleotides which form the chain, and the chain, itself, which has that sequence of nucleotides. ("Sequence" is used in the same way in referring to RNA chains, linear chains made of ribonucleotides.) The gene includes regulatory and control sequences, sequences which can be transcribed into an RNA molecule, and may contain sequences with unknown function. The majority of the RNA transcription products are messenger RNAs (mRNAs), which include sequences which are translated into polypeptides and may include sequences which are not translated. It should be recognized that small differences in nucleotide sequence for the same gene can exist between different bacterial strains, or even within a particular bacterial strain, without altering the identity of the gene.

Thus, "expressed bacterial gene" means that, in a bacterial cell of interest, the gene is transcribed to form RNA molecules. For those genes which are transcribed into mRNAs, the mRNA is translated to form polypeptides. More generally, in this context, "expressed" means that a gene product is formed at the biological level which would normally have the relevant biological activity (i.e., RNA or polypeptide level).

As used herein in referring to the relationship between a specified nucleotide sequence and a gene, the term "corresponds" or "corresponding" indicates that the specified sequence identifies the gene. Therefore, a sequence which will uniquely hybridize with a gene from the relevant bacterium corresponds to that gene (and the converse). In general, for this invention, the specified sequences have the same sequence (a low level of sequencing error or individual variation does not matter) as portions of the gene or flanking sequences. Similarly, correspondence is shown by a transcriptional, or reverse transcriptional relationship. Many genes can be transcribed to form mRNA molecules. Therefore, there is a correspondence between the entire DNA sequence of the gene and the mRNA which is, or might be, transcribed from that gene; the correspondence is also present for the reverse relationship, the messenger RNA corresponds with the DNA of the gene. This correspondence is not limited to the relationship between the full sequence of the gene and the full sequence of the mRNA, rather it also exists between a portion or portions of the DNA sequence of the gene and a portion or portions of the RNA sequence of the mRNA. Specifically it should be noted that this correspondence is present between a portion or portions of an mRNA which is not normally translated into polypeptide and all or a portion of the DNA sequence of the gene.

Similarly, the DNA sequence of a gene or the RNA sequence of an mRNA "corresponds" to the polypeptide encoded by that gene and mRNA. This correspondence between the mRNA and the polypeptide is established through the translational relationship; the nucleotide sequence of the mRNA is translated into the amino acid sequence of the polypeptide. Then, due to the transcription relationship between the DNA of the gene and the mRNA, there is a "correspondence", between the DNA and the polypeptide.

The term "administration" or "administering" refers to a method of giving a dosage of an antibacterial pharmaceutical composition to a mammal, where the method is, e.g., topical, oral, intravenous, transdermal, intraperitoneal, or intramuscular. The preferred method of administration can vary depending on various factors, e.g., the components of the pharmaceutical composition, the site of the potential or actual bacterial infection, the bacterium involved, and the severity of an actual bacterial infection.

The term "active against" in the context of compounds, agents, or compositions having antibacterial activity indicates that the compound exerts an effect on a particular bacterial target or targets which is deleterious to the in vitro and/or in vivo growth of a bacterium having that target or targets. In particular, a compound active against a bacterial gene exerts an action on a target which affects an expression product of that gene. This does not necessarily mean that the compound acts directly on the expression product of the gene, but instead indicates that the compound affects the expression product in a deleterious manner. Thus, the direct target of the compound may be, for example, at an upstream component which reduces transcription from the gene, resulting in a lower level of expression. Likewise, the compound may affect the level of translation of a polypeptide expression product, or may act on a downstream component of a biochemical pathway in which the expression product of the gene has a major biological role. Consequently, such a compound can be said to be active against the bacterial gene, against the bacterial gene product, or against the related component either upstream or downstream of that gene or expression product. While the term "active against" encompasses a broad range of potential activities, it also implies some degree of specificity of target. Therefore, for example, a general protease is not "active against" a particular bacterial gene which produces a polypeptide product. In contrast, a compound which inhibits a particular enzyme is active against that enzyme and against the bacterial gene which codes for that enzyme.

The term "mammal" refers to any organism of the Class Mammalia of higher vertebrates that. nourish their young with milk secreted by mammary glands, e.g., mouse, rat, and, in particular, human, dog, and cat.

By "comprising" it is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

A DNA containing a specific bacterial gene is obtainable using a shorter, unique probe(s) with readily available molecular biology techniques. If the method for obtaining such gene is properly performed, it is virtually certain that a longer DNA sequence comprising the desired sequence (such as the full coding sequence or the full length gene sequence) will be obtained. Thus, "obtainable by" means that an isolation process will, with high probability (preferably at least 90%), produce a DNA sequence which includes the desired sequence. Thus, for example, a full coding sequence is obtainable by hybridizing the DNA of two PCR primers appropriately derived from the sequences of SEQ ID NO. 1–105 corresponding to a particular complementing clone to a *Staphylococcus aureus* chromosome, amplifying the sequence between the primers, and purifying the PCR products. The PCR products can then be used for sequencing the entire gene or for other manipulations. Those skilled in the art will understand the included steps, techniques, and conditions for such processes. However, the full coding sequence or full gene is clearly not limited to a specific process by which the sequence is obtainable. Such a process is only one method of producing the final product.

A "coding sequence" or "coding region" refers to an open reading frame (ORF) which has a base sequence which is normally transcribed in a cell (e.g., a bacterial cell) to form RNA, which in most cases is translated to form a polypeptide. For the genes for which the product is normally a polypeptide, the coding region is that portion which encodes the polypeptide, excluding the portions which encode control and regulatory sequences, such as stop codons and promoter sequences.

In a related aspect, the invention provides a method for treating a bacterial infection in a mammal by administering an amount of an antibacterial agent effective to reduce the infection. The antibacterial agent specifically inhibits a biochemical pathway requiring the expression product of a gene corresponding to one of the genes identified in the first aspect above. Inhibition of that pathway inhibits the growth of the bacteria in vivo. In particular embodiments, the antibacterial agent inhibits the expression product of one of the identified genes.

In the context of the coding sequences and genes of this invention, "homologous" refers to genes whose expression results in expression products which have a combination of amino acid sequence similarity (or base sequence similarity for transcript products) and functional equivalence, and are therefore homologous genes. In general such genes also have a high level of DNA sequence similarity (i.e., greater than 80% when such sequences are identified among members of the same genus, but lower when these similarities are noted across bacterial genera), but are not identical. Relationships across bacterial genera between homologous genes are more easily identified at the polypeptide (i.e., the gene product) rather than the DNA level. The combination of functional equivalence and sequence similarity means that if one gene is useful, e.g., as a target for an antibacterial agent, or for screening for such agents, then the homologous gene is likewise useful. In addition, identification of one such gene serves to identify a homologous gene through the same relationships as indicated above. Typically, such homologous genes are found in other bacterial species, especially, but not restricted to, closely related species. Due to the DNA sequence similarity, homologous genes are often identified by hybridizing with probes from the initially identified gene under hybridizing conditions which allow stable binding under appropriately stringent conditions (e.g., conditions which allow stable binding with approximately 85% sequence identity). The equivalent function of the product is then verified using appropriate biological and/or biochemical assays.

In this context, the term "biochemical pathway" refers to a connected series of biochemical reactions normally occurring in a cell, or more broadly a cellular event such as cellular division or DNA replication. Typically, the steps in such a biochemical pathway act in a coordinated fashion to produce a specific product or products or to produce some other particular biochemical action. Such a biochemical pathway requires the expression product of a gene if the absence of that expression product either directly or indirectly prevents the completion of one or more steps in that pathway, thereby preventing or significantly reducing the production of one or more normal products or effects of that pathway. Thus, an agent specifically inhibits such a biochemical pathway requiring the expression product of a particular gene if the presence of the agent stops or substantially reduces the completion of the series of steps in that pathway. Such an agent, may, but does not necessarily, act directly on the expression product of that particular gene.

The term "in vivo" in the context of a bacterial infection refers to the host infection environment, as distinguished, for example, from growth of the bacteria in an artificial culture medium (e.g., in vitro).

The term "antibacterial agent" refers to both naturally occurring antibiotics produced by microorganisms to suppress the growth of other microorganisms, and agents synthesized or modified in the laboratory which have either bactericidal or bacteriostatic activity, e.g., β-lactam antibacterial agents, glycopeptides, macrolides, quinolones, tetracyclines, and aminoglycosides. In general, if an antibacterial agent is bacteriostatic, it means that the agent essentially stops bacterial cell growth (but does not kill the bacteria); if the agent is bacteriocidal, it means that the agent kills the bacterial cells (and may stop growth before killing the bacteria).

The term, "bacterial gene product" or "expression product" is used to refer to a polypeptide or RNA molecule which is encoded in a DNA sequence according to the usual transcription and translation rules, which is normally expressed by a bacterium. Thus, the term does not refer to the translation of a DNA sequence which is not normally translated in a bacterial cell. However, it should be understood that the term does include the translation product of a portion of a complete coding sequence and the translation product of a sequence which combines a sequence which is normally translated in bacterial cells translationally linked with another DNA sequence. The gene product can be derived from chromosomal or extrachromosomal DNA, or even produced in an in vitro reaction. Thus, as used herein, an "expression product" is a product with a relevant biological activity resulting from the transcription, and usually also translation, of a bacterial gene.

In another related aspect, the invention provides a method of inhibiting the growth of a pathogenic bacterium by contacting the bacterium with an antibacterial agent which specifically inhibits a biochemical pathway requiring the expression product of a gene selected from the group of genes corresponding to SEQ ID NO. 1–105 or a homologous gene. Inhibition of that pathway inhibits growth of the bacterium. In particular embodiments, the antibacterial agent inhibits the expression product of one of the identified genes. Also in preferred embodiment, the antibacterial agent is a compound having a structure as described in the first aspect above.

The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated.

A "pathogenic bacterium" includes any bacterium capable of infecting and damaging a mammalian host, and, in particular, includes *Staphylococcus aureus*. Thus, the term includes both virulent pathogens which, for example, can cause disease in a previously healthy host, and opportunistic pathogens which can only cause disease in a weakened or otherwise compromised host.

Similarly, the invention provides a method of prophylactic treatment of a mammal by administering a compound active against a gene selected from the group of genes corresponding to SEQ ID NO. 1–105 to a mammal at risk of a bacterial infection.

A mammal may be at risk of a bacterial infection, for example, if the mammal is more susceptible to infection or if the mammal is in an environment in which infection by one or more bacteria is more likely than in a normal setting. Therefore, such treatment can, for example, be appropriate for an immuno-compromised patient.

Also provided is a method of screening for an antibacterial agent by determining whether a test compound is active against one of the genes identified in the first aspect. In a particular embodiment the method is performed by providing a bacterial strain having a mutant form of a gene selected from the group of genes corresponding to SEQ. ID. NOS. 1–105 or a mutant gene homologous to one of those genes. The mutant form of the gene confers a growth conditional phenotype, e.g., a temperature-sensitive phenotype, on the bacterial strain having that mutant form. A comparison bacterial strain having a normal form of the gene is also provided and the two strains of bacteria are separately contacted with a test compound under semi-permissive growth conditions. The growth of the two strains in the presence of the test compound is then compared; a reduction in the growth of the bacterial strain having the mutant form compared to the growth of the bacterial strain having the normal form of the gene indicates that the test compound is active against the particular gene.

In this context, a "mutant form" of a gene is a gene which has been altered, either naturally or artificially, changing the base sequence of the gene, which results in a change in the amino acid sequence of an encoded polypeptide. The change in the base sequence may be of several different types, including changes of one or more bases for different bases, small deletions, and small insertions. By contrast, a normal form of a gene is a form commonly found in a natural population of a bacterial strain. Commonly a single form of a gene will predominate in natural populations. In general, such a gene is suitable as a normal form of a gene, however, other forms which provide similar functional characteristics may also be used as a normal gene. In particular, a normal form of a gene does not confer a growth conditional phenotype on the bacterial strain having that gene, while a mutant form of a gene suitable for use in these methods does provide such a growth conditional phenotype.

As used in this disclosure, the term "growth conditional phenotype" indicates that a bacterial strain having such a phenotype exhibits a significantly greater difference in growth rates in response to a change in one or more of the culture parameters than an otherwise similar strain not having a growth conditional phenotype. Typically, a growth conditional phenotype is described with respect to a single growth culture parameter, such as temperature. Thus, a temperature (or heat-sensitive) mutant (i.e., a bacterial strain having a heat-sensitive phenotype) exhibits significantly reduced growth, and preferably no growth, under non-permissive temperature conditions as compared to growth under permissive conditions. In addition, such mutants preferably also show intermediate growth rates at intermediate, or semi-permissive, temperatures. Similar responses also result from the appropriate growth changes for other types of growth conditional phenotypes.

Thus, "semi-permissive conditions" are conditions in which the relevant culture parameter for a particular growth conditional phenotype is intermediate between permissive conditions and non-permissive conditions. Consequently, in semi-permissive conditions the bacteria having a growth conditional phenotype will exhibit growth rates intermediate between those shown in permissive conditions and non-permissive conditions. In general, such intermediate growth rate is due to a mutant cellular component which is partially functional under semi-permissive conditions, essentially fully functional under permissive conditions, and is non-functional or has very low function under non-permissive conditions, where the level of function of that component is related to the growth rate of the bacteria.

The term "method of screening" means that the method is suitable, and is typically used, for testing for a particular property or effect in a large number of compounds. Therefore, the method requires only a small amount of time for each compound tested; typically more than one compound is tested simultaneously (as in a 96-well microtiter plate), and preferably significant portions of the procedure can be automated. "Method of screening" also refers to determining a set of different properties or effects of one compound simultaneously.

Since the essential genes identified herein can be readily isolated and the gene products expressed by routine methods, the invention also provides the polypeptides encoded by those genes. Thus, the invention provides a method of screening for an antibacterial agent by determining the effects of a test compound on the amount or level of activity of a polypeptide gene product of one of the identified essential genes. The method involves contacting cells expressing such a polypeptide with a test compound, and determining whether the test compound alters the amount or level of activity of the expression product. The exact determination method will be expected to vary depending on the characteristics of the expression product.

Such methods can include, for example, antibody binding methods, enzymatic activity determinations, and substrate analog binding assays.

It is quite common in identifying antibacterial agents, to assay for binding of a compound to a particular polypeptide where binding is an indication of a compound which is active to modulate the activity of the polypeptide.

Thus, by identifying certain essential genes, this invention provides a method of screening for an antibacterial agent by contacting a polypeptide encoded by one of the identified essential genes, or a biologically active fragment of such a polypeptide, with a test compound, and determining whether the test compound binds to the polypeptide or polypeptide fragment.

In addition, to simple binding determinations, the invention provides a method for identifying or evaluating an agent active on one of the identified essential genes. The method involves contacting a sample containing an expression product of one of the identified genes with the known or potential agent, and determining the amount or level of activity of the expression product in the sample.

In a further aspect, this invention provides a method of diagnosing the presence of a bacterial strain having one of the genes identified above, by probing with an oligonucleotide at least 15 nucleotides in length, which specifically hybridizes to a nucleotide sequence which is the same as or complementary to the sequence of one of the bacterial genes identified above. In some cases, it is practical to detect the presence of a particular bacterial strain by direct hybridization of a labeled oligonucleotide to the particular gene. In other cases, it is preferable to first amplify the gene or a portion of the gene before hybridizing labeled oligonucleotides to those amplified copies.

In a related aspect, this invention provides a method of diagnosing the presence of a bacterial strain by specifically detecting the presence of the transcriptional or translational product of the gene. Typically, a transcriptional (RNA) product is detected by hybridizing a labeled RNA or DNA probe to the transcript. Detection of a specific translational (protein) product can be performed by a variety of different tests depending on the specific protein product. Examples would be binding of the product by specific labeled antibodies and, in some cases, detection of a specific reaction involving the protein product.

As used above and throughout this application, "hybridize" has its usual meaning from molecular biology. It refers to the formation of a base-paired interaction between nucleotide polymers. The presence of base pairing implies that at least an appreciable fraction of the nucleotides in each of two nucleotide sequences are complementary to the other according to the usual base pairing rules. The exact fraction of the nucleotides which must be complementary in order to obtain stable hybridization will vary with a number of factors, including nucleotide sequence, salt concentration of the solution, temperature, and pH.

The term, "DNA molecule", should be understood to refer to a linear polymer of deoxyribonucleotides, as well as to the linear polymer, base-paired with its complementary strand, forming double-strand DNA (dsDNA). The term is used as equivalent to "DNA chain" or "a DNA" or "DNA polymer" or "DNA sequence":, so this description of the term meaning applies to those terms also. The term does not necessarily imply that the specified "DNA molecule" is a discrete entity with no bonding with other entities. The specified DNA molecule may have H-bonding interactions with other DNA molecules, as well as a variety of interactions with other molecules, including RNA molecules. In addition, the specified DNA molecule may be covalently linked in a longer DNA chain at one, or both ends. Any such DNA molecule can be identified in a variety of ways, including, by its particular nucleotide sequence, by its ability to base pair under stringent conditions with another DNA or RNA molecule having a specified sequence, or by a method of isolation which includes hybridization under stringent conditions with another DNA or RNA molecule having a specified sequence.

References to a "portion" of a DNA or RNA chain mean a linear chain which has a nucleotide sequence which is the same as a sequential subset of the sequence of the chain to which the portion refers. Such a subset may contain all of the sequence of the primary chain or may, contain only a shorter sequence. The subset will contain at least 15 bases in a single strand.

However, by "same" is meant "substantially the same"; deletions, additions, or substitutions of specific nucleotides of the sequence, or a combination of these changes, which affect a small percentage of the full sequence will still leave the sequences substantially the same. Preferably this percentage of change will be less than 20%, more preferably less than 10%, and even more preferably less than 3%. "Same" is therefore distinguished from "identical"; for identical sequences there cannot be any difference in nucleotide sequences.

As used in reference to nucleotide sequences, "complementary" has its usual meaning from molecular biology. Two nucleotide sequences or strands are complementary if they have sequences which would allow base pairing between the strands according to the usual pairing rules. This does not require that the strands would necessarily base pair at every nucleotide; two sequences can still be complementary with a low level of base mismatch such as that created by deletion, addition, or substitution of one or a few (up to 5 in a linear chain of 25 bases) nucleotides, or a combination of such changes.

Further, in another aspect, this invention provides a pharmaceutical composition appropriate for use in the methods of treating bacterial infections described above, containing a compound active on a bacterial gene selected from the group of genes described above and a pharmaceutically acceptable carrier. In a preferred embodiment, the compound has a structure as described in the first aspect above. Also, in a related aspect the invention provides a novel compound having antibacterial activity against one of the bacterial genes described above.

In a further related aspect a method of making an antibacterial agent is provided. The method involves screening for an agent active on one of the identified essential genes by providing a bacterial strain having a mutant form of one of the genes corresponding to SEQ ID NO. 1–105, or a homologous gene. As described above, the mutant form of the gene confers a growth conditional phenotype. A comparison bacterial strain is provided which has a normal form of said gene. The bacterial strains are contacted with a test compound in semi-permissive growth conditions, and the growth of the strains are compared to identify an antibacterial agent. The identified agent is synthesized in an amount sufficient to provide the agent in a therapeutically effective amount to a patient.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); *Goodman and Gilman's: The Pharmacological Basis of Therapeutics*, 8th Ed., Pergamon Press.

Consistent with the usage of "anti-bacterial agent" herein, the term "anti-bacterial activity" indicates that the presence of a particular compound in the growth environment of a bacterial population reduces the growth rate of that population, without being a broad cellular toxin for other categories of cells.

As is described below in the Detailed Description of the Preferred Embodiments, bacterial strains expressing a mutated form of one of the above identified genes, which confers a growth conditional phenotype, are useful for evaluating and characterizing the gene as an antibacterial target and for screening for antibacterial agents. Therefore, this invention also provides a purified bacterial strain expressing a mutated gene which is a mutated form of one of the bacterial genes identified above, where the mutated gene confers a growth conditional phenotype.

Similarly, this invention provides a recombinant bacterial cell containing an artificially inserted DNA construct which contains a DNA sequence which is the same as or complementary to one of the above-identified bacterial genes or a portion of one of those genes. Such cells are useful, for example, as sources of probe sequences or for providing a complementation standard for use in screening methods.

The term "recombinant bacterial cell" has its usual molecular biological meaning. The term refers to a microbe into which has been inserted, through the actions of a person, a DNA sequence or construct which was not previously found in that cell, or which has been inserted at a different location within the cell, or at a different location in the chromosome of that cell. Such a term does not include natural genetic exchange, such as conjugation between naturally occurring organisms. Thus, for example, a recombinant bacterium could have a DNA sequence inserted which was obtained from a different bacterial species, or may contain an inserted DNA sequence which is an altered form of a sequence normally found in that bacteria.

As described above, the presence of a specific bacterial strain can be identified using oligonucleotide probes. Therefore this invention also provides such oligonucleotide probes at least 15 nucleotides in length, which specifically hybridize to a nucleotide sequence which is the same as or complementary to a portion of one of the bacterial chains identified above.

In a related aspect this invention provides an isolated or purified DNA sequence at least 15 nucleotides in length, which has a nucleotide base sequence which is the same as or complementary to a portion of one of the above-identified bacterial genes. In particular embodiments, the DNA sequence is the same as or complementary to the base sequence of the entire coding region of one of the above-identified bacterial genes. Such an embodiment may in addition contain the control and regulatory sequence associated with the coding sequence.

Use of the term "isolated" indicates that a naturally occurring material or organism (e.g., a DNA sequence) has been removed from its normal environment. Thus, an isolated DNA sequence has been removed from its usual cellular environment, and may, for example, be in a cell-free solution or placed in a different cellular environment. For a molecule, such as a DNA sequence, the term does not imply that the molecule (sequence) is the only molecule of that type present.

It is also advantageous for some purposes that an organism or molecule (e.g., a nucleotide sequence) be in purified form. The term "purified" does not require absolute purity; instead, it indicates that the sequence, organism, or molecule is relatively purer than in the natural environment. Thus, the claimed DNA could not be obtained directly from total human DNA or from total human RNA. The claimed DNA sequences are not naturally occurring, but rather are obtained via manipulation of a partially purified naturally occurring substance (genomic DNA clones). The construction of a genomic library from chromosomal DNA involves the creation of vectors with genomic DNA inserts and pure individual clones carrying such vectors can be isolated from the library by clonal selection of the cells carrying the library.

In a further aspect, this invention provides an isolated or purified DNA sequence which is the same as or complementary to a bacterial gene homologous to one of the above-identified bacterial genes where the function of the expression product of the homologous gene is the same as the function of the product of one of the above-identified genes. In general, such a homologous gene will have a high level of nucleotide sequence similarity and, in addition, a protein product of homologous gene will have a significant level of amino acid sequence similarity. However, in addition, the product of the homologous gene has the same biological function as the product of the corresponding gene identified above.

Similarly, the invention provides an isolated or purified DNA sequence which has a base sequence which is the same as the base sequence of a mutated bacterial gene selected from one of the genes identified in the first aspect where the expression of this DNA sequence or the mutated bacterial gene confers a growth conditional phenotype in the absence of expression of a gene which complements that mutation. Such an isolated or purified DNA sequence can have the base sequence which varies slightly from the base sequence of the original mutated gene but must contain a base sequence change or changes which are functionally equivalent to the base sequence change or changes in the mutated gene. In most cases, this will mean that the DNA sequence has the identical bases at the site of the mutation as the mutated gene.

As indicated above, by providing the identified essential genes, the encoded expression products are also provided. Thus, another aspect concerns a purified, enriched, or isolated polypeptide, which is encoded by one of the identified essential genes. Such a polypeptide may include the entire gene product or only a portion or fragment of the encoded product. Such fragments are preferably biologically active fragments which retain one or more of the relevant biological activities of the full size gene product.

Other features and advantages of the invention will be apparent from the following description of the preferred embodiments, and from the claims.

BRIEF DESCRIPTION OF THE FIGURES

FIG. 2 presents the hypersensitivity profiles of a set of temperature sensitive mutants of Salmonella, for a variety of antibacterial agents with characterized modes of action, compared to the sensitivity profile of wild type.

FIG. 9 is a diagram for two S. aureus mutants, illustrating that a greater number of growth inhibitory hits are identified at higher temperatures using heat sensitive mutants. Compounds were identified as hits if the growth of the mutant was inhibited by at least 50% and the inhibition of growth of the mutant was at least 30% higher than the inhibition of growth of a wild type strain.

FIG. 12 presents the fold increase in sensitivity of a set of Staphylococcus aureus temperature sensitive mutants for a variety of compounds which inhibit growth of Staphylococcus aureus wild type, but which have uncharacterized targets of action.

DESCRIPTION OF THE PREFERRED EMBODIMENTS

Figure 1:
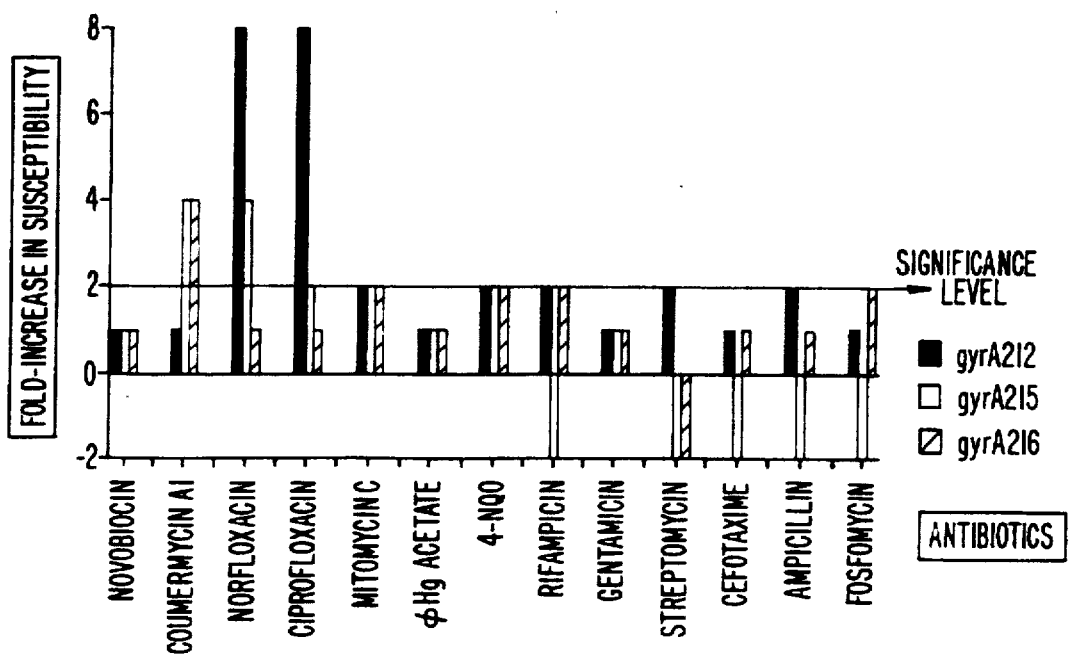
FIG. 1 shows the fold increase in sensitivity toward 12 antibacterial agents and a generally toxic agent for 3 temperature sensitive mutants of Salmonella typhimurium. These are mutants of DNA gyrase subunit A (gyrA212, gyrA215, and gyrA216, grown at a semi-permissive temperature (35_C.). Hypersensitivity is observed to antibacterial agents acting on DNA gyrase, but not to other classes of drugs or toxic agents. The data demonstrate that growth conditional mutations in a known target cause hypersensitivity to target inhibitors.

I. General Approach for Identification of Target Genes

As was briefly described in the Summary above, this invention concerns essential genes in Staphylococcus

*aureus*. This organism is a serious pathogen which frequently carries resistance to a variety of existing antibiotic agents. Such resistant strains of *S. aureus* are a particular problem in settings where antibacterial agents are intensively used, such as in hospitals. To overcome the therapeutic difficulties posed by the existing resistant strains, it is highly desirable that new classes of antibiotic drugs be found, particularly ones which are active against new bacterial targets. While such bacterial targets are usually (though not always) proteins, the targets can be identified by first identifying the bacterial genes which encode proteins (or RNA transcripts) that are essential for growth of the bacteria.

Identification of these genes which are essential for growth of the bacteria was accomplished by isolating conditional lethal mutant strains. Such mutant strains will grow under permissive conditions, but will not grow, or grow very poorly under non-permissive conditions. For the bacterial genes described herein, temperature sensitive mutants provided the growth conditional phenotype. The particular gene in each strain which was mutated to confer a growth conditional phenotype was then identified by isolating recombinant derivatives of the mutant strains. These recombinant strains each contained a DNA insert which, when expressed, would complement the defective gene and thus would allow growth under non-permissive conditions. These DNA inserts were provided by a genomic library of a normal *S. aureus* chromosome. The ability of the DNA insert in the recombinant strain to complement the defective product of the mutated gene showed that the DNA insert contained essentially a complete gene corresponding to a particular mutated gene. The vectors carrying each of these DNA inserts were constructed such that the *S. aureus* chromosomal insert could be amplified by PCR using flanking primer sequences. Each of the amplified *S. aureus* inserts was then partially sequenced, in general from both the 5' and 3' ends. This sequencing was, in general, single pass sequencing and, thus, the specified sequences may contain a low level of sequence errors compared to the actual gene sequence. Since the partial sequences at the 5' and 3' ends bracket the complete gene, such partial sequences uniquely identify and provide that complete gene without interference from a low level of sequencing error. The complete gene and gene sequence can be reliably obtained by any of several different methods. For example, probes can be constructed based on the partial sequences provided, which can be used to probe genomic or cDNA libraries of *S. aureus*. Clones containing the corresponding 5' and 3' sequences can then be further characterized and sequenced to provide the complete gene. In another approach, the partial 5' and 3' sequences can be used to construct PCR primer sequences which can be used to amplify the sequence between those primers and likewise provide the complete gene. In yet another approach, equivalent growth conditional mutant strains can be obtained by following the same or a similar process of mutagenizing the base *S. aureus* strain, and then likewise obtaining the complete gene by isolating complementing clones which correspond to the sequences provided, from a genomic or cDNA library. It should again be noted that, for any of these approaches, a low level of sequencing error in the sequence presented herein does not matter, since the stringency of the hybridizing conditions can be readily adjusted to provide the appropriately specific binding. While the genes identified in this invention are highly useful as targets for novel antibacterial therapy, the genes and parts of those genes are also useful to provide probes which can be used to identify the presence of a particular bacteria carrying a particular gene. In addition, the growth conditional mutant strains described above are also useful as tools in methods for screening for antibacterial agents which target that gene (targeting the corresponding normal gene). The methods involved in the identification of the mutant strains complementing recombinant clones and the particular genes are described in more detail below.

A. Bacterial Strain Selection

The growth conditional mutant strains and recombinant strains herein are based on *S. aureus* strain 8325-4. This strain has been the subject of substantial genetic characterization and is appropriate for use in the approach described herein. It is believed to be free of transposons, phage or extrachromosomal elements. Numerous other strains of *S. aureus* can likewise be used. However, it is advantageous to select a strain which has few, or preferably no, transposons or extrachromosomal elements, as such elements can complicate the genetic analysis.

B. Isolation of Conditional Lethal Mutants (general)

Heat-sensitive mutants were obtained after diethyl sulfate (DES; SIGMA Chemical) mutagenesis of strain 8325-4. Briefly, single colonies were inoculated into LB broth in individual wells of a 96-well microtiter plate and grown overnight (35° C., 18 h). Culture supernatants (10 μl) were diluted into λ-dilution buffer (λdil; 500 μl) and then treated with DES (5 μl). After a short incubation period (20 min at 37° C.), the treated cultures were serially diluted with λdil into microtiter plates. After an additional incubation period (8–12 h. at 37° C.), appropriate dilutions (50 μl each of 10 E-2 and 10 E-3) were plated onto TS agar plates and incubated overnight (30° C., 18 h). The plates were replica-printed onto two Tryptic-soy (TS) plates and incubated either at 30° C. or 43° C. (permissive and non-permissive conditions, respectively). Colonies growing at 30° C. but not at 43° C. were isolated and their ts phenotype was subsequently confirmed in a second round of plating. Only one ts mutant was picked from an original singe-colony culture to assure that the mutants isolated were independent from each other. Indepetidently-derived colonies with the appropriate phenotype are identified by direct screening on rich solid media at a permissive temperature (30° C.), as it obviates selection of mutants deficient in metabolic pathways, such as aromatic amino acid biosynthesis. No penicillin enrichment is employed, as it would counterselect mutant strains that are strongly bactericidal at the non-permissive temperature. A preliminary collection of 100 independent condition-lethal mutants and 71 non-independent mutants was made. This collection has been supplemented with additional condition-lethal mutants.

C. Creation of the *S. aureus* Shuttle Library

The *S. aureus* strain used for the preparation of genomic DNA for library construction as well as for the generation of conditional-lethal (temperature sensitive) mutants described in this document is a derivative of NCTC 8325, designated as 8325-4 (Novick, R. P., 1990). The 8325 parent strain is one of the better-characterized strains of *S. aureus*, with genetic and physical map data available in the current literature (Pattee, P. A., 1990). The 8325-4 derivative strain has all the chromosomal elements of the parent, with the exception of integrated (i.e., prophage and transposon DNA) and extrachromosomal (i.e., plasmid DNA) elements endogenous to the parent.

Cloning and subcloning experiments utilized the commercially-available *E. coli* strains JM109 (Promega) and DH5alpha (GIBCO-BRL). All enzymes cited (i.e., restriction endonucleases, ligases and phosphatases) were obtained commercially (NEB, Promega). All DNA cloning and manipulations are described in the current literature (Sambrook, et al., 1989). Parent plasmids pE194 and pUC19 have been described previously (Horinouchi, S. et al., 1982; Yanisch-Perron, C. et al., 1985) Recombinant constructs for use in a S. aureus host were first electroporated (Gene Pulser, BioRad) into S. aureus strain RN4220 (a restriction-deficient but methylase-proficient strain; Novick, R. P., 1990) before transduction into the target strain for complementation and cross-complementation analyses.

D. Library Construction

The shuttle plasmid vector used was pMP16, constructed by cloning the entire length of the natural S. aureus plasmid pE194 (linearized with Cla I) into the Nar I site of pUC19 (Yanisch-Perron et al., 1985). This new construct replicates and offers antibiotic resistance selections in both E. coli and S. aureus. It also provides blue-white screening to facilitate scoring of insert-containing clones. Carefully purified genomic DNA from S. aureus strain 8325-4 was partially digested (Sau3A I) and fragments of 2–8 kb were isolated by sucrose gradient centrifugation. DNA fragments isolated in this manner were then used for constructing two different libraries. In library A, the DNA fragments were directly cloned into pMP16, which had been linearized (Bam HI) and dephosphorylated (CIP). The DNA mixture was ligated (T4 DNA ligase) and transformed into E. coli DH5alpha. Library A thus constructed contains about 60,000 independent clones, 60% of which have inserts. In constructing library B, the ends of the Sau3A I fragments were partially filled with dGTP and dATP, ligated with linearized (Sal I) pMP16 that was partially filled with dCTP and dTTP, and transformed into E. coli. The advantage of partially filling the ends is that DNAs with the same ends can no longer ligate to each other; the majority of the ligation occurs between the vector and inserts, significantly increasing the percentage of insert-containing clones. In addition, the chance that two unrelated insert fragment are fortuitously ligated in the same clone is greatly reduced by using this strategy. Library B consists of 50,000 independent clones with >98% containing inserts. Both library A and library B contain at least a 50-fold representation of the S. aureus genome.

Clones from the two libraries were pooled and plasmid DNA extracted. The DNAs were used to transform S. aureus strain RN4220. About 100,000 erythromycin resistant transformants were pooled and infected with bacteriophage φ11 at a multiplicity of infection (MOI) of 0.01 to generate phage lysates containing the shuttle library plasmids. The lysates were then used to introduce the shuttle plasmids into ts mutants by transduction to isolate complementing clones.

E. Isolation of Complementing Clones (general)

The lysate from library B was first chosen for transduction of the ts mutants because of its higher insert frequency. The ts mutants were grown either in TS broth or on TS agar plates overnight (18 h). The cells were resuspended in TS broth containing $CaCl_2$ (5 mM) to an $OD_{600}$ between 2–3. The lysate from library B (10–50 μl) was added to the resuspended cells (2 ml) and incubated at 30° C. with slow shaking (20 m). Ice-cold sodium citrate (20 mM; 1 ml) was added and the culture was centrifuged to pellet the cells. After removing the supernatant, the pellet was resuspended in ice-cold sodium citrate (20 mM; 500 μl). A small aliquot (about 1/5000 of the total volume) was plated on a TSA-ery-citrate plate (TS agar containing 5 μg/ml erythromycin and 500 μg/ml sodium citrate) and incubated at 30° C. overnight (18 h). The total number of erythromycin-resistant transductants screened were estimated from this plate; at least 200,000 transductants were screened for each ts mutant to assure that the library population was well represented.

The rest of the cells were plated onto the same selection media (3–5 plates), incubated at 30° C. for 5 h and then at 43° C. overnight (18 h). Individual colonies that appeared on the 43° C. plates were isolated and infected with φ11 to generate lysates.

The lysates prepared from these individual colonies were then used to transduce the same ts mutants as described above, using much smaller volumes of cells (0.1 ml) and lysates (1–3 μl) to facilitate testing of large number of lysates. Equal amounts of the transduced cultures were plated onto two sets of TSA-ery-citrate plates and incubated at either 30 or 43° C. Individual lysates that generated similar numbers of transductants at 30 and 43° C. were scored as complementing clones. Among the first 96 ts mutants studied, complementing clones were isolated for 60 (63%) of the mutants; 57 were from library B and 3 were from library A.

To test whether different ts mutants carry mutations in the same or closely linked genes, cross complementation was performed to evaluate the ability of positive clones of one ts mutant to complement another mutant. The results showed that, while some positive clones failed to complement any ts mutants other than their primary mutant, other clones were able to complement additional mutants. Taken together, the cross complementation studies identified 38 loci on the S. aureus chromosome, each consisting of at least one essential gene.

All the positive clones for the 60 ts mutants were twice streaked on TSA-ery-citrate plates and grown at 43° C. to eliminate φ11 prophage from the host cells. Plasmid DNA was extracted from these complementing clones and transformed into E. coli. The plasmids were prepared from the E. coli clones and used for restriction mapping and subcloning of the inserts.

F. Strategy for DNA Sequencing of Complementing Clones (general)

Complementing clones were subcloned into a sequencing vector (pGEM3Zf(+); Promega) containing regions of DNA flanking the multiple cloning site (T7 and SP6 primer annealing sites) to facilitate plasmid-based automated sequencing. Clones larger than 1.54 kB were cut with restriction endonucleases (BamHI, HindIII, EcoRI; NEB) and then subcloned into the same sequencing vector. DNA sequence ladders were generated by thermocycle sequencing procedures based upon the use of fluorescent-labeled primers (one of T7, SP6, M13 forward and M13 reverse; ABI), a thermostable DNA polymerase (AmpliTaq; Perkin Elmer/ABI) and dideoxy terminator chemistry (Sanger, et al, 1977, Proc. Natl. Acad. Sci. USA 74:54463). Data were acquired on an ABI 373A automated DNA sequencer (ABI) and processed using the PRISM sequence analysis software (ABI). The nucleotide sequences disclosed herein represent the range of highest quality data acquired in one pass for each clone. All DNA sequence data are reported with the same directionality, 5' to 3', regardless of which strand (i.e., coding or anti-coding) is sequenced. Some DNA sequence is reported using standard IUB codes in cases where sequence ambiguities could not be absolutely resolved in first-pass sequence.

For the sequences identified herein as SEQ ID NO. 1–105, the sequences corresponding to each complementing clone identify and provide the coding sequence (gene) responsible for providing that complementation. Therefore, the sequences corresponding to each complementing clone correspond to a particular essential gene.

G. DNA Sequence Analysis of Complementing Clones
Similarity Searching (general)

Sequence data were analyzed for similarity to existing publicly-available database entries both at the nucleic acid level and the (putative) polypeptide level; the current releases and daily cumulative updates of these databases are maintained at the NCBI and are freely accessible. The programs BLASTN (Altschul, et al., 1990, *J. Mol. Biol.* 215:403–410) and FASTA (Pearson, et al., 1988, *Proc. natl. Acad. Sci. USA* 85:2444–2448) were used to search the nucleic acid databases GenBank (Release 89.0) and EMBL (Rel. 43.0), while the programs BLASTX and TFASTA were used to search the protein databases SwissProt (Rel. 30.0), PIR (Rel. 45.0) and GenPept (Rel 89.0). For reporting the results of the similarity searching below, the following abbreviations of bacterial species names are used:

Bsu=*Bacillus subtilis*
Eco=*Escherichia coli*
Zmo=*Zymomonas mobilis*
Bme=*Bacillus megaterium*
Lme=*Leuconostoc mesenteriodes*
Sxy=*Staph. xylosys*
Sca=*Staph. carnosus*
Sau=*Staph. aureus*
Hin=*Haemophilus influenzae*
Seq=*Strep. equisimilis*
Bca=*Bacillus caldolyticus*
Kpn=*Klebsiella pneumoniae*
Mle=*Mycobacterium leprae*

H. DNA Sequence of Complementing Clones

Mutant NT 6—Clone pMP33: an Example of Complementing ORFs with Literature Precedent in *Staph. aureus*.

The ORF complementing the heat-sensitive phenotype of *S. aureus* mutant NT6 described here was identified by sequencing subclones of pMP33, an *E. coil/S. aureus* shuttle vector containing a 2.3 kilobase-pair (kb) insert of parental (i.e. wild-type) genomic DNA. The subclones, pMP1006 (0.5 kb), pMP1007 (0.9 kb) and pMP 1008 (0.9 kb), were generated by EcoRI and HindIII digestion of the parent clone and ligation into pGEM3Zf(+), a commercially available vector (Promega, Inc.) suitable for double-stranded DNA sequencing applications.

PCR-based methods (PRISM Dye Primer DNA Sequencing Kit; ABI, Inc.) were employed to generate DNA sequence data from the SP6 promoter of each of the subclones. Electrophoresis and detection of fluorescently-labelled DNA sequence ladder on an ABI 373A automated DNA sequencer (ABI, Inc.) yielded the following sequence data:

```
subclone 1006, a 500 kb Hind III fragment
1006.seq Length: 400 nt
    1 AAATAATCTA AAAATTGGTA GTNCTCCTTC AGATAAAAAT CTTACTTTAA   SEQ ID NO. 4

51 CACCATTCTT TTNAACTNNT TCCGTGTTTC TTTTTCTAAG TCCATCCATA

101 TTTTNAATGA TGTCATCTGC TGTTTTATCT TTTAAATCTA ACACTGAGTG

151 ATAACGGATT TGTAGCACAG GATCAAATCC TTTATGGAAT CCAGTATGTT

201 CAAATCCTAA GTTACTCATT TTATCAAAGA ACCAATCATT ACCAGCATTA

251 CCTGTAATCT CGCCATCATG ATTCAAGTAT TGATATGGTA AATATGGATC

301 GNTATGTAGG TATAGNCAAC GATGTTTTTT AACATATTTT GGATAATTCA

351 TTAAAGNAAA AGTGTACGAG TNCTTGATTT TCATANTCAA TCACTGGACC subclone 1007, a 900 bp Hind III fragment
1007.seq Length: 398 nt
    1 TGCGTGAAAT NACTGTATGG CNTGCNATCT GTAAAGGCAC CAAACTCTTT   SEQ ID NO. 5

51 AGCTGTTAAA TTTGTAAACT TCATTATCAT TACTCCTATT TGTCTCTCGT

101 TAATTAATTT CATTTCCGTA TTTGCAGTTT TCCTATTTCC CCTCTGCAAA

151 TGTCAAAAAT AATAAATCTA ATCTAAATAA GTATACAATA GTTAATGTTA

201 AAACTAAAAC ATAAACGCTT TAATTGCGTA TACTTTTATA GTAATATTTA

251 GATTTTNGAN TACAATTTCA AAAAAAGTAA TATGANCGTT TGGGTTTGCN

301 CATATTACTT TTTTNGAAAT TGTATTCAAT NTTATAATTC ACCGTTTTTC

351 ACTTTTTNCA AACAGTATTC GCCTANTTTT TTTAAATCAA GTAAACTT subclone 1008, a 920 bp EcoR I/Hind III fragment
1008.seq Length: 410 nt
    1 GTAATGACAA ATNTAACTAC AATCGCTTAA AATATTACAA AGACCGTGTG   SEQ ID NO. 6

51 TNAGTACCTT TAGCGTATAT CAACTTTAAT GAATATATTA AAGAACTAAA

101 CGAAGAGCGT GATATTTTAA ATAAAGATTT AAATAAAGCG TTAAAGGATA

151 TTGAAAAACG TCCTGAAAAT AAAAAAGCAC ATAACAAGCG AGATAACTTA
```

```
201  CAACAACAAC TTGATGCAAA TGAGCAAAAG ATTGAAGAAG GTAAACGTCT

251  ACAAGANGAA CATGGTAATG AATTACCTAT CTCTNCTGGT TTCTNCTTTA

301  TCAATCCATT TGANGTTGTT TATTATGCTG GTGGTACATC AAATGCATTC

351  CGTCATTTTN CCGGAAGTTA TGCAGTGCAA TGGGAAATGA TTAATTATGC

401  ATTAAATCAT
```

Figure 23:
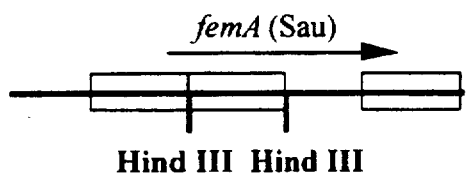

A partial restriction map of clone pMP33 appears in FIG. 23, with open boxes to represent the percentage of the clone for which DNA sequence has been obtained in one pass.

Analysis of these data reveals identity (>90%, including sequence ambiguities in first-pass sequence) at both the nucleotide and (predicted) amino acid-level to the femA gene of S. aureus (Genbank ID M23918; published in Berger-Baechi, B. et al., Mol. Gen. Genet. 219 (1989) 263–269). The nucleotide sequence identities to the Genbank entry indicate that complementing clone PMP33 contains the complete ORF encoding the FemA protein along with the necessary upstream elements for its expression in S. aureus. The figure demonstrates the relative position of the subclones along with the location of the ORF encoding the FemA protein.

Mutant NT64/Clone pMP98: an Example of Complementing ORFs Without Direct Literature Precedent, but Identifiable by Similarity to Genes from Other Bacteria The ORF(s) complementing the heat-sensitive phenotype of S. aureus mutant NT64 described here were identified by sequencing a subclone of pMP98, an E. coli/S. aureus shuttle vector containing a 2.9 kb insert of parental (i.e. wild-type) genomic DNA. The subclone, pMP1038, was generated by EcoRI and HindIII digestion of pMP98 and ligation into pGEM3Zf(+), a commercially available vector (Promega, Inc.) suitable for use in automated fluorescent sequencing applications. Using fluorescently-labelled dye primers (T7 and SP6; ABI, Inc.), a total of 914 bp of sequence from the two edges of the sublone was generated.

```
subclone 1038, a 2800 bp genomic fragment
1038.sp6 Length: 417 nt
   1  GTGATGGATT AAGTCCTAAA TTTNNATTCG CTTTCTTGTC TTTTTAATCT   SEQ ID NO. 106

51  TTTTCAGACA TTTTATCGAT TTCACGTTTT GTATACTTAG GATTTAAATA

101  GGCATTAATT GTTTTCTTGT CCAAAAATTG ACCATCTTGA TACAAATATT

151  TATCTGTTGG AAATACTTCT TTACTTAAGT NCAATAAACC ATCTTCAAAG

201  TCGCCGCCAT TATAACTATT TGCCATGTTA TCTTGTAAAA GTCCTCTTGC

251  CTGGNTTTCT TTAAATGGTA ACAATGTACG NTAGTTATCA CCTTGTACAT

301  TTTTATCCGT TGCAATTTCT TNTACTTGAT TTGAACTATT GTTATGTTTT

351  NAATTATCTT TTCCCAGCCT GGGTCATCCT TATGGTTAHC ACAAGCAGCG

401  AGTATAAAGG TAGCTGT 1038.t7 Length: 497 nt
   1  TAATGTAGCA ATTACAAGGC CTGAAGAGGT GTTATATATC ACTCATGCGA   SEQ ID NO. 107

51  CATCAAGAAT GTNATTTGGN CGCCCTCAGT CAAATATGCC ATCCAGNTTT

101  TNAAAGGAAA TTCCAGAATC ACTATTAGAA AATCATTCAA GTGGCAAACG

151  ACAAACGGTA CAACCTNNGG CAAAACCTTT TNCTAAACGC GGNTTTTGTC

201  AACGGNCAAC GTCAACGGNN AANCAAGTAT TNTNATCTGN TTGGAATNTT

251  GGTGGCAANG TGGTGCNTAA NGNCNCCGGG GGGAGGCATT GTNNGTAATT

301  TTAACGNGGA NAATGGCTCN NTCGGNCTNG GTNNTATNTT TTATTCACAC

351  AGGGNCGCGN CANGTTTTTT TTGTNGGATT TTTTTCCCCC NTTTTTNAAA

401  AGGNGGGGTN TTNNGGGTGG CTGNTTTANT NGTCTCNGNG TGGNCGTGNN

451  TCATTNNTTT TTTTNTTNNA TCCAAGCCTT NTATGACTTT NNTTGGG
```

Figure 20:
FIG. 20 is a partial restriction map of the S. aureus clone insert (complementing mutant NT64), showing the position of the initial left and right sequences obtained.

Similarity searches at the nucleotide and (putative) amino acid level reveal sequence identity from the left-most (T7) edge of the clone to the Genbank entry for pcrA, a putative helicase from *S. aureus* (Genbank ID M63176; published in Iordanescu, S. M. and Bargonetti, J. *J. Bacteriol.* 171 (1989) 4501–4503). The sequence identity reveals that the pMP98 clone contains a C-terminal portion of the ORF encoding pcrA, but that this ORF is unlikely to be responsible for complementation of the NT64 mutant. The Genbank entry extends 410 bp beyond the 3' end of the pcrA gene, and does not predict any further ORFs. Similarity searches with data obtained from the right-most (SP6) edge reveal no significant similarities, indicating that the complementing ORF in pMP98 is likely to be unpublished for *S. aureus*. A partial restriction map of clone pMP98 appears in FIG. 20 (there are no apparent restriction sites for BamH I, EcoR I, or Hind III); the relative position and orientation of the identified (partial) ORF corresponding to the PcrA protein is indicated by an arrow:

From the preliminary sequence data, the following PCR primers were designed:

pMP98(+): 5'-CTG AAG AGG TGT TAT ATA TCA C-3' SEQ ID NO. 108 pMP98(−): 5'-GTG ATG GAT TAA GTC CTA AAT T-3' SEQ ID NO. 109

These primers were used to amplify the 2.9 kb genomic DNA fragment in one round of PCR amplification directly from *S. aureus* genomic DNA (parental strain 8325-4). Similar strategies using PCR primers designed from partial sequences can be used for amplifying the genomic sequence (or a cloned genomic sequence) corresponding to the additional complementing clones described below. Additional primers based upon the obtained sequence were designed to generate further DNA sequence data by primer-walking, using the dye terminator strategy (PRISM DyeDeoxy Terminator Kit; ABI, Inc.).

pMP98.b(+): 5'-CTC AGT CAA ATA TGC CAT CCA G-3' SEQ ID NO. 110 pMP98.b(−): 5'-CTT TAA ATG GTA ACA ATG TAC G-3' SEQ ID NO. 111

Figure 41:
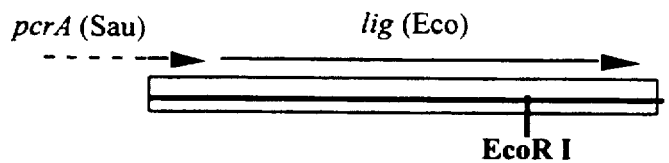

The following sequence data were obtained, as depicted in the partial restriction map in FIG. 41:

```
clone pMP98
pMP98  Length: 2934 nt
    1 CATGAAATGC AAGAAGAACG TCGTATTTGT TATGTAGCAA TTACAAGGGC    SEQ ID NO. 36

51 TGAAGAGGTG TTATATATCA CTCATGCGAC ATCAAGAATG TTATTTGGTC

101 GCCCTCAGTC AAATATGCCA TCCAGATTTT TAAAGGAAAT TCCAGAATCA

151 CTATTAGAAA ATCATTCAAG TGGCAAACGA CAAACGATAC AACCTAAGGC

201 AAAACCTTTT GCTAAACGCG GATTTAGTCA ACGAACAACG TCAACGAAAA

251 AACAAGTATT GTCATCTGAT TGGAATGTAG GTGACAAAGT GATGCATAAA

301 GCCTGGGGAG AAGGCATGGT GAGTAATGTA AACGAGAAAA ATGGCTCAAT

351 CGAACTAGAT ATTATCTTTA AATCACAAGG GCCAAAACGT TTGTTAGCGC

401 AATTTGCACC AATTGAAAAA AAGGAGGATT AAGGGATGGC TGATTTATCG

451 TCTCGTGTGA ACGRDTTACA TGATTTATTA AATCAATACA GTTATGAATA

501 CTATGTAGAG GATAATCCAT CTGTACCAGA TAGTGAATAT GACAAATTAC

551 TTCATGAACT GATTAAAATA GAAGAGGAGC ATCCTGAGTA TAAGACTGTA

601 GATTCTCCAA CAGTTAGAGT TGGCGGTGAA GCCCAAGCCT CTTTCAATAA

651 AGTCAACCAT GACACGCCAA TGTTAAGTTT AGGGAATGCA TTTAATGAGG

701 ATGATTTGAG AAAATTCGAC CAACGCATAC GTGAACAAAT TGGCAACGTT

751 GAATATATGT GCGAATTAAA AATTGATGGC TTAGCAGTAT CATTGAAATA

801 TGTTGATGGA TACTTCGTTC AAGGTTTAAC ACGTGGTGAT GGAACAACAG

851 GTTGAAGATA TTACCGRAAA TTTAAAAACA ATTCATGCGA TACCTTTGAA

901 AATGAAAGAA CCATTAAATG TAGAAKTYCG TGGTGAAGCA TATATGCCGA

951 GACGTTCATT TTTACGATTA AATGAAGAAA AAGAAAAAAA TGATGAGCAG

1001 TTATTTGCAA ATCCAAGAAA CGCTGCTGCG GGATCATTAA GACAGTTAGA

1051 TTCTAAATTA ACGGCAAAAC GAAAGCTAAG CGTATTTATA TATAGTGTCA

1101 ATGATTTCAC TGATTTCAAT GCGCGTTCGC AAAGTGAAGC ATTAGATGAG

1151 TTAGATAAAT TAGGTTTTAC AACGAATAAA AATAGAGCGC GTGTAAATAA

1201 TATCGATGGT GTTTTAGAGT ATATTGAAAA ATGGACAAGC CAAAGAAGAG
```

-continued

```
1251 TTCATTACCT TATGATATTG ATGGGATTGT TATTAAGGTT AATGATTTAG

1301 ATCAACAGGA TGAGATGGGA TTCACACAAA AATCTCCTAG ATGGGCCATT

1351 GCTTATAAAT TTCCAGCTGA GGAAGTAGTA ACTAAATTAT TAGATATTGA

1401 ATTAAGTATT GGACGAACAG GTGTAGTCAC ACCTACTGCT ATTTTAGAAC

1451 CAGTAAAAGT AGCTGGTACA ACTGTATCAA GAGCATCTTT GCACAATGAG

1501 GATTTAATTC ATGACAGAGA TATTCGAATT GGTGATAGTG TTGTAGTGAA

1551 AAAAGCAGGT GACATCATAC CTGAAGTTGT ACGTAGTATT CCAGAACGTA

1601 GACCTGAGGA TGCTGTCACA TATCATATGC CAACCCATTG TCCAAGTTGT

1651 GGACATGAAT TAGTACGTAT TGAAGGCGAA GTTAGCACTT CGTTGCATTA

1701 ATCCAAAATG CCAAGCACAA CTTGTTGAAG GATTGATTCA CTTTGTATCA

1751 AGACAAGCCA TGAATATTGA TGGTTTAGGC ACTAAAATTA TTCAACAGCT

1801 TTATCAAAGC GAATTAATTA AAGATGTTGC TGATATTTTC TATTTAACAG

1851 AAGAAGATTT ATTACCTTTA GACAGAATGG GGCAGAAAAA AGTTGATAAT

1901 TTATTAGCTG CCATTCAACA AGCTAAGGAC AACTCTTTAG AAAATTTATT

1951 ATTTGGTCTA GGTATTAGGC ATTTAGGTGT TAAAGCGAGC CAAGTGTKAG

2001 CAGAAAAATA TGAAACGATA GATCGATTAC TAACGGTAAC TGAAGCGGAA

2051 TTAGTAGAAT TCATGATATA GGTGATAAAG TAGCGCAATC TGTAGTTACT

2101 TATTTAGCAA ATGAAGATAT TCGTGCTTTA ATTCCATAGG ATTAAAAGAT

2151 AAACATGTTA ATATGATTTA TGAAGGTATC CAAAACATCA GATATTGAAG

2201 GACATCCTGA ATTTAGTGGT AAAACGATAG TACTGACTGG TAAGCTACAT

2251 CCAAATGACA CGCAATGAAG CATCTAAATG GCTTGCATCA CCAAGGTGCT

2301 AAAGTTACAA GTAGCGTTAC TAAAAATACA GATGTCGTTA TTGCTTGTGA

2351 AGATGCAGGT TCAAAATTAA CAAAAGCACA AAGTTTAGGT ATTGAAATTT

2401 GGACAGAGCA ACAATTTGTA GATAAGCAAA ATGAATTAAA TAGTTAGAGG

2451 GGTATGTCGA TGAAGCGTAC ATTAGTATTA TTGATTACAG CTATCTTTAT

2501 ACTCGCTGCT TGTGGTAACC ATAAGGATGA CCAGGCTGGA AAAGATAATC

2551 AAAAACATAA CAATAGTTCA AATCAAGTAA AAGAAATTGC AACGGATAAA

2601 AATGTACAAG GTGATAACTA TCGTACATTG TTACCATTTA AAGAAAGCCA

2651 GGCAAGAGGA CTTTTACAAG ATAACATGGC AAATAGTTAT AATGGCGGCG

2701 ACTTTGAAGA TGGTTTATTG AACTTAAGTA AAGAAGTATT TCCAACAGAT

2751 AAATATTTGT ATCAAGATGG TCAATTTTTG GACAAGAAAA CAATTAATGC

2801 CTATTTAAAT CCTAAGTATA CAAAACGTGA AATCGATAAA ATGTCTGAAA

2851 AAGATAAAAA AGACAAGAAA GCGAATGAAA ATTTAGGACT TAATCCATCA

2901 CACGAAGGTG AAACAGATCG ACCTGCAGKC ATGC
```

From this data, a new ORF in the pMP98 clone was identified as having significant similarity to lig, the gene encoding DNA ligase from *E. coli*: (Genbank ID M30255; published in Ishino, Y., et al., *Mol. Gen. Genet.* 204(1986), 1–7). The revised clone map of pMP98, including the predicted size and orientation corresponding to the putative DNA ligase ORF, is shown in FIG. 41:

The DNA ligase protein from *E. coli* is composed of 671 amino acids; a polypeptide translated from *S. aureus* DNA sequence acquired above matches the C-terminal 82 amino acids of the *E. coli* DNA ligase with a 52% sequence identity and a 67% sequence similarity; this level of similarity is considered significant when comparing proteins from Gram-negative and Gram-positive bacteria. Since the predicted coding region of the *S. aureus* gene for DNA ligase is small enough to be contained within clone pMP98 and the gene for DNA ligase is known to be essential to survival for many bacterial species, NT64 is concluded to contain a ts mutation in the gene for DNA ligase.

Mutant NT42/Clone pMP76: an Example of Complementing ORFs with Unknown Function The ORF(s) complementing the temperature-sensitive phenotype of *S. aureus* mutant NT42 described here was identified by sequencing subclones of pMP0076, an *E. coli*/*S. aureus* shuttle vector containing a 2.5 kb insert of parental (i.e. wild-type) genomic DNA. The subclones, pMP1026 (1.1 kb) and pMP1027 (1.3 kb), were generated by EcoRI and BamHI digestion of the parent clone and ligation into pGEM3Zf(+), a commercially available vector (Promega, Inc.) suitable for double-stranded DNA sequencing applications.

PCR-based methods (PRISM Dye Primer DNA Sequencing Kit; ABI, Inc.) were employed to generate DNA sequence data from the SP6 and T7 promoters of both of the subclones. Primer walking strategies were used to complete the sequence contig. Electrophoresis and detection of fluorescently-labelled DNA sequence ladder on an ABI 373A automated DNA sequencer (ABI, Inc.) yielded the following sequence data:

```
clone pMP76
pMP7E  Length: 2515 nt
    1 CSYCGGWACC CGGGGATCCT CTAGAGTCGA TCGTTCCAGA ACGTATTCGA    SEQ ID NO. 37

51 ACTTATAATT ATCCACAAAG CCGTGTAACA GACCATCGTA TAGGTCTAAC

101 GCTTCAAAAA TTAGGGCAAA TTATGGAAGG CCATTTAGAA GAAATTATAG

151 ATGCACTGAC TTTATCAGAG CAGACAGATA AATTGAAAGA ACTTAATAAT

201 GGTGAATTAT AAAGAAAAGT TAGATGAAGC AATTCATTTA ACACAACAAA

251 AAGGGTTTGA ACAAACACGA GCTGAATGGT TAATGTTAGA TGTATTTCAA

301 TGGACGCGTA CGGACTTTGT AGTCCACATG CATGATGATA TGCCGAAAGC

351 GATGATTATG AAGTTCGACT TAGCATTACA ACGTATGTTA TTAGGGAGAG

401 CCTATACAGT ATATAGTTGG CTTTGCCTCA TTTTATGGTA GAACGTTTGA

451 TGTAAACTCA AATTGTTTGA TACCAAGACC TGAAACTGAA GAAGTAATGT

501 TGCATTTCTT ACAACAGTTA GAAGATGATG CAACAATCGT AGATATCGGA

551 ACGGGTAGTG GTGTACTTGC AATTACTTTG AAATGTTGAA AAGCCGGATT

601 TAAATGTTAT TGCTACTGAT ATTTCACTTG AAGCAATGAA TATGGCTCCG

651 TAATAATGCT GAGAAGCATC AATCACAAAT ACAATTTTTA ACAGGGGATG

701 CATTAAAGCC CTTAATTAAT GAAGGTATCA ATTTGAACGG CTTTGATATC

751 TAATCCMCCA TATATAGATG AAAAAGATAT GGTTACGATG TCTCCMACGG

801 TTACGAAATT CGAACCACAT CAGGCATTGT TTGCAGATAA CCATGGATAT

851 GCTATTTATG AATCAATCAT GGAAGATTTA CCTCACGTTA TGGAAAAAGG

901 CAGCCCAGTT GTTTTTGAAA TTGGTTACAA TCAAGGTGAG GCACTTAAAT

951 CAATAATTTT AAATAAATTT CCTGACAAAA AAATCGACAT TATTAAAGAT

1001 ATAAATGGCC ACGATCGAAT CGTCTCATTT AAATGGTAAT TAGAAGTTAT

1051 GCCTTTGCTA TGATTAGTTA AGTGCATAGC TTTTTGCTTT ATATTATGAT

1101 AAATAAGAAA GGCGTGATTA AGTTGGATAC TAAAATTTGG GATGTTAGAG

1151 AATATAATGA AGATTTACAG CAATATCCTA AAATTAATGA AATAAAAGAC

1201 ATTGTTTTAA ACGGTGGTTT AATAGGTTTA CCAACTGAAA CAGTTTATGG

1251 ACTTGCAGCA AATGCGACAG ATGAAGAAGC TGTAGCTAAA ATATATGAAG

1301 CTAAAGGCCG TCCATCTGAC AATCCGCTTA TTGTTCATAT ACACAGTAAA

1351 GGTCAATTAA AAGATTTTAC ATATACTTTG GATCCACGCG TAGAAAAGTT

1401 AATGCAGGCA TTCTGGCCGG GCCCTATTTC GTTTATATTG CCGTTAAAGC

1451 TAGGCTATCT ATGTCGAAAA GTTTCTGGAG GTTTATCATC AGTTGCTGTT

1501 AGAATGCCAA GCCATTCTGT AGGTAGACAA TTATTACAAA TCATAAATGA

1551 ACCTCTAGCT GCTCCAAGTG CTAATTTAAG TGGTAGACCT TCACCAACAA
```

```
-continued
1601 CTTTCAATCA TGTATATCAA GATTTGAATG GCCGTATCGA TGGTATTGTT

1651 CAAGCTGAAC AAAGTGAAGA AGGATTAGAA AGTACGGTTT TAGATTGCAC

1701 ATCTTTTCCT TATAAAATTG CAAGACCTGG TTCTATAACA GCAGCAATGA

1751 TTACAGAAAT AMTTCCGAAT AGTATCGCCC ATGCTGATTA TAATGATACT

1801 GAACAGCCAA TTGCACCAGG TATGAAGTAT AAGCATTACT CAACCCAATA

1851 CACCACTTAC AATTATTACA GATATTGAGA GCAAAATTGG AAATGACGGT

1901 AAAGATTRKW MTTCTATAGC TTTTATTGTG CCGAGTAATA AGGTGGCGTT

1951 TATACCAAGT GARSCGCAAT TCATTCAATT ATGTCAGGAT GMCAATGATG

2001 TTAAACAAGC AAGTCATAAT CTTTATGATG TGTTACATTC ACTTGATGAA

2051 AATGAAAATA TTTCAGCGGC GTATATATAC GGCTTTGAGC TGAATGATAA

2101 TACAGAAGCA ATTATGAATC GCATGTTAAA AGCTGCAGGT AATCACATTA

2151 TTAAAGGATG TGAACTATGA AGATTTTATT CGTTTGTACA GGTAACACAT

2201 GTCGTAGCCC ATTAGCGGGA AGTATTGCAA AAGAGGTTAT GCCAAATCAT

2251 CAATTTGAAT CAAGAGGTAT ATTCGCTGTG AACAATCAAG GTGTTTCGAA

2301 TTATGTTGAA GACTTAGTTG AAGAACATCA TTTAGCTGAA ACGACCTTAT

2351 CGCAACAATT TACTGAAGCA GATTTGAAAG CAGATATTAT TTTGACGATG

2401 TCGTATTCGC ACAAAGAATT AATAGAGGCA CACTTTGGTT TGCAAAATCA

2451 TGTTTTCACA TTGCATGAAT ATGTAAAAGA AGCAGGAGAA GTTATAGATC

2501 GACCTGCAGG CATGC
```

Figure 42:
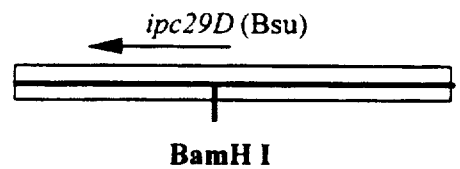

Analysis of the DNA sequence data at the nucleotide level reveals no significant similarity to data in the current release of the Genbank or EMBL databases. Analysis of the predicted ORFs contained within clone pMP76 reveals a high degree of similarity to two open reading frames identified in *B. subtilis*; "ipc29D" and "ipc31D" (EMBL entry Z38002). A partial restriction map of pMP76 is depicted in FIG. 42, along with an open box to indicate the percentage of the clone for which DNA sequence has been obtained. The relative orientation and predicted size of the "ipc29D" ORF is indicated by an arrow:

These two ORFs identified from the EMBL entry Z38002 were predicted from genomic sequence data and are denoted as "putative"; no characterization of expression or function of the predicted gene products has been reported in the literature. A similarity has been noted between the predicted Ipc31D-like polypeptide and the SUA5 gene product from yeast (*S. cerevisiae*), but functional characterization still remains to be performed. Hence, the ORFs contained within clone pMP76 represent putative polypeptides of uncertain function, but are known to be responsible for restoring a wild-type phenotype to NT42.

In addition to the illustrative sequences described above, the following sequences of clones complementing heat sensitive mutants of *S. aureus* similarly provide essential genes.

Mutant: NT3

Phenotype: temperature sensitivity

Figure 21:
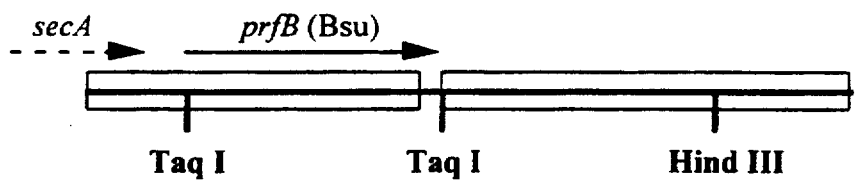
FIGS. 21–90 are partial restriction maps of each of the S. aureus clone inserts for which sequences are described herein, showing the relative fraction of the insert for which nucleotide sequence is described, as well as the approximate positions of identified open reading frames (ORFs).

Sequence map: Mutant NT3 is complemented by plasmid pMP27, which contains a 3.9 kb insert of *S. aureus* genomic DNA. The partial restriction map of the insert is depicted in FIG. 21; open boxes along part of the length of the clone indicate the portions of the clone for which DNA sequence has been obtained (this contig is currently being completed). Database searches at both the nucleic acid and protein levels reveal strong similarity at both the peptide and nucleic acid level to the C-terminal fragment of the SecA protein from *S. carnosus* (EMBL Accession No. X79725) and from *B. subtilis* (Genbank Accession No. D10279). Since the complete SecA ORF is not contained within clone pMP27, SecA is unlikely to be the protein responsible for restoring mutant NT3 to a wild-type phenotype. Further strong peptide-level similarities exist between the DNA sequence of a Taq I subclone of pMP27 and the prfB gene, encoding Peptide Release Factor II, of *B. subtilis* (Genbank D10279; published in Pel et al., 1992, *Nucl. Acids Res.* 20:4423–4428). Cross complementation analysis (data not shown) suggests that a mutation in the prfB gene is most likely to be responsible for conferring a temperature-sensitive phenotype to mutant NT3 (i.e. it is an essential gene).

DNA sequence data: The following DNA sequence data represents the sequences at the left-most and right-most edges of clone pMP27, using standard M13 forward and M13 reverse sequencing primers, and then extending via primer walking strategies. The sequences below can be used to design PCR primers for the purpose of amplification from genomic DNA with subsequent DNA sequencing.

clone pMP27 (forward and reverse contigs)
pMP27.forward   Length: 1739 nt

```
   1 CTCGCAGCCG NYAKYCGWAA ATGGTCCAAT GTACTCCATC CATCACTGCA    SEQ ID NO. 1
  51 TCAACCTTAC CTGTTTCTTC GTTCGTACGA TGATCTTTCA CCATTGAGTA
 101 TGGATGGAAA ACATATGATC TAATTTGGCT TCCCCAGCCG ATTTCTTTTT
 151 GTTCGCCACG AATTTCAGCC ATTTCACGTG CCTGCTCTTC CAATTTTAAT
 201 TGATATAATT TAGACTTTAA CATTTTCATA GCTGCTTCAC GGTTTTTAAT
 251 TTGAGAACGT TCATTTTGGT TATTAACAAC TATACCTGAG GGGTGGTGGG
 301 TAATTCGTAT TGCCGATTCA GTTTTGTTAA TATGCTGACC ACCTGCACCA
 351 GAAGCTCTGA ATGTATCAAC TGTAATATCA TCCGGATTGA TTTCAATCTC
 401 TATTTCATCA TTATTAAAAT CTGGAATAAC GTCGCATGAT GCAAATGATG
 451 TATGACGACG TCCTGATGAA TCAAAGGGAG AAATTCGTAC TAGTCGGTGT
 501 ACACCTTTTT CAGCTTTTAA ATAACCATAA GCATTATGCC CTTTGATGAG
 551 CAATGTTACA CTTTTAATCC CCGCTTCATC CCCAGGTAGA TAATCAACAG
 601 TTTCAACTTT AAAGCCTTTC TTCTCAACAA TAACGTTGAT ACATTCTAAA
 651 TAGCATATTA GCCCAATCTT GAGACTCCGT GCCACCTGCA CCAGGATGTA
 701 ACTCTAGAAT TGCGTTATTG GCATCGTGAG GCCCATCTAA TAATAATTGC
 751 AATTCGTATT CATCCACTTT AGCCTTAAAA TTAATGACCT CTTGCTCTAA
 801 GTCTTCTTTC ATTTCCTTCA TCAAATTCTT CTTGTAATAA ATCCCAAGTA
 851 GCATCCATGT CATCTACTTC TGCTTGTAGT GTTTTATAAC CATTAACTAT
 901 TGCTTTTAAC GCATTATTTT TATCTATAAT ATCTTGCGCT TTCGTTTGGT
 951 TATCCCAAAA ATTAGGTTCT GCCATCATTT CTTCATATTC TTGAATATTA
1001 GTTTCTTTGT TCTCTAAGTC AAAGAGACCC CCTAATTTGT GTTAAATCTT
1051 GATTATACTT ATCTATATTT CGTTTGATTT CTGATAATTC CATAGCATTC
1101 GCTCCTATTT ATATTTCAAT TCAAGTCATT GATTTGCATC TTTTATAATG
1151 CTAAATTTTA ACATAATTTT GTTAAATAAC AATGTTAAGA AATATAAGCA
1201 CACTGACAAT TAGTTTATGC ATTTATTGTT TAAAAAWGCA GTACATTTAT
1251 GCATCGACAT ATGCCTAAAC CGATTTTTTA AAACTAAGTA CATAACAACG
1301 TTTAACAACT TCTTCACATT TTTTAAAGTA TTTAACGCTT GTAAAATAAA
1351 AAGACTCCTC CCATAACACA AACTATAGGT GTTTAATTGG AAGGAGTTAT
1401 TTTATATCAT TTATTTTCCA TGGCAATTTT TGAATTTTTT ACCACTACCA
1451 CATGGACAAT CATCGTTACG ACCAACTTGA TCGCCTTTAA CGATTGGTTT
1501 CGGTTTCACT TTTTCTTTAC CATCTTCAGC TGAAACGTGC TTCGCTTCAC
1551 CAAACTCTGT TGTTTTTTCA CGTTCAATAT TATCTTCAAC TTGTACTACA
1601 GATTTTAAAA TGAATTTACA AGTATCTTCT TCAATATTTT GCATCATGAT
1651 ATCAAATAAT TCATGACCTT CATTTTGATA GTCACGTAAT GGATTTTGTT
1701 GTGCATAAGA ACGTAAGTGA ATACCTTGAC GTAATTGAT
``` pMP27.reverse   Length: 2368 nt

```
   1 CTGCAGGTCG ATCTGCATCT TGATGTTTAT GAAATTCGAG TTGATCTAGT    SEQ ID NO. 2
  51 AATTAAATAA CCAGCTAATA ATGACACTAC ATCAGKAAGA ATAATCCACT
 101 CGTTATGGAA ATACTCTTTA TAGATTGAGG CACCAATTAA AATTAATGTC
 151 AGAATAGTAC CGACCCATTT ACTTCTTGTT ATTACACTAA ATAAATACTAC
```

-continued

```
 201 CAAGACACAT GGAAAGAATG CTGCGCTAAA ATACCATATC ATTCATTTTC
 251 CTCTTTTCTT TTATTTAAAA TGTTCATGGT TGTTTCTCTT AATTCTGTTC
 301 TAGGTATAAA GTTTTCAGTC AACATTTCTG GAATGATATT ATTAATAAAA
 351 TCTTGTACAG ATGCTAAATG GTCAAATTGA ATAATTGTTT CTAGACTCAT
 401 TTCATAAATT TCGAAAAATA ATTCTTCGGG ATTACGKTTT TGTATTTCTC
 451 CAAATGTTTC ATAAAGCAAA TCAATTTTAT CAGCAACTGA AAGTATTTGG
 501 CCTTCTAATG AATCATCTTT ACCTTCTTGC AGTCGTTGCT TATAAACATC
 551 TCTATATTGT AATGGAATTT CTTCTTCAAT AAAGGTCTCT ACCATTTCTT
 601 CTTCAACTTG CGAAAATAAT TTTTTTAATT CACTACTCGC ATATTTAACA
 651 GGTGTTTTTA TATCACCAGT AAACACTTCG GSGAAATCAT GATTTAATGC
 701 TTTTTCATAT AAGCTTTTCC AATTAAYCTT TCTCCATGAT ATTCTTCAAC
 751 TGTTGCTAGA TATTGTGCAA TTTTAGTTAC TTTAAAGGAG TGTGCTGCAA
 601 CATTGTGTTC AAAATATTTA AATTTTCCAG GTAATCTTAT AAGTCTTTCC
 851 ATATCTGATA ATCTTTTAAA ATATTGATGT ACACCCATTT CAATTACCTC
 901 CTCCATTAAT TAATCATAAA TTATACTTTC TTTTTACATA TCAATCAATT
 951 AAATATCATT TAAATATCTT CTTTATATAA CTCTGATTAA ATGATACCAA
1001 AAAATCCTCT CAACCTGTTA CTTAAACAGG CTAAGAGGGT AGTCTTGTCT
1051 TGATATATTA CTTAGTGGAT GTAATTATAT TTTCCTGGAT TTAAAATTGT
1101 TCTTGAAGAT TTAACATTAA ATCCAGCATA GTTCATTTTC AGAAACAGTA
1151 ATTGTTCCMT TTAGGGTTTA CAGATTCAAC AACACCAACA TGTCCATATG
1201 GACCAGCAGC TGTTTGGAAA ATAGCGCCAA CTTCTGGKGT TTTATCTACT
1251 TTTAAATCCT GCAACTTTTG CTGCGTAATT CCAGTTATTT GCATTGCCCC
1301 ATAAACTTCC TATACTTCTA CCTAATTGTG CACGACGATC GAAAGCATAA
1351 TATGTGCAGT TTCCATAAGC ATATAAGTTT CCTCTGTTAG CAACTGATTT
1401 ATTGTAGTTA TGTGCAACAG GTACAGTGGG TACTGATTTT TGTACTGGAG
1451 CAGGTTTGTA TGCTACATTA ACTGTCTTAG TTACTGCTTG CTTAGGTGCT
1501 TGCTTAACTA CTACTTTTTT AGATGCTTGT TGTACAGGTT GTTTTACTAC
1551 CTTTTTAGCT TGGCTTGCTT TTCTTACTGG TGATTTAACC GCTTTAGTTT
1601 GTTTCACTTT ATTTTGAGGC ACAAGTGAAA TCACGTCACC AGGAAAAATT
1651 AAAGGTGTTA CACCAGGATT GTATTGAATA TAATTGATTC AACGTTAAGT
1701 GATGCTCTTA AAGCAATCTT ATATTAATGA ATCGCCAGCA ACTACTGTWT
1751 AAGTTGTCGG TGATTGCGTT TGTGCTTGAA CATTTGATAC ATAATTATGT
1801 TGAACAGGTG TTTTTACTTG TGTGCCATGT TGTTGTGCAT GTGCKGCATT
1851 ATTTAAAGCK AAAAAAGCTA ACACTGACGA AACCGTCACT GWAAGARART
1901 TTTTCATCTK GCTGTCATTC CTTTGCTGTW AGTATTTTAA GTTATGCAAA
1951 TACTATAGCA CAATACATTT TGTCCAAAAG CTAATTGTTA TAACGANGTA
2001 ATCAAATGGT TAACAANATN AANAGAAGAC AACCGTNTAT CATAGNGGNA
2051 AANGTAGNCA TACCATGNAA TTGAGAACGT TNTCAANAAN TAANTCAATA
2101 CCNTGAAAAT CGCCATAGGN AATATTACNA AATGCACACT GCATATGNTG
2151 NTTAACAAA CACNACTTTT NANAAATATA NTCTAACTCT ATCTACCGAA
```

-continued

```
2201 TTGNACTTAA ATATTCATAA ANAAATNATA TTCNAAAATC TAATTTACAA

2251 TTTATTTAGC TACCTTTAAA AAANCNNAAA ACCGACGNCC TTTTAGAGCC

2301 TCGGTTTTTA NATATATNTT AATCGTGCGA CATTGTCTGT TTTNAATNTG

2351 ATTCGACTCT AGNGGATC
```

Figure 22:
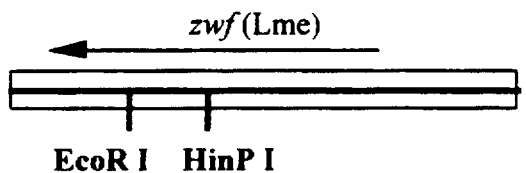

Mutant: NT5
Phenotype: temperature sensitivity
Sequence map: Mutant NT5 is complemented by plasmid pMP628, which contains a 2.5 kb insert of S. aureus genomic DNA. The partial restriction map of the insert is depicted in FIG. 22. Database searches at both the nucleic acid and protein levels reveal strong similarity between one of the ORFs contained within clone pMP628 and the zwf gene from a variety of species, which encodes the Glucose-6-Phosphate Dehydrogenase (G6PD) protein (EC 1.1.1.49).

The strongest similarity is demonstrated in the Genbank entry for G6PD (Accession No. M64446; published in Lee, W. T. et al. *J. Biol. Chem.* 266 (1991) 13028–13034.) from *Leuconostoc mesenteriodes*, here abbreviated as "Lme".

DNA sequence data: The following DNA sequence data represents the complete first-pass sequence of pMP628; the sequence below can be used to design PCR primers for the purpose of amplification from genomic DNA with subsequent DNA sequencing.

```
clone pMP628
pMP62B  Length. 2494 nt
     1 AATCATTTTA AATGATTGAT CAAGATGGTA TGGCGAAAGA CCAACGTAAT    SEQ ID NO. 3

51 CACTTAATTC TTGCAAATTG AAAGGCTCTA ATAAACGATC TTCAATATAA

101 ACAATTGCCT GTTGTATTTG CTTGATAACG TCCAAAACTT TCACTCCAAT

151 TAATTCAATC ATTTATTTTT ATTCTACATT ATTTCTATAA ATTATACACC

201 CATTTGTTCA ATGATTATTA AAATAGTTTT GGGCATTGTA AAATATAATT

251 TCATAATATA GTCTAGAAAA AAAGCGAATG ATAGAACAAT TGATTTACTT

301 GATTCGTAAT CAATCCTTGT CATTCGCTCA TTTATTTTTG TTTAACATGT

351 GCGTTTTAAT TCAATTATTG AATATCGTCC CACCAATGGT TACCATCACG

401 AGCAAGTAGT AAATCACTTT CTAATGGACC ATTAGTACCT GATTCATAGT

451 TAGGGAATTC TGGATCAACC ATATTCCATT CATCTTGGAA TTGCATCAAC

501 AAATTTCCAT GTTGATTTTA ATTCTTCCCA GTGCGTGAAG TTAGTGGCAT

551 CACCTTTAAG ACAATCAAAT AATAGATTTT CATATGCATC TACAGTATTC

601 ATTTTATCTT GAGCGCTCAT TGAGTAAGAC AATTGGACAG GTTCTGTTTC

651 GATACCTTGT GTWTTTTTCT TAGCATTTAR ATGTAAAGAT ACACCTTCAT

701 TAGGTTGGAT ATTGATTANT AATAGGTTTG AATCTAACAG TTTATCAGTT

751 TCATAGTATA AGTTCATTGG TACTTCTTTA AATTCAACGA CAACTTGAAT

801 TGTTTTAGAT TTCATACGTT TACCAGTACG GATATAGAAT GGTACACCAG

851 CCCATCTAAA GTTATCAATT GTTAATTTAC CTGAAACAAA GGTAGGTGTG

901 TTAGAGTCAT CTGCAACGCG ATCTTCATCA CGGTATGCTT TAACTTGTTT

951 ACCATCGATA TAGCCTTCGC CATATTGACC ACGAACAAAG TTCTTTTTAA

1001 CATCTTCAGA TTGGAAATGA CGCAGTGATT TAAGTACTTT TAACTTTCTC

1051 AGCACGGATA TCTTCACTAT TTAAACTAAT AGGTGCTTCC ATAGCTAATA

1101 ATGCAACCAT TTGTAACATG TGGTTTTGCA CCATATCTTT TAGCGCGCCA

1151 CTTGATTCAT AATAACCACC ACGATCTTCA ACACCTAGTA TTTCAGAAGA

1201 TGTAACYYGG ATGTTTGAAA TATATTTGTT ATTCCATAAT GGTTCAAACA

1251 TCGCATTCGC AAAACGTAAT ACCTCGATAT TTTGAACCAT GTCTTTTCCT
```

-continued

```
1301 AAATAGTGGT CMATACGRTA AATTTCTTCT TCTTTAAATG ATTTACGAAT

1351 TTGATTGTTT AATGCTTCGG CTGATTTTAA ATCACTACCG AATGGTTTTT

1401 CGATAACAAG GCGTTTAAAT CCTTTTGTAT CAGTAAGACC AGAAGATTTT

1451 AGATAATCAG AAATAACGCC AAAGAATTGT GGTGCCATTG CTAAATAGAA

1501 TAGTCGATTA CCTTYTAATT CAAATTGGCT ATCTAATTCA TTACTAAAAT

1551 CTAGTAATTT CTTGATAGCT TTCTTCATTA CTAACATCAT GTCTATGATA

1601 GAAGACATGT TCCATAAACG CGTCAATTTT GTTTGTATCT TTWACGTGCT

1651 TTTGAATTGA TGATTTTAAC TTGATTACGG AAATCATCAT TAGTAATGTC

1701 ACGACGTCCA ATACCGATGA TGGCAATATG TTCATCTAAA TTGTCTTGTT

1751 GGTAGAGATG GAATATTGAT GGAAACAACT TACGATGGCT TAAGTCACCA

1801 GTTGCACCAA AGATTGTGAT TAAACATGGG ATGTGTTTGT TTTTAGTACT

1851 CAAGATTAAA ACCTCAATTC WYMCATTAGA TATATSATTT ATTATKAYMM

1901 GATAATCCAT TTCAGTAGGT CATACMATAT GYTCGACTGT ATGGAGTKTC

1951 TTAAATGAAA TATCGATTCA TGTATCATGT TTAATGTGAT AATTATTAAT

2001 GATAAGTATA ACGTAATTAT CAAAATTTAT ATAGTTATGT CTAACGTTAA

2051 AGTTAGAAAA ATTAACTAGC AAAGACGAAT TTTTAACAGA TTTTGATTCA

2101 AGTATAAATT AAAACTAAAT TGATACAAAT TTTATGATAA AATGAATTGA

2151 AGAAAAGGAG GGGCATATAT GGAAGTTACA TTTTTTGGAA CGAGTGCAGG

2201 TTTGCCTACA AAAGAGAGAA ATACACAAGC AATCGCCTTA AATTTAGAAC

2251 CATATTCCAA TTCCATATGG CTTTTCGACG TTGGTGAAGG TACACAGCAC

2301 CAAATTTTAC ATCATGCAAT TAAATTAGGA AAAGTGACAC ATATATTTAT

2351 TACTCATATG CATGGCGATC ATATTTTTGG TTTGCCAGGA TTACTTTCTA

2401 GTCGTTCTTT TCAGGGCGGT GAACAGAAGC CGCTTACATT GGTTGGACCA

2451 AAAGGAATTA AAGCATATGT GGAAATGTCT ATGAATTTAT CAGA
```

Mutant: NT6
Phenotype: temperature sensitivity
Sequence map: Mutant NT6 is complemented by plasmid pMP33, which contains a 2.3 kb insert of *S. aureus* genomic DNA. The partial restriction map of the insert is depicted in FIG. 23; open boxes along part of the length of the clone indicate the percentage of the clone for which DNA sequence has been obtained. Database searches at both the nucleic acid and protein levels reveal identity to the *S. aureus* femA gene, encoding a protein involved in peptidoglycan crosslinking (Genbank Accession No. M23918; published in Berger-Baechi, B., et al., *Mol. Gen. Genet.* 219, (1989) 263–269). The pMP33 clone contains the complete fema ORF (denoted in relative length and direction by an arrow ) as well as 5' and 3' flanking DNA sequences, suggesting that it is capable to direct expression of the FemA protein.

DNA sequence data: The following DNA sequence represents sequence data acquired from subclones 1006, 1007 and 1008, using standard sequencing methods and the commercially-available primers T7 and SP6:

```
Subclone 1006, a 500 bp Hind III fragment
1006.sp6 Length: 400 nt
     1 AAATAATCTA AAAATTGGTA GTNCTCCTTC AGATAAAAAT CTTACTTTAA    SEQ ID NO. 4

51 CACCATTCTT TTNAACTNNT TCCGTGTTTC TTTTTCTAAG TCCATCCATA

101 TTTTNAATGA TGTCATCTGC TGTTTTATCT TTTAAATCTA ACACTGAGTG

151 ATAACGGATT TGTAGCACAG GATCAAATCC TTTATGQAAT CCAGTATGTT

201 CAAATCCTAA GTTACTCATT TTATCAAAGA ACCAATCATT ACCAGCATTA

251 CCTGTAATCT CGCCATCATG ATTCAAGTAT TGATATGGTA AATATGGATC
```

```
301 GNTATGTAGG TATAGNCAAC GATGTTTTTT AACATATTTT GGATAATTCA

351 TTAAAGNAAA AGTGTACGAG TNCTTGATTT TCATANTCAA TCACTGGACC

Subclone 1007, a 900 bp Hind III fragment
1007.sp6 Length: 398 nt
  1 TGCGTGAAAT NACTGTATGG CNTGCNATCT GTAAAGGCAC CAAACTCTTT    SEQ ID NO. 5

51 AGCTGTTAAA TTTGTAAACT TCATTATCAT TACTCCTATT TGTCTCTCGT

101 TAATTAATTT CATTTCCGTA TTTGCAGTTT TCCTATTTCC CCTCTGCAAA

151 TGTCAAAAAT AATAAATCTA ATCTAAATAA GTATACAATA GTTAATGTTA

201 AAACTAAAAC ATAAACGCTT TAATTGCGTA TACTTTTATA GTAATATTTA

251 GATTTTNGAN TACAATTTCA AAAAAAGTAA TATGANCGTT TGGGTTTGCN

301 CATATTACTT TTTTNGAAAT TGTATTCAAT NTTATAATTC ACCGTTTTTC

351 ACTTTTTNCA AACAGTATTC GCCTANTTTT TTTAAATCAA GTAAACTT subclone 1008, a 900 bp Hind ZI fragment
1008.sp6 Length: 410 nt
  1 GTAATGACAA ATNTAACTAC AATCGCTTAA AATATTACAA AGACCGTGTG    SEQ ID NO. 6

51 TNAGTACCTT TAGCGTATAT CAACTTTAAT GAATATATTA AAGAACTAAA

101 CGAAGAGCGT GATATTTTAA ATAAAGATTT AAATAAAGCG TTAAAGGATA

151 TTGAAAAACG TCCTGAAAAT AAAAAAGCAC ATAACAAGCG AGATAACTTA

201 CAACAACAAC TTGATGCAAA TGAGCAAAAG ATTGAAGAAG GTAAACGTCT

251 ACAAGANGAA CATGGTAATG AATTACCTAT CTCTNCTGGT TTCTNCTTTA

301 TCAATCCATT TGANGTTGTT TATTATGCTG GTGGTACATC AAATGCATTC

351 CGTCATTTTN CCGGAAGTTA TGCAGTGCAA TGGGAAATGA TTAATTATGC

401 ATTAAATCAT
```

Figure 24:
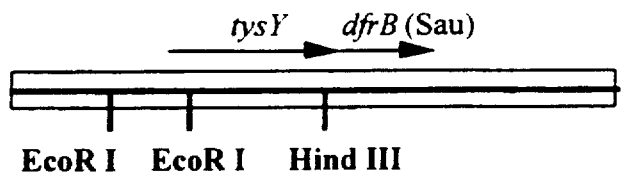

Mutant: NT8
Phenotype: temperature sensitivity
Sequence map: Mutant NT8 is complemented by plasmid pMP34, which contains a 3.5 kb insert of *S. aureus* genomic DNA. The partial restriction map of the insert is depicted in FIG. 24. Database searches at both the nucleic acid and protein levels reveal identity to the DNA sequence for the dfrB (dihydrofolate reductase [EC 1.5.1.3]; EMBL entry Z16422, published in Dale, G. E. et al. *Antimicrob. Agents Chemother.* 37 (1993) 1400–1405) and tysY (thymidylate synthase [EC 2.1.1.45]; EMBL entry X13290, published in Rouch, D. A. et al. *Mol. Microbiol.* 3 (1989) 161–175) genes of *S. aureus*. The relative size and orientations of the genes, along with sequence identities, are depicted as arrows in the restriction map:

DNA sequence data: The following DNA sequence represents data acquired from clone pMP34, starting with M13 forward and M13 reverse primers and applying primer walking strategies to complete the contig:

```
clone pMP34                                                 SEQ ID NO. 7
pMP34 Length: .3479 nt
  1 AAGCTTCATT AAAAACTTTC TTCAATTTAT CAACATATTC AATGACGTTA

51 GCATGTGCGA CACCAACGGA YTKSAKKTCA TGATCTCCTA TAAATTCAGC

101 AATTTCCTTT TTCAAGTATT GGATACTAGA ATTTTGAGTT CTCGCATTGT

151 GCACAAGCTC TAAGCGACCA TCATCTAGTG TACCAATTGG TTTAATTTTC

201 ATAAGATTAC CAATCAAACC TTTTGTTTTA CTAATTCTGC CACCTTTAAT

251 TAATTGATTC AATTGCCCTA TAACTACAAA TAATTTAATG TTTTCTCTTA

301 AATGATTTAA CTTTTTAACT ATTTCAGAAG TTGAGACACC TTCTTTTACA

351 AGCTCTACTA GGTGTTGTAT TTGATACCCT AAACCAAAAG AAATAGATTT

401 TGAATCAATA ACAGTTACAT TAGCATCTAC CATTTGACTT GCTTGGTAAG

451 CAGTGTTATA TGTACCACTT AATCCTGAAG AAAGATGAAT ACTTATGATT
```

-continued

```
 501 TCAGAGCCAT CTTTTCCTAG TTCTTCATAA GCAGATATAA ATTCACCTAT
 551 GGCTGGCTGA CTTGTCTTTA CATCTTCATC ATTTTCAATA TGATTAATAA
 601 ATTCTTCTGA TGTAATATCT ACTTGGTCAA CGTATGAAGC TCCTTCAATA
 651 GTTAAACTTA AAGGAATTAC ATGWATGTTG TTTGCTTCTA ARTATTCTTT
 701 AGATAAATCG GATGTTGAGT CTGTTACTAT AATCTGTTTT GTCATGGTCG
 751 TTTTCCCCCT TATTTTTTAC GAATTAAATG TAGAAAGGTA TGTGGAATTG
 801 TATTTTTCTC ATCTAGTTTA CCTTCAACTG AAGAGGCAAC TTCCCAGTCT
 851 TCAAATGTAT AAGGTGGAAA GAACGTATCA CCACGGAATT TACCTTCAAT
 901 AACAGTAATA TACATGTCGT CCACTTTATC AATCATTTCT TCAAATAATG
 951 TTTGCCCTCC AAATATGAAA ACATGGCCCG GTAGTTGGTA AATATCTTCA
1001 ATAGARTGAA TTACATCAAC GCCCTCTACG TTGAAACTTG TATCTGAAGT
1051 AAGTACAACA TTTCGACGAT TCGGTAGTGG TTTACCAATC GATTCAAATG
1101 TCTTACGACC CATTACTAAA GTATGACCTG TTGATAATTT TTTAACATGC
1151 TTCAAATCAT TTGGTAGGTG CCAAGGTAAT TGATTTTCAA AACCAATTAC
1201 TCGTTGCAAG TCATGTGCAA CTAGAATGGA TAAAGTCATA ATTATCCTCC
1251 TTCTTCTATC ATTTCATTTT TTATTACTAA GTTATCTTTA ATTTAACACA
1301 ATTTTTATCA TAAAGTGTGA TAGAAATAAT GATTTTGCAT AATTTATGAA
1351 AACGTTTAAC ACAAAAAAGT ACTTTTTTGC ACTTGAAAAT ACTATGATGT
1401 CATTTKGATG TCTATATGGT TAGCTAAYTA TGCAATGACT ACAMTGCTAT
1451 KGGAGCTTTT ATKGCTGGAT GTGATTCATA GTCAACAATT TCCAMAATCT
1501 TCATAATTTA TGTCGAAAAT AGACTTGTCA CTGTTAATTT TTAATGTTGG
1551 AGGATTGAAG CTTTCACGTG CTAATGGTGT TKCGMATCGC ATCAATATGA
1601 TTTGAATAAA TATGTGCATC TCCAAATGTA TGCACAAATT CACCCACTTC
1651 AAGTCCACAT TTCTTTGGCA ATAAGGTGTG TCAATAAAGC GTAGCYTGCG
1701 ATATTAAATG GCACACCTAA AAAGATATCT GCGCTACGTT GGTATAACTG
1751 GCAACTTAAC TTACCATCTT GGACATAAAA CTGGAACATG GTATGACAAG
1801 GCGGAAGTGC CATTGTATCA ATTTCTGTTG GATTCCATGC AGATACGATG
1851 TGTCGCCTTG AATCTGGATT ATGCTTAATT TGTTCAATTA CTGTTTTAAG
1901 TTGATCAAAA TGATTACCAT CTTTATCAAC CCAATCTCGC CMATTGTTTA
1951 CCATAAACAT TTCCTAAATC CCCGAATTGC TTCGCAAATG TATCATCTTC
2001 AAGAATACGT TGCTTAAATT GTTTCATTTG TTCTTTATAT TGTTCGTTAA
2051 ATTCAGGATC ACTCAATGCA CGATGCCCGA AATCTGTCAT ATCTGGACCT
2101 TTATACTCGT CTGATTTGAT ATAATTTTCA AAAGCCCATT CGTTCCATAT
2151 ATTATTATTA TATTTTAATA AGTATTGGAT GTTTGTATCT CCTTTAATGA
2201 ACCATAATAA TTCGGTTGCT ACTAATTTAA AAGAAACTTT CTTTGTCGTT
2251 AATAGTGGAA ATCCTTTAGA TAAGTCAAAG CGAAGTTGAT GACCAAATTT
2301 CGAAATCGTA CCTGTATTTG TGCGATCATT TCGTGTATTT CCTATTTCTA
2351 AAACTTCTTC ACAAAGACTG TGATATGCTG CATCAAATGA ATTTCAACAT
2401 ATGCGATAAC ACCTCATTTT CATTATTTAT AGTATGTATA TTTAGTTTGA
2451 TATAACTTAA CTTTATGTAG CATTTTGTTA TCACTCATTT TAGGAATATG
```

-continued

```
2501 ATATTAATAT CATGAATTCC GTTACTTTAT TTATAAAATG CTGATTAAGT
2551 ACCTACCCCA TCGTAACGTG ATATATGTTT CCAATTGGTA ATTGTTTACC
2601 CAAATCTATA ACTTTAATGC TAAAAAATTT TAAAAAAGAG GTTAACACAT
2651 GATTTGAATA TTATGTTTGA TGTCCTATTA AAACAGTTAA ATTTCTAGAA
2701 AATATAGTTG GTAAAAACGG ACTTTATTTA ACAAATAGAA TACAACTATA
2751 TTCTCTATTT TCAATGACAG ACACCATTTT TAATATTATA AAATGTGTTA
2801 ACCTTTATAT TTATTTATGT GTACTATTTA CAATTTTCGT CAAAGGCATC
2851 CTTTAAGTCC ATTGCAATGT CATTAATATC TCTACCTTCG ATAAATTCTC
2901 TAGGCATAAA ATAAACTAAA TCTTGACCTT TGAATAAAGC ATACGAAGGA
2951 CTAGATGGTG CTTGCTGAAT GAATTCTCGC ATTGTAGCAG TTGCTTCTTT
3001 ATCTTGCCCA GCAAAAACTG TAACTGTATT TGTAGGTCTA TGTTCATTTT
3051 GTGTTGCAAC TGCTACTGCA GCTGGTCTTG CTAATCCAGC TGCACAGCCG
3101 CATGTAGAGT TAATAACTAC AAAAGTAGTG TCATCAGCAT TTACTTGGTT
3151 CATATACTCC GATACTGCTT CGCTCGTTTC TAAACTTGTA AAACCATTTT
3201 GAGTTAATTC GCCACGCATT TGTTGCGCAA TTTCTTTCAT ATAAGCATCA
3251 TAYGCATTCA TATTTAATTC CTCCAATTAA ATTGTTCTGT TTGCCATTTG
3301 TYTCCATACT GAACCAAGYG CTTCAYCTCC GTTTTCAATA TCGAGATATG
3351 GCCATTTCAA TTTGTAATTT AACWTCAAAC GCMTKGTCAK KAATATGGGS
3401 WTTTAGKGCG GGAAGMTGMT YWGCATWACS WTCATSAWAG ATAWACAYAG
3451 CARCAYSCCA CYTWAYGAKT TTMWKTGGA
```

Figure 25:
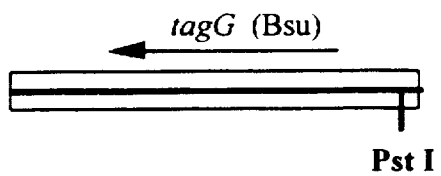

Mutant: NT12
Phenotype: temperature sensitivity
Sequence map: Mutant NT12 is complemented by pMP37, which contains a 2.9 kb insert of *S. aureus* genomic DNA. A partial restriction map is depicted FIG. 25. Database searches at both the nucleic acid and peptide levels reveal significant similarities to the protein encoded by the tagG gene, an integral membrane protein involved in the assembly of teichoic acid-based structures, from *B. subtilis* (Genbank Accession No. U13832; published in Lazarevic, et al., *Mol. Microbiology*, 16 (1995) 345–355).

DNA sequence data: The following DNA sequence data represents the sequence of clone pMP37, using standard M13 forward and M13 reverse sequencing primers and then completing the sequence contig via primer walking strategies. The sequences below can be used to design PCR primers for the purpose of amplification from genomic DNA with subsequent DNA sequencing.

```
clone pMP37                                              SEQ ID NO. 8
pMP37 Length: 2875 nt
    1 GTGGTTCCCT GTCATTYTRA TATCCATCAA ACCTTTATTA ATACACGTRG
   51 CTATCGAAGC ATTTTGTAAT TGTATTAATG AAATATGCTT GAGTYCTCTT
  101 TGTAACCGTT CAATCATAGG AATTGTTTGA TCAGTAGAAC CACCATCAAT
  151 ACAAAGGATT CTATAGTGTT CTTTACTCTC AATAGATATT AACAATTGTC
  201 GAATTGTTGC CTCATTATTA CATGTAGGTA TGATTATCGT AAACCTCATT
  251 TTGTCACCAT CTTATCTATA TATTCTGTGA GCTGATGTAA ACTTTTATCA
  301 GTATTATACT TATGCCAATC TTTAAATAAC GGACTTAATA GATGTTCTTT
  351 TTCTTGTATC GTCATTATTA AATCTTCTTC AGTATACACT TTGTAGCTAT
  401 CCGGTATTGC TTTGTAAAAT TGATTCAGGC CTCTCACCTG ATCATATGTT
  451 CCTTCATCAT ACACATAAAA TATAGTTGGA ATATCTAACA AGCTAGCTTC
  501 TATTGGCAGC GAACTATAGT CGCTAATAAT TATATCTGAC ATTAGCATTA
```

-continued

```
 551 ATGTAGACGT GTCGATTGAA GATACGTCAT CAATGTCTGA ATCTTCAATT
 601 GATGGATGTA ATTTATTAAT CAGTGTATAT CCTGGTAAAC ATTTTTCAAA
 651 ATAAGCTTTA TCAATAGCCC TATTATCTGC TTTATCTTCT CTATATGTTG
 701 GTACATATAA TACCAACTTA TTTGTAATTC CATATTTATC CTTTAACTCT
 751 GCCTTAACCG TTGCTCTATC AGCTGTGTAA TATTTATTAA TTCTCGGAAG
 801 CCCAAAATAC AGCATTTGCT CTTCTGTTGC ACCTAAAGAC TGTTTAAAAC
 851 ATTGTGACAT TTGTTCACAA CCCACTAAGT TAAAAATCCG TCGCTTGATA
 901 AACTTTACGG TACTGCTGAA CCATTGCCTT GTCAGACACA TCGACTTGAT
 951 GATCTGTTAA GCCAAAGTTT TTTAATGCAC CACTTGCATG CCACGTTTGA
1001 ACAATGTGTT TGATTAGAAK TCTTATTATA TCCACCTAGC MATAGGTAAT
1051 AATTATCGAT AATAATCATC TGCGCGCTTT TCAAAGCCTT AATTTGTTTT
1101 ACCAATGTTC GATTAGTCAT TTCTATCACA TCAACATCGT CGCTAAGTTC
1151 AGATAAATAA GGCGCTTGTT TTGGTGTTGT TAAAACAGTT TTCTGATACG
1201 ACGAATTATT TAATGCTTTG ATGATAGGCT TAATATCTTC TGGAAAAGTC
1251 ATCATAAATA CGATATGCGG TTTATCAATC ACTTGAGGSG TAWTCATTTW
1301 AGRAAGTATT CGAACTACCA AATGATAAAA TTTCTTTATT AAAAACGTTC
1351 ATAATAACAC CAACTTAATA TGTTATTTAA CTTAAATTAT AAACAAAAAT
1401 GAACCCCACT TCCATTTATT AATGGTTAGC GGGGTTTCGT CATATAAATA
1451 TATTACAAGA AGTCTGCAAA TTGATCTCTA TATTTCATGT GTWAGTACGC
1501 MCCMATTGCA AAGAAAATGG CAACAATACC GAAATTGTAT AACATTAATT
1551 TCCAATGATC CATGAAATAC CATTCGTGAT ATAAAATTGC TGCACKKTWT
1601 KATTMAKCWR TAMRGTMAAC TRGMTKATAT TTCATCATTK SATGAATTAA
1651 ACCACTGATA CCATGGTTCT TTGGTAGCCA CAAAATTGGT GAAAAGTAAA
1701 ATAATATTCT TAATATTGGC TTGCATTAAC ATTTGTGTAT CTCTAACTAA
1751 CAACACCGAG TGTTGATGTT AATAACGTCA CCGAGGCAGT TAAGAAAAAA
1801 CAAAACGGTA CATATATCAA TAATTGAATG ATATGTATTG ATGGATAAAT
1851 ACCAGTAAAC ATACATGCAA TTATCACAAG TAAAAGTAAG CCTAAATGTC
1901 CATAAAATCT ACTTGTCACA ATATATGTCG GTATTATCGA TAACGAAAAG
1951 TTCATTTTCG ATACTTGATT AAACTTTTGT GTAATTGCTT TAGTACCTTC
2001 TAAAATACCT TGGTTGATGA AGAACCACAT ACTGATACCA ACCAATAACC
2051 AATAAACAAA AGGTACACCA TGAATTGGTG CATTACTTCT TATTCCTAAT
2101 CCAAAAACCA TCCAGTAAAC CATAATTTGC ATAACAGGGT TAATTAATTC
2151 CCAAGCCACA CCTAAATAGT TACTATGATT GATAATTTTA ACTTGAAACT
2201 GAGCCAGTCT TTGAATTAAA TAAAAGTTCT WTASATGTTC TTTAAAAACT
2251 GTTCCTATTG CTGACATTCC ATTAAACCAC ACTTTCAAAT GTTTAACTAT
2301 TTCTCTAACT TAACTAAATA GTATTATAAT AATTGTTGTA AATACTATCA
2351 CTAWACATGG ATGCTATCAA AATTATTGTC TAGTTCTTTA AAATATTAGT
2401 TTATTACAAA TACATTATAG TATACAATCA TGTAAGTTGA AATAAGTTTA
2451 GTTTTTAAAT ATCATTGTTA TCATTGATGA TTAACATTTT GTGTCAAAAC
2501 ACCCACTCTG ATAATAACAA AATCTTCTAT ACACTTTACA ACAGGTTTTA
```

-continued

```
2551 AAATTTAACA ACTGTTGAGT AGTATATTAT AATCTAGATA AATGTGAATA

2601 AGGAAGGTCT ACAAATGAAC GTTTCGGTAA ACATTAAAAA TGTAACAAAA

2651 GAATATCGTA TTTATCGTAC AAATAAAGAA CGTATGAAAG ATGCGCTCAT

2701 TCCCAAACAT AAAAACAAAA CATTTTTCGC TTTAGATGAC ATTAGTTTAA

2751 AAGCATATGA AGGTGACGTC ATAGGGCTTG TTGGCATCAA TGGTTCCGGC

2801 AAATCAACGT TGAGCAATAT CATTGGCGGT TCTTTGTCGC CTACTGTTGG

2851 CAAAGTGGAT CGACCTGCAG TCATA
```

Figure 26:
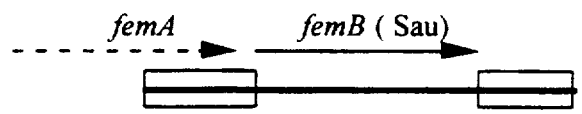

Mutant: NT14
Phenotype: temperature sensitivity
Sequence map: Mutant NT14 is complemented by plasmid pMP40, which contains a 2.3 kb insert of *S. aureus* genomic DNA. The partial restriction map of the insert is depicted in FIG. 26 (no Eco RI, Hind III, Bam HI or Pst I sites are apparent); open boxes along part of the length of the clone indicate the percentage of the clone for which DNA sequence has been obtained. Database searches at both the nucleic acid and protein levels reveal identity to the *Staph.* *aureus* femB gene, encoding a protein involved in peptidoglycan crosslinking (Genbank Accession No. M23918; published in Berger-Baechi, B., et al., Mol. Gen. Genet. 219, (1989) 263–269). The pMP40 clone contains the complete FemB ORF (denoted in relative length and direction by an arrow ) as well as 5' and 3' flanking DNA sequences, suggesting that it is capable to direct expression of the FemB protein; the relation of the femA gene is also depicted to demonstrate the extent of identity between the clone and the Genbank entry.

DNA sequence data: The following DNA sequence data represents the sequences at the left-most and right-most edges of clone pMP40 obtained with the standard DNA sequencing primers T7 and SP6, and can be used to demonstrate identity to part of the published sequence (Genbank No. M23918):

```
1015.t7  LENGTH: 453 nt                                          SEQ ID NO. 9
   1 CTTAAAATAT TACAAAGACC GTGTGTNAGT ACCTTNAGCG TATATCAACT

51 TTAATGAATA TATTAAAGAA CTAAACGAAG AGCGTGATAT TTTAAATAAA

101 GATTTAAATA AAGCGTTAAA GGATATTGAA AAACGTCCTG AAAATAAAAA

151 AGCACATAAC AAGCGAGATA ACTTACAACA ACAACTTGAT GCAAATGAGC

201 AAAAGATTGA NGACGGTAAA CGTCTACAAG ANGANCATGG TAATGNTTTA

251 CCTATCTCTC CTGGTTTCTC CTTTATCAAT CCNTTTGANG TTGTTTATTA

301 TGCTGGTGGT ACATCAAATG CNTTCCGTCA TTTTNCCGGA NGTTATGCNG

351 TGCAATGGGA AATGNTTAAT TTTGCATTAA ATCATGGCAT TGNCCGTTAT

401 AATTNCTATG GTGTTAGTGG TNAATTTNCA GNAGGTGCTG AAGATGCTGG

451 TGT 1015.sp6 LENGTH: 445 nt                                         SEQ ID NO. 10
   1 ATGCTCAGGT CGATCATACA TCTATCATCA TTTTAATTTC TAAAATACAA

51 ACTGAATACT TTCCTAGAAT NTNANACAGC AATCATTGCT CATGCATTTA

101 ATAAATTACA ATTAGACAAA TATGACATTT GATATCACAC ACTTGCAAAC

151 ACACACATAT ATAATCAGAC ATAAATTGTT ATGCTAAGGT TTATTCACCA

201 AAANTATAAT ACATATTGGC TTGTTTTGAG TCATATTGNN TGANTTANAA

251 NGTATACTCA ACTCANTCAT TTNCAAATNG GTTGTGCAAT TCNTATTTNT

301 NTTTCTTGCA ATCCCTTGTT AAACTTGTCA TTTNATATAT CATTNTTCGG

351 GGCTTTATTA AAANNCATNT NNNACNGNGC CTATNGNNTC NNTNACTATN

401 NGCCCTAACA TCATTTTCNT CTNTTTCTTA TTTTTTACGG GATTT
```

Figure 27:
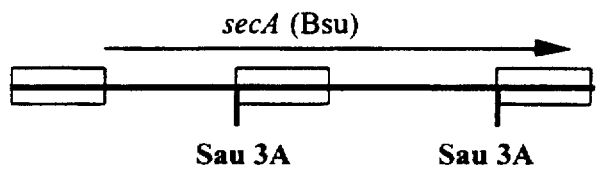

Mutant: NT15
Phenotype: temperature sensitivity
Sequence map: Mutant NT15 is complemented by plasmid pMP102, which contains a 3.1 kb insert of *S. aureus* genomic DNA. The partial restriction map of the insert is depicted in FIG. 27; open boxes along part of the length of the clone indicate the percentage of the clone for which DNA sequence has been obtained. Database searches at both the nucleic acid and protein levels reveal strong identity at both the peptide and nucleic acid level to the SecA protein from *S. carnosus* (Genbank Accession No. X79725; submitted in 1994, unpublished as of 1995); the relative size and location of the secA gene predicted from similarity to the *S. carnosus* gene is depicted below by an arrow. The SecA protein is involved in the protein secretory pathway and serves an essential cellular function.

```
DNA sequence data:                                            SEQ ID NO. 11
clone pMP102
pMP102.forward Length: 719 nt
    1 GATCRAGGAG ATCAAGAAGT GTTTGTTGCC GAATTACAAG AAATGCAAGA

51 AACACAAGTT GATAATGACG CTTACGATGA TAACGAGATA GAAATTATTC

101 GTTCAAAAGA ATTCAGCTTA AAACCAATGG ATTCAGAAGA AGCGGTATTA

151 CAAATGAATC TATTAGGTCA TGACTTCTTT GTATTCACAG ACAGAGAAAC

201 TGATGGAACA AGTATCGTTT ACCGCCGTAA AGACGGTAAA TATGGCTTGA

251 TTCAAACTAG TGAACAATAA ATTAAGTTTA AAGCACTTGT GTTTTTGCAC

301 AAGTGCTTTT TTATACTCCA AAAGCAAATT ATGACTATTT CATAGTTCGA

351 TAATGTAATT TGTTGAATGA ACATAGTGA CTATGCTAAT GTTAATGGAT

401 GTATATATTT GAATGTTAAG TTAATAATAG TATGTCAGTC TATTGTATAG

451 TCCGAGTTCG AAAATCGTAA AATATTTATA ATATAATTTA TTAGGAAGTT

501 ATAATTGCGT ATTGAGAATA TATTTATTAG TGATAAACTT GTTTGACACA

551 GAATGTTGAA TGAATTATGT CATAAATATA TTTATATTGA TCTACCAATG

601 AGTAAATAAN TATAATTTCC TAACTATAAA TGATAAGANA TATGTTGTNG

651 GCCCAACAGT TTTTTGCTAA AGGANCGAAC GAATGGGATT TTATCCAAAA

701 TCCTGATGGC ATAATAAGA pMP102.reverse Length: 949 nt                                 SEQ ID NO. 12
    1 CTTTACCATC TTCAGCTGAA ACGTGCTTCG CTTCACCAAA CTCTGTTGTT

51 TTTTCACGTT CAATATTATC TTCAACTTGT ACTACAGATT TTAAAATGAA

101 TTTACAAGTA TCTTCTTCAA TATTTTGCAT CATGATATCA AATAATTCAT

151 GACCTTCATT TTGATAGTCA CGTAATGGAT TTTGTTGTGC ATAAGAACGT

201 AAGTGAATAC CTTGACGTAA TTGATCCATT GTGTCGATAT GATCAGTCCA

251 ATGGCTATCA ATAGAACGAA GTAAAATCAT ACGCTCAAAC TCATTCATTT

301 GTTCTTCTAA GATATCTTTT TGACTTTGAT ATGCTGCTTC AATCTTAGCC

351 CAAACGACTT CGAAAATATC TTCAGGATCT TTACCTTTGA TATCATCCTC

401 TGTAATGTCA CCTTCTTGTA AGAAGATGTC ATTAATGTAG TCGATGAATG

451 GTTGATATTC AGGCTCGTCA TCTGCTGTAT TAATATAGTA ATTGATACTA

501 CGTTGTAACG TTGAACGTAG CATTGCATCT ACAACTTGAG AGCTGTCTTC

551 TTCATCAATA ATACTATTTC TTTCGTTATA GATAATTTCA CGTTGTTTAC

601 GTAATACTTC ATCGTATTCT AAGATACGTT TACGCGCGTC GAAGTTATTA

651 CCTTCTACAC GTTTTTGTGC TGATTCTACA GCTCTTGATA CCATTTTTGA

701 TTCAATTGGT GTAGAGTCAT CTAAACCTAG TCGGCTCATC ATTTTCTGTA

751 AACGTTCAGA ACCAAAACGA AATCATTAAT TCATCTTGTA ATGATAAATA

801 GAAGCGACTA TCCCCTTTAT CACCTTGACG TCCAGAACGA CCACGTAACT

851 GGTCATCAAT ACGACGAAGA TTCATGTCGC TCTGTACCTA TTACTGCTAA

901 ACCGCCTAAT TCCTCTACGC CTTCACCTAA TTTGATATCT GTACCACGA
```

-continued

```
pMP102.subclone Length: 594 nt                              SEQ ID NO. 13
    1 GGGGATCAAT TTANAGGACG TACAATGCCA GGCCGTCGTT NCTCGGAAGG

51 TTTACACCAA GCTATTGAAG CGAGGAAAGG CGTTCAAATT CAAAATGAAA

101 TCTAAAACTA TGGCGTCTAT TACATTCCAA AACTATTTCA GAATGTACAA

151 TAAACTTGCG GGTATGACAG GTACAGCTAA AACTGAAGAA GAAGAATTTA

201 GAAATATTTA TAACATGACA GTAACTCAAA TTCCGACAAA TAAACCTGTG

251 CAACGTAACG ATAAGTCTGA TTTAATTTAC ATTAGCCAAA AAGGTAAATT

301 TGATGCAGTA GTAGAAGATG TTGTTGAAAA ACACAAGGCA GGGCAACCMG

351 TGCTATTAGG TACTGTTGCA GTTGAGACTT CTGTATATAT TTCAAATTTA

401 CTTAAAAAAC GTGGTATCCG TCATGATGTG TTAAATGCGA RAAATCATGA

451 MCGTGAAGCT GAAATTGTTG CAGGCGCTGG RCAAAAAGGT GCCGTTACTA

501 TTGCCACTAM CATGGCTGGT CGTGGTACAG ATATCAAATT AGGTGAAGGC

551 GTTANAANGA AATTAGGCGG TTTANCCAGT AATANGTTCA GAAG
```

Figure 28:
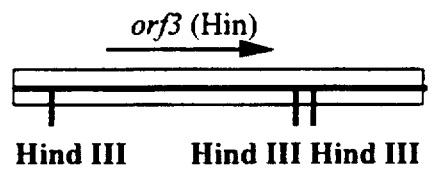

Mutant: NT16
Phenotype: temperature sensitivity
Sequence map: Mutant NT16 is complemented by plasmid pMP44, which contains a 2.2 kb insert of *S. aureus* genomic DNA. The partial restriction map of the insert is depicted in FIG. 28. Database searches at both the nucleic acid and protein levels reveal significant similarity at the peptide level to an ORF (orf3) of unknown function in the serotype "A" capsulation locus of *H. influenzae* (Genbank Accession No. Z37516); similarity also exists at the protein level to the tagB gene of *B. subtilis* (Genbank Accession No. X15200), which is involved in teichoic acid biosynthesis. Based upon the peptide level similarities noted, it is possible that the ORF(s) contained within this clone are involved in some aspect of membrane biogenesis, and should make an excellent screening target for drug development. No significant similarities are observed at the nucleic acid level, strengthening the stance that clone pMP44 represents a novel gene target(s).

DNA sequence data: The following DNA sequence data represents the sequence generated by primer walking through clone pMP44, starting with standard M13 forward and M13 reverse sequencing primers. The sequence below can be used to design PCR primers for the purpose of amplification from genomic DNA with subsequent DNA sequencing.

```
clone pMP44                                                  SEQ ID NO. 14
pMP44 Length: 2192 nt
    1 GCATGMCTGC AGGTCGATCY SYTGAACAGT CATCAACTAC AACCACTTCA

51 AATTCAGTTT TCGGAAAATC TTGTTTCGCA AGGCTATTAA GTAATTCTGT

101 TATATACTTT TCTGAATTGT ATGTTGGAAC TATTACTGAA AATTTCATCA

151 TTATACCTCT CCCACTTTGA CTACTATATA AACTTAGCTA CCAAATAAAT

201 TTCTGACTAA ACGCTCACTT GATCGGCCAT CTTGATATTT AAAATGTTTA

251 TCTAAGAATG GAATGACTTT TTCTCCTTCA TAATCTTCAT TGTCCAAGGC

301 GTCCATTAAT GCGTCAAATG ATTGCACAAT TTTACCTGGA ACAAATGATT

351 CATATGGTTC ATAAAAATCA CGCGTCGTAA TATAATCTTC TAAATCAAAT

401 GCATAGAAAA TCATTGGCTT TTTAAATACT GCATATTCAT ATATTAAAGA

451 TGAATAGTCA CTAATTAATA AATCTGTTAT GAACAGTATA TCATTAACTT

501 CTCTAAAGTC AGAAACGTCA ACAAAATATT GTTTATGTTT GTCTGCAATA

551 TTAAGTCTAT TTTTCACAAA TGGATGCATT TTAAATAATA CAACCGCGTT

601 ATTTTTTTCG CAATATCTTG CTAAACGTTC AAAATCAATT TTGAAAAATG

651 GGTAATGTGC TGTACCATGA CCACTACCTC TAAATGTTGG TGCGAAAAGA

701 ATGACTTTCT TACCTTTAAT AATTGGTAAT TCATCTTCCA TCTCTTGTTT

751 GATCTGTGTC GCATAAGCTT CATCAAATAG TACATCAGTA CGTTGGGAAC
```

-continued

```
 801 ACCTGTAGGC ACTACATTTT TCTCTTTAAT ACCAAATGCT TCAGCGTAGA
 851 ATGGAATATC GGTTTCAAGA TGATACATAA GCTTTTGTAT AAGCTACGGA
 901 TGATTTAATG AATCAATAAA TGGTCCACCC TTTTTACCAG TACGACTAAA
 951 GCCAACTGTT TTAAAGGCAC AACGGCATG CCATACTTGA ATAACTTCTT
1001 GAGAACGTCT AAAACGCACT GTATAAATCA ATGGGTGAAA GTCATCAACA
1051 AAGATGTAGT CTGCCTTCCC AAGTAAATAT GGCAATCTAA ACTTGTCGAT
1101 GATGCCACGT CTATCTGTAA TATTCGCTTT AAAAACAGTG TGAATATCAT
1151 ACTTTTTATC TAAATTTTGA CGTAACATTT CGTTATAGAT GTATTCAAAG
1201 TTTCCAGACA TCGTTGGTCT AGAGTCTGAT GTGAACAACA CCGTATTCCC
1251 TTTTTTCAAG TGGAAAAATT TCGTCGTATT AAATATCGCT TTAAAAATAA
1301 ATTGTCTTGT ATTAAATGAT TGTTTGCGGA AATACTTACG TAATTCTTTA
1351 TATTTACGRA CGATATAAAT ACTTTTAAMT TCCCGGAGTC GTTACAACAA
1401 CATCAAGGAC AAATTCATTA ACATCGCTAG AAATTTCAGG TGTAACAGTA
1451 TAAACCGTTT TCTTTCGAAA TGCCGCCTTT TCTAAATTCT TTTAGGTAAG
1501 TCTGCAATAA GAAATTGATT TTACCATTTT GTGTTTCTAA TTCGYTGTAT
1551 TCTTCTTCTT GTTCTGGCTT TAGATTTTGA TATGCATCAT TAATCAACAT
1601 CTGGGTTTAA CTGTGCAATA TAATCAAGTT CTTGCTCATT CACTAATAAG
1651 TACTTATCTT CAGGTAAGTA ATAACCATTA TCTAAGATAG CTACATTGAA
1701 ACGACAAACG AATTGATTCC CATCTATTTT GACATCATTC GCCTTCATTG
1751 TACGTGTCTC AGTTAAATTT CTTAATACAA AATTACTATC TTCTAAATCT
1801 AGGTTTTCAC TATGTCCTTC AACGAATAAC TGAACACGTT CCCAATAGAT
1851 TTTAYCTATA TATATCTTAC TTTTAACCAA CGTTAATTCA TCCTTTTCTA
1901 TTTACATAAT CCATTTTAAT ACTGTTTTAC CCCAAGATGT AGACAGGTCT
1951 GCTTCAAAAG CTTCTGTAAG ATCATTAATT GTTGCAATTT CAAATTCTTG
2001 ACCTTTTAAA CAACGGCTAA TTTATCTAAC AATATCTGGG TATTGAATGT
2051 ATAAGTCTAA CAACATCTTG GAAATCTTTT GAACCACTTC GACTACTACC
2101 AATCAACGTT AGTCCTTTTT CCAATACTAG AACGTGTATT AACTTCTACT
2151 GGGAACTCAC TTACACCTAA CAGTGCAATG CTTCCTTCTG GT
```

Figure 29:
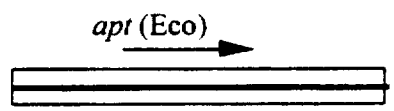

Mutant: NT17
Phenotype: temperature sensitivity
Sequence map: Mutant NT17 is complemented by plasmid pMP45, which contains a 2.4 kb insert of *S. aureus* genomic DNA. The partial restriction map of the insert is depicted in FIG. 29. Database searches at both the nucleic acid and protein levels reveal a strong similarity to the product of the apt gene, encoding adenine phosphoribosyl transferase (EC 2.4.2.7) from *E. coli* (Genbank Accession No. M14040; published in Hershey, H. V. et al. *Gene* 43 (1986) 287–293). DNA sequence data: The following DNA sequence data represents the sequence generated by primer walking into clone pMP45, starting with standard M13 forward and M13 reverse sequencing primers. The sequence below can be used to design PCR primers for the purpose of amplification from genomic DNA with subsequent DNA sequencing:

```
clone pMP45                                              SEQ ID NO. 15
pMP45 Length: 2431 nt
   1 ATGCAGGTCG ATCNCCTNGT TTATTCNGNT TCATCATTTT CCGATAAATA
  51 CTGTAAATAT GNNTAGGTCT ACCATTTATA TCGCCTTCGA TATTCATTCG
 101 GTCCATTTCA GTACGTATTC TATCAATAGC CGTTTCGATA TACGCTTCAC
 151 GTTCACTACG TTTCTTCTTC ATTAAATTGA CTATTCTAAA ATATTGCACA
```

```
 201 TTATCAATAT AACGAAGAGC CGKATCTTCT AGTTCCCATT TGATTGTATT
 251 AATACCAAGA CGATGTGCTA ATGGTGCATA AATTTCTAAT GTTTCTCGAG
 301 AAATTCTAAT TTGKTTTTCG CGCGGSATGG STTTCAAGGT ACGCATATTA
 351 TGTAATCTGT CTGCTAATTT CAMCAAAATT ACGCGTACAT CTTTGGCAAT
 401 CGCAATAAAT AACTTGSGAT GATTTTCAGC TTGTTGTTCT TCTTTTGAGC
 451 GGTATTTTAC TTTTTTAAGC TTCGTCACAC CATCAACAAT TCGAGCAACT
 501 TCTTCATTGA ACATTTCTTT TACATCTTCA AATGTATACG GTGTATCTTC
 551 AATTACATCA TGCAAAAAAC CTGCGACAAT CGTCGGTCCG TCTAATCGCA
 601 TTTCTGTTAA AATACCTGCA ACTTGTATAG GATGCATAAT GTATGGTAAT
 651 CCGTTTTTTC GGAACTGACC TTTATGTGCT TCATAACCAA TATGATAGCT
 701 TTTTAAAACA TACTCATATT CATCTGCTGA CAAATATGAT TTTGCTTTGT
 751 GAAGAACTTC GTCTGCACTA TATGGATATT CGTTGTTCAT TATATGATAC
 801 ACCCCATTCA TATTTATTAC TTCGCCTTTA AACAATGGAT TTAGGTACTC
 851 TTGTTGAATA GTATTTGTCC CACACCAATC ATACGTCCGT CGACGATAAA
 901 TATTTATCCT GTCGTGCATT AATCGTAATA TTAATTTTAC TTGAGCGAGT
 951 TTAATTTGTA TACTATTCCT ACTTTTAAAA CTTTTACAAA AATTCGACCT
1001 AAATCTACTG TTTCATTTTT TAAATATTAG TTCTATGATA CTACAATTTA
1051 TGARATAAAT AAACGAWGTT ATTAAGGTAT AATGCTCMAT CATCTATCAT
1101 TTTCAGTAAA TAAAAAATCC AACATCTCAT GTTAAGAAAA CTTAAACAAC
1151 TTTTTTAATT AAATCATTGG TYCTTGWACA TTTGATRGAA GGATTTCATT
1201 TGATAAAATT ATATTATTTA TTATTCGTCG TATGAGATTA AACTMATGGA
1251 CATYGTAATY TTTAAWAKTT TTCMAATACC AWTTAAAWKA TTTCAATTCA
1301 AATTATAAAW GCCAATACCT AAYTACGATA CCCGCCTTAA TTTTTCAACT
1351 AATTKTATKG CTGYTCAATC GTACCACCAG TAGCTAATAA ATCATCTGTA
1401 ATTRRSACAG TTGACCTGGK TTAATTGCAT CTTKGTGCAT TGTYAAAACA
1451 TTTGTACCAT ATTCTAGGTC ATAACTCATA ACGAATGACT TCACGAGGTA
1501 ATTTCCCTTC TTTTCTAACA GGTGCAAAGC CAATCCCCAT KGAATAAGCT
1551 ACAGGACAGC CAATGATAAA GCCAACGSGC TTCAGGTCCW ACAACGATAT
1601 CAAACATCTC TGTCTTTTGC GTATTCWACA ATTTTATCTG TTGCATAGCC
1651 ATATGCTTCA CCATTATCCA TAATTGTAGT AATATCCTTG AAACTAACAC
1701 CTGGTTTCGG CCAATCTTGA ACTTCTGATA CGTATTGCTT TAAATCCATT
1751 AATATTTCCT CCTAAATTGC TCACGACAAT TGTGACTTTA TCCAATTTTT
1801 TATTTCTGAA AAATCTTGAT ATAATAATTG CTTTTCAACA TCCATACGTT
1851 GTTGTCTTAA TTGATATACT TTGCTGGAAT CAATCGATCT TTTATCAGGT
1901 TGTTGATTGA TTCGAATTAA ACCATCTTCT TGTGTTACAA ATTTAAGTC
1951 TAAGAAAACT TTCAACATGA ATTTAAGTGT ATCTGGTTTC ACACTTAAAT
2001 GTTGACACAA TAACATACCC TCTTTCTGGA TATTTGTTTC TTGTTTAGTT
2051 ATTAATGCTT TATAACACTT TTTAAAAATA TCCATATTAG GTATACCATC
2101 GAAGTAAATC GAATGATTAT GTTGCAAAAC TATAKAAAGW TGAGAAAATT
2151 GCAGTTGTTG CAAGGAATTA GACAAGTCTT CCATTGACGT TGGTAAATCT
```

-continued

```
2201 CTTAATACTA CTTTATCAGT TTGTTGTTTA ATTTCTTCAC CATAATAATA

2251 TTCATTCGCA TTTACTTTAT CACTTTTAGG ATGAATAAGC ACGACAATAT

2301 TTTCATCATT TTCTGTAAAA GGTAAACTTT TTCGCTTACT TCTATAATCT

2351 AATATTTGCT GTTCATTCAT CGCAATATCT TGAATAATTA TTTGCGGTGA

2401 TTGATTACCA TTCCATTCGT TGATTTGAAC A
```

Figure 30:
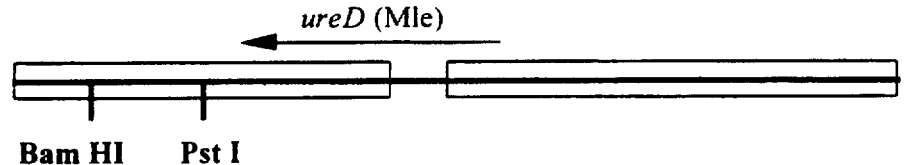

Mutant: NT18
Phenotype: temperature sensitivity
Sequence map: Mutant NT18 is complemented by pMP48, which contains a 4.7 kb insert of *S. aureus* genomic DNA. A partial restriction map is depicted in FIG. 30, along with open boxes to indicate the percentage of the clone for which DNA sequence has been obtained; the sequence contig will be completed shortly. Database searches at both the nucleic acid and peptide levels reveal a strong peptide-level similarity to the ureD gene product, encoding a putative regulatory protein with strong similarities to the phosphomannomutase and the phosphoglucomutase from *E. coli*. The right-most sequence contig from the diagram below is responsible for complementing mutant NT102, described later; however, the full pMP48 clone described here is required for complementing mutant NT18. Based upon genomic organization and peptide-level similarities, it is highly likely that mutants NT18 and NT102 represent two different proteins in the same biochemical pathway.

DNA sequence data: The following DNA sequence data represents the sequence obtained from clone pMP48, starting with standard M13 forward and M13 reverse sequencing primers and applying primer walking strategies to augment the sequence contigs. The sequences below can be used to design PCR primers for the purpose of amplification from genomic DNA with subsequent DNA sequencing:

clone pMP48                                                            SEQ ID NO. 16
pMP48.forward Length: 2018 nt

```
   1 GCATCAGTTG GTACTTTAAA TAAATGTGCA GTACCAGTCT TAGCAACATT

51 TACAGTTGCT AATTCAGTAT TTTTCTTAGC ATCTTTAATA ACTAAATTTG

101 TTGCACCTTG CTTACTATTC GTTTGCATAG TAGTAAAGTT AATAATTAAT

151 TCTGAATCTG GTTTTACATT TACAGTTTTT GAAATACCGT TAAAGTTACC

201 ATGATCTGTA GAATCATTTG CATTCACACG ACCTAATGCA GCCACGTTTC

251 CTTTAGCTTG ATAGTTTTGA GGGTTATTCT TATCAAACAT ATCGCTTCGT

301 CTTAATTCTG AGTTAACGAA ACCAATCTTA CCGTTGTTAA TTAATGAATA

351 ACCATTTACT TTATCTGTAA CAGTTACAGT TGGATCGTGC CTATTCTCAT

401 CTGTTGATAT GGCAGGATCA TCAAATGTTA ATGTCGTATT AATACTGCCT

451 TCACCAGTAT TGCTAGCATT TGGATCTTGA GTTTGTGCGT TTGCTGCTAT

501 AGGTGCTGCT GGTTGCGCTG CTGCTGGANC ATTCGCTGGC TGTGTTTGAT

551 TTGCCGGTGT TGCATTATTA TWAGGTGTTG CTTGGTTATT TCCTTGACCT

601 GCTTGGTWTG CCGGTGTTGC TTGATTTCCA GGTTGTGCAT GTGCAACGTT

651 ATTCGGATCA GCTTGATCAC CTTGTCCAGC TGGTTGTGTA TTTGGTTGTG

701 CTGCTCCTCC TGCTGGATTA GCCTGTCCAC CTTGGTTTGC TGGTTGTACT

751 GCTGGTTGTC CTTGGTTGGC AGGTGCAGCT GGCTGTGCTG TAGGATTAGC

801 TTGAGCACCA GCATTTGCGT TAGGCTGTGT ATTGGCATCA GCTGGTTGTG

851 CTGGTTGATT TTGTGCAGGC TGATTTTGCT CTGCTGCAKA CGCTGTTGTC

901 GGGTTAGTAG ATATAAAAGT AACAGTGGCA ATTAAAGCTG AAAAAATACC

951 GACATTAAAT TTTCTGATAC TAAATTTTTG TTGTCTGAAT AAATTCATTA

1001 AGTCATCCTC CTGGTTGATT ATTCTCGCTG TTAAATGATT TCACTTAATC

1051 AACTGTTAAG ATAAGTAGTA GCATCTGCGT TAAAAACACA AAGCAACTCT

1101 ATCTAATTAA AATTAATTTT ATCATCATTA TATATTGAGT ACCAGTGTAT
```

-continued

```
1151 TTTATATTAC ATATTGATTA CTTTGTTTTT ATTTTGTTTA TATCATTTTA
1201 CGTTTGTACT ATAAATTATT TCTACAAACA CAAAAAACCG ATGCATACGC
1251 ATCGGCTCAT TTGTAATACA GTATTTATTT ATCTAATCCC ATTTTATCTT
1301 GAACCACATC AGCTATTTGT TGTGCAAATC TTTCAGCATC TTCATCAGTT
1351 GCTGCTTCAA CCATGACACG AACTAATGGT TCTGTTCCAG AAGGTCTTAC
1401 TAAAATTCGA CCTTCTCCAT TCATTTCTAC TTCTACTTTA GTCATAACTT
1451 CTTTAACGTC AACATTTTCT TCAACACGAT ATTTATCTGT TACGCGTACG
1501 TTAATTAATG ATTGTGGATA TTTTTTCATT TGTCCAGCTA ATTCACTTAG
1551 TGATTTACCA GTCATTTTTA TTACAGAAGC TAATTGAATA CCAGTTAATA
1601 AACCATCACC AGTTGTATTG TAATCCAYCA TAACGATATG TCCARATKGT
1651 TCTCCACCTA AGTTATAATT ACCGCGAMGC ATTTCTTCTA CTACATATCT
1701 GTCGCCAACT TTAGTTTTAT TAGATTTAAT TCCTTCTTGT TCAAGCGCTT
1751 TGTAAAAACC TAAATTACTC ATAACAGTAG AAAACGAATC ATGTCATTAT
1801 TCAATTCTTG ATTTTTATGC ATTTCTTGAC CAATAATAAA CATAATTTGG
1851 TCACCGTCAA CGATTTGACC ATTCTCATCT ACTGCTATGA TTCTGTCTCC
1901 ATCGCCGTCA AATGCTAACC CAAAATCACT TTCAGTTTCA ACTACTTTTT
1951 CAGCTAATTT TCAGGATGTG TAAAGCCACA TTTCTCATTG ATATTATATC
2001 CATCAGGGAC TACATCCA
``` pMP48.reverse Length: 2573 nt           SEQ ID NO. 17

```
   1 ATTCGAGCTC GGTACCCGKG GATCCTSYAG AGTCGATCCG CTTGAAACGC
  51 CAGGCACTGG TACTAGAGTT TTGGGTGGTC TTAGTTATAG AGAAAGCCAT
 101 TTTGCATTGG AATTACTGCA TCAATCACAT TTAATTTCCT CAATGGATTT
 151 AGTTGAAGTA AATCCATTGA TTGACAGTAA TAATCATACT GCTGAACAAG
 201 CGGTTTCATT AGTTGGAACA TTTTTTGGTG AAACTTTATT ATAAATAAAT
 251 GATTTGTAGT GTATAAAGTA TATTTTGCTT TTTGCACTAC TTTTTTTAAT
 301 TCACTAAAAT GATTAAGAGT AGTTATAATC TTTAAAATAA TTTTTTTCTA
 351 TTTAAATATA TGTTCGTATG ACAGTGATGT AAATGATTGG TATAATGGGT
 401 ATTATGGAAA ATATTACCC GGAGGAGATG TTATGGATTT TTCCAACTTT
 451 TTTCAAAACC TCAGTACGTT AAAAATTGTA ACGAGTATCC TTGATTTACT
 501 GATAGTTTGG TATGTACTTT ATCTTCTCAT CACGGTCTTT AAGGGAACTA
 551 AAGCGATACA ATTACTTAAA GGGATATTAG TAATTGTTAT TGGTCAGCAG
 601 ATAATTWTGA TATTGAACTT GACTGCMACA TCTAAATTAT YCRAWWYCGT
 651 TATTCMATGG GGGGTATTAG CTTTAANAGT AATATTCCAA CCAGAAATTA
 701 GACGTGCGTT AGAACAACTT GGTANAGGTA GCTTTTTAAA ACGCNATACT
 751 TCTAATACGT ATAGTAAAGA TGAAGAGAAA TTGATTCAAT CGGTTTCAAA
 801 GGCTGTGCAA TATATGGCTA AAAGACGTAT AGGTGCATTA ATTGTCTTTG
 851 AAAAAGAAAC AGGTCTTCAA GATTATATTG AAACAGGTAT TGCCAATGGA
 901 TTCAAATATT TCGCAAGAAC TTTTAATTAA TGTCTTTATA CCTAACACAC
 951 CTTTACATGA TGGTGCAAKG ATTATTCAAG GCACGAARAT TGCAGCAGCA
1001 GCAAGTTATT TGCCATTGTC TGRWAGTCCT AAGATATCTA AAAGTTGGGT
1051 ACAAGACATA GAGCTGCGGT TGGTATTTCA GAAGTTATCT GATGCATTTA
```

-continued

```
1101 CCGTTATTGT ATCTGAAGAA ACTGGTGATA TTTCGGTAAC ATTTGATGGA

1151 AAATTACGAC GAGACATTTC AAACCGAAAT TTTTGAAGAA TTGCTTGCTG

1201 AACATTGGTT TGGCACACGC TTTCAAAAGA AAGKKKTGAA ATAATATGCT

1251 AGAAAKTAAA TGGGGCTTGA GATTTATTGC CTTTCTTTTT GGCATTGTTT

1301 TTCTTTTTAT CTGTTAACAA TGTTTTTGGA AATATTCTTT AAACACTGGT

1351 AATTCTTGGT CAAAAGTCTA GTAAAACGGA TTCAAGATGT ACCCGTTGAA

1401 ATTCTTTATA ACAACTAAAG ATTTGCATTT AACAAAAGCG CCTGAAACAG

1451 TTAATGTGAC TATTTCAGGA CCACAATCAA AGATAATAAA AATTGAAAAT

1501 CCAGAAGATT TAAGAGTAGT GATTGATTTA TCAAATGCTA AAGCTGGAAA

1551 ATATCAAGAA GAAGTATCAA GTTAAAGGGT TAGCTGATGA CATTCATTAT

1601 TCTGTAAAAC CTAAATTAGC AAATATTACG CTTGAAAACA AAGTAACTAA

1651 AAAGATGACA GTTCAACCTG ATGTAAGTCA GAGTGATATT GATCCACTTT

1701 ATAAAATTAC AAAGCAAGAA GTTTCACCAC AAACAGTTAA AGTAACAGGT

1751 GGAGAAGAAC AATTGAATGA TATCGCTTAT TTAAAAGCCA CTTTTAAAAC

1801 TAATAAAAAG ATTAATGGTG ACACAAAAGA TGTCGCAGAA GTAACGGCTT

1851 TTGATAAAAA ACTGAATAAA TTAAATGTAT CGATTCAACC TAATGAAGTG

1901 AATTTACAAG TTAAAGTAGA GCCTTTTAGC AAAAAGGTTA AAGTAAATGT

1951 TAAACAGAAA GGTAGTTTRS CAGATGATAA AGAGTTAAGT TCGATTGATT

2001 TAGAAGATAA AGAAATTGAA TCTTCGGTAG TCGAGATGAC TTMCAAAATA

2051 TAAGCGAAGT TGATGCAGAA GTAGATTTAG ATGGTATTTC AGAATCAACT

2101 GAAAAGACTG TAAAAATCAA TTTACCAGAA CATGTCACTA AAGCACAACC

2151 AAGTGAAACG AAGGCTTATA TAAATGTAAA ATAAATAGCT AAATTAAAGG

2201 AGAGTAAACA ATGGGAAAAT ATTTTGGTAC AGACGGAGTA AGAGGTGTCG

2251 CAAACCAAGA ACTAACACCT GAATTGGCAT TTAAATTAGG AAGATACGGT

2301 GGCTATGTTC TAGCACATAA TAAAGGTGAA AAACACCCAC GTGTACTTGT

2351 AGGTCGCGAT ACTAGAGTTT CAGGTGAAAT GTTAGAATCA GCATTAATAG

2401 CTGGTTTGAT TTCAATTGGT GCAGAAGTGA TGCGATTAGG TATTATTTCA

2451 ACACCAGGTG TTGCATATTT AACACGCGAT ATGGGTGCAG AGTTAGGTGT

2501 AATGATTTCA GCCTCTCATA ATCCAGTTGC AGATAATGGT ATTAAATTCT

2551 TTGSCTCGAC CNCCNNGCTN GCA
```

Figure 31:
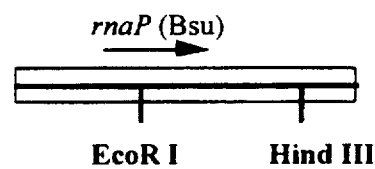

Mutant: NT19
Phenotype: temperature sensitivity
Sequence map: Mutant NT19 is complemented by pMP49, which contains a 1.9 kb insert of *S. aureus* genomic DNA. A partial restriction map is depicted FIG. 31. Database searches at both the nucleic acid and peptide levels reveal strong similarity at the nucleic acid level to the rnpA gene, which encodes the catalytic RNA component RNAse P, from the bacilli *B. megaterium*, *B. subtilis*, and *B. stearothermophilus* as well as from other prokaryotes. The strongest similarity observed is to the rnpA Genbank entry from *B. subtilis* (Genbank Accession No. M13175; published in Reich, C. et al. *J. Biol. Chem.*, 261 (1986) 7888–7893).
DNA sequence data: The following DNA sequence data represents the sequence of clone pMP49, starting with the standard M13 forward and M13 reverse sequencing primers and applying primer walking strategies to complete the sequence contig. The sequences below can be used to design PCR primers for the purpose of amplification from genomic DNA with subsequent DNA sequencing:

clone pMP49   SEQ ID NO. 18
pMP49 Length: 1962 nt

```
   1 GTGCTTCCAC CAATACGTTC CACCATATGG AGGATTTCCA ATTAACGCCA
  51 CCGGTTCTTC TGTATCAATT GTTAATGTAT TGACATCTTT TACACTAAAT
 101 TTAATAATAT CAGACAACCC AACTTCTTCA GCGTTACGCT TAGCAATCTC
 151 TACCATTTCT GGATCGATAT CAGAAGCATA TACTTCGATT TCTTTATCAT
 201 AATCAGCCAT CTTATCCGCT TCATCACGGT AATCATCATA AATATTTGCT
 251 GGCATGATGT TCCATTGCTC TGATACGAAC TCGCGATTAA AACCAGGTGC
 301 GATATTTTGA GCAATTAAAC AAGCTTCTAT AGCTATTGTA CCCGAACCGC
 351 AAAATGGATC AATTAAAGGT GTATCACCTT TCCAGTTTGC AAGACGGATT
 401 AAACTTGCTG CCAACGTTTC TTTAATTGGT GTTTCACCTT GTGCTAATCT
 451 ATAACCACGT CTGTTCAAAC CAGAACCTGA TGTGTCGATA GTCAATAATA
 501 CATTATCTTT TAAAATGGCA ACTTCAACAG GGTATTTGGC ACCTGATTCA
 551 TTTAACCAAC CTTTTTCGTT ATATGCGCGA CGTAATCGTT CAACAATAGC
 601 TTTCTTAGTT ATCGCCTGAC AATCTGGCAC ACTATGTAGT GTTGATTTAA
 651 CGCTTCTACC TTGAACTGGG AAGTTACCCT CTTTATCAAT TATAGATTCC
 701 CAAGGGAGCG CTTTGGTTTG TTCGAATAAT TCGTCAAACG TTGTTGCGTW
 751 AAAACGTCCA ACAACAATTT TGATTCGGTC TGCTGTGCGC AACCATAAAT
 801 TTGCCTTTAC AATTGCACTT GCGTCTCCTT CAAAAAATAT ACGACCATTT
 851 TCAACATTTG TTTCATAGCC TAATTCTTGA ATTTCCCTAG CAACAACAGC
 901 TTCTAATCCC ATCGGACAAA CTGCAAGTAA TTGAAACATA TATGATTCTC
 951 CTTTTATACA GGTATTTTAT TCTTAGCTTG TGTTTTTTAT ACATTTCCAA
1001 CAAATTTAAT CGCTGATACA TTAACGCATC CGCTTACTAT TTTAAAACAA
1051 GGCAGTGTCA TTATATCAAG ACAAGGCGTT AATTTAAGT GTCTTCTTTY
1101 CATGAAAAAA GCTCTCCMTC ATCTAGGAGA GCTAAACTAG TAGTGATATT
1151 TCTATAAGCC ATGTTCTGTT CCATCGTACT CATCACGTGC ACTAGTCACA
1201 CTGGTACTCA GGTGATAACC ATCTGTCTAC ACCACTTCAT TTCGCGAAGT
1251 GTGTYTCGTT TATACGTTGA ATTCCGTTAA CAAGTGCTC CTACCAAATT
1301 TGGATTGCTC AACTCGAGGG GTTTACCGCG TTCCACCTTT TATATTTCTA
1351 TAAAAGCTAA CGTCACTGTG GCACTTTCAA ATTACTCTAT CCATATCGAA
1401 AGACTTAGGA TATTTCATTG CCGTCAAATT AATGCCTTGA TTTATTGTTT
1451 CAYCAAGCRC GAACACTACA ATCATCTCAG ACTGTGTGAG CATGGACTTT
1501 CCTCTATATA ATATAGCGAT TACCCAAAAT ATCACTTTTA AAATTATAAC
1551 ATAGTCATTA TTAGTAAGAC AGTTAAACTT TTGTATTTAG TAATTATTTA
1601 CCAAATACAG CTTTTTCTAA GTTTGAAATA CGTTTTAAAA TATCTACATT
1651 ATTTGAAGAT GTATTTGTTG TTGTATTATT CGAAGAAAAA CTTTTATTGT
1701 CCTGAGGTCT TGATGTTGCT ACACGTAGTC TTAATTCTTC TAATTCTTTT
1751 TTAAGTTTAT GATTCTCTTC TGATAATTTT ACAACTTCAT TATTCATATC
1801 GGCCATTTTT TGATAATCAG CAATAATGTC ATCTAAAAAT GCATCTACTT
```

-continued

```
1851 CTTCTCTTCT ATAGCCACGA GCCATCGTTT TTTCAAAATC TTTTTCATAA

1901 ATATCTTTTG CTGATAATTT CAATGAAACA TCTGACATTT TTTCCACCTC

1951 ATTAGAAACT TT
```

Figure 32:
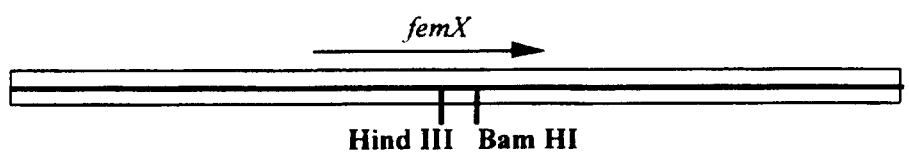

Mutant: NT23
Phenotype: temperature sensitivity
Sequence map: Mutant NT23 is complemented by pMP55, which contains a 5.2 kb insert of *S. aureus* genomic DNA. A partial restriction map is depicted FIG. 32. Database searches at both the nucleic acid and peptide levels reveal limited similarity at the protein level only to *S. aureus* proteins FemA and FemB, suggesting that clone pMP55 contains a new Fem-like protein. Since the Fem proteins are involved in peptidoglycan formation, this new Fem-like protein is likely to make an attractive candidate for screening antibacterial agents. Since clone pMP55 does not map to the same location as the femAB locus (data not shown here), the protein is neither FemA nor FemB and represents a novel gene.

DNA sequence data: The following DNA sequence data represents the sequence of clone pMP55, starting with the standard M13 forward and M13 reverse sequencing primers and applying primer walking strategies to complete the sequence contig. The sequences below can be used to design PCR primers for the purpose of amplification from genomic DNA with subsequent DNA sequencing:

```
clone pMP55, a 5000 bp genomic fragment              SEQ ID NO. 19
pMP55 Length: 5253 nt
    1 TAACTGGACT ACWACCGCCA ACTRAGTATT GAATTGTTTT AACATGCTTT

51 TCCTGTTTTA AATATTTTTA AACATCTTTC GCATGATTCA ACACTGCTTG

101 CTCCGTTTCA CCAGGCTTCG GTGTATAAGT AATAGCTAAA AATTTATCGT

151 CACCTGCTGA AATAAAGCTA GTGCCTAGTC TCGGTCCTCC AAATACAATA

201 GTTGCAACCA AAATTAATGT ACTTAATATA ATTWCAATCC ACTTATGATT

251 TAATGACCAA TGTAATACTT TTTTATAAGT TGTACTAACA ACACCTAATC

301 CTTCTTGATG TTGTTTATTA CGACGTTTAA CGCCTTTTTT AAATAGTGTA

351 GCTGCCAACG CTGGAACGAG TGTAATTGAC ACTAATAACG ATGCTAATAA

401 ACTAAATGCA ATAGCCAATG CAAAAGGTCT AAACATTTCG CCTACTGAAC

451 CTGATACAAA CACAAGTGGT AAGAAGACGA TAATAGKAAC TAGTGTCGAT

501 GRCATTATTG GTTTAAATAC TTCAGTTGTC GCACTGATAA TTAAATTTTC

551 ACCTTTTAGT TGGTTCTTCT GAATCTGTTA AGCGTCGATA AATATTTTCA

601 MCAACTACAA TCGAATCGTC TATCACACGT CCAATCGCTA CTGTTAATGC

651 ACCTAACGTT AGTATATTCA ATGAMACATC ACTCAATTTC AGAGCAATAA

701 GCGSCATAAG AAGTGATAAC GGMATCGATA TMATAGAAAT TGCCGTCGTA

751 CGAATGTTTC TTAAAAACAG CAAAATAACT ATAATTGCCA CGRATTGTAC

801 CTAATGATGC TTTTTCAACC ATCGTATAAA GTGATTTCTC AACAGGCTTT

851 GCAGTATCCA TTGTTTTTGT GACATTAAAA TCTTTATTTT CATCAACGAA

901 TGTATCAATT TTACGTTGTA CATCTTTGGC TACTTGAACT GTATTGGCAT

951 CTTGAGCTTT AGTTATTTGT AGATTAACCG CATCCTTTCC ATTCGTTTTA

1001 GAAATAGAAG TACGCACATC ACCAACTGTA ATATCAGCTA AATCTCCTAG

1051 TTTCGCTGTC GGCATACCAC TTATATTATT TGGTGCTGAC GCTTTTGAAT

1101 TTTGCTGTGG TGATGCCTGA TTAACGTCTG ACATGGCTGA AATTTTGTTT

1151 ATTGTCACTT TGGGATTGAG ATTGCCCTTG TCCTCCTGCC AACGTTAATG

1201 GAATATTTAT GTTTTTAAAA GCATCAACAG ATTGATATTG ACCATCAACA

1251 ACAATTGATT TATCTTTATC ACCAAATTGG AACAATCCAA GTGGCGTTGT

1301 TCTTGTTGCC GTTTTTAGAT AGTTTTCTAC ATCATCAGCA GTCAACCCAT
```

-continued

```
1351 ATTTTCAAGT TCATTTTGCT TAAATTTAAG GGTGATTTCA CGGTTCGTCT
1401 GCCCATTTAA TTGCGCATTT TGNACACCAT CTACCGTTTG CAATTTTGGT
1451 ATNAATTGTT CATTCAGTAC TTTCGTTACT TTTTTCAAGT CATTCNCTTT
1501 ATTTGAAAAT GAATATGCTA AAACCGGAAA AGCATCCATC GAATTACGTC
1551 NTANTTCTGG TTGACCAACT TCATCTTTAA ATTTAATTTT NTNTATTTCT
1601 NTTNTAAGCT GTTCTTCTGC TTTATCCAAA TCTGTATTMT TTTCATATTC
1651 AACTGTTACA ATTGAAGCAT TTTGTATGGA TTGCGTTTTA ACATTTTTCA
1701 CATATGCCAA TGATCTTACY TGAWTGTCAA TTTTACTACT TATTTCATCT
1751 TGGGTACTTT GTGGCGTTGC ACCCGGCATT GTTGTTGTAA CTGGAATAAC
1801 TGGATKTTGT ACATTTGGTA KTAATTCTMA TTTCAATTTA GCACTCGCAT
1851 ATACACCGCC AAGACAACT WAAACAACCA TTAMAAAGAT AGCAAACYTA
1901 TTCCCTAAAA RGAAAATTGT AATAGCTTTT TTAWCAACAG TMCTYCCCCC
1951 TCTTTCACTA WAATTCAAAA AATTATTTTA CTCAACCATY CTAWWWTGTG
2001 TAAAAAAAAT CTGAACGCAA ATGACAGYCT TATGAGCGTT CAGATTTCAG
2051 YCGTTAATCT ATTTYCGTTT TAATTTACGA GATATTTTAA TTTTAGCTTT
2101 TGTTAAACGC GGTTTAACTT GCTCAATTAA TTGGYACAAT GGCTGATTCA
2151 ATACATAATC AAATTCACCA ATCTTTTCAC TTAAGTATGT TCCCCACACT
2201 TTTTTAAATG CCCATAATCC ATAATGTTCT GAGTCTTTAT CTGGATCATT
2251 ATCTGTACCA CCGAAATCGT AAGTTGTTGC ACCATGTTCA CGTGCATACT
2301 TCATCATCGT ATACTGCATA TGATGATTTG GTAAAAAATC TCTAAATTCA
2351 TTAGAAGACG CACCATATAA GTAATATGAT TTTGAGCCAG CAAACATTAA
2401 TAGTGCACCA GAAAGATAAA TACCTTCAGG ATGTTCCTTT TCTAAAGCTT
2451 CTAGGTCTCG TTTTAAATCT TCATTTTTAG CAATTTTATT TTGCGCATCA
2501 TTAATCATAT TTTGCGCTTT TTTAGCTTGC TTTTCAGATG TTTTCATCTT
2551 CTGCTGCCAT TTAGCAATTT CGGCATGAAG TTCATTCAAT TCTTGATTTA
2601 CTTTCGCTAT ATTTTCTTTT GGATCCAACT TTACTAAAAA TAGTTCAGCA
2651 TCTCCATCTT CATGCAACGC ATCATAAATA TTTTCAAAGT AACTAATATC
2701 ACGCGTTAAG AAGCCATCGC GTTCCCCAGT GATTTTCATT AACTCAGCAA
2751 ATGTTTTTAA ACCTTCTCTA TCAGATCGTT CTACTGTCGT ACCTCGCTTT
2801 AAAGCCAAGC GCACTTTTGA ACGATTTCGG CGTTCAAAAC TATTTAATAA
2851 CTCATCATCA TTTTTATCAA TTGGTGTAAT CATAGTCATA CGTGGTTGGA
2901 TGTAGTCTTT TGATAAACCT TCTTTAAATC CTTTATGTTT AAAACCAAGC
2951 GCTTTCAAAT TTTGCAAAGC ATCTGTRCCT TTATCAACTT CAACATCAGG
3001 ATCGRTTTTA ATTGCATACG CTTTCTCAGC TTTAGCAATT TCTTTTGGAC
3051 TGTCTAACMA TGSMTTTAAC GYTTCTTTAT TACTATTAAT CAACAACCAA
3101 AACCMCGCGR RAWTATWACM TAGSGTATAA GGTAATTTAG GTACTTTTTT
3151 AAAAAGTAAC TGCGCAACAC CCTGAAACTT SMCCGTCACG ACCTACAGCG
3201 ATTCTTCGCG CGTACCATCC AGTTAATTTC TTTGTTTCTG CCCATTTCGT
3251 TAATTGTAAT AAATCTCCAT TTGGGTGGGR WTTWACAAAT GCGTCATGTT
3301 CCTGATTAGG KGATATGCAT CTTTTCCATG ATTTATGATA TCTCCTTCTA
```

```
3351 TTTAACAATA CCTTTAATTA TACAGTTTGT ATCTTATAGT GTCGATTCAG

3401 AGCTTGTGTA AGATTTGAAC TCTTATTTTT GGAAATGTCC ATGCTCCAAT

3451 TAATAGTTTA GCAAGTTCAA ATTTACCCAT TTAATTGTG AATCATTTTA

3501 TATCTATGTT TCGTGTTAAA TTTAATGTTA TCGTACARTT AATACTTTTC

3551 AACTAGTTAC CTATACTTCA ATATACTTTC ATCATCTAAC ACGATATTCA

3601 TTTCTAARAA TGAACCAACT TGACTTCAAT GAATAAATTT TTCCTCAAGC

3651 AACCACATTA ATGTTCATAT ACAATTACCC CTGTTATAAT GTCAATAATC

3701 TAACAATGAG GTGTTGATA TGAGAACAAT TATTTTAAGT CTATTTATAA

3751 TTATGRACAT CGTTGCAATC ATTATGACAT TGAGTCAACC TCTCCACCGT

3801 GAATTACTTT AGTTTACGGG TTATACTTAT CTTTTTCACA TTTATATTAT

3851 CAATCTTTTT CATTTTAATT AAGTCATCAC GATTAAATAA TATATTAACG

3901 ATTMWWTCCA TTGTGCTTGT CATTATTCAT ATGGGCATTC TCGCTCATAG

3951 CACTTACGTA TATTTATACT AATGGTTCAA AGCGATAAAT AGCACCTCTG

4001 ATAAAAATTG AATATGGTGA AGTTGCTTGT GCGTCTTTTA TGATAACCGA

4051 ATGATATTTT GAAACTTTAC CATCTTCAAT TCTAAAATAA ATATCATCAT

4101 TTTTTAAAAT CAAATCTGTG TAATGGTCAT TTYKTCHACA ATGTCCATAT

4151 CAARCCATTT CAACCAATTC GATACTGTWK GTGATCGGTT TTTACTTTTC

4201 ACAATAACAG TTTCAAWTGA AAATTGTTTT TGAAAATATT TTTGCAATTT

4251 TTTAGTACGC ATGGAATCAC TTTCTTCCCA TTGAATAAAA AATGGTGGCT

4301 TAATTTCATC ATCATCCTGA TTCATTATAT AAAGCAATTG CCACTTTACC

4351 TWCACCATCT TTATGTGTAT CTCTTTCCAT TTGAATCGGC CCTACTACTT

4401 CAACCTGCTC ACTNTGTAGT TTATTTTTAA CTGCCTCTAT ATCATTTGTA

4451 CGCAAACAAA TATTTATTAA AGCCTTGCTC ATACTTCTCT TGAACAATTT

4501 GAGTAGCAAA AGCGACTCCG CCTTCTATCG TTTTTGCCAT CTTTTTCAAC

4551 TTTTCATTAT TTTACTACAT CTAGTAGCTC AAGATAATTT CATTGATATW

4601 ACCTAAKKTA TTGAATGTTC CATATTTATG ATGATACCCA CCTGAATGTA

4651 ATTTTATAAC ATCCTCCTGG AAAACTAAAC CGATCTAACT GATCTATATA

4701 ATGAATGATG TGATCANATT TCAATATCAT TAGTATCCCC CTATTTACAT

4751 GTAATTACGC TTATTTTAAA CAAAGTAWAA TTATTTTTGC YCTTAATAAT

4801 TATATAKTGA YYYCWAATTG CTCCCGTTTT ATAATTACTA TTGTTGTAAA

4851 ARGGTTAGCT AAGCTAACTA TTTTGCCTTA GGAGATGTCA CTATGCTATC

4901 ACAAGAATTT TTCAATAGTT TTATAACAAT ATAYCGCCCC TATTTAAAAT

4951 TAGCCGAGCC GATTTTAGRA AAACACAATA TATATTATGG CCAATGGTTA

5001 ATCTTACGCG ATATCGCTAA ACATCAGCCC ACTACTCTCA TTGNAATTTC

5051 ACATAGACGG GCAATTGAAA AGCCTACTGC AAGAAAAACT TTAAAAGCTC

5101 TAATAGGAAA TGACCTTATW ACAGTAGAAA ACAGNTTAGA GGATAAACNA

5151 CAAAAGNTTT TAACTTTAAC ACCTAAAGGG CATKAATTAT ATGAGATTGT

5201 TTGTCTTGAT GNACAAAAGC TCCNACAAGC AGNNAGTTGC CAAAACAAAG

5251 ATT
```

Mutant: NT27

Phenotype: temperature sensitivity

Figure 33:

Sequence map: Mutant NT27 is complemented by pMP59, which contains a 3.2 kb insert of *S. aureus* genomic DNA. A partial restriction map is depicted FIG. 33. Database searches at both the nucleic acid and peptide levels reveal strong peptide-level similarities to two hypothetical ORFs from *B. subtilis*. These hypothetical ORFs are also found in other bacteria, but in all cases, nothing has been reported in the literature about the functions of the corresponding gene products.

DNA sequence data: The following DNA sequence data represents the sequence of clone pMP59, starting with the standard M13 forward and M13 reverse sequencing primers and applying primer walking strategies to complete the sequence contig. The sequences below can be used to design PCR primers for the purpose of amplification from genomic DNA with subsequent DNA sequencing:

```
clone pMP59                                                    SEQ ID NO. 20
pMP59 Length: 3263 nt
    1 ACATTGAMAA AGATCACCCA TTACAACCAC ATACAGATGC AGTAGAAGTT
   51 TAAAACACAT TTTTCTAATT ATCAAAGCTT AGGATAAATA TGATGTCCTA
  101 AGCTTTTCCT TTTACAACTT TTTCGAATAA ACAACAGTTA AATATATTCA
  151 CCTTTCTACC AAACTTTTTA TCCCCTCATT TAAATTTTAC CGGKYTCATA
  201 TAAAATCCTT TAATTCTTTC TTAACATTAW TTTWTWATCT CTACATYTAT
  251 TTTAATAAAT AGAACTGCAC ATTTATTCGA AATACTTAGA TTTCTAGTGA
  301 GATAAACTGC TTTATTTATT ATCATTCATC ATGTAAAATA AGATTTAACT
  351 GAAATTTTAG TGTTATTTCA CTAATTTTTT AAAATGAACG ACATGATGAA
  401 CCTAGTTATT AACCAAATCG TTATTAAGTT ACATTATAGA GATGATTGGA
  451 ATGAATTTAT CGATATATAC TCCAATACGA TTTTACTAGG GTTAACAATA
  501 AATTAAACAA ACATTCTTAG GAGGRATTTT TAACATGGCA GTATTTAAAG
  551 TTTTTTATCA ACATAACAGA GTACGAGGTR RTTGTGCGTG AAAATACACA
  601 ATCACTTTAT GTTGAAGCTC ARACAGAAGA ACAAGTAGCG TCGTTACTTG
  651 AAAGATCGTA ATTTTAATAT CGAATTTATC ACTAAATTAG AGGGCGCACA
  701 TTTAGATTAC GAAAAAGAAA ACTCAGCAAC ACTTTAATGT GGAGATTGCT
  751 AAATAATGAA ACAATTACAT CCAAATGAAG TAGGTGTATA TGCACTTGGA
  801 GGTCTAGGTG AAATCGGTAA AAATACTTAT GCAGTTGAGT ATAAAGACGA
  851 AATAAGCATT ATCGATGCCG GTATCAAATT CCCTGATGAT AACTTATTAG
  901 GGATTGCATA TGTTATACCT GACTACACAT ATCTAGTTCA AAACCAAGAT
  951 AAAATTGTTG GCCTATTTAT AACACATGGT CACGAAGACC ATATAGGCGG
 1001 TGTGCCCTTC CTATTAAAAC AACTTAATAT ACCTATTTAT GGTGGTCCTT
 1051 TAGCATTAGG TTTAATCCGT AATAAACTTG AAGAAACATC ATTTATTACG
 1101 TACTGCTAAA CTAAATGAAA TCAATGAGGA CAGTGTGATT AAATCTAAGC
 1151 ACTTTACGAT TTCTTTCTAC TTAACTACAC ATAGTATTCC TGAAACTTAT
 1201 GGCGTCATCG TAGATACACC TGAAGGAAAA KTAGTTCATA CCGGTGACTT
 1251 TAAATTTGAT TTTACACCTG TAGGCAAACC AGCAAACATT GCTAAAATGG
 1301 CTCAATTAGG CGAAGAAGGC GTTCTATGTT TACTTTCAGA CTCAACAAAT
 1351 TCACTTGTGC CTGATTTTAC TTTAAGCGAA CGTTGAAGTT GGTCAAAACG
 1401 TTAGATAAGA TCTTCCGTAA TTGTAAAGGT CCGTATTATA TTTGCTACCT
 1451 TCGCTTCTAA TATTTACCGA GTTCAACAAG CAGTTGAAGC TGCTATCAAA
 1501 AATAACCGTA AAATTGTTAC KTTCGGTCCG TTCGATGGGA AACAATATTA
 1551 AAATAGKTAT GGAACTTGGT TATATTAAAG CACCACCTGA AACATTTATT
```

-continued

```
1601 GAACCTAATA AAATTAATAC CGTACCGAAG CATGAGTTAT TGATACTATG

1651 TACTGGTTCA CAAGGTGAAC CAATGGCAGC ATTATCTAGA ATTGCTAATG

1701 GTACTCATAA GCAAATTAAA ATTATACCTG AAGATACCGT TGTATTTAGT

1751 TCATCACCTA TCCCAGGTAA TACAAAAAGT TATTAACAGA ACTATTAATT

1801 CCTTGTATAA AGCTGGTGCA GATGTTATCC ATAGCAAGAT TTCTAACATC

1851 CATACTTCAG GGCATGGTTC TGAAGGGTGA TCAACAATTA ATGCTTCCGA

1901 TTAATCAAGC CGAAATATTT CTTACCTATT CATGGTGAAT ACCGTATGTT

1951 AAAAGCACAT GGTGAGACTG GTGTTGAATG CGSSKTTGAA GAAGATAATG

2001 TCTTCATCTT TGATATTGGA GATGTCTTAG CTTTAACACM CGATTCAGCA

2051 CGTAAAGCTG KTCGCATTCC ATCTGGTAAT GWACTTGTTG ATGGTAGTGG

2101 TATCGGTGAT ATCGGTAATG TTGTAATAAG AGACCGTAAG CTATTATCTG

2151 AAGAAGGTTT AGTTATCGTT GTTGTTAGTA TTGATTTTAA TACAAATAAA

2201 TTACTTTCTG GTCCAGACAT TATTTCTCGA GGATTTGTAT ATATGAGGGA

2251 ATCAGGTCAA TTAATTTATG ATGCACAACG CMAAAWCMAA ACTGATGTTT

2301 ATTAGTWAGT TWAATCCAAA ATAAAGAWAT TCAATGGCAT CAGATTAAAT

2351 CTTCTATCAT TGAAACATTA CAACCTTATT TATTKGAAAA AACAGCTAGR

2401 AAACCAATGA TTTTACCAGT CATTATGGAA GGTAAACGAA CAAAARGAAT

2451 CAAACAATAA ATAATCAAAA AGCTACTAAC TTTCAAGTGA AGTTTTAATT

2501 AAACTCACCC ACCCATTGTT AGTAGCTTTT TCTTTATATA TGATGAGCTT

2551 GAGACATAAA TCAATGTTCA ATGCTCTACA AAGTTATATT GGCAGTAGTT

2601 GACTGAACGA AAATGCGCTT GTWACAWGCT TTTTTCAATT STASTCAGGG

2651 GCCCCWACAT AGAGAATTTC GAAAAGAAAT TCTACAGGCA ATGCGAGTTG

2701 GGGTGTGGGC CCCAACAAAG AGAAATTGGA TTCCCCAATT TCTACAGACA

2751 ATGTAAGTTG GGGTGGGACG ACGGAAATAA ATTTTGAGAA AATATCATTT

2801 CTGTCCCCAC TCCCGATTAT CTCGTCGCAA TATTTTTTTC AAAGCGATTT

2851 AAATCATTAT CCATGTCCCA ATCATGATTA AAATATCACC TATTTCTAAA

2901 TTAATATTTG GATTTGGTGA AATGATGAAC TCTTTGCCTC GTTTAATTGC

2951 AATAATGTTA ATTCCATATT GTGCTCTTAT ATCTAAATCA ATGATAGACT

3001 GCCCCGCCAT CTTTTCAGTT GCTTTCAATT CTACAATAGA ATGCTCGTCT

3051 GCCAACTCAA GATAATCAAG TACACTTGCA CTCGCAACAT TATGCGCNAT

3101 ACGTCTACCC ATATCACGCT CAGGGTGCAC AACCGTATCT GCTCCAATTT

3151 TATTTAAAAT CTTTGCNTGA TAATCATTTT GTGCTCTTAG CAGTTACTTT

3201 TTTTACACCT AACTCTTTTA AAATTAAAGT CGTCAACGTA CTTGNTTGAA

3251 TATTTTCACC AAT
```

Figure 34:
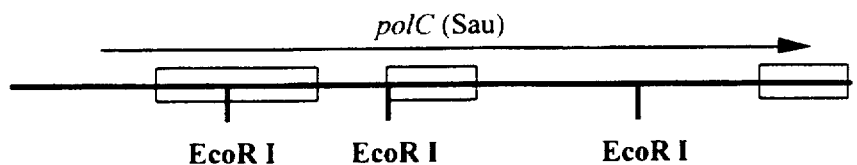

Mutant: NT28
Phenotype: temperature sensitivity
Sequence map: Mutant NT28 is complemented by pMP60, which contains a 4.7 kb insert of *S. aureus* genomic DNA. A partial restriction map is depicted FIG. 34, along with open boxes to indicate the percentage of the clone for which DNA sequence has been obtained. Database searches at both the nucleic acid and peptide levels reveal identity of clone pMP60 at both the nucleic acid and peptide levels to the polc gene, encoding DNA Polymerase III alpha subunit, from *S. aureus* (Genbank Accession No. Z48003; unpublished as of 1995). The relative size and orientation of the complete ORF encoding Pol III is depicted by an arrow in the map.

Figure 35:
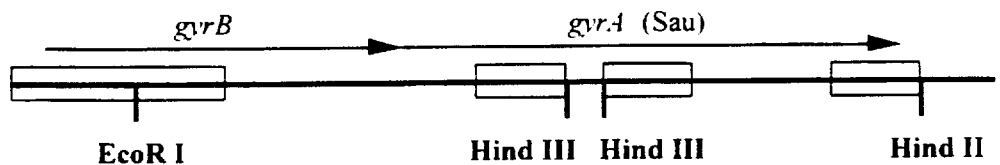

DNA sequence data: The following DNA sequence data was generated by using the standard sequencing primers SP6 and T7, and can be used to demonstrate identity between clone pMP60 and Genbank entry Z48003:

subclone 1022, a 900 bp EcoR I fragment                    SEQ ID NO. 21
1022.sp6 Length: 510 nt
          1 GGGTACCGAG CTCGAATTCG AGGTGTACGG TAGAAATACT TCACCAATGA
         51 TGCACTTACA ATTTTAAATA GATTTTNAAG ACCTTGTTGG TTTTGTACAA
        101 TTAATGTGAC ATGACTAGGT CTTGCACGTT TATATGCATC TNCATTACTG
        151 AGTTTTTTGT TGATTTCGTT ATGATTTAAT ACGCCTAATT CTTTCATTTG
        201 TTGAACCATT TTNATGAAAA TGTAAGCTGT TGCTTCTGTA TCATAAATGG
        251 CACGGTGATG TTGCGTTAAT TCTACGCCAT ATTTTTTAGC CAAGAAATTC
        301 AAACCATGTT TACCATATTC AGTATTAATC GTACGNGATA ATTCTAAAGT
        351 ATCGNTAACA CCATTCGTTG ATGGTCCAAA CCCAAGACGT TCATATCCCG
        401 TATCGATGNN GCCCATATCA AACGGAGCAT TATGCGTTAC GGTTTTCGNA
        451 TCGGCAACCC TTCTTAAACT CTGTAAGNAC TTCTTCATTT CAGGGGATCT
        501 NCTANCATAT subclone 1023, a 1200 bp EcoR I fragment                   SEQ ID NO. 22
1023.sp6 Length: 278 nt
          1 GGGTACCGAG CTCGAATTCT ACACGCTTTT CTTCAGCCTT ATCTTTTTTT
         51 GTCGCTTTTT TAATCTCTTC AATATCAGAC ATCATCATAA CTAAATCTCT
        101 AATAAATGTA TCTCCTTCAA TACGNCCTTG AGCCCTAACC CATTTACCAA
        151 CANTTAGNGC TTTAAAATGT TCTAAATGCT CTTTGTTTTT ACGAGTAAAC
        201 ATTTTTAAAA CTAAAGNGTC CGTATAGTCT GTCACTTTAA TTTCTACGGT
        251 ATGGNGGCCA CTTTTAAGTT CTTTTAAG subclone 1024, a 1400 bp EcoR I fragment                   SEQ ID NO. 23
1024.sp6 Length: 400 nt
          1 GGGTACCGAG CTCGAATTCT GGTACCCCAA ATGTACCTGT TTTACATAAA
         51 ATTTCATCTT CAGTAACACC CAAACTTTCA GGTGTACTAA ATATCTGCAT
        101 AACTNCTTTA TCATCTACAG GTATTGTTTT TGGNTCAATT CCTGATAAAT
        151 CTTGAAGCAT ACGAATCATT GTTGGNTCAT CGTGTCCAAG TATATCANGT
        201 TTTAATACAT TATCATGAAT AGAATGGAAA TCAAAATGTG TCGTCATCCA
        251 TGCTGAATTT TGATCATCGG CAGGATATTG TATCGGCGTA AAATCATAAA
        301 TATCCATGTA ATCAGGTACT ACAATAATAC CCCCTGGNTG CTGTCCAGTT
        351 GTACGTTTAA CACCTGTACA TCCTTTAACG NGTCGATCTA TTTCAGCACC subclone 1025, a 1200 bp EcoR I/ Hind III fragment         SEQ ID NO. 24
1025.sp6 Length: 528 nt
          1 GATCATTTGC ATCCATAGCT TCACTTATTT NTCCAGAAGC TAGCGTACAA
         51 TCATTTAAAT CTACGCCACC TTCTTTATCA ATAGAGATTC TAAGAAAATN
        101 ATCTCTACCC TCTTTGACAT ATTCAACGTC TACAAGTTCA AAATTCAAGT
        151 CTTCCATAAT TGGTTTAACA ATCACTTCTA CTTGTCCTGT AATTTTNCTC
        201 ATACAGGCCT CCCTTTTTGG CAAATAGAAA AGAGCGGGAA TCTCCCACTC
        251 TTCTGCCTGA GTTCACTAAT TTTTAAGCAA CTTAATTATA GCATAAGTTT
        301 ATGCTTGAAA CAAATGACTT CACTATTAAT CAGAGATTCT TGTAAAAGTT
        351 TGTCCCTTTA TTTCACCATT ACATTTGAAT NGNCTCGTNA GNCATTGTAA
        401 AGAGATNCGG GCATAATTTT GTGTCCAGCA TCAATTTTGG TATTTCTTGT
        451 CTTACGGCTT ACGGTTNATT AAATACCTNG GTTTTTTNTC TTTTACCTNT
        501 NATATNTCGN ANGNTGGGNT TTTTCNNG Mutant: NT29
Phenotype: temperature sensitivity
Sequence map: Mutant NT29 is complemented by pMP62, which contains a 5.5 kb insert of *S. aureus* genomic DNA. A partial restriction map is depicted FIG. 35, along with open boxes to indicate the percentage of the clone for which DNA sequence has been obtained. Database searches at both the nucleic acid and peptide levels reveal identity between clone pMP62 and the gyrBA locus of *S. aureus* (Genbank Accession No. M86227; published in Margerrison, E. E., et al. *J. Bacteriology*, 174 (1992) 1596–1603), which encodes DNA gyrase (EC 5.99.1.3). Arrows above the restriction map indicate relative size and position of the ORFs, demonstrating that both gyrB and gyrA genes are fully contained within clone pMP62 and are likely to be expressed.

DNA sequence data: The following DNA sequence data are those obtained from subclones of clone pMP62, using standard sequencing conditions and the primers T7 or SP6. These data can be used to demonstrate identity between the pMP62 clone and Genbank entry M86227.

```
subclone 29.2e.a, a 550 bp EcoR I fragment                    SEQ ID NO. 25
29.2e.a.sp6 LENGTH: 557 nt
              1 CAGCCGACAG TTNACAACCA GCNTCACCGT NAGACAGCAA ACGCCACAAA

51 CTACAAGGNT CCAAATGNCT AGACAATACT GGTGNAAGGC ANGTAATAAT

101 ACGACATTAA CATTTGATGA TCCTGCCATA TCAACAGNTC AGAATAGACA

151 GGATCCAACT GTAACTGTTA CAGATAAAGT AAATGGTTAT TCATTAATTA

201 ACAACGGTAA GATTGGTTTC GTTAACTCAG AATTAAGACG AAGCGATATG

251 TTTGATAAGA ATAACCCTCA AAACTATCAA GCTAAAGGAA ACGTGGCTGC

301 ATTAGGTCGT GTGAATGCAA ATGATTCTAC AGATCATGGT AACTTTAACG

351 GTATTTCAAA AACTGTAAAT GTAAAACCAG NTTCAGAATT AATTATTAAC

401 TTTACTACTA TGCAAACCGG ATAGTNAGCA AGGTGCAACA AATTTAGTTA

451 TTAAAGGATG CTAAGGAANN TACTGNNTTA GCACCTGTAA AATGTTGCTT

501 AGGCTGGTCC TGCACATTTA TTTTAAGGTC CNNCTTGTNC TGNTNGGCTC

551 TNGGGGG 29.2e.a.t7 LENGTH: 527 nt                                     SEQ ID NO. 26
              1 GTCGATCAGC ATCATTGGTA CTTTAAATAA ATGTGCAGTA CCAGTCTTAG

51 CAACATTTAC AGTTGCTAAT TCAGTATTTT CNTTAGCATC TTTAATAACT

101 AANTTTTTNG CACCTTGCNT ACTATTCGTT TGCATAGTAG TAAAGTTAAT

151 AATTAATTCT GANTCTGGTT TTACATTTAC AGTTTTTGAA ATACCGTTAA

201 AGTTACCATG ANCTGTAGNA TCATTTGCNT TCACACGGCC TAATGCAGCC

251 NCGGTTCCTT TAGCTTGATA GTTTTGAGGG GTATTCTTAT CAAACATATC

301 GNTTCGGCTT AATTCTGAGG TAACTGGNAC CNATCTTTAC CNTTGTTAAT

351 TAATGGNTTC CCCTTTACNT TAATCTGTAA CAGTTACAGT TGGGTCCCCG

401 TCTATTCTCA TCTGTTGGTA TGGCAGGGTC ACCACAATGN TAATGTCGGT

451 TTATACTGGN NTCNCCCGNA TTGCTTAGGT TTGGNGCTTG NGGTGTGCGN

501 TTNCTNGCTT CAGGGGNCTG CTGGGTT subclone 29.2h.2a, a 1800 bp Hind III fragment                SEQ ID NO. 27
29.2h.2a.sp6 LENGTH: 578 nt
              1 TGTGAGCTCC CATNACCACC AGTGCGNNCA TTGCCTGGGC TACCGTTTGT

51 CAATTTAAAG TCTTCATCTT TAAAGAAAAT TTCAGTACCA TGTTTTTTAA

101 GTACAACAGT TGCACCTAAA CGATCAACTG CTTCACGATT ACGCTCATAT

151 GTCTGTTCCT CAATAGGAAT ACCACTTAAT CGTTCCCATT CTTTGAGGTG

201 TGGTGTAAAG ATCACACGAC ATGTAGGTAA TTGCGGTTTC AGTTTACTAA

251 AGATTGTAAT CGCATCGCCG TCTACGATTA AATTTTGATG CGGTTGTATA

301 TTTTGTAGTA GGAATGTAAT GGCATTATTT CCTTTGAAAT CAACGCCAAG
```

-continued

```
    351 ACCTGGACCA ATTAGTATAC TGTCAGTCAT TTCAATCATT TTCGTCAACA
    401 TTTTCGTATC ATTAATATCA ATAACCATCG CTTCTGGGCA ACGAGAATGT
    451 AATGCTGAAT GATTTGTTGG ATGTGTAGTA CAGTGATTAA ACCACTACCG
    501 CTAAATACAC ATGCACCGAG CCGCTAACAT AATGGCACCA CCTAAGTTAG
    551 CAGATCGGCC CTCAGGATGA AGTTGCAT
```

29.2h.2a.t7 LENGTH: 534 nt                              SEQ ID NO. 28
```
      1 CGAGCCAGCA GNTTGCAGCG GCGTGTCCCA TAACTAAGGT GGTGCCATTA
     51 TGTNAGCGGC TCGTCCATGT NTATTTGGCG GTAGTGGTTT AATCACTGTA
    101 GCTACACATC CAACAAATCA TTCAGCATTA CATTCTCGTN GCCCAGAAGC
    151 GATGGTTATT GATATTAATG ATACGAAAAT NTTGACGAAA ATNATTGAAA
    201 TGACTGACAG TATACTAATN GGNCCAGGTC TTGGCGTTGA TTTCAAAGGA
    251 AATAATGCCA TTNCATTCCT ACTACAAAAT ATACAACCGC ATCAAAATTT
    301 AANCGTAGAC GGCGNTGCGA TTNCAATCTT TNGTAAACTG NAACCGCAAT
    351 TACCTACATG TNGTGTGNNC TTNACACCAC ACCTCAAAGG NNTGGGNCGG
    401 TTANGTGGTA TTCCNNTTGN GGACAGGCAT ATGGNGCGTA ATCGTGNAGC
    451 AGTTGNTCGT TTAGGNGCAC TNTNGTCCTT AAAAAACATG GTCTGNATNT
    501 CCTTTAANGN NGNNGCTTTA AATTGGCAAT CGGT
``` subclone 29.2he, 2400 bp Hind III, EcoR I fragment      SEQ ID NO. 29
29.2he.1.sp6 LENGTH: 565 nt
```
      1 ACCATTCACA GTGNCATGCA TCATTGCACA CCAAATGNTG TTTGAAGAGG
     51 TGTTTGTTTG TATAAGTTAT TTAAAATGAC ACTAGNCATT TGCATCCTTA
    101 CGCACATCAA TAACGACACG CACACCAGTA CGTAAACTTG TTTCATCACG
    151 TAAATCAGTG ATACCGTCAA TTTTCTTGTC ACGAACGAGC TCTGCAATTT
    201 TTTCAATCAT ACGAGCCTTA TTCACTTGGA AAGGAATTTC AGTGACAACA
    251 ATACGTTGAC GTCCGCCTCC ACGTTCTTCA ATAACTGCAC GAGAACGCAT
    301 TTGAATTGAA CCACGNCCTG TTTCATATGC ACGTCTAATA CCACTCTTAC
    351 CTAAAATAAG TCCNGCAGTT GGGGAATCAG GACCTTCAAT ATCCTCCATT
    401 AACTCAGCAA ATTGNAATNT CAAGGGGTCT TTACTTTAAG GCTNAGNNCA
    451 CCCTTGGTTA ATTCTGTTAA GTTATTGTGG TGGGATATTT CGGTTGCCAT
    501 NCCTNCCNCG GGTACCCNNA TGCACCCNTT GGGTAATNAG GNTTGGGGGT
    551 TTGTGCCCGG TAAGC
```

29.2he.1.t7 Length: 558 nt                              SEQ ID NO. 30
```
      1 CGCAAAACGT CANCAGAANG NACTNCCTAA TGCACTAATG AAGGGCGGTA
     51 TTAAATCGTA CGTTGAGTTA TTGANCGNAA AATAAAGGAA CCTATTCATG
    101 AATGAGCCAA TTTATATTCA TCAATCTAAA GATGATATTG ANGTAGAAAT
    151 TGCNATTCAN TATAACTCAG GATATGCCAC AAATCTTTTA ACTTACGCAA
    201 ATAACATTCA TACGTATGAN GGTGGTACGC ATGANGACGG ATTCAAACGT
    251 GCATTTACGC GTGTCTTAAA TAGTTATGGT TTAAGTAGCA AGATTNTGTA
    301 AGANGGAAAA GNTAGNCTTT CTGGTGAAGN TACACGTGAA GGTATNNCNG
    351 CNNTTNTATC TNTCAAACNT GGGGNTCCNC AATTGGAGG TCAAACGGGG
    401 CAAAAATTTG GGNNTTCTGT AGTGCGTCAN GTTGTNGGTN AATTATTCNN
    451 NGNGNCTTTT TACNGTTTTN CTTTGNAAAT CCNCNAGTCG GNCGTNCNGT
```

-continued

```
501 GGTTTNNAAA AGGGTTTTTT GNGGCACGTG NACGTGTTNT TCGGAAAAAA

551 AGCGGGTT
```

Figure 36:
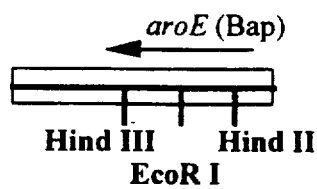

Mutant: NT31
Phenotype: temperature sensitivity
Sequence map: Mutant NT31 is complemented by pMP64, which contains a 1.4 kb insert of *S. aureus* genomic DNA. A partial restriction map is depicted FIG. 36. Database searches at both the nucleic acid and peptide levels reveal strong similarity at the nucleic acid and peptide levels to the aroE gene of *B. aphidicola* (Genbank Accession No. U09230; unpublished as of 1995), which encodes the shikimate-5-dehydrogenase protein (EC 1.1.1.25). Strong similarities also exist at the peptide level to the aroE genes from *E. coli* and *P. aeruginosa*. The size and relative position of the predicted AroE ORF within the pMP64 clone is depicted in the restriction map by an arrow.

DNA sequence data: The following DNA sequence data represents the sequence of clone pMP64, starting with the standard M13 forward and M13 reverse sequencing primers and applying primer walking strategies to complete the sequence contig. The sequences below can be used to design PCR primers for the purpose of amplification from genomic DNA with subsequent DNA sequencing:

```
clone pMP64                                              SEQ ID NO. 31
pMP64 Length: 1508 nt
         1 AGTSGWTCCG TGTGCATAGG TRTGAACTTT GAACCACCAC GTTTAATTTC

51 ATCGTCACAA ATATCTCCAA AACCAAGCTC GTCGATAATC ATCTGTATCA

101 TTGTTAATCT GTGCTGAACG TCTATAAAAT CATGGTGCTT TTTCAATGGA

151 GACATAAAAC TAGGTAAAAA ATAAAATTCA TCTGGCTGTA ATTCATGAAA

201 TACTTCGCTA GCTACTATCA TATGTGCAGT ATGGATAGGG TTAAACTGAC

251 CGCCGTAAAG TACTATCTTT TTCATTATTA TGGCAATTCA ATTTCTTTAT

301 TATCTTTAGA TTCTCTATAA ATCACTATCA TAGATCCAAT CACTTGCACT

351 AATTCACTAT GAGTAGCTTC GCTTAATGTT TCAGCTAATT CTTTTTTATC

401 ATCAAAGTTA TTTTGTAGTA CATGTACTTT AATCAATTCT CTGTTTTCTA

451 ACGTATCATC TATTTGTTTA ATCATATTTT CGTTGATACC GCCTTTTCCA

501 ATTTGAAAAA TCGGATCAAT ATTGTGTGCT AAACTTCTTA AGTATCTTTT

551 TTGTTTGCCA GTAAGCATAT GTTATTCTCC TTTTAATTGT TGTAAAACTG

601 CTGTTTTCAT AGAATTAATA TCAGCATCTT TATTAGTCCA AATTTTAAAG

651 CTTTCCGCAC CCCTGGTAAA CAAACATATC TAAGCCATTA TAAATATGGT

701 TTCCCTTGCG CTCTGCTTCC TCTAAAATAG GTGTTTTATA CGGTATATAA

751 ACAATATCAC TCATTAAAGT ATTGGGAGAA AGATGCTTTA AATTAATAAT

801 ACTTTCGTTA TTTCCAGCCA TACCCGCTGG TGTTGTATTA ATAACGATAT

851 CGAATTCAGC TAAATAACTT TTCAGCATCT GCTAATGAAA TTTGGTTTAT

901 ATTTAAATTC CAAGATTCAA AACGAGCCAT CGTTCTATTC GCAACAGTTA

951 ATTTGGGCTT TACAAATTTT GCTAATTCAT AAGCAATACC TTTACTTGCA

1001 CCACCTGCGC CCAAAATTAA AATGTATGCA TTTTCTAAAT CTGGATAAAC

1051 GCTGTGCAAT CCTTTAACAT AACCAATACC ATCTGTATTA TACCCTATCC

1101 ACTTGCCATC TTTTATCAAA ACAGTGTTAA CTGCACCTGC ATTAATCGCT

1151 TGTTCATCAA CATAATCTAA ATACGGTATG ATACGTTCTT TATGAGGAAT

1201 TGTGATATTA AAGCCTTCTA ATTCTTTTTT CGAAATAATT TCTTTAATTA

1251 AATGAAAATC TTCAATTGGA ATATTTAAAG CTTCATAAGT ATCATCTAAT

1301 CCTAAAGAAT TAAAATTTGC TCTATGCATA ACGGGCGACA AGGAATGTGA

1351 AATAGGATTT CCTATAACTG CAAATTTCAT TTTTTTAATC ACCTTATAAA
```

-continued

```
1401 ATAGAATTTC TTAATACAAC ATCAACATTT TTAGGAACAC GAACGATTAC

1451 TTTAGCCCCT GGTCCTATAG TTATAAAGCC TAGACCAGAG ATCGACCTGC

1501 AGGCAGCA
```

Figure 37:
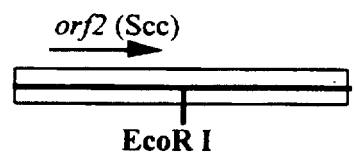

Mutant: NT33a
Phenotype: temperature sensitivity
Sequence map: Mutant NT33a is complemented by pMP67, which contains a 1.8 kb insert of S. aureus genomic DNA. A partial restriction map is depicted FIG. 37. Database searches at both the nucleic acid and peptide levels reveal strong peptide-level similarities to ORFs of unknown function in Synechoccocus sp. (identified as "orf2" in Genbank Accession No. L19521), M. tuberculosis (Genbank Accession No. U00024) and E. coli (Genbank Accession No. M86305).

DNA sequence data: The following DNA sequence data represents the sequence of clone pMP59, starting with the standard M13 forward and M13 reverse sequencing primers and applying primer walking strategies to complete the sequence contig. The sequences below can be used to design PCR primers for the purpose of amplification from genomic DNA with subsequent DNA sequencing:

clone pMP67
pMP67 Length: 1810 nt

SEQ ID NO. 32

```
   1 CGCGTCTTCC AAATTTCNAA AGCTGTAAAA AGTTATTAAA TCAAATCTTG

51 CGAATTTGGA TNTAGAGGCA CAATCTGANG TTTATAAAAN TAATGCAGAT

101 AGAGCTTTAA AAGCNTTGTC AAAACGTGAT ATTCAATTTG ATNTCATTTT

151 CTTAGATCCA CCTTATAATA AAGGTCTCAT TGATAAAGCT TTAAAACTAA

201 TTTCAGAGTT TAATTTATTG AAAGAAAATG GTATCATCGT TTGTGAATTT

251 AGCAATCATG AAGAAATAGA TTATCAACCG TTTAATATGA TTAAACGTTA

301 CCATTATGGG TTGACAGACA CATTGTTATT AGAAAAGGGA GAATAGCATG

351 GAACATACAA TAGCGGTCAT TCCGGGTAGT TTTGACCCCA TTACTTATGG

401 TCATTTAGAC ATTATTGAGA GAAGTACAGA TAGATTTGAT GAAATTCATG

451 TCTGTGTTCT TAAAAATAGT AAAAAAGAAG GTACGTTTAG TTTAAAAGAG

501 CGTATGGATT TAATTGAACA ATCTGTTAAA CATTTACCTA ATGTCAAGGT

551 TCATCAATTT AGTGGTTTAC TAGTCGATTA TTGTGAACAA GTAGGAGCTA

601 AAACAATCAT ACGTGGTTTA AGAGCAGTCA GTGATTTTGA ATATGAATTA

651 CGCTTAACTT CMATGAATAA AAAGTTGAAC AATGAAATTG AAACGTTATA

701 TATGATGTCT AGTACTAATT ATTCATTTAT AAGTTCAAGT ATTGTTAAAG

751 AAGTTGCAGC TTATCGAGCA GATATTTCTG AATTCGTTCC ACCTTATGTT

801 GAAAAGGCAT TGAAGAAGAA ATTTAAGTAA TAAAAATAAC AGTATTTTAG

851 GTTTATCATG GTTTACAATC CTAAAATACT GTTTTCATTT GTTAACGATA

901 TTGCTGTATG ACAGGCGTGT TGAAATCTGT TTGTTGTTGC CCGGTTATTG

951 CATTGTATAT GTGTGTTGCT TTGATTTCAT TTGTGAAGTA ATGTGCATTG

1001 CTTTTGTTAA TATGGGTTAT ATATTGTCTT TCTGGGAACG CTGTTTTTAA

1051 ATGCTTTAAA TATTGTCTGC CACGGTCGTT CATCGCTAAT ACTTTAACTG

1101 CGTGAATGTT ACTCGTAACA TCTGTAGGTT TAATGTTTAA TAATACATTC

1151 ATTAACAGTC TTTGGATATG CGTATATGTA TAACGCTTTG TTTTTAGTAA

1201 TTTTACAAAA TGATGAAAAT CAGTTGCTTC ATAAATGTTA GATTTCAAAC

1251 GATTTTCAAA ACCTTCAGTA ACAGTATAAA TATTTTTTAA TGAATCTGTA

1301 GTCATAGCTA TGATTTGATA TTTCAAATAT GGAAATATTT GATTTAATGT

1351 WATATGAGGT GTTACGTACA AGTGTTGAAT ATCTTTAGGT ACCACATGAT
```

-continued

```
1401 GCCAATGATC ATCTTGACTA ATGATTGATG TTCTAATAGA TGTACCACTT

1451 SCAAACTGAT GGTGTTGAAT TAATGAATCA TGATGTTGAG CATTTTCTCG

1501 TTTGATAGAA ATTGCATTGA TGTTTTTAGC ATTTTTAGCA ATTGCTTTCA

1551 GGTAACTAAT ACCAAGTATG TTGTTAGGAC TTGCTAGTGC TTCATGATGC

1601 TCTAATAATT CGCTAATGAT ACGAGGGTAG CTTTTACCTT CTTTTACTTT

1651 TNGTGAAAAG GATTCAGATN GTTCAATTTC ATTAATNCTG NGTGCTAATT

1701 GCTTTAANGT TTNGATATCA TTATTTTCAC TACCAAATGC AATGGTATCG

1751 ACACTCATAT AATCNGCGAC TTNAACGGCT AGTTCGGCCA AGGGATCGAC

1801 CGGCAGGCAG
```

Figure 38:
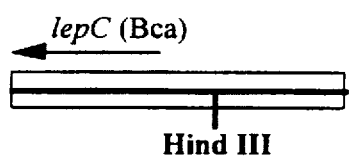

Mutant: NT33b
Phenotype: temperature sensitivity
Sequence map: Mutant NT33b is complemented by pMP636, which contains a 1.8 kb insert of *S. aureus* genomic DNA. A partial restriction map is depicted FIG. 38. Database searches at both the nucleic acid and peptide levels reveal strong peptide-level similarities to the lepC gene product, encoding signal peptidase I (EC 3.4.99.36) from *B. caldolyticus* (abbreviated as "Bca" in the sequence map).

DNA sequence data: The following DNA sequence data represents the sequence of clone pMP636, starting with the standard M13 forward and M13 reverse sequencing primers and applying primer walking strategies to complete the sequence contig. The sequences below can be used to design PCR primers for the purpose of amplification from genomic DNA with subsequent DNA sequencing:

clone pPMP636  SEQ ID NO. 33
pMP636 Length: 1876 nt

```
   1 TCTGAATGAT CTARACGGAT TAAATTATTT AGCTGGTAAA ACAATCGACG

51 AAGTTAACAC AAAAGCATTC GAAGGTACAT TATTAGCGCA TACTGATGGT

101 GGTGTTCCTA ACATGGTAGT GAACATTCCA CAATTAGATG AAGAAACTTT

151 CGGTTACGTC GTATACTTCT TCGAACTTGC TTGTGCAATG AGTGGATACC

201 AATTAGGCGT AAATCCATTT AACCAACCTG GTGTAGAAGC ATATAAACAA

251 AACATGTTCG CATTATTAGG TAAACCTGGT TTTGAAGACT TGAAAAAAGA

301 ATTAGAAGAA CGTTTATAAA ATACATTACT TCAAAGATTA GTGAAGTTTG

351 AAAAGATAGA ACTAGACGTT AACTATTTAA AGCATATTTT CGAGGTTGTC

401 ATTACAAATG TAAAAATGTA ATGACAACCT CGTTTTTATT TATATGCAAG

451 AACTAGGTTA CTAGCTAATG TGACAAGATG TTWAGAGAAA ATTAAAGATA

501 AAATAATATC TGCCTTACAA TAATATTGTT ATACTACTAG AGACTGATTT

551 ATTAGCATGA TTACATGTTA ATGTTTCTTT ACTTAGTAAT TAACTTTRTA

601 ATGTAARAHT AATTATCTTC ADCCAHAGAA AGGGATTGAT GATTTGTCGT

651 WTCMTCAATT AGAAGAATGG TTTGAGATAT KTCGACAGTT TGGTWTTTA

701 CCTGGATTTA TATTGTTATA TATTAGAGCT NTAATTCCAG TATTTCCTTT

751 ARCACTCTAT ATTTAATTA ACATTCAAGC TTATGGACCT ATTTTAGGTA

801 TATTGATTAG TTGGCTTGGA TTAAATTTCTG GAACATTTAC AGTCTATTTG

851 ATCTGTAAAC GATTGGTGAA CACTGAGAGG ATGCAGCGAA TTAAACAACG

901 TACTGCTGTT CAACGCTTGA TTAGTTTTAT TGATCGCCAA GGATTAATCC

951 CATTGTTTAT TTTACTTTGT TTTCCTTTTA CGCCAAATAC ATTAATAAAT

1001 TTTGTAGCGA GTCTATCTCA TATTAGACCT AAATATTATT TCATTGTTTT

1051 GGCATCATCA AAGTTAGTTT CAACAATTAT TTTAGGTTAT TTAGGTAAGG
```

-continued

```
1101 AAATTACTAC AATTTTAACG CATCCTTTAA GARGGATATT AATGTTAGTT

1151 GGTGTTGGTT GTATTTTGGA TTGTTGGAAA AAAGTTAGAA CAGCATTTTA

1201 TGGGATCGAA AAAGGAGTGA CATCGTGAAA AAAGTTGTAA AATATTTGAT

1251 TTCATTGATA CTTGCTATTA TCATTGTACT GTTCGTACAA ACTTTTGTAA

1301 TAGTTGGTCA TGTCATTCCG AATAATGATA TGYMCCCAAC CCTTAACAAA

1351 GGGGATCGTG TTATTGTWAA TAAAATTAAA GTAACATTTA ATCAATTGAA

1401 TAATGGTGAT ATCATAACAT ATAGGCGTGG TAACGGAGAT ATATACTAGT

1451 CGAATTATTG CCAAACCTGG TCAATCAATG GCGTTTCGTC AGGGACAATT

1501 ATACCGTGAT GACCGACCGG TTGACGCATC TTATGCCAAG AACAGAAAAA

1551 TTAAAGATTT TAGTTTGCGC AATTTTAAAG AATTAGGATG GTGATATTAT

1601 TCCGCCAAAC AATTTTGTTG TGCTAAATGA TCAAGATAAT AACAAGCACG

1651 ATTCAAGACA ATTTGGTTTA ATCGATAAAA AGGATATTAT TGGTAATGTT

1701 AGTTTACGAT ACTATCCTTT TTCAAAATGG ACTGTTCAGT TCAAATCTTA

1751 AAAAGAGGTG TCAAAATTGA AAAAAGAAAT ATTGGAATGG ATTATTTCAA

1801 TTGCAGTCGC TTTTGTCATT TTATTTATAG TAGGTAAATT TATTGTTACG

1851 CCATATACAA TTAAAGGTGA ATCAAT
```

Figure 39:
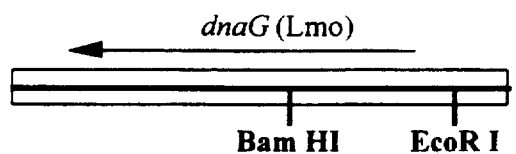
Figure 40:
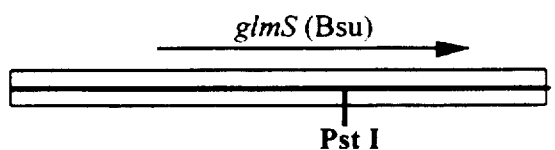

Mutant: NT36
Phenotype: temperature sensitivity
Sequence map: Mutant NT36 is complemented by pMP109, which contains a 2.7 kb insert of S. aureus genomic DNA. A partial restriction map is depicted FIG. 39. Database searches at both the nucleic acid and peptide levels reveal identity at one end of the pMP109 clone to the plaC gene from S. aureus (Genbank Accession No. M63177), encoding a DNA-directed RNA polymerase (EC 2.7.7.6). Since clone pMP109 does not contain the entire plaC ORF, the complementation of mutant NT36 by clone pMP109 is not likely to be due to the presence of this gene. Further analysis of clone pMP109 reveals strong similarity at the peptide level to the dnaG gene of L. monocytogenes (Genbank Accession No. U13165; published in Lupski et al., 1994, Gene 151:161–166), encoding DNA primase (EC 2.7.7. -); these similarities also extend to the dnaG genes of L. lactis, B. subtilis, and E. coli. The relative size and location of the dnaG ORF within clone pMP109 is denoted by an arrow in the sequence map.

DNA sequence data: The following DNA sequence data represents the sequence of clone pMP109, starting with the standard M13 forward and M13 reverse sequencing primers and applying primer walking strategies to complete the sequence contig. The sequences below can be used to design PCR primers for the purpose of amplification from genomic DNA with subsequent DNA sequencing:

```
clone pMP109                                              SEQ ID NO. 34
pMP109 Length: 2687 nt
          1 TATGATGATG GTAAAGATCC TAAAGGATTA CCTAAAGCTG ATATTGTTTT

51 ACTTGGTATT TCGAGAACTT CAAAGACACC ATTATCTCAG TATTTAGCGC

101 ATAAGAGTTA CAAAGTTATG AATGTACCGA TTGTACCAGA AGTGACACCG

151 CCAGATGGCT TATATGATAT TAATCCAAAG AAATGTATCG CACTTAAAAT

201 AAGTGAAGAA AAATTAAATC GCATTAGAAA AGAGCGACTA AAACAATTAG

251 GACTAGGTGA CACAGCTCGA TATGCAACAG AAGCACGAAT TCAAGAAGAA

301 TTGAATTACT TTGAAGAAAT CGTAAGTGAA ATTGGATGTC CTGTCATTGA

351 TGTTTCTCAA AAAGCAATCG AAGAAACAGC AAACGATATA ATCCATTATA

401 TTGAACAAAA TAAATCGAAA TGATTTCATT TTTGTCGAAA ATTAGGTATA

451 ATAGTATAAC TAATGCTTAA TAGGTGATTT AATTTGCGAA TAGATCAATC

501 GATCATTAAT GAAATAAAAG ATAAAACCGA CATTTTAGAC TTGGTAAGTG

551 AATATGTWAA ATTAGAAAAG AGAGGACGCA ATTATATAGG TTTGTGTCCT
```

-continued

```
 601 TTTCATGATG AAAAGACACC TTCATTTACA GTTTCTGAAG ATAAACAAAT
 651 TTGTCATTGT TTTGGTTGTA AAAAGGTGG CAATGTTTTC CAATTTACTC
 701 AAGAAATTAA AGACATATTC ATTTGTTGAM GCGGTTAAAG AATTAGGTGG
 751 WTAGRGTTAA TGTTTGCTGT AGRTATTGAG GCAMCACAAT CTTWACTCAA
 801 ATGTYCAAAT TSCTTCTSRY GRTTTACAAA TGATTGACAW TGCATGGRGT
 851 TAWTACAAGR ATTTTATTAT TACGCTTTAA CAAAGACAGT CGAAGGCGAA
 901 CAAGCATTAA CGTACTTACA AGAACGTGGT TTTACAGATG CGCTTATTAA
 951 AGAGCGAGGC ATTGGCTTTG CACCCGATAG CTCACATTTT TGTCATGATT
1001 TTCTTCAAAA AAAGGGTTAC GATATTGAAT TAGCATATGA AGCCGGATTA
1051 TWATCACGTA ACGAAGAAAA TTTCAGTTAT TTACGATAGA TTYCGAAAYC
1101 GTATTATGTT YCCTTTGAAA AATGCGCAAG GAAGAATTGT TGGATATTCA
1151 GGTCGAACAT ATACCGGTCA AGAACCAAAA TACTTAAATA GTCCTGAAAC
1201 ACCTATCTTT CAAAAAAGAA AGTTGTTATA CAACTTAGAT AAAGCGCGTA
1251 AATCAATTAG AAAATTAGAT GAAATCGTAT TACTAGAAGG TTTTATGGAT
1301 GTTATAAAAT CTGATACTGC TGGCTTGAAA AACGTTGTTG CAACAATGGG
1351 TACACAGTTG TCAGATGAAC ATATTACTTT TATACGAAAG TTAACATCAA
1401 ATATAACATT AATGTTTGAT GGGGATTTTG CGGGTAGTGA AGCAACACTT
1451 AAAACAGGTY CAAAATTTGT TACAGCAAGG GCTAAATGTR TTTKTTATAC
1501 AATTGCCATC AGGCATGGAT CCGGATGAAT ACATTGGTAA GTATGGCAAC
1551 GATGCATTTM CTGCTTTTST AAAAAATGAC AAAAAGTCAT TTSCACATTA
1601 TAAAGTGAGT ATATTAAAAG ATGAAATTGC ACATAATGAC CTTTCATATG
1651 AACGTTATTT GAAAGAMCTA AGTCATGATA TTTCGCTTAT GAAATCATCG
1701 ATTTTGCAAC AAAAGGCTTT AAATGATGTT GCACCATTTT TCAATGTTAG
1751 TCCTGAGCAA TTAGCTAACG AAATACAATT CAATCAAGCA CCAGCCAATT
1801 ATTATCCAGA AGATGAGTAT GGCGGTTACA TTGAACCTGA GCCAATTGGT
1851 ATGGCACAAT TTGACAATTT GAGCCGTCAA GAAAAAGCGG AGCGAGCATT
1901 TTTAAAACAT TTAATGAGAG ATAAAGATAC ATTTTTAAAT TATTATGAAA
1951 GTGTTGATAA GGATAACTTC ACAAATCAGC ATTTAAATA TGTATTCGAA
2001 GTCTTACATG ATTTTTATGC GGAAAATGAT CAATATAATA TCAGTGATGC
2051 TGTGCAGTAT GTTAATTCAA ATGAGTTGAG AGAAACACTA ATTAGCTTAG
2101 AACAATATAA TTTGAATGAC GAACCATATG AAAATGAAAT TGATGATTAT
2151 GTCAATGTTA TTAATGAAAA AGGACAAGAA ACAATTGAGT CATTGAATCA
2201 TAAATTAAGG GAAGCTACAA GGATTGGCGA TGTAGAATTA CAAAAATACT
2251 ATTTACAGCA AATTGTTGCT AAGAATAAAG AACGCATGTA GCATGTGATT
2301 TTAAAGAATA ATACGAATAA TGATTATGTC AAAATGTATA AGGGTAAATG
2351 ATAGTTACCG CATTTAAACA ACACTATTGA AAAATAAATA TTGGGATTAG
2401 TTCCAATTTG TAAAATAAAA TTAAAAATAT GGATGAATTA ATTAAGAATT
2451 TAGTTTAAAA TAGCAATATT GAATAAATTT CGAATGTTCA TATTTAAAAT
2501 CGGGAGGCCG TTTCATGTCT GATAACACAG TTAAAATTAA AAAACAAACA
2551 ATTGATCCGA CATTAACATT AGAAGATGTT AAGAAGCAAT TAATTGAAAA
```

```
2601 AGGTAAAAAA GAGGGTCATT TAAGTCATGA AAAAATTGCT GAAAAACTTC

2651 AGAATTTTGA TATCGACTCT GATCAAATGG ATGATTT
```

Mutant: NT37
Phenotype: temperature sensitivity
Sequence map: Mutant NT37 is complemented by pMP72, which contains a 2.8 kb insert of *S. aureus* genomic DNA. A partial restriction map is depicted 40. Database searches at both the nucleic acid and peptide levels reveal a strong similarity at the peptide level to the glmS gene of *B. subtilis* (Genbank Accession No. U21932; published in Morohoshi, F. et al. *J. Bacteriol.* 175 (1993) 6010–6017), which encodes the protein L-glutamine-D-fructose-6-phosphate amidotransferase (EC 2.6.1.16). The relative location and predicted size of this ORF is designated by an arrow in the sequence map.

DNA sequence data: The following DNA sequence data represents the sequence of clone pMP72, starting with the standard M13 forward and M13 reverse sequencing primers and applying primer walking strategies to complete the sequence contig. The sequences below can be used to design PCR primers for the purpose of amplification from genomic DNA with subsequent DNA sequencing:

```
clone pMP72                                                  SEQ ID NO. 35
pMP72 Length: 2800 nt
         1 NTNAATTAAC ATGCGAGGNC ACCCCTTTAT TGCTACTCCA TACTTCTCAT

51 AAAATCATAT TAACATAACA CCCTTAATTG TCAGACTATT NAAATAAATA

101 AAACACTTCA TTTTTACGCA TTTCTGCCAA ATTAAGATGA AGTAAAAGCT

151 AAGTCGACCT AAAAAAGCAC CCTTCTAGTC GATTAATCTA AAAGGGGTGC

201 CATATACTTT AATTTTAATA CATGATTGAT TCTAAAAAAG TGAATTATTC

251 CACAGTAACT GATTTAGCAA GGTTACGTGG TTTATCAACA TCTAAATCTC

301 TGTGTAATGC TGCATAGTAT GAAATTAATT GTAATGCAAC CACTGATACT

351 AATGGCGTTA ACAATTCATG TACATGAGGA ATGACATAAG TGTCGCCTTC

401 TTTTTCAAGA CCCTCCATAG AAATAATACA TGGATGTGCA CCACGTGCTA

451 CTACCTCTTT AACGTTACCA CGAATTGATA AATTAACTTT CTCTTGTGTT

501 GCTAAACCTA CAACTGGTGT ACCTTCTTCG ATTAAGGCAA TTGTACCATG

551 TTTAAGTTCT CCACCAGCAA AACCTTCTGC TTGAATGTAA GAAATTTCTT

601 TAAGTTTTAA CGCACCTTCT AAACTTACGT TATAGTCAAT AGTACGTCCG

651 ATAAANAATG CATTGCGTGT TGTTTCTAAG AAATCTGTAG CAATTTGTTC

701 CATAATTGGT GCATCGTCAA CAATTGCTTC TATTGCTGTT GTTACTTTTG

751 CTAATTCTCT CAATAAATCA ATATCTGCTT CACGACCATG CTCTTTTGCA

801 ACGATTTGAG ACAAGAWTGA TAATACTGCA ATTTGTGCAG WATAWGCTTT

851 TGTAGATGCA ACTGCGAWTT CAGGGACCCG CGTGTAATAA CAATGTGTGG

901 TCTGCTTCAC GTTGATAAAG TTGAACCTGC AACATTAGTG ATTGTTAATG

951 AWTTATGAMC TAATTTATTA GTTWCAACTA AATACGGCGC GGCTATCTGG

1001 CAGTTTCACC TGATTGAGAA ATATAAACGA ACAATGGTTT TTAAGATAAT

1051 AATGGCATGT TGTAGACAAA CTCTGATGCA ACGTGTACTT CAGTTGGTAC

1101 GCCAGCCCAT TTTTCTAAAA ATTCTTTACC TACTAAACCT GCATGGTAGC

1151 TTGTACCTGC TGCAATAACG TAAATGCGGT CTGCTTCTTT AACATCATTG

1201 ATGATGTCTT GATCAATTTT CAAGTTACCT TCTGCATCTT GATATTCTTG

1251 AATAATACGA CGCATTACTG CTGGTTGTTC ATGALTTTCT TTTAACATGT

1301 AGTGTGCATA AACACCTTTT TCAGCATCTG ATGCATCAAT TTCAGCAATA

1351 TATGAATCAC GTTCTACAAC GTTTCCATCT GCATCTTTAA TAATAACTTC
```

```
-continued
1401 ATCTTTTTTA ACAATAACGA TTTCATGGTC ATGGRTTTCT TTATATTCGC

1451 TTGTCACTTG TAACATTGCA AGTGCGTCTG ATGCGATAAC ATTGAAACCT

1501 TCACCAACAC CTAATAATAA TGGTGATTTA TTTTTAGCAA CATAGATTGT

1551 GCCTTTGHCT TCAGCATCTA ATAAACCTAA TGCATATGAA CCATGTAATA

1601 ATGACACAAC TTTTGTAAAT GCTTCTTCAG TTGAAAGTCC TTGATTTGAA

1651 AAGTATTCAA CTAATTGAAC GATAACTTCT GTATCTGTTT CTGAAATGAA

1701 TGATACACCT TGTAAGTATT CACCTTTTAA CTCTTCATAG TTTTCAATAA

1751 CACCGTTATG AACTAGAGTA AAACGGCCAT TTGATGATTG ATGTGGATGA

1801 GAGTTTTCAT GATTCGGTAC ACCGTGTGTT GCCCAACGTG TGTGACCGAT

1851 TCCAACAGGT CCATTCAAAA TCGCTACTAT CAGCAACTTT ACGTAATTCT

1901 GCAATACGAC CTTTTTCTTT AAATACAGTT GTATTATCAT YATTTACTAC

1951 TGCGATACCT GCAGAGTCAT AACCTCTGTA TTCTAATTTT TCTACAACCT

2001 TTTAATAATA ATTTCTTTGG CATTATCATA GCCAATATAA CCAACAATTC

2051 CACACATAAC GACATTTTCC TCCATATTGG AATAGTACGS GTAAATTATG

2101 ATTTATTGCC GATAATTTAG ATTGACAATC TGCTTTCATA ATATAAATAG

2151 GAACATGCTA TCATCGCATT CATCCATAAC AAATTAAGCA TAGTTATTTT

2201 TACAACTATA CAAATTGCTC ACACTGTACT TTCCATATTA ATATTTTTTA

2251 TATTCAATTT CTGGCGATCT TATTAACTTT GTCCATTAAG TCACCCTAAT

2301 GTTTTACTTA ATAAGCTAAC GAATGAGCCA CATCCGGGAT AGCATCCGCC

2351 GATCTATTCG ATCACTATCC TCTTCGTCTA CAAATACATA TATTGCACTC

2401 TATAAAGGCC ACTCATATAT TAACCTTTAA TCTTCAAATA CAAATATTTA

2451 TTTGCACAGG CGCTTTAACT GTACTGCCGA ACTTTCCCCC TTTCCATTAA

2501 TCATTATTGT ACAACGGTGT TGTTTTGTTT TGCAAATATT TTCACAATAA

2551 AATTTTAAAA ATCCTAAAAC AATTTTTTTG TTTTACTTTT TCAAAATATC

2601 TATACTGTCA CATTGATGAC ACTTTATTTA ATTTTGTCAC ATTTATTTTG

2651 ACAAAGTTGA TTTTTGTTTA TATTGAGTAA CAAGTAACCT CTCTATACAC

2701 TATATATAGT CACATATATT AAAAAAGAGG TGTAAACATG TCACAAACTG

2751 AAGAAAAAAA AGGAATTGGT CGTCGTGTTC AAGCATTTGG ATCGACCGCA
```

Mutant: NT41/64
Phenotype: temperature sensitivity
Sequence map: Mutants NT41 and NT64 are complemented by pMP98, which contains a 2.9 kb insert of *S. aureus* genomic DNA. A partial restriction map is depicted FIG. 41. Database searches at both the nucleic acid and peptide levels reveal identity at both the peptide and nucleic acid levels to the C-terminal fragment of the pcrA gene from *S. aureus* (Genbank Accession No. M63176; published in Iordanescu, S. M. et al. *J. Bacteriol.* 171 (1989) 4501–4503), encoding DNA helicase (EC 3.6.1. -). Since only a small portion of the C-terminal fragment of the helicase protein is contained within clone pMP98, the pcrA gene is unlikely to be responsible for restoring a wild-type phenotype to mutants NT41 and 64. Further analysis reveals strong peptide level similarity to the lig gene of *E. coli*(Genbank Accession No. M30255; published in Ishino, y. et al., *Mol. Gen. Genet.* 204 (1986) 1–7), encoding the protein DNA ligase (EC 6.5.1.2). The relative location and predicted size of the ORF encoding the putative *S. aureus* lig gene is depicted by an arrow in the sequence map.

DNA sequence data: The following DNA sequence data represents the sequence of clone pMP98, starting with the standard M13 forward and M13 reverse sequencing primers and applying primer walking strategies to complete the sequence contig. The sequences below can be used to design PCR primers for the purpose of amplification from genomic DNA with subsequent DNA sequencing:

clone pMP98  
pMP98 Length: 2934 nt

SEQ ID NO. 36

```
   1 CATGAAATGC AAGAAGAACG TCGTATTTGT TATGTAGCAA TTACAAGGGC
  51 TGAAGAGGTG TTATATATCA CTCATGCGAC ATCAAGAATG TTATTTGGTC
 101 GCCCTCAGTC AAATAAGCCA TCCAGATTTT TAAAGGAAAT TCCAGAATCA
 151 CTATTAGAAA ATCATTAACA TGGCAAACGA CAAACGATAC AACCTAAGGC
 201 AAAACCTTTT GCTAAACGGT GATTTAGTCA ACGAACAACG TCAACGAAAA
 251 AACAAGTATT GTCATCTGAT TGGAATAAGC GTGACAAAGT GATGCATAAA
 301 GCCTGGGGAG AAGGCATGGT GAGTAATGCC AACGAGAAAA ATGGCTCAAT
 351 CGAACTAGAT ATTATCTTTA AATCACAAGG GCCAAAACGT TTGTTAGCGC
 401 AATTTGCACC AATTGAAAAA AAGGAGGATT AAGGGATGGC TGATTTATCG
 451 TCTCGTGTGA ACGRDTTACA TGATTTATTA AATCAATACA GTTATGAATA
 501 CTATGTAGAG GATAATCCAT CTGTACCAGA TAGTGAATAT GACAAATTAC
 551 TTCATGAACT GATTAAAATA GAAGAGGAGC ATCCTGAGTA TAAGACTGTA
 601 GATTCTCCAA CAGTTAGAGT TGGCGGTGAA GCCCAAGCCT CTTTCAATAA
 651 AGTCAACCAT GACACGCCAA TGTTAAGTTT AGGGAATGCA TTTAATGAGG
 701 ATGATTTGAG AAAATTCGAC CAACGGATAC GTGAACAAAT TGGCAACGTT
 751 GAATATATGT GCGAATTAAA AATTGATGGC TTAGCAGTAT CATTGAAATA
 801 TGTTGATGGA TACTTCGTTC AAGGTTTAAC ACGTGGTGAT GGAACAACAG
 851 GTTGAAGATA TTACCGRAAA TTTAAAAACA ATTCATGCGA TACCTTTGAA
 901 AATGAAAGAA CCATTAAATG TAGAAKTYCG TGGTGAAGCA TATATGCCGA
 951 GACGTTCATT TTTACGATTA AATGAAGAAA AGAAAAAAAA TGATGAGCAG
1001 TTATTTGCAA ATCCAAGAAA CGCTGCTGCG GGATCATTAA GACAGTTAGA
1051 TTCTAAATTA ACGGCAAAAC GAAAGCTAAG CGTATTTATA TATAGTGTCA
1101 ATGATTTCAC TGATTTCAAT GCGCGTTCGC AAAGTGAAGC ATTAGATGAG
1151 TTAGATAAAT TAGGTTTTAC AACGAATAAA AATAGAGCGC GTGTAAATAA
1201 TATCGATGGT GTTTTAGAGT ATATTGAAAA ATGGACAAGC CAAAGAAGAG
1251 TTCATTACCT TATGATATTG ATGGGATTGT TATTAAGGTT AATGATTTAG
1301 ATCAACAGGA TGAGATGGGA TTCACACAAA AATCTCCTAG ATGGGCCATT
1351 GCTTATAAAT TTCCAGCTGA GGAAGTAGTA ACTAAATTAT TAGATATTGA
1401 ATTAAGTATT GGACGAACAG GTGTAGTCAC ACCTACTGCT ATTTTAGAAC
1451 CAGTAAAAGT AGCTGGTACA ACTGTATCAA GAGCATCTTT GCACAATGAG
1501 GATTTAATTC ATGACAGAGA TATTCGAATT GGTGATAGTG TTGTAGTGAA
1551 AAAAGCAGGT GACATCATAC CTGAAGTTGT ACGTAGTATT CCAGAACGTA
1601 GACCTGAGGA TGCTGTCACA TATCATATGC AACCCATTG TCCAAGTTGT
1651 GGACATGAAT TAGTACGTAT TGAAGGCGAA GTTAGCACTT CGTTGCATTA
1701 ATCCAAAATG CCAAGCACAA CTTGTTGAAG GATTGATTCA CTTTGTATCA
1751 AGACAAGCCA TGAATATTGA TGGTTTAGGC ACTAAAATTA TTCAACAGCT
1801 TTATCAAAGC GAATTAATTA AGATGTTGC TGATATTTTC TATTTAACAG
1851 AAGAAGATTT ATTACCTTTA GACAGAATGG GGCAGAAAAA AGTTGATAAT
1901 TTATTAGCTG CCATTCAACA AGCTAAGGAC AACTCTTTAG AAAATTTATT
1951 ATTTGGTCTA GGTATTAGGC ATTTAGGTGT TAAAGCGAGC CAAGTGTKAG
```

-continued

```
2001 CAGAAAAATA TGAAACGATA GATCGATTAC TAACGGTAAC TGAAGCGGAA

2051 TTAGTAGAAT TCATGATATA GGTGATAAAG TAGCGCAATC TGTAGTTACT

2101 TATTTAGCAA ATGAAGATAT TCGTGCTTTA ATTCCATAGG ATTAAAAGAT

2151 AAACATGTTA ATATGATTTA TGAAGGTATC CAAAACATCA GATATTGAAG

2201 GACATCCTGA ATTTAGTGGT AAAACGATAG TACTGACTGG TAAGCTACAT

2251 CCAAATGACA CGCAATGAAG CATCTAAATG GCTTGCATCA CCAAGGTGCT

2301 AAAGTTACAA GTAGCGTTAC TAAAAATACA GATGTCGTTA TTGCTGGTGA

2351 AGATGCAGGT TCAAAATTAA CAAAAGCACA AAGTTTAGGT ATTGAAATTT

2401 GGACAGAGCA ACAATTTGTA GATAAGCAAA ATGAATTAAA TAGTTAGAGG

2451 GGTATGTCGA TGAAGCGTAC ATTAGTATTA TTGATTACAG CTATCTTTAT

2501 ACTCGCTGCT TGTGGTAACC ATAAGGATGA CCAGGCTGGA AAAGATAATC

2551 AAAAACATAA CAATAGTTCA AATCAAGTAA AAGAAATTGC AACGGATAAA

2601 AATGTACAAG GTGATAACTA TCGTACATTG TTACCATTTA AAGAAAGCCA

2651 GGCAAGAGGA CTTTTACAAG ATAACATGGC AAATAGTTAT AATGGCGGCG

2701 ACTTTGAAGA TGGTTTATTG ATCTTAAGTA AAGAAGTATT TCCAACAGAT

2751 AAATATTTGT ATCAAGATGG TCAAAAGTTG GACAAGAAAA CAATTAATGC

2801 CTATTTAAAT CCTAAGTATA CAAAAAGTGA AATCGATAAA ATGTCTGAAA

2851 AAGATAAAAA AGACAAGAAA GCGAATGAAA ATTTAACACT TAATCCATCA

2901 CACGAAGGTG AAACAGATCG ACCTGCAGKC ATGC
```

Mutant: NT42
Phenotype: temperature sensitivity
Sequence map: Mutant NT42 is complemented by pMP76, which contains a 2.5 kb insert of *S. aureus* genomic DNA. A partial restriction map is depicted FIG. 42. Database searches at both the nucleic acid and peptide levels reveal strong similarity at the peptide level to ORFs of unknown function in *B. subtilis* (Genbank Accession No. Z38002; characterization of the Ipc29D polypeptide is unpublished as of 1995). Strong similarity is also noted to the SUA5 protein from the yeast *S. cerevisiae*, which is described as being essential for normal growth (published in Na, J. G. et al. *Genetics* 131 (1992) 791–801).

DNA sequence data: The following DNA sequence data represents the sequence of clone pMP76, starting with the standard M13 forward and M13 reverse sequencing primers and applying primer walking strategies to complete the sequence contig. The sequences below can be used to design PCR primers for the purpose of amplification from genomic DNA with subsequent DNA sequencing:

clone pMP76　　　　　　　　　　　　　　　　　　SEQ ID NO. 37
pMP76 Length: 2515 nt

```
  1 CSYCGGWACC CGGGGATCCT CTAGAGTCGA TCGTTCCAGA ACGTATTCGA

51 ACTTATAATT ATCCACAAAG CCGTGTAACA GACCATCGTA TAGGTCTAAC

101 GCTTCAAAAA TTAGGGCAAA TTATGGAAGG CCATTTAGAA GAAATTATAG

151 ATGCACTGAC TTTATCAGAG CAGACAGATA AATTGAAAGA ACTTAATAAT

201 GGTGAATTAT AAAGAAAAGT TAGATGAAGC AATTCATTTA ACACAACAAA

251 AAGGGTTTGA ACAAACACGA GCTGAATGGT TAATGTTAGA TGTATTTCAA

301 TGGACGCGTA CGGACTTTGT AGTCCACATG CATGATGATA TGCCGAAAGC

351 GATGATTATG AAGTTCGACT TAGCATTACA ACGTATGTTA TTAGGGAGAG

401 CCTATACAGT ATATAGTTGG CTTTGCCTCA TTTTATGGTA GAACGTTTGA

451 TGTAAACTCA AATTGTTTGA TACCAAGACC TGAAACTGAA GAAGTAATGT

501 TGCATTTCTT ACAACAGTTA GAAGATGATG CAACAGCGGT AGATATCGGA

551 ACGGGTAGTG GTGTACTTGC AATTACTTTG AAATGACGAA AAGCCGGATT
```

-continued

```
 601 TAAATGTTAT TGCTACTGAT ATTTCACTTG AAGCAATGAA TATGGGTCCG
 651 TAATAATGCT GAGAAGCATC AATCACAAAT ACAATTTTTA ACAGGGGATG
 701 CATTAAAGCC CTTAATTAAT GAAGGTATCA AKTTGAACGG CTTTGATATC
 751 TAATCCMCCA TATATAGATG AAAAAGATAT GGTTACGATG TCTCCMACGG
 801 TTACGARLTT CGAACCACAT CAGGCATTGT TTGCAGATAA CCATGGATAT
 851 GCTATTTATG AATCAATCAT GGAAGATTTA CCTCACGTTA TGGAAAAAGG
 901 CAGCCCAGTT GTTTTTGAAA TTGGTTACAA TCAAGGTGAG GCACTTAAAT
 951 CAATAATTTT AAATAAATTT CCTGACAALA AAATCGACAT TATTAAAGAT
1001 ATAAATGGCC ACGATCGAAT CGTCTCATTT AAATGGTAAT TAGAAGTTAT
1051 GCCTTTGCTA TGATTAGTTA AGTGCATAGC TTTTTGCTTT ATATTATGAT
1101 AAATAAGAAA GGCGTGATTA AGTTGGATAC TAAAATTTGG GATGTTAGAG
1151 AATATAATGA AGATTTACAG CAATATCCTA AAATTAATGA ATAALLGAC
1201 ATTGTTTTAA ACGGTGGTTT AATAGGTTTA CCAACTGAAA CAGTTTATGG
1251 ACTTGCAGCA AATGCGACAG ATGAAGAAGC TGTAGCTAAA ATATATGAAG
1301 CTAAAGGCCG TCCATCTGAC AATCCGGGTA TTGTTCATAT ACACAGTAAA
1351 GGTCAATTAA AAGATTTTAC ATATACTTTG GATCCACGCG TAGAAAAGTT
1401 AATGCAGGCA TTCTGGCCGG GCCCTATTTC GTTTATATTG CCGTTAAAGC
1451 TAGGCTATCT ATGTCGAAAA GTTTCTGGAG GTTTATCATC AGTTGCTGTT
1501 AGAATGCCAA GCCATTCTGT AGGTAGACAA TTATTACAAA TCATAAATGA
1551 ACCTCTAGCT GCTCCAAGTG CTAATTTAAG TGGTAGACCT TCACCAACAA
1601 CTTTCAATCA TGTATATCAA GATTTGAATG GCCGTATCGA TGGTATTGTT
1651 CAAGCTGAAC AAAGTGAAGA AGGATTAGAA AGTACGGTTT TAGATTGCAC
1701 ATCTTTTCCT TATAAAATTG CAAGACCTGG TTCTATAACA GCAGCAATGA
1751 TTACAGAAAT AMTTCCGAAT AGTATCGCCC ATGCTGATTA TAATGATACT
1801 GAACAGCCAA TTGCACCAGG TATGAAGTAT AAGCATTACT CAACCCAATA
1851 CACCACTTAC AATTATTACA GATATTGAGA GCAAAATTGG AAATGACGGT
1901 AAAGATTRKW MTTCTATAGC TTTTATTGTG CCGAGTAATA AGGTGGCGTT
1951 TATACCAAGT GARSCGCAAT TCATTCAATT ATGTCAGGAT GMCAATGATG
2001 TTAAACAAGC AAGTCATAAT CTTTATGATG TGTTACATTC ACTTGATGAA
2051 AATGAAAATA TTTCAGCGGC GTATATATAC GGCTTTGAGC TGAATGATAA
2101 TACAGAAGCA ATTATGAATC GCATGTTAAA AGCTGCAGGT AATCACATTA
2151 TTAAAGGATG TGAACTATGA AGATTTTATT CGTTTGTACA GGTAACACAT
2201 GTCGTAGCCC ATTAGCGGGA AGTATTGCAA AAGAGGTTAT GCCAAATCAT
2251 CAATTTGAAT CAAGAGGTAT ATTCGCTGTG AACAATCAAG GTGTTTCGAA
2301 TTATGTTGAA GACTTAGTTG AAGAACATCA TTTAGCTGAA ACGACCTTAT
2351 CGCAACAATT TACTGAAGCA GATTTGAAAG CAGATATTAT TTTGACGATG
2401 TCGTATTCGC ACAAAGAATT AATAGAGGCA CACTTTGGTT TGCAAAATCA
2451 TGTTTTCACA TTGCATGAAT ATGTAAAAGA AGCAGGAGAA GTTATAGATC
2501 GACCTGCAGG CATGC
```

Figure 43:
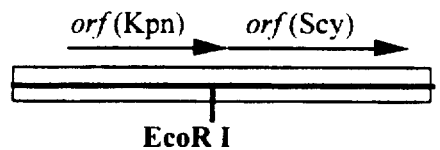

Mutant: NT47
Phenotype: temperature sensitivity
Sequence map: Mutant NT47 is complemented by pMP639, which contains a 2.6 kb insert of *S. aureus* genomic DNA. A partial restriction map is depicted FIG. 43, along with open boxes to indicate the percentage of the clone for which DNA sequence has been obtained. Database seachers at both the nucleic acid and peptide levels reveal strong similarity at the peptide level to two hypothetical ORFs of unknown function, one from *K. pneumonia* and one from Synechocystis spp. (abbreviated as "Kpn" and "Scy" in the diagram below. Experiments are currently underway to determine which ORF (or both) is an essential gene. The relative orientation and predicted size of these uncharacterized ORFs with respect to the partial restriction map of clone pMP639 are depicted by arrows in the map.

DNA sequence data: The following DNA sequence data represents the sequence of clone pMP639, starting with the standard M13 forward and M13 reverse sequencing primers and applying primer walking strategies to complete the sequence contig. The sequences below can be used to design PCR primers for the purpose of amplification from genomic DNA with subsequent DNA sequencing:

```
clone pMP639                                                    SEQ ID NO. 38
pMP639 Length: 2635 nt
           1 ATTCTCTGTG TTGGGGCCCC TGACTAGAGT TGAAAAAAGC TTGTTGCAAG
          51 CGCATTTTCA TTCAGTCAAC TACTAGCAAT ATAATATTAT AGACCCTAGG
         101 ACATTGATTT ATGTCCCAAG CTCCTTTTAA ATGATGTATA TTTTTAGAAA
         151 TTTAATCTAG ACATAGTTGG AAATAAATAT AAAACATCGT TGCTTAATTT
         201 TGTCATAGAA CATTTAAATT AACATCATGA AATTCGTTTT GGCGGTGAAA
         251 AAATAATGGA TAATAATGAA AAAGAAAAAA GTAAAAGTGA ACTATTAGTT
         301 GTAACAGGTT TATCTGGCGC AGGTAAATCT TTGGTTATTC AATGTTTAGA
         351 AGACATGGGA TATTTTTGTG TAGATAATCT ACCACCAGTG TTATTGCCTA
         401 AATTTGTAGA GTTGATGGAA CAAGGGAAAT CCATCCTTAA GAAAAAGTGG
         451 CAATTGCAAT TGATTAAGA RGTAAGGAAC TATTTAATTC ATTAGTTGCA
         501 GTAGTGGATA AAGTTCAAAA GTTGAAAGTG ACGTCATCAT TGATGTTATG
         551 TTTTTAGAAG CAAGTACTGA AAAATTAATT TCAAGATATA AGGAAACGCG
         601 TCCKTGCACA TCCTTTGATG GAACAAGGTT AAAAGATCGT TAATCAATGC
         651 MATTAATGAT GAGCGAGAGC ATTTGTCTCA AATTAGAAGT ATAGCTAATT
         701 TTGTTATAGA TAACTACAAA GTTATCACCT AAAGAATTAA AAGAACGCAT
         751 TCGTCGATAC TATGAAGATG AAGAGTTTGA AACTTTTACA ATTAATGTCA
         801 CAAGTTTCGG TTTTAAACAT GGGATTCAGA TGGATGCAGA TTTAGTATTT
         851 GATGTACGAT TTTTACCAAA TCCATATTAT GTAGTAGATT TAAGACCTTT
         901 AACAGGATTA GATAAAGACG TTTATAATTA TGTTATGAAA TGGAAAGAGA
         951 CGGAGATTTT TCTTTGAAAA ATTAACTGAT TTGTTAGATT TTATGATACC
        1001 CGGGTWTAAA AAAGAAGGGA AATCTCAATT AGTAATTGCC ATCGGTTGTA
        1051 CGGGTGGGAC AACATCGATC TGTAGCATTA GCAGAACGAC TAGGTWATTA
        1101 TCTAAATGAA GTWTTTGAAT ATAATGTTTA TGTGCATCAT AGGGACGCAC
        1151 ATATTGAAAG TGGCGAGAAA AAATGAGACA AATAAAAGTT GTACTTATCG
        1201 GGTGGTGGCA CTGGCTTATC AGTTATGGCT AGGGGATTAA GAGAATTCCC
        1251 AATTGATATT ACGGCGATTG TAACAGTTGC TGATAATGGT GGGAGTACAG
        1301 GGAAAATCAG AGATGAAATG GATATACCAG CACCAGGAGA CATCAGAAAT
        1351 GTGATTGCAG CTTTAAGTGA TTCTGAGTCA GTTTTAAGCC AACTTTTTCA
        1401 GTATCGCTTT GAAGAAAATC AAATTAGCGG TCACTCATTA GGTAATTTAT
        1451 TAATCGCAGG TATGACTAAT ATTACGAATG ATTTCGGACA TGCCATTAAA
        1501 GCATTAAGTA AAATTTTAAA TATTAAAGGT AGAGTCATTC CATCTACAAA
```

-continued

```
1551 TACAAGTGTG CAATTAAATG CTGTTATGGA AGATGGAGAA ATTGTTTTTG

1601 GAGAAACAAA TATTCCTAAA AAACATAAAA AAATTGATCG TGTGTTTTTA

1651 GAACCTAACG ATGTGCAACC AATGGAAGAA GCAATCGATG CTTTAAGGGA

1701 AGCAGATTTA ATCGTTCTTG GACCAGGGTC ATTATATACG AGCGTTATTT

1751 CTAACTTATG TTKTGAATGG TATTTCAGAT GCGTTWATTC ATTCTGATGC

1801 GCCTAAGCTA TATGTTTCTA ATGTGATGAC GCAACCTGGG GAAACAGATG

1851 GTTATAGCGT GAAAGATCAT ATCGATGCGA TTCATAGACA AGCTGGACAA

1901 CCGTTTATTG ATTATGTCAT TTGTAGTACA CAAACTTTCA ATGCTCAAGT

1951 TTTCAAAAAA TATGAAGAAA AACATTCTAA ACCAGTTGAA GTTAATAAGG

2001 CTGAACTKGA AAAAGAAAGC ATAAATGTAA AAACATCTTC AAATTTAGTT

2051 GAAATTTCTG AAAATCATTT AGTAAGACAT AATACTAAAG TGTTATCGAC

2101 AATGATTTAT GACATAGCTT TAGAATTAAT TAGTACTATT CCTTTCGTAC

2151 CAAGTGATAA ACGTAAATAA TATAGAACGT AATCATATTA TGATATGATA

2201 ATAGAGCTGT GAAAAAATG AAAATAGACA GTGGTTCTAA GGTGAATCAT

2251 GTTTTAAATA AGAAAGGAAT GACTGTACGA TGAGCTTTGC ATCAGAAATG

2301 AAAAATGAAT TAACTAGAAT AGACGTCGAT GAAATGAATG CAAAAGCAGA

2351 GCTCAGTGCA CTGATTCGAA TGAATGGTGC ACTTAGTCTT TCAAATCAAC

2401 AATTTGTTAT AAATGTTCAA ACGGAAAATG CAACAACGGC AAGACGTATT

2451 TATTCGTTGA TTAAACGTGT CTTTAATGTG GAAGTTGAAA TATTAGTCCG

2501 TAAAAAAATG AAACTTAAAA AAAATAATAT TTATATTTGT CGTACAAAGA

2551 TGAAAGCGAA AGAAATTCTT GATGAATTAG GAATTTTAAA AGACGGCATT

2601 TTTACGCATG AAATTGATCG ACCTGCAGGC ATGCA
```

Mutant: NT51

Phenotype: temperature sensitivity

Figure 44:
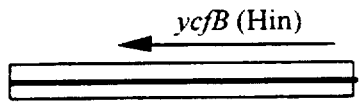

Sequence map: Mutant NT51 is complemented by pMP86, which contains a 1.9 kb insert of *S. aureus* genomic DNA. A partial restriction map is depicted FIG. 44 (there are no apparent restriction sites for EcoR I, Hind III, or BamH I). Database searches at both the nucleic acid and peptide levels reveal strong similarity at the peptide level to an ORF of undetermined function in *H. influenzae* (Genbank Accession No. U32702):

DNA sequence data: The following DNA sequence data represents the sequence of clone pMP86, starting with the standard M13 forward and M13 reverse sequencing primers and applying primer walking strategies to complete the sequence contig. The sequences below can be used to design PCR primers for the purpose of amplification from genomic DNA with subsequent DNA sequencing:

```
             clone pMP86                                              SEQ ID NO. 39
             pMP86 Length: 1952 nt
               1 TGCATGTACA GCAGGCTCTA CACAACCGTC GCATGTTTTA GATGCAATGT

51 TCGAAGATGA GGAGCGATCA AATCATTCGA TTCGATTTAG TTTTAACGAA

101 TTGACTACTG AAAATGAAAT TAATGCAATT GTAGCTGAAA TTCATAAAAT

151 ATATTTAAA TTTAAGGAGG AGTCATAATT GTCAAATAAA GATATAACGT

201 GTTGTCGTTG GTATGTCAGG CGGTGTAGAT AGTTCTGTAA CAGCCCACGT

251 CTTAAAAGAA CAAGGTTATG ATGTCATTGG CATATTTATG AAAAACTGGG

301 ATGACACTGA CGAAAATGGC GTATGTACTG CAACTGAAGA TTACAACGAT

351 GTTATTGAAG TGTGTAATCA AATGGGCATT CCGTATTACG CTGTTAATTT

401 TGAAAAAGAA TATTGGGATA AAGTCTTTAC GTATTTCTTA GATGAATACA

451 AAAAAGGTCG TACTCCAAAT CCAGACGTTA TGTGTAATAA AGAAATTAAG
```

-continued

```
 501 TTTAAAGCCT TTTTAGATCA TGCGATGAAT TTAGGTGCAG ATTATGTAGC

551 AACAGGACAT TACGCACGCA TACATCGTCA TGAASRTGGT CATGTTGAAA

601 TGTTACGTGG TGTAGATAAT AATAAAGATC ARACATACTK CWKGMATGCA

651 AKTATCTCAA CAACAACTTT CAAAAGTGAT GTTCCCAATT GGCGACATCG

701 AAAAGAGTGA AGTGCGTCGA ATTGCTGAAG AACAAGGACT TGTTACTGCT

751 AAGAAAAAAG ATTCTACAGG CATTTGTTTT ATCGGCGAAA AAAACTTTAA

801 AACATTTTTA TCACAATATT TACCTGCACA ACCGGGTGAT ATGATAACAC

851 TTGATGGTAA GAAAATGGGT AAACATAGTG GTTTGATGTA TTACACAATA

901 GGACAAAGAC ATGGATTAGG TATAGGTGGG AGATGGCGAT CCTTGGTTTG

951 TTGTCGGTAA AAACCTAAAA GATAATGTTT TATATGTWGA ACAAGGATCC

1001 ATCACGATGC ATTATACAGT GATTACTTAA TTGCTTCAGA CTATTCATTT

1051 GTAAATCCCA GAAGATAATG ACTTAGATCA AGGTTTTGAA TGTACAGCTA

1101 AATTTAGATA TCGCCAAAAA GATACGAAAG TTTTTGTGAA ACGTGAAAAA

1151 CGACCATGCA CTACGTGTTA CTTTTGCTGA GCCAGTAAGA GCAATCACAC

1201 CTGGACAAGC AGTTGTTTTT TATCAAGGTG ATGTGTTGTC TTGGTGGTGC

1251 AACAATTGAC GATGTKTTCA AAAATGAAGG TCAATTAAAT TATGTTGTAT

1301 ANACAATGGC AACAATAAAT TACTTATTTG AAGTTTCNAC GTTGAAAATG

1351 ACGAAAGACA GTTTTTGATG AGAATAATTC ATGAGGATAG AGTCTGGGAC

1401 ATCACAATGT CCTAGGCTCT ACAATGTTAT ATKGGCGGGA CCACAACATA

1451 GAGAATTTCG TAAAGAAATT CWACAGGCAA TGCCAGTTGG GGATAACGAA

1501 TTTAATTTTG TTAAAATATC ATTTCTGTCC CACTCCCTAT GCATGAATCT

1551 AATTATGTAT TCTTATTTTT AAGTACATAA TAGTGGTGGC TAATGTGGAA

1601 GAACCATTAC ATAATAAACC GTTAATGGTT CTTAAGCATT TYTATTCCAT

1651 TCCCGCTTTT TCATGAATGA AGATGATATT AGATTATATT TTATTCGTTG

1701 TTAAGTGATT CGAGACATAC AATTTATCAA GATGTTTATA ATTGATGAGA

1751 AATGAGGTTC GTAAATGATA GATCAACAAA CAATTTATCA ATACATACAA

1801 AATGGAAAAA TAGAAGAAGC GTTACAAGCA TTGTTCGGAA ATATCGAAGA

1851 AAATCCTACA ATTATTGAAA ATTATATTAA TGCTGGTATC GTACTTGCTG

1901 ATGCGAATGA GATTGAAAAG GCAGAGCGTT TTTTCCAAAA AGCTTTAACA

1951 AT
```

Figure 45:

Mutant: NT52
Phenotype: temperature sensitivity
Sequence map: Mutant NT52 is complemented by pMP87, which contains a 2.3 kb insert of *S. aureus* genomic DNA. A partial restriction map is depicted FIG. 45. Database searches at both the nucleic acid and peptide levels strong peptide-level similarity to the kimE gene product, encoding mevalonate kinase (EC 2.7.1.36), from *M. thermoautotrophicum* (abbreviated as "Mth" in the sequence map).

DNA sequence data: The following DNA sequence data represents the sequence of clone pMP87, starting with the standard M13 forward and M13 reverse sequencing primers and applying primer walking strategies to complete the sequence contig. The sequences below can be used to design PCR primers for the purpose of amplification from genomic DNA with subsequent DNA sequencing:

```
clone pMP87                                              SEQ ID NO. 40
pMP87 Length: 2273 nt
           1 TAACCAATAT TGATAAAACC TTGATGTGTT TCGTGTCAAT GACATACCAT
          51 ATCGACTAGG TACCTTTTTA GAATGTTGAT TAATCACAAC AAATATCATG
         101 GCAAGGTCAT CTTCAAAATG ATTCGATTCA AGTGGAACGG CATATGACGT
         151 CTCATCACTA TACCCTTTTT CCCATTCTGC AAATCCACCA TAAATACTAC
         201 GCGACGCAGA ACCCGAACCA ATTCGCGCCA ATCTCGATAA ATCCTTATCT
         251 GACAGCTGCA TGTCTAGCGC TTGATTACAA GCTGCTGCTA AAGCTGCATA
         301 TGCGCTTGCC GATGAAGCCA ACCCTGCTGC TGTTGGTACA AAATTGTCGC
         351 TTTCAATTTC TGCATACCAA TCGATGCCAG CTCTATTTCT GACAATATCC
         401 ATATATTTTG AAATTTTCTC TAATTCTTTG CCACTAACCT TTTCACCATT
         451 CAACCAAAAT TGATCCTGTG TTAACTGGTC GTTAAAAGTG ACTTTCGTTT
         501 CAGTGTWAAA TTTTTCTAAT GTWACAGATA TGCTATTATT CATTGGAATG
         551 ATTAGTGCTT CATCTTWTTT ACCCCAATAT TTTATAAGTG CAATATTCGT
         601 ATGTGCACGT GCTTTGCCAC TTTTAATCAA CGCATTAACC TCCTAAATTC
         651 TCAATCCAAG TATGTGCTGC ACCAGCTTTT TCTACAGCTT TTACAATATT
         701 TTTCGCTGTT GGTAAATCTT TGGCAAGCAA TAACATACTT CCACCACGAC
         751 CAGCGCCAGT AAGTTTTCCA GCAATCGCAC CATTTTCTTT ACCAATTTTC
         801 ATTAATTGTT CTATTTTATC ATGACTAACT GTCAACGCCT TTAAATCCGC
         851 ATGACATTCA TTAAAAATAT CCGCTAAGGS TTCAAAGTTA TGATGTTCAA
         901 TCACATCACT CGCACGTAAA ACTAACTTAC CGATATGTTT TACATGTGAC
         951 ATGTACTGAG GGTCCTCACA AAGTTTATGA ACATCTTCTA CTGCTTGTCT
        1001 TGTTGAACCT TTCACACCAG TATCTATAAC AACCATATAG CCGTCTAAAC
        1051 TTAACGTTTT CAACGTTTCA GCATGACCTT TTTGGAACCA AACTGGTTTG
        1101 CCTGATACAA TCGTTTGCGT ATCAATACCA CTTGGTTTAC CATGTGCAAT
        1151 TTGCTCTGCC CAATTAGCCT TTTCAATGAG TTCTTCTTTC GTTAATGATT
        1201 TCCCTAAAAA ATCATAACTT GCACGAACAA AAGCAACCGC GACAGCTGCA
        1251 CTCGATCCTA ATCCACGTGA TGGTGGTAAA TTCGTTTGGA TCGTTACTGC
        1301 TAGCGGCTCT GTAATATTAT TTAATTCTAC AAAACGGTTC ACCAAAGAMT
        1351 TAAGATGGTC AGGCGCATCA TATAAACATA CCATCGTAAA ACATCGCTTT
        1401 TAATAGAGGA ATAGTTCCCG CTCTCTAAGG TTCTATTAAA ACTTTGATTT
        1451 TAACCGGCGT TAAACGGTAC TGCAATAGCA GGCTCTCCAA ATGTAACAGC
        1501 ATGTTCTCCT ATTAAAATAA TCTTACCTGT CGATTCCCCA TATCCTTTTC
        1551 TTGTCATGTC AATATCACCT TTTATATTTA TCCTAWACTT GATTCATTAT
        1601 TTTTATTTAT TAGTAAAAGA CATCATATTC TAAGTKGCAW ACGCATTCGC
        1651 GTTAAATTTC ATTGCAGTCT TTATCTCACA TTATTCATAT TATGTATAAT
        1701 CTTTATTTTG AATTTATATT TGACTTAACT TGATTAGTAT AAAACTAACT
        1751 TTCGTTTACT TCAAAGTTTA AATCTTATCG AGTGATATTT CAGATTCTTT
        1801 ATCTTTTTAT AAAATAGCCC TACAATTTAT AATTTTCCAC CCTAACTATA
        1851 ATACTACAAA TAATAATTGG AATATATAGA TTTACTACTA AAGTATTAGA
        1901 ACATTTCAAT AGAAGGTCGT TTCTTTCATA GTCATACGCA TTATATATAC
```

```
                                  -continued
1951 CCTATTCTCA ATCTATTTAA TACGTAAAAC ATGAAATTTT CTTATTAAAT

2001 TTATTATTTC CATCATATCA TTACTTTTAA TTTAATGATG TTCAATTTAA

2051 ATATTAGGTC AATAACATAT TTATGCTTTT TATGGATACT TTCAAAAATA

2101 ACAGCCCCAA ACGATAACTT GAAAGGGGCT GTTAAATATT TAACTATTGC

2151 ATTTGATCKA TCATTYTMKW GKWTCYYYSR RTMMYKWKMT CRAAATACGT

2201 ATCGTATCTT TGCCATTCTT CTTGAGTAAT TGGCGTCATA TTTAATACAC

2251 CGCCAAGATC GACCTGCAGG CAT
```

Figure 46:
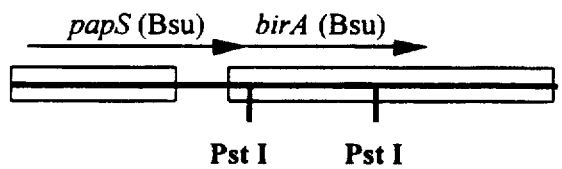

Mutant: NT53
Phenotype: temperature sensitivity
Sequence map: Mutant NT53 is complemented by pMP143, which contains a 3.0 kb insert of *S. aureus* genomic DNA. A partial restriction map is depicted FIG. 46, along with open boxes to indicate the percentage of the clone for which DNA sequence has been obtained. Database searches at both the nucleic acid and peptide levels reveal strong similarity at the peptide level to papS, encoding poly-A polymerase (EC 2.7.7.19) from *B. subtilis*(Genbank Accession No. L38424; published in Bower, S. et al. *J. Bacteriol.* 9 (1995) 2572–2575). Also included in this clone is the gene homolog for birA, which encodes biotin [acetyl-CoA-carboxylase] ligase and functions as a biotin operon repressor protein.

DNA sequence data: The following DNA sequence data represents the sequence of clone pMP143, starting with the standard M13 forward and M13 reverse sequencing primers and applying primer walking strategies to augment the sequence contigs. The sequences below can be used to design PCR primers for the purpose of amplification from genomic DNA with subsequent DNA sequencing:

```
        clone pMP143                                              SEQ ID NO. 41
        pMP143.forward Length: 928 nt
            1 TCCTCTAGAG TCGATCAATA TGAGTATTAT TATCAAAAAA TGCTAAATNA

51 GCATAACAAA AGTAAAGGCG AGTAATAATA TGGATAAATC ATTATTTGAA

101 YAGGCAAGGC CTATATTAGA ACAAATTCAA GACAATGGTT TTNAAGCATA

151 TTATGTAGGT GGCTCTGTAA GAGATTATGT CATGGGAAGA AATATTCATG

201 ATATAGATAT CACAACAAGT GCAACGNCGG ATGAAATAGA ATCTATCTTT

251 AGTCATACGA TACCTGTAGG TAAAGAACAT GGCACGATAA ATGTAGTTTT

301 TAATGATGAA AATTATGAAG TGACAACATT CCGGGCTGAA GAAGATTATG

351 TCGATCACCG TAGACCAAGT GGTGTTACAT TTGTYCGTGA TTTATACGAR

401 GATTTGCAAC GACGAGATTT CACGATGAAT GCGATAGAAT GGATACAGCA

451 TACAAATTGT ATGATTATTT TGATGGTCAA CAAGATATTA ATAATCGAWT

501 AATAAGAACT GTAGGTATAG CTGAGGAACG TTCCAAGAAG ATGCTTTACG

551 TATGATTCGA TGTTTAAGGT TCCAGTCACA ATTATCATTT GATATTGCAA

601 CGGAAACATT CGAAGCGATG CGTATACAAA TGGCAGATAT TAAATTTTTA

651 TCAATTGAGC GTATAGTGAT TGAACTAACT AAATTAATGC GAGGTATTAA

701 TGTTGAAAAG AGTTTTAATC ATTTAAAATC GCTGAAAGCA TTTAATTATA

751 TGCCGTATTT CGAACATCTT GATATGAATC AAATTAATGT AACTGAAGCA

801 ATTGATTTAG AATTGTTGAT TGCTATAGTA TCAGTTAAAT TTGATATTAA

851 TTACTCATTG AAGCCTTTAA AGCTAAGTTA ACCGACAAGT TAAAAGATAT

901 CAATCAATAT ATTCAAATTA TGAATGCA pMp143.reverse Length: 2119 nt                            SEQ ID NO. 42
            1 TGCATGCCTG CAGGTCGATC TAATATAGTT TCCGCTAAAT ATAATTGTTG

51 CGGTCGATAT GTTAAGCCAR GTYGATCTAC AGCTTTGCTA TATAAAGACT

101 TCAAGCTGCC ATTATAATTT GTTGTCGGCT TTTTAAAATC AACTTGCTTA

151 CGATAGATAA TCTGTTCGAA CTTTTCGTAC GATTTATCCA ATGGCTTTGC
```

-continued

```
 201 ATCATATTGC CTAACCATCT CAAAGAAAAT ATCATACAAA TCGTATTTCA
 251 ACTGTTTACT TAAATAATAT AATTGCTTCA AAGTATCTAA CGGTAACTTT
 301 TCAAATTTTT CAAAAGCTAA TATCATCAAT TTAGCAGTAG TAGCGGCATC
 351 TTCGTCAGCT CGATGGGCAT TTGCTAAGGT AATACCATGT GCCTCTGCTA
 401 ATTCACTTAA TTGATAGCTT TTATCTGTAG GAAAAGCTAT TTTAAAGATT
 451 TCTAGTGTAT CTATAACTTT TTTGGGACGA TATTGAATAT TACAATCTTT
 501 AAATGCCTTT TTAATAAAAT TCAAATCAAA ATCTACATTA TGAGCTACAA
 551 AAATGCAATC TTTWATCTTA TCGTAGATTT CTTGTGCAAC TTGATTAAAA
 601 TATGGCGCTT GTTGTAGCAT ATTTKCTTCA ATGGATGTTA ACGCWTGAAT
 651 GAACGGCGGA AWCTCTAAAT TTGTTCTAAT CATAGAATGA TATGTATCAA
 701 TAATTTGGTT ATTGCGSACA AACGTTATAC CAATTTGAAT GATATCGTCA
 751 AAATCTAATT GGTTGCCTGT TGTTTCCAAA TCCACAACGG CATAGGTTGC
 801 CATACCCATA GCTATCTCTC CTTGCTTTAG TGTTAAAAAT CTATATCTGC
 851 ACTAATTAAA CGGTGTGATT CACCCGCTTC ATCTCTAACA ATTAGATAGC
 901 CATCGTAATC TAAATCAATT GCTTGTCCTT TAAACTGTTT ATCATTTTCT
 951 GTAAATAGCA ACGTTCTATT CCAAATATTA GAAGCTGCAG TATATTCTTC
1001 ACGAATTTCA GAAAAAGGTA ACGTTAAAAA TTGATTATAT CTTTTTYCAA
1051 TTTCTAGAAG TAATATCTCT AAAAATTGAT ATCTATCTAA TTWATTTTTA
1101 TCATGTAATT GTATACTTGT TGCTCTATGT CTAATACTTY CATCAAAGTT
1151 TTCTAGTTGT TTGCGTTCAA ATTAATACCT ATACCACATA TTATTGCTTC
1201 TATACCATCC ATTATTAGCA ACCATTTCAG TTAAGAAACC ACACACTTTA
1251 CCATTATCAA TAAATATATC ATTCGGCCAT TTCACTTTGA CTTCATCTTG
1301 ACTAAAATGT TGAATCGCAT CTCTTATCCC TAATGCAATA AATAAATTAA
1351 ATTTAGATAT CATTGAGAAT GCAACGTTAG GTCTTAACAC GACAGACATC
1401 CAAAGTCCTT GCCCTTTTGA AGAACTCCAA TGTCTATTAA ATCGCCCACG
1451 ACCTTTCGTT TGTTCATCAC TCAAGATAAA AAATGAAGAT TGATTTCCAA
1501 CAAGTGACTT TTTCGCAGCA AGTTGTGTAG AATCTATTGA ATCGTATACT
1551 TCACTAAAAT CAAACAAAGC AGAACTTTTT GTATATTGGT CTATTATACC
1601 TTGATACCAA ATATCTGGGA GCTGTTGTAA TAAATGCCCT TTATGATTTA
1651 CTGAATCTAT TTTACATCCC TCTAACTTTA ATTGGTCAAT CACTTTTTTT
1701 ACTGCAGTGC GTGGAAATAT TAAGTTGATT CCGCAATGCT TTGTCCAGAA
1751 TATATAATTC GGTTTATTTT TATAGAGTAA TTGAAGTTAC ATCTTGACTA
1801 TATTTTNACA TGATTATCCA CCCATTTCAA AATTNCAGTT TCTNCGTTGC
1851 TTACTTTACC TGTNACAATC GCTATCTCAA TTTGTCTTAG CACATCTTTT
1901 AACCACGGAC CACTTTTGGC ATTTAAATGT GCCATAAGTA CACCGCCATT
1951 AACCATCATG TCTTTNCTAT TATGCATAGG TAAACGATGT AATGTTTCAT
2001 CAATCGTTTG AAGGTTAACG CTTAATGGTT CATGTCCTTG GTATCATAAC
2051 GCCTGTNTCA AGCGTTCTNC AANCATGTAC AGTTTTTCAA TGTGGNGTGT
2101 CCGNATTAAC GCTATTCAA
```

Figure 47:
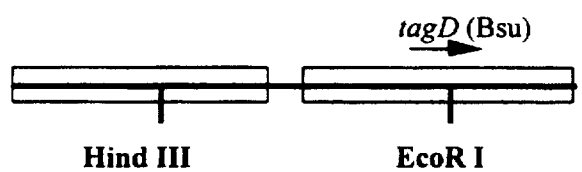

Mutant: NT54
Phenotype: temperature sensitivity
Sequence map: Mutant NT54 is complemented by pMP145, which contains a 3.1 kb insert of *S. aureus* genomic DNA. A partial restriction map is depicted FIG. 47, along with open boxes to indicate the percentage of the clone for which DNA sequence has been obtained. Database searches at both the nucleic acid and peptide levels reveal identity at the nucleic acid level and peptide level to the C-terminal portion of the pbp4 gene, encoding D,D-carboxy peptidase (EC 3.4.16.4) from *S. aureus* (Genbank Accession No. U29454; unpublished as of July, 1995). Since clone pMP146 does not contain the complete Pbp4 ORF, this gene is unlikely to be responsible for restoring mutant NT54 to a wild-type phenotype. Cross complementation with clone pMP91, which contains a 5.2 kb insert of *S. aureus* genomic DNA, reveals that only 800 additional base pairs downstream (3' to) the Pbp4 ORF are necessary for complementation (data not shown). DNA sequence of this region reveals strong similarity at the nucleic acid and peptide levels to the tagD gene, encoding glycerol-3-phosphate cytidylyl transferase (EC 2.7.7.39), from *B. subtilis* (Genbank Accession No. M57497; published in Mauel, C. et al., *J. Gen. Microbiol.* 137 (1991) 929–941). The tagD gene of *B. subtilis* has been reported to be an essential gene and is therefore likely to be a good candidate for screen development. The relative size and location of the TagD ORF with respect to clone pMP145 is depicted. by an arrow in the restriction map.

DNA sequence data: The following DNA sequence data represents the sequence of the right-most portion of clone pMP145, starting with the standard M13 reverse sequencing primer and applying primer walking strategies to complete the sequence contig. The sequence below can be used to design PCR primers for the purpose of amplification from genomic DNA with subsequent DNA sequencing:

```
clone pMP145                                              SEQ ID NO. 43
pMP145 Length: 1407 nt

1 TTCACAGTGT TGTCGGGATA CGATATAGTA CACTGTACAG TACGNTGGAG

51 ATTTATTAGA TTTTCACAGA ATTNTGAAAA TAAGACNACG GGTCATGGAA

101 ATGTTACTAT TACCTGAACA AAGGCTATTA TATAGTGATA TGGTTGNTCG

151 TATTTTATTC AATAATTCAT TAAAATATTA TATGAACGAA CACCCAGCAG

201 TAACGCACAC GACAATTCAA CTCGTAAAAG ACTATATTAT GTCTATGCAG

251 CATTCTGATT ATGTATCGCA AAACATGTTT GACATTATAA ATACAGTTGA

301 ATTTATTGGT GAGAATTGGG ATAGAGAAAT ATACGAATTG TGGCGACCAA

351 CATTAATTCA AGTGGGCATT AATAGGCCGA CTTATAAAAA ATTCTTGATA

401 CAACTTAAAG GGAGAAAGTT TGCACATCGA ACAAAATCAA TGTTAAAACG

451 ATAACGTGTA CATTGATGAC CATAAACTGC AATCCTATGA TGTGACAATA

501 TGAGGAGGAT AACTTAATGA AACGTGTAAT AACATATGGC ACATATGACT

551 TACTTCACTA TGGTCATATC GAATTGCTTC GTCGTGCAAG AGAGATGGGC

601 GATTATTTAA TAGTAGCATT ATCAACAGAT GAATTTAATC AAATTAAACA

651 TAAAAAATCT TATTATGATT ATGAACAACG AAAAATGATG CTTGAATCAA

701 TACGCTATGT CRTATTTAGT CATTCCAGAA AAGGGCTGGG GACAAAAAGA

751 AGACGATGTC GAAAAATTTC ATGTAGATGT TTTTGTTATG GGACATGACT

801 GGGAAGGTGA ATTCGACTTC TTAAAGGATA AATGTGAAGT CATTTATTTA

851 AAACGTACAG AAGGCATTTC GACGACTAAA ATCAAACAAG AATTATATGG

901 TAAAGATGCT AAATAAATTA TATAGAACTA TCGATACTAA ACGATAAATT

951 AACTTAGGTT ATTATAAAAT AAATATAAAA CGGACAAGTT TCGCAGCTTT

1001 ATAATGTGCA ACTTGTCCGT TTTTAGTATG TTTTATTTTC TTTTTCTAAA

1051 TAAACGATTG ATTATCATAT GAACAATAAG TGCTAATCCA GCGACAAGGC

1101 ATGTACCACC AATGATAGTG AATAATGGAT GTTCTTCCCA CATACTTTTA

1151 GCAACAGTAT TTGCCTTTTG AATAATTGGC TGATGAACTT CTACAGTTGG

1201 AGGTCCATAA TCTTTATTAA TAAATTCTCT TGGATAGTCC GCGTGTACTT

1251 TACCATCTTC GACTACAAGT TTATAATCTT TTTTACTAAA ATCACTTGGT

1301 AAAACATCGT AAAGATCATT TTCAACATAA TATTTCTTAC CATTTATCCT
```

-continued

```
1351 TTGCTCACCT TTAGACAATA TTTTTACATA TTTATACTGA TCAAATGAVC

1401 GTTCCAT
```

Figure 48:
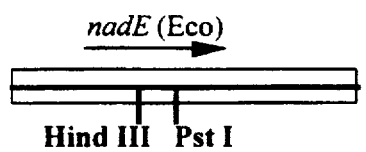

Mutant: NT55
Phenotype: temperature sensitivity
Sequence map: Mutant NT55 is complemented by pMP92, which contains a 2.0 kb insert of *S. aureus* genomic DNA. A partial restriction map is depicted FIG. 48. Database searches at both the nucleic acid and peptide levels reveal strong peptide-level similarity to the nadE gene product, encoding the nitrogen regulatory protein NH3-dependent NAD synthetase (EC 6.3.5.1), from *E. coli* (Genbank Accession No. M15328; published in Allibert, P. et al. *J. Bacteriol.* 169 (1987) 260–271).

DNA sequence data: The following DNA sequence data represents the sequence of clone pMP92, starting with the standard M13 forward and M13 reverse sequencing primers and applying primer walking strategies to complete the sequence contig. The sequences below can be used to design PCR primers for the purpose of amplification from genomic DNA with subsequent DNA sequencing:

```
          clone pMP92                                           SEQ ID NO. 44
          pMP92 Length: 1996 nt
             1 TCCTCTAGAG TCGATCGTAT TAAATTATCA AATAACGCTG AAAAGGTTAC

51 GACGCCAGGT AAGAAAAATG TATATCGCAT TATAAACAAG AAAACAGGTA

101 AGGCAGAAGG CGATTATATG ACTTTGGAAA ATGAAAATCC ATACGATGAA

151 CAACCTTTAA AATTATTCCA TCCAGTGCAT ACTTATAAAA TGAAATTTAT

201 AAAATCTTTC GAAGCCATTG ATTTGCATCG TAATATTTAT GAAAATGGTA

251 AATTAGTATA TCAAATGCCA ACAGAAGATG AATCACGTGA ATATTTAGCA

301 CTAGGATTAC AATCTATTTG GGATGAAAAT AAGCGTTTCC TGAATCCACA

351 AGAATATCCA GTCGATTTAA GCAAGGCATG TTGGGATAAT AAACATAAAC

401 GTATTTTTGA AGTTGCGGAA CACGTTAAGG AGATGGAAGA AGATAATGAG

451 TAAATTACAA GACGTTATTG TACAAGAAAT GAAAGTGAAA AAGCGTATCG

501 ATAGTGCTGA AGAAATTATG GAATTAAAGC AATTTATAAA AAATTATGTA

551 CAATCACATT CATTTATAAA ATCTTTAGTG TTAGGTATTT CAGGAGGACA

601 GGATTCTACA TTAGTTGGAA AACTAGTACA AATGTCTGTT AACGAATTAC

651 GTGAAGAAGG CATTGATTGT ACGTTATTG CAGTTAAATT ACCTTATGGA

701 GTTCAAAAAG ATGCTGATGA AGTTGAGCAA GCTTTGCGAT TCATTGAACC

751 AGATGAAATA GTAACAGTCA ATATTAAGCC TGCAGTTGAT CAAAGTGTGC

801 AATCATTAAA AGAAGCCGGT ATTGTTCTTA CAGATTTCCA AAAAGGAAAT

851 GAAAAAGCGC GTGAACGTAT GAAAGTACAA TTTTCAATTG CTTCAAACCG

901 ACAAGGTATT GTAGTAGGAA CAGATCATTC AGCTGAAAAT ATAACTGGGT

951 TTTATACGAA GTACGGTGAT GGTGCTGCAG ATATCGCACC TATATTTGGT

1001 TTGAATAAAC GACAAGGTCG TCAATTATTA GCGTATCTTG GTGCGCCAAA

1051 GGAATTATAT GAAAAAACGC CAACTGCTGA TTTAGAAGAT GATAAACCAC

1101 AGCTTCCAGA TGAAGATGCA TTAGGTGTAA CTTATGAGGC GATTGATAAT

1151 TATTTAGAAG GTAAGCCAGT TACGCCAGAA GAACAAAAAG TAATTGAAAA

1201 TCATTATATA CGAAATGCAC ACAAACGTGA ACTTGCATAT ACAAGATACA

1251 CGTGGCCAAA ATCCTAATTT AATTTTTTCT TCTAACGTGT GACTTAAATT

1301 AAATATGAGT TAGAATTAAT AACATTAAAC CACATTCAGC TAGACTACTT

1351 CAGTGTATAA ATTGAAAGTG TATGAACTAA AGTAAGTATG TTCATTTGAG

1401 AATAAATTTT TATTTATGAC AAATTCGCTA TTTATTTATG AGAGTTTTCG
```

-continued

```
1451 TACTATATTA TATTAATATG CATTCATTAA GGTTAGGTTG AAGCAGTTTG

1501 GTATTTAAAG TGTAATTGAA AGAGAGTGGG GCGCCTTATG TCATTCGTAA

1551 CAGAAAATCC ATGGTTAATG GTACTAACTA TATTTATCAT TAACGTTTGT

1601 TATGTAACGT TTTTAACGAT GCGAACAATT TTAACGTTGA AAGGTTATCG

1651 TTATATTGCT GCATCAGTTA GTTTTTTAGA AGTATTAGTT TATATCGTTG

1701 GTTTAGGTTT GGTTATGTCT AATTTAGACC ATATTCAAAA TATTATTGCC

1751 TACGCATTTG GTTTTTCAAT AGGTATCATT GTTGGTATGA AAATAGAAGA

1801 AAAACTGGCA TTAGGTTATA CAGTTGTAAA TGTAACTTCA GCAGAATATG

1851 AGTTAGATTT ACCGAATGAA CTTCGAAATT TAGGATATGG CGTTACGCAC

1901 TATGCTGCGT TTGGTAGAGA TGGTAGTCGT ATGGTGATGC AAATTTTAAC

1951 ACCAAGAAAA TATGAACGTA AATTGATGGA TACGATAAAA AATTTA
```

Figure 49:
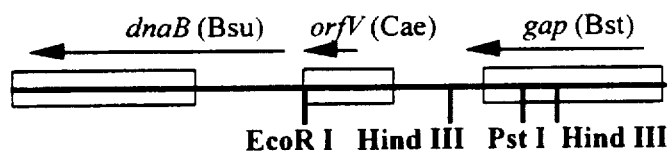

Mutant: NT57
Phenotype: temperature sensitivity
Sequence map: Mutant NT57 is complemented by pMP94, which contains a 3.6 kb insert of *S. aureus* genomic DNA. A partial restriction map is depicted FIG. 49, along with open boxes to indicate the percentage of the clone for which DNA sequence has been obtained. Database searches at both the nucleic acid and peptide levels reveal significant similarity at the peptide level to the gap gene, encoding glyceraldehyde-3-phosphate dehydrogenase (EC 1.2.1.12), from a number of prokaryotes and eukaryotes (e.g. Genbank Accession No. M24493, for the corresponding gene from *B. stearothermophilus*; published in Branlandt, C. et al., 1989, Gene 75:145–155). From the opposite sequence contig, a strong peptide-level similarity is noted to the dnaB gene product, encoding an essential protein involved in the initiation of DNA replication, from *B. subtilis* (Genbank Accession No. M15183; published in Hoshino, T. et al. *Proc. Natl. Acad. Sci. USA* 84 (1987) 653–657). Also of significance is the similarity of a subclone sequence to an ORF of unknown function, conserved among prokaryotes including *E. coli*, *M. leprae*, *C. acetobutylicum*, *H. influenzae* and *B. subtilis* (e.g. "orf 168" from Genbank Accession No. D28752). The relative orientations and predicted sizes of the ORFs identified in this entry are denoted by arrows in the restriction map.

DNA sequence data: The following DNA sequence data represents the partial sequence of clone pMP94, starting with the standard M13 forward and M13 reverse sequencing primers and applying primer walking strategies to augment the sequence contigs as well as obtain subclone sequence data. The sequences below can be used to design PCR primers for the purpose of amplification from genomic DNA with subsequent DNA sequencing:

```
clone pMP94                                              SEQ ID NO. 45
pMP94.forward Length: 1017 nt
    1 CTTYGARCTC GGTACCCGGG GMTCCTCTAR AGTCGATCTT TATACTCTTG

51 TAACACATTT AAGTCTTCAT CAATCATAGC ATTCGTTAAT TCAGCTCGAT

101 GCGCTTCCAA AAATTGCTTA ACATCTGGGT CATWGATGTC TCCTGATTTT

151 ATCTTTTCTA TTCTTTTTTC AAAGTCCTGC GACGTGTTAA TTATACTTTT

201 AAATTGCTTC ATTATTGACT GTCCTCCTCC CATTTTTTAG ATAATTTATC

251 TAGAAATGCT TGTCGATCTT GCTCTAATTG TTGATCATCT ACGCTATTAT

301 CTTTAGCCGA ATCTTCTTCA CTAGGTTTAT CTCTATTTTC TAACCATTTA

351 GGTGTTTTTT CTTTTGAAAT ACGATTACGC TGCCCATAGT ATGAACCACG

401 CTTTTGGTAA TTTCCGCTAG AACCCTCATT TTTAGGTTGA TTAACTTTTT

451 TAGCGTAATT ATATGCTTCT TTAGCTGTCT TAATACCTTT TTTCTTCCAA

501 TTTGATGCTA TTTCCAAAAT ATACGCTTTA GGAAGTTTCA TATCTTCTTT

551 TAACATGACA AATTGCAACA AAATATTAAT GACGCCAAAA GACATTTTTT

601 CACGTTTCAA TTAATTCTTC AACCATTGTC TTTTGCGATA TAGTTGGTYC

651 TGATTCAGAM CAAGAAGCTA ACATATCAAT TGGACTCGTT TGTTCAAGTA

701 ACTCAAACCA TTCATCACTT TGTGGCTTTG GATTCACTTC TGAAGATTTG
```

-continued

```
 751 CCCGCCGAAG ATGATGTAGC AGGAGATTTC ACCTGTAATT TAGGCATTTG

801 ATTTTCGTGT TCCATTAAGT AATACGAGCG TGCTTGTTTA CGCATTTCTT

851 CAAAGGATAA CTGTTGTCCA CTTGTAATTG AATTTAAAAT AACATGCTTC

901 ATGCCATCTG CTGTTAAACC ATATAAATCN CGAATTGTGT TATTAAACCC

951 TTGCATCTTG GTAACAATGT CTTGACTAAT AAATGTTTAC CTAACATTGT

1001 CTCCACATTT CNANTCC
``` pMP94.reverse Length: 1035 nt                                SEQ ID NO. 46

```
   1 TGCATGCCTG CAGGTCGATC AAGGGGTGCT TTTAATGTCA AGAATATTG

51 CAATTRATGG TATGGGTAGA ATTGGAAGAA TGGTATTACG TATTGCATTA

101 CAAAATAAAA ATTTAAATGT AGTAGCGATA AATGCTAGTT ATCCACCCGA

151 AACAATTGCA CATTTAATCA ATTACGATAC GACACATGGA AAATATAATC

201 TAAAAGTTGA ACCGATTGAA ATGGATTGC AAGTTTGAGA TCATAAAATT

251 AAATTGGTTG CTGATCGCAA TCCTGAAAAC TTGCCATGGA AAGAATTAGA

301 TATCGATATT GCTATAGATG CAACTGGTAA ATTTAATCAT GGTGATAAAG

351 CCATCGCACA TATTAAAGCA GGTGCCAAAA AAGTTTTGTT AACTGGTCCT

401 TCAAAAGGTG GACATGTTCA AATGGTAGTT AAAGGCGTAA ATGATAACCA

451 ATTAGATATA GAAGCATTTG ACATTTTTAG TAATGCTTCA TGTACTACTA

501 ATTGCATTGG TCCAGTTGCA AAAGTTTTAA ATAATCAGTT TGGGAATAGT

551 TAATGGTTTA ATGACTACTG TTCACGCTAT TACAAATGAC CAAAAAAATA

601 TTGATAATCC MCATAAAGAT TTAAGACGTG CACGTTCATG TWATGGAAGC

651 ATTATTCCTA CTTCTACTGG TGCGGCGAAA GCTTTAAAAG AAGTATTACC

701 AGAATTAGAA GGTAAATTAC ACGGCATGGC ATTACGTTGT ACCAACAAAG

751 AATGTATCGC TCGTTGATTT AGTTGTTGAT TTAGAAAAAG AAGTAACTGC

801 AGAAGAANTA AACCAAGCTT TGAAAATGC AGGTTTAGAA GGTATCATAG

851 AANTCGAACA TCACCACTAG TGTCTGTTGA TTTTAATACT AATCCCAATT

901 CAGCTATTAT TGATGCCAAA CCACNATGTC ATGTTCCGGG AAATAAGTAA

951 ANTTATTGCT TGGTATGAAN ATGAATGGGG TTATTCCAAT AAATTGTTAA

1001 NNTTGCNGAA CAAATTGGAC NCTTTGGANT CCAAA
``` pMP94.subclone Length: 483 nt                                SEQ ID NO. 47

```
   1 CTCCGTTTGT TTTCGCTTAA ATCCCTTGC ATCGATGCTA ACAATTGATC

51 AACATCTTTA AATTCTTTAT AGACTGATGC AAATCTAACA TATGAAACTT

101 GATCAACATG CATTAACAAG TTCATAACGT GTTCACCTAT ATCTCGTGAA

151 GACACTTCCG TATGACCTTC ATCTCGTAAT TGCCATTCAA CCTTGTTAGT

201 TATGACTTCA AGTTGTTGAT ATCTAACTGG TCGTTCTCA CAAGAACGCA

251 CAAGTCCATT AAGTTATCTT TTCTCTTGAA AACTGCTCTC TTGTGCCATC

301 TTTTTTCACA ACTATAAGCT GACTAACTTC GATATGNTTC AAATGTTAGT

351 GGAAACGTTG TTTCCACAAT TTTCACATTC TCTTCGTCTT CCGAAATGGC

401 ATTTAATTCA TCGGGCATGC CTTGAATCTA CAACTTTAGA ATTGTGTTAG

451 AATTACATTT CGGGCATTTC ATTACATCAC CTC
```

Figure 50:
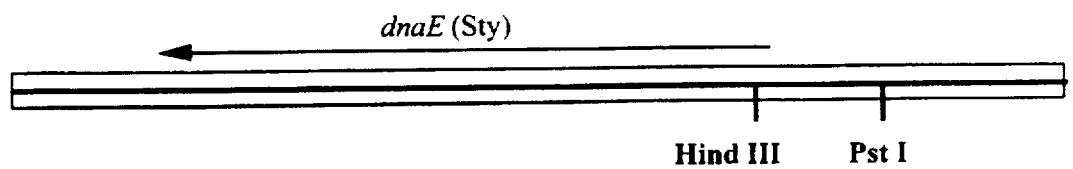

Mutant: NT68
Phenotype: temperature sensitivity
Sequence map: Mutant NT68 is complemented by pMP163, which contains a 5.8 kb insert of *S. aureus* genomic DNA. A partial restriction map is depicted FIG. 50. Database searches at both the nucleic acid and peptide levels reveal strong peptide-level similarities to the dnaE gene, encoding DNA polymerase III alpha subunit (EC 2.7.7.7), from Gram-negative bacteria such as *S. typhimurium* (Genbank Accession No. M29701; published in Lancey, E. D., et al. *J. Bacteriol.* 171 (1989) 5581–5586). This mutant is distinct from NT28, described previously as having a mutation in the polC gene which also encodes. an alpha subunit of DNA polymerase III (found so far in Gram-positive bacteria).

Although dnaE and polC putatively encode proteins of the same enzymatic function, in *S. aureus* these two genes are quite distinct and may or may not encode proteins of redundant function; since the DNA sequences of each are less than 65% identical, they are confirmed as being two distinct essential genes.

DNA sequence data: The following DNA sequence data represents the sequence generated by primer walking through clone pMP163, starting with standard M13 forward and M13 reverse sequencing primers and completing the sequence contig via primer walking strategies. The sequence below can be used to design PCR primers for the purpose of amplification from genomic DNA with subsequent DNA sequencing.

clone pMP163  SEQ ID NO. 48
pMP163 Length: 5718 nt

```
   1 CTCGGTACCC GGGGATCGTC ATGGAATACC GGAATATTAG TTTCTTTTTT
  51 CAATCGTTCT TCAATTTCAA AACAACGTGG TGCCGAAATA TCCTCTAAAT
 101 TAATACCACC ATAATTAGGT TCTAACAACT TAACTGTTTT AATGATTTCT
 151 TCGGTATCAG TTGTATTTAA CGCAATAGGC ACCCCATTGA TACCAGCGAA
 201 GCTTTTGAAT AATACTGCTT TACCTTCCAT TACAGGAATA CTTGCTTCAG
 251 GTCCAATGTT ACCTAAACCT AATACCGCTG TTCCATCAGT AATAACTGCA
 301 ACTGTATTTC CTTTAATTGT GTAATCATAT ACTTTTCTTT TATCTTCATA
 351 AATATCTTTA CACGGTTCAG CAACGCCAGG TGAGTATGCT AAACTTAATT
 401 CCTCTTTATT AGTAACTTTT ACATTTGGTT TAACTTCTAA TTTACCTTGA
 451 TTACGTTTGT GCATTTCCAA TGCTTCATCT CTTAATGACA TGAAATCAGC
 501 CCCTAATTCA ATATTTATTT TTAAAAAATA ACTTGGATAA AACGCATTAC
 551 ATTATAAAAG TAAAAATATT GGGTAATCTG AATGARTAAG AATTTATGGT
 601 TTTGATTATG TAACACAAAT AGCGATAAAC GATAATAAAA TAATATTTAT
 651 AAAGATACAT TAAACCATAC TATCTAAAGA TATACCTTTA ATTATTATAA
 701 TGGATAGCAA AAACCAATAT ATCAAAAAGT TATTATTTTT CCGCACGATA
 751 TATCGACAAA ATTCTTTACT CAATTTATGT ATACTGCTTT TTGTGCTAAT
 801 TATTCTTATG GATTAATCAA TAATGTAAAG TGAAACTCAT AAAAATAATA
 851 AGCATAAAAA ACTAATATAA ACGCAAACTG ATGGTTAAAA AATATCTAAC
 901 CATCAGTTTA CTATATCATA ATTTATTAGT TGATAAAAGT TATATAAGCC
 951 TAATATCACT AGGGTTAAAG GGATTGTATA AAATTATTAA ACATACTATC
1001 TTTTTGATTA ATATAGCCTA AAGTAGTCAT TTGTTTAATC GTTTCATCAT
1051 AAAAGGATAA CACAACATCA TTAGCATTCT CTTTCGTAGC TTTAATCATC
1101 TCTTCAAACA TATCTATTTG TGATTTATTT CTAATTATAA TTTGTTTGGC
1151 AAATGCTAAT TTTTGTTCTT CAAAAGTGGC TAATGTCTGA ATCTCATTTA
1201 TAATTAGTTG ACGTTGTTGC TTTCTATGGT CAAATTTCCC GCTAACTATA
1251 AACAAGTCAT TATGTGATAA CAACTCTTCG TACTTTTTAA ACTGATTAGG
1301 GAAAATCACA CCATCTAAAG TTTCAATGCC ATCATTTAAT GTTGACGAAT
1351 GCCATATTTT GACCATTTTT AGTTCGAATT TGTTTAACTT TATCAAACTG
1401 TACTAATATA GGTTTATAAT TCTGCGCGTT ACTCAATTTA AATATCGTTA
1451 AATATTGTTT GGCAACAAAC TTTTTATCTA CTGGGTGTTG CGAAACATAA
```

-continued

```
1501 AATCCTAAAT ATTCTTTTTC GTACTGACTA ATAAGTGCAT CAGGCAATTC
1551 TTCTTTATCT TCATACATCT GTTTTGGCGT TAAAATATCA AATAAAAAAC
1601 CATCTTGTTC AATGTTTAAA TCGCCATCCA ACACTTGATC AATAGCTTGC
1651 AACAACGTTG AACGTGTTTT ACCAAAAGCA TCAAACGCTC CCACTAAAAT
1701 CAGTGCTTCA AGTAACTTTC TCGTTWTGAM YCTCTTCGGT ATACGTCTAG
1751 CAWAATCAAA GAAATCTTTA AATTTGCCGT TCTGATAACG TTCATCAACA
1801 ATCACTTTCA CACTTTGATA ACCAACACCT TTAATTGTAC CAATTGATAA
1851 ATAAATGCCT TCTTGGGAAG GTTTATAAAA CCAATGACTT TCGTTAATGT
1901 TCGGTGGCAA TATAGTGATA CCTTGTTTTT TTGCTTCTTC TATCATTTGA
1951 GCAGTTTTCT TCTCACTTCC AATAACATTA CTTAAAATAT TTGCGTAAAA
2001 ATAATTTGGA TAATGGACTT TTAAAAAGCT CATAATGTAT GCAATTTTAG
2051 AATAGCTGAC AGCATGTGCT CTAGGAAAAC CATAATCAGC AAATTTCAGA
2101 ATCAAATCAA ATATTTGCTT ACTAATGTCT TCGTGATAAC CATTTTGCTT
2151 TGSMCCTTCT ATAAAATGTT GACGCTCACT TTCAAGAACA GCTCTATTTT
2201 TTTTACTCAT TGCTCTTCTT AAAATATCCG CTTCACCATA ACTGAAGTTT
2251 GCAAATGTGC TCGCTATTTG CATAATTTGC TCTTGATAAA TAATAACACC
2301 GTAAGTATTT TTTAATATAG GTTCTAAATG CGGATGTAAA TATTGAACTT
2351 TGCTTGGATC ATGTCTTCTT GTAATGTAAG TTGGAATTTC TTCCATTGGA
2401 CCTGGTCTAT ACAAGAAGT TACAGCAACA ATATCTTCAA AGTGTTCCGG
2451 CTTTAATTTT TTTAATACAC TTCTTACACC GTCAGACTCT AATTGGAATA
2501 TGCCAGTCGT ATCTCCTTGC GACAACAATT CAAACACTTT TGATCATCA
2551 AACGGAATCT TTTCGATATC AATATTAATA CCTAAATCTT TTTTGACTTG
2601 TGTTAAGATT TGATGAATAA TCGATAAGTT TCTCAACCCT AGAAAATCTA
2651 TTTTTAATAA CCCAATACGT YCGGCTTCAG TCATTGTCCA TTGCGTTAAT
2701 AATCCTGTAT CCCCTTTCGT TAAAGGGGCA TATTCATATA ATGGATGGTC
2751 ATTAATAATA ATYCCTGCCG CATGTGTAGA TGTATGTCTT GGTAAACCTT
2801 CTAACTTTTT ACAAATACTG AACCAGCGTT CATGTCGATG GTTTCGATGT
2851 ACAAACTCTT TAAAATCGTC AATTTGATAT GCTTCATCAA GTGTAATTCC
2901 TAATTTATGT GGGATTAAAC TTGAAAATTT CATTTAATGT AACTTCATCA
2951 AACCCCATAA TTCTTCCAAC ATCTCTAGCA ACTGCTCTTG CAAGCAGATG
3001 AMCGAAAGTC ACAATTCCAG ATACATGTAG CTCGCCATAT TTTTCTTGGA
3051 CGTACTGAAT GACCCTTTCT CGGCGTGTAT CTTCAAAGTC AATATCAATA
3101 TCAGGCATTG TTACACKTTC TGGGTTTAAA AAACGTTCAA ATAATAGATT
3151 GAATTTAATA GGATCAATCG TTGTAATTCC CAATAAATAA CTGACCAGTG
3201 AGCCAGCTGA AGAACCACGA CCAGGACCTA CCATCACATC ATTCGTTTTC
3251 GCATAATGGA TTAAATCACT WACTATTAAG AAATAATCTT CAAAACCCAT
3301 ATTAGTAATA ACTTTATACT CATATTTCAA TCGCTCTAAA TAGACGTCAT
3351 AATTAAGTTC TAATTTTTTC AATTGTGTAA CTAAGACACG CCACAAATAT
3401 TTTTTAGCTG ATTCATCATT AGGTGTCTCA TATTGAGGAA GTAGAGATTG
3451 ATGATATTTT AATTCTGCAT CACACTTTTG AGCTATAACA TCAACCTGCG
```

-continued

```
3501 TTAAATATTT CTTGGTTAAT ATCTAATTGA TTAATTTCCT TTTTCAGTTA
3551 AAAAATGTGC ACCAAAATCT TTCTTGATCA TGAATTAAGT CTAATTTTGT
3601 ATTGTCTCTA ATAGCTGCTA ATGCAGAAAT CGTATCGGCA TCTTGACGTG
3651 TTTGGTAACA AACATTTTGA ATCCAAACAT GTTTTCTACC TTGAATCGAA
3701 ATACTAAGGT GGTCCATATA TGTGTCATTA TGGGTTTCAA ACACTTGTAC
3751 AATATCACGA TGTTGATCAC CGACTTTTTT AAAAATGATA ATCATATTGT
3801 TAGAAAATCG TTTTAATAAT TCAAACGACA CATGTTCTAA TGCATTCATT
3851 TTTATTTCCG ATGATAGTTG ATACAAATCT TTAATCCAT CATTATTTTT
3901 AGCTAGAACA ACTGTTTCGA CTGTATTTAA TCCATTTGTC ACATATATTG
3951 TCATACCAAA ATCGGTTTA ATGTTATTTG CTATACATGC ATCATAAAAT
4001 TTAGGAAAAC CATACAATAC ATTGGTGTCA GTTATGGCAA GTGCATCAAC
4051 ATTTTCAGAC ACAGCAAGTC TTACGGCATC TTCTATTTTT AAGCTTGAAT
4101 TTAACAAATC ATAAGCCGTA TGAATATTTA AATATGCCAC CATGATTGAA
4151 TGGCCCCTTT CTATTAGTTA AGTTTTGTGC GTAAAGCTGT AGCAAGTTGC
4201 TCAAATTCAT CCCAGCTGTC CAACTGAAAY TCCTGACGCA TTCGGATGAC
4251 CACCGCCACC AAAATCTTGC GCAATATCAT TAATAATCAA TTGCCCTTTA
4301 GAACGTAATC GACATCTGAT TTCATTACCT TCATCGACTG CAAATACCCA
4351 TATTTTCAAG CCTTTGATGT CAGCAATTGT ATTAACAAAC TGAGATGCTT
4401 CATTTGGCTG AATACCGAAT TGCTCCAATA CATCTTCAGT TATTTTAACT
4451 KGGCAGAATC CATCATCCAT AAGTTCGAAA TGTTGYAAAA CATAACCTTG
4501 AAACGGCAAC ATTKYTGGGT CCTTCTCCAT CATTTTATTT AAAAGCGCAT
4551 TATGATCAAT ATCATGCCCA ATTAACTTTC CAGCAATTTC CATAGTATGT
4601 TCWGAGGTAT TGTTAAAAAG GRGATCGCCC AGTATCACCG ACGATACCAA
4651 GATATAAAAC GCTCGCGATA TCTTTATTAA CAATTGCTTC ATCATTAAAA
4701 TGTGAGATTA AATCGTAAAT GATTTCACTT GTAGATGACG CGTTCGTATT
4751 AACTAAATTA ATATCACCAT ACTGATCAAC TGCAGGATGA TGATCTATTT
4801 TAATAAGTYT ACGACCTGTA CTATAACGTT CATCGTCAAT TCGTGGAGCA
4851 TTGGCAGTAT CACATACAAT TACAAGCGCA TCTTTATATG TTTTATCATC
4901 AATGTTATCT AACTCTCCAA TAAAACTTAA TGATGATTCC GCTTCACCCA
4951 CTGCAAATAC TTGCTTTTGC GGAAATTTCT GCTGAATATA GTATTTAAA
5001 CCAAGTTGTG AACCATATGC ATCAGGATCK RSTYTARMRK RTCYSYGKMT
5051 AMYRATTGYA TCGTTGTCTT CGATACATTT CATAATTTCA TTCAAAGTAC
5101 TAATCATTTT CAWACTCCCT TTTTAGAAA AGTGGCTTAA TTTAAGCATT
5151 AGTCTATATC AAAATATCTA AATTATAAAA ATTGTTACTA CCATATTAAA
5201 CTATTTGCCC GTTTTAATTA TTTAGATATA TATATTTTCA TACTATTTAG
5251 TTCAGGGGCC CCAACACAGA GAAATTGGAC CCCTAATTTC TACAAACAAT
5301 GCAAGTTGGG GTGGGGCCCC AACGTTTGTG CGAAATCTAT CTTATGCCTA
5351 TTTTCTCTGC TAAGTTCCTA TACTTCGTCA AACATTTGGC ATATCACGAG
5401 AGCGCTCGCT ACTTTGTCGT TTTGACTATG CATGTTCACT TCTATTTTGG
5451 CGAAGTTTCT TCCGACGTCT AGTATGCCAA AGCGCACTGT TATATGTGAT
```

```
5501 TCAATAGGTA CTGTTTTAAT ATACACGATA TTTAAGTTCT CTATCATGAC

5551 ATTACCTTTT TTAAATTTAC GCATTTCATA TTGTATTGTT TCTTCTATAA

5601 TACTTACAAA TGCCGCTTTA CTTACTGTTC CGTAATGATT GATTAAAAGT

5651 GGTGAAACTT CTACTGTAAT TCCATCTTGA TTCATTGTTA TATATTTGGC

5701 GATTTGATCC TCTAGAGT
```

Figure 51:
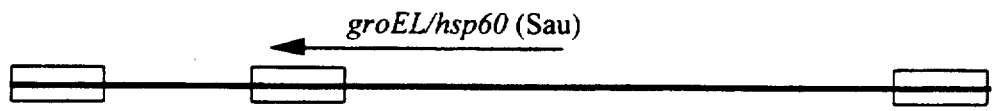

Mutant: NT78
Phenotype: temperature sensitivity
Sequence map: Mutant NT78 is complemented by pMP115, which contains a 5.3 kb insert of *S. aureus* genomic DNA. A partial restriction map is depicted FIG. 51, along with open boxes to indicate the percentage of the clone for which DNA sequence has been obtained. Database searches at both the nucleic acid and peptide levels reveal no significant similarities between the sequences obtained at the left-most and right-most edges and any published sequences. The sequence generated from a Msp I subclone, however, matches at both the nucleic acid and peptide level to hsp60, encoding the GroEL protein from *S. aureus* (Genbank Accession No. D14711). The relative size and orientation of the GroEL ORF is depicted by an arrow; other proteins (i.e.

GroES) are known to reside near the identified ORF and will be confirmed by further DNA sequencing.

DNA sequence data: The following DNA sequence data represents the sequence generated bye sequencing the left-most and rightmost edges of pMP115 and its subclone 78.3, starting with standard M13 forward and M13 reverse sequencing primers. The sequence below can be used to design PCR primers for the purpose of amplification from genomic DNA with subsequent DNA sequencing.

```
         clone pMP115, a 5,300 bp genomic fragment            SEQ ID NO. 49
         pMP115.m13f Length: 513 nt
           1 TTCTTGCCTC CCAATCGCCT AATAGCCCTN AAAACTACTT TTTTTAATCT

51 ATAGGCGATG TAAAAATACC ATATATTGAN GGTGCTATAC CTCCTAAAAT

101 AGCAGTTCCC AAAGTTGTCA TTACTGAAAT TACTGCGAAA GTATCATCCG

151 AAAGCAATAA ATTCAAACTA ATGCATTGTT TATTACCCAT CGAATTTATT

201 GACCAAATAG CTAGAGAAAT AAACAACCCA AAATTTAAAA TAAATGATAT

251 AGTAATAGCA ATTGTTTACA AAACACGGAA TTTTTCATTT TTATTTATAT

301 TATCCATTTT NCTCCCTTTT NCTTAAATCA TTTTATTATA TATTNCAATA

351 ATCAATCTGA AATGTTGATG TAATTTGNNA AAAATATCAT ACTTTTNCTC

401 CTGAAAACCT CCCTAAATCA TCAATATGGN AATCNGTTTT NGGGTATTGC

451 GNTTNCAACT CTTTTAAANC TCACTCNTTC TTCTCATCGN CTTAACCGTA

501 CTATCANTAA AAT
         pMP115.m13r Length: 533 nt                             SEQ ID NO. 50
           1 CTGAGCTGCT TNCANNNCCA NTNTGAAAAA GCCCCCAGNN CAGCCCGNTT

51 NCAAAACAAC GNCTNCATTT GAANCCCCAT GAAAAAGAAC GAATTTTGAC

101 AATGGNTTAA AAAACANGNA AGATAATAAG AAAAAGTGCC GTCAACTTCA

151 TATAGTAAAA GTTGGCTAGC AATTGTATGT NCTATGATGG TGGTATTTTC

201 AATCATGCTA TTCTTATTTG TAAAGCGAAA TAAAAAGAAA AATAAAAACG

251 AATCACAGCG ACGNTAATCC GTGTGTGAAT TCGTTTTTTT TATTATGGAA

301 TAAAAATGTG ATATATAAAA TTCGCTTGTC CCGTGGCTTT TTTCAAAGCC

351 TCAGGNTTAA GTAATTGGAA TATAACGNCA AATCCGTTTT GTAACATATG

401 GGTAATAATT GGGAACAGCA AGCCGTTTTG TCCAAACCAT ATGCTAATGN

451 AAAAATGNCA CCCATACCAA AATAAACTGG GATAAATTTG GNATCCATTA

501 TGTGCCTAAT GCAAATNCCT NATGACCTTC CTT
```

The following DNA sequence data were acquired using standard sequencing methods and the commercially-available T7 and SP6 primers and can be used to demonstrate identity to the GroEL protein from *S. aureus*:

```
78.3.sp6 Length: 568 nt                                  SEQ ID NO. 51
    1 CCGACAGTCG TTCCCNTCAT GCAAAATATG GGGGCTAAAC TCAGTTCAAG

51 AAGTCGGCAA ATAAGACAAA TGAAATTGCC TGGTGACGGT AGNACAACTG

101 CAACAGTATT AGCTCAAGCA ATGATTCAAG AAGGCTTGAA AAATGTTACA

151 AGTGGTGCGA ACCCAGTTGG TTTACGACAA GGTATCGACA AAGCAGTTAA

201 AGTTGCTGTT GAAGCGTTAC ATGAAAATTC TCAAAAGTT GAAAATAAAA

251 ATGAAATTNC GCAAGTAGGT GCGNTTTCAG CAGCAGATGN AGNAATTNGA

301 CGTTATATTT CTGAAGCTAT NGGNAAAGTA GGTAACGNTG GTGTCATTAC

351 ANTTNTNGGG TCAAATGGGC TNTNCACTNN NCTNGANGTG GTTGNNGGTG

401 TNCNATTTGA TCNNNGTTAT CANTCACCNN CTATNGTTAC TGCTTCNGCT

451 AAAATGGTTG CTGCNTTTGG NCGCCCCTAC ATTTTTGTNA CNGCTTNGGG

501 ANTCTCGTCT TTNCNCGATT CTTTCCCCTT TTTGGCCCNT GGGNAATCTT

551 TTNGGNCNCC CTTTATTT
```

Figure 52:
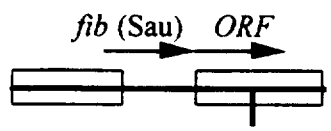

Mutant: NT81
Phenotype: temperature sensitivity
Sequence map: Mutant NT81 is complemented by clone 81-3, which contains a 1.7 kb insert of *S. aureus* genomic DNA. A partial restriction map is depicted FIG. 52, along with open boxes to indicate the percentage of the clone for which DNA sequence has been obtained. Database searches at both the nucleic acid and peptide levels reveal identity to the fib locus, encoding a fibrinogen binding protein, from *S. aureus* (Genbank Accession No. X72013; published in Boden, M. K. et al., *Mol. Microbiol.* 12 (1994) 599–606.)

The relative size and orientation of the Fib ORF with respect to the restriction map is depicted by an arrow; also identified in this analysis is an ORF of unknown function downstream from (3' to) the Fib ORF.

DNA sequence data: The following DNA sequence data represent the sequences at the left-most and right-most edges of subclones pMP1043 and pMP1042, using standard SP6 and T7 sequencing primers. The sequences below can be used to design PCR primers for the purpose of amplification from genomic DNA with subsequent DNA sequencing:

```
subclone 1042, a 400 bp Hind III fragment                SEQ ID NO. 52
1042.con Length: 437 nt
    1 CAAYTTAGYC AACTACTACC AATATAGCAC TAGAACTGGA AATGATAATT

51 TAATATTGKG CACTTTTTSA TTGKTTAAAC ATGTACATAT TTNAAAAAAT

101 AGGAGAGCAA AGKAAATAAT TGATATAGTT ATTTTSAGAG TAATCCTAGG

151 AACTATTGTA TTTATATTTS TCTCCCCTAC TTTTAAATGT CATTCATTAT

201 ACATAAGCAT TTTGATATAG AATTTATCAC ATATGCAAAT TGAAAACAGG

251 TTAAGACCAT TTTTTGTCTC AACCTGTTTT ATTTATTATC TATTTTTAAT

301 TTCATCAATT TCTTTGTATA TTTTTYCTAA TGCAACTTTA GCATCAGCCA

351 TTGATACGAA ATCATTTTYC TTAAGTGCCG CTTTAGCTCT ATATTCATTC

401 ATYATAATCG TACGTTTATA ATATGGATTT ACGTTGA subclone 1043, a 1300 bp EcoR I/Hind III fragment         SEQ ID NO. 53
1043.t7 Length: 659 nt
    1 CCCGATTCGA GCTCGGTACC GGNGATCCTC TAGAGTCGAT CTATCAAGCA

51 GTAAATGAAA AAATGGACAT TAATGATATT AATATCGACA ATTTCCAATC

101 TGTCTTTTTT GACGTGTCTA ATTTGAATTT AGTAATTCTA CCAACGTTAA

151 TCATTAGCTG GGTCACAATA TTTAACTATA GAATGAGAAG TTACAAATAA

201 AATCTATGAG ATTATACCTN CAGACACCAA CATTCAAATG GTGTCTTTTN

251 TGTTGTGTGG TTTTATTTNT GAAATNCGAA AAAGTAGAGG CATGAATTTT

301 GTGACTAGTG TATAAGTGCT GATGAGTCAC AAGATAGATA GCTATATTTT

351 GTCTATATTA TAAAGTGTTT ATAGNTAATT AATAATTAGT TAATTTCAAA
```

-continued

```
401 AGTTGTATAA ATAGGATAAC TTAATAAATG TAAGATAATA ATTTGGAGGA

451 TAATTAACAT GAAAAATAAA TTGATAGCAA AATCTTNATT AACATTAGGG

501 GCAATAGGTA TTACTACAAC TACAATTGCG TCAACAGCAG ATGCGAGCGA

551 AGGATACGGT CCAAGAGAAA AGAAACCAGT GAGTATTAAT CACAATATCG

601 NAGAGTACAA TGATGGTACT TTTAATATCA ATCTTGANCA AAATTACTCA

651 ACAACCTAA
```

```
1043.sp6 Length: 298 nt                              SEQ ID NO. 54
   1 AATNCTCCTC CNATGNTTTA TNATGAAACT AACTTTAAGT NAAATATTTN

51 TCCAGACTAC TTGCATCTCC NTTATNCCCT TCTATAGTTN CTATCCCAGT

101 TNATGATAAA AGTAATGCTA ATGTNCCTGT NAATATATAT TTNTAAAATT

151 NNATTATAAG CNCTCCTTAA AATTNATACT TACTGAGTAT ATAGTCAATT

201 TNNGGACAAT TACATTAACC TGTCATTAAA TNGATTACTT TTTNNATTAA

251 CAAAAATTAA CATAACATTT AATTAATTNT TTCCNGATAN CAGCAACG
```

Figure 53:
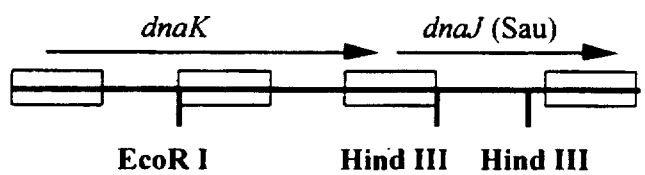

Mutant: NT86
Phenotype: temperature sensitivity
Sequence map: Mutant NT86 is complemented by pMP121, which contains a 3.4 kb insert of *S. aureus* genomic DNA. A partial restriction map is depicted FIG. 53, along with open boxes to indicate the percentage of the clone for which DNA sequence has been obtained. Database searches at both the nucleic acid and peptide levels reveal identity at the nucleic and peptide levels to the dnaK/dnaJ genes, encoding Hsp70 and Hsp40, from *S. aureus* (Genbank Accession No. D30690; published in Ohta, T. et al. *J. Bacteriol.* 176 (1994) 4779–4783). Cross complementation studies (plasmid pMP120; data not shown) reveal that the ORF responsible for restoring a wild-type phenotype to mutant NT86 codes for Hsp40. The relative sizes and orientations of the identified genes are depicted in the restriction map by arrows.
DNA sequence data: The following DNA sequence data represent the sequences at the left-most and right-most edges of clone pM121, using standard M13 forward and M13 reverse sequencing primers. The sequences below can be used to design PCR primers for the purpose of amplification from genomic DNA with subsequent DNA sequencing:

```
clone pMP121, a 3400 bp genomic fragment              SEQ ID NO. 55
pMP121.m13f Length: 535 nt
   1 TCCAAATATT CACCAAGCTG TAGTTCAAGA TGATAACCCT NATTTTAANT

51 CTGGCGAAAT CACTCAAGAN CTACAAAAAG GATACAAGCT TAAAGATAGA

101 GTATTAAGAC CATCANTGGT CAAAGTAAAC CAATAACTTA AATTTGGCGA

151 AAAGACATTG TTTAAAATTA ANTTAATTTA ATGATTAATT GGAGGGATTT

201 TTTTATGAGT AAAATTTTTG GTATAGACTT AGGTACAACA NATTCATGTG

251 TAACAGTATT AGANGGCGAT GAGCCAAAAG TAATTCAAAA CCCTGANGGT

301 TCACGTACAA CACCATCTGT NGTAGCTTTC AAAAATGGAG AAACTCAAGT

351 TGGTGGAGTA GCAAAACGTC AAGCTATTAC AAACCCAAAC ACTGTTCANT

401 CTATTAGNCG TCATATGGGT ACTGNTTATA ANGTAGATAT TGAGGGTAAA

451 TCATACACAC CACAAGNNNT CTCAGCTNTG NTTTTNCAAA ACTTANNANT

501 TNCAGCTGNA GTNATTTAGG TGNGNNNGTT GNCAA
```

```
pMP121.m13r Length: 540 nt                            SEQ ID NO. 56
   1 ATGACTGCAG GTCGATCCAT GATTTACAAG TATATTGGTA GCCAATTCTA

51 CTGCTTCATG ATTAATAATA ATTGAAAGCT CTGTCCAGTT CATACTTTAT

101 TCTCCCTTAA AGAATCTTTT TGNTCTATCT TTAAAATTCG AAGGTTGTTC

151 ATTAATTTCT TCACCATTTA ATTGGGCAAA TTCTTTCATT AGTTCTTTNT

201 GTCTATCTGT TAATTTAGTA GGCGTTACTA CTTTAATATC AACATATAAA

251 TCTCCGTATC CATAGCCATG AACATTTTTT ATACCCTTTT CTTTTAAGCG
```

```
-continued
301 GAATTGCTTA CCTGTTTGTG TACCAGCAGG GGATTGTTAA CATAACTTCA

351 TTATTTAATG TTGGTATTTT TATTTCATCG CCTAAAGCTG CTTGTGGGAA

401 GCTAACATTT AATTTGNAAT AAATATCATC ACCATCACGT TTAAATGTTT

451 CAGATGGTTT AACTCTAAAT ACTACGTATT AATCANCAGG AGGTCCTCCA

501 TTCACGGCTG GAGAGGCTTC AACAGCTAAT CTTATTTGGT
```

The following DNA sequence data were acquired using standard sequencing methods and the commercially-available T7 and SP6 primers and can be used to demonstrate identity to the Hsp40 protein from S. aureus.

(guanine-N1-) methyltransferase (EC 2.1.1.31), from various prokaryotes, including S. marcescens (Genbank Accession No. L23334; published in Jin, S. et al. Gene 1 (1994) 147–148), H. influenzae, E. coli, and S. typhimurium. The

```
subclone 1116, a 1400 bp Ecor I/Hind III fragment          SEQ ID NO. 57
1116.sp6 Length: 536 nt
    1 TTTATAATTT CATCTNTTGA AGCATCCTTA CTAATGCCTA AAACTTCATA

51 ATAATCTCTT TTGGCCACAG CTATCTCTCC TTTNCTNAAT TAACTCATAT

101 AGTTTAACGT AATATGTCAT ACTATCCAAA TAAAAAGCCA AAGCCAATGT

151 NCTATTGACT TTNACTTTTC ANATCATGAC AACATTCTAA TTGTATTGTT

201 TAATTATTTT NTGTCGTCGT CTTTNACTTC TTTAAATTCA GCATCTTCTA

251 CAGTACTATC ATTGTTTTNA CCAGCATTAG CACCTTGTNT TGTTGTTGCT

301 GTTGAGCCGC TTGCTCATAT ACTTTTNCTG NTAATTCTTG ANTCACTTTT

351 TCAAGTTCTT CTTTTTTAGA TTTANTATCT TCTATATNCT TGACCTTTCT

401 AANGCAGTTT TAAGAGCGTC TTTTTTCCTC TTTCTGCAGT TTTTTTATAC

451 TTCCTTTCAC CGTNATTTTT CGGCTTATTT CAGTTAAANG TTTTTCCANC

501 TTGGGTNTAN CTATGGCTAG NAAAGNTTCG NTTCCT 1116.t7 LENGTH: 537 nt                                     SEQ ID NO. 58
    1 AAGATAAAAT GGCATTACAA CGTTTNAAAG ATGCTGCTGA AAAANCTAAA

51 AAAGACTTAT CAGGTGTATC ACAAACTCAA ATCTCATTAC CATTTATCTC

101 AGCTGGTGAA AACGGTCCAT TACACTTAGA AGTAAACTTA ACTCGTNCTA

151 AATTTGAAGA ATTATCAGAT TCATTAATTA GAAGANCAAT GGAACCTACA

201 CGCCAAGCAA TGAAAGACGC TGGCTTAACA AACTCAGATA TCGATAAAGT

251 TATCTTAGTT GGTGGNTCAA CTCGTATTCC AGCAGTACAA GANGCTGTCA

301 AAAAAGAAAT CGGTAAAGAG CCTAACAAAG GAGTAAACCC GGNCGAAGTA

351 GGTGGCAATG GGNGCTGCAA TCCAAGGTGG CGTTATTCAC AGGTGACGTT

401 TAAAGACGTG TATTATTAGG NCGTAACACC ACTATCTTTA GGTATTAAA

451 TTTTAGGTGG NCGTATGNAT TACGGTAATT GAACGTAACA CTACGGTTCC

501 TNCATTCTAA NTCTCAAAAT CTNTTCAACA GCAGTT
```

Mutant: NT89

Phenotype: temperature sensitivity

Figure 54:
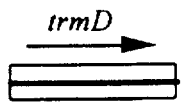

Sequence map: Mutant NT89 is complemented by pMP122, which contains a 0.9 kb insert of S. aureus genomic DNA. A partial restriction map is depicted FIG. 54, along with open boxes to indicate the percentage of the clone for which DNA sequence has been obtained. Database searches at both the nucleic acid and peptide levels reveal a high level of similarity at the peptide level to the trmD gene, encoding predicted size and relative orientation of the TrmD ORF is depicted by an arrow.

DNA sequence data: The following DNA sequence data represent the sequences at the left-most and right-most edges of clone pM122, using standard M13 forward and M13 reverse sequencing primers. The sequence below can be used to design PCR primers for the purpose of amplification from genomic DNA with subsequent DNA sequencing; it can also be used to demonstrate similarity to the trmD gene of S. marcescens:

```
clone pMP122, a 925 bp genomic fragment              SEQ ID NO. 59 pMP122.con Length: 925 nt

1 CTAGAGTCGA TCTAAAGAAT ATNTAANTCC TNATATKSCT GATGTTGTAA
  51 AAGAAGTGGA TGTTGAAAAT AAAAAAATTA TCATCACGCC AATGGAAGGA
 101 TTGTTGGATT AATGAAAATT GATTATTTAA CTTTATTTCC TGAAATGTTT
 151 GATGGTGTTT TAAATCATTC AATTATGAAA CGTGCCCANG AAAACAATAA
 201 ATTACAAATC AATACGGTTA ATTTTAGAGA TTATGCAATT AACAAGCACA
 251 ACCAAGTAGA TGATTATCCG TATGGTGGCG GWCAAGGTAT GGTGTTAAAG
 301 CCTGACCCTG TTTTTAATGC GATGGAAGAC TTAGATGTCA CAGAMCAAAC
 351 ACGCGTTATT TTAATGTGTC CACAAGGCGA GCCATTTTCA CATCAGAAAG
 401 CTGTTGATTT AAGCAAGGCC GACCACATCG TTTTCATATG CGGACATTAT
 451 GAAGGTTACG ATGAACGTAT CCGAACACAT CTTGTCACAG RTGAAATATC
 501 AATGGGTGAC TATGTTTTAA CTGGTGGAGA ATTGCCAGCG ATGACCATGA
 551 CTGATGCTAT TGTTAGACTG ATTCCAGGTG TTTTAGGTAA TGNACAGTCA
 601 CATCAAGACG ATTCATTTTC AGATGGGTTA TTAGAGTTTC CGCAATATAC
 651 ACGTCCGCGT GAATTTAAGG GTCTAACAGT TCCAGATGTT TTATTGTCTG
 701 GAAATCATGC CAATATTGAT GCATGGAGAC ATGAGCAAAA GTTGAACCGC
 751 ACATATAATN AAAGACCTGA CTTAATTNNA AAATACCCAT TAANCCAATG
 801 GCAGCATAAG GCAAATCATT CAGNAAANAT CATTAAAATC AGGTATTNGT
 851 AAAAAGGTTN AGTGATTGTG NNNAACNNNN TNGNATGTGG CAAACATNCN
 901 AANTACATCC TGGAAGGACC TCACG
```

Mutant NT94

Phenotype: temperature sensitivity

Figure 55:
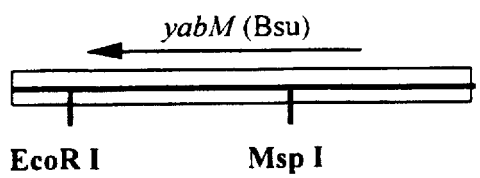

Sequence map: Mutant NT94 is complemented by pMP170, which contains a 2.5 kb insert of *S. aureus* genomic DNA. A partial restriction map is depicted FIG. 55. Database searches at both the nucleic acid and peptide levels reveal strong peptide-level similarities to yabM, a hypothetical ORF of uncharacterized function from *B. subtilis*, noted as being similar to the spoVB gene from *B. subtilis*; further similarities are noted to hypothetical ORFs from *E. coli* and *H. influenzae*.

DNA sequence data: The following DNA sequence data represents the sequence generated by primer walking through clone pMP170, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP170                                         SEQ ID NO. 60 pMP170 Length: 2531 nt

1 TGGYTTRTTT CAACATAATA TAGACATTTY CAATGTTATT CTATTAATTC
  51 TCCACGAAAC TGTTATCTTA TCGTTTTCTG GTTCTAATAT GTGTTTTTTG
 101 GGTGATTTAA TTACTTGTTC CGTTGAACAT TTACAAGGCC TTTTTTAAGT
 151 TAACTGTTTG ACCTCATTAC GTGTACCGAC GCCCATATTT GCTAAAAATT
 201 TATCTATTCT CATCGTAAAA ACCTAACTCT ACGTCTTAAT TTTTCAGGAA
 251 TTTCACCTAA GAATTCGTCC GCAAGACGCG TTTTAATTGT GAWTGTACCG
 301 TAAATTAGAA TACCTACTGT AACACCTAAA ATAATAATGA TTAAGTWACC
 351 AAGTTTTAGT AGGTYCTAAR AATARATTTG CAAGGNAAAA TACTAATTCT
 401 ACACCTAGCA TCATAATNNT GNATACAAGG ATATWTWTGC AAAATGGATC
```

-continued

```
 451 CCAACTATAG CTGAATTTAA ACTTCGCATA TWTTTTAAGR ATWTAGRAAT
 501 TACATCCMAT TGCAAATAAT TAATGCGATA CTAGTACGTA AAATTGCACC
 551 AGGTGTATGG AATAACATAA TTAATGGATA GTTTAACGCT AACTTGATAA
 601 CTACAGAAGC TAAAATAACA TAAACTGTTA ATTTCTGTTT ATCTATACCT
 651 TGTAANATNG ATGCCGTTAC ACTTAATAGT GAAATYAGTA TTGCTACAGG
 701 CGCATAATAK AATAATAAGC GACTACCATC ATGGTTAGGG TCATGACCTA
 751 WAACAATTGG ATCGTAACCA TAGATAAACT GTGAAATTAA TGGTTGTGCC
 801 AAGGCCATAA TCYCCAATAC TAGCTGGGAA CAGTTATAAA CATTWAGTTA
 851 CACCAATTAG ATGTTCCTAA TTTGATGATG CATTTCATGT AAGCGACCTT
 901 CTGCAAATGT TTTTGTAATA TAAGGAATTA AACTCACTGC AAAACCAGCA
 951 CTTAATGATG TCGGAATCAT TACAATTTTA TTAGTTGACA TATTTAGCAT
1001 ATTAAAGAAT ATATCTTGTA ACTGTGAAGG TATACCAACT AAAGATAAAG
1051 CACCGTTATG TGTAAATTGA TCTACTAAGT TAAATAATGG ATAATTCAAA
1101 CTTACAATAA CGAACGGTGA TACTATAAGC AATAATTTCT TTATACATCT
1151 TGCCATATGA CACATCTATA TCTGTGTAAT CAGATTCGAC CATACGATCA
1201 ATATTATGCT TACGCTTTCT CCAGTAATAC CAGAGTGTGR ATATRCCAAT
1251 AATCGCACCA ACTGCTGCTG CAAAAGTAGC AATACCATTG GCTAATAAAA
1301 TAGAGCCATC AAAGACATTT AGTACTAAAT AACTTCCGAT TAATATGAAA
1351 ATCACGCGTG CAATTTGCTC AGTTACTTCT GACACTGCTG TTGGCCCCAT
1401 AGATTTATAA CCTTGGAATA TCCCTCTCCA TGTCGCTAAT ACAGGAATAA
1451 AGATAACAAC CATACTAATG ATTCTTATAA TCCAAGTTAA TATCATCCGA
1501 CTGACCAACC GTTTTTATCA TGAATGTTTC TAGCTAATGT TAATTCAGAA
1551 ATATAAGGTG YTAAGAAATA CAGTACCAAG AAACCTAAAA CACCGGTAAT
1601 ACTCATTACA ATAAAAYTCG ATTTATAAAA WTTCTGACTT WACTTTAWAT
1651 GCCCCAATAG CATTATATTT CGCAACATAT TTCGAAGCTG CTAATGGTAC
1701 ACCTGCTGTC GCCAACTGCA ATTGCAATAT TATATGGTGC ATAAGCGTWT
1751 GTTGAACGGS GCCATATTTT CTTGTCCCNC CAATTAAATA GTTGAATGGA
1801 ATGATAAAAA GTACGCCCAA TACCTTGGTA ATTAATATAC TAATGGTAAT
1851 TAAAAAGGTT CCACGCACCA TTTCTTTACT TTCACTCATT ACGAATCTCC
1901 CTATCTCATG TTTATTAAAG TTTTGTAAAC TAAAAGCTGT TTCTCTGTAA
1951 AATCATTTTT CATTATTATG AATATATCAC AAAACTTTAT TTCATYGTCG
2001 TATATTTCAA TGGAATTATC CATAACAAAA TTATCAACAC ATTGTCATTG
2051 AATACTAGAT TTTGATTAGA ATATTACGAA ATTTCATATA AACATTATAC
2101 TACTATTTGA GATGAACATC GCATAACAGT AGAAAAATCA TTCTTATCAT
2151 ACACATACAT CTTCATTTTT TATGAAGTTC ACATTATAAA TATATTCAAC
2201 ATAATTGTCA TCTCATAACA CAAGAGATAT AGCAAAGTTT AAAAAAGTAC
2251 TATAAAATAG CAATTGAATG TCCAGTAACA AATTTGGAGG AAGCGTATAT
2301 GTATCAAACA ATTATTATCG GAGGCGGACC TAGCGGCTTA ATGGCGGCAG
2351 TAGCWGCAAG CGAACAAAGT AGCAGTGTGT TACTCATTGA AAAAAGAAA
2401 GGTCTAGGTC GTAAACTCAA AATATCTGGT GGCGGTAGAT GTAACGTAAC
```

```
-continued
2451 TAATCGAYTA CCATATGCTG AAATTATTCA AGGAACATTC CCTGGAAATG

2501 GGAAATTTTY ATCATAGTTC CCTTTTCAAT T
```

Figure 56:
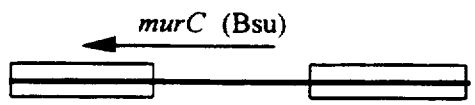

Mutant: NT96
Phenotype: temperature sensitivity
Sequence map: Mutant NT96 is complemented by pMP125, which contains a 2.6 kb insert of *S. aureus* genomic DNA. A partial restriction map is depicted FIG. 56, along with open boxes to indicate the percentage of the clone for which DNA sequence has been obtained. Database searches at both the nucleic acid and peptide levels reveal strong similarities at the peptide level to the murC gene product, encoding UDP-N-Acetyl muramoyl-L-alanine synthase (EC 6.3.2.8), from *B. subtilis* (Genbank Accession No. L31845).

DNA sequence data: The following DNA sequence data represent the sequences at the left-most and right-most edges of clone pM125, using standard M13 forward and M13 reverse sequencing primers. The sequences below can be used to design PCR primers for the purpose of amplification from genomic DNA with subsequent DNA sequencing:

```
            clone pMP125                                    SEQ ID NO. 61 pMP125.forward Length: 889 nt

1 TCGAGCTCGG TACCCGGGGA TCCTCTAGAG TCGATCTACA GAGCTGTTTA

51 ACGTTTGTAC TGAGTCACCG ATACCTTTAA CAGCATCTAC AACTGAGTTT

101 AAACGATCTA CTTTACCTTG GATATCCTCA GTTAAACGGT TTACTTTATG

151 AAGTAAATCT GTTGTTTCAC GAGTAATACC TTGAACTTGA CCTTCTACAC

201 CGTCAAGTGT TTTTGCAACA TAATCTAAGT TTTTCTTAAC AGAATTTAAT

251 ACAGCTACGA TACCGATACA TAAAATTAAG AATGCAATCG CAGCGATAAT

301 TCCAGCAATT GGTAAAATCC AATCCATTAA AAACGCCTCC TAATTAACAT

351 GTAATAATGT CATTAATAAT AAATACCCAT ACTACTCTAT TATAAACATA

401 TTAAAACGCA TTTTTCATGC CTAATTTATC TAAATATGCA TTTTGTAATT

451 TTTGAATATC ACCTGCACCC ATAAATGAAA ATAACAGCAT TATCAAATTG

501 TTCTAATACA TTAATAGAAT CTTCATTAAT TAACGATGCA CCTTCAATTT

551 TATCAATTAA ATCTTGTWTC GTTAATGCGC CAGTATTTTC TCTAATTGAT

601 CCAAAAATTT CACAATAAGA AATACACGAT CTGCTTTACT TAAACTTTCT

651 GCAAATTCAT TTAAAAATGC CTGTGTTCTA GAGAAAGTGT GTGGTTTGAN

701 ATACTGCAAC AACTTCTTTA TGTGGATATT TCTTTCGTGC GGTTTCAATT

751 GNNGCACTAA NTTCTCTTGG ATGGTGTNCA TAATCAGCTA CATTAACTTG

801 ATTTGCGATT GTAGTNTCAT NGANNGACGT TTAACNCCAC CAACGTTTCT

851 AATGCTTCTT TAANATTGGG ACATCTAACT TCTCTAAA pMP125.reverse Length: 902 nt                      SEQ ID NO. 62

1 GCATGCCTGC AGGTCGATCC AAAAATGGTT GAATTAGCTC CTTATAATGG

51 TTTGCCMMMT TTRGTTGCCA CCGKTAATTA CAGATGTCMA AGCCAGCTAC

101 ACAGAGTTTG AAAAKGGSCC STWGAAAGGA AATGGAACGA ACGTKATAAG

151 TTATTTGCCA CATTACCATG TACGTAATAT AACAGCCATT TAACAAAAAA

201 GCCACCATAT GATGAAAGAW TGCCAAAAAT TGTCATTGTA ATTGATGAGT

251 TGGCTGATTT AATGATGATG GCTCCGCAAG AAGTTGAACA GTCTATTGCT

301 AGAATTGCTC AAAAAGCGAG AGCATGTGGT ATTCATATGT TAGTAGCTAC

351 GCAAAGACCA TCTGTCAATG TAATTACAGG TTTAATTAAA GCCAACATAC

401 CAACAAGAAT TGCATTTATG GTATCATCAA GTGTAGATTC GAGAACGATA
```

-continued

```
451 TTAGACAGTG GTGGAGCAGA ACGCTTGTTA GGATATGGCG ATATGTTATA

501 TCTTGGTAGC GGTATGAATA AACCGATTAG AGTTCAAGGT ACATTTGTTT

551 CTGATGACGA AATTGATGAT GTTGTTGATT TTATCAAACA ACAAAGAGAA

601 CCGGACTATC TATTTGAAGA AAAAAGAAAT TGTTGAAAAA AACACAAACA

651 CMATCMCMAG ATGAATTATT TGATGATGTT TGTGCATTTA TGGTTAATGA

701 AGGACATATT TCAACATCAT TAATCCAAAG ACATTTCCAA ATTGGCTATA

751 ATAGAGCAGC AAGAATTATC GATCAATTAG AAGCAACTCG GTTATGTTTC

801 GAGTGCTAAT NGGTTCAAAA ACCNAGGGAT GTTTATGTTA CGGAAGCCGA

851 TTTTAAATAA AGAATAATTT ATGATTAAGG ATTTTTATAT AATGGACACC

901 CC
```

Figure 57:
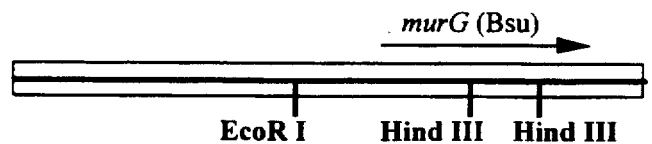

Mutant: NT99
Phenotype: temperature sensitivity
Sequence map: Mutant NT99 is complemented by pMP176, which contains a 3.6 kb insert of *S. aureus* genomic DNA. A partial restriction map is depicted FIG. 57. Database searches at both the nucleic acid and peptide levels reveal strong similarity at the peptide level to the murG gene, encoding UDP-GlcNAc:undecaprenyl-pyrophosphoryl-pentapeptide transferase, from *B. subtilis* (Genbank Accession No. D10602; published in Miyao, A. et al. *Gene* 118 (1992) 147–148.) Cross complementation studies (data not shown) have demonstrated that the minimal amount of clone pMP176 required for restoring a wild-type phenotype to mutant NT99 is contained in the right-half of the clone and contains the entire (predicted) murG ORF; the predicted size and orientation of this ORF is depicted in the restriction map by an arrow.

DNA sequence data: The following DNA sequence data represents the sequence generated by primer walking through clone pMP176, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP176                                        SEQ ID NO. 63 pMP176 Length: 3592 nt

1 GATCCTTATT CTGAATATTT AACAAAWGCA ACAAACGAAA TCCCTTTGAA

51 TGAAAGGTGT TTCAGGTGCA TTTTKTAGGT ATTGGTGCAG AAAATGCAAA

101 AGAAAAATGA ATCAAATTAT GGTTACTAGT CCTATGAAGG GWTCTCCAGC

151 AGAACGTGCT GGCATTCGTC CTAAAGATGT CATTACTAAA GTAAATGGAA

201 AATCAATTAA AGGTAAAGCA TTAGATGAAG TTGTCAAAGA TGTTCGTGGT

251 AAAGAAAACA CTGAAGTCAC TTTAACTGTT CAACGAGGTA GTGAAGAAAA

301 AGACGTTAAG ATTAAACGTG RAAAAATTCA TGTTAAAAGT GTTGAGTATW

351 AGRAAAAAGG TAAAGTTGGA GTTATTACTA TTAATAAATT CCAGAMTGAT

401 ACATCCAGGT GRATTGAAAG ATGCAGTTCT AAAAGCTCAC CAAAGATGGT

451 TTGWAAAAGA TTGTTTTAGA TTTAAGAAAT AATCCAGGTG GACTACTAGA

501 TGAAGCTGTT AAAATGGCAA ATATTTTTAT CGATAAAGGA AAAACTGTTG

551 TTAAACTARA AAAAGGTAAA GATACTGAAG CAATTCNNAC TTCTAATGAT

601 GCGTTAAAAG AAGCGAAAGA CATGGATATA TCCATCTTAG TGAATGAAGG

651 TTCNGCTNGC GCTTCTGAAG TGTTTACTGG TGCGCTAAAA GACTNTAATA

701 AAGCTAAAGT TTATGGGTCA AAAACATTCG GCAAAGGTGT CGTACAAACT

751 ACAAGAGAGT TTAAGGGATG GTTCATTGTT AAAATATACT GAAATGGAAA

801 TGGTTAACGC CAGATGGTCA TTATATTCAC NGTACAAGGC ATNAAACCAG

851 TATTAAAAWT GGTTTATCAG CTTTAGGTTA ATCTTTTAAA TGTCATTCCT
```

-continued

```
 901 AATACGANAA CATTTAAAGT TNGGAGACGA TGAATCTAAA ATATTAAAAC
 951 TATTAAAAWT GGTTTATCAG CTTTAGGTTA TAAAGTTGAT AAATGGAATC
1001 AACGCCAATT TGGATAAAGC TTTAGAAAAT CAAGTTAAAG CTTYCCAMCA
1051 AGCGAATAAA CTTGAGGTAM YKGGKGAWTT TAATAAAGAA ACGAATAATA
1101 AATTTACTGA GTTATTAGTT GAAAAAGCTA ATAAACATGA TGATGTTCTC
1151 GATAAGTTGA TTAATATTTT AAAATAAGCG ATACACACTA CTAAAATTGT
1201 ATTATTATTA TGTTAATGAC ACGCCTCCTA AATTTGCAAA GATAGCAATT
1251 TAGGAGGCGT GTTTATTTTT ATTGACGTCT AACTCTAAAA GATATAAATT
1301 AGACATTTAC AAATGATGTA ATAACGCAA TTTCTATCAT CGCTGATAAC
1351 AATTCATGGT TTAATATGCA ATGAGCATAT ACTTTTTAAA TAGTATTATT
1401 CACTAGTTTT AACAATCAAT TAATTGGTAT ATGATACTTT TATTGGTTAT
1451 TTTTATCCCA TAGTGTGATA AWTACTATTT TTCATTCAYA ATAAAGGTTT
1501 AAAGCATGTT AATAGTGTGT TAAGATTAAC ATGTACTGAA AAACATGTTT
1551 WACAATAATG AATATAAGGA KTGACGTTAC ATGAWCCGTC CTAGGTAAAA
1601 TCTCMGAWTT AGATCAAATC TTAAATCTAG TAGAAGAAGC AAAAGAATTA
1651 ATGAAAGAAC ACGACAACGA GCAATGGGAC GATCAGTACC CACTTTTAGA
1701 ACATTTTGAA GAAGATATTG CTAAAGATTA TTTGTACGTA TTAGAGGAAA
1751 ATGACAAAAT TTATGGCTTT ATTGTTGTCG ACCAAGACCA AGCAGAATGG
1801 TATGATGACA TTGACTGGCC AGTAAATAGA GAAGGCGCCT TTGTTATTCA
1851 TCGATTAACT GGTTCGAAAG AATATAAAGG AGCTGCTACA GAATTATTCA
1901 ATTATGTTAT TGATGTAGTT AAAGCACGTG GTGCAGAAGT TATTTTAACG
1951 GACACCTTTG CGTTAAACAA ACCTGCACAA GGTTTATTTG CCAAATTTGG
2001 ATTTCATAAG GTCGGTGAAC AATTAATGGA ATATCCGCOM TATGATAAAG
2051 GTGAACCATT TTATGCATAT TATAAAAATT TAAAAGAATA GAGGTAATAT
2101 TAATGACGAA AATCGCATTT ACCGGAGGGG GAACAGTTGG ACACGTATCA
2151 GTAAATTTWA RTTTAATTCC AACTGCATTA TCACAAGGTT ATGGARGCGC
2201 TTTATATTGG TTCTAAAAAT GGTATTGAAA GAGAGAATGA TTGAWTCACC
2251 AACTACCCRG AAATTAAGTA TTATCCTATT TCGGAGTGKT AAATTAAGAA
2301 GATATATTTC TTTAGAAAAT GCCAAAGACG TATTTAAAGT ATTGAAAGGT
2351 ATTCTTGATG CTCGTAAAGT TTTGAAAAAA GAAAAACCTG ATCTATTATT
2401 TTCAAAAGGT GGATTTGTAT CTGTGCCTGT TGTTATTGCA GCCAAATCAT
2451 TAAATATACC AACTATTATT CATGAATCTG ACTTAACACC AGGATTAGCG
2501 AATAAGATAG CACTTAAATT TGCCAAGAAA ATATATACAA CATTTGAAGA
2551 AACGCTAAAC TACTTACCTA AAGAGAAAGC TGATTTTATT GGAGCAACAA
2601 TTCGAGAAGA TTTAAAAAAT GGTAATGCAC ATAATGGTTA TCAATTAACA
2651 GGCTTTWATG RAAATAAAAA AGTTTTACTC GTYATGGGTG GAAGCTTWGG
2701 AAGTAAAAAA TTAAATAGCA TTATTCGCGA AAACTTAGAT GCATTTATTA
2751 CAACAATATC AAGTGATACA TTTAACTGGT AAAGGATTAA AAGATGCTCA
2801 AGTTAAAAAA TCAGGATATA TACAATATGA ATTTGTTAAA GNGGATTTAA
```

-continued

```
2851 TAGGTTTAGA TCAATCCCGA GGCGACCAAA TTGACANTGC AAATCATTTT

2901 GCGATTTATG GAGTTCTTAA CATTACGTNT ACCAATGTTA TTAGTACCAT

2951 TAGGTTTAGA TCAATCCCGA GGCGACCAAA TTGACANTGC AAATCATTTT

3001 GCTGATAAAG GATATGCTAA AGCGATTGAT GAAGAACAAT TAACAGCACA

3051 AATTTTATTA CAAGAACTAA ATGAAATGGA ACAGGAAAGA ACTCGAATTA

3101 TCAATAATAT GAAATCGTAT GAACAAAGTT ATACGAAAGA AGCTTTATTT

3151 GATAAGATGA TTAAAGACGC ATTGAATTAA TGGGGGGTAA TGCTTTATGA

3201 GTCAATGGAA ACGTATCTCT TTGCTCATCG TTTTTACATT GGTTTTTGGA

3251 ATTATCGCGT TTTTCCACGA ATCAAGACTT GGGAAATGGA TTGATAATGA

3301 AGTTTATGAG TTTGTATATT CATCAGAGAG CTTTATTACG ACATCTATCA

3351 TGCTTGGGGC TACTAAAGTA GGTGAAGTCT GGGCAATGTT ATGTATTTCA

3401 TTACTTCTTG TGGCATATCT CATGTTAAAG CGCCACAAAA TTGAAGCATT

3451 ATTTTTTGCA TTAACAATGG CATTATCTGG AATTTTGAAT CCAGCATTAA

3501 AAAATATATT CGATAGAGAA AGGACCTGAC ATTGCTGGCG TTTGAATTGG

3551 ATGATTAACA GGRTTTAGTT TTCCTGAGCG GTCATGCTAT GG
```

Figure 58:

Mutant: NT102
Phenotype: temperature sensitivity
Sequence map: Mutant NT102 is complemented by pMP129, which contains a 2.5 kb insert of *S. aureus* genomic DNA. A partial restriction map is depicted FIG. 58 (there are no apparent restriction sites for EcoR I, Hind III, Bam HI or Pst I). Database searches at both the nucleic acid and peptide levels reveal strong similarity to one hypothetical ORF of unknown function from Synechocystis spp.; another ORF with no apparent homolog on the current databases is also predicted to be contained in this clone. The predicted sizes and orientations of these two hypothetical ORFs is depicted in the map.

DNA sequence data: The following DNA sequence data represents the sequence generated by primer walking through clone pMP129, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP129                                           SEQ ID NO. 64 pMP129 Length: 2573 nt

1 ATTCGAGCTC GGTACCCGKG GATCCTSYAG AGTCGATCCG CTTGAAACGC

51 CAGGCACTGG TACTAGAGTT TTGGGTGGTC TTAGTTATAG AGAAAGCCAT

101 TTTGCATTGG AATTACTGCA TCAATCACAT TTAATTTCCT CAATGGATTT

151 AGTTGAAGTA AATCCATTGA TTGACAGTAA TAATCATACT GCTGAACAAG

201 CGGTTTCATT AGTTGGAACA TTTTTTGGTG AAACTTTATT ATAAATAAAT

251 GATTTGTAGT GTATAAAGTA TATTTTGCTT TTTGCACTAC TTTTTTTAAT

301 TCACTAAAAT GATTAAGAGT AGTTATAATC TTTAAAATAA TTTTTTTCTA

351 TTTAAATATA TGTTCGTATG ACAGTGATGT AAATGATTGG TATAATGGGT

401 ATTATGGAAA AATATTACCC GGAGGAGATG TTATGGATTT TTCCAACTTT

451 TTTCAAAACC TCAGTACGTT AAAAATTGTA ACGAGTATCC TTGATTTACT

501 GATAGTTTGG TATGTACTTT ATCTTCTCAT CACGGTCTTT AAGGGAACTA

551 AAGCGATACA ATTACTTAAA GGGATATTAG TAATTGTTAT TGGTCAGCAG

601 ATAATTWTGA TATTGAACTT GACTGCMACA TCTAAATTAT YCRAWWYCGT

651 TATTCMATGG GGGGTATTAG CTTTAANAGT AATATTCCAA CCAGAAATTA
```

-continued

```
 701 GACGTGCGTT AGAACAACTT GGTANAGGTA GCTTTTTAAA ACGCNATACT
 751 TCTAATACGT ATAGTAAAGA TGAAGAGAAA TTGATTCAAT CGGTTTCAAA
 801 GGCTGTGCAA TATATGGCTA AAAGACGTAT AGGTGCATTA ATTGTCTTTG
 851 AAAAAGAAAC AGGTCTTCAA GATTATATTG AAACAGGTAT TGCCAATGGA
 901 TTCAAATATT TCGCAAGAAC TTTTAATTAA TGTCTTTATA CCTAACACAC
 951 CTTTACATGA TGGTGCAAKG ATTATTCAAG GCACGAAARAT TGCAGCAGCA
1001 GCAAGTTATT TGCCATTGTC TGRWAGTCCT AAGATATCTA AAAGTTGGGT
1051 ACAAGACATA GAGCTGCGGT TGGTATTTCA GAAGTTATCT GATGCATTTA
1101 CCGTTATTGT ATCTGAAGAA ACTGGTGATA TTTCGGTAAC ATTTGATGGA
1151 AAATTACGAC GAGACATTTC AAACCGAAAT TTTTGAAGAA TTGCTTGCTG
1201 AACATTGGTT TGGCACACGC TTTCAAAAGA AAGKKKTGAA ATAATATGCT
1251 AGAAAKTAAA TGGGGCTTGA GATTTATTGC CTTTCTTTTT GGCATTGTTT
1301 TTCTTTTTAT CTGTTAACAA TGTTTTTGGA AATATTCTTT AAACACTGGT
1351 AATTCTTGGT CAAAAGTCTA GTAAAACGGA TTCAAGATGT ACCCGTTGAA
1401 ATTCTTTATA CAACTAAAG ATTTGCATTT AACAAAAGCG CCTGAAACAG
1451 TTAATGTGAC TATTTCAGGA CCACAATCAA AGATAATAAA AATTGAAAAT
1501 CCAGAAGATT TAAGAGTAGT GATTGATTTA TCAAATGCTA AAGCTGGAAA
1551 ATATCAAGAA GAAGTATCAA GTTAAAGGGT TAGCTGATGA CATTCATTAT
1601 TCTGTAAAAC CTAAATTAGC AAATATTACG CTTGAAAACA AAGTAACTAA
1651 AAAGATGACA GTTCAACCTG ATGTAAGTCA GAGTGATATT GATCCACTTT
1701 ATAAAATTAC AAAGCAAGAA GTTTCACCAC AAACAGTTAA AGTAACAGGT
1751 GGAGAAGAAC AATTGAATGA TATCGCTTAT TTAAAAGCCA CTTTTAAAAC
1801 TAATAAAAAG ATTAATGGTG ACACAAAAGA TGTCGCAGAA GTAACGGCTT
1851 TTGATAAAAA ACTGAATAAA TTAAATGTAT CGATTCAACC TAATGAAGTG
1901 AATTTACAAG TTAAAGTAGA GCCTTTTAGC AAAAAGGTTA AAGTAAATGT
1951 TAAACAGAAA GGTAGTTTRS CAGATGATAA AGAGTTAAGT TCGATTGATT
2001 TAGAAGATAA AGAAATTGAA TCTTCGGTAG TCGAGATGAC TTMCAAAATA
2051 TAAGCGAAGT TGATGCAGAA GTAGATTTAG ATGGTATTTC AGAATCAACT
2101 GAAAAGACTG TAAAAATCAA TTTACCAGAA CATGTCACTA AAGCACAACC
2151 AAGTGAAACG AAGGCTTATA TAAATGTAAA ATAAATAGCT AAATTAAAGG
2201 AGAGTAAACA ATGGGAAAAT ATTTTGGTAC AGACGGAGTA AGAGGTGTCG
2251 CAAACCAAGA ACTAACACCT GAATTGGCAT TTAAATTAGG AAGATACGGT
2301 GGCTATGTTC TAGCACATAA TAAAGGTGAA AAACACCCAC GTGTACTTGT
2351 AGGTCGCGAT ACTAGAGTTT CAGGTGAAAT GTTAGAATCA GCATTAATAG
2401 CTGGTTTGAT TTCAATTGGT GCAGAAGTGA TGCGATTAGG TATTATTTCA
2451 ACACCAGGTG TTGCATATTT AACACGCGAT ATGGGTGCAG AGTTAGGTGT
2501 AATGATTTCA GCCTCTCATA ATCCAGTTGC AGATAATGGT ATTAAATTCT
2551 TTGSCTCGAC CNCCNNGCTN GCA
```

Figure 59:
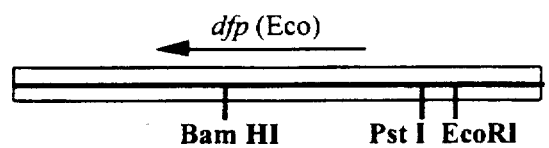

Mutant: NT114
Phenotype: temperature sensitivity
Sequence map: Mutant NT114 is complemented by pMP151, which contains a 3.0 kb insert of *S. aureus* genomic DNA. A partial restriction map is depicted FIG. 59. Database searches at both the nucleic acid and peptide levels reveal strong similarity at the peptide level to the dfp gene, encoding a flavoprotein affecting pantothenate metabolism and DNA synthesis, from *E. coli* (Genbank Accession No. L10328; published in Lundberg, L. G. et al. *EMBO J.* 2 (1983) 967–971). The predicted size and orientation of the Dfp ORF is represented by an arrow in the restriction map. DNA sequence data: The following DNA sequence data represents the sequence generated by primer walking through clone pMP151, starting with standard M13 forward and M13 reverse sequencing primers and completing the sequence contig via primer walking strategies. The sequence below can be used to design PCR primers for the purpose of amplification from genomic DNA with subsequent DNA sequencing.

clone pMP151                                                          SEQ ID NO. 65 pMP151 Length: 2976 nt

```
   1 GRTCGACTCT AGAGTCGATC TTTAAATGGG TCTCTTTCAA CAACCGCGTC
  51 ATATTTTTMA ACATAACCTT TTTTRATAAG TCCATCTAAA CTGGATTTTR
 101 AAAAGCCCAT ATCCTCAATA TCAGTTAAAA ATATTGTTTT ATGTTGTTCT
 151 TCAGACAAGT AAGCATACAA ATCGTATTGT TTAATAACTT TCTCCAACTT
 201 AGCTAATACT TCATCAGGAT GATACCCTTC AATGACACGA ACAGCACGCT
 251 TGGTTTTTTT AGTTATATTT TGTGTGAGAA TCGTTTTTTC TTCAACGATA
 301 TCATCTTTTA ACAACTTCAT AAGCAATTGA ATATCATTAT TTTTTTGCGC
 351 ATCTTTATAA TAATAGTAAC CATGCTTATC AAATTTTTGT AATAAAGCTG
 401 AAGGTAGCTC TATGTCATCT TTCATCTTAA ATGCTTTTTT ATACTTCGCT
 451 TTAATAGCAC TCGGAAGCAT CACTTCTAGC ATAGAAATAC GTTTAATGAC
 501 ATGAGTTGAA CCCATCCACT CACTTAAAGC TATTAATTCT GATGTTAATT
 551 CTGGTTGTAT ATCTTTCACT TCTATGATTT TTTTTAACTT CGAAACGTCA
 601 AGTTGTGCAT CAGGTTCTGC TGTTACTTCC ATTACATAAC CTTGAATCGT
 651 TCTTGGTCCA AAAGGTACAA TTACACGCAC ACCAGGTTGG ATGACAGATT
 701 CGAGTTGTTC GGGAATTATA TAATCAAATT TATAGTCAAC GCTCTTCGAC
 751 GCGACATCGA CTATGACTTT CGCTATCATT ATKGCCACCT AGTTTCTAGT
 801 TCATCTAAAA TTTGTGCAGC WAATACTACK TTTTKNCCTT YCTTGATATT
 851 TACKTTTTCA TTAKTTTTAA AATGCATTGT CAATTCATTA TCATCAGAAC
 901 TAAATCCGAT AGACATATCC CCAACATTAT TTGAAATAAT CACATCTGCA
 951 TTTTTCTTGC GTAATTTTTG TTGTGCATAA TTTTCAATAT CTTCAGTCTC
1001 TGCTGCAAAG CCTATTAAAT ACTGTGATGT TTTATGTTCA CCTAAATATT
1051 TAAGAATGTC TTTAGTACGT TTAAAAGATA CTGACAAATC ACCATCCTGC
1101 TTTTTCATCT TATGTTCCTA ATACATCAAC CGGTGTATAG TCAGATACGG
1151 CTGCTGCTTT TACAACAATA TYTTGTTCCG TYAAATCGGC TTGTCACTTG
1201 GTTCAAACAT TTCTTCAGGC ACTTTGRACA TGAATAACTT CAATATCTTT
1251 TGGATCCTCT AGTGTTGTAG GACCAGCAAC TAACGTCACG ATAGCTCCTC
1301 GATTTCGCAA TGCTTCAGCT ATTGCATAGC CCATTTTTCC AGAAGAACGA
1351 TTGGATACAA ATCTGACTGG ATCGATAACT TCAATAGTTG GTCCTGCTGT
1401 AACCAATGCG CGTTTATCTT GAAATGAACT ATTAGCTAAA CGATTACTAT
1451 TTTGAAAATG AGCATCAATT ACAGAAACGA TTTGAAGCGG TTCTTCCATA
1501 CGTCCTTTAG CAACATAACC ACATGCTAGA AATCCGCTTC CTGGTTCGAT
```

-continued

```
1551 AAAATGATAC CCATCTTCTT TTAAAATATT AATATTTTGC TGCGTTACGT

1601 TTATTTTCAT ACATATGCAC ATTCATAGCA GGCGCAATAA ATTTCGGTGT

1651 CTCTCTTGCT AGCAACGTTG ATGTCACCAA ATCATCAGCA ATACCTACAC

1701 TCAATTTTGC AATTGTATTT GCCGTTGCAG GTGCAACAAT GATTGCATCK

1751 GCCCAATCCA CCTAATGCAA TATGCTGTAT TTCTGGAAGG ATTTTYTTCT

1801 ATAAAAGTAT CTGTATAAAC AGCATTTCGA MTTATTGCTT GAAATGCTAA

1851 TGGTGTCACA AATTTTTGTG CGTGATTCGT TAAACATAAC GCGAACTTCA

1901 TAACCCAGAT TGTGTTAACT TACTTGTCAA ATCAATTGCT TTATATGCCG

1951 CAATGCCACC TGTAACGGCT AATAATATTT TCTTCATATT CAATCTCCCT

2001 TAAATATCAC TATGACATTT ACGCTTTACA TCATCATATG CGCACAAATG

2101 TTGGATAAAC TAAAAAAACA CACCTACATA GGTGCGTTTG ATTTGGATAT

2151 GCCTTGACGT ATTTGATGTA ACGTCTAGCT TCACATATTT TTAATGGTCG

2201 AAACTATTCT TTACCATAAT AATCACTTGA AATAACAGGG CGAATTTTAC

2251 CGTCAGCAAT TTCTTCTAAC GCTCTACCAA CTGGTTTAAA TGAATGATAT

2301 TCACTTAATA ATTCAGTTTC AGGTTGTTCA TCAATTTCAC GCGCTCTTTT

2351 CGCTGCAGTT GTTGCAATTA AATACTTTGA TTTAATTTGT GACGTTAATT

2401 GGTTTAAAGG TGGATTTAAC ATTATTTTTT AGCCTCCAAA ATCATTTTTC

2451 TATACTTAGC TTCTACGCGC TCTCTTTTTA AGTGCTCAGC TTCTACAATA

2501 CATTGAATTC TATTCTTCGC AAGTTCTACT TCATCATTAA CTACAACGTA

2551 ATCGTATAAA TTCATCATTT CAACTTCTTT ACGCGCTTCG TTAATACGAC

2601 TTTGTATTTT CTCATCAGAT TCTGTTCCTC TACCTACTAA TCGCTCTCTC

2651 AAGTGTTCTA AACTTGGAGG TGCTAAGAAA ATAAATAGCG CATCTGGAAA

2701 TTTCTTTCTA ACTTGCTTTG CACCTTCTAC TTCAATTTCT AAAAATACAT

2751 CATGACCTTC GTCCATTGTA TCTTTAACAT ATTGAACTGG TGTACCATAA

2801 TAGTTGCCTA CATATTCAGC ATATTCTATA AATTGGTCAT CTTTGATTAA

2851 AGCTTCAAAC GCATCCCTAG TTTTAAAAAA GTAATCTACG CCATTCAACW

2901 TCACCTTCAC GCATTTGACG TGTTGTCATT GGAATAGRAG AGCTTRANNG

2951 ATGTATNGNG ATCGACCTGC AGTCAT
```

Mutant: NT124 pheonotype: temperature sensitivity

Figure 60:
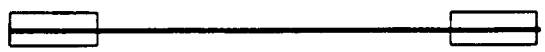

Sequence map: Mutant NT124 is complemented by plasmid pMP677, which carries a 3.0 kb insert of wild-type *S. aureus* genomic DNA. A partial restriction map is depicted in FIG. 60 with open boxes to depict the current status of the contig project; no apparent restriction sites for EcoR I, HinD III, BamH I or Pst I are present. Database searches at the nucleic acid and (putative) polypeptide levels against currently available databases reveal no significant similarities to known genes at this time.

DNA seqeunce data: The following DNA sequence data represents the sequence generated from clone pMP677, starting with standard M13 forward and M13 reverse sequencing primers; the sequence contig will be completed later via primer walking strategies. The sequence below can be used to design PCR primers for the purpose of amplification from genomic DNA with subsequent DNA sequencing.

clone pMP677  SEQ ID NO. 66 pMP677.forward Length: 540 nt

```
  1 TACCCGGGGA CCTTGAAAAA TACCTGGTGT ATCATACATA AATGANGTGT
 51 CATCTANAGG AATATCTATC ATATCTNAAG TTGTTCCAGG GANTCTTGAA
101 GTTGTTACTA CATCTTTTTC ACCAACACTA GCTTCAATCA GTTTATTAAT
151 CAATGTAGAT TTCCCAACAT TCGTTGTCCC TACAATATAC ACATCTTCAT
201 TTTCTCGAAT ATTCGCAATT GATGATAATA AGTCNTNTNT GCCCCAGCCT
251 TTTTCAGCTG AAATTAATAC GACATCGTCA GCTTCCAAAC CATATTTTCT
301 TGCTGTTCGT TTTAACCATT CTTTAACTCG ACGTTTATTA ATTTGTTTCG
351 GCAATAAATC CAATTTATTT GCTGCTAAAA TGATTTTTTT GTTTCCGACA
401 ATACGTTTAA CTGCATTAAT AAATGATCCT TCAAAGTCAA ATACATCCAC
451 GACATTGACG ACAATACCCT TTTTATCCGC AAGTCCTGAT AATAATTTTA
501 AAAAGTCTTC ACTTTCTAAT CCTACATCTT GAACTTCGTT
``` pMP677.reverse Length: 519 nt  SEQ ID NO. 67

```
  1 GACGCGTAAT TGCTTCATTG AAAAAATATA TTTGTNGAAA GTGGTGCATG
 51 ACAAATGTAC TGCTCTTTTT GTAGTGTATC AGTATTGTGA TGTTTTAATG
101 AGAATATTAT ATGAATCATT ATGAAATTTA ATAAAAATAA AAGAAATGAT
151 TATCATTTTT TCTTATATAC TGTTAAACGG TTTGGAATTT TTAGGTATAC
201 ACTGTATTGG TTGATATAAC TCAACTAATA ATTGCGAACA GAGTATTTCA
251 AATTGAAAAG TATTATGAGC GTGATACATA ATCAAAATTG TAGGCTCAAG
301 AACCACTACA TAATAAACCA TAAGCGGTTC TTTATCATTT ATGTCTCGCT
351 CTCAAATGTA AATTAATAAT TGTTTTGGGG GAGTTTGAAG TTAAATATTT
401 AACAGGATTT ATTTTAATAT TATTGTTAGA AGGAATTTTT ACAAATTCAG
451 CGAGTGCAAT CGAATATTCA GACTTACATC ATAAAAGTAA GTTGATTCA
501 AAGCGTCCTA AGTTAATGC
```

Figure 61:
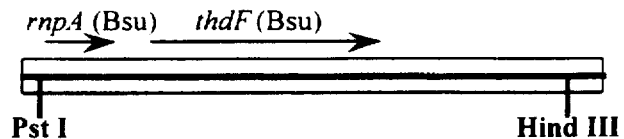

Mutant: NT125
Phenotype: temperature sensitivity
Sequence map: Mutant NT125 is complemented by plasmid pMP407, which carries a 3.3 kb insert of wild-type *S. aureus* genomic DNA. A partial restriction map is depicted in FIG. 61. Database searches at the nucleic acid and (putative) polypeptide levels against currently available databases reveal strong peptide level similarities to rnpA (Genbank Accession No. X62539), encoding the protein component of RNAseP (EC 3.1.26.5), and thdF (Genbank Accession No. X62539), a hypothetical ORF with similarities to the thiophene/furan oxidase from *E. coli*.

DNA sequence data: The following DNA sequence data represents the sequence generated by primer walking through clone pMP407, starting with standard M13 forward and M13 reverse sequencing primers and completing the sequence contig via primer walking strategies. The sequence below can be used to design PCR primers for the purpose of amplification from genomic DNA with subsequent DNA sequencing.

clone pMP407  SEQ ID NO. 68 pMP407 Length: 3308 nt

```
  1 ACCAATATAT GCATCTGAAC GACTTAATAT CTTTTCGCCT GTGTTTAACA
 51 CTTTACCTGC AGCGTTAATA CCTGCCATCA ATCCTTGTCC TGCTGCTTCT
101 TCATAACCAG ATGTACCATT AATTTGACCT GCAGTATATA AGTTTTTAAT
151 CATTTTCGTT TCAAGTGTAG GCCATAACTG CGTTGGCACA ATCGCATCAT
201 ATTCAATTGC GTAGCCGGCA CGCATCATAT CTGCTTTTTC AAGACCTGGT
```

-continued

```
 251 ATCGTCTCTA ACATTTGACG TTGCACATGT TCAGGAAGAC TTGTNGACAA
 301 TCCTTGCACA TATACTTCAT TTGTATTAAC GACCTTCAGG CTCTAAGAAA
 351 AAGTTGATGT CGCGGCTTAT CATTAAATCG AACAAATTTA TCTTCAATTG
 401 AAGGGCAATA ACGTGGCCCG GTTCCTTTAA TCATCCCTGA ATACATTGCA
 451 GATAGATGTA AATTATCATC GATAACTTTG TGTGTTTCAN CATTAGTATA
 501 CGTTAGCCAA CATGGCAATT GATCKAMYAT ATATTCTGTT GTTTCAAAGC
 551 TGAATGCACG ACCTACATCG TCACCTGGTT GTATTTCAGT CTTCGAATAR
 601 TCAATTGTTT TTGAATTGTA CACGGCGGWG GTGTACCTGT TTTAAAACGA
 651 ACAATATCAA AACCAAGTTC TCTTARATGK GKSTGATAAT GTGATTGATG
 701 GTAATTGGTG GATTTGGTCC ACTTGAATAC TTCATATTAC CTAAAATGAT
 751 TTCACCACGT ATRAAATGTT GCCCGTWGTA ATAATTACTG CTTTAGATAA
 801 ATACTCTGTA CCAATATTTG TACGTACACC TTKAACTGTC ATTAWCTTCT
 851 ATAAKAAGTT CGTCTACCAT ACCTTGCATT AATATGCAAA TTTTCTTCAT
 901 CTTCAATCAM GCGTTTCATT TCTTGTTGAT AAAGTACTWT AKCTGCTTGC
 951 GCCKCTWAGT GCTCTTACAR CAGGTCCTTT AACTGTATTT AACATTCTCA
1001 TTTGAATGTG TGTTTTATCG ATTGTTTTTG CCATTTGTCC ACCTAAAGCA
1051 TCAATTTCAC GAACAACGAT ACCTTTAGCT GGTCCACCTA CAGATGGGTT
1101 ACATGGCATA AATGCAATAT TATCTAAATT TATTGTTAGC ATTAATGTTT
1151 TAGCACCACG TCTTGCAGAT GCTAAACCTG CTTCTACACC TGCATGTCCC
1201 GCACCTATAA CGATTACATC ATATTCTTGA ACCACAATAT AAACCTCCTT
1251 ATTTGATATC TTACTAGCCK TCTTAAGACG GTATTCCGTC TATTTCAATT
1301 ACTATTTACC TAAGCAGAAT TGACTGAATA ACTGATCGAT GAGTTCATCA
1351 CTTGCAGTCT CACCAATAAT TTCTCCTAAT ATTTCCCAAG TTCTAGTTAA
1401 ATCAATTTGT ACCATATCCA TAGGCACACC AGATTCTGCT GCATCAATCG
1451 CMTCTWGTAT CGTTTGTCTT GCTTGTTTTA ATACCGAAAT ATGTCTTGAA
1501 TTAGAAACAT AAGTCATATC TTGATTTTTG TACTTCTCCA CCAAAGAACA
1551 AATCTCGAAT TTGTATTTCT AATTCATCAA TACCTCCTTG TTTTAACATT
1601 GAAGTTTGAA TTAATGGCGT ATCACCTATC ATATCTTTAA CTTCATTAAT
1651 ATCTATGTTT TGCTCTAAAT CCATTTTATT AACAATTACG ATTACATCTT
1701 CATTTTTAAC CACTTCATAT AATGTGTAAT CTTCTTGAGT CAATGCTTCG
1751 TTATTGTTTA ATACAAATAA AATTAAGTCT GCTTGGCTAA GAGCCTTTCT
1801 AGAGCGTTCA ACACCAATCT TCTCTACTAT ATCTTCTGTC TCACGTATAC
1851 CAGCAGTATC AACTAATCTT AATGGCACGC CACGAACATT GACGTAMTCT
1901 TCTAAGACAT CTCTAGTAGT ACCTGCTACY TCAGTTACAA TCGCTTTATT
1951 ATCTTGTATT AAATTATTTA ACATCGATGA TTTACCTACG TTTGGTTTAC
2001 CAACAATAAC TGTAGATAAA CCTTCACGCC ATAATTTTAC CCTGCGCACC
2051 GGTATCTAAT AAACGATTAA TTTCCTGTTT GATTTCTTTA GACTGCTCTA
2101 AAAGAAATTC AGTAGTCGCA TCTTCAACAT CATCGTATTC AGGATAATCA
2151 ATATTCACTT CCACTTGAGC GAGTATCTCT AATATAGATT GACGTTGTTT
2201 TTTGATTAAG TCACTTAGAC GACCTTCAAT TTGATTCATC GCAACTTTAG
```

-continued

```
2251 AAGCTCTATC TGTCTTCGAG CGAWWAAAGT CCATAACTGY TTCAGCTTGA

2301 GATAAATCAA TACGACCATT TAAAAAGGCA MGTTTTGTAA ATTCAACCTG

2351 GCTCAGCCAT TCTAGCGCCA TATGTCATAG TAAGTTCCAG CACTCTATTA

2401 ATCGTTAAAA TACCACCATG ACAATTAATT TCTATAATAT CTTCGCGTGT

2451 AAATGTTTTT GGCGCTCTTA ACACAGACAC CATAACTTNT TCAACCATTC

2501 TTTAGACTCT GGATCAATAA TATGACCGTA ATTAATCGTA TGTGATGGAA

2551 CATCATTTAA AAGATGTTTT CCTTTATATA ATTTGTCAGC AATTTCAACG

2601 GCTTGCGGTC CAGACAATCG AACAATTCCA ATTGCCCCTT CACCCATTGG

2651 TGTTGAAATA CTCGTAATTG TATCTAAATC CATATTGCTA CTCGCCTCCT

2701 TCAACGATGT GAATACATTT TAAAGTAAGT TATTATAACC CTAAGGTCAG

2751 TCTTAACGTT TGTCTGAGGT AAGACTTCGG GATGTGTTGA GTGGTTAATG

2801 TTTTCCTTCC CCTACCCTAT CCTTACTTAA TCTTTTTATT AAAAACTTTG

2851 GCAATTTTAA GTACGTGCTC AAGACTATTC TGTATTTGTA AAGTCGTCAT

2901 ATCTTTAGCT GGCTGTCTTG CTATTACAAT AATATCTTTG GCCAATATAT

2951 GCGACTTATG TACTTTGAAA TTTTCACGTA TTGCTCTTTT AATCTTGTTT

3001 CTTAACACTG CATTACCTAG TTTTTTAGAA ACACTAATAC CTAAGCGAAA

3051 ATGGTCTATT TCTTTATTAT TACAAGTGTA TACAACAAAT TGTCTGTTGG

3101 CTACAGAATG ACCTTTTTTA TATATTCTCT GAAAATCTGC ATTCTTTTTA

3151 ATTCGGTAAG CTTTTTCCAA TAACATCACT CGCTTATTTA TCGTTTTTAT

3201 TTGAAGCTAT ATTTAAACTT CTATTGAGCT TATAACATAA ATTTCTATTT

3251 ATTCTTAATT TAAACGAAAA AAAAGATCGA CTCTAGAGGA TCCCCGGGTA

3301 CCGAGCTC
```

Figure 62:
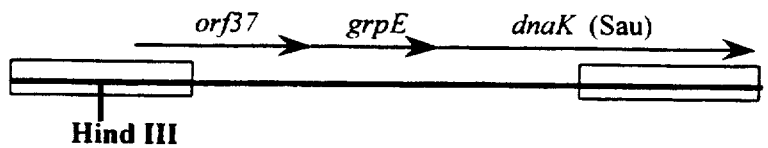

Mutant: NT144
Phenotype: temperature sensitivity
Sequence map: Mutant NT144 is complemented by plasmid pMP414, which carries a 4.5 kb insert of wild-type *S. aureus* genomic DNA. A partial restriction map is depicted in FIG. 62. Database searches at the nucleic acid and (putative) polypeptide levels against currently available databases reveal identity to the Hsp70 locus from *S. aureus* (Genbank Accession No. D30690), including an additional 600 bp of unpublished sequence upstream of the Genbank entry. Experiments are underway to determine which ORF in this contig is the essential gene.

DNA sequence data: The following DNA sequence data represents the sequence generated from clone pMP414, starting with standard M13 forward and M13 reverse sequencing primers; the sequence contig will be completed later via primer walking strategies. The sequence below can be used to design PCR primers for the purpose of amplification from genomic DNA with subsequent DNA sequencing.

clone pMP414                                          SEQ ID NO. 69 pMP414.forward Length: 1004 nt

```
  1 AGTTACGGCT TAATACTTGA ACCNAAAACC CAATTTTATA ATATGTATAG

51 AAAAGGCTTG CTCAAACTTG CTAATGAGGA TTTAGGTGCT GACATGTATC

101 AGTTGCTGAT GTCTAANATA GAACAATCTC CTTTCCATCA ATACGAAATA

151 TCTAATTTTG CATTAGATGG CCATGANTCN NAACATAATA AGGTTTACTG

201 GTTAATGAG GAATATTATG GATTTGGAGC AGGTGCAAGT GGTTATGTAN

251 ATGGTGTGCG TTATACGAAT ATCAATCCAG TGAATCATTA TATCAAAGCT

301 ATNAATAAAG AAAGTAAAGC AATTTTAGTA TCAAATAAAC CTTCTTTGAC
```

-continued

```
351 TGAGAGAATG GAAGAAGAAA TGTTTCTTGG GTTGCGTTTA AATGAAAGTG

401 TGAGTAGTAG TAGGTTCAAA AAGAAGTTTG ACCAATCTAT TGAAAGTGTC

451 TTTGGTCAAA CAATAAATAA TTTAAAAGAG AAGGAATTAA TTGTAGAAAA

501 AGAACGATGT GATTGCACTT ACAAATAGAG GGAAAGTCAT ANGTAATGAG

551 GTTTTTGAAG CTTTCCTAAT CAATGATTAA GAAAAATTGA AATTTCGAGT

601 CTTTAACATT GACTTANTTT GACCAATTTG ATAAATTATA ATTAGCACTT

651 GAGATAAGTG AGTGCTAATG AGGTGAAAAC ATGANTACAG ATAGGCAATT

701 GAGTATATTA AACGCAATTG TTGAGGATTA TGTTGATTTT GGACAACCCG

751 TTGGTTCTAA AACACTAATT GAGCGACATA ACTTGAATGT TAGTCCTGCT

801 ACAATTAGAA ATGAGATGAA ACAGCTTGAA GATTTAAACT ATATCGAGAA

851 GACACATAGT TCTTCAGGGC GTTCGCCATC ACAATTAGGT TTTAGGTATT

901 ATGTCAATCG TTTACTTGAA CAAACATCTC ATCAAAAAAC AAATAAATTA

951 AGACGATTAA ATCAATTGTT AGTTGAGAAC AATATGATGT TTCATCAGCA

1001 TTGA
``` pMP414.reverse Length: 1021 nt                                   SEQ ID NO. 70

```
  1 CCTGCAGGTC GATCCTGACA ACATTCTAAT TGTATTGTTT ANTTATTTTT

51 TGTCGTCGTC TTTTACTTCT TTAAATTCAG CATCTTCTAC AGTTCTATCA

101 TTGTTTTGAC CAGCATTAGC ACCTTGTGCT TGTTGTTGCT GTTGAGCCGC

151 TTGCTCATAT ACTTTGCTG ATAATTCTTG AATCACTTTT TCAAGTTCTT

201 CTTTTTTAGA TTTAATATCT TCTATATCTT GACCTTCTAA AGCAGTTTTA

251 AGAGCGTCTT TTTTCTCTTC AGCAGATTTT TTATCTTCTT CACCGATATT

301 TTCGCCTAAA TCAGTTAAAG TTTTTTCAAC TTGGAATACT AGACTGTCAG

351 CTTCGTTTCT TAAGTCTACT TCTTCACGAC GTTTTTTATC TGCTTCAGCG

401 TTAACTTCAG CATCTTTTAC CATACGGTCR ATTTCTTCGT CTGATAATGA

451 AGAACTTGAT TGAATTGTAA TTCTTTGTTC TTTATTTGTA CCTAAGTCTT

501 TTGGCAGTTA CATTTACAAT ACCGTTTTTA TCGATATCAA ACGTTACTTC

551 AATTTGGAGG TTTACCACCG TTTCARMWGG TGGAATATCA GTCAATTGGA

601 ATCTACCAAG TGTTTTATTA TCCGCAGCCA TTGGACGTTC ACCTTGTAAT

651 ACGTGTACAT CTACTGATGG TTGATTATCT ACTGCTGTTG AATAGATTTG

701 AGATTTAGAT GTAGGAATCG TAGTGTTACG TTCAATTAAC GTATTCATAC

751 GTCCACCTAA AATTTCAATA CCTAAAGATA GTGGTGTTAC GTCTAATAAT

801 ACTACGTCTT TAACGTCACC TGTGATAACG CCACCTTGGA TTGCAGCTCC

851 CATTGCCACT ACTTCGTCCG GGTTTACTCC TTTGTTAGGC TCTTTACCGA

901 TTTCTTTTTT GACAGCTTCT TGTACTGCTG AATACGAAT TGATCCACCA

951 ACTAAGATAA CTTCATCGAT ATCTGANTTT GTTAAGCCAG CGTCTTTCAT

1001 TGCTTGGCGT GTAGGTCCAT C
```

Figure 63:
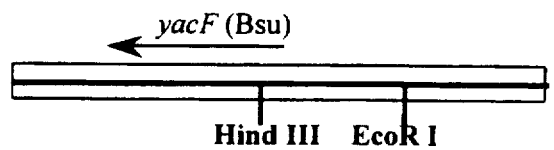

Mutant: NT152
Phenotype: temperature sensitivity
Sequence map: Mutant NT152 is complemented by plasmid pMP418, which carries a 3.0 kb insert of wild-type *S. aureus* genomic DNA. A partial restriction map is depicted in FIG. 63. Database searches at the nucleic acid and (putative) polypeptide levels against currently available databases reveal limited peptide-level similarity to yacF, a hypothetical ORF, from *B. subtilis* (Genbank Accession No. D26185).

DNA sequence data: The following DNA sequence data represents the sequence generated by primer walking through clone pMP418, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP418
pMP418 Length: 3010 nt
    1 ATGCCTGCAG GTCGATCACG ATGNAAGTCA TTCAATAAGA ATGATTATGASEQ ID NO. 71
   51 AAATAGAAAC AGCAGTAAGA TATTTTCTAA TTGAAAATCA TCTCACTGCT
  101 GTTTTTTAAA GGTTTATACC TCATCCTCTA AATTATTTAA AAATAATTAA
  151 TGGTATTTGA GCACGTTTAG CGACTTTATG ACTGACATTA CCAATTTCCA
  201 TTTCTTGCCA GATATTCAAA CCACGTGTAC TCAAAATGAT AGCTTGGTAT
  251 GTACCTCCAA TAGTAATTTC AATAACTTTG TCTGTTGAAC ACTAAGAGCA
  301 ATTTTAATTT CATAATGTGT TGTAAACATT TTTTTTGATT GGAGTTTTTT
  351 TCTGAGTTAA ACGATATCCT GATGTATTTT TAATTTTGCA CCATTTCCAA
  401 AAGGATAAGT GACATAAGTA AAAAGGCATC ATCGGGAGTT ATCCTATCAG
  451 GAAAACCAAG ATAATACCTA AGTAGAAAAG TGTTCAATCC GTGTTAAATT
  501 GGGAAATATC ATCCATAAAC TTTATTACTC ATACTATAAT TCAATTTTAA
  551 CGTCTTCGTC CATTTGGGCT TCAAATTCAT CGAGTARTGC TCGTGCTTCT
  601 GCAATTGATT GTGTGTTCAT CAATTGATGT CGAAGTTCGC TAGCGCCTCT
  651 TATGCCACGC ACATAGATTT TAAAGAATCT ACGCAAGCTC TTGAATTGTC
  701 GTATTTCATC TTTTTCATAT TTGTTAAACA ATGATAAATG CAATCTCAAT
  751 AGATCTAATA GTTCCTTGCT TGTGTGTTCG CGTGGTTCTT TTTCAAAAGC
  801 GAATGGATTG TGGAAAATGC CTCTACCAAT CATGACGCCA TCAATGCCAT
  851 ATTTTTCTGC CAGTTCAAGT CCTGTTTTTC TATCGGGAAT ATCACCGTTA
  901 ATTGTTAACA ATGTATTTGG TGCAATTTCG TCACGTAAAT TTTTAATAGC
  951 TTCGATTAAT TCCCAATGTG CATCTACTTT ACTCATTTCT TTACGTTGTA
 1001 CGAAGATGAA TAGATAAATT GGCAATGTCT TGTTCGAAGA CAKTGCTTCA
 1051 ACCAATCTTT CCATTCATCG ATTTCATAKT AGCCAAGGCG TGTTTTTAAC
 1101 ACTTTACCGG AASCCCACCT GCTTTAGTCG CTTGAATAAT TTCGGCAGCA
 1151 ACGTCAGGTC TTAAGATTAA GCCGGANCCC TTACCCTTTT TAGCAACATT
 1201 TGCTACAGGA CATCCCATAT TTAAGTCTAT GCCTTTAAAG CCCATTTTAG
 1251 CTAATTGAAT ACTCGTTTCA CGGAACTGTT CTGGCTTATC TCCCCATATA
 1301 TGAGCGACCA TCGGCTGTTC ATCTTCACTA AAAGTTAAGC GTCCGCGCAC
 1351 ACTATGTATG CCTTCAGGGT GGCAAAAGCT TTCAGTATTT GTAAATTCAG
 1401 TGAAAACAC ATCCRGTCTA GNTGCTTCAN TTACAACGTG TCGAAAGACG
 1451 ATATCTGTAA CGTCTTCCAT TGGCGCCAAA ATAAAAAATG GACGTGGTAA
 1510 TTCACTCCAA AAATTTTCTT TCATAATATA TTTATACCCT CTTTATAATT
 1551 AGTATCTCGA TTTTTTATGC ATGATGATAT TACCACAAAA GCNTAACTTA
 1601 TACAAAAGGA ATTTCAATAG ATGCAACCAT TKGAAAAGGG AAGTCTAAGA
 1651 GTAGTCTAAA ATAAATGTTG TGGTAAGTTG ATCAATACAA AGATCAAGGA
 1701 TTATAGTATT AAATTGTTCA TTATTAATGA TACACTACTT ATGAATATGA
 1751 TTCAGAATTT TCTTTGGCTA CTNCTTACAG TAAAGCGACC TTTTAGTTAT
 1801 CTTATAACAA AGACAAATTT CTAAAGGTGA TATTATGGAA GGTTTAAAGC
```

```
-continued
1851 ATTCTTTAAA AAGTTTAGGT TGGTGGGATT NATTTTTTGC GATACCTATT

1901 TTTCTGCTAT TCGCATACCT TCCAAACTNT AATTTTATAA NCATATTTCT

1951 TAACATTGTT ATCATTATTT TCTTTTCCNT AGGTTTGATT TTAACTACGC

2001 ATATAATTAT AGATAAAAYT AAGAGCAACA CAGGGTGAAT CATTAATACG

2051 GAATGTGATT AAAACATAAA ACTGAAGGAG CGATTACAAT GGCGACTAAG

2101 AAAGATGTAC ATGATTTATT TTTAAATCAT GTGAATTCAA ACGCGGTTAA

2151 GACAAGAAAG ATGATGGGAG AATATATTAT TTATTATGAT GGCGTGGTTA

2201 TAGGTGGTTT GTATGATAAT AGATTATTGG TCAAGGCGAC TAAAAGTGCC

2251 CAGCAGAAAT TGCAAGATAA TACATTAGTT TCGCCATATC CAGGTTTCTA

2301 AAGAAATGAT ATTAATTTTA GACTTTACCG AAGCAACAAA TCTCACTGAT

2351 TTATTTAAGA CCATAAAAAA TGATTTGAAA AAGTGAAGTA GTGAAGTGTG

2401 GGTGCAGAGA GAACTAAGCC CATCGWTAAA TGGTCGCTTG TTAAAGAAGA

2451 GTGACGGTCA CTCTTCTTTA TGTGCATATT TTATTTTGTC TGTTTBGTTA

2501 ACAAGCAGCA GTGTAACAAA TATGAGTAAG GATAAAATGA GTATAATATA

2551 GAAACCGAAT TTATCATTAA TTTCATTAAT CCATCTTCCT AAAAATGGAG

2601 CAATTAAACT TTGCAGTAAC AATGAAATTG ACGTCCATAT CGTAAATGAG

2651 CGACCGACAT ATTTATCTGA AACAGTGTTC ATTATAGCWG TATTCATATA

2701 AATTCTGATT GATGAAATTG AGTAGCCTAG TATAAAKGAT CCTATGAATA

2751 AGTAAAATGC TGAGTTTATC CAAATAAATA GTGCKGAATT TATGACTRRC

2801 TATGAAATAT AACAAAAATA TCACATACTT TAGKTGAGAT TTTCTTSGAA

2851 AGAATAGCTG AAATTAAACC TGCACATAAT CCTCCAATGC CATATAACAT

2901 ATCTGAAMAA CCAAAKTGTA CAGACCGAAA GTTTTAAAAC ATTATAAACA

2951 TATCCTGGTA ATGATATGTT AAAGATCGAC TCTAGAGGAT CCCCGGNTAC

3001 CGAGCTCGAA
```

Mutant: NT156 phenotype: temperature sensitivity

Figure 64:
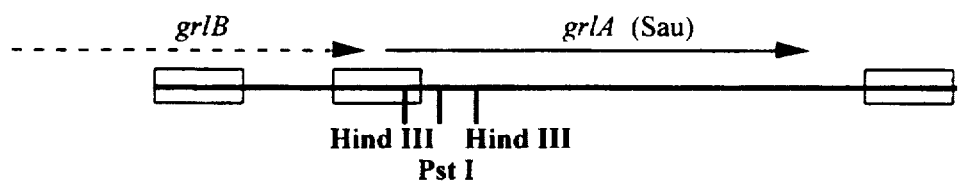

Sequence map: Mutant NT156 is complemented by plasmids pMP672 and pMP679, which carry 4.5 kb inserts of wild-type S. aureus genomic DNA. A partial restriction map is depicted in FIG. 64. Database searches at the nucleic acid and (putative) polypeptide levels against currently available databases reveal identity to the grlBA locus, a known essential gene encoding DNA topoisomerase (EC 5.99.1.3), from S. aureus (Genbank Accession No. L25288; published in Ferrero, L. et al. Mol. Microbiol. 13 (1994) 641–653).

DNA sequence data: The following DNA sequence data represents the sequence generated from clone pMP679, starting with standard M13 forward and M13 reverse sequencing primers; the sequence contig will be completed later via primer walking strategies. The sequence below can be used to design PCR primers for the purpose of amplification from genomic DNA with subsequent DNA sequencing.

```
clones pMP676 and pMP672
pMP679.forward Length: 548 nt
  1 ATCGGTACCC GGGGACCAAT ANACAGAAAG TATATTAAGT TTNGTAAATASEQ ID NO. 72

51 ATGTACGTAC TNAAGATGGT GGTACACATG AAGTTGGTTT TAAAACAGCA

101 ATGACACGTG TATTTAATGA TTATGCACGT CGTATTAATG AACTTAAAAC

151 AAAAGATAAA AACTTAGATG GTAATGATAT TCGTGAAGGT TTAACAGCTG

201 TTGTGTCTGT TCGTATTCCA GAAGAATTAT TGCAATTTGA ANGACAAACG

251 AAATCTAAAT TGGGTACTTC TGAAGCTAGA AGTGCTGTTG ATTCAGTTGT
```

```
-continued
301 TGCAGACAAA TTGCCATTCT ATTTAGAAGA AAAAGGACAA TTGTCTAAAT

351 CACTTGTGGA AAAAAGCGAT TAAAGCACAA CAAGCAAGGG AAGCTGCACG

401 TAAAGCTCGT GAAGATGCTC GTTCAGGTAA GAAAAACAAG CGTAAAGACA

451 CTTTGCTATC TGGTAAATTA ACACCTGCAC AAAGTTAAAA ACACTGGAAA

501 AAAATGAATT GTATTTAGTC GAAGGTGATT CTGCGGGAAG TTCAGCAA
pMP679.reverse Length: 541 nt
    1 ACTGCAGGTC GAGTCCAGAG GWCTAAATTA AATAGCAATA TTACTAAAAC SEQ ID NO. 73

51 CATACCAATG TAAATGATAG CCATAATCGG TACAATTAAC GAAGATGACG

101 TAGCAATACT ACGTACACCA CCAAATATAA TAATAGCTGT TACGATTGCT

151 AAAATAATAC CTGTGATTAC TGGACTAATA TTATATTGCG TATTTAACGA

201 CTCCGCAATT GTATTAGATT GCACTGTGTT AAATACAAAT GCAAATGTAA

251 TTGTAATTAA AATCGCAAAT ACGATACCTA GCCATTTTTG ATTTAAACCT

301 TTAGTAATAT AGTAAGCTGG ACCACCACGG GAATCCACCA TCTTTATCAT

351 GTACTTTATA AACCTGAGCC AAAGTCGCTT CTATAAATGC ACTCGCTGCA

401 CCTATAAATG CAATAACCCA CATCCAAAAT ACTGCACCTG GACCGCCTAA

451 AACAATCGCA GTCGCAACAC CAGCAATATT ACCAGTACCA ACTCTCGAAC

501 CAGCACTAAT CGCAAATGCT TGGAATGGCG AAATACCCTT C
pMP672.forward Length: 558 nt
    1 AGGGTCTNNC ACGGTACCCG GGGNCCAATT WGATGAGGAG GAAATCTAGT SEQ ID NO.74

51 GAGTGAAATA ATKCAAGATT TATCACTTGA AGATGTTTTA GGTGATCGCT

101 TTGGAAGATA TAGTAAATAT ATTATTCAAG AGCGTGCATT GCCAGATGTT

151 CGTGATGGTT TAAAACCAGT ACAACGTCGT ATTTTATATG CAATGTATTC

201 AAGTGGTAAT ACACACGATA AAAATTTCCG TAAAAGTGCG AAAACAGTCG

251 GTGATGTTAT TGGTCAATAT CATCCACATG GGAGACTCCT CAGTGTACGA

301 AGCAATGGTC CGTTTAAGTC AAGACTGGAA GTTACGACAT GTCTTAATAG

351 AAATGCATGG TAATAATGGT AGTATCGATA ATGATCCGCC AGCGGCAATG

401 CGTTACACTG AAGCTAAGTT AAGCTTACTA GCTGAAGAGT TATTACGTGA

451 TATTAATAAA GAGACAGTTT CTTTCATTCC AAACTATGAT GATACGACAC

501 TCCGAACCAA TGGTATTGCC ATCAAGAATT TCCTAACTTA CTAAKTGAAT

551 GGTTCTAC
```

Figure 65:
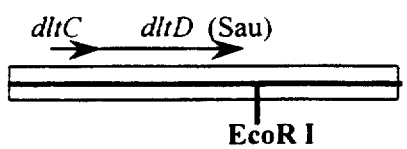

Mutant: NT160
Phenotype: temperature sensitivity
Sequence map: Mutant NT160 is complemented by plasmid pMP423, which carries a 2.2 kb insert of wild-type *S. aureus* genomic DNA. A partial restriction map is depicted in FIG. 65. Database searches at the nucleic acid and (putative) polypeptide levels against currently available databases reveal identity to the Dlt locus of *S. aureus* (Genbank Accession No. D86240; unpublished). The pMP423 clone completely contains the genes dltC, encoding a putative D-Alanine carrier protein, and dltD, encoding a putative "extramembranal protein". Further subcloning and recomplementation experiments already in progress will demonstrate whether one or both of the ORFs encode essential genes.

DNA sequence data: The following DNA sequence data represents the sequence generated by primer walking through clone pMP423, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP423
pMP423 Length: 2234 nt
    1 AGTCGATCTT TATTCTACAT GTCTCGTAAA AAATTATTGA AGAGTCAATT SEQ ID NO. 75

51 TGCAATGTCT AACGTGGCAT TCTTAATCAA CTTCTTCATA ATGGGAATTT
```

-continued

```
 101 GGCATGGTAT CGAAGTGTAT TACATTGTTT ATGGTTTATA CCATGCAGCA
 151 TTGTTTATAG GTTATGGCTA TTATGAACGT TGGCGTAAGA AACATCCGCC
 201 ACGTTGGCAA ATGGTTTCA  CAACAGCACT TAGCATTGTG ATTACATTCC
 251 ACTTTGTAAC ATTTGGCTTT TTAATCTTCT CAGGTAAACT TATATAATAA
 301 AGGAGAATTT AATTATGGAA TTTAGAGAAC AAGTATTAAA TTATTTAGCA
 351 GAAGTAGCAG AAAAATGATA TTGTAAAAGA AAATCCAGAC GTAGAAATTT
 401 TTGAAGAAGG TATTATTGAT TCTTTCCAAA CAGTTGGATT ATTATTAGAG
 451 ATTCAAAATA AACTTGATAT CGAAGTATCT ATTATGGACT TTGATAGAAG
 501 ATGAGTGGGC MACACCAAAT AAAATCGTTG AAGCATTAGA AGAGTTACGA
 551 TGAAATTAAA ACCTTTTTTA CCCATTTTAA TTAGTGGAGC GGTATTCATT
 601 GTCTTTCTAT TATTACCTGC TAGTTGGTTT ACAGGATTAG TAAATGAAAA
 651 GACTGTAGAA GATAATAGAA CTTCATTGAC AGATCAAGTA CTAAAAGGCA
 701 CACTCAWTCA AGATAAGTTA TACGAATCAA ACAAGTATTA TCCTATATAC
 751 GGCTCTAGTG AATTAGGTAA AGATGACCCA TTTAATCCTG CAATTGCATT
 801 AAATAAGCAT AACGCCAACA AAAAAGCATT CTTATTAGGT GCTGGTGGTT
 851 CTACAGACTT AATTAACGCA GTTGAACTTG CATCACAGTT ATGATAAATT
 901 AAAAGGTTAA GAAATTAACA TTTATTATTT CACCACAATG GTTTACAAAC
 951 CCATGGTTTA ACGAATCCAA AACTTTGATG CTCSTATGTC TCAAACTCMA
1001 ATTAATCAAA TGTTCCCASC AGAAAAACAT GTCTACTGAA TTAAAACGTC
1051 GTTATGCACA ACGTTTATTA CAGTTTCCAC ATGTACACAA TAAAGAATAC
1101 TTGAAATCTT ATGCTAAAAA CCCTAAAGAA ACTAAAGRTA GTTATATTTC
1151 TGGKTTTWAA RAGAGATCAA TTGATTAAAA TAGAAGCGAT TAAATCATTG
1201 TTTGCAATGG ATAAATCTCC ATTAGAACAT GTTAAACCCT GCTACAAAAC
1251 CAGACGCTTC TTGGGATGAG ATGAAACAAA AAGCAGTTGA AATTGGTAAA
1301 GCTGATACTA CATCGAATAA ATTTGGTATT AGAGATCAAT ACTGGAAATT
1351 AATTCCAAGA AAGTAAGCCG TTAAAGTTAG ACGTTGACTA CGAATTCMAT
1401 GTTWATTCTC CCAGAATTCC MAGATTTAGA ATTACTTGTW AAAAMMATGC
1451 KTGCTGCTGG TGCAGATGTT CAATATGTAA GTATTCCATC AAACGGTGTA
1501 TGGTATGACC ACATTGGTAT CGATAAAGAA CGTCGTCAAG CAGTTTATAA
1551 AAAAATCCAT TCTACTGTTG TAGATAATGG TGGTAAAATT TACGATATGA
1601 CTGATAAAGA TTATGAAAAA TATGTTATCA GTGATGCCGT ACACATCGGT
1651 TGGAAAGGTT GGGTTTATAT GGATGAGCAA ATTGCGAAAC ATATGAAAGG
1701 TGAACCACAA CCTGAAGTAG ATAAACCTAA AAATTAAAAT ACAAATAGCA
1751 CATAACTCAA CGATTTTGAT TGAGCGTATG TGCTATTTTT ATATTTTAAA
1801 TTTCATAGAA TAGAATAGTA ATATGTGCTT GGATATGTGG CAATAATAAA
1851 ATAATTAATC AGATAAATAG TATAAAAATAA CTTTCCCATC AGTCCAATTT
1901 GACAGCGAAA AAAGACAGGT AATAACTGAT TATAAATAAT TCAGTATTCC
1951 TGTCTTTGTT GTTATTCATA ATATGTTCTG TTAACTTAAT ATCTTTATAT
2001 TAGAATACTT GTTCTACTTC TATTACACCA GGCACTTCTT CGTGTAATGC
2051 ACGCTCAATA CCAGCTTTAA GAGTGATTGT AGAACTTGGG CATGTACCAC
```

```
2101 ATGCACCATG TAATTGTAAT TTAACAATAC CGTCTTCCAC GTCAATCAAT

2151 GAGCAGTCGC CACCATCACG TAATAAAAAT GGACGAAGAC GTTCAATAAC

2201 TTCTGCTACT TGATCGACCT GCAGGCATGC AAGC
```

Mutant: NT166

Phenotype: temperature sensitivity

Figure 66:
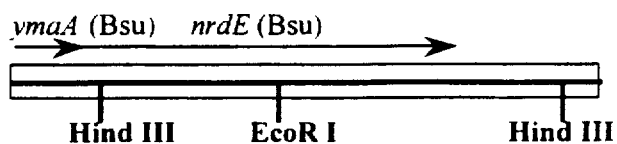

Sequence map: Mutant NT166 is complemented by plasmid pMP425, which carries a 3.3 kb insert of wild-type *S. aureus* genomic DNA. A partial restriction map is depicted in FIG. 66. Database searches at the nucleic acid and (putative) polypeptide levels against currently available databases reveal strong peptide-level similarities to nrdE, encoding ribonucleotide diphosphate reductase II (EC 1.17.4.1), from *B. subtilis* (Genbank Accession No. Z68500), and ymaA, a hypothetical ORF, from *B. subtilis* (same Genbank entry).

DNA sequence data: The following DNA sequence data represents the sequence generated by primer walking through clone pMP425, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP425
pMP425 Length: 3305 nt
    1 GAGCTCGGTA CCCGGGGATC CTCTAGAGTC GATCCAATGA AAATAATATASEQ ID NO. 76

51 TTTTTCATTT ACTGGAAATG TCCGTCGTTT TATTAAGAGA ACAGAACTTG

101 AAAATACGCT TGAGATTACA GCAGAAAATT GTATGGAACC AGTTCATGAA

151 CCGTTTATTA TCGTTACTGG CACTATTGGA TTTGGAGAAG TACCAGAACC

201 CGTTCAATCT TTTTTAGAAG TTAATCATCA ATACATCAGA GGTGTGGCAG

251 CTAGCGGTAA TCGAAATTGG GGACTAAATT TCGCAAAAGC GGGTCGCACG

301 ATATCAGAAG AGTATAATGT CCCTTTATTA ATGAAGTTTG AGTTACATGG

351 GAAAAAACAA AGACGTTATT GAATTTAAGA ACAAGGTGGG TAATTTTAAT

401 GAAAACCATG GAAGAGAAAA AGTACAATCA TATTGAATTA AATAATGAGG

451 TCACTAAACG AAGAGAAGAT GGATTCTTTA GTTTAGAAAA AGACCAAGAA

501 GCTTTAGTAG CTTATTTAGA AGAAGTAAAA GACAAAACAA TCTTCTTCGA

551 CACTGAAATC GAGCGTWTAC GTTMTTTAGT AGACMACGAT TTTTATTTCA

601 ATGTGTTTGA TATWTATAGT GAAGCGGATC TAATTGAAAT CACTGATTAT

651 GCAAAATCAA TCCCGTTTAA TTTTGCAAGT TATATGTCAG CTAGTAAATT

701 TTTCAAAGAT TACGCTTTGA AAACAAATGA TAAAAGTCAA TACTTAGAAG

751 ACTATAATCA ACACGTTGCC ATTGTTGCTT TATACCTAGC AAATGGTAAT

801 AAAGCACAAG CTAAACAATT TATTTCTGCT ATGGTTGAAC AAAGATATCA

851 ACCAGCGACA CCAACATTTT TAAACGCAGG CCGTGCGCGT TCGTGGTGGA

901 GCTAGTGTTC ATTGTTTCCT TATTAGAAGT TGGATGGACA GCTTAAATTC

951 AATTTAACTT TATTGGATTC AACTGCAAAA CAATTAAGTW AAATTGGGGG

1001 CGGCGTTTGC MATTAACTTA TCTAAATTGC GTGCACGTGG TGAAGCAATT

1051 AAAGGAATTA AAGGCGTAGC GAAAGGCGTT TTACCTATTG CTAAGTCACT

1101 TGAAGGTGGC TTTAGCTATG CAGATCAACT TGGTCAACGC CCTGGTGCTG

1151 GTGCTGTGTA CTTAAATATC TTCCATTATG ATGTAGAAGA ATTTTTAGAT

1201 ACTAAAAAAG TAAATGCGGA TGAAGATTTA CGTTTATCTA CAATATCAAC

1251 TGGTTTAATT GTTCCATCTA AATTCTTCGA TTTAGCTAAA GAAGGTAAGG

1301 ACTTTTATAT GTTTGCACCT CATACAGTTA AAGAAGAATA TGGTGTGACA

1351 TTAGACGATA TCGATTTAGA AAAATATTAT GATGACATGG TTGCAAACCC
```

-continued

```
1401 AAATGTTGAG AAAAAGAAAA AGAATGCGCG TGAAATGTTG AATTTAATTG
1451 CGCMAACACA ATTACAATCA GGTTATCCAT ATTTAATGTT TAAAGATAAT
1501 GCTAACAGAG TGCATCCGAA TTCAAACATT GGACAAATTA AAATGAGTAA
1551 CTTATGTACG GAAATTTTCC AACTACAAGA AACTTCAATT ATTAATGACT
1601 ATGGTATTGA AGACGAAATT AAACGTGATA TTTCTTGTAA CTTGGGCTCA
1651 TTAAATATTG TTAATGTAAT GGAAAGCGGA AAATTCAGAG ATTCAGTTCA
1701 CTCTGGTATG GACGCATTAA CTGTTGTGAG TGATGTAGCA AATATTCAAA
1751 ATGCACCAGG AGTTAGAAAA GCTAACAGTG AATTACATTC AGTTGKTCTT
1801 GGGTGTGATG AATTWACACG GTTACCTAGC AAAAAATAAA ATTGGTTATG
1851 AGTCAGAAGA AGCAAAAGAT TTTGCAAATA TCTTCTTTAT GATGATGAAT
1901 TTCTACTCAA TCGAACGTTC AATGGAAATC GCTAAAGAGC GTGGTATCAA
1951 ATATCAAGAC TTTGAAAAGT CTGATTATGC TAATGGCAAA TATTTCGAGT
2001 TCTATACAAC TCAAGAATTT GAACCTCAAT TCGAAAAAGT ACGTGAATTA
2051 TTCGATGGTA TGGCTATTCC TACTTCTGAG GATTGGAAGA AACTACAACA
2101 AGATGTTGAA CAATATGGTT TATATCATGC ATATAGATTA GCAATTGCTC
2151 CAACACAAAG TATTTCTTAT GTTCAAAATG CAACAAGTTC TGTAATGCCA
2201 ATCGTTGACC AAATTGAACG TCGTACTTAT GGTAAATGCG GAAACATTTT
2251 ACCCTATGCC ATTCTTATCA CCACAAACAA TGTGGTACTA CAAATCAGCA
2301 TTCAATACTG ATCAGATGAA ATTAATCGAT TTAATTGCGA CAATTCAAAC
2351 GCATATTGAC CAAGGTATCT CAACGATCCT TTATGTTAAT TCTGAAATTT
2401 CTACACGTGA GTTAGCAAGA TTATATGTAT ATGCGCACTA TAAAGGATTA
2451 AAATCACTTT ACTATACTAG AAATAAATTA TTAAGTGTAG AAGAATGTAC
2501 AAGTTGTTCT ATCTAACAAT TAAATGTTGA AAATGACAAA CAGCTAATCA
2551 TCTGGTCTGA ATTAGCAGAT GATTAGACTG CTATGTCTGT ATTTGTCAAT
2601 TATTGAGTAA CATTACAGGA GGAAATTATA TTCATGATAG CTGTTAATTG
2651 GAACACACAA GAAGATATGA CGAATATGTT TTGGAGACAA AATATATCTC
2701 AAATGTGGGT TGAAACAGAA TTTAAAGTAT CAAAAGACAT TGCAAGTTGG
2751 AAGACTTTAT CTGAAGCTGA ACAAGACACA TTTAAAAAAG CATTAGCTGG
2801 TTTAACAGGC TTAGATACAC ATCAAGCAGA TGATGGCATG CCTTTAGTTA
2851 TGCTACATAC GACTGACTTA AGGAAAAAAG CAGTTTATTC ATTTATGGCG
2901 ATGATGGAGC AAATACACGC GAAAAGCTAT TCACATATTT TCACAACACT
2951 ATTACCATCT AGTGAAACAA ACTACCTATT AGATGAATGG GTTTTAGAGG
3001 AACCCCATTT AAAATATAAA TCTGATAAAA TTGTTGCTAA TTATCACAAA
3051 CTTTGGGGTA AGAAGCTTC GATATACGAC CAATATATGG CCAGAGTTAC
3101 GAGTGTATTT TTAGAAACAT TCTTATTCTT CTCAGGTTTC TATTATCCAC
3151 TATATCTTGC TGGTCAAGGG AAAATGACGA CATCAGGTGA AATCATTCGT
3201 AAAATTCTTT TAGATGAATC TATTCATGGT GTATTTACCG GTTTAGATGC
3251 ACAGCATTTA CGAAATGAAC TATCTGAAAG TGAGAAACAA AAAGCAGATC
3301 GACCT
```

173

Figure 67:
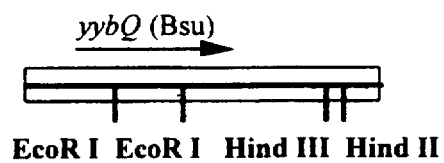

Mutant: NT 199
Phenotype: temperature sensitivity
Sequence map: Mutant NT199 is complemented by plasmid pMP642, which carries a 3.6 kb insert of wild-type *S. aureus* genomic DNA. A partial restriction map is depicted in FIG. 67. Database searches at the nucleic acid and (putative) polypeptide levels against currently available databases reveal strong peptide-level similarities to yybQ, an uncharacterized ORFs identified in *B. subtilis* from genomic sequencing efforts.

174

DNA sequence data: The following DNA sequence data represents the sequence generated by primer walking through clone pMP642, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP642
pMP642 Length: 1945 nt
    1 TTGATAGTTT ATTGGAGAGA AAGAAGTATT AATCAAGTCG AAATCGTTGG SEQ ID NO. 77
   51 TGTATGTACC GATATTTGCG TGTTACATAC AGCAATTTCT GCATACAACT
  101 TAGGTTATAA AATTTCAGTA CCTGCTGAGG GAGTGGCTTC ATTTAATCAA
  151 AAAGGGCATG AATGGGCACT TGCACATTTC AAAAACTCAT TAGGTGCAGA
  201 GGTAGAACAA CACGTTTAAA TCGTGCTAAA ATAATTATAA AGAATACAAT
  251 TTACAAGGGA GATATTTGAC AATGGCTAAA ACATATATTT TCGGACATAA
  301 GAATCCAGAC ACTGATGCAA TTTCATCTGC GATTATTATG GCAGAATTTG
  351 AACAACTTCG AGGTAATTCA GGAGCCAAAG CATACCGTTT AGGTGATGTG
  401 AGTGCARAAA CTCAATTCGC GTTAGATACA TTTAATGTAC CTGCTCCGGA
  451 ATTATTAACA GATGATTTAG ATGGTCAAGA TGTTATCTTA GTTGATCATA
  501 ACGAATTCCA ACAAGTTCT GATACGATTG CCTCTGCTAC AATTAAGCAT
  551 GTAATTGATC ATCACAGAAT TGCAAATTTC GAAACTGCTG GTCCTTTATG
  601 TTATCGTGCT GAACCAGTTG GTTGTACAGC TACAATTTTA TACAAAATGT
  651 TTAGAGAACG TGGCTTTGAA ATTAAACCTG AAATTGCCGG TTTAATGTTA
  701 TCAGCAATTA TCTCAGATAG CTTACTTTTC AAATCACAAC ATGTACACAA
  751 CAAGATGTTA AAGCAGCTGA AGAATTAAAA GATATTGCTA AAGTTGATAT
  801 TCAAAAGTAC GGCTTTAGTA TGTTAAAAGC AGGTGCTTCA ACAACTGATA
  851 AATCAGTTGA ATTCTTATTA AACATGGATG CTAAATCATT TACTATGGGT
  901 GACTATGKGA YTCGTATTGC AACAAGTTAA TGCTGTTGAC CTTGACGAAG
  951 TGTTAAWTCG TAAAGAAGAT TTAGAAAAAG AAATGTTAGC TGTAAGTGCA
 1001 CAAGAAAAAT ATGACTTATT TGTACTTGTT GTTACKGACA TCATTAATAG
 1051 TGATTCTAAA ATTTTAGTTG TAGGTGCTGA AAAAGATAAA GTTGGCGAAG
 1101 CATTCAATGT TCAATTAGAA GATGACATGG CCYTCTTATC TGGTGTCGTW
 1151 TCTCGAAAAA AACAAATCGT ACCTCAAATC ACTGAAGCAT AACAAAATA
 1201 ATACTATATT ACTGTCTAAT TATAGACATG TTGTATTTAA CTAACAGTTC
 1251 ATTAAAGTAG AATTTATTTC ACTTTCCAAT GAACTGTTTT TTATTTACGT
 1301 TTGACTAATT TACAACCCTT TTTCAATAGT AGTTTTTATT CCTTTAGCTA
 1351 CCCTAACCCA CAGATTAGTA ATTTCTATAC AATTCCCCTT TTGTCTTAAC
 1401 ATTTTCTTAA AATATTTGCG ATGTTGAGTA TAAATTTTTG TTTTCTTCCT
 1451 ACCTTTTTCG TTATGATTAA AGTTATAAAT ATTATTATGT ACACGATTCA
 1501 TCGCTCTATT TTCAACTTTC AACATATATA ATTCGAAAGA CCATTTAAAA
 1551 TTAACGGCCA CAACATTCAA ATCAATTAAT CGCTTTTTCC AAAATAATCA
```

-continued

```
1601 TATAAGGAGG TTCTTTTCAT TATGAATATC ATTGAGCAAA AATTTTATGA

1651 CAGTAAAGCT TTTTTCAATA CACAACAAAC TAAAGATATT AGTTTTAGAA

1701 AAGAGCAATT AAAGAAGTTA AGCAAAGCTA TTAAATCATA CGAGAGCGAT

1751 ATTTTAGAAG CACTATATAC AGATTTAGGA AAAAATAAAG TCGAAGCTTA

1801 TGCTACTGAA ATTGGCATAA CTTTGAAAAG TATCAAAATT GCCCGTAAGG

1851 AACTTAAAAA CTGGACTAAA ACAAAAAATG TAGACACACC TTTATATTTA

1901 TTTCCAACAA AAAGCTATAT CAAAAAAGAA CCTTATGGAA CAGTT
```

Mutant: NT 201

Phenotype: temperature sensitivity

Figure 68:
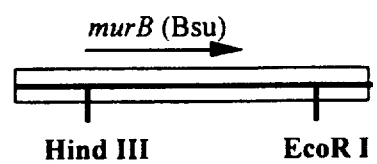

Sequence map: Mutant NT201 is complemciitcd by plasmid pMP269, which carries a 2.6 kb insert of wild-type *S. aureus* genomic DNA. A partial restriction map is depicted in FIG. 68. Database searches at the nucleic acid and (putative) polypeptide levels against currently available databases reveal strong peptide-level similarity to ylxc, encoding a putative murB homolog (UDP-N-acetylenolpyruvoylglucosamine reducmtase), in *B. subtilis* (Genbank Accession No. M31827). The predicted relative size and orientation of the ylxC gene is depicted by an arrow in the map.

DNA sequence data: The following DNA sequence data represents the sequence generated by primer walking through clone pMP269, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP269
pMP269 Length: 2590 nt
   1 TCGAACTCGG TACCCGGGGA TCCTCTAGAG TCGATCAACT ACAACTACAA SEQ ID NO. 78

51 TTAAACAAAT TGAGGAACTT GATAAAGTTG TAAAATAATT TTAAAAGAGG

101 GGAACAATGG TTAAAGGTCT TAATCATTGC TCCCCTCTTT TCTTTAAAAA

151 AGGAAATCTG GGACGTCAAT CAATGTCCTA GACTCTAAAA TGTTCTGTTG

201 TCAGTCGTTG GTTGAATGAA CATGTACTTG TAACAAGTTC ATTTCAATAC

251 TAGTGGGCTC CAAACATAGA GAAATTTGAT TTTCAATTTC TACTGACAAT

301 GCAAGTTGGC GGGGCCCAAA CATAGAGAAT TCAAAAAGG AATTCTACAG

351 AAGTGGTGCT TTATCATGTC TGACCCACTC CCTCTAATGT TTTGACTATG

401 TTGTTTAAAT TTCAAAATAA ATATGATAGT GATATTTACA GCGATTGTTA

451 AACCGAGATT GGCAATTTGG ACAACGCTCT ACCATCATAT ATTCATTGAT

501 TGTTAATTCG TGTTTGCATA CACCGCATAA GATTGCTTTT TCGTTAAATG

551 AAGGCTCAGA CCAACGCTTA ATGGCGTGCT TTTCAAACTC ATTATGGCAC

601 TTATAGCATG GATAGTATTT ATTACAACAT TTAAATTTAA TAGCAATAAT

651 ATCTTCTTCG GTAAAATAAT GGCGACAGCG TGTTTCAGTA TCGATTAATG

701 AACCATAAAC TTTAGGCATA GACAAAGCTC CTTAACTTAC GATTCCTTTG

751 GATGTTCACC AATAATGCGA ACTTCACGAT TTAATTCAAT GCCAAWTTTT

801 TCTTTGACGG TCTTTTGTAC ATAATGAATA AGGTTTTCAT AATCTGTAGC

851 AGTTCCATTG TCTACATTTA CCATAAAACC AGCGTGTTTG GTTGAAACTT

901 CAACGCCGCC AATACGGTGA CCTTGCAAAT TAGAATCTTG TATCAATTTA

951 CCTGCAAAAT GACCAGGCGG TCTTTGGAAT ACACTACCAC ATGAAGGATA

1001 CTCTAAAGGT TGTTTAAATT CTCTACGTTC TGTTAAATCA TCCATTTTAG

1051 CTTGTATTTC AGTCATTTTA CCAGGAGCTA AAGTAAATGC AGCTTCTAAT

1101 ACAACTAANT GTTCTTTTTG AATAATGCTA TTACNATAAT CTAACTCTAA
```

-continued

```
1151 TTCTTTTGTT GTAAGTTTAA TTAACGAGCC TTGTTCGTTT ACGCAAAGCG

1201 CATRGTCTAT ACAATCTTTA ACTTCGCCAC CATAAGCGCC AGCATTCATA

1251 TACACTGCAC CACCAATTGA ACCTGGAATA CCACATGCAA ATTCAAGGCC

1301 AGTAAGTGCG TAATCACGAG CAACACGTGA GACATCAATA ATTGCAGCGC

1351 CGCTACCGGC TATTATCGCA TCATCAGATA CTTCCGATAT GATCTAGTGA

1401 TAATAAACTA ATTACAATAC CGCGAATACC ACCTTCACGG ATAATAATAT

1451 TTGAGCCATT TCCTAAATAT GTAACAGGAA TCTCATTTTG ATAGGCATAT

1501 TTAACAACTG CTTGTACTTC TTCATTTTTA GTAGGGGTAA TGTAAAAGTC

1551 GGCATTACCA CCTGTTTTAG TATAAGTGTA TCGTTTTAAA GGTTCATCAA

1601 CTTTAATTTT TTCAKTYGRS MTRARKKSWT GYAAAGCTTG ATAGATGTCT

1651 TTATTTATCA CTTCTCAGTA CATCCTTTCT CATGTCTTTA ATATCATATA

1701 GTATTATACC AATTTTAAAA TTCATTTGCG AAAATTGAAA AGRAAGTATT

1751 AGAATTAGTA TAATTATAAA ATACGGCATT ATTGTCGTTA TAAGTATTTT

1801 TTACATAGTT TTTCAAAGTA TTGTTGCTTT TGCATCTCAT ATTGTCTAAT

1851 TGTTAAGCTA TGTTGCAATA TTTGGTGTTT TTTTGTATTG AATTGCAAAG

1901 CAATATCATC ATTAGTTGAT AAGAGGTAAT CAAGTGCAAG ATAAGATTCA

1951 AATGTTTGGG TATTCATTTG AATGATATGT AGACGCACCT GTTGTTTTAG

2001 TTCATGAAAA TTGTTAAACT TCGCCATCAT AACTTTCTTA GTATATTTAT

2051 GATGCAAACG ATAAAACCCT ACATAATTTA AGCGTTTTTC ATCTAAGGAT

2101 GTAATATCAT GCAAATTTTC TACACCTACT AAAATATCTA AAATTGGCTC

2151 TGTTGAATAT TTAAAATGAT GCGTACCGCC AATATGTTTT GTATATTTTA

2201 CTGGGCTGTC TAAGAGGTTG AATAATAATG ATTCAATTTC AGTGTATTGT

2251 GATTGAAAAC AATTAGTTAA ATCACTATTA ATGAATGGTT GAACATTTGA

2301 ATACATGATA AACTCCTTTG ATATTGAAAA TTAATTTAAT CACGATAAAG

2351 TCTGGAATAC TATAACATAA TTCATTTTCA TAATAAACAT GTTTTTGTAT

2401 AATGAATCTG TTAAGGAGTG CAATCATGAA AAAAATTGTT ATTATCGCTG

2451 TTTTAGCGAT TTTATTTGTA GTAATAAGTG CTTGTGGTAA TAAAGAAAAA

2501 GAGGCACAAC ATCMATTTAC TAAGCAATTT AAAGATGTTG AGCAAACACA

2551 WAAAGAATTA CAACATGTCA TGGATAATAT ACATTTGAAA
```

Figure 69:

Mutant: NT304
Phenotype: temperature sensitivity
Sequence map: Mutant NT304 is complemented by plasmid pMP450, which carries a 3.3 kb insert of wild-type *S. aureus* genomic DNA. A partial restriction map is depicted in FIG. 69. Database searches at the nucleic acid and (putative) polypeptide levels against currently available databases reveal strong peptide-level similarities from the left-most contig below and the dod gene product, encoding pentose-5-phosphate epimerase (EC 5.1.3.1), from *S. oleraceae* (Genbank Accession No. L42328).

DNA sequence data: The following DNA sequence data represents the sequence generated from clone pMP450, starting with standard M13 forward and M13 reverse sequencing primers; the sequence contig will be completed via primer walking strategies. The sequence below can be used to design PCR primers for the purpose of amplification from genomic DNA with subsequent DNA sequencing.

```
clone pMP450
pMP450.forward Length: 1019 nt
  1 ATTCGAGCTC GGTACCCGGG GATCCTCTAG AGTCGCTCGA TAACTTCTATSEQ ID NO. 79

51 ATGAACATCA TGTTTATAAT ATGCTTTTTT CAATAATAAC TGAATTGCCC
```

-continued

```
 101 CAAAAAAGTG ATCTAATCGT CCGCCTGTTG CACCATAAAT TGTAATACTA
 151 TCAAATCCAA GTGCAACAGC TTTATCAACC GCTAAAGCTA AATCCGTATC
 201 AGCTTTTTCA GCTTGAACTG GTTTGATTTG TAACTGTTCT GTTAGAAGTT
 251 GGCGTTCTTC TTTACTGACT GAATCAAAGT CTCCCACTGA GAAAAAGGG
 301 ATAATTTGAT GCTTCAATAA AATCAAAGCA CCTCTATCAA CGCCGCCCCA
 351 TTTACCTTCA TTACTTTTGG CCCAAATATC TTGCGGCAAG TGTCGATCAG
 401 AACATAATAA ATTTATATGC ATATACACTC AACCTTTCAA TGCTTGTGTT
 451 GACTTTTTTA TAATCCTCTT GTTTAAAGAA AAATGAACCT GTTACTAGCA
 501 TTGTTAGCAC CATTTTCAAC ACAAACTTTC GCTGTTATCG GTATTTACGC
 551 CTCCATCAAC TTCAATATCA AAGTTTAATT GACGTTCCAT TTTAATAGCA
 601 TTAAGACCCG CTATTTTTTC TACGCATTGA TCAATAAATG ATTGACCACC
 651 AAACCCTGGG TTAACTGTCA TCACTAGTAC ATAATCAACA ATGTCTAAAA
 701 TAGGTTCAAT TTGTGATATT GGTGTACCAG GATTAATTAC TACACCAGCT
 751 TTTTTATCTA AATGTTTAAT CATTTGAATA GCACGATGAA ATATGAGGCG
 801 TTGATTCGAC ATGAATTGNA AATCATATCG GCACCATGTT CTGCAAATGA
 851 TGCAATATAC TTTTCTGGAA TTTTCAATCA TCAAATGTAC GTCTATANGT
 901 AATGTTGTGC CTTTTCTTAC TGCATCTAAT ATTGGTAAAC CAATAGATAT
 951 ATTAGGGACA AATTGACCAT CCATAACATC AAAATGAACT CCGTCGAANC
1001 CCGGCTTCTC CAGTCGTTT
pMP450.reverse Length: 1105 nt
   1 CNTGCATGCC TGCAGGTCGA TCTANCAAAG CATATTAGTG AACATAAGTC SEQ ID NO. 80
  51 GAATCAACCT AAACGTGAAA CGACGCAAGT ACCTATTGTA AATGGGCCTG
 101 CTCATCATCA GCAATTCCAA AAGCCAGAAG GTACGGTGTA CGAACCAAAA
 151 CCTAAAAAGA AATCAACACG AAAGATTGTG CTCTTATCAC TAATCTTTTC
 201 GTTGTTAATG ATTGCACTTG TTTCTTTTGT GGCAATGGCA ATGTTTGGTA
 251 ATAAATACGA AGAGACACCT GATGTAATCG GGAAATCTGT AAAAGAAGCA
 301 GAGCAAATAT TCAATAAAAA CAACCTGAAA TTGGGTAAAA TTTCTAGAAG
 351 TTATAGTGAT AAATATCCTG AAAATGAAAT TATTAAGACA ACTCCTAATA
 401 CTGGTGAACG TGTTGAACGT GGTGACAGTG TTGATGTTGT TATATCAAAG
 451 GGSCCTGAAA AGGTTAAAAT GCCAAATGTC ATTAATTTAC CTAAGGAGGA
 501 AGCCTTGCAG AAATTAAAAT CCGTTAGGTC TTAAAGATGT TACGATTGAA
 551 AAAGTWTATA ATAATCCAAG CGCCMAAAGG ATACATTGCA AATCAAAKTG
 601 TTAMCCGCAA ATACTGAAAT CGCTATTCAT GATTCTAATA TTAAACTATA
 651 TGAATCTTTA GGCATTAAGC AAGTTTATGT AGAAGACTTT GAACATAAAT
 701 CCTTTAGCAA AGCTAAAAAA GCCTTAGAAG AAAAAGGGTT TAAAGTTGAA
 751 AGTAAGGAAG AGTATAGTGA CGATATTGAT GAGGGTGATG TGATTTCTCA
 801 ATCTCCTAAA GGAAAATCAG TAGATGAGGG GTCAACGATT TCATTTGTTG
 851 TTTCTAAAGG TAAAAAAAGT GACTCATCAG ATGTCNAAAC GACAACTGAA
 901 TCGGTAGATG TTCCATACAC TGGTNAAAAT GATAAGTCAC AAAAAGTTCT
 951 GGTTTATCTT NAAGATAANG ATAATGACGG TTCCACTGAA AAAGGTAGTT
1001 TCGATATTAC TAATGATCAC GTTATAGACA TCCTTTAAGA ATTGAAAAAG
```

```
                                              -continued
1051 GGAAAACGCA GTTTTATTGT TAAATTGACG GTAAACTGTA CTGAAAAAAA

1101 NTCGC
```

Figure 70:
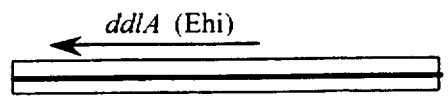

Mutant: NT 310
Phenotype: temperature sensitivity
Sequence map: Mutant NT310 is complemented by plasmid pMP364, which carries a 2.4 kb insert of wild-type *S. aureus* genomic DNA. A partial restriction map is depicted in FIG. 70; there are no apparent restriction sites for EcoR I, BamH I, HinD III or Pst I. Database searches at the nucleic acid and (putative) polypeptide levels against currently available databases reveal strong similarities to the ddlA gene product from *E. hirae*, which encodes D-Ala-D-Ala ligase (EC 6.3.2.4); similarities are also noted to the functionally-similar proteins VanA and VanB from *E. faecium* and the VanC protein from *E. gallinarum*. The predicted relative size and orientation of the ddlA gene is depicted by an arrow in the restriction map.

DNA sequence data: The following DNA sequence data represents the sequence generated by primer walking through clone pMP364, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP364
pMP364 Length: 2375 nt
    1 AATATGACAG AACCGATAAA GCCAAGTTCC TCTCCAATCA CTGAAAAGAT SEQ ID NO. 81

51 AAAGTCAGTA TGATTTTCAG GTATATAAAC TTCACCGTGA TTGTATCCTT

101 TACCTAGTAA CTGTCCAGAA CCGATAGCTT TAAGTGATTC AGTTAAATGA

151 TAGCCATCAC CACTACTATA TGTATAGGGG TCAAGCCATG AATTGATTCG

201 TCCCATTTGA TACAGTTGGA CACCTAATAA ATTTTCAATT AATGCGGGTG

251 CATATAGAAT ACCTAAAATG ACTGTCATTG CACCAACAAT ACCTGTAATA

301 AAGATAGGTG CTAAGATACG CCATGTTATA CCACTTACTA ACATCACACC

351 TGCAATAATA GCAGCTAATA CTAATGTAGT TCCTAGGTCA TTTTGCAGTA

401 ATATTAAAAT ACTTGGTACT AACGAGACAC CAATAATTTT GAAAAATAAT

451 AACAAATCAC TTTGGAATGA TTTATTGAAT GTGAATTGAT TATGTCTAGA

501 AACGACACGC GCTAATGCTA AAATTAAAAT AATTTTCATG AATTCAGATG

551 GCTGAATACT GATAGGGCCA AACGTGTTYC AACTTTTGGC ACCATTGATA

601 ATAGGTGTTA TAGGTGACTC AGGAATAACG AACCAGCCTA TTWATAWTAG

651 ACAGATTAAG AAATACAATA AATATGTATA ATGTTTAATC TTTTTAGGTG

701 AAATAAACAT GATGATACCT GCAAAAATTG CACCTAAAAT GTAATAAAAA

751 ATTTGTCTGA TACCGAAATT AGCACTGTAT TGACCACCGC CCATTGCCGA

801 GTTAATAAGC AGAACACTGA AAATTGCTAA AACAGCTATA GTGGCTACTA

851 ATACCCAGTC TACTTTGCGA AGCCAATGCT TATCCGGCTG TTGACGAGAT

901 GAATAATTCA TTGCAAACTC CTTTTATACT CACTAATGTT TATATCAATT

951 TTACATGACT TTTTAAAAAT TAGCTAGAAT ATCACAGTGA TATCAGCYAT

1001 AGATTTCAAT TTGAATTAGG AATAAAATAG AAGGGAATAT TGTTCTGATT

1051 ATAAATGAAT CAACATAGAT ACAGACACAT AAGTCCTCGT TTTTAAAATG

1101 CAAAATAGCA TTAAAATGTG ATACTATTAA GATTCAAAGA TGCGAATAAA

1151 TCAATTAACA ATAGGACTAA ATCAATATTA ATTTATATTA AGGTAGCAAA

1201 CCCTGATATA TCATTGGAGG GAAAACGAAA TGACAAAAGA AAATATTTGT

1251 ATCGTTTTTG GAGGGAAAAG TGCAGAACAC GAAGTATCGA TTCTGACAGC

1301 AYWAAATGTA TTAAATGCAR TAGATAAAGA CAAATATCAT GTTGATATCA

1351 TTTATATTAC CAATGATGGT GATTGGAGAA AGCAAAATAA TATTACAGCT
```

-continued

```
1401 GAAATTAAAT CTACTGATGA GCTTCATTTA GAAAAATGGA GAGGCGCTTG

1451 AGATTTCACA GCTATTGAAA GAAAGTAGTT CAGGACAACC ATACGATGCA

1501 GTATTCCCAT TATTACATGG TCCTAATGGT GAAGATGGCA CGATTCAAGG

1551 GCTTTTTGAA GTTTTGGATG TACCATATGT AGGAAATGGT GTATTGTCAG

1601 CTGCAAGTTT CTATGGACAA ACTTGTAATG AAACAATTAT TTGAACATCG

1651 AGGGTTACCA CAGTTACCTT ATATTAGTTT CTTACGTTCT GAATATGAAA

1701 AATATGAACA TAACATTTTA AAATTAGTAA ATGATAAATT AAATTACCCA

1751 GTCTTTGTTA AACCTGCTAA CTTAGGGTCA AGTGTAGGTA TCAGTAAATG

1801 TAATAATGAA GCGGAACTTA AAGGAGGTAT TAAAGAAGCA TTCCAATTTG

1851 ACCGTAAGCT TGTTATAGAA CAAGGCGTTA ACGCAACGTG AAATTGAAGT

1901 AGCAGTTTTA GGAAATGACT ATCCTGAAGC GACATGGCCA GGTGAAGTCG

1951 TAAAAGATGT CGCGTTTTAC GATTACAAAT CAAAATATAA AGGATGGTAA

2001 GGTTCAATTA CAAATTCCAG CTGACTTAGA CGGAAGATGT TCAATTAACG

2051 GCTTAGAAAT ATGGCATTAG AGGCATTCAA AGCGACAGAT TGTTCTGGTT

2101 TAGTCCGTGC TGATTTCTTT GTAACAGAAG ACAACCAAAT ATATATTAAT

2151 GAAACAAATG CAATGCCTGG ATTTACGGCT TTCAGTATGT ATCCAAAGTT

2201 ATGGGAAAAT ATGGGCTTAT CTTATCCAGA ATTGATTACA AAACTTATCG

2251 AGCTTGCTAA AGAACGTCAC CAGGATAAAC AGAAAAATAA ATACAAAATT

2301 SMCTWAMTGA GGTTGTTATK RTGATTAAYG TKACMYTAWA GYAAAWTCAA

2351 TCATGGATTN CCTTGTGAAA TTGAA
```

Figure 71:
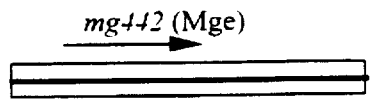

Mutant: NT 312
Phenotype: temperature sensitivity
Sequence map: Mutant NT312 is complemented by plasmid pMP266, which carries a 1.5 kb insert of wild-type *S. aureus* genomic DNA. A partial restriction map is depicted in FIG. 71; there are no apparent restriction sites for EcoR I, BamH I, HinD III or Pst I. Database searches at the nucleic acid and (putative) polypeptide levels against currently available databases reveal strong peptide-level similarities to mg442, a hypothetical ORF from *M. genetalium*, and limited similarities to G-proteins from human and rat clones; this probably indicates a functional domain of a new Staph. protein involved in GTP-binding. The ORF contained within clone pMP266 is novel and likely to be a good candidate for screen development.

DNA sequence data: The following DNA sequence data represents the sequence generated by primer walking through clone pMP266, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP266
pMP266 Length: 1543 nt
      1 AATCATTTTC AGTTTATCAT TAAACAAATA TATTGAACYM MYMAAAATGTSEQ ID NO. 82

51 CATACTGATA AAGATGAATG TCACTTAATA AGTAACTTAG ATTTAACAAA

101 TGATGATTTT TAATTGTAGA AAACTTGAAA TAATCACTTA TACCTAAATC

151 TAAAGCATTG TTAAGAAGTG TGACAATGTT AAAATAAATA TAGTTGAATT

201 AATGAATTTG TTCTAYAATT AACAKGTTWT WGAWTTTAAT AATGAGAAAA

251 GAATTGACGA AAGTAAGGTG AATTGAATGG TTATTCMATG GTATCCAGGA

301 CMTATGGCGA AAAGCCAAAA GAGAAGTAAG TGAACAATTA AMAAAAGTAG

351 ATGTAGTGTT TGAACTAGTA GATGCAAGAA TTCCATATAG TTCAAGAAAC

401 CCTATGATAG ATGAAGTTAT TAACCAAAAA CCACGTGTTG TTATATTAAA
```

```
                              -continued
 451 TAAAAAAGAT ATGTCTAATT TAAATGAGAT GTCAAAATGG GAACAATTTT

501 TTATTGATAA AGGATACTAT CCTGTATCAG TGGATGCTAA GCACGGTAAA

551 AATTTAAAGA AAGTGGAAGC TGCAGCAATT AAGGCGACTG CTGAAAAATT

601 TGAACGCGAA AAAGCGAAAG GACTTAAACC TAGAGCGATA AGAGCAATGA

651 TCGTTGGAAT TCCAAATGTT GGTAAATCCA CATTAATAAA TAAACTGGCA

701 AAGCGTAGTA TTGCGCAGAC TGGTAATAAA CCAGGTGTGA CCAAACAACA

751 ACAATGGATT AAAGTTGGTA ATGCATTACA ACTATTAGAC ACACCAGGGA

801 TACTTTGGCC TAAATTTGAA GATGAAGAAG TCGGTAAGAA GTTGAGTTTA

851 ACTGGTGCGA TAAAAGATAG TATTGTGCAC TTAGATGAAG TTGCCATCTA

901 TGGATTAAAC TTTTTAATTC AAAATGATTT AGCGCGATTA AAGTCACATT

951 ATAATATTGA AGTTCCTGAA GATGCMGAAA TCATAGCGTG GTTTGATGCG

1001 ATAGGGAAAA AACGTGGCTT AATTCGACGT GGTAATGAAA TTGATTACGA

1051 AGCAGTCATT GAACTGATTA TTTATGATAT TCGAAATGCT AAAATAGGAA

1101 ATTATTGTTT TGATATTTTT AAAGATATGA CTGAGGAATT AGCAAATGAC

1151 GCTAACAATT AAAGAAGTTA CGCAGTTGAT TAATGCGGTT AATACAATAG

1201 AAGAATTAGA AAATCATGAA TGCTTTTTAG ATGAGCGAAA AGGTGTTCAA

1251 AATGCCATAG CTAGGCGCAG AAAAGCGTTA GAAAAAGAAC AAGCTTTAAA

1301 AGAAAAGTAT GTTGAAATGA CTTACTTTGA AAATGAAATA TTAAAAGAGC

1351 ATCCTAATGC TATTATTTGT GGGATTGATG AAGTTGGAAG AGGACCTTTA

1401 GCAGGTCCAG TCGTTGCATG CGCAACAATT TTAAATTCAA ATCACAATTA

1451 TTTGGGCCTT GATGACTCGA AAAAAGTACC TGTTACGAAA CGTCTAGAAT

1501 TAAATGAAGC ACTAAAAAAT GAAGTTACTG YTTTTGCATA TGG
```

Figure 72:
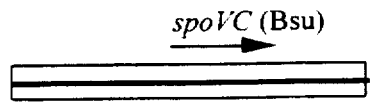

Mutant: NT 318
Phenotype: temperature sensitivity
Sequence map: Mutant NT318 is complemented by plasmid pMP270, which carries a 2.2 kb insert of wild-type *S. aureus* genomic DNA. A partial restriction map is depicted in FIG. 72; there are no apparent restriction sites for EcoR I, BamH I, HinD III, or Pst I. Database searches at the nucleic acid and (putative) polypeptide levels against currently available databases reveal strong similarities to the spoVC gene from *B. subtilis*, a gene identified as being important in sporulation, and the pth gene from *E. coli*, which encodes aminoacyl-tRNA hydrolase (EC 3.1.1.29). It is highly likely that the spoVC and pth gene products are homologues and that the essential gene identified here is the Staph. equivalent. The predicted relative size and orientation of the spoVC gene is depicted by an arrow in the restriction map.

DNA sequence data: The following DNA sequence data represents the sequence generated by primer walking through clone pMP270, starting with standard M13 forward and M13 reverse sequencing primers and completing the sequence contig via primer walking strategies. The sequence below can be used to design PCR primers for the purpose of amplification from genomic DNA with subsequent DNA sequencing.

```
     clone pMP270
     pMP270 Length: 2185 nt
       1 TTAAACAATT AAGAAAATCT GGTAAAGTAC CAGCASYAGT ATACGGTTAC SEQ ID NO. 83

51 GGTACTAAAA ACGTGTCAGT TAAAGTTGAT GAAGTAGAAT TCATCAAAGT

101 TATCCGTGAA GTAGGTCGTA ACGGTGTTAT CGAATTAGGC GTTGGTTCTA

151 AAACTATCAA AGTTATGGTT GCAGACTACC AATTCGATCC ACTTAAAAAC

201 CAAATTACTC ACATTGACTT CTTWKCAATC AATATGAGTG AAGAACGTAC

251 TGTTGAAGTA CCAGTTCAAT TAGTTGGTGA AGCAGTAGGC GCTAAAGAAA

301 GGCGGCGTTA GTTGAACAAC CATTATTCAA CTTAGAAAGT AACPGCTACT

351 CCAGACAATA TTCCAGAAGC AATCGAAGTA GACATTACTG AATTAAACAT
```

-continued

```
 401 TAACGACAGC TTAACTGTTG CTGATGTTAA AGTAACTGGC GACTTCAAAA
 451 TCGAAAACGA TTCAGCTGAA TCAGTAGTAA CAGTAGTTGC TCCAACTGAA
 501 GAACCAACTG AAGAAGAAAT CGAAGCCTAT GGAAGGCGAA CAMCAAACTG
 551 AAGAACCAGA AGTTGTTGGC GAAAGCAAAG AAGACGAAGA AAAAACTGAA
 601 GAGTAATTTT AATCTGTTAC ATTAAAGTTT TTATACTTTG TTTAACAAGC
 651 ACTGTGCTTA TTTTAATATA AGCATGGTGC TTTTKGTGTT ATTATAAAGC
 701 TTAATTAAAC TTTATWACTT TGTACTAAAG TTTAATTAAT TTTAGTGAGT
 751 AAAAGACATT AAACTCAACA ATGATACATC ATAAAAATTT TAATGTACTC
 801 GATTTTAAAA TACATACTTA CTAAGCTAAA GAATAATGAT AATTGATGGC
 851 AATGGCGGAA ATGGATGTT GTCATTATAA TAATAAATGA AACAATTATG
 901 TTGGAGGTAA ACACGCATGA AATGTATTGT AGGTCTAGGT AATATAGGTA
 951 AACGTTTTGA ACTTACAAGA CATAATATCG GCTTTGAAGT CGTTGATTAT
1001 ATTTTAGAGA AAAATAATTT TTCATTAGAT AAACAAAAGT TTAAAGGTGC
1051 ATATACAATT GAACGAATGA ACGGCGATAA AGTGTTATTT ATCGAACCAA
1101 TGACAATGAT GAATTTGTCA GGTGAAGCAG TTGCACCGAT TATGGATTAT
1151 TACAATGTTA ATCCAGAAGA TTTAATTGTC TTATATGATG ATTTAGATTT
1201 AGAACAAGGA CAAGTTCGCT TAAGACAAAA AGGAAGTGCG GGCGGTCACA
1251 ATGGTATGAA ATCAATTATT AAAATGCTTG GTACAGACCA ATTTAAACGT
1301 ATTCGTATTG GTGTGGGAAG ACCAACGAAT GGTATGACGG TACCTGATTA
1351 TGTTTTACAA GCGTTTTCAA ATGATGAAAT GGTAACGATG GGAAAAAGTT
1401 ATCGAACACG CAGCACGCGC AATTGAAAAG TTTGTTGAAA CATCACRATT
1451 TGACCATGTT ATGAATGAAT TTAATGGTGA AKTGAAATAA TGACAATATT
1501 GACAMCSCTT ATAAAAGAAG ATAATCATTT TCAAGACCTT AATCAGGTAT
1551 TTGGACAAGC AAACACACTA GTAACTGGTC TTTCCCCGTC AGCTAAAGTG
1601 ACGATGATTG CTGAAAAATA TGCACAAAGT AATCAACAGT TATTATTAAT
1651 TACCAATAAT TTATACCAAG CAGATAAATT AGAAACAGAT TTACTTCAAT
1701 TTATAGATGC TGAAGAATTG TATAAGTATC CTGTGCAAGA TATTATGACC
1751 GAAGAGTTTT CAACACAAAG CCCTCAACTG ATGAGTGAAC GTATTAGAAC
1801 TTTAACTGCG TTAGCTCCAA GGTAAGAAAG GGTTATTTAT CGTTCCTTTA
1851 AATGGTTTGA AAAGTGGTT AACTCCTGTT GAAATGTGGC AAAATCACCA
1901 AATGACATTG CGTGTTGGTG AGGATATCGA TGTGGACCAA TTTMWWAACA
1951 AATTAGTTAA TATGGGGTAC AAACGGGAAT CCGTGGTATC GCATATTGGT
2001 GAATTCTCAT TGCGAGGAGG TATTATCGAT ATCTTTCCGC TAATTGGGGA
2051 ACCAATCAGA ATTGAGCTAT TGATACCGA AATTGATTCT ATTCGGGATT
```

-continued

```
2101 TTGATGTTGA AACGCAGCGT TCCAAAGATA ATGTTGAAGA AGTCGATATC

2151 ACAACTGCAA GTGATTATAT CATTACTGAA GAAGT
```

Mutant: NT 321

Phenotype: temperature sensitivity

Figure 73:
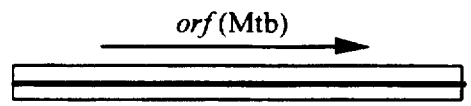

Sequence map: Mutant NT321 is complemented by plasmid pMP276, which carries a 2.5 kb insert of wild-type *S. aureus* genomic DNA. A partial restriction map is depicted in FIG. 73; no apparent sites for HinD III, EcoR I, BamH I or Pst I are present. Database searches at the nucleic acid and (putative) polypeptide levels against currently available databases reveal strong peptide-level similarities to a hypothetical ORF of unknown function from *M. tuberculosis* (Genbank Accession No. Z73902).

DNA sequence data: The following DNA sequence data represents the sequence generated by primer walking through clone pMP276, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP276
pMP276 Length: 2525 nt
   1 AATCTGTTCC TACTACAATA CCTTGTCGGT TTGAAGCACC NGAAAATNGTSEQ ID NO. 84

51 ACTTTCATAC GTTCACGCGC TTTTTCATTT CCTTTTTGGA AATCTGTAAG

101 AACAATACCG GCTTCTTTTA ATGATTGCAC ACTTTGATCA ACTGCAGGCT

151 TAATATTGAC TGTTACTATT TCATCTGGTT CAATGAATCG CAAAGCTTGC

201 TCAACTTCAT CAGCATCTTT TTGAACTCCA TAAGGTAATT TAACTGCAAT

251 AAACGTACAA TCAATGCCTT CTTCACGTAA TTCGTTAACA GACATTTGTA

301 CTAGTTTTCC AACTAATGTA GAATCCTGTC CTCCTGAAAT ACCTAACACT

351 AAAGATTTTA TAAATGAATG TGATTGTACA TAATTTTTTA TAAATTGCTT

401 TAATTCCATA ATTTCTTCAG CACTATCGAT ACGCTTTTTC ACTTTCATTT

451 CTTGTACAAT AACGTCTTGT AATTTACTCA TTATCTTCTT CCATCTCCTT

501 AACGTGTTCC GCAACTTCAA AAATACGTTT ATGTTTATTA TCCCAACATG

551 CCTTGCTTAA ATCGACTGGA TATTCTTGTG GATTCAGGAA ACGCTTATTT

601 TCATCCCAAA TAGATTGTAA TCCTAGTGCT AAATATTCAC GTGATTCATC

651 TTCTGTTGGC ATTTGATATA CTAATTTACC ATTTTCATAA ATATTATGAT

701 GCAAATCAAT GGCTTCGAAA GATTTTATAA ATTTCATTTT ATAAGTATGC

751 ACTGGATGGA ATAATTTTAA AGGTTGTTCA TCGTATGGAT TTTCATTTTC

801 CAAAGTAATA TAATCGCCTT CTGCCTTACC TGTTTTCTTG TTTATAATGC

851 GATATACATT TTTCTTACCT GGCGTCGTAA CCTTTTCAGC GTTATTTGAT

901 AATTTAATAC GATCACTATA TGAACCATCT TCATTTTCAA TAGCTACAAG

951 TTTATATACT GCACCTAATG CTGGTTGATC GTATCCTGTA ATCAGCTTTG

1001 TACCAACGCC CCAAGAATCT ACTTTTGCAC CTTGTGCTTT CAAACTCGTA

1051 TTCGTTTCTT CATCCAAATC ATTAGAYGCG ATAATTTTAG TTTCAGTAAA

1101 TCCTGYTTCA TCAAGCATAC GTCTTGCYTC TTTAGATAAA TAAGCGATAT

1151 CTCCAGAATC TAATCGAATA CCTAACAAAG TTAATTTTGT CACCTAATTC

1201 TTTTGCAACT TTTATTGCAT TTGGCACGCC AGATTTAAA GTATGGAATG

1251 TATCTACTAG GAACACACAA TTTTTATGTC TTTCAGCATA TTTTTTGAAG

1301 GCAACATATT CGTCTCCATA AGTTGGACA AATGCATGTG CATGTGTACC

1351 AGACACAGGT ATACCAAATA ATTTTCCCCG CCCTAACATT ACTTGTAGAA

1401 TCAAAGCCCC CGATGTAAGC AGCTCTAGCG CCCCACAATG CTGCATCAAT
```

```
-continued
1451 TTCTTGCGCA CGACGTGTTA CCAAACTCCA TTAATTTATC ATTTGATGCA

1501 ATTTGACGAA ATTCTGCTAG CCTTTGTTGT AATTAATGTA TGGAAATTTA

1551 CAATGTTTAA TAAAATTGTT CTATTAATTG CGCTTGAATC AATGGTGCTT

1601 CTACGCGTAA CAATGGTTCG TTACCAAAGC ATAATTCGCC TTCTTGCATC

1651 GAACGGATGC TGCCTGTGAA TTTTAAATCT TTTAAATATG ATAAGAAATC

1701 ATCCTTGTAG CCAATAGACT TTAAATATTC CAAATCAGAT TCTGAAAATC

1751 CAAAATGTTC TATAAAATCA ATGACGCGTT TTAAACCATT AAAAACAGCA

1801 TAGCCACTAT TAAATGGCAT TTTTCTAAAA TACAAATCAA ATACAGCCAT

1851 TTTTTCATGA ATATTATCAT TCCAATAACT TTCAGCCATA TTTATTTGAT

1901 ATAAGTCATT ATGTAACATT AAACTGTCGT CTTCTAATTG GTACACTTGT

1951 ATCTCTCCAA TCGACCTAAA TATTTTCTTA CATTTTATCA TAATTCATTT

2001 TTTTATATAC ATAAGAGCCC CTTAATTTCC ATCTTTTTAA TTAAAATCAA

2051 CCAACAATTT AATGACATAT ACATAATTTT TAAGAGTATT TTAATAATGT

2101 AGACTATAAT ATAAAGCGAG GTGTTGTTAA TGTTATTTAA AGAGGCTCAA

2151 GCTTTCATAG AAAACATGTA TAAAGAGTGT CATTATGAAA CGCAAATTAT

2201 CAATAAACGT TTACATGACA TTGAACTAGA AATAAAAGAA ACTGGGACAT

2251 ATACACATAC AGAAGAAGAA CTTATTTATG GTGCTAAAAT GGCTTGGCGT

2301 AATTCAAATC GTTGCATTGG TCGTTTATTT TGGGATTCGT TGGGTGTCAT

2351 TGATGCAAGA GATGTTACTG ACGAAGCATC GTTCTTATCA TCAATTACTT

2401 ATCATATTAC ACAGGCTACA AATGAAGGTA AATTAAAGCC GTATATTACT

2451 ATATATGCTC CAAAGGATGG ACCTAAAATT TTCAACAATC AATTAATTCG

2501 CTATGCTGGC TATGACAATT GTGGT
```

Mutant: NT 325

Phenotype: temperature sensitivity

Figure 74:
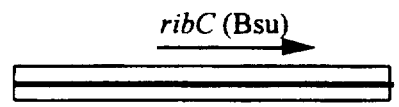

Sequence map: Mutant NT325 is complemented by plasmid pMP644, which carries a 2.1 kb insert of wild-type *S. aureus* genomic DNA. A partial restriction map is depicted in FIG. 74; no apparent sites for HinD III, EcoR I, BamH I or Pst I are present. Database searches at the nucleic acid and (putative) polypeptide levels against currently available databases reveal significant peptide-level similarities to the ribC gene product, a protein exhibiting regulatory functions, from *B. subtilis* (Genbank Accession No. x95312; unpublished).

DNA sequence data: The following DNA sequence data represents the sequence generated by primer walking through clone pMP644, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP644
pMP644 Length: 2181 nt
    1 ATCGATAGGA AGAAGTACAA CGACTGAAGA TCAAACGGGT GATACATTGGSEQ ID NO. 85

51 AAACAAAAGG TGTACACTCA GCAGATTTTA ATAAGGACGA TATTGACCGA

101 TTGTTAGAAA GTTTTAAAGG TATCATTGAA CAAATTCCGC CGATGTACTC

151 ATCCGTCAAA GTAAATGGTA AAAAATTATA TGAATATGCG CGTAATAATG

201 AAACAGTTGA AAGACCAAAG CGTAAAGTTA ATATTAAAGA CATTGGGCGT

251 ATATCTGAAT TAGATTTTAA AGAAAATGAG TGTCATTTTA AAATACGCGT

301 CATCTGTGGT AAAGGTACAT ATATTAGAAC GCTAGCAACT GATATTGGTG

351 TGAAATTAGG CTTTCCGGCA CATATGTCGA AATTAACACG AATCGAGTCT
```

```
 401 GGTGGATTTG TGTTGAAAGA TAGCCTTACA TTAGAACAAA TAAAAGAACT

451 TCATGAGCAG GATTCATTGC AAAATAAATT GTTTCCTTTA GAATATGGAT

501 TAAAGGGTTT GCCAAGCATT AAAATTAAAG ATTCGCACAT AAAAAAACGT

551 ATTTTAAATG GGCAGAAATT TAATAAAAAT GAATTTGATA ACAAAATTAA

601 AGACCAAATT GTATTTATTG ATGATGATTC AGAAAAAGTA TTAGCAATTT

651 ATATGGTACA CCCTACGAAA AGAATCAGAA ATTAAACCTA AAAAAGTCTT

701 TAATTAAAGG AGATAGAATT TATGAAAGTT CATAGAAAGT GACACATCCT

751 ATACAATCCT AAACAGTTAT ATTACAGGAG GATGTTGCAA TGGGCATTCC

801 GGATTTTTCG ATGGCATGCA TAAAGGTCAT GACAAAGTCT TTGATATATT

851 AAACGAAATA GCTGAGGCAC GCAGTTTAAA AAAAGCGGTG ATGACATTTG

901 ATCCGCATCC GTCTGTCGTG TTTGAATCCT AAAAGAAAAC GAACACGTTT

951 TTACGCCCCT TTCAGATAAA ATCCGAAAAA TTACCCACAT GATATTGATT

1001 ATTGTATAGT GGTTAATTTT TCATCTAGGT TTGCTAAAGT GAGCGTAGAA

1051 GATTTTGTTG AAAATTATAT AATTAAAAAT AATGTAAAAG AAGTCATTGC

1101 TGGTTTTGAT TTTAACTTTT GGTAAATTTG GAAAAGGTAA TATGACTGTA

1151 ACTTCAAGAA TATGATGCGT TTAATACGAC AATTGTGAGT AAACAAGAAA

1201 TTGAAAATGA AAAAATTTCT ACAACTTCTA TTCGTCAAGG ATTTAATCAA

1251 TGGTGAGTTG CCAAAAAGGC GAATGTATGG CTTTTAGGCT ATATATATTT

1301 CTTATTAAAA GGCACTGTAG TGCATCATCA AAAAAGGGGA AGAACTATTG

1351 GCTTCCCCAA CAGCTAACAT TCAACCTAGT GATGATTATT TGTTACCTCG

1401 TAAAGGTGTT TATGCTGTTA GTATTGAAAT CGGCAGAGAA AATAAATTAT

1451 ATCGAGGGGT AGCTAACATA GGTGTAAAGC CAACATTTCA TGATCCTAAC

1501 AAAGCAGAAG TTGTCATCGA AGTGAATATC TTTGACTTTG AGGATAATAT

1551 TTATGGTGAA CGAGTGACCG TGAATTGGCA TCATTTCTTA CGTCCTGAGA

1601 TTAAATTTGA TGGTATCGAC CCATTAGTTA AACAAATGAA CGATGATAAA

1651 TCGCGTGCTA AATATTTATT AGCAGTTGAT TTTGGTGATG AAGTAGCTTA

1701 TAATATCTAG AGTTGCGTAT AGTTATATAA ACAATCTATA CCACACCTTT

1751 TTTCTTAGTA GGTCGAATCT CCAACGCCTA ACTCGGATTA AGGAGTATTC

1801 AAACATTTTA AGGAGGAAAT TGATTATGGC AATTTCACAA GAACGTAAAA

1851 ACGAAATCAT TAAAGAATAC CGTGTACACG AAACTGATAC TGGTTCACCA

1901 GAAGTACAAA TCGCTGTACT TACTGCAGAA ATCAACGCAG TAAACGAACA

1951 CTTACGTACA CACAAAAAAG ACCACCATTC ACGTCGTGGA TTATTAAAAA

2001 TGGTAGGTCG TCGTAGACAT TTATTAAACT ACTTACGTAG TAAAGATATT

2051 CAACGTTACC GTGAATTAAT TAAATCACTT GGTATCCGTC GTTAATCTTA

2101 ATATAACGTC TTTGAGGTTG GGGCATATTT ATGTTCCAAC CCTTAATTTA

2151 TATTAAAAAA GCTTTTTRCA WRYMTKMASR T
```

Figure 75:
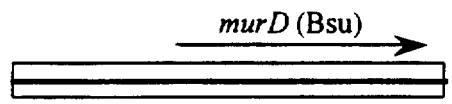

Mutant: NT 333
Phenotype: temperature sensitivity
Sequence map: Mutant NT333 is complemented by plasmid pMP344, which carries a 2.3 kb insert of wild-type *S. aureus* genomic DNA. A partial restriction map is depicted in FIG. 75; no apparent restriction sites for EcoR I, HinD III, BamH I or Pst I are present. Database searches at the nucleic acid and (putative) polypeptide levels against currently available databases reveal significant similarities to the murD gene product from *B. subtilis*, which encodes udp-MurNAc-dipeptide::D-Glu ligase (EC 6.3.2.9); similarities are also noted to the equivalent gene products from *E. coli* and *H. influenzae*. The predicted relative size and orientation of the murD gene is depicted by an arrow in the map.

DNA sequence data: The following DNA sequence data represents the sequence generated by primer walking through clone pMP344, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP344
pMP344 Length: 2424 nt
    1 ACATTAAAAA GGATGAAATT TGGTCAAAGT ATTCGAGAAG AAGGTCCACA SEQ ID NO. 86
   51 AAGCCATATG AAGAAGACTG GTACACCAAC GATGGGTGGA CTAACATTTC
  101 TATTAAGTAT TGTGATAACG TCTTTGGTGG CTATTATATT TGTAGATCAA
  151 GCWAATCCAA TCATACTGTT ATTATTTGTG ACGATTGGTT TTGGGTTAAT
  201 TGGTTCTTAT ACGATGATTA TATTATTGTT GTTAAAAAGA ATAACCAAGG
  251 TTTAACAAGT AAACAGAAGT TTTTGGCGCA AATTGGTATT GCGATTATAT
  301 TCTTTGTTTT AAGTAATGTG TTTCATTTGG TGAATTTTTC TACGAGCATA
  351 CATATTCCAT TTACGAATGT AGCAATCCCA CTATCATTTG CATATGTTAT
  401 TTTCATTGTT TTTTGGCAAG TAGGTTTTTC TAATGCAGTA AATTTAACAG
  451 ATGGTTTAGA TGGATTAGCA ACTGGACTGT CAATTATCGG ATTTACAATG
  501 TATGCCATCA TGAGCTTTGT GTTAGGAGAA ACGGCAATTG GTATTTCTG
  551 TATCATTATG TTGTTTGCAC TTTTAGGATT TTTACCATAT AACATTAACC
  601 CTGCTAAAGT GTTTATGGGA GATACAGGTA GCTTAGCTTT AGGTGGTATA
  651 TTTGCTACCA TTTCAATCAT GCTTAATCAG GAATTATCAT TAATTTTTAT
  701 AGGTTTAGTA TTCGTAATTG AAACATTATC TGTTATGTTA CAAGTCGCTA
  751 GCTTTAAATT GACTGGAAAG CGTATATTTA AAATGAGTCC GATTCATCAT
  801 CATTTTGAAT TGATAGGATG GAGCGAATGG AAAGTAGTTA CAGTATTTTG
  851 GGCTGTTGGT CTGATTTCAG GTTTAATCGG TTTATGGATT GGAGTTGCAT
  901 TAAGATGCTT AATTATACAG GGTTAGAAAA TAAAAATGTW TTAGTTGTCG
  951 GTTTGGCAAA AAGTGGTTAT GAAGCAGCTA AATTATTAAG TAAATTAGGT
 1001 GCGAATGTAA CTGTCAATGA TGGAAAAGAC TTATCACAAG ATGCTCATGC
 1051 AAAAGATTTA GAWTCTATGG GCATTTCTGT TGTAAGTGGA AGTCATCCAT
 1101 TAACGTTGCT TGATAATAAT CCAATAATTG TTAAAAATCC TGGAATACCC
 1151 TTATACAGTA TCTATTATTG ATGAAGCAGT GAAACGAGGT TTGAAAATTT
 1201 TAACAGAAGT TGAGTTAAGT TATCTAATCT CTGAAGCACC AATCATAGCT
 1251 GTAACGGGTA CAAATGGTAA AACGACAGTT ACTTCTCTAA TTGGAGATAT
 1301 GTTTAAAAAA AGTCGCTTAA CTGGAAGATT ATCCGGCAAT ATTGGTTATG
 1351 TTTGCATCTA AAGTWGCACA AGAAGTWAAG CCTACAGATT ATTTAGTTAC
 1401 AGAGTTGTCG TCATTCCAGT TACTTGGAAT CGAAAAGTAT AAACCACACA
 1451 TTGCTATAAT TACTAACATT TATTCGGCGC ATCTAGATTA CCATGRAAAT
 1501 TTAGAAAACT ATCAAAATGC TAAAAAGCAA ATATATAAAA ATCAAACGGA
 1551 AGAGGATTAT TTGATTTGTA ATTATCATCA AAGACAAGTG ATAGAGTCGG
 1601 AAGAATTAAA AGCTAAGACA TTGTATTTCT CAAACTCAAC AAGAAGTTGA
 1651 TGGTATTTAT ATTAAAGATG RTTTATCGT TTATAAAGGT GTTCGTATTA
 1701 TTAACACTGA AGATCTAGTA TTGCCTGGTG AACATAATTT AGAAAATATA
 1751 TTAGCCAGCT GKGCTKGCTT GTATTTWAGY TGGTGTACCT ATTAAAGCAA
```

```
                              -continued
1801 TTATTGATAG TTWAAYWACA TTTTCAGGAA TAGAGCATAG ATTGCAATAT

1851 GTTGGTACTA ATAGAACTTA ATAAATATTA TAATGATTCC AAAGCAACAA

1901 ACACGCTAGC AACACAGTTT GCCTTAAATT CATTTAATCA ACCAATCATT

1951 TGGTTATGTG GTGGTTTGGA TCGGAGGGAA TGAATTTGAC GAACTCATTC

2001 CTTATATGGA AAATGTTCGC GCGATGGTTG TATTCGGACA AACGAAAGCT

2051 AAGTTTGCTA AACTAGGTAA TAGTCAAGGG AAATCGGTCA TTGAAGCGAA

2101 CAATGTCGAA GACGCTGTTG ATAAAGTACA AGATATTATA GAACCAAATG

2151 ATGTTGTATT ATTGTCACCT GCTTGTGCGA GTTGGGATCA ATATAGTACT

2201 TTTGAAGAGC GTGGAGAGAA ATTTATTGAA AGATTCCGTG CCCATTTACC

2251 ATCTTATTAA AGGGTGTGAG TATTGATGGA TGATAAAACG AAGAACGATC

2301 AACAAGAATC AAATGAAGAT AAAGATGAAT TAGAATTATT TACGAGGAAT

2351 ACATCTAAGA AAAGACGGCA AAGAAAAAGW TCCTCTAGAG TCGACCCTGC

2401 AGGCATGCAA GCTTGGCGTA NCC
```

Mutant: NT 346

Phenotype: temperature sensitivity

Figure 76:
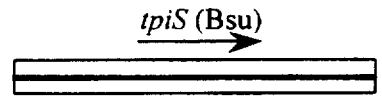

Sequence map: Mutant NT346 is complemented by plasmid pMP347, which carries a 2.1 kb insert of wild-type *S. aureus* genomic DNA. A partial restriction map is depicted in FIG. 76; no apparent restriction sites for EcoR I, HinD III, BamH I or Pst I are present. Database searches at the nucleic acid and (putative) polypeptide levels against currently available databases reveal strong similarities to the tpis gene from *B. subtilis*, which encodes triose phosphate isomerase (EC 5.3.1.1); similarities are also noted to the equivalent gene products from *B. megaterium* and *S. stearothermophilus*. The predicted relative size and orientation of the tpis gene is depicted by an arrow in the restriction map.

DNA sequence data: The following DNA sequence data represents the sequence generated by primer walking through clone pMP347, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP347
pMP347 Length: 2094 nt
    1 CACATAAACC AGTTGTTGCT ATTTTAGGTG GAGCAAAAGT ATCTGACAAA  SEQ ID NO. 87

51 ATTAATGTCA TCAAAAACTT AGTTAACATA GCTGATAAAA TTATCATCGG

101 CGGAGGTATG GCTTATACTT TCTTAAAAGC GCAAGGTAAA GAAATTGGTA

151 TTTCATTATT AGAAGAAGAT AAAATCGACT TCGCAAAAGA TTTATTAGAA

201 AAACATGGTG ATAAAATTGT ATTACCAGTA GACACTAAAG TTGCTAAAGA

251 ATTTTCTAAT GATGCCAAAA TCACTGTAGT ACCATCTGAT TCAATTCCAG

301 CAGACCAAGA AGGTATGGAT ATTGGACCAA ACACTGTAAA ATTATTTGCA

351 GATGAATTAG AAGGTGCGCA CACTGTTGTT ATGGAATGGA CCTATGGGTT

401 GTTATTCGAG TTCAGTAACT TTGCACAAGG TACAATTGGT GTTTGTTAAA

451 GCAATTGCCA ACCTTAAAGA TGCCATTACG ATTATCGGTG GCGGTGATTC

501 AGCCTGCAGC AGCCATCTCT TTAGGTTTTT GAAAATGACT TCACTCMTAT

551 TTCCACTGGT GGCGGCSCKC CATTAGAKTA CCTAGAAGGT WAAGAATGCC

601 TGGTWTCMAA GCAAYCAWTA WTAAWTAATA AAGTGATAGT TTAAAGTGAT

651 GTGGCATGTT TGTTTAACAT TGTTACGGGA AAACAGTCAA CAAGATGAAC

701 ATCGTGTTTC ATCAACTTTT CAAAAATATT TACAAAAACA AGGAGTTGTC

751 TTTAATGAGA ACACCAATTA TAGCTGGTAA CTGGAAAATG AACAAAACAG

801 TACAAGAAGC AAAAGACTTC GTCAATACAT TACCAACACT ACCAGATTCA
```

```
-continued
 851 AAAGAAKTWR AATCAGTWAT TTGTTGCMCC AGCMATTCAA TTAGATGCAT

901 TAACTACTGC AGTTWAAGAA GGAAAAGCAC AAGGTTTAGA AATCGGTGCT

951 CAAAATNCGT ATTTCGAAGA AATGGGGCTT MACAGTGAAA KTTTCCAGTT

1001 GCATAGCAGA TTAGGCTTAA AAAGTTGTAT TCGGTCATTC TGAACTTCGT

1051 GAATATTCCA CGGAACCAGA TGAAGAAATT AACAAAAAAG CGCACGTATT

1101 TTCAAACATG GAATGAMTCC AATTATATGT GTTGGTGAAA CAGACGAAGA

1151 GCGTGAAAGT GGTAAAGCTA ACGATGTTGT AGGTGAGCAA GTTAAAGAAA

1201 GCTGTTGCAG GTTTATCTGA AGATCAAACT TAAATCAGTT GTAATTGCTT

1251 ATGAACCAAT CTGGGCAATC GGAACTGGTA AATCATCAAC ATCTGAAGAT

1301 GCAAATGAAA TGTGTGCATT TGTACGTCAA ACTATTGCTG ACTTATCAAG

1351 CAAAGAAGTA TCAGAAGCAA CTCGTATTCA ATATGGTGGT AGTGTTAAAC

1401 CTAACAACAT TAAAGAATAC ATGGCACAAA CTGATATTGA TGGGGCATTA

1451 GTAGGTGGCG CATCACTTAA AGTTGAAGAT TTCGTACAAT TGTTAGAAGG

1501 TGCAAAATAA TCATGGCTAA GAAACCAACT GCGTTAATTA TTTTAGATGG

1551 TTTTGCGAAC CGCGAAAGCG AACATGGTAA TGCGGTAAAA TTAGCAAACA

1601 AGCCTAATTT TTNGATCGGT TNATTACCAA CCAAATATCC CAACCGAACT

1651 TCAAAATTCG AAGGCGAGTG GCTTAAGATG TTGGACTACC CTGAAGGACA

1701 AATGGGTAAC TCAGAAGTTG GTCATATGAA TATCGGTGCA GGACGTATCG

1751 TTTATCAAAG TTTAACTCGA ATCAATAAAT CAATTGAAGA CGGTGATTTC

1801 TTTGAAAATG ATGTTTTAAA TAATGCAATT GCACACGTGA ATTCACATGA

1851 TTCAGCGTTA CACATCTTTG GTTTATTGTC TGACGGTGGT GTACACAGTC

1901 ATTACAAACA TTTATTTGCT TTGTTAGAAC TTGCTAAAAA ACAAGGTGTT

1951 GAAAAAGTTT ACGTACACGC ATTTTTAGAT GGCCGTGACG TAGATCAAAA

2001 ATCCGCTTTG AAATACATCG AAGAGACTGA AGCTAAATTC AATGAATTAG

2051 GCATTGGTCA ATTTGCATCT GTGTCTGGTC GTTATTATGC ANTG
```

Figure 77:
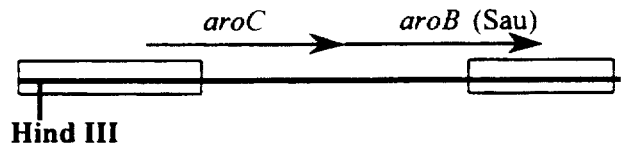

Mutant: NT348
phenotype: temperature sensitivity
Sequence map: Mutant NT348 is complemented by plasmid pMP649, which carries a 3.3 kb insert of wild-type *S. aureus* genomic DNA. A partial restriction map is depicted in FIG. 77; no apparent restriction sites for EcoR I, HinD III, BamH I or Pst I are present. Database searches at the nucleic acid and (putative) polypeptide levels against currently available databases reveal DNA sequence identities to two different Genbank entries for *S. aureus* DNA. The left-most contig below matches Genbank Accession No. U31979, which includes the complete aroC gene, encoding 5-enolpyruvylshikimate 3-phosphate phospholyase (EC 4.6.1.4), and the N-terminal portion of the aroB gene, encoding 5-dehydroquinate hydrolyase (EC 4.2.1.10); the right-most contig matches Genbank Accession No. L05004, which includes the C-terminal portion of the aroB gene. Neither Genbank entry described contains the complete DNA sequence of pMP649. Further experiments are underway to determine whether one or both of the genes identified in clone pMP649 are essential.

DNA sequence data: The following DNA sequence data represents the sequence generated from clone pMP649, starting with standard M13 forward and M13 reverse sequencing primers; the sequence contig will be completed via primer walking strategies. The sequence below can be used to design PCR primers for the purpose of amplification from genomic DNA with subsequent DNA sequencing.

```
clone pMP649
pMP649.forward Length: 954 nt
  1 GGGGWYYCTC TAGAGYCGAC CTRCAGGCAT SCAAGCTTBA CCAGGWTCAA    SEQ ID NO. 88

51 TTAGAGGTRA TTWAGGTTTA RCTKTTSGTV GAADTATCAT BMTCGGTTCA

101 GATTCCTGAG AGTCTGCTGA ACGTGAAATT AATCTATGGT TTAATGAAAA
```

-continued

```
151 TGAAATTACT AGCTATGCTT CACCACGTGA TGCATGGTTA TATGAATAAA

201 ATATAAACTG TAAACCTTTA CGATTTATTT ATAAAGGTAG AAAGGGTTTT

251 GTTATGTGGT TAGTCATTAT GATTATACAT AACAAGGCCC GTTTTTTATG

301 TTGTAGTAAA TTACTTGAAA AATTTTATAG TTTTTTGGTA ACACGTATTA

351 AAAAGAGAGG AATATTCTTT ATCAAATGAA ACTAAACAGA GAGAAGGGGT

401 TGTTAAAATG AAGAATATTA TTTCGATTAT TTTGGGGATT TTAATGTTCT

451 TAAAATTAAT GGAATTACTA TATGGTGCTA TATTTTTAGA TAAACCACTT

501 AATCCTATAA CAAAAATTAT TTTTATACTG ACTCTCATTT ATATTTTTA

551 TGTATTAGTA AAAGAATTGA TTATATTTTT GAAGTCAAAG TATAACAAAA

601 GCGCTTAACA TATGTTTATT TTAATATCAT AATTTTTTTA AACGGGACTG

651 ATTAACYTTT ATTAATAATT AACAGTTCGT TCTTTTGTAT TAAGAAATGT

701 AGTCAGTATA TTATTTGCTA AAGTTGCGAT ACGATTATAT TAAAACGGCT

751 AATCATTTTT AATTAATGAT TATATGATGC AACTGTTTAG AAATTCATGA

801 TACTTTTCTA CAGACGAATA TATTATAATT AATTTTAGTT CGTTTAATAT

851 TAAGATAATT CTGACATTTA AAATGAGATG TCATCCATTT TCTTAATTGA

901 GCTTGAAAAC AAACATTTAT GAATGCACAA TGAATATGAT AAGATTAACA

951 ACAT
``` pMP649.reverse Length: 841 nt

```
  1 CTTTMAWKRC CTRAACCACT TAACAAACCT GCCAATAATC GTGTTGTCGT    SEQ ID NO. 89

51 ACCAGAATTA CCTGTATACA ATACTTGATG TGGCGTGTTA AAAGATTGAT

101 ATCCTGGGGA AGTCACAACT AATTTTTCAT CATCTTCTTT GATTTCTACA

151 CCTAACAGTC GGAAAATGTC CATCGTACGA CGACAATCTT CGCCAAGTAG

201 TGGCTTATAT ATAGTAGATA CACCTTCAGC TAGCGACGCC AACATGATTG

251 CACGGTGTGT CATTGACTTA TCGCCCGGCA CTTCTATTTC GCCCTTTAAC

301 GGACCTGAAA TATCAATGAT TTGTTCATTT ACCATTTCAT TCACCTACTT

351 AAAATATGTT TTTAATTGTT CACATGCATG TTGTAATGTT AGTTGATCAA

401 CATGTTGTAC AACGATATCT CCAAATTGTC TAATCAAGAC CATTTGTACA

451 CCTTGCTTAT CATTCTTTTT ATCACTTAGC ATATATTGGT ATAACGTTTC

501 AAAATCCAAG TCAGTTATCA TGTCTAAAGG ATAGCCGAGT TGTATTAAAT

551 ATTGAATATA ATGATTAATA TCATGCTTAG RATCAAACAA AGCATTCGCA

601 ACTATAAATT GATAGATAAT GCCAACCATC ACTGACATGA CCATGAGGTA

651 TTTTATGATA GTATTCAACA GCATGACCAA ATGTATGACC TAAATTTAAR

701 AATTTACGTA CACCTTGTTC TTTTTSATCT GGCGAATAAC AATATCCAGC

751 TTSGTTTCAA TACCTTTRGS AATWTATTTR TCCATACCAT TTAATGACTG

801 TAATATCTCT CTATCTTTAA AGTGCTGTTC GATATCTTGC G
```

Figure 78:
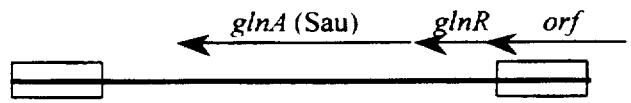

Mutant: NT359
phenotype: temperature sensitivity
Sequence map: : Mutant NT359 is complemented by plasmid pMP456, which carries a 3.2 kb insert of wild-type *S. aureus* genomic DNA. A partial restriction map is depicted in FIG. 78; no apparent restriction sites for EcoR I, HinD III, BamH I or Pst I are present. Database searches at the nucleic acid and (putative) polypeptide levels against currently available databases reveal identity to the glnRA locus of *S. aureus* (Genbank Accession No. X76490), also referred to as the femC locus; mutations localized to femC have been reported in the scientific literature to display an increased sensitivity to the bacterial cell-wall synthesis inhibitor methicillin.

DNA sequence data: The following DNA sequence data represents the sequence generated from clone pMP456, starting with standard M13 forward and M13 reverse sequencing primers; the sequence contig will be completed via primer walking strategies. The sequence below can be used to design PCR primers for the purpose of amplification from genomic DNA with subsequent DNA sequencing.

```
clone pMP456
pMP456.forward Length: 568 nt
  1 CCGGGGATCC TCTAGAGTCG ATCTTTGCAT TCTTTAAGCT TAAATTTTCT  SEQ ID NO. 90

51 ATTCTTCTTT CTCTACGGCG CATAGCATTA ATATTACCGT AACTTATCCC

101 AGTATCTTTA TTAATTTGAT AACTCGATAT CTCTTTGTTT TCTATCAATT

151 CTTTGATTGT ATTGAATATT TCATCATAGC AATTCATAAA TTAGATGAGG

201 CGAAATTTTT AATTTTTTAG AATATCAATA GTANTATAAC TAAAATGAAA

251 ATACCGATCG ATAAACAAAA AGATATTTTT TGTTTTGTTT CTCTTTTCAT

301 ATAGTATTAC CCCCTTAATA ATGCGTAGTA AGGTCCCTCT TTTCGGGGTC

351 TTACCTTANA AACGTTCTGC AAATGAATTC GATGAGAAGT AATATGAATA

401 TGGCTATTTT CAAGTAATAC TCAACGTTTT CGCGACGTTC TTTTATCGCC

451 TCATCTCATC ACCTCCAAAT ATATTAAAAT TCATGTGAAC TAAAATATAA

501 AATGGTCTTC CCCAGCTTTA AAAAAATAAA TACATAAAAC ATTTTACTTG

551 GACCAAAACT TGGACCCC pMP456.reverse Length: 581 nt
  1 ATGCCTGCAG GTCGATCATT AATTAAAAAC CCTGGCGGTG GTTTAGCTAA  SEQ ID NO. 91

51 GATTGGTGGA TACATTGCTG GTAGAAAAGA TTTAATTGAA CGATGTGGTT

101 ATAGATTGAC AGCACCTGGT ATTGGTAAAG AAGCGGGTGC ATCATTAAAT

151 GCATTGCTTG AAATGTATCA AGGTTTCTTT TTAGCACCAC ACGTTGTCAG

201 TCAGAGTCTT AAAGGTGCAT TGTTTACTAG TTTATTTTTA GAAAAAATGA

251 ATATGAACAC AACGCCGAAG TACTACGAAA AACGAACTGA TTTAATTCAA

301 ACAGTTAAAT TTGAAACGAA AGAACAAATG ATTTCATTTT GTCAAAGTAT

351 TCAACACGCA TCCCCAATTA ATGCACATTT TAGTCCANAA CCTAGTTATA

401 TGCCTGGTTA CGAAGATGAT GTTATTATGG CAGCTGGTAC GTTTATTCAA

451 GGTTCATCCG ATTGAATTAT CTGCAGATGG ACCTATTCGT CCTCCTTATG

501 AAGCATATGT TCAAGGANGA TTAACATATG AACACGTTAA AATTGCTGTT

551 GACAAGANCT GTTTAATCAG TTTGAAAAAA C
```

Mutant: NT371 phenotype: temperature sensitivity

Figure 79:
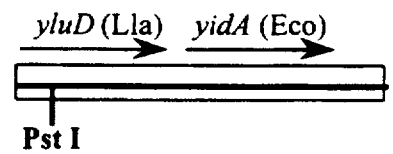

Sequence map: : Mutant NT371 is complemented by plasmid pMP461, which carries a 2.0 kb insert of wild-type *S. aureus* genomic DNA. A partial restriction map is depicted in FIG. 79. Database searches at the nucleic acid and (putative) polypeptide levels against currently available databases reveal strong peptide-level similarities to yluD, a hypothetical ABC transporter (Genbank Accession No. M90761), and yidA, a hypothetical ORF of unknown function (Genbank Accession No. L10328).

DNA sequence data: The following DNA sequence data represents the sequence generated by primer walking through clone pMP461, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone PMP461
pMP461 Length: 2001 nt
   1 CGGGGATCCT CTAAAGTCGA TCAAATTGGG CGAATGAAGC AAGGAAAAAC  SEQ ID NO. 92

51 AATTTTAAAA AAGATTTCTT GGCAAATTGC TAAAGGTGAT AAATGGATAT

101 TATATGGGTT GAATGGTGCT GGCAAGACAA CACTTCTAAA TATTTTAAAT

151 GCGTATGAGC CTGCAACATC TGGAACTGTT AACCTTTTCG GTAAAATGCC

201 AGGCAAGGTA GGGTATTCTG CAGAGACTGT ACGACAACAT ATAGGTTTTG

251 TATCTCATAG TTTACTGGAA AAGTTTCAAG AGGGTGAAAG AGTAATCGAT

301 GTGGTGATAA GCGGTGCCTT TAAATCAATT GGTGTTTATC AAGATATTGA

351 TGATGAGATA CGTAATGAAG CACATCAATT ACTTAAATTA GTTGGAATGT

401 CTGCTAAAGC GCAACAATAT ATTGGTTATT TATCTACCGG TGAAAAACAA

451 CGAGTGATGA TTGCACGAGC TTTAATGGGG CAACCCCAGG TTTTAATTTT

501 AGATGAGCCA GCAGCTGGTT TAGACTTTAT TGCACGAGAA TCGTTGTTAA

551 GTATACTTGA CTCATTGTCA GATTCATATC CAACGCTTGC GATGATTTAT

601 GTGACGCACT TTATTGAAGA AATAACTGCT AACTTTTCCA AAATTTTACT

651 GCTAAAAGAT GGCCAAAGTA TTCAACAAGG CGCTGTAGAA GACATATTAA

701 CTTCTGAAAA CATGTCACGA TTTTTCCAGA AAAATGTAGC AGTTCAAAGA

751 TGGAATAATC GATTTTCTAT GGCAATGTTA GAGTAAATAT TTTGCAAATA

801 ATAAGTAATA ATGACAAAAT TTAATTAAGA TAAAATGGAC AGTGGAGGGC

851 AATATGGATA ACGTTAAAAG CAATATTTTT GGACATGGAT GGAACAATTT

901 TACATTGAAA ATAATCCAAG CATCCAACGT WTACGAAAGA TGTTCATTAA

951 TCAATTGGAG AGAGAAAGGA TATWAAGTAT TTTTGGSCAA CAGGACGTTC

1001 GCATTCTGAA ATACATCMAA YTTGTACCTC AAGATTTTGC GGTTAATGGC

1051 ATCATTAGTT CAAATGGAAC AATTGGAGAA GTAGATGGAG AAATTATCTT

1101 CAAGCATGGT TTATCATTGG CTCAAGTGCA ACAAATTACT AATTTAGCTA

1151 AGCGCCAACA AATTTATTAT GAGGTATTTC CTTTTGAAGG TAATAGAGTT

1201 TCTTTAAAAG AAGATGAAAC ATGGATGCGA GATATGATTC GTAGTCAAGA

1251 TCCTATTAAT GGCGTAAGTC ATAGTGAATG GTCTTCAAGA CAAGATGCGC

1301 TTGCTGGTAA GATAGATTGG GTAACTAAGT TTCCTGAAGG TGAATATTCA

1351 AAAATTTATC TATTCAGTTC TAATTTAGAA AAAATAACAG CATTTAGAGA

1401 TGAATTAAAG CAAAATCATG TGCAACTACA GATTAGTGTT TCAAATTCAT

1451 CAAGATTTAA TGCGGAAACA ATGGCTTATC AAACTGATAA AGGTACAGGC

1501 ATTAAAGAAA TGATTGCACA TTTTGGTATT CATCAAGAAG AAACGTTAGT

1551 TATTGGAGAT AGCGACAATG ATAGAGCAAT GTTTGAATTT GGTCATTATA

1601 CAGTTGCTAT GAAAAATGCA CGCCCTGAAA TCCAAGCATT AACTTCAGAT
```

-continued

```
1651 GTAACGGCAT ACACGAATGA AGAGGATGGC GCAGCAAAAT ATTTAGCAGA

1701 GCATTTTTTA GCTGAATAAT AAAATAGGTA GTTATTTATT ATTTAATTTA

1751 CAATAGTTGA TGAGTAATGT ACAAAGAGCA GTAAAGTTAT TTTCTATTAG

1801 AAAATGTCTT ACTGCTCTTT TGTATGCTTA TAAATATTTG AATCATCTAT

1851 ATTTAATTGG ACAAACTCTA TGAGAATAAA TATTGTTAAA ACTAATAAGA

1901 TAGGAAATTC ATTGATTTTG AATAATATTT CTTGTTTTAA GGTTTAACTA

1951 TTGAATTGTA TACTTCTTTT TTTAGTAGCA ACAGATCGAC CTGCAGGCAT

2001 A
```

Figure 80:
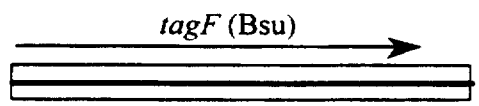

Mutant: NT 379
Phenotype: temperature sensitivity
Sequence map: Mutant NT379 is complemented by plasmid pMP389, which carries a 2.5 kb insert of wild-type S. aureus genomic DNA. A partial restriction map is depicted in FIG. 80; no apparent restriction sites for EcoR I, HinD III, BamH I or Pst I are present. Database searches at the nucleic acid and (putative) polypeptide levels against currently available databases reveal strong similarities to the tagF gene from B. subtilis, which encodes a protein involved in the biosynthesis of teichoic acid polymers (Genbank Accession No. X15200). The Tag genes of B. subtilis have been identified as essential and are expected to make good candidates for screen development. The predicted relative size and orientation of the tagF gene is depicted by an arrow in the restriction map.

DNA sequence data: The following DNA sequence data represents the sequence generated by primer walking through clone pMP389, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP389
pMP389 Length: 2522 nt
   1 GANCTCGGTA CCCGGGdATG CCTSYAGAGT CGATCGCTAC CACCTTGAAT  SEQ ID NO. 93

51 GACTTCAATT CTTTCATCAG AAATTTTGAA TTTTCTAAGT GTATCTTTCG

101 TATGCGTCAT CCATTGTTGT GGCGTCGCGA TAATAATTTT TTCAAAATCA

151 TTAATTAAAA TAAATTTTTC TAATGTATGG ATTAAAATCG GTTTGTTGTC

201 TAAATCTAAA AATTGTTTAG GTAAAGGTAC GTTACCCATT CTTGAGCCTA

251 TACCTCCAGC TAGAATACCA GCGTATTTCA TAAAATACTT CCTCCATTCA

301 ACTATATCTA TATTTAATTA TTTAAATTTC GTTGCATTTT CCAATTGAAA

351 ACTCATTTTA AAATCAAAAC TCTAAATGTC TGTGTATTAC TTAAAATTAT

401 ACATATTTTG CTTATATTTT AGCATATTTT GTTTAAACCT ATATTACATT

451 ATATCAGACG TTTTCATACA CAAATAATAA CATACAAGCA AACATTTCGT

501 TTATTATTTA TATCACTTAA CTAATTAATT TATAATTTTT TATTGTTTTT

551 AAGTTATCAC TTAAAAATCG TTTGGCAAAT TCGTTGTGAC GCTTGTCCAT

601 CTTCTAATGA ACAGAATTTT TGATAAAATA CCGTTCGTGC TTCAATATAC

651 TCATTTGCAG TCTCATCGAT TTGTTTTAAT GCATCAATGA GTGCTGTTTG

701 ATTTTCAACA ATTGGAMCTG GCAACTCTTT TTTATAATCC ATGTAAAAAC

751 CTCTAAGCTC ATCGCCATAT TTATCTAAGT CATATGCATA GAAAATTTGC

801 GGACGCTTTA ATACACCGAA GTCGAACATG ACAGATGAGT AGTCGGTAAC

851 TAACGCATCG CTGATTAAGT TATAAATCCG AAATGCCTTC ATAATCTGGA

901 AAMGTCTTTC AACAAAATCA TCAATGTTCA TCAATAACGY GTCAACAACT

951 AAATAATGCA KGCGTAATAA AATAACATAA TCATCATCCA GCGCTTTACG

1001 CAAAGCTTCT ATATCAAAGT TAACATTAAA TTGATATGAA CCCTTCTCGG
```

```
-continued
1051 AATCGCTTCA TCGTCAACGC CAAGTTGGCG CGTACATAAT CAACTTTTTT

1101 ATCTAATGGA ATATTTAATC TTGTCTTAAT ACCATTAATA TATTCAGTAT

1151 CATTGCGTTT ATGTGATAAT TTATCATTTC TTGGATAACC TGTTTCCAAA

1201 ATCTTATCTC GACTAACATG AAATGCATTT TGAAATATCG ATGTCGAATA

1251 TGGATTAGGT GACACTAGAT AATCCCACCG TTGGCTTTCT TTTTTAAAGC

1301 CATCTTGGTA ATTTTGAGTA TTTGTTCCTA GCATTTTAAC GTTACTAATA

1351 TCCAAACCAA TCTTTTTTAA TGGCGTGCCA TGCCATGTTT GTAAGTACGT

1401 CGTTCGCGGT GATTTATATA ACCAATCTGG TGTACGTGTG TTAATCATCC

1451 ACGCTTTCGC WCTTGGCATC GCTAAAAACC ATTTCATTGA AAACTTTGTA

1501 ACATATGGTA CATTGTGCTG TTGGAATATG TGTTCATATC CTTTTTTCAC

1551 ACCCCATATT AATTGGGCAT CGCTATGTTC AGTTAAGTAT TCATATAATG

1601 CTTTGGGGTT GTCGCTGTAT TGTTTACCAT GAAAGCTTTC AAAATAAATT

1651 AGATTCTTGT TTGGCAATTT TGGATAGTAA TTTAAAAGTC GTATATATAC

1701 TATGTTCTAT CAATTTTTTA ATTGTATTTT TAATCATGTC GTACCTCCGA

1751 CGTGTTTTTG TAATTATATT AATATGTATG AGCAAGCTCA TTGTAACCAT

1801 GCCTATTATA GCATTTCATC ATAAAATACA TTTAACCATT ACACTTGTCG

1851 TTAATTATCA TACGAAATAC ATGATTAATG TACCACTTTA ACATAACAAA

1901 AAATCGTTAT CCATTCATAA CGTATGTGTT TACACATTTA TGAATTAGAT

1951 AACGATTGGA TCGATTATTT TATTTWACAA AATGACAATT CAGTTGGAAG

2001 GTGATTGCTT TTGATTGAAT CGCCTTATGC ATGAAAAATC AAAAGGTTAT

2051 TCTCATTGTA TAGTCCTGCT TCTCATCATG ACATGTTGCT CACTTCATTG

2101 TCAGAACCCT TCTTGAAAAC TATGCCTTAT GACTCATTTG CATGGCAAGT

2151 AATATATGCC AACATTAGCG TCTAAACAAA TCTTTGACTA AACGTTCACT

2201 TGAGCGACCA TCTTGATATT TAAAATGTTT ATCTAAGAAT GGCACAACTT

2251 TTTCAACCTC ATAATCTTCA TTGTCCAAAG CATCCATTAA TGCATCAAAG

2301 GACTGTACAA TTTTACCTGG AACAAATGAT TCAAATGGTT CATAGAAATC

2351 ACGCGTCGTA ATGTAATCTT CTAAGTCAAA TGCATAGAAA ATCATCGGCT

2401 TTTTAAATAC TGCATATTCA TATATTAAAG ATGAATAATC ACTAATCAAC

2451 AAGTCTGTAA CAAAGAGAAT ATCGTTWACT TCASGRTCGA TCGACTCTAG

2501 AGGATCCCCG GGTACCGAGC TC
```

Figure 81:
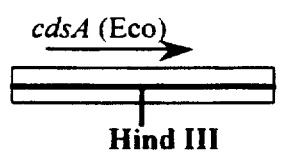

Mutant: NT 380
Phenotype: temperature sensitivity
Sequence map: Mutant NT380 is complemented by plasmid pMP394, which carries a 1.3 kb insert of wild-type *S. aureus* genomic DNA. A partial restriction map is depicted in FIG. 81. Database searches at the nucleic acid and (putative) polypeptide levels against currently available databases reveal strong similarities to the cdsA gene product from *E. coli* (Genbank Accession No. M11330), which encodes osphatidate cytidylyltransferase (EC 2.7.7.41); the cdsA gene product is involved in membrane biogenesis and is likely to be a good candidate for screen development. The predicted relative size and orientation of the cdsA gene is depicted by an arrow in the restriction map.

DNA sequence data: The following DNA sequence data represents the sequence generated by primer walking through clone pMP394, starting with standard M13 forward and M13 reverse sequencing primers and completing the sequence contig via primer walking strategies. The sequence below can be used to design PCR primers for the purpose of amplification from genomic DNA with subsequent DNA sequencing.

clone pMP394
pMP394 Length: 1335 nt
```
   1 CAGAGTTGTT AATTCGTACT TCAGGAGAAC AAAGAATAAG TAATTTCTTG   SEQ ID NO. 94

51 ATTTGGCAAG TTTCGTATAG TGAATTTATC TTTAATCAAA AATTATGGCC

101 TGACTTTGAC GAAGATGAAT TAATTAAATG TATAAAAATT TATCAGTCAC

151 GTCAAAGACG CTTTGGCGGA TTGARTGAKG AGKATRTATA GTATGAAAGT

201 TAGAACGCTG ACAGCTATTA TTGCCTTAAT CGTATTCTTG CCTATCTTGT

251 TAAAAGGCGG CCTTGTGTTA ATGATATTTG CTAATATATT AGCATTGATT

301 GCATTAAAAG AAATTGTTGA ATATGAATAT GATTAAATTT GTTTCAGTTC

351 CTGGTTTAAT TAGTGCAGTT GGTCTTATCA TCATTATGTT GCCACAACAT

401 GCAGGGCCAT GGGTACAAGT AATTCAATTA AAAAGTTTAA TTGCAATGAG

451 CTTTATTGTA TTAAGTTATA CTGTCTTATC TAAAAACAGA TTTAGTTTTA

501 TGGATGCTGC ATTTTGCTTA ATGTCTGTGG CTTATGTAGG CATTGGTTTT

551 ATGTTCTTTT ATGAAACGAC ATCAGAAGGA TTACATTACA TATTATATGC

601 CTTTTTAATT GTTTGGCTTA CAGATACAGG GGCTTACTTG TTTGGTAAAA

651 TGATGGGTTA AACATAAGCT TTGGCCAGTA ATAAKTCCGA ATAAAACAAT

701 CCGAAGGATY CATAGGTGGC TTGTTCTGTA GTTTGATAGT ACCACTTGCA

751 ATGTTATATT TTGTAGATTT CAATATGAAT GTATGGATAT TACTTGGAGT

801 GACATTGATT TTAAGTTTAT TTGGTCAATT AGGTGATTTA GTGGAATCAG

851 GATTTAAGCG TCATTTNGGC GTTAAAGACT CAGGTCGAAT ACTACCTGGA

901 CACGGTGGTA TTTTAGACCG ATTTGACAGC TTTATGTTTG TGTTACCATT

951 ATTAAATATT TTATTAATAC AATCTTAATG CTGAGAACAA ATCAATAAAC

1001 GTAAAGAGGA GTTGCTGAGA TAATTTAATG AATCCTCAGA ACTCCCTTTT

1051 GAAAATTATA CGCAATATTA ACTTTGAAAA TTATACGCAA TATTAACTTT

1101 GAAAATTAGA CGTTATATTT TGTGATTTGT CAGTATCATA TTATAATGAC

1151 TTATGTTACG TATACAGCAA TCATTTTTAA AATAAAAGAA ATTTATAAAC

1201 AATCGAGGTG TAGCGAGTGA GCTATTTAGT TACAATAATT GCATTTATTA

1251 TTGTTTTTGG TGTACTAGTA ACTGTTCATG AATATGGCCA TATGTTTTTT

1301 GCGAAAAGAG CAGGCATTAT GTGTCCAGAA TTTGC
```

Figure 82:
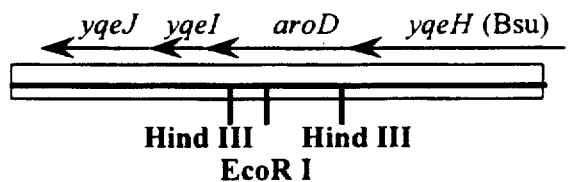

Mutant: NT401
phenotype: temperature sensitivity
Sequence map: Mutant NT401 is complemented by plasmid pMP476, which carries a 2.9 kb insert of wild-type S. aureus genomic DNA. A partial restriction map is depicted in FIG. 82. Database searches at the nucleic acid and (putative) polypeptide levels against currently available databases reveal sequence identity in the middle of the clone to pMP64, the complementing clone to NT31 (described previously). Since pMP64 does not cross complement NT401, and pMP476 contains additional DNA both upstream and downstream, the essential gene is likely to reside in the flanking DNA. The remaining DNA that completely contains an ORF is that coding for yqeJ, a hypothetical ORF from B. subtilis (Genbank Accession No. D84432)

DNA sequence data: The following DNA sequence data represents the sequence generated by primer walking through clone pMP476, starting with standard M13 forward and M13 reverse sequencing primers and completing the sequence contig via primer walking strategies. The sequence below can be used to design PCR primers for the purpose of amplification from genomic DNA with subsequent DNA sequencing.

clone pMP476
pMP476 Length: 2902 nt
```
   1 GAGCTCGGTA CCCGGGGATC CTCTAGAGTCGATCATTACC TAATTCGTAT   SEQ ID NO. 95

51 TGTCGAACAA TTTGATACAT TTTACCTAAA TCATCATATT TACAGAAATC
```

-continued

```
 101 ATGTAATACA CCTGCTAATT CTACTTTACT AGTGTCTCCA TCATAAATTT

151 CTGCCRATTT AATCGCTGTT TCTGCAACTC TTAAAGAATG ATTGATRACG

201 TTTCTCTGGA CAGTTTCTCT TTTGCAAGCC GTTTTGCTTT TTCAATGTWC

251 ATATAATCCT TCCCCCTTAA TATAGTTTTC AACGGATTTA GGAACAAGAA

301 CTTGGATAGA TTTCCCTTCA CTAACTCTTT GTCGAATCAT TGTCGAACTT

351 ATATCTACCC TAGGTATCTG AATTGCAATC ATAGCATTTT CAACATTTTG

401 ACTATTTTTG TCTCGATTTA CAACTACAAA AGTAACCATT TCTTTTAAGT

451 ATTCAATTTG ATACCATTTC TCTAGTTGGT TATACTGATC CGTCCCAATA

501 ACAAAGTACA ACTCACTGTC TTTGTGTTGC TCCTTGAATG CCTTGATCGT

551 GTCATAGGTA TAACTTTGAC CACCACGTTT AATTTCATCG TCACAAATAT

601 CTCCAAAACC AAGCTCGTCG ATAATCATCT GTATCATTGT TAATCTGTGC

651 TGAACGTCTA TAAAATCATG GTGCTTTTTC AATGGAGAMA WAAAAMWARR

701 WAAAAAATAA AATTCATCTG GCTGTAATTC ATGAAATACT TCGCTAGCTA

751 CTATCATATG TTGCAGTATG GATAGGGTTA AACTGACCGC CGTAAAGTAC

801 TATCTTTTTC ATTATTATGG CAATTCAATT TCTTTATTAT CTTTAGATTC

851 TCTATAAATC ACTATCATAG ATCCAATCAC TTGCACTAAT TCACTATGAA

901 KTAGCTTCCG CTTAATGTTT CCAGCTAATY CTTTTTTATC ATCAAAGTTT

951 ATTTTGTTAK TACATGTTAC TTTAATCAAT YCTCTGTTTT CYAACGTTAT

1001 CATCTATTTG TTTAATCATA TTTTCGTTGA TACCGCCTTT TCCAATTTGA

1051 AAAATCGGAT CAATATTGTG TGCTAAACTT CTTAAGTATC TTTTTTGTTT

1101 GCCAGTAAGC ATATGTTATT CTCCTTTTAA TTGTTGTAAA ACTGCTGTTT

1151 TCATAGAATT AATATCAGCA TCTTTATTAG TCCAAATTTT AAAGCWTTCC

1201 GCACCCTGGT AAACAAACAT ATCTAAGCCA TTATAAATAT GGTTTCCCTT

1251 GCGCTCTGCT TCCTCTAAAA TAGGTGTTTT ATACGGTATA TAAACAATAT

1301 CACTCATTAA AGTATTGGGA GAAAGAGCTT TAAATTAATA ATACTTTCGT

1351 TATTTCCAGC CATACCCGCT GGTGTTGTAT TAATAACGAT ATCGAATTCA

1401 GCTAAATACT TTTCAGCATC TGCTAATGAA ATTTGGTTTA TATTTAAATT

1451 CCAAGATTCA AAACGAGCCA TCGTTCTATT CGCAACAGTT AATTTGGGCT

1501 TTACAAATTT TGCTAATTCA TAAGCAATAC CTTTACTTGC ACCACCTGCG

1551 CCCAAAATTA AAATGTATGC ATTTTCTAAA TCTGGATAAA CGCTGTGCAA

1601 TCCTTTAACA TAACCAATAC CATCTGTATT ATACCCTATC CACTTGCCAT

1651 CTTTTATCAA AACAGTGTTA ACTGCACCTG CATTAATCGC TTGTTCATCA
```

-continued

```
1701 ACATAATCTA AATACGGTAT GATACGTTCT TTATGAGGAA TTGTGATATT

1751 AAASCCTTCT AATTYTTTTT TSGAAATAAT TTCTTTAATT AAATGAAAAA

1801 TTYTTCAATT GGGAATATTT AAAGCTTCAT AAGTATCATC TTAATCCTAA

1851 AGAATTAAAA TTTGCTCTAT GCATAACGGG CGACAAGGAA TGTGAAATAG

1901 GATTTCCTAT AACTGCAAAT TTCATTTTTT TAATCACCTT ATAAAATAGA

1951 ATTYTTTAAT ACAACATCAA CATTTTTAGG AACACGAACG ATTACTTTAG

2001 CCCCTGGTCC TATAGTTATA AAGCCTAGAC CAGAGATCAT AACATCGCGT

2051 TTCTCTTTGC CTGTTTCAAG TCTAACAGCC TTTACCTCAT TAAGATCAAA

2101 ATTTTGTGGA TTTCCAGGTG GCGTTAATAA ATCGCCAAGT TGATTACGCC

2151 ATAAATCATT AGCCTTCTCC GTTTTAGTAC GATGTATATT CAAGTCATTA

2201 GAAAAGAAAC AAACTAACGG ACGTTTACCA CCTGAWACAT AATCTATGCG

2251 CGCTAGACCG CCGAAGAATA ATGTCKGCGC CTCATTTAAT TGATATACGC

2301 GTTGTTTTAT TTCTTTCTTA GGCATAATAA TTTTCAATYC TTTTTCACTA

2351 ACTAAATGCG TCATTTGGTG ATCTTGAATA ATACCTGGTG TATCATACAT

2401 AAATGATGTT TCATCTAAAG GAATATCTAT CATATCTAAA GTTGYTTCCA

2451 GGGAATCTTG AAGTTGTTAC TACATCTTTT TCACCAACAC TAGCTTCAAT

2501 CAGTTTATTA ATCAATGTAG ATTTCCCAAC ATTCGTTGTC CCTACAATAT

2S51 ACACATCTTC ATTTTCTCGA ATATTCGCAA TTGATGATAA TAAGTCGTCT

2601 ATGCCCCAGC CTTTTTCAGC TGAAATTAAT ACGACATCGT CAGCTTCCAA

2651 ACCATATTTT CTTGCTGTTC GTTTTAACCA TTCTTTAACT CGACGTTTAT

2701 TAATTTGTTT CGGCAATAAA TCCAATTTAT TTGCTGCTAA AATGATTTTT

2751 TTGTTTCCGA CAATACGTTT AACTGCATTA ATAAATGATC CTTCAAAGTC

2801 AAATACATCC ACGACATTGA CGACAATACC CTTTTTATCC GCAAGTCCTG

2851 ATAATAATTT TAAAAAGTCT TCACTTTCTA ATCCTACATC TTGAACTTCG

2901 TT
```

Figure 83:
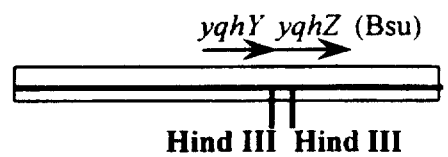

Mutant: NT423
phenotype: temperature sensitivity
Sequence map: : Mutant NT423 is complemented by plasmid pMP499, which carries a 2.0 kb insert of wild-type *S. aureus* genomic DNA. A partial restriction map is depicted in FIG. 83. Database searches at the nucleic acid and (putative) polypeptide levels against currently available databases reveal strong peptide-level similarities to yqhY, a hypothetical ORF identified from a genomic sequencing effort in *B. subtilis* (Genbank Accession No. D84432), and yqhZ, a hypothetical ORF from *B. subtilis* bearing similarity to the nusB gene product from *E. coli* (Genbank Accession No. M26839; published in Imamoto, F. et al. *Adv. Biophys.* 21 (1986) 175–192). Since the nusB gene product has been demonstrated to be involved in the regulation of transcription termination in *E. coli*, it is likely that either one or both of the putative genes identified in this sequence contig encode essential functions.

DNA sequence data: The following DNA sequence data represents the sequence generated by primer walking through clone pMP499, starting with standard M13 forward and M13 reverse sequencing primers and completing the sequence contig via primer walking strategies. The sequence below can be used to design PCR primers for the purpose of amplification from genomic DNA with subsequent DNA sequencing.

clone pMP499
pMP499 Length: 1916 nt
```
   1 AGTCGATCAA AGCCAATGTT CCAGTTGTTC CTGGTAGTGA CGGTTTAATG    SEQ ID NO. 96
  51 AAAGACGTCT CAGAAGCTAA GAAAATCGCC AAAAAAATTG GCTATCCGGT
 101 CATCATTAAA GCTACTGCTG GCGGTGGCGG AAAAGGTATC CGTGTTGCTC
 151 GTGATGAAAA AGAACTTGAA ACTGGCTTCC GAATGACAGA ACAAGAAGCT
 201 CAAACTGCAT TTGGTAATGG TGGACTTTAT ATGGAGAAAT TCATCGAAAA
 251 CTTCCGCCAT ATTGAAATCC AAATTGTTGG GGACAGCTAT GGTAATGTAA
 301 TTCATTTAGG AGAACGTGAT TGTACAATTC AAAGACGTNT GCAGAAATTA
 351 GTGGAAGAAG CACCTTCCCC NATTTTAGAT GATGAAACAC GTCGTGAAAT
 401 GGGAAATGCC GCAGTTCGTG CAGCGAAAGC TGTAAATTAT GAAAATGCGG
 451 GAACAATTGA GTTTATATAT GATTTAAATG ATAATAAATT TTATTTTATG
 501 GAAATGAATA CACGTATTCA AGTAGAACAT CCTGTAACTG AAATGGTAAC
 551 AGGAATTGAT TTAGTTAAAT TACAATTACA AGTTGCTATG GGTGACGTGT
 601 TACCGTATAA ACAAGAAGAT ATTAAATTAA CAGGACACGC AATTGAATTT
 651 AGAATTAATG CTGAAAATCC TTACAAGAAC TTTATGCCAT CACCAGGTAA
 701 AATTGAGCAA TATCTTGCAC CAGGTGGATA TGGTGTTCGA ATAGAGTCAG
 751 CATGTTATAC TAATTATACG ATACCGCCAT ATTATGATTC GATGGTAGCG
 801 AAATTAATCA TACATGAACC GACACGAGAT GARGCGATTA TGGSTGGCAT
 851 TCGTGCACTA ARKGRAWTTG TGGTTYTTGG GTATTGATAC AACTATTCCA
 901 TTTCCATATT AAATTATTGA ATAACGGATA TATTTAGGAA GCGGTAAATT
 951 TAATACAAAC TTTTTAGAAG CAAAATAGCA TTATTGAATG ATGAAAGGTT
1001 AATAGGAGGT CMATCCCMTG GTCAAAGTAA CTGATTATTC MAATTCMAAA
1051 TTAGGTAAAG TAGAAATAGC GCCAGAAGTG CTATCTGTTA TTGCAAGTAT
1101 AGCTACTTCG GAAGTCGAAG GCATCACTGG CCATTTTGCT GAATTAAAAG
1151 AAACAAATTT AGAAAAGTT AGTCGTAAAA ATTTAAGCCG TGATTTAAAA
1201 ATCGAGAGTA AAGAAGATGG CATATATATA GATGTATATT GTGCATTAAA
1251 ACATGGTGTT AATATTTCAA AAACTGCAAA CAAAATTCAA ACGTCAATTT
1301 TTAATTCAAT TTCTAATATG ACAGCGATAG AACCTAAGCA AATTAATATT
1351 CACATTACAC AAATCGTTAT TGAAAAGTAA TGTCATACCT AATTCAGTAA
1401 TTAAATAAAG AAAAATACAA ACGTTTGAAG GAGTTAAAAA TGAGTCGTAA
1451 AGAATCCCGA GTGCAAGCTT TTCAAACTTT ATTTCAATTA GAAATGAAGG
1501 ACAGTGATTT AACGATAAAT GAAGCGATAA GCTTTATTAA AGACGATAAT
1551 CCAGATTTAG ACTTCGAATT TATTCATTGG CTAGTTTCTG GCGTTAAAGA
1601 TCACGAACCT GTATTAGACG AGACAATTAG TCCTTATTTA AAAGATTGGA
1651 CTATTGCACG TTTATTAAAA ACGGATCGTA TTATTTTAAG AATGGCAACA
1701 TATGAAATAT TACACAGTGA TACACCTGCT AAAGTCGTAA TGAATGAAGC
1751 AGTTGAATTA ACAAAACAAT TCAGTGATGA TGATCATTAT AAATTTATAA
1801 ATGGTGTATT GAGTAATATA AAAAAATAAA ATTGAGTGAT GTTATATGTC
1851 AGATTATTTA AGTGTTTCAG CTTTAACGAA ATATATTAAA TATAAATTTG
1901 ATCGACCTGC AGGCAT
```

Mutant: NT432 phenotype: temperature sensitivity

Figure 84:
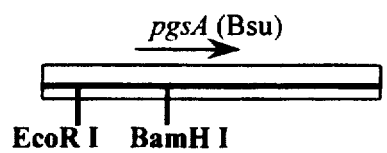

Sequence map: : Mutant NT432 is complemented by plasmid pMP500, which carries a 1.9 kb insert of wild-type *S. aureus* genomic DNA. A partial restriction map is depicted in FIG. 84. Database searches at the nucleic acid and (putative) polypeptide levels against currently available databases reveal strong peptide-level similarities to the pgsA gene product, encoding CDP-diacylglycerol:glycerol-3-phosphate 3-phosphatidyltransferase (PGP synthase; EC 2.7.8.5) from *B. subtilis* (Genbank Accession No. D50064; published in Kontinen, V. P. et al. *FEBS lett.* 364 (1995) 157–160).

DNA sequence data: The following DNA sequence data represents the sequence generated by primer walking through clone pMP500, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP500
pMP500 Length: 1932 nt
   1 CGGGGATCCT CTAGAGTCGA TCCGTTTGGT GGTGGTTTTG GTTTCTTCGA SEQ ID NO. 97

51 GTAAGTGTAA GGAGGCTATG AATTGARRAC GGTCGGTGAA GCGCTAAAAG

101 GTANACGTGA AAGGTTAGGA ATGACTTYAA CAGAATTAGA GCAACGTACT

151 GGAATTAANC GTGAAATGCT AGTGCATATT GAAAATAATG AATTCGATCA

201 ACTACCGAAT AAAAATTACA GCGAAGGATT TATTAGAAAA TATGCAAGCG

251 TAGTAAATAT TGAACCTAAC CAATTAATTC AAGCTCATCA AGATGAAATT

301 CCATCGAACC AGAGCCGAAT GGGACGAAGT AATTACAGTT TTCAATAGAT

351 AATAAAGACT TACGATTATA AGAGTAAATC AAAGANAGCC AATACAATTA

401 TTAGTAATCA TGGGTTATTA CAGTTTTAAT AACTTTATTG TTATGGATCA

451 TGTTAGTTTT AATATTTTAA CAGAAATAAA TTAGTGAGAA ATGAGGATGT

501 TATAATGAAT ATTCCGAACC AGATTACGGT TTTTAGAGTT AGTGTTAATA

551 CCAGTTTTTA TATTGTTTGC GTTAGTTGAT TTTGGATTTG GCAATGTGTC

601 ATTTCTAGGA GGATATGAAA TAAGAATTGA GTTATTAATC AGTGGTTTTA

651 TTTTTATATT GGCTTCCCTT AGCGATTTTG TTGATGGTTA TTTAGCTAGA

701 AAATGGAATT TAGTTACAAA TATGGGGAAA TTTTTGGATC CATTAGCGGA

751 TAAATTATTA GTTGCAAGTG CTTTAATTGT ACTTGTGCAA CTAGGACTAA

801 CAAATTCTGT AGTAGCAATC ATTATTATTG CCAGAGAATT TGCCGTAACT

851 GGTTTACGTT TACTACAAAT TGAACAAGGA TTCCGTAAGT TGCAGCTGGT

901 CCAATTTAGG TWAAAWTWAA AACAGCCAGT TACTATGGTT AGCMAWTWAC

951 TTGGTTGTTW ATTAAGKTGA TCCCATTGGG CAACATTGAT TGGTTTGTCC

1001 ATTARGACAA ATTTTAATTA TAACATTGGC GTTATWTTTW ACTATCYTAT

1051 CTGGTATTGA ATAACTTTTA TAAAGGTAGA GATGTTTTTA AACAAAAATA

1101 AATATTTGTT TATACTAGAT TTCATTTTCA TATGGAATCT AGTTTTTTTA

1151 ATCCCAATTT TAGAAATTAG CCACGCAATT GTTTATAATG ATATATTGTA

1201 AAACAATATT TGTTCATTTT TTTAGGGAAA ATCTGTAGTA GCATCTGATA

1251 CATTGAATCT AAAATTGATG TGAATTTTTA AATGAAATAC ATGAAAAAAT

1301 GAATTAAACG ATACAAGGGG GATATAAATG TCAATTGCCA TTATTGCTGT

1351 AGGCTCAGAA CTATTGCTAG GTCAAATCGC TAATACCAAC GGACAATTTC

1401 TATCTAAAGT ATTTAATGAA ATTGGACAAA ATGTATTAGA ACATAAAGTT

1451 ATTGGAGATA ATAAAAAACG TTTAGAATCA AGTGTAACGT CATGCGCTAG

1501 AAAAATATGA TACTGTTATT TTAACAGGTG GCTTAGGTCC TACGAAAGAT

1551 GACTTAACGA AGCATACAGT GGCCCAGATT GTTGGTAAAG ATTTAGTTAT
```

-continued

```
1601 TGATGAGCCT TCTTTAAAAT ATATTGAAAG CTATTTTGAG GAACAAGGAC

1651 AAGAAATGAC ACCTAATAAT AAACAACAGG CTTTAGTAAT TGAAGGTTCA

1701 ACTGTATTAA CAAATCATCA TGGCATGGCT CCAGGAATGA TGGTGAATTT

1751 TGAAAACAAA CAAATTATTT TATTACCAGG TCCACCGAAA GAAATGCAAC

1801 CAATGGTGAA AAATGAATTG TTGTCACATT TTATAAACCA TAATCGAATT

1851 ATACATTCTG AACTATTAAG ATTTGCGGGA ATAGGTGAAT CTAAAGTAGA

1901 AACAATATTA ATAGATCGAC CTGCAGGCAT GC
```

Figure 85:
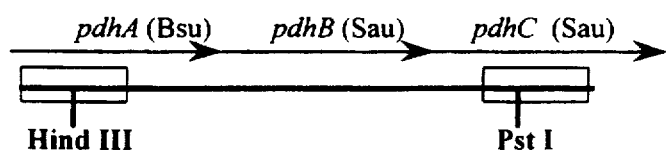

Mutant: NT435
phenotype: temperature sensitivity
Sequence map: Mutant NT435 is complemented by plasmid pMP506, which carries a 3.2 kb insert of wild-type *S. aureus* genomic DNA. A partial restriction map is depicted in FIG. 85. Database searches at the nucleic acid and (putative) polypeptide levels against currently available databases reveal strong peptide-level similarity from the left-most contig (shown below) to the pdhA gene product, encoding the E1-alpha subunit of pyruvate dehydrogenase, from *B. subtilis*. The right-most contig below demonstrates DNA sequence identity to the pdhC gene, encoding the E2 chain of dihydrolipoamide acetyltransferase (EC 2.3.1.12), from *S. aureus* (Genbank Accession No. X58434). This Genbank entry also contains the pdhB gene upstream, encoding the E1-beta subunit of pyruvate dehydrogenase (EC 1.2.4.1); since the pMP506 clone contains the region upstream of pdhC, it is predicted that the essential gene identified by mutant NT435 is pdhb. Further sequencing is currently underway to prove this assertion.

DNA sequence data: The following DNA sequence data represents the sequence generated from clone pMP506, starting with standard M13 forward and M13 reverse sequencing primers; the sequence contig will be completed via primer walking strategies. The sequence below can be used to design PCR primers for the purpose of amplification from genomic DNA with subsequent DNA sequencing.

```
clone pMP506
pMP506.forward Length: 619 nt
  1 ATTCGAGCTC GGTACCCGGG GATCCTCTAN AGTCGATCTT ACGGATGAAC  SEQ ID NO. 98

51 AATTAGTGGA ATTAATGGAA AGAATGGTAT GGACTCGTAT CCTTGATCAA

101 CGTTCTATCT CATTAAACAG ACAAGGACGT TTAGGTTTCT ATGCACCAAC

151 TGCTGGTCAA GAAGCATCAC AATTAGCGTC ACAATACGCT TTAGAAAAAG

201 AAGATTACAT TTTACCGGGA TACAGAGATG NTCCTCAAAT TATTTGGCAT

251 GGTTTACCAT TAACTGAAGC TTTCTTATTC TCAAGAGGTC ACTTCAAAGG

301 AAATCAATTC CCTGAAGGCG TTAATGCATT AAGCCCACAA ATTATTATCG

351 GTGCACAATA CATTCAAGCT GCTGGTGTTT GCATTTGCAC TTAAAAAACG

401 TTGGTAAAAA TGCAGTTGCA ATCACTTACA CTGGTTGACG GTGGTTCTTC

451 ACAAGGTTGA TTTCTACGAA GGTATTAACT TTGCAGCCAG CTTTATAAAG

501 CACCTGGCAA TTTTCCGTTA TTCAAAACAA TAACTATGCA ATTTCAACAC

551 CCAAGAANCA AGCNAACTGC TGCTGAAACA TTACTCAAAA ACCATTGCTG

601 TAGTTTTCCT GGTATCCAT

PMP506.reverse Length: 616 nt
  1 CTTGCATGCC TGCAGGTCGA TCANCATGTT TAACAACAGG TACTAATAAT  SEQ ID NO. 99

51 CCTCTATCAG TGTCTGCTGC AATACCGATA TTCCAGTAAT GTTTATGAAC

101 GATTTCACCA GCTTCTTCAT TGAATGAAGT GTTAAGTGCT GGGTATTTTT

151 TCAATGCAGA AACAAGTGCT TTAACAACAT AAGGTAAGAA TGTTAACTTA

201 GTACCTTGTT CAGCTGCGAT TTCTTTAAAT TTCTTACGGT GATCCCATAA

251 TGCTTGAACA TCAATTTCAT CCATTAATGT TACATGAGGT GCAGTATGCT

301 TAGAGTTAAC CATTGCTTTC GCAATTGCTC TACGCATAGC AGGGATTTTT
```

```
351 TCAGTTGTTT CTGGGAAGTC GCCTTCTAAT GTTACTGCTG CAGGTGCTGC

401 AGGAGTTTCA GCAACTTCTT CACTTGTAGC TGAAGCAGCT GATTCATTTG

451 AAGCTGTTGd TGCACCACCA TTTAAGTATG CATCTACATC TTCTTTTGTA

501 ATACGACCAT TTTTTACCAG ATCCAGAAAC TGCTTTAATG TTTAACACCT

551 TTTTCACGTG CGTTATTTAC TTACTGAAGG CATTGCTTTA AACAGTCTGT

601 TTTCATCTAC TTCCTC
```

Mutant: NT437 phenotype: temperature sensitivity

Figure 86:

Sequence map: Mutant NT437 is complemented by plasmid pMP652, which carries a 3.1 kb insert of wild-type *S. aureus* genomic DNA. A partial restriction map is depicted in FIG. 86; no apparent restriction sites for EcoR I, HinD III, BamH I or Pst I are present. Database searches at the nucleic acid and (putative) polypeptide levels against currently available databases reveal no significant similarities at this time.

Current efforts are underway to complete the sequence contig and identify the essential gene contained in clone pMP652.

DNA sequence data: The following DNA sequence data represents the sequence generated from clone pMP652, starting with standard M13 forward and M13 reverse sequencing primers; the sequence contig will be completed via primer walking strategies. The sequence below can be used to design PCR primers for the purpose of amplification from genomic DNA with subsequent DNA sequencing.

```
clone pMP652
pMP652.forward Length: 655 nt
  1 GTACCGGGGA TCGTCACTTA NCCTCTCTAT TTCAATTTCA ACTTATTTCG SEQ ID NO.
                                                            100

51 TCATCAAGTA TATGTGTTAT GCTTTTATAA CTTTGATTTC AATTCTATCA

101 ATATCTGTGA CATTGATAAC ATCGGACATA CGGTCTTCTT GTAACTTTTT

151 ATCCAATTCA AATGTATACT TTCCATAGTA TTTCTTTTTG ACTGTAATTT

201 TTCCTGTACT CATTTCACCG TAAAGACCAT AATTATCAAT AAGGTATTTT

251 CTTAATTTAA AATCAATCTC TTTCAATGAC ATCGCTTCTT TATCTATTTT

301 AAATGGGAAA AAGTCATAAT CATATTCACC AGTATGATCT TCTTTAATAA

351 CTCTTGCTTC TGCTATTAGG TCGACAGCTT TATCGTTTGC ACTCGTGATA

401 CCCCCAATAG AGTACTTTGC ACCTTCAAAT CTCTTATCCT CATTAACGTA

451 AAATATATTA AGAWTACGAW KKTACACCCG TATGATAATG TTTGCTTATC

501 TTTGCCAATT AAAGCAATAT TATTAACAGA ATTACCATCT ATGATATTCA

551 TAAATTTAAT ACTTGGTTGA ATGAAACTGG ATATAACCTG TCMCATTTTT

601 AATATTCMAT ACTAGGTTGA ATWATAATAA GCTTTTAATT TTTKGCTATT

651 TTCCC
pMP652.reverse Length: 650 nt
  1 GTCGACTCTA GAGGACTGCG TAATAACCTA TGAAAAATGA TATGAGCAAC SEQ ID NO.
                                                            101

51 GCCGCTCTGC TTTGCCGCAT ATACTAAATT TTCCACTTCA GGAATACGTT

101 TGAATGATGG ATGGATAATA CTTGGAATAA ACACAACGGT ATCCATTCCT

151 TTAAATGCTT CTACCATGCT TTCTTGATTA AAATAATCTA ATTGTCGAAC

201 AGGAACTTTT CCGCGCCAAT CTTCTGGAAC TTTCTCAACA TTTCTAACAC

251 CAATGTGAAA ATGATCTATG TGATTTGCAA TGGCTTGATT TGTAATATGT

301 GTGCCTAAAT GACCTGTAGC ACCTGTTAAC ATAATATTCA TTCACTTCAT

351 CTCCTAATCT TTATATACAT AACATAATAC TTATTTGATG GTTTTCAAAA

401 CATTTGATTT TATAAAAAAT TCTAATCTGT ATTTATTGTC GACGTGTATA

451 GTAAATACGT AAATATTANT AATGTTGAAA ATGCCGTAAT GACGCGTTTT
```

-continued

```
501 AGTTGATGTG TTTCACTAAT ATCATTGAAA ATTTTAATCA GGTACTACGA

551 CAATATGAAG TCTGTTTTGT GTCTGAAAAT TTTACAGTTT TTAAAATAAA

601 AATGGTATAA GTTGTGATTT GGTTTAAAAA ANAATCTCGA CGGATAANAA
```

Figure 87:
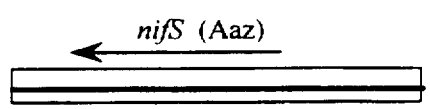

Mutant: NT438
phenotype: temperature sensitivity
Sequence map: : Mutant NT438 is complemented by plasmid pMP511, which carries a 2.3 kb insert of wild-type *S. aureus* genomic DNA. A partial restriction map is depicted in FIG. 87; no apparent restriction sites for EcoR I, HinD III, BamH I or Pst I are present. Database searches at the nucleic acid and (putative) polypeptide levels against currently available databases reveal strong peptide-level similarities to the nifS gene product, encoding a protein involved in the response pathway for nitrogen assimilation, from *A. azollae* (Genbank Accession No. L34879; published in Jackman, D. M. et al. *Microbiology* 141, pt.9 (1995) 2235–2244).

DNA sequence data: The following DNA sequence data represents the sequence generated by primer walking through clone pMP511, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP511
pMP511 Length: 2341 nt
     1  CTTGCATGCC TGCAGGTCGA TCTTTATTAT NATCTACACC ACGTANCATT  SEQ ID NO. 102

51  TCAACATGAC CACGNTCATG ACGATGTATG CGTGCGTAAW GTCCTGTKGY

101  WACATAATCK GCACCTAAAT TCATCGCATG ATCTAAAAAG GCTTTAAACT

151  TAATTTCTTT ATWAMACATA ACGTCTGGAT TTGGAGTACG ACCTTTTTTG

201  TATTCATCTA AGAAATACGT AAAGACTTTA TCCCAATATT CTTTTTCAAA

251  ATTAACAGCG TAATACGGAA TGCCAATTTG ATTACACACT TCAATAACAT

301  CGTTGTAATC TTCAGTTGCA GTACATACGC CATTTTCGTC AGTGTCATCC

351  CAGTTTTTCA TAAATATGCC AATGACATCA TAACCTTGTT CTTTTAAGAC

401  GTGGGCTGTT ACAGAACTAT CTACACCGCC TGACATACCA ACGACAACAC

451  GTTATATCTT TATTTGACAA TTATGACTCC TCCTTAAATT TAAAATATAT

501  TTTATGAATT TCAGCTACAA TTGCATTAAT TTCATTTTCA GTAGTCAATT

551  CGTTAAAACT AAATCGAATC GAATGATTTG ATCGCTCCTC ATCTTCGAAC

601  ATTGCATCTA AAACATGCGA CGGTTGTGTA GAGCCTGCTG TACATGCAGA

651  TCCAGACGAC ACATAGATTT GTGCCATATC CAACAATGTT AACATCGTTT

701  CAACTTCAAC AAACGGAAAA TATAGATTTA CAATATGGCC TGTAGCATCC

751  GTCATTGAAC CATTTAATTC AAATGGAATC GCTCTTTCTT GTAATTTAAC

801  TAAAAATTGT TCTTTTAAAT TCATTAAATG AATATTGTTA TCGTCTCGAT

851  TCTTTTCTGC TAATTGTAAT GCTTTAGCCA TCCCAACAAT TTGCGCAAGA

901  TTTTCAKTGC CTAGCACGGC GTTTCAATTC TTGTTCACCG CCAAGTTGAG

951  GATAATCTAG TGTAACATGG TCTTTAACTA GTAATGCACC GACACCTTTT

1001  GGTCCGCCAA ACTTATGAGC AGTAATACTC ATTGCGTCGA TCTCAAATTC

1051  GTCAAWCTTA ACATCAAGAT GTCCAATTGC TTGAACCGCA TCAACATGGA

1101  AATATGCATT TGTCTCAGCA ATAATATCTT GAATATCATA AATTTGTTGC

1151  ACTGTGCCAA CTTCATTATT TACAAACATA ATAGATACTA AAATCGTCTT

1201  ATCTGTAATT GTTTCTTCAA GTTTGATCTA AATCAATAGC ACCTGTATCA

1251  TCARCATCTA GATATGTTTA CATCAAAACC TYCTCGCTCT AATTGTTCAA

1301  AAACATGTAA CACAGAATGA TGTTCAATCT TCGATGTGAT AATGTGATTA
```

-continued

```
1351  CCCAATTGTT CATTTGCTTT TACTATGCCT TTAATTGCCG TATTATTCGA
1401  TTCTGTTGCG CCACTCGTAA ATATAATTTC ATGTGTATCT GCACCAAGTA
1451  ATTGTGCAAT TTGACGTCTT GACTCATCTA AATATTTACG CGCATCTCTT
1501  CCCTTAGCAT GTATTGATGA TGGATTACCA TAATGCGAAT TGTAAATCGT
1551  CATCATCGCA TCTACTAACT TCAGGTTTTA CTGGTGTGGT CGCAGCATAA
1601  TCTGCATAAA TTTCCCATGT TTGGACAACT CCTCACAATT TTATCAATGT
1651  TCCAATAATA GCACCTTAAC ATACTATTTT TCTAACTTTT CTGTTTAACT
1701  TTATTTATAA TGTTTTTAAT TATATTTTAC CATTTTCTAC ACATGCTTTT
1751  CGATAGGCTT TTTTAAGTTT ATCGCTTTAT TCTTGTCTTT TTTATAAATT
1801  TTAGTATTTG CAGATATTTT TTTATTTGTA AAATGTAACG TACTATTATT
1851  TTGGTTATGA GCAATTTAAT ATTTATCTGG TTATTCGGAT TGGTATACTT
1901  CTTATATCAT AAAAAAGGAA GGACGATATA AAAATGGCGG ATTAAATATT
1951  CAGCAKKAAA CCTTGTCCCT ATTCGAGAAG GTGAAGATGA ACAAACAGCA
2001  ATTAATAATA TGGTTAATCT CGCACAACAT TTAGACGAAT TATCATATGA
2051  AAGATATTGG ATTGCTGAAC ACCATAACGC TCCCAACCTA GTAAGTTCAG
2101  CAACTGCTTT ATTAATTCAA CATACGTTAG AACATACGAA ACACATACGT
2151  GTAGGTTCTG GAGGCATCAT GTTACCTAAT CATGCTCCAT TAATCGTTGC
2201  GGAACAATTT GGCACGATGG CAACATTATT TCCAAATCGT GTCGATTTAG
2251  GATTAGGACG TGCACCTGGA ACAGATATGA TGACCGCAAG TGCATTAAGA
2301  CGAGATCGAC TNTAGAGGAT CCCCGGGTAC CGAGCTCGAA T
                                                        35
```

Figure 88:
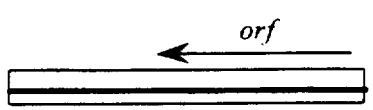

Mutant: NT462
phenotype: temperature sensitivity
Sequence map: :Mutant NT462 is complemented by plasmid pMP540, which cdrries a 2.0 kb insert of wild-type *S. aureus* genomic DNA. A partial restriction map is depicted in FIG. 88; no apparent restriction sites for EcoR I, HinD III, BamH I or Pst I are present. Database searches at the nucleic acid and (putative) polypeptide levels against currently available databases reveal limited peptide-level similarity to a transposase-like protein from *S. aureus*; the putative function of the ORF contained in clone pMP540 is unclear and will require further characterization.

DNA sequence data: The following DNA sequence data represents the sequence generated by primer walking through clone pMP540, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP540
pMP540 Length: 2026 nt
    1  AAGGAAACCA CCAACACCTG CGCCAACTAA ACCKCCTGTT AGTGCAGAAA    SEQ ID NO. 103
   51  TAACGCTAAT AGCCCCCGCA CCTAAAGCAG CTRKNGTTTT TGTATATGCA
  101  GAAGAAAGAT ATAATGTTGC AGTATCTTTA CCTGTTTCTA CATATTGAGT
  151  TTTACCCGCT CTCAATTGGT CTTCAGCTTT ATATTTNTWT ATTTCTTCTW
  201  TAGTAAATAT ATCTTCCRGT TTATAACCTT TTTTCTCAAG TTCATCAAAT
  251  AAATTTWGGT TACTCAAATA TATTACCTTT GCTTGAGAAT GGTCTAACTT
  301  ATCTTCAGCA TGAGCTACAT CTGAATTATA GAGATAATGA AATTGGACTA
  351  ACAAATAATA CACCAGCAGC TRRTAATAAG AGATTTTTAA TTCGTTTTTC
  401  ATTAGTTTCT TTTAGATGAT TTTTGTATTT AGATTTCGTA TAAACAGAAA
  451  CTAGATTTTT TCATGATCGA CCTATCTTTT GTCCAGATAC AGTGAGACCT
```

-continued

```
 501  TGTCATTTAA ATGATTTTTA ATTCGTCTTG TACCAGAGAC TTTTCTATTA
 551  GAATTAAAAA TATTTATGAC GGCTGTTCTA TGTTTGAATC ATCTTTAGTG
 601  ATTTTATTAT CTTTTCTTTT TATAGAATCA TAATAGGTAC TTCTTAGTAT
 651  TATCAGGACT TTACACATTG NTGATACTGA ATANTGATGT GCATTCTTTT
 701  GAATGACTTC TATTTTTGCC CCATAATCAG CGCTACTTGC TTTAAAATAT
 751  CGTGCTCCAT TTTAAAATGT TGAACTTCTT TGCGTAATTT AATCAGGTCT
 801  TTTTCTTCAT CCGATAAGTT ATCTTGGTGA TTGAATGTAC CCGTGTTTTG
 851  ATGTTGCTTT ATCCATTTTC CTACATTTTA TAACCGCCAT TTACAAACGT
 901  CGAAKGTGTG AAATCATACT CGCGTWTAAT TTCATTCCTA GGCTTACCAT
 951  TTTTATATAA TCTAACCATT TGTAACTTAA ACTCTGAACT AAATGATCTT
1001  CTTTCTCTTG TCATAATAAA ATCGCCTACT TTCTTAAATT AACAATATCT
1051  ATTCTCATAG AATTTGTCCA ATTAAGTGTA GACGATTCAA TCTATCAGCT
1101  AGAATCATAT AACTTATCAG AAGCAAGTGA CTGTGCWTGT ATATTTGCCG
1151  MTGATATAAT AGTAGAGTCG CCTATCTCTC AGGCGTCAAT TTAGACGCAG
1201  AGAGGAGGTG TATAAGGTGA TGCTYMTTTT CGTTCAACAT CATAGCACCA
1251  GTCATCAGTG GCTGTGCCAT TGCGTTTTTY TCCTTATTGG CTAAGTTAGA
1301  CGCAATACAA AATAGGTGAC ATATAGCCGC ACCAATAAAA ATCCCCTCAC
1351  TACCGCAAAT AGTGAGGGGA TTGGTGTATA AGTAAATACT TATTTTCGTT
1401  GTCTTAATTA TACTGCTAAT TTTTCTTTTT GTAAAATATG CAAGGTTTTA
1451  AAGAGAAACA TCAAGAACTA AAAAAGGCTY TATGTCAAAT TGGACTGATG
1501  CGTTCAATAT CCGAAGTTAA GCAACTAAAC ATTGCTTAAC TTCCTTTTTA
1551  CTTTTTGGAG CGTAAAGTTT TGAACATAAT AATATTCGAT TGCGCAAATG
1601  ATTGTAACTT CCATAACCAA AAGATGTACG TTTAATTAAT TTTATTTTGT
1651  TATTTATACC TTCTAAAGGA CCATTTGATA AATTGTAATA ATCAATGGTT
1701  ACACTATTAA AAGTGTCACA AATTCTTATG AATCTGGCAT AAACTTTGAA
1751  TTAACTAAAT AAGTAAGAAA ACCTCGGCAC TTTATCATTT TAATAGTGTC
1801  GAGATTTTTA TAGATACTAC AAATATTTAT AACATAGTTA AACTCATCTA
1851  ATGACTTATA TTTTTGTTTC ATCACAATAT GAACAATTAT TTATTGGACG
1901  TATTTTGCTC TTTTTTTATT TCAGAAACTG ACTTAGGATT TTTATTAAAT
1951  TTTCTACCCA ATTCATCTGT ATAAGAAATA TCGGTATCAA ATTTAGAATC
2001  ATCAACAGAT CGACCTGCAG GCATGC
```

Mutant: NT482 phenotype: temperature sensitivity

Figure 89:
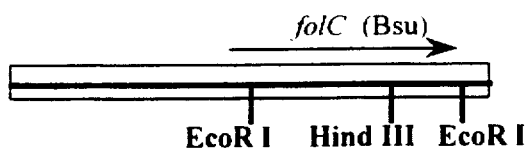

Sequence map: : Mutant NT482 is complemented by plasmid pMP560, which carries a 2.7 kb insert of wild-type *S. aureus* genomic DNA. A partial restriction map is depicted in FIG. 89. Database searches at the nucleic acid and (putative) polypeptide levels against currently available databases reveal strong similarity at the peptide-level to the folC gene product, encoding folyl polyglutamate synthase (FGPS), from *B. subtilis* (Genbank Accession No. L04520; published in Mohan, S. et al., *J. Bacteriol.* 171 (1989) 6043–6051.)

DNA sequence data: The following DNA sequence data represents the sequence generated by primer walking through clone pMP560, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP560
pMP560 Length: 2736 nt
   1 TGCCTGCAGG TCGATCTTCT ATGTAAATAA TCAAATGACG TTTCTTCTAT  SEQ ID NO. 104

51 AGATATAAAT TGATATASAA AACTAAAAAT ACAACTGCAA CTATAAGATA

101 ACAATACTAC CAAATGACAA CCTCCTTATG TAAATTATAG TTAGTTATTA

151 CCAAAATGTA AATATACACT ATTTTTCAAG AATTGAACCG CTTTTTCATT

201 TAAATTTTTC AATATTGCTA AGCATAATTG ATGGATACTT TAACAACCCA

251 TTACTGCTCG GCAAAATTAA TAATGGCAAG AAATTGAACC TTATAAACAC

301 ATACGATTTA GAGCATAAAA AATAACCATG AAGCTCTACC TATTGATTAA

351 ATARATTCTT CATGGCTATT TTAGTTTTAG TTTTATAATG &TTCAAAGTC

401 TAATTTTGAT TTAACTTCAC TTATGAAATA CAGACTACCG GTAATTACTA

451 ATGTATCACC TTGATAATTT TTTATAAATT CAACGTAGTC ATCTACTAAT

501 TGTATTTCAT CATTTTCAAT ACTACCTACA ATTTCTTCTT TGCGTAACGC

551 TTTCGGAAAA TCAAATTCAG TTGCATAAAA CGTATGCGCA ATTAAACTTA

601 AATGTTTGAC CATCTCGTTA ATCGGTTTTC CGTTTATTGC TGASAACAAA

651 ATATCTACTT TTTCTTTATC ATGGTACTGT TTAATTGTAT CAATTAGAGC

701 ATCTATACTC TCTGAATTAT GYGCGCCATC CAAAATGATT AAAGGYTTGT

751 CATGCACCTG CTCAATACGT CCAGTCCAAC GAACTGATTC AATACCGTCT

801 ATCATCTTAT TGAAATCTAA TTCAATTAAT CCTTGTTCAT TTAATTCAAT

851 AAGAGCTGTT ATGGCTAATG CAGCAAWTTT GTTTCTGATG TTTCACCTAA

901 CATGCTTAAA ATGATTGTTT CTAATTCATA ATCTTTATAA CGGTAAGTTA

951 AATTCATCAT TTTGCGATAC AACAACAATT TCTCTATCTA ATTCAATGGC

1001 TTTGCATGTT GTTCAATTGC GCGTTCACGA ACATATTTTA ATGCATCTTC

1051 ATTTTTTACA GCATATATCA CTGGAACKTT AGGSTTTATA ATCGCGCCYT

1101 TATCCCTAGC AATATCTAGA TAAGTACCAC CTAAAATATC TGTATGGTCT

1151 AGACCGATAC TAGTTAAGAT TGATAAAACC GGTGTAAAGA CATTTGTCGA

1201 ATCGTTCTTT ATACCCAATC CAGCCTCAAC AATGACAAAA TCAACAGGAT

1251 GTATTTCACC AAAATATAAA AACATCATCG CTGTGATTAT TTCGAATTCA

1301 GTTGCAAMMM CTAAATCTGT TTCAMSTTCC ATCATTTCAA TTAACTGGTT

1351 TAATACGTGA TACTAATTCT AACAATAGCG TCATTTGATA TTGGCAACAC

1401 CATTTAGRAT AATTCGTTCA TTAAATGTTT CAATAAACGG CGACGTAAAT

1451 GTACCTACTT CATAACCATT TTCAACTAAA GCTGTTCTAA GGTAAGCAAC

1501 TGTAGAGCCT TTACCATTTG TGCCACSKAC ATGAATACCC TTAATGWTAT

1551 TTTGAGGATT ATTAAATTGT GCTAGCATCC ATTCCATACG TTTAACACCT

1601 GGTTTGATGC CAAATTTAGT TCTTTCGTGT ATCCAATACA AGCTCTCTAG

1651 GTAATTCATT GTTACTAACT CCTATGCTTT TAATTGTTCA ATTCTTGCCT

1701 TCACACCATC ATATTTTTCT TGATAATCTT GTTTTTTACG TTTTTCTTCA

1751 TTTATAACCT TTTCAGGTGC TTTACTTACA AAGTTTTCAT TAGAGAGCTT

1801 TTTATCTACT CTATCTAATT CGCTTTGAAG TTTAGCTAAT TCTTTTTCCA

1851 AACGGCTGAT TTCCTTATCC ATATCAATTA GCCCTTCTTA ATGGTAATAC

1901 CCACTTTACC TGCAATTACA ACTGATGTCA TTGCTTTCTC AGGAATTTCC
```

-continued

```
1951  AACGTCAGTG CTAATATTTA AGGTACTAGG ATTACAGAAT TTGATTAAAT
2001  AATCTTTGTT TTGTGATAAA GTTGTTTCAA TTTCTTTATC TTTAGCTTGA
2051  ATTAAAATAG GTATTTCTTT AGACAATGGC GTATTTACTT CTACACGTGA
2101  TTGTCTTACA GATTAATGA TTTCAACAAG TGGTKGCATT GTTTGTTAAC
2151  TTTCTTCAAA AATCAATGAT TCACGCACTT CTGGCCATGA AGCTTTAACA
2201  ATTGTGTCAC CTTCATGTGG TAAACTTTGC CATATTTTCT CTGTTACAAA
2251  TGGCATGAAT GGATGTAGCA TTCTCATAAT ATTGTCTAAA GTATAACTCA
2301  ATACTGAACG TGTAACTTGT TTTTGTTCTT CATCATTACT ATTCATTGGA
2351  ATTTTACTCA TTTCAATGTA CCAATCACAG AAATCATCCC AAATGAAATT
2401  ATATAATGCA CGTCCAACTT CGCCGAATTC ATATTTGTCA CTTAAATCAG
2451  TAACTGTTGC AATCGTTTCA TTTAAACGTG TTAGAATCCA TTTATCTGCT
2501  AATGATAAGT TACCACTTAA ATCGATATCT TCAACTTTAA AGTCTTCACC
2551  GATATTCATT AAACTGAAAC GTGCCCCATT CCAGATTTTA TTGATAAAGT
2601  TCCACACTGA CTCAACTTTT TCAGTTGAGT ATCTTAAATC ATGTCCTGGA
2651  GATGAACCTG TTGCTAAGAA GTAACGCAAG CTATCAGCAC CGTATTCGTC
2701  AATAACATCC ATTGGATCGA CCTGCAGGCA TGCAAG
```

Figure 90:
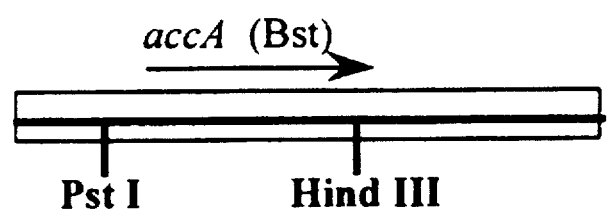

Mutant: NT486
phenotype: temperature sensitivity
Sequence map: : Mutant NT486 is complemented by plasmid pMP567, which carries a 2.3 kb insert of wild-type *S. aureus* genomic DNA. A partial restriction map is depicted in FIG. 90; no apparent restriction sites for EcoR I, HinD III, BamH I or Pst I are present. Database searches at the nucleic acid and (putative) polypeptide levels against currently available databases reveal strong peptide-level similarities to the accA gene product, encoding the alpha subunit of acetyl-CoA-carboxylase carboxyl transferase (EC 6.4.1.2), from *B. stearothermophilus* (Genbank Accession No. D13095); this gene product forms part of an enzyme complex responsible for fatty acid biosynthesis and is thought to be essential.

DNA sequence data: The following DNA sequence data represents the sequence generated by primer walking through clone pMP567, starting with standard M13 forward and M13 reverse sequencing primers and completing the sequence contig via primer walking strategies. The sequence below can be used to design PCR primers for the purpose of amplification from genomic DNA with subsequent DNA sequencing.

```
clone pMP567
pMP567 Length: 2255 nt
    1  CNCGNNAGCG ANGTNGCCGA GGATCCTCTA GAGTCNATCG GTTATCGGTG   SEQ ID NO. 105
   51  AAAAGATATG TCGCATCATT GATTACTGCA CTGAGAACCG TTTACCATTT
  101  ATTCTTTTCT CTGCAAGTGG TGGTGCACGT ATGCAAGAAG TATTATTTC
  151  CTTGATGCAA ATGGGTAAAA CCAGTGTATC TTTAAAACGT CATTCTGACG
  201  CTGGACTATT ATATATATCA TATTTAACAC ATCCAACTAC TGGTGGTGTA
  251  TCTGCAAGTT TTGCATCAGT TGGTGATATA AATTTAAGTG AGCCAAAAGC
  301  GTTGATAGGT TTTGCAGGTC GTCGAGTTAT TGAACAGACA ATAAACGAAA
  351  AATTGCCAGA TGATTTCCAA ACTGCAGAAT TTTTATTAGA GCATGGACAA
  401  TTGGATAAAG TTGTACATCG TAATGATATG CGTCAAACAT TGTCTGAAAT
  451  TCTAAAAATC CATCAAGAGG TGACTAAATA ATGTTAGATT TTGAAAAACC
  501  ACTTTTTGAA ATTCGAAATA AAATTGAATC TTTAAAAGAA TCTCAAGATA
  551  AAAATGATGT GGATTTACCA AAGAAGAATT TGACATGCCT TGAARCGTCM
  601  TTGGRACGAG AAACTAAAAA AATATATACA AATCTAAAAC CATGGGATCG
  651  TGTGCAAATT GCGCGTTTGC AAGAAAGACC TACGACCCTA GATTATATTC
```

-continued

```
 701   CATATATCTT TGATTCGTTT ATGGAACTAC ATGGTGATCG TAATTTTAGA
 751   GATGATCCAG CAATGATTGG TGGTATTGGC TTTTTAAATG GTCGTGCTGT
 801   TACAGTYRTK GGACAACAAC GTGGAAAAGA TACWAAAGAT RATATTTATC
 851   GAAATTTTKG GTATGGCGCA TCCAGAAGGT TATCGAAAAG CATTACGTTT
 901   AATGAAACAA GCTGAAAAAT TCAATCGTCC TATCTTTACA TTTATAGATA
 951   CAAAAGGTGC ATATCCTGGT AAAGCTGCTG AAGAACGTGG ACAAAGTGAA
1001   TCTATCGCAA CAAATTTGAT TGAGATGGCT TCATTAAAAG TACCAGTTAT
1051   TGCGATTGTC ATTGKYGAAG GTGGCAGTGG AGGTGCTCTA GGTATTGGTA
1101   TTGCCAATAA AGYATTGATG TTAGAGAATA GTACTTACTC TGWTATATCT
1151   CCTGAAGGTG CAGCGGCATT ATTATGGAAA GACAGTAATT TGGCTAAAAT
1201   YGCAGCTGAA ACAATGAAWA TTACTGCCCA TGATATTAAG CAATTAGGTA
1251   TTATAGATGA TGYCATTTCT GAACCACTTG GCGGTGCACA TAAAGATATT
1301   GAACAGCAAG CTTTAGCTAT TAAATCAGCG TTTGTTGCAC AGTTAGATTC
1351   ACTTGAGTCA TTATCAACGT GATGAAATTG CTAATGATCG CTTTGAAAAA
1401   TTCAGAAATA TCGGTTCTTA TATAGAATAA TCAACTTGAG CATTTTTATG
1451   TTAAATCGAT ACTGGGTTTT ACCATAAATT GAAGTACATT AAAACAATAA
1501   TTTAATATTT AGATACTGAA TTTTTAACTA AGATTAGTAG TCAAAATTGT
1551   GGCTACTAAT CTTTTTTTAA TTAAGTTAAA ATAAAATTCA ATATTTAAAA
1601   CGTTTACATC AATTCAATAC ATTAGTTTTG ATGGAATGAC ATATCAATTT
1651   GTGGTAATTT AGAGTTAAAG ATAAATCAGT TATAGAAAGG TATGTCGTCA
1701   TGAAGAAAAT TGCAGTTTTA ACTAGTGGTG GAGATTCACC TGGAATGAAT
1751   GCTGCCGTAA GAGCAGTTGT TCGTACAGCA ATTTACAATG AAATTGAAGT
1801   TTATGGTGTG TATCATGGTT ACCAAGGATT GTTAAATGAT GATATTCATA
1851   AACTTGAATT AGGATCRAGT TGGGGATACG ATTCAGCGTG GAGGTACATT
1901   CTTGTATTCA GCAAGATGTC CAGAGTTTAA GGAGCAAGAA GTACGTAAAG
1951   TTGCAATCGA AAACTTACGT AAAAGAGGGA TTGAGGGCCT TGTAGTTATT
2001   GGTGGTGACG GTAGTTATCG CGGTGCACAA CGCATCAGTG AGGAATGTAA
2051   AGAAATTCAA ACTATCGGTA TTCCTGGTAC GATTGACAAT GATATCAATG
2101   GTACTGATTT TACAATTGGA TTTGACACAG CATTAAATAC GATTATTGGC
2151   TTAGTCGACA AAATTAGAGA TACTGCGTCA AGTCACGCAC GAACATTTAT
2201   CATTGAAGCA ATGGGCCGTG ATTGTGGAGT CATCTGGAGT CGACCTGCTA
2251   GTCTT
```

II. Homologous Genes

As described above, the use of genes from other pathogenic bacterial strains and species which are homologous to the identified genes from *Staphylococcus aureus* is also provided. Such homologous genes not only have a high level of sequence similarity with the particular *S. aureus* genes, but also are functional equivalents. This means that the gene product has essentially the same biological activity. Therefore, the homologous genes are identifiable, for example, based on a combination of hybridization of all or a portion of one gene to its homologous counterpart, and the ability of the homologous gene to complement the growth conditional mutant of *S. aureus* under non-permissive conditions. The ability of the homologous gene to hybridize with sequences from the *S. aureus* gene provides that homologous gene using generally accepted and used cloning techniques. The ability of the homologous gene to complement a defective *S. aureus* gene demonstrates that the genes are essentially equivalent genes found in different bacteria.

Specific examples of methods for identifying homologous genes are described in Van Dijl et al., U.S. Pat. No. 5,246,838, issued Sep. 21, 1993. In addition to the direct hybridization methods for identifying and isolating homologous genes mentioned above, Van Dijl et al. describe the isolation of homologous genes by isolating clones of a host bacterial strain which contain random DNA fragments from a donor microorganism. In those clones a specific host gene has been inactivated (such as by linkage with a regulatable promoter), and inserted homologous genes are identified by the complementation of the inactivated gene function. Homologous genes identified in this way can then be sequenced.

If the function of the product of a specific host gene is known, homologous gene products can often be isolated (by assaying for the appropriate activity) and at least partially sequenced (e.g., N-terminal sequencing). The amino acid sequence so obtained can then be used to deduce the degenerate DNA base sequence, which can be used to synthesize a probe(s) for the homologous gene. A DNA library from another microorganism is then probed to identify a clone(s) containing a homologous gene, and the clone insert sequenced.

These and other methods for identifying homologous genes are well-known to those skilled in the art. Therefore, other persons can readily obtain such genes which are homologous to the genes corresponding to SEQ ID NO. 1–105.

III. Evaluation of Gene as Therapeutic Target

A. General Considerations

While the identification of a particular bacterial gene as an essential gene for growth in a rich medium characterizes that gene as an antibacterial target, it is useful to characterize the gene further in order to prioritize the targets. This process is useful since it allows further work to be focused on those targets with the greatest therapeutic potential. Thus, target genes are prioritized according to which are more likely to allow identification of antibacterial agents which are:

1. Highly inhibitory to the target in relevant pathogenic species;
2. Cause rapid loss of bacterial viability;
3. Not have frequently arising resistance mechanisms;
4. Have high selectivity for the bacterial target and little, or preferably no, effect on the related mammalian targets;
5. Have low non-specific toxicity to mammals; and
6. Have appropriate pharmacodynamic and physical properties for use as a drug.

Consequently, target genes are prioritized using a variety of methods, such as those described below.

B. Methods for Recognizing Good Targets

Essential genes can be characterized as either bactericidal or bacteriostatic. Earlier work with Salmonella mutants established that the bactericidal/bacteriostatic distinction was a characteristic of inhibition of the specific gene, rather than of a mutant allele, and could be characterized in vitro. (Schmid et al., 1989, *Genetics* 123:625–633. ) Therefore, preferred targets (high priority) are those which are highly bactericidal when inhibited, causing cell death. A subset of the bactericidal essential genes can be identified as strongly bactericidal, resulting in rapid cell death when inhibited.

In *S. typhimurium*, inhibition of strongly bactericidal genes was shown to result in one of the following effects:

1. Cell lysis (such genes generally involved in cell wall biosynthesis);
2. Inhibition of protein synthesis;
3. DNA degradation; or
4. Entry into non-recoverable state involving cell cycle related genes.

In vivo switch

In addition to the prioritization of gene targets based on the observed in vitro phenotypes, further evaluation of a specific gene as a potential therapeutic target is performed based on the effects observed with loss of that gene function in vivo. One approach is the use of null mutants in which the mutant gene product is inactive at 37° C. In the case of essential genes for which temperature sensitive mutants were previously isolated, those mutant strains can be used in this evaluation if the gene product is essentially inactive at 37° C. If such a temperature sensitive mutant has not previously been isolated but a complementing clone of some growth conditional mutant is available, then the required null mutants can generally be isolated through the use of localized mutagenesis techniques (Hong and Ames, 1971, *Proc. Natl. Acad. Sci. USA* 68:3158–3162). The evaluation then involves the comparison of the in vivo effects of the normal strain and the mutant strain.

The comparison involves determinations of the relative growth in vivo, relative bactericidal phenotype in vivo and differences in response in various infection models.

In addition to gene target evaluations using null mutant experiments, related evaluations can be performed using "in vivo switch" methods. Such methods allow control of the expression of a gene in vivo, and so provide information on the effects of inhibiting the specific gene at various time points during the course of an infection in a model infection system. In effect, an in vivo switch provides a mimic of the administration of an inhibitor of a gene, even if such an inhibitor has not yet been identified.

Such in vivo switch methods can be carried out by using recombinant strains of a pathogenic bacterium, which carry a test gene transcriptionally linked with an artificially controllable promoter. One technique for doing this is to use the natural promoter for the test gene, and insert an operator site in a position so that transcription will be blocked if a repressor molecule is bound to the operator. Expression of the repressor molecule is then placed under artificial control by linking the gene for the repressor with a promoter which can be controlled by the addition of a small molecule. For example, a β-lactamase receptor/repressor/promoter system can be used to control expression of a lac repressor, which, in turn, will bind to a lac operator site inserted in the test gene. These DNA constructs are then inserted into bacteria in which the endogenous copy of the test gene has been inactivated, and those bacteria are used in various infection models. Therefore, for this system, the test gene will be expressed prior to administration of a β-lactam. However, when a β-lactam with little or no intrinsic antibacterial activity (e.g., CBAP) is administered to an animal infected with the recombinant bacteria, the β-lactam induces production of lac repressor. The lac repressor molecule then binds to the lac operator, stopping (turning off) expression of the test gene.

The method can be extended by administering the β-lactam (or other appropriate controller molecule) at different times during the course of an infection, and/or according to different schedules of multiple dosing. Also, many different designs of in vivo switch may be used to provide control over the test gene. In general, however, such a method of target evaluation provides information such as:

1. a measure of the "cidalness" of the target gene following inhibition of that gene;
2. a benchmark against which to measure chemical inhibitors as they are identified, since the in vivo switch can mimic complete inhibition of the gene;
3. an estimate of the efficacy of inhibitor use at different time points in an infection process; and
4. an estimate of the efficacy of inhibitor use in various types of infections, in various in vivo environments.

Information of this nature is again useful for focusing on the gene targets which are likely to be the best therapeutic targets.

C. In vivo Evaluation of Microbial Virulence and Pathogenicity

Using gene target evaluation methods such as the null mutant and in vivo switch methods described above, the identified target genes are evaluated in an infection model system. (References herein to the use of animals or mammals should be understood to refer to particular infection models. Other infection systems may be used, such as cell-based systems as surrogates for whole organism models, or systems to evaluate possible antimicrobial targets of pathogens of organisms other than animals (e.g., plants). The criteria for evaluation include the ability of the microbe to replicate, the ability to produce specific exoproducts involved in virulence of the organism, and the ability to cause symptoms of disease in the animals.

The infection models, e.g., animal infection models, are selected primarily on the basis of the ability of the model to mimic the natural pathogenic state of the pathogen in an organism to be treated and to distinguish the effects produced by activity or by loss of activity of a gene product (e.g., a switch in the expression state of the gene). Secondarily, the models are selected for efficiency, reproducibility, and cost containment. For mammal models, rodents, especially mice, rats, and rabbits, are generally the preferred species. Experimentalists have the greatest experience with these species. Manipulations are more convenient and the amount of materials which are required are relatively small due to the size of the rodents.

Each pathogenic microbe (e.g., bacterium) used in these methods will likely need to be examined using a variety of infection models in order to adequately understand the importance of the function of a particular target gene.

A number of animal models suitable for use with bacteria are described below. However, these models are only examples which are suitable for a variety of bacterial species; even for those bacterial species other models may be found to be superior, at least for some gene targets and possibly for all. In addition, modifications of these models, or perhaps completely different animal models are appropriate with certain bacteria.

Six animal models are currently used with bacteria to appreciate the effects of specific genes, and are briefly described below.

1. Mouse Soft Tissue Model

The mouse soft tissue infection model is a sensitive and effective method for measurement of bacterial proliferation. In these models (Vogelman et al., 1988, *J. Infect. Dis.* 157: 287–298) anesthetized mice are infected with the bacteria in the muscle of the hind thigh. The mice can be either chemically immune compromised (e.g., cytoxan treated at 125 mg/kg on days −4, −2, and 0) or immunocompetent. The dose of microbe necessary to cause an infection is variable and depends on the individual microbe, but commonly is on the order of $10^5$–$10^6$ colony forming units per injection for bacteria. A variety of mouse strains are useful in this model although Swiss Webster and DBA2 lines are most commonly used. Once infected the animals are conscious and show no overt ill effects of the infections for approximately 12 hours. After that time virulent strains cause swelling of the thigh muscle, and the animals can become bacteremic within approximately 24 hours.

This model most effectively measures proliferation of the microbe, and this proliferation is measured by sacrifice of the infected animal and counting colonies from homogenized thighs.

2. Diffusion Chamber Model

A second model useful for assessing the virulence of microbes is the diffusion chamber model (Malouin et al., 1990, *Infect. Immun.* 58: 1247–1253; Doy et al., 1980, *J. Infect. Dis.* 2: 39–51; Kelly et al., 1989, *Infect. Immun.* 57: 344–350. In this model rodents have a diffusion chamber surgically placed in the peritoneal cavity. The chamber consists of a polypropylene cylinder with semipermeable membranes covering the chamber ends. Diffusion of peritoneal fluid into and out of the chamber provides nutrients for the microbes. The progression of the "infection" can be followed by examining growth, the exoproduct production or RNA messages. The time experiments are done by sampling multiple chambers.

3. Endocarditis Model

For bacteria, an important animal model effective in assessing pathogenicity and virulence is the endocarditis model (J. Santoro and M. E. Levinson, 1978, *Infect. Immun.* 19: 915–918). A rat endocarditis model can be used to assess colonization, virulence and proliferation.

4. Osteomyelitis Model

A fourth model useful in the evaluation of pathogenesis is the osteomyelitis model (Spagnolo et al., 1993, *Infect. Immun.* 61: 5225–5230). Rabbits are used for these experiments. Anesthetized animals have a small segment of the tibia removed and microorganisms are microinjected into the wound. The excised bone segment is replaced and the progression of the disease is monitored. Clinical signs, particularly inflammation and swelling are monitored. Termination of the experiment allows histolic and pathologic examination of the infection site to complement the assessment procedure.

5. Murine Septic Arthritis Model

A fifth model relevant to the study of microbial pathogenesis is a murine septic arthritis model (Abdelnour et al., 1993, *Infect. Immun.* 61: 3879–3885). In this model mice are infected intravenously and pathogenic organisms are found to cause inflammation in distal limb joints. Monitoring of the inflammation and comparison of inflammation vs. inocula allows assessment of the virulence of related strains.

6. Bacterial Peritonitis Model

Finally, bacterial peritonitis offers rapid and predictive data on the virulence of strains (M. G. Bergeron, 1978, *Scand. J. Infect. Dis. Suppl.* 14: 189–206; S. D. Davis, 1975, *Antimicrob. Agents Chemother.* 8: 50–53). Peritonitis in rodents, preferably mice, can provide essential data on the importance of targets. The end point may be lethality or clinical signs can be monitored. Variation in infection dose in comparison to outcome allows evaluation of the virulence of individual strains.

A variety of other in vivo models are available and may be used when appropriate for specific pathogens or specific genes. For example, target organ recovery assays (Gordee et al., 1984, *J. Antibiotics* 37:1054–1065; Bannatyne et al., 1992, *Infect.* 20:168–170) may be useful for fungi and for bacterial pathogens which are not acutely virulent to animals. For additional information the book by Zak and Sande (EXPERIMENTAL MODELS IN ANTIMICROBIAL CHEMOTHERAPY, O. Zak and M. A. Sande (eds.), Academic Press, London (1986) is considered a standard.

It is also relevant to note that the species of animal used for an infection model, and the specific genetic make-up of that animal, may contribute to the effective evaluation of the effects of a particular gene. For example, immunoincompetent animals may, in some instances, be preferable to immuno-competent animals. For example, the action of a competent immune system may, to some degree, mask the effects of altering the level of activity of the test gene product as compared to a similar infection in an immuno-incompetent animal. In addition, many opportunistic infections, in fact, occur in immuno-compromised patients, so modeling an infection in a similar immunological environment is appropriate.

In addition to these in vivo test systems, a variety of ex vivo models for assessing bacterial virulence may be employed (Falkow et al., 1992, Ann. Rev. Cell Biol. 8:333–363). These include, but are not limited to, assays which measure bacterial attachment to, and invasion of, tissue culture cell monolayers. With specific regard to S. aureus, it is well documented that this organism adheres to and invades cultured endothelial cell monolayers (Ogawa et al., 1985, Infect. Immun. 50: 218–224; Hamill et al., 1986, Infect. and Imm. 54:833–836) and that the cytotoxicity of ingested S. aureus is sensitive to the expression of known virulence factors (Vann and Proctor, 1988, Micro. Patho. 4:443–453). Such ex vivo models may afford more rapid and cost effective measurements of the efficacy of the experiments, and may be employed as preliminary analyses prior to testing in one or more of the animal models described above.

IV. Screening Methods for Antibacterial Agents
A. Use of Growth Conditional Mutant Strains
1. Hypersensitivity and TS Mutant Phenoprints In addition to identifying new targets for drug discovery, the growth conditional mutants are useful for screening for inhibitors of the identified targets, even before the novel genes or biochemical targets are fully characterized. The methodology can be whole-cell based, is more sensitive than traditional screens searching for strict growth inhibitors, can be tuned to provide high target specificity, and can be structured so that more biological information on test compounds is available early for evaluation and relative prioritization of hits.

Certain of the screening methods are based on the hypersensitivity of growth conditional mutants. For example, conditionally lethal ts mutants having temperature sensitive essential gene functions are partially defective at a semi-permissive temperature. As the growth temperature is raised, the mutated gene causes a progressively crippled cellular function. It is the inherent phenotypic properties of such ts mutants that are exploited for inhibitor screening.

Each temperature sensitive mutant has secondary phenotypes arising from the genetic and physiological effects of the defective cellular component. The genetic defect causes a partially functional protein that is more readily inhibited by drugs than the wild type protein. This specific hypersensitivity can be exploited for screening purposes by establishing "genetic potentiation" screens. In such screens, compounds are sought that cause growth inhibition of a mutant strain, but not of wild type, or greater inhibition of the growth of a mutant. strain than of a wild type strain. Such compounds are often (or always) inhibitors of the wild type strain at higher concentrations.

Also, the primary genetic defect can cause far-reaching physiological changes in the mutant cells, even in semi-permissive conditions. Necessity for full function of biochemically related proteins upstream and downstream of the primary target may arise. Such effects cause hypersensitivity to agents that inhibit these related proteins, in addition to agents that inhibit the genetically defective cellular component. The effects of the physiological imbalance will occur through metabolic interrelationships that can be referred to as the "metabolic web". Thus, in some cases, the initial genetic potentiation screen has the ability to identify inhibitors of either the primary target, or biochemically related essential gene targets.

With sufficient phenotypic sensors, a metabolic fingerprint of specific target inhibition can be established. Therefore, the mutant strains are evaluated to identify a diverse repertoire of phenotypes to provide this phenotypic fingerprint, or "phenoprint". These evaluations include hypersensitivities to known toxic agents and inhibitors, carbon source utilization, and other markers designed to measure specific or general metabolic activities for establishing a mutant phenoprint that will aid in interpretation of inhibitor profiles.

2. Determination of Hypersusceptibility Profiles

As an illustration of the hypersusceptibility profiles for a group of bacterial ts mutant strains, the minimal inhibitory concentrations (MICs) of various drugs and toxic agents were determined for a set of Salmonella typhimurium temperature-sensitive essential gene mutants.

The MICs were measured by using a standard micro broth dilution technique following the recommendations of the National Committee for Clinical Laboratory Standards (1994). Bacteria were first grown in Mueller-Hinton broth at 30° C., diluted to $10^5$ cfu/ml and used to inoculate 96-microwell plates containing two-fold dilutions of antibiotics in Mueller-Hinton broth. Plates were incubated for 20 h at a semi-permissive temperature (35° C.) and the MIC was determined as the lowest dilution of antibiotic preventing visible growth.

A two-fold difference in the susceptibility level of the mutant strain compared to that of the parental strain is within the limits of the experimental variation and thus a $\geq$4-fold decrease in MIC was considered as a significant hypersusceptibility.

EXAMPLE 1

Hypersensitivity of S. aureus secA Mutants

The secA mutant strain NT65 was found to be more sensitive to compound MC-201,250. The MIC of this compound on NT65 is 0.62 μg/ml and that on the wild type strain is 50 μg/ml. The inhibitory effect of MC-201,250 on secA mutants increased as screening temperatures increased. Other secA mutants, which may represent different alleles of the gene, are also hypersensitive to this compound by varying degrees, examples are shown in Table 1 below.

TABLE 1

| Hypersensitivity of secA Alleles to MC201,250 | |
|---|---|
| Strain | MIC (μg/ml) |
| NT65 | 0.62 |
| NT328 | 1.25 |
| NT74 | 2.5 |
| NT142 | 5 |
| NT15 | 10 |
| NT67 | 10 |
| NT122 | 10 |
| NT112 | 20 |
| NT368 | 20 |
| NT413 | 20 |
| Wild Type (WT) | 50 |

Furthermore, introduction of the wild type secA allele into NT65 raised the MIC to the wild type level. These data suggest that the hypersensitivity results from the secA mutation in the mutants.

To Further demonstrate that the hypersensitivity to MC-201,250 is due to the secA mutation that causes the temperature sensitivity, heat-resistant revertants, both spontaneous and UV-induced, were isolated from NT65 and tested for their responses to the compound. In a parallel experiment, MC-201250-resistant revertants were also isolated from NT65 and tested for their growth at nonpermissive temperatures. The results showed that revertants able to grow at 43° C. were all resistant to MC-201250 at the wild type level (MIC=50 µg/ml) and vice versa. Revertants able to grow at 39° C. but not at 43° C. showed intermediate resistance to MC-201,250 (MIC=1.25–2.5 µg/ml and vice versa. The correlation between the heat-sensitivity and MC-201,250-sensitivity strongly suggests that the secA gene product may be the direct target for MC-201,250.

The benefits of using hypersensitive mutants for screening is apparent, as this inhibitor would have not been identified and its specificity on secA would have not been known if wild type cells rather than the mutants were used in whole cell screening at a compound concentration of 10 µg/ml or lower.

EXAMPLE 2

Hypersensitivity of *S. typhimurium* gyr Mutants

The specific hypersensitivity of temperature sensitive mutations in a known target to inhibitors of that target is shown in FIG. 1 with the susceptibility profile of three ts *S. typhimurium* mutant alleles of the gyrase subunit A (gyrA212, gyrA215 and gyrA216) grown at a semipermissive temperature (35° C.). The graph shows the fold-increases in susceptibility to various characterized antibacterial agents compared to that observed with the wild-type parent strain. The data demonstrate the highly specific hypersusceptibility of these mutants to agents acting on DNA gyrase. Susceptibility to other classes of drug or toxic agents is not significantly different from the parent strain (within 2-fold).

In addition, different mutant alleles show unique hypersensitivity profiles to gyrase inhibitors. Coumermycin inhibits the B-subunit of the gyrase, while norfloxacin, ciprofloxacin, and nalidixic acid inhibit the A-subunit. One mutant shows hypersusceptibility to coumermycin (gyrA216), one to coumermycin and norfloxacin (gyrA215), and another to norfloxacin and ciprofloxacin (gyrA212). Note that a mutation in the gyrase subunit A (gyrA215) can cause hypersensitivity to B-subunit inhibitors and could be used to identify such compounds in a screen. In addition, some gyrA mutant strains show no hypersensitivity to known inhibitors; potentially, these strains could be used to to identify novel classes of gyrase inhibitors. Overall these results show that a selection of mutated alleles may be useful to identify new classes of compounds that affect gyrase function including structural subunit-to-subunit interactions. Thus, use of the properties of the crippled gyrase mutants in a screen provides a great advantage over biochemical-based screens which assay a single specific function of the target protein in vitro.

EXAMPLE 3

Hypersensitivity Profiles of Salmonella ts Mutants

Demonstration of the generalized utility of hypersensitive screening with the conditional lethal mutants has been obtained (FIG. 2) by collecting hypersensitivity profiles from partly characterized Salmonella conditional ts mutants. The table shows the increased susceptibility of the mutant strains to various characterized antibacterial agents compared to the wild-type parent strain. A two-fold difference in the susceptibility level is within the limits of the experimental variation and thus a $\geq$4-fold difference is significant.

A variety of hypersusceptibility profiles is observed among the ts mutants. These profiles are distinct from one another, yet mutants with related defects share similar profiles. The parF mutants, which have mutations closely linked to the Salmonella topoisomerase IV gene, are hypersusceptible to gyrase subunit B inhibitors (black circle), although these mutants are also susceptible to drugs affecting DNA or protein metabolism. Similarly, specficly within the hypersusceptibility profiles of two out of four ts mutants (SE7583, SE7587, SE5119 and SE5045) having possible defects in the cell wall biosynthesis machinery are also observed (mutants dapA and murCEFG, black diamond). The latter mutants are also susceptible to other agents and share their hypersusceptibility profile with a mutant having a defect in the incorporation of radioactive thymidine (SE5091).

Figure 3:
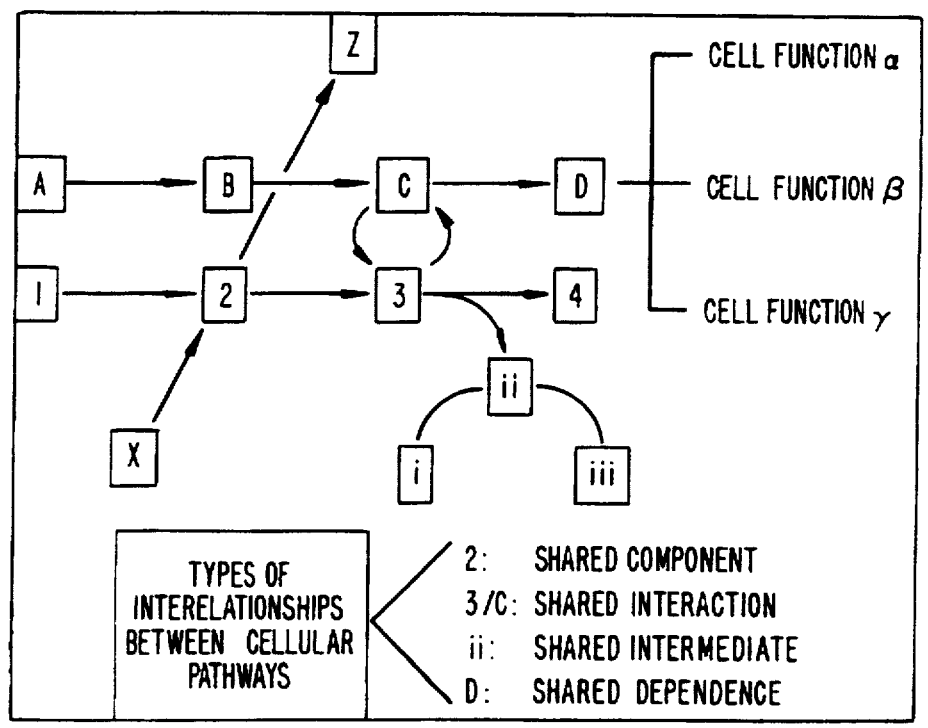
FIG. 3 illustrates a variety of types of interactions which exist between different essential genes, and which can create differential responses in screens using growth conditional mutants.

Thus, the hypersensitivity profiles actually represent recognizable interrelationships between cellular pathways, involving several types of interactions as illustrated in FIG. 3. The patterns created by these profiles become signatures for targets within the genetic/metabolic system being sensitized. This provides a powerful tool for characterizing targets, and ultimately for dereplication of screening hits. The hypersusceptibility profiles have been established for 120 Salmonella and 14 *Staphylococcus aureus* ts mutants with a selection of 37 known drugs or toxic agents The growth conditional mutants are also used in gene sensor methodology, e.g., using carbon utilization profiles. Ts mutants fail to metabolize different carbon sources in semi-permissive growth conditions. The carbon sources not utilized by a specific mutant or group of mutants provide additional phenotypes associated with the crippled essential function. Moreover, some of these carbon source markers were also not used by the wild type strain exposed to sub-MIC concentrations of known drugs affecting the same specific cellular targets or pathways. For example, a sublethal concentration of cefamandole prevented the Salmonella wild type parent strain from metabolizing the same carbon source that was not used by either the dapA or the murCEFG mutant.

In combination, interrelationships within and between essential cellular pathways are manifested in hypersensitivity and biosensor profiles that together are employed for highly discriminatory recognition of targets and inhibitors. This information provides recognition of the target or pathway of compound action.

B. Screening Strategy and Prototypes

1. Strain Validation and Screening Conditions

Hypersensitive strains (not growth conditional) have been successfully used in the past for discovery of new drugs targeting specific cellular pathways. (Kamogashira and Takegata, 1988, *J. Antibiotics* 41:803–806; Mumata et al., 1986, *J. Antibiotics* 39:994–1000.) The specific hypersensitivities displayed by ts-conditional mutants indicates that use of these mutants in whole cell screening provides a rapid method to develop target-specific screens for the identification of novel compounds. However, it is beneficial to eliminate mutants that will not be useful in semi-permissive growth conditions. Such mutant alleles may have nearly wild type function at the screening assay temperature. The simplest method for validating the use of ts mutants is to select those which show a reduced growth race at the semi-restrictive growth temperature. A reduced growth rate indicates that the essential gene function is pzartially defective. More specific methods of characterizing the partial defect of a mutant strain are available by biochemical or physiological assays.

2. Multi-Channel Screening Approach

The phenoprint results above, demonstrate that ts mutants show specific hypersusceptibility profiles in semi-oermissive growth conditions. As a screening tool, the mutant inhibition profile characterizes the effects of test compounds on specific bacterial pathways. Because the mutants are more sensitive than wild type strains, compounds with weak inhibition activity can be identified.

Figure 4:
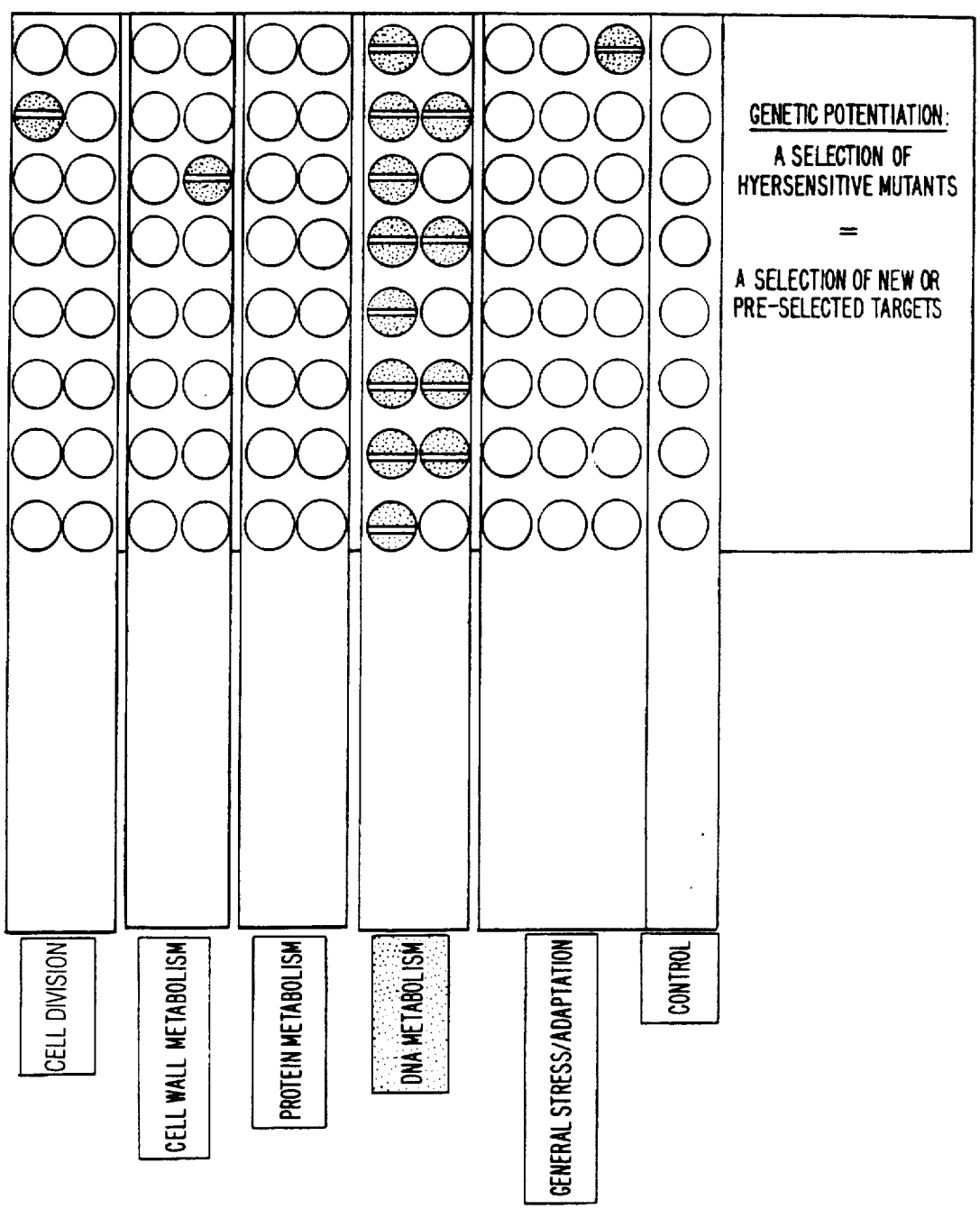
FIG. 4 illustrates a possible arrangement of a multichannel screen plate using conditional. growth mutants with mutations affecting 5 different cellular processes plus controls.

An example of a multi-channel screen for inhibitors of essential genes is shown in FIG. 4. In this screen design, one plate serves to evaluate one compound. Each well provides a separate whole-mutant cell assay (i.e., there are many targets per screening plate). The assays are genetic potentiation in nature, that is, ts-hypersensitive mutants reveal compounds that are growth inhibitors at concentrations that do not inhibit the growth of the wildtype strain. The profile of mutant inhibition provides insight into the compound's target of inhibition. The ts mutants are grouped by their hypersensitivity profiles to known drugs or by their related defective genes. The figure illustrates the hypothetical growth inhibition results (indicated by "-") that would be obtained with a new antibacterial agent targeting DNA/RNA metabolism.

Different multi-channel screen designs can it soecific needs or purposes. The choice of a broadly-designed screen (such as in FIG. 4), or one focused on specific cellular pathways, or even specific targets can be made by the appropriate choice of mutants. More specific screen plates would use mutants of a specific gene target like DNA gyrase, or mutants in a specific pathway, such as the cell division pathway.

Figure 5:
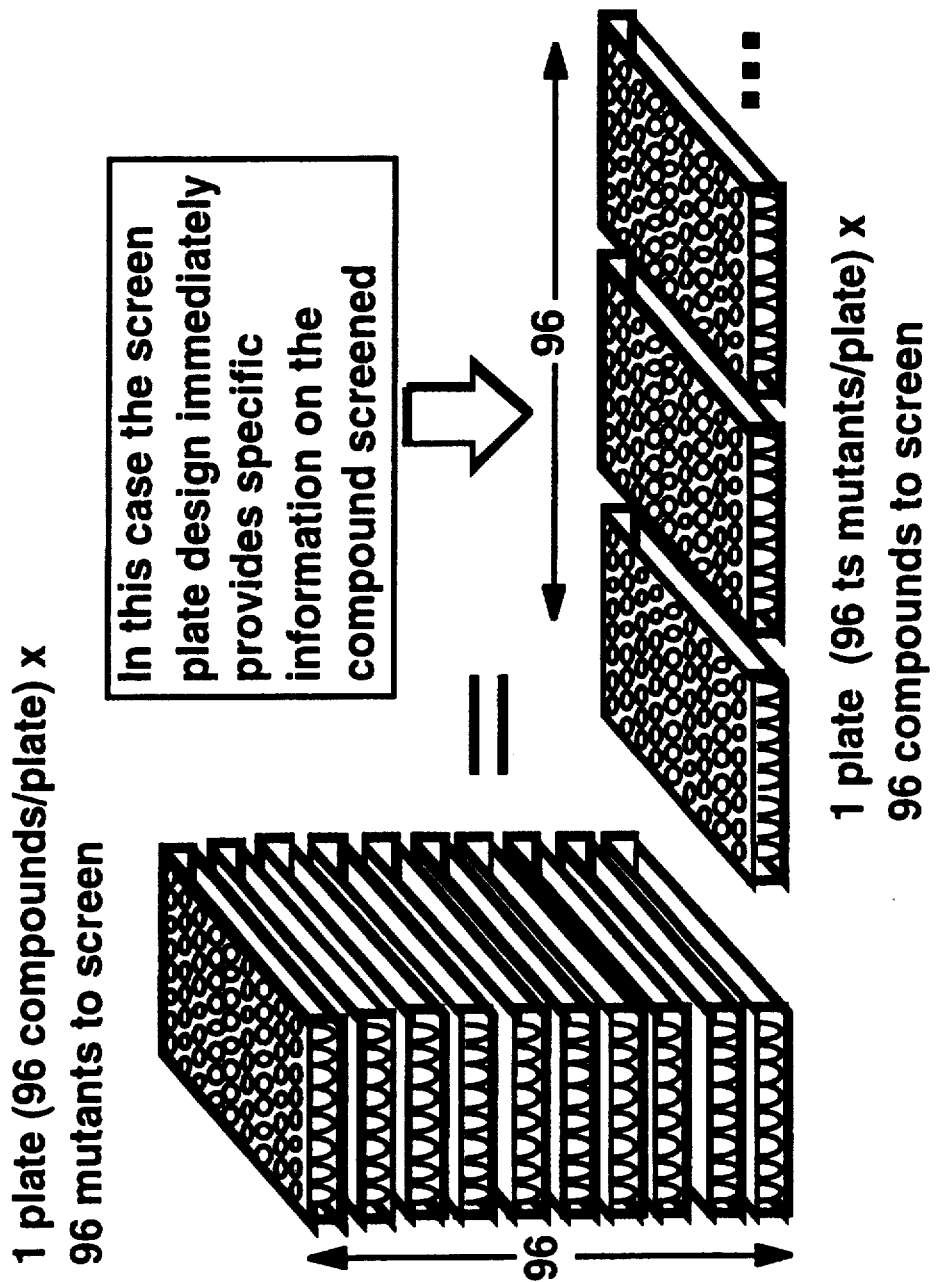
FIG. 5 illustrates 2 alternative multichannel screen designs in which either multiple compounds are screened using a single growth conditional mutant on each plate, or in which multiple growth conditional mutants are used on each plate to create an inhibition profile of a single compound.

The use of the 96-well multi-channel screen format allows up to 96 different assays to characterize a single compound. As shown in FIG. 5, this format provides an immediate characterization or profile of a single compound.

The more traditional format, using up to 96 different compounds per plate, and a single assay can also be readily accommodated by the genetic potentiation assays.

In comparing the two formats, the multi-channel screen format is generally compound-focused: prioritization of compounds run through the screen will occur, as decisions are made about which compounds to screen first. Each plate provides an immediate profile of a compound. The more traditional format is target-focused: prioritization of targets will occur, as decisions are made about the order of targets or genetic potentiation screens to implement.

In a preferred strategy for screening large compound libraries, a "sub-library" approach is taken. In this approach, the compound library is divided into a number of blocks or "sub-libraries". All of the selected ts mutants are screened against one block of the compounds. The screen is carried out in 96-well plates and each plate serves to test 80 compounds (one compound per well) on one mutant strain. After a block of compounds are screened, the mutant collection is moved on to test the next compound block.

The advantage of this stategy is that the effect of a compound on all the selected mutant strains can be obtained within a relatively short time. This provides compound-focused information for prioritization of compounds in follow-up studies. Since this strategy has only one mutant instead of many mutants on a plate, cross comtamination between different strains and the testing of different mutants at different temperatures (or with other changes in assay conditions) are no longer problems. Moreover, this strategy retains the same compound arrangement in all compound plates, thus saving time, effort and compounds as compared to screening one compound against many mutants on one plate, for compound focused analysis.

EAXMPLE 4

Prototype Screening Protocol

*S. aureus* bacterial cells from pre-prepared frozen stocks are diluted into Mueller-Hinton (MH) broth to an OD600 of about 0.01 and grown at 30° C. till OD600=0.5. Cells are diluted 1,000-fold into MH broth and 50 μl is added to each well of 96-well plates to which 40 μl of MH broth and 10 μl of test compound (varying concentraticns) are added. No-compound wells with or without cells are included as controls. The total volume in each well is 100 μl. The plates are incubated at an appropriate screening temperature for 20 hr and OD600 are read. The effect of each compound on a mutant is measured against the growth control and % of inhibition is calculated. Wild type cells are screened at the same conditions. The % of inhibition of a compound on a mutant and that on the wild type cell are compared, and compounds that show higher inhibition on the mutant than on the wild type are identified.

3. Screening Method Refinement

Certain testing parameters for the genetic potentiation screening methods can significantly affect the identification of growth inhibitors, and thus can be manipulated to optimize screening efficiency and/or reliabilty. Notable among these factors are variable thermosensitivity of different ts mutants, increasing hypersensititivy with increasing temperature, and "apparent" increase in hypersensitivity with increasing compound concentration.

a. Variable Thermosersitivity

Figure 6:
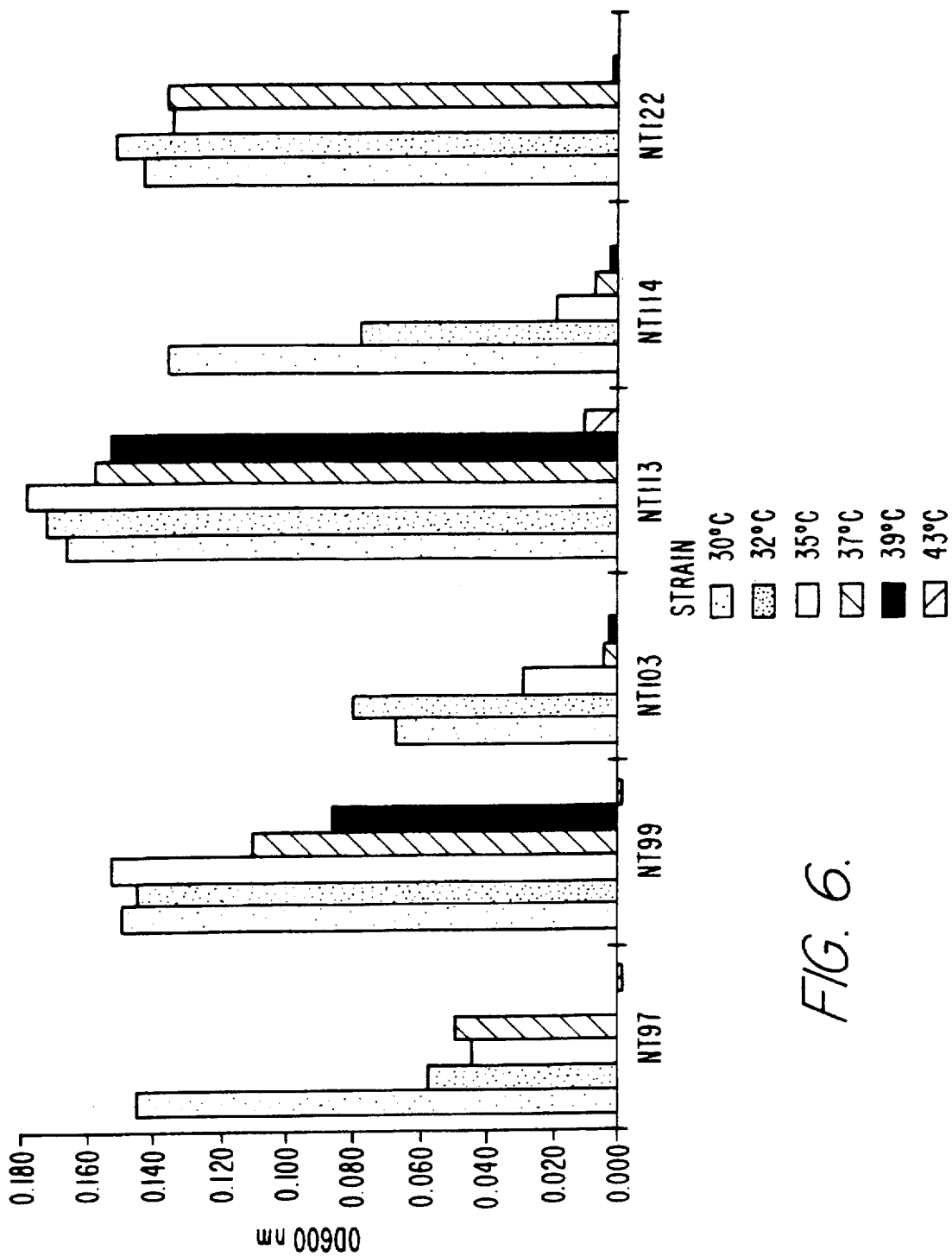
FIG. 6 is a bar graph showing the. different heat sensitivity proviles for 6 S. aureus heat sensitive mutant strains. The growth of each strain is shown at 6 different temperatures ranging from 300° C. to 43° C.
Figure 7:
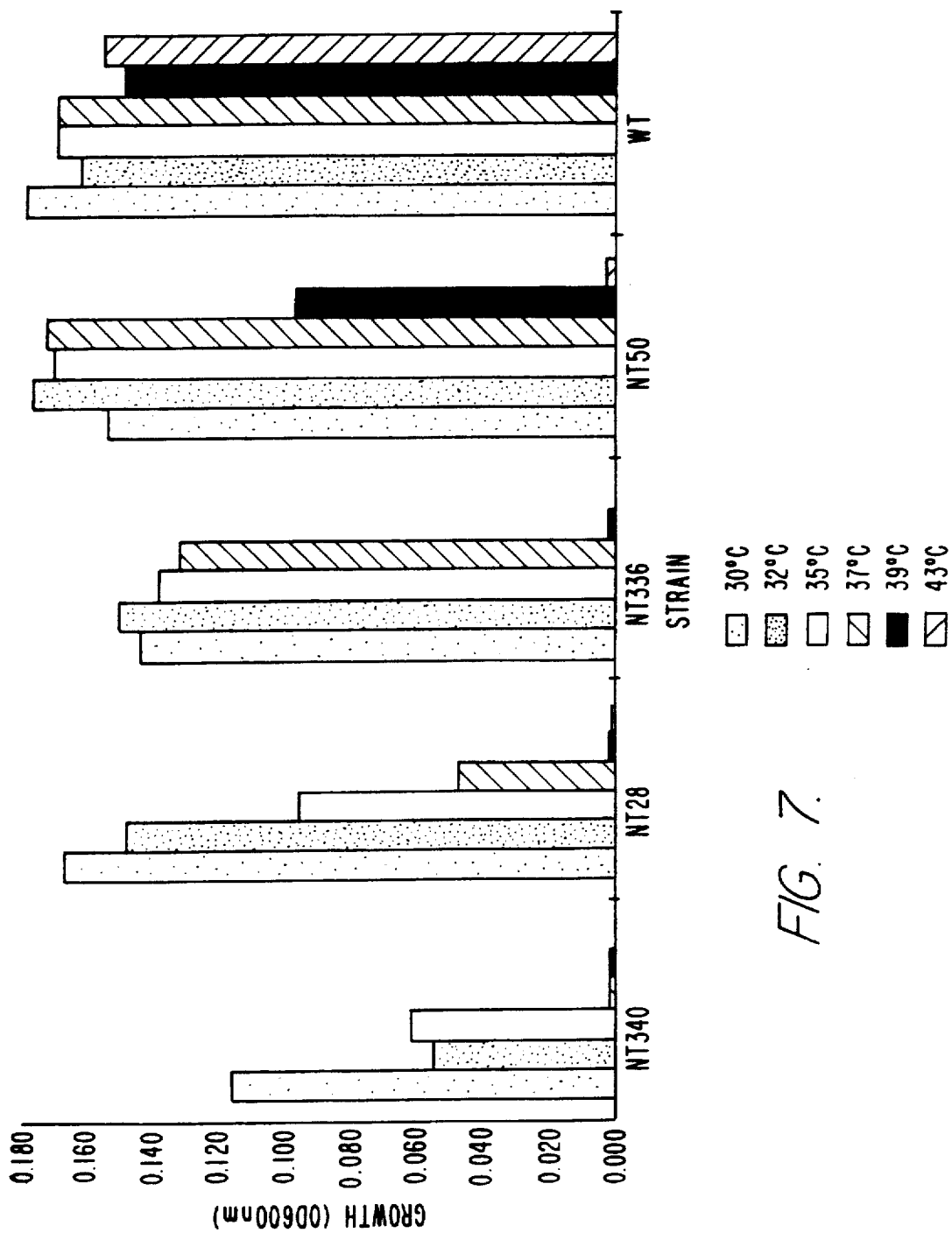
FIG. 7 is a bar graph showing the different heat sensitivity profiles for 4 different S. aureus polC heat sensitive mutants and a wild type strain. The growth of each strain is shown at 6 different temperatures ranging from 30° C. to 43° C.
Figure 8:
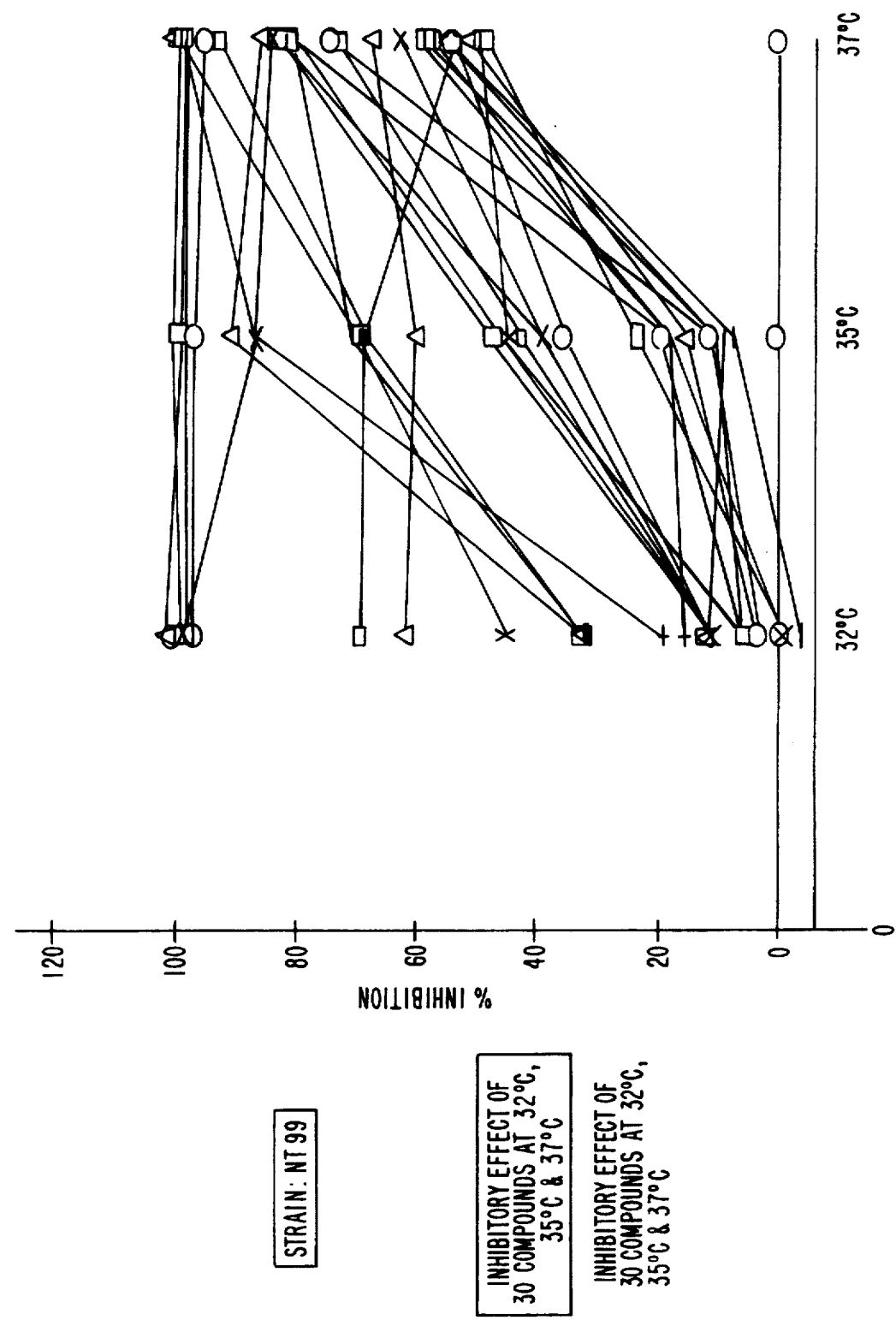
FIG. 8 is a graph showing the differences in hypersensitivity of one S. aureus heat sensitive strain (NT99) toward 30 inhibitory compounds at 3 different temperatures.

To use *S. aureus* ts mutants in genetic potentiation screening, the growth of these mutants at different temperatures were measured to determine screening temperatures for each of these mutants. The results showed that different ts mutants have quite different maximum growth temperatures (MGT). The MGTs of some mutants are as high as 39° C., while those of others are 37° C., 35° C., 32° C. or even 30° C. (FIG. 6). Furthermore, different mutants that have mutations in the same gene may have quite different MGTs, as illustrated in FIG. 7 for several polC mutants. Thus, different screening temperatures should be chosen for these mutants in order to accommodate the different growth preferences.

b. Raisina Screening Temperature Makes ts Mutants More Sensitive to Certain Compounds To demonstrate that the ts mutants are more sensitive to potential inhibitors at elevated temperature, the effect of different temperatures on the sensitivity of several ts mutants to a subset of compounds was examined. FIG. 8 shows the inhibitory effect of 30 compounds on mutant NT99 at 3 different temperatures, 32° C., 35° C., and 37° C. Most of these compounds showed increasing inhibitory effect as temperature increased from 32° to 35° C. then to 37° C. Consequently, more hits were identified at 37° C. (FIG. 9). In fact, all the hits identified at 32° C. and 35° C. were included in the 37° C. hits. On the other hand, little difference was observed when the compounds were tested on wild type cells at the same three different temperatures (data not shown).

The temperature effect as mentioned above can be used to control hit rates in the screening. Higher screening temperature can be used to produce more hits for mutants that have low hit rates. Similarly, if a mutant shows a very high hit rate, the number of hits can be reduced by using lower screening temperatures to facilitate hit prioritizaion.

c. Inceasing Compound Concentrations Affect Apparent Hypersensitivity

Figure 10:
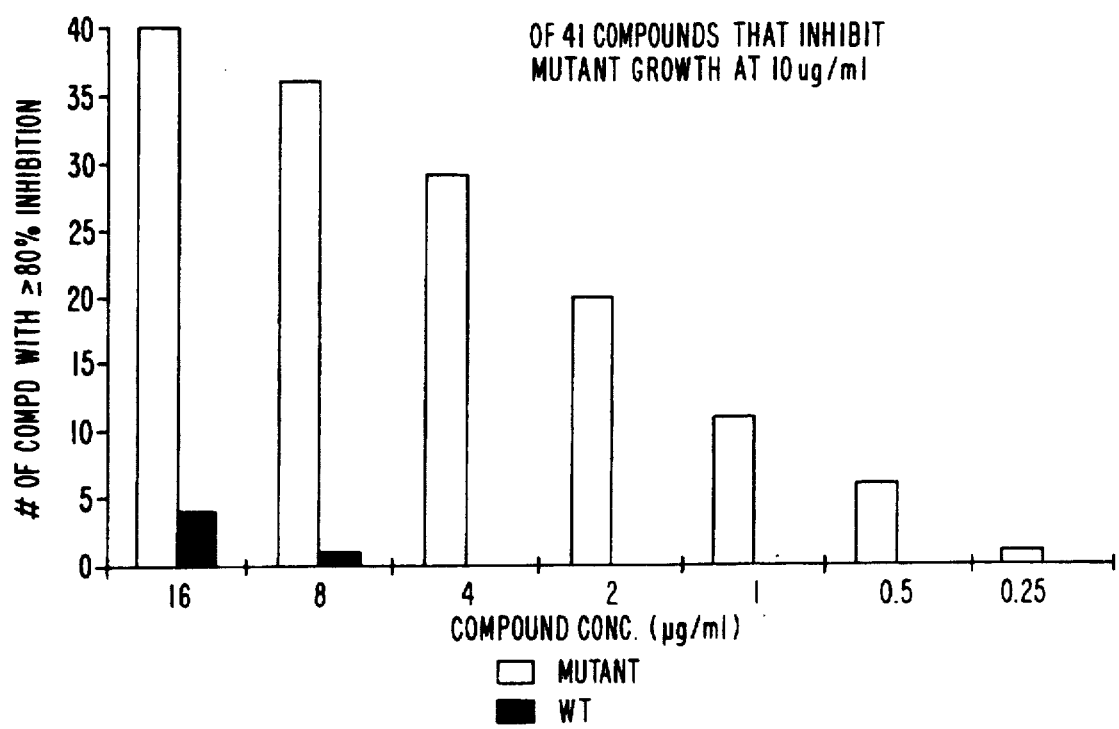
FIG. 10 is a bar diagram illustrating the effect of test compound concentration on the number of hits identified, showing that, in general, more compounds are identified as hits at higher concentrations.

The concentration of compounds used in the screening is an important parameter in determining the hit rates and the amount of follow-up studies. The concentration of 10 µg/ml has been used in piloting screening studies. To examine whether screening at lower concentrations can identify a similar set of hits, 41 compounds previously scored as hits were screened agaist their corresponding hypersensitive mutants at lower concentrations. Results in FIG. 10 showed that the number of compounds to which the target mutants were still hypersensitive ($\geq 80\%$ inhibition) decreased as the screening concentrations decreased. At 2 µg/ml, only 20 out of 41 hit compounds were able to be identified as hits that inhibit the mutants by $\geq 80\%$, and at 1 µg/ml only 11, or 27%, of the compounds still fell into this catagory. These data suggest that screening at concentrations <2 µg/ml may miss at least half of the hits that would be identified at 10 µg/ml. On the other hand, screening at concentrations higher than 10 µg/ml may result in large number of low quality hits and create too much work in hit confirmation and follow-up studies. At 10 µg/ml, a hit may appear as a growth nhibitor for both the mutant and wild type strains. This should not be a major problem since lower concentrations of the compound can be tested in the follow-up studies to differentiate its effect on the mutant and the wild type.

4. Evaluation of Uncharacterized Known Growth Inhibitors

In addition to testing known inhibitors of cellular pathways, uncharacterized growth inhibitors identified in other whole-cell screens were also evaluated using temperature sensitive mutants. These growth inhibitors had uncharacterized targets of action. These compounds were previously shown to cause some growth inhibition of the *S. aureus* strain 8325-4 at 5 mg/ml. The compounds were subsequently tested using a range of concentrations against a collection of *S. aureus* ts mutants (all derived from *S. aureus* 8325-4), to determine the MIC values, relative to wild type. FIG. 12 summarizes the data generated using 52 *S. aureus* ts mutants and 65 growth inhibitor compounds (47 compounds not shown). The table reports the fold-increase in susceptibility of the ts mutants compared with the wild-type parent strain; values within two-fold of wildtype have been left blank in the table for ease of identifying the significant hypersensitive values.

The effects of the 65 test compounds on the ts mutants were mostly selective: for most compounds, a limited number of mutants were hypersensitive. Approximately one-third of all compounds showed identical inhibition of mutant and wild type strains (i.e., no mutants were hypersensitive to these compounds). Two compounds in FIG. 12 showed strong inhibitory effects on about 50% of the mutants tested (compounds 00-2002 and 00-0167). Two additional compounds showed identical inhibition profiles (compounds 30-0014 and 20-0348, FIG. 12). A preliminary analysis of these profiles is provided below.

The genetic basis of the hypersensitivity has been substantiated by two criteria. First, one compound (10-0797) strongly inhibited two mutants (NT52 and NT69) that both affect the same gene. Secondly, complementation of the temperature sensitive phenotype of these mutants resulted in loss of hypersensitivity.

Figure 11:
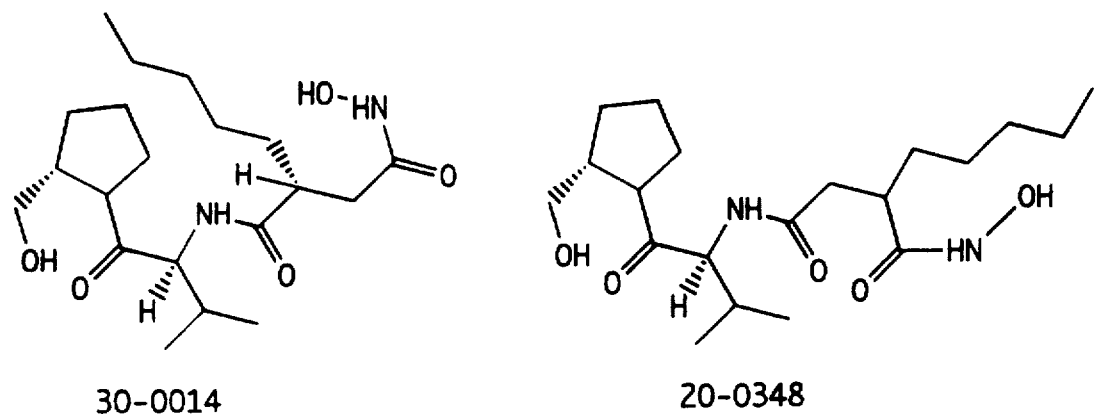
FIG. 11 presents the structures of two compounds which exhibited the same inhibition profiles for a set of temperature sensitive Staphylococcus aureus mutants, showing the structural similarity of the compounds.

Furthermore, the two compounds that had identical inhibition profiles (30-0014 and 20-0348) have very similar structures (FIG. 11). Thus, the hypersensitivity profile provides a pattern that allows recognition of compounds with similar targets of action, even when the target may be poorly defined. The strong similarity in the structures of these compounds makes their common target of action likely. Based on the mutants that were inhibited (secA , dnaG, and 3 uncharacterized mutants) the target of action of these compounds is not yet defined.

It is preferable to perform a screen of the uncharacterized inhibitors against a larger number of ts mutants. This screen employs preset compound concentrations and obtains the mutant inhibition profile for each compound. Computing the difference in the relative growth of parent and mutant strains in the presence of compounds provides a compound profile similar to that obtained by the MIC determinations of the first screen above.

A wide range of test compounds can be screened. Test compounds that are inhibitory for the wild type parent strain at the pre-selected concentration in the first screening run are retested at a lower concentration to generate an inhibition profile. Data analysis from the screens described above showed that a significant growth reduction of mutant strains compared to the parent strain in the presence of the test compounds is a reasonable indicator of selective compound activity.

Further, compounds for testing can include compounds that show no growth inhibition of the wild type strain. The hypersensitivity of the mutant strains provides the ability to identify compounds that target an essential cellular function, but which lack sufficient potency to inhibit the growth of the wild type strain. Such compounds are modified using medicinal chemistry to produce analogs with increased potency.

Figure 13:
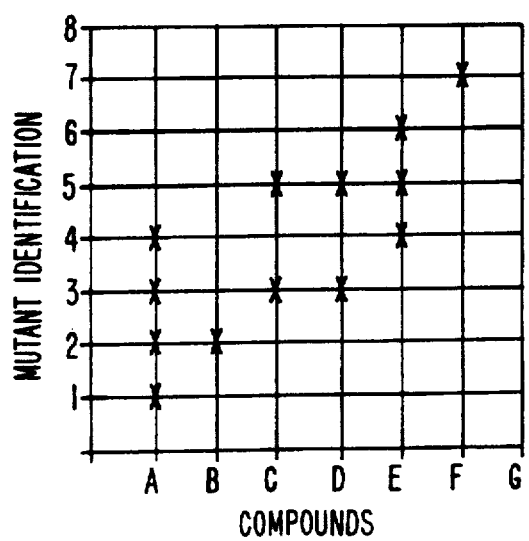
FIG. 13 illustrates the types of anticipated inhibition profiles of different growth conditional mutants for a variety of test compounds, indicating that the number of mutants affected by a particular compound is expected to vary.

The grid shown in FIG. 13 represents different mutant inhibition profiles anticipated from screening of growth inhibitors, where "x" denotes inhibition of a particular mutant by a particular compound at. concentrations much lower than for wildtype.

This grid shows compounds that cause growth inhibition of more than one mutant (compounds A,C,D,E), compounds that inhibit just one mutant (compounds B,F) and one compound that inhibits no mutants (compound G). In addition, this profile identifies mutants inhibited by no compound (mutant 8), a single compound (mutants 1,6,7), and several compounds (mutants 2,3,4,5). In the preliminary screens described above, compounds were identified that fit some of these anticipated inhibition profiles (see FIG. 14).

In the preliminary screen, compounds that inhibit the growth of the wild type strain were diluted to a point where growth inhibition of wild type no longer occurred. In this situation, only mutants that are hypersensitive to a particular compound will fail to grow. Thus, even compounds considered "generally toxic" should show some specificity of action, when assayed with the hypersensitive mutant strains.

In the simplest interpretation, compounds that cause growth inhibition inhibit the function of one essential macromolecule. Some compounds may specifically inhibit more than one target macromolecule. However, since one of the targets will be most sensitive to inhibition, one target can be considered the primary target. Thus, a one-to-one correspondence between inhibitors and targets can be established. However, both the data, and less simplistic reasoning provide exceptions to the simple one-to-one relationship between targets and inhibitors. Further analysis and understanding of the complicating effects is necessary to make full use of the data. Some of the complicating effects are discussed below.

a. Compounds That Affect Many Mutants.

Certain compounds, such as detergents that target membrane integrity, or DNA incercalators, will have "general", rather than specific targets. These "general targets" are not the product of a single gene product, but rather are created by the action of many gene products. Thus, in analyzing hypersensitivity profiles, compounds that affect many mutants may indicate action on a "general target". The profiles of known membrane active agents, and intercalators will provide information to recognize uncharacterized compounds with similar effects.

Compounds that cause growth inhibition of more than one mutant may also arise when the affected mutants are metabolically related. These mutants may affect the same gene, or the same biochemical pathway. For example, mutants defective in one of many cell wall biosynthetic steps may show hypersensitivity to compounds that inhibit any of these steps. Evidence for this type of effect was observed in the hypersensitivity patterns of known inhibitors (see FIG. 2). This concept can be broadened to include effects caused by the "metabolic web", in which far-reaching consequences may arise through characterized and uncharacterized interrelationships between gene products and their functions.

Figure 14:
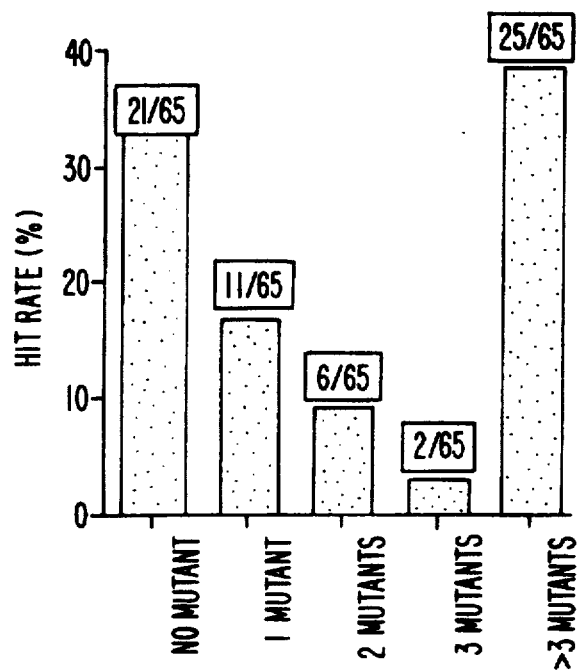
FIG. 14 shows the proportion of compounds (from a total of 65) which significantly inhibited the growth of varying numbers of temperature sensitive mutants in a screen of uncharacterized growth inhibitors of Staphylococcus aureus.
Figure 15:
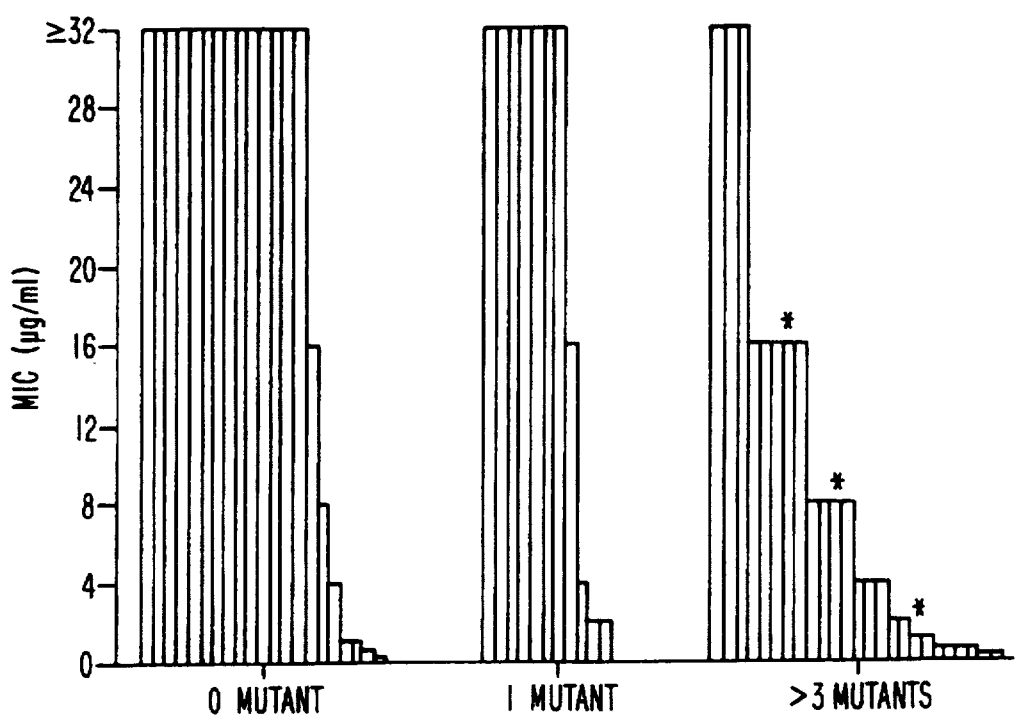
FIG. 15 shows the potency (MIC values) of a number of growth inhibitors which affected 0, 1 or more than 3 temperature sensitive mutants of Staphylococcus aureus in a screen of uncharacterized growth inhibitors.

Overall, the hit rate was high when we considered all compounds that were more active on mutants than on the parent strain. The histogram in FIG. 14 shows the hit rate for compounds that affected one, two, three, or more than three mutants in our prototype screen. The large number of compounds that affected more than three different mutants was at least partly explained by the greater potency this group of compounds. FIG. 15 illustrates the potency of some of the hits found in the screen as evaluated by the MIC obtained for the parent strain S. aureus 8325-4.

In the prototype screen, compounds affecting more than 3 mutants were generally more potent but some may also be considered broadly toxic. The columns identified by an asterisk in FIG. 15 represent 3 out of 4 compounds that were also shown to be inhibitors of Salmonella typhimurium in another whole cell screen. Consequently, only the most hypersusceptible strain of a group of mutants affected by the same compound should be considered as the primary target. However, the entire mutant inhibition profile of a specific compound is very useful and should be considered as its actual fingerprint in pattern recognition analysis.

b. Compounds that Affect Few (or no) Mutants.

Since all compounds assayed in the preliminary screen inhibit the growth of the wild type strain to some degree (initial basis of pre-selection), such compounds indicate that the mutant population is not sufficiently rich to provide a strain with a corresponding hypersensitive target.

c. Mutants Affected by Many Compounds.

Figure 16:
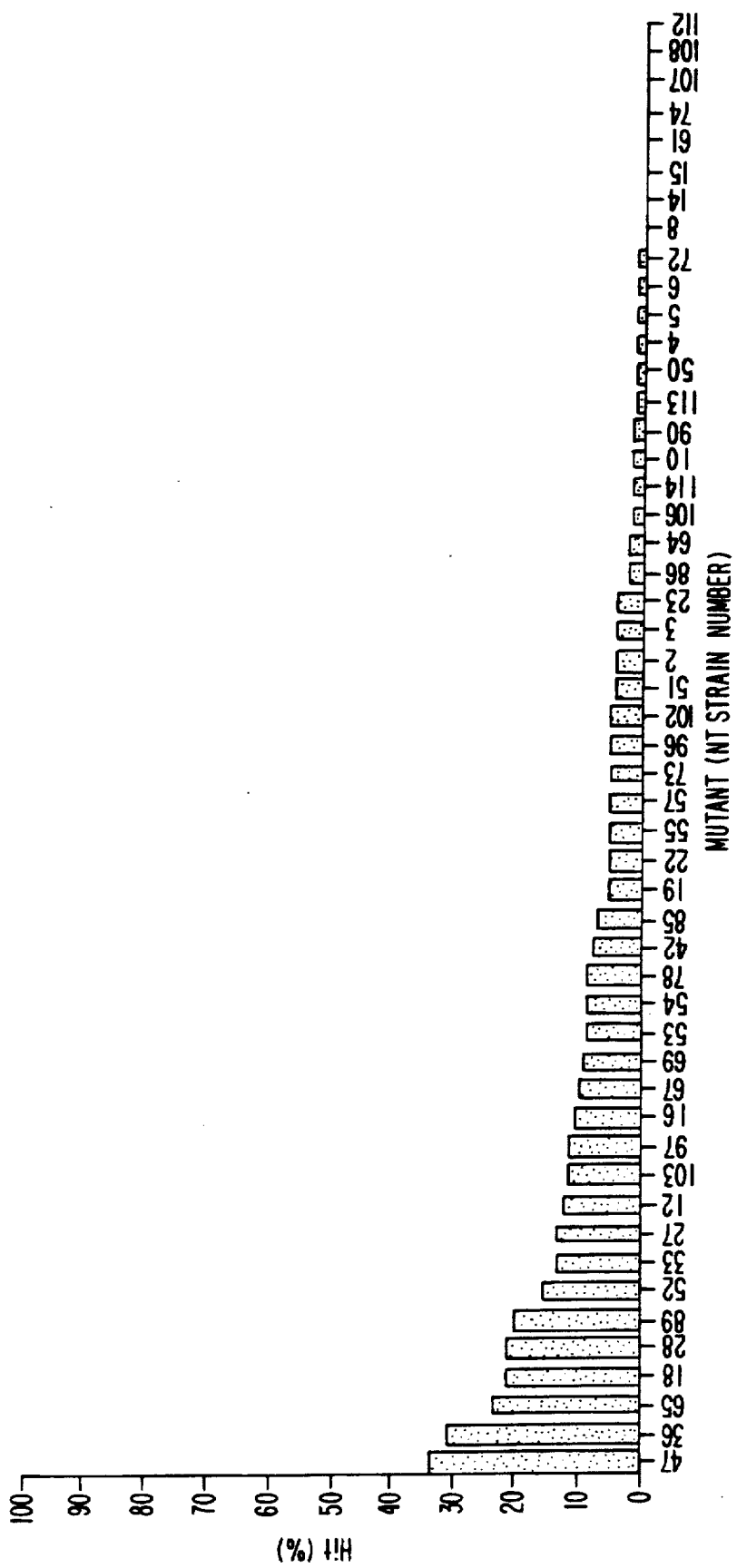
FIG. 16 shows the number of hits for each of the temperature sensitive mutants of Staphylococcus aureus in a screen of 65 uncharacterized growth inhibitors.

Another complication of the simple one-to-one compound/target relationship will arise because of mutants that are inhibited by many different compounds. The relative number of compounds (% hits) that inhibited the growth of each mutant in the S. aureus pilot is shown in FIG. 16. Several mutants were affected by many compounds. Several distinct causes of this are apparent. First, some mutants may have defects in the membrane/barrier that cause hyperpermeability to many different compounds. Such mutants will have higher intracellular concentrations of many compounds, which will inhibit metabolically unrelated targets. Other mutants may have defects that have far-reaching consequences, because their gene products sit at critical points in the metabolic web. Still other mutants may have specific alleles that are highly crippled at the assay temperature. For these mutants, the metabolic web consequences are large because the specific allele has created a highly hypersensitive strain.

d. Mutants Affected by Few or No Compounds.

For the mutants that were hypersusceptible to fewer compounds, it is possible that their mutations affect a limited metabolic web, that mutations provide a true specificity that was yet not revealed by any compound, or that these mutants have nearly full activity at the assay temperature. This analysis stresses the importance of strain validation as indicated above.

In interpreting these patterns, the number of mutants screened and the total number of targets are also important variables. These numbers provide a simple probabilistic estimate of the fraction of the compounds that should have a one-to-one correspondence with a mutant target in the sample that was screened.

6. Prioritization of Hits and Downstream Development

The early steps in a multi-channel genetic potentiation screen include the following:

Pre-selection of mutant strains for screening

Pre-selection of desired test compounds based on structural features, biolocical activity, etc. (optional)

Testing of the chosen compounds at a pre-determined concentration, preferably in the range 1–10 µg/ml.

Analysis of inhibitory profiles of compounds against the mutant population and selection of interesting hits Confirmation of the selective inhibitory activity of the interesting hits against specific mutants Secondary evaluation of prioritized hits.

Genetic potentiation assays provide a rapid method to implement a large number of screens for inhibitors of a large number of targets. This screening format will test the capacity of rapid high-throughput screening. The capability to screen large numbers of compounds should generate a large number of "hits" from this screening. Limitations in downstream development through medicinal chemistry, pharmacology and clinical development will necessitate the prioritization of the hits. When large numbers of hits are available, each with reasonable in vitro activity, prioritization of hits can proceed based on different criteria. Some of the criteria for hit characterization include:

chemical novelty chemical complexity, modifiability pharmacological profile toxicity profile target desirability, ubiquity, selectivity Secondary tests will be required not only for the initial evaluation of hits, but also to support medicinal chemistry efforts. While the initial genetic potentiation tests will be sufficient to identify and confirm hits, selection of hits for further development will necessitate establishment of the specific target of action. Equipped with the gene clones, selection of resistant alleles provides early evidence for the specific target. Subsequent efforts to establish a biochemical assay for rapid, specific and sensitive tests of derivative compounds will be aided by the over-expression and purification of the target protein, sequence analysis of the ORF to provide early insight into novel target function, as well as a variety of physiological and biochemical tests comparing the mutant and wild type strain to confirm the novel target function, and aid in the establishment of biochemical assays for the targets.

7. Identification of Specific Inhibitors of Gene Having Unknown Function

In a piloting screening study, a number of compounds were identified as inhibitors for mutants with mutations located in open reading frames whose functions are not known. Some of the open reading frames have been previously identified in other bacteria while others show little homology to the current Genbank sequence collection. An example is mutant NT94, whose complementing clones contain an open reading frame that is homologous to a spoVB-like gene in *B. subtilis*. While the function of the gene is not clear in either *B. subtilis* or *S. aureus*, NT94 is hypersensitive to many compounds tested, as illustrated in Table 2 below.

TABLE 2

Hit Rates in Genetic Potentiation Screen

| Number of mutants n, on which cmpds active | | Confirmed Hits | |
| --- | --- | --- | --- |
| | | 39 mutants | NT94 |
| n = 1 or 2 | Average hit rate | 0.03% | 1.06% |
| | Hit rate range among mutants | 0–0.31% | |
| n = >3 | Average hit rate | 0.17% | 1.39% |
| | Hit rate range among mutants | 0–0.72% | |

In fact, NT94 had the highest hit rate among the 40 mutant strains tested. Among the NT94 hits, 4 compounds share similar chemical structures (FIGS. 19A–D) The MICs of these compounds on NT94 are 0.25–2 μg/ml, which are 16–256 fold lower than those on the wild type cells (32–64 μg/ml). The similarity in the compound structures suggests a common and specific mechanism of the inhibitory effect on NT94.

Furthermore, the hypersensitivity to these compounds can be abolished by introducing 2 or more copies of the wild type gene into NT94. A correlation between the copy number of the wild type gene and the tolerance to the compounds has been observed. Cells with 2 copies of the wild type gene are slightly more resistant (2-fold increase in MIC) to MC-207,301 and MC-207,330 than the wild type cells which has one gene copy; cells carrying complementing plasmids (about 20–50 copies per cell) are much more resistant (8–16 fold increase in MIC). Such a gene dosage effect further suggests that either the gene product itself or its closely related functions of the open reading frame affected in NT94 is the target of the hit compounds.

8. Multi-Channel Screen Advantages

Figures 17, 18:
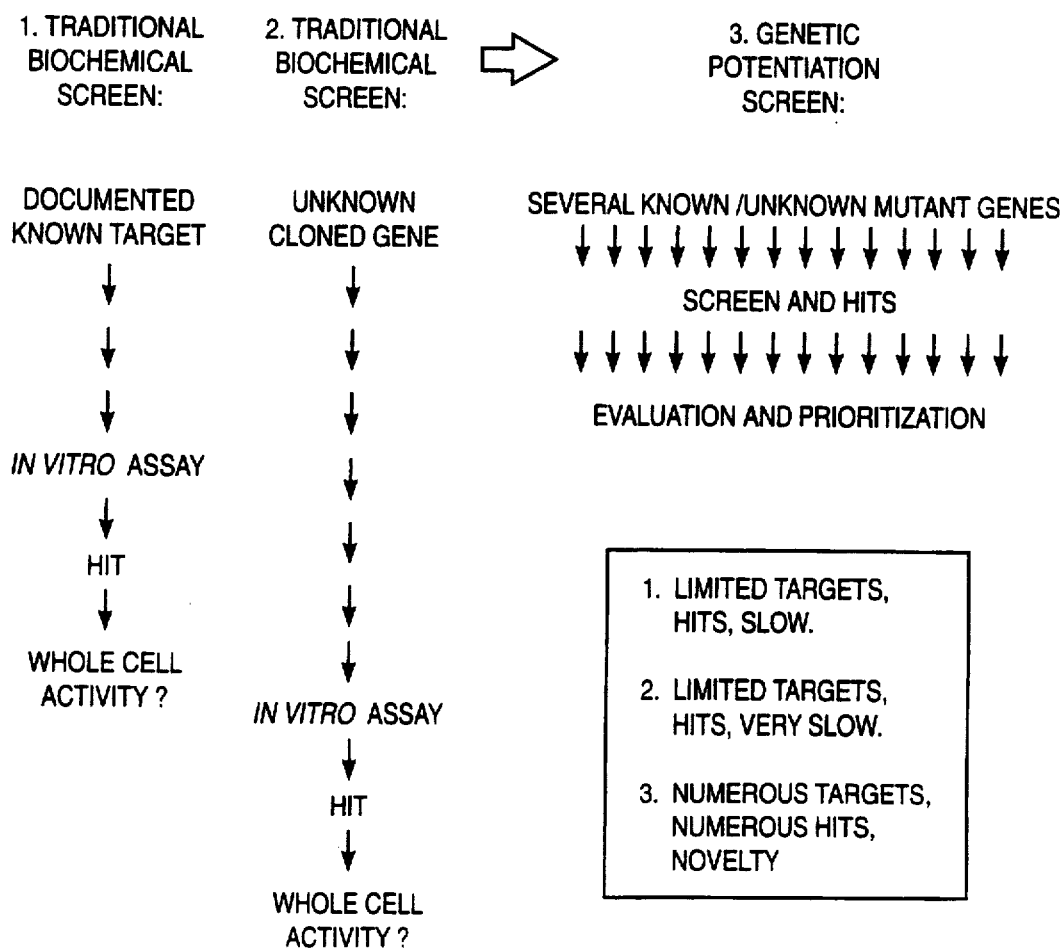
FIG. 17 shows some advantages of a multichannel genetic potentiation screen using growth conditional mutants over traditional biochemical screens with either a known target or an unknown cloned gene.
FIG. 18 illustrates a strategy for selecting dominant lethal mutants for use in screens for antibacterial agents, not requiring hypersensitivity.
Figure 19:
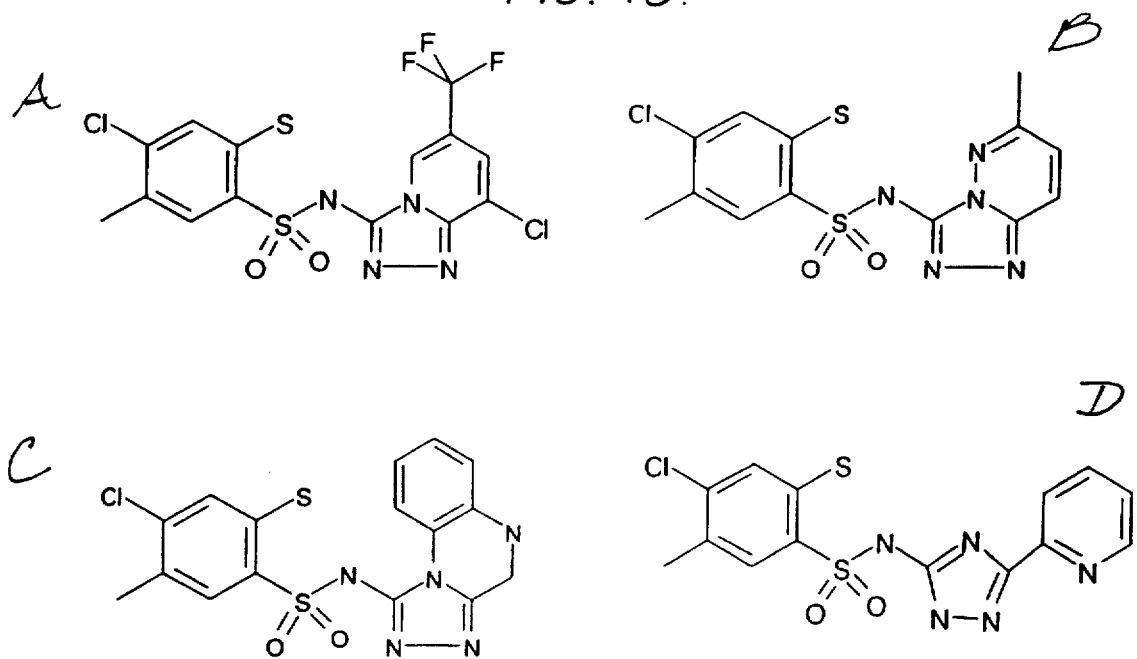
FIG. 19A–D are structures of four compounds which were identified as hits on mutant NT94.

As depicted by the *S. aureus* example shown above, multi-channel screen design rapidly leads to the identification of hits and provide some of the necessary specificity information to prioritize compounds for further evaluation. FIG. 17 illustrates the advantages of a genetic potentiation approach as the basis of a screen design.

Overall, an approach using whole-cell genetic potentiation of ts mutants includes the selectivity of the biochemical screens (it is target-specific, or at least pathway-specific) and it is more sensitive than traditional screens looking for growth inhibitors due to the hypersensitive nature of the mutants. This genetic potentiation approach also provides a rapid gene-to-screen technology and identifies hits even before the genes or biochemical targets are fully characterized.

9. Alternatives to Ts Hypersensitivity Screening

There are a number of additional strategies that can be undertaken to devise target-based whole cell screens, as well as binding or biochemical type screens. In order to implement these strategies, knowledge of the existence of the gene, the DNA sequence of the gene, the hypersensitivity phenotype profile, and the conditional mutant alleles will provide significant information and reagents. Alternative strategies are based on:

over- and under-expression of the target gene dominant mutant alleles hypersensitive mutant alleles a. Over- and Under-expression of Target Genes.

There are numerous examples of over-expression phenotypes that range from those caused by 2-fold increases in gene dosage (Anderson and Roth, 1977, *Ann. Rev. Microbiol.* 31:473–505; Stark and Wahl, 1984, *Ann. Rev. Biochem.* 53:447–491) to multi-fold increases in dosage which can be either chromosomal-encoded (Normark et al., 1977, *J. Bacteriol.* 132:912–922), or plasmid-encoded (Tokunaga et al., 1983, *J. Biol. Chem.* 258:12102–12105). The phenotypes observed can be analog resistance (positive selection for multiple copies, negative selection for inhibition phenotype) or growth defects (negative selection for multiple copies, but positive selection for inhibition phenotype).

Over-expression can be achieved most readily by artificial promoter control. Such screens can be undertaken in *E. coli* where the breadth of controllable promoters is high. However, this method loses the advantage gained by whole cell screening, that of assurance that the compound enters the pathogen of interest. Establishing controllable promoters in *S. aureus* will provide a tool for screening not only in *S. aureus* but most likely in other Gram-positive organisms. An example of such a controllable promoter is shown by controlled expression of the agr P3 promoter in the in vivo switch construction.

b. Dominant Alleles.

Dominant alleles can provide a rich source of screening capabilities. Dominant alleles in essential genes will prevent growth unless conditions are established in which the alleles are non-functional or non-expressed. Methods for controlled expression (primarily transcriptional control) will provide the opportunity to identify dominant mutant alleles that prevent cell growth under conditions of gene product expression.

Equally useful will be mutant alleles that are dominant, but conditionally functional. A single mutation may provide both the dominant and conditional-growth phenotype. However, utilizing the existing collection of temperature sensitive alleles, mutagenesis with subsequent selection for a dominant allele may provide more mutational opportunities for obtaining the necessary dominant conditional alleles. There is precedent for such additive effects of mutations on the protein phenotype (T. Alber, 1989, *Ann. rev. Biochem.* 58:765–798) as well as evidence to suggest that heat-sensitive mutations, which generally affect internal residues (Hecht et al., 1983, *Proc. Natl. Acad. Sci. USA* 80:2676–2680), will occur at different locations in the protein different than dominant mutations, one type of which will affect protein-protein interactions, which are more likely on the protein surface.

The use of dominant conditional double mutants may have an additional advantage, since the hypersensitivity phenotypes may remain the same in the double mutant as in the single conditional mutant allele. In this case, a merodiploid carrying two copies of the target gene—one wild type, and one carrying the dominant conditional doubly mutant gene—would provide a sophisticated screening strain (see FIG. 18). The screen would rely on the hypersensitivity of the dominant protein to inhibitor compounds. Under conditions of the dominant protein's function, cells will not grow, while inhibition of the dominant protein will allow cell growth. The temperature sensitive allele provides a basis for hypersensitivity of the dominant protein, relative to the wild type protein.

c. Hypersensitive Mutant Alleles

Additional mutants that display more pronounced hypersensitivities than the original conditional lethal mutants can be sought. Selection or screening procedures are based on the initial secondary phenotype profiles. These new highly hypersensitive alleles need not have a conditional growth defect other than that observed in the presence of the toxic agent or inhibitor. Such highly hypersensitive alleles provide strong target specificity, and high sensitivity to weak inhibitors. Such hypersensitive alleles can readily be adapted for screens with natural products, and with synthetic or combinatorial libraries of compounds in traditional screen formats.

d. Compound Binding and Molecular Based Assays and Screens

As indicated above, knowledge and possession of a sequence encoding an essential gene also provides knowledge and possession of the encoded product. The sequence of the gene product is provided due to the known genetic code. In addition, possession of a nucleic acid sequence encoding a polypeptide provides the polypeptide, since the polypeptide can be readily produced by routine methods by expressing the corresponding coding sequence in any of a variety of expression systems suitable for expressing procaryotic genes, and isolating the resulting product. The identity of the isolated polypeptide can be confirmed by routine amino acid sequencing methods.

Alternatively, once the identity of a polypeptide is known, and an assay for the presence of the polypeptide is determined, the polypeptide can generally be isolated from natural sources, without the necessity for a recombinant coding sequence. Such assays include those based on antibody binding, enzymatic activity, and competitive binding of substrate analogs or other compounds.

Consequently, this invention provides purified, enriched, or isolated products of the identified essential genes, which may be produced from recombinant coding sequences or by purification from cells naturally expressing the gene.

For use of binding assays in screening for compounds active on a specific polypeptide, it is generally preferred that the binding be at a substrate binding site, or at a binding site for an allosteric modulator, or at another site which alters the relevant biological activity of the molecule. However, simple detection of binding is often useful as a preliminary indicator of an active compound; the initial indication should then be confirmed by other verification methods.

Binding assays can be provided in a variety of different formats. These can include, for example, formats which involve direct determination of the amount of bound molecule, either while bound or after release; formats involving indirect detection of binding, such as by determination of a change in a relevant activity, and formats which involve competitive binding. In addition, one or more components of the assay may be immobilized to a support, though in other assays, the assays are performed in solution. Further, often binding assays can be performed using only a portion of a polypeptide which includes the relevant binding site. Such fragments can be constructed, for example, by expressing a gene fragment which includes the sequence coding for a particular polypeptide fragment and isolating the polypeptide fragment, though other methods known to those skilled in the art can also be used. Thus, essential genes identified herein provide polypeptides which can be utilized in such binding assays. Those skilled in the art can readily determine the suitable polypeptides, appropriate binding conditions, and appropriate detection methods.

Provision of a purified, enriched, or isolated polypeptide product of an essential gene can also allow use of a molecular based (i.e., biochemical) method for screening or for assays of the amount of the polypeptide or activity present in a sample. Once the biological activities of such a polypeptide are identified, one or more of those activities can form the basis of an assay for the presence of active molecules of that polypeptide. Such assays can be used in a variety of ways, for example, in screens to identify compounds which alter the level of activity of the polypeptide, in assays to evaluate the sensitivity of the polypeptide to a particular compound, and in assays to quantify the concentration of the polypeptide in a sample.

10. Antibacterial Compounds Identified by Hypersensitive Mutant Screening

Using the genetic potentiation screening methods described above, a number of compounds have been identified which inhibit growth of *S. aureus* cell. These compounds were identified as having activity on the NT94 mutant described above, and so illustrate the effectiveness of the claimed screening methods. These results further illustrate that the genes identified by the temperature sensitive mutants are effective targets for antibacterial agents. The identified compounds have related structures, as shown in FIGS. 19A–D These compounds can be generally described by the structure shown below:

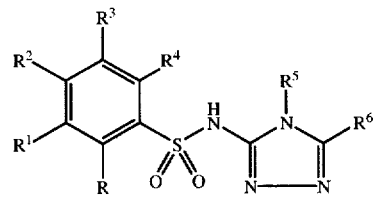

in which
  R, $R^1$, $R^2$, and $R^3$ are independently H, alkyl ($C_1$–$C_5$), or halogen;
  $R^4$ is H, alkyl ($C_1$–$C_5$), halogen, SH, or S-alkyl ($C_1$–$C_3$);
  $R^5$ is H, alkyl ($C^1$–$C^5$), or aryl ($C_6$–$C_{10}$);
  $R^6$ is CH2NH2, alkyl (C1–C4), 2-pyridyl, 3-pyridyl, 4-pyridyl, 2-furyl, 3-furyl, 2-thienyl, 3-thienyl, or aryl ($C_6$–$C_{10}$);

or
  $R^5$ and $R^6$ together are —C($R^7$)=C($R^8$)—C($R^9$)=C($R^{10}$)—, —N=C($R^8$)—C($R^9$)=C($R^{10}$)—, —C($R^7$)=N—C($R^9$)=C($R^{10}$)—, —C($R^7$)=C($R^8$)—N=C($R^{10}$)—, or —C($R^7$)=C($R^8$)—C($R^9$)=N—;

in which
  $R^7$, $R^8$, $R^9$, and $R^{10}$ are independently H, alkyl ($C_1$–$C_5$), halogen, fluoroalkyl ($C_1$–$C_5$);

or
  $R^7$ and $R^8$ together are —CH=CH—CH=CH—.

Thus, the invention includes antibacterial compositions containing the described compounds, and the use of such compositions in methods for inhibiting the growth of bacteria and methods for treating a bacterial infection in an animal.

V. Description of Compound Screening Sources and Sub-structure Search Method

The methods of this invention are suitable and useful for screening a variety of sources for possible activity as inhibitors. For example, compound libraries can be screened, such as natural product libraries, combinatorial libraries, or other small molecule libraries.

In addition, compounds from commercial sources can be tested, this testing is particularly appropriate for commercially available analogs of identified inhibitors of particular bacterial genes.

Compounds with identified structures from commercial sources can be efficiently screened for activity against a particular target by first restricting the compounds to be screened to those with preferred structural characteristics. As an example, compounds with structural characteristics causing high gross toxicity can be excluded. Similarly, once a number of inhibitors of a specific target have been found, a sub-library may be generated consisting of compounds which have structural features in common with the identified inhibitors. In order to expedite this effort, the ISIS computer program (MDL Information Systems, Inc.) is suitable to perform a 2D-substructure search of the Available Chemicals Directory database (MDL Information Systems, Inc.). This database contains structural and ordering information on approximately 175,000 commercially available chemical compounds. Other publicly accessible chemical databases may similarly be used.

VI. In vivo Modeling: Gross Toxicity

Gross acute toxicity of an identified inhibitor of a specific gene target may be assessed in a mouse model. The inhibitor is administered at a range of doses, including high doses, (typically 0–100 mg/kg, but preferably to at least 100 times the expected therapeutic dose) subcutaneously or orally, as appropriate, to healthy mice. The mice are observed for 3–10 days. In the same way, a combination of such an inhibitor with any additional therapeutic components is tested for possible acute toxicity.

VII. Pharmaceutical Compositions and Mode of Administration

The particular compound that is an antibacterial agent can be administered to a patient either by itself, or in combination with another antibacterial agent, or in pharmaceutical compositions where it is mixed with suitable carriers or excipient(s). A combination of an inhibitor of a particular gene with another antibacterial agent can be of at least two different types. In one, a quantity of an inhibitor is combined with a quantity of the other antibacterial agent in a mixture, e.g., in a solution or powder mixture. In such mixtures, the relative quantities of the inhibitor and the other antibacterial agent may be varied as appropriate for the specific combination and expected treatment. In a second type of combination an inhibitor and another antibacterial agent can be covalently linked in such manner that the linked molecule can be cleaved within the cell. However, the term "in combination" can also refer to other possibilities, including serial administration of an inhibitor and another antibacterial agent. In addition, an inhibitor and/or another antibacterial agent may be administered in pro-drug forms, i.e. the compound is administered in a form which is modified within the cell to produce the functional form. In treating a patient exhibiting a disorder of interest, a therapeutically effective amount of an agent or agents such as these is administered. A therapeutically effective dose refers to that amount of the compound(s) that results in amelioration of symptoms or a prolongation of survival in a patient, and may include elimination of a microbial infection.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. It is preferable that the therapeutic serum concentration of an efflux pump inhibitor should be in the range of 0.1–100 µg/ml.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture Such information can be used to more accurately determine useful doses in humans. Levels in plasma may be measured, for example, by HPLC.

The exact formulation, route of administration and dosage can be chosen by the individual physician in view of the patient's condition. (See, e.g., Fingl et al., in THE PHARMACOLOGICAL BASIS OF THERAPEUTICS, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific infection being treated, such agents may be formulated and administered systemically or locally. Techniques for formulation and administration may be found in *Remington's Pharmaceutical Sciences*, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art, into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers including excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

VIII. Use of Gene Sequences as Probes and Primers

In addition to the use of the growth conditional mutant strains as described above, DNA sequences derived from the identified genes are also useful as probes to identify the presence of bacteria having the particular gene or, under suitable conditions, a homologous gene. Similarly, such probes are useful as reagents to identify DNA chains which contain a sequence corresponding to the probe, such as for identifying clones having a recombinant DNA insert (such as in a plasmid). For identifying the presence of a particular DNA sequence or bacterium having that sequence it is preferable that a probe is used which will uniquely hybridize with that sequence. This can be accomplished, for example, by selecting probe sequences from variable regions, using hybridization conditions of suitably high stringency, and using a sufficiently long probe (but still short enough for convenient preparation and manipulation. Preferably, such probes are greater than 10 nucleotides in length, and more preferably greater than 15 nucleotides in length. In some cases, it is preferable that a probe be greater than 25 nucleotides in length. Those skilled in the art understand how to select the length and sequence of such probes to achieve specific hybridization. In addition, probes based on the specific genes and sequences identified herein can be used to identify the presence of homologous sequences (from homologous genes). For such purposes it is preferable to select probe sequences from portions of the gene which are not highly variable between homologous genes. In addition, the stringency of the hybridization conditions can be reduced to allow a low level of base mismatch.

As mentioned above, similar sequences are also useful as primers for PCR. Such primers are useful as reagents to amplify the number of copies of one of the identified genes or of a homologous gene. As with probes, it is preferable that the primers specifically hybridize with the corresponding sequence associated with one of the genes corresponding to SEQ ID NO. 1–105. Those skilled in the art understand how to select and utilize such primers.

The embodiments herein described are not meant to be limiting to the invention. Those of skill in the art will appreciate the invention may be practiced by using any of the specified genes or homologous genes, for uses and by methods other than those specifically discussed, all within the breadth of the claims.

Other embodiments are within the following claims.

What is claimed is:

1. A method of screening for an antibacterial agent, comprising determining whether a test compound is active against an essential bacterial gene selected from the group consisting of the essential genes corresponding to SEQ ID NO. 14, 16, 37, 38, 43, 59, 65, 66 and 67, 68 and 71, or a gene having an equivalent function and at least 85% sequence identity thereto.

2. The method of claim 1, comprising
   a. providing a bacterial strain having a mutant form of an essential gene selected from the group consisting of the essential genes corresponding to SEQ ID NO. 14, 16, 37, 38, 43, 59, 65, 66 and 67, 68, and 71, wherein said mutant form of the gene confers a growth conditional phenotype;
   b. providing comparison bacteria of a bacterial strain having a normal form of said gene;
   c. contacting bacteria of said bacterial strains with a test compound in semi-permissive growth conditions;
   d. determining whether the growth of said bacteria having said mutant form of a gene is reduced in the presence of said test compound compared to the growth of said comparison bacteria.

3. A method of screening for an antibacterial agent, comprising:
   a) contacting a cell expressing a polypeptide encoded by an essential gene selected from the group consisting of the essential genes corresponding to SEQ ID NO. 14, 16, 37, 38, 43, 59, 65, 66 and 67, 68, and 71 with a test compound; and
   b) determining whether the amount or level of activity of said polypeptide is altered;
   wherein an alteration in said amount or level of activity of said polypeptide is indicative of a useful antibacterial agent.

4. A method of screening for an antibacterial agent, comprising:
   a) contacting a polypeptide or a biologically active fragment thereof with a test compound, wherein said polypeptide is encoded by an essential gene selected from a group consisting of the essential genes corresponding to SEQ ID NO. 14, 16, 37, 38, 43, 59, 65, 66 and 67, 68, and 71; and
   b) determining whether said test compound binds to said polypeptide or said fragment;
   wherein said binding of said test compound to said polypeptide or said fragment is indicative of a useful antibacterial agent.

5. A method for evaluating an agent active on an essential gene selected from a group consisting of the essential genes corresponding to SEQ ID NO. 14, 16, 37, 38, 43, 59, 65, 66 and 67, 68, and 71, comprising:
   a) contacting a sample containing an expression product of said gene with said agent; and
   b) determining the amount or level of activity of said expression product in said sample.

6. A method for making an antibacterial agent, comprising:
   a) screening for an agent active on one of the essential genes corresponding to SEQ ID NO. 14, 16, 37, 38, 43, 59, 65, 66 and 67, 68, and 71 by
   providing a bacterial strain having a mutant form of an essential gene selected from the essential genes corresponding to SEQ ID NO. 14, 16, 37, 38, 43, 59, 65, 66 and 67, 68, and 71, wherein said mutant form of the gene confers a growth conditional phenotype,
   providing comparison bacteria of a bacterial strain having a normal form of said gene,
   contacting bacteria of said bacterial strains with a test compound in semi-permissive growth conditions, and
   determining whether the growth of said bacteria having said mutant form of a gene is reduced in the presence of said text compound compared to the growth of said comparison bacteria; and
   b) synthesizing said agent in an amount sufficient to provide said agent in a therapeutically effective amount to a patient.

7. The method of claim 1, wherein said gene corresponds to SEQ ID NO. 14.

8. The method of claim 2, wherein said gene corresponds to SEQ ID NO. 14.

9. The method of claim 3, wherein said gene corresponds to SEQ ID NO. 14.

10. The method of claim 4, wherein said gene corresponds to SEQ ID NO. 14.

11. The method of claim 5, wherein said gene corresponds to SEQ ID NO. 14.

12. The method of claim 6, wherein said gene corresponds to SEQ ID NO. 14.

13. The method of claim 1, wherein said gene corresponds to SEQ ID NO. 16.

14. The method of claim 2, wherein said gene corresponds to SEQ ID NO. 16.

15. The method of claim 3, wherein said gene corresponds to SEQ ID NO. 16.

16. The method of claim 4, wherein said gene corresponds to SEQ ID NO. 16.

17. The method of claim 5, wherein said gene corresponds to SEQ ID NO. 16.

18. The method of claim 6, wherein said gene corresponds to SEQ ID NO. 16.

19. The method of claim 1, wherein said gene corresponds to SEQ ID NO. 37.

20. The method of claim 2, wherein said gene corresponds to SEQ ID NO. 37.

21. The method of claim 3, wherein said gene corresponds to SEQ ID NO. 37.

22. The method of claim 4, wherein said gene corresponds to SEQ ID NO. 37.

23. The method of claim 5, wherein said gene corresponds to SEQ ID NO. 37.

24. The method of claim 6, wherein said gene corresponds to SEQ ID NO. 37.

25. The method of claim 1, wherein said gene corresponds to SEQ ID NO. 38.

26. The method of claim 2, wherein said gene corresponds to SEQ ID NO. 38.

27. The method of claim 3, wherein said gene corresponds to SEQ ID NO. 38.

28. The method of claim 4, wherein said gene corresponds to SEQ ID NO. 38.

29. The method of claim 5, wherein said gene corresponds to SEQ ID NO. 38.

30. The method of claim 6, wherein said gene corresponds to SEQ ID NO. 38.

31. The method of claim 1, wherein said gene corresponds to SEQ ID NO. 43.

32. The method of claim 2, wherein said gene corresponds to SEQ ID NO. 43.

33. The method of claim 3, wherein said gene corresponds to SEQ ID NO. 43.

34. The method of claim 4, wherein said gene corresponds to SEQ ID NO. 43.

35. The method of claim 5, wherein said gene corresponds to SEQ ID NO. 43.

36. The method of claim 6, wherein said gene corresponds to SEQ ID NO. 43.

37. The method of claim 1, wherein said gene corresponds to SEQ ID NO. 59.

38. The method of claim 2, wherein said gene corresponds to SEQ ID NO. 59.

39. The method of claim 3, wherein said gene corresponds to SEQ ID NO. 59.

40. The method of claim 4, wherein said gene corresponds to SEQ ID NO. 59.

41. The method of claim 5, wherein said gene corresponds to SEQ ID NO. 59.

42. The method of claim 6, wherein said gene corresponds to SEQ ID NO. 59.

43. The method of claim 1, wherein said gene corresponds to SEQ ID NO. 65.

44. The method of claim 2, wherein said gene corresponds to SEQ ID NO. 65.

45. The method of claim 3, wherein said gene corresponds to SEQ ID NO. 65.

46. The method of claim 4, wherein said gene corresponds to SEQ ID NO. 65.

47. The method of claim 5, wherein said gene corresponds to SEQ ID NO. 65.

48. The method of claim 6, wherein said gene corresponds to SEQ ID NO. 65.

49. The method of claim 1, wherein said gene corresponds to SEQ ID NO. 66 and 67.

50. The method of claim 2, wherein said gene corresponds to SEQ ID NO. 66 and 67.

51. The method of claim 3, wherein said gene corresponds to SEQ ID NO. 66 and 67.

52. The method of claim 4, wherein said gene corresponds to SEQ ID NO. 66 and 67.

53. The method of claim 5, wherein said gene corresponds to SEQ ID NO. 66 and 67.

54. The method of claim 6, wherein said gene corresponds to SEQ ID NO. 66 and 67.

55. The method of claim 1, wherein said gene corresponds to SEQ ID NO. 68.

56. The method of claim 2, wherein said gene corresponds to SEQ ID NO. 68.

57. The method of claim 3, wherein said gene corresponds to SEQ ID NO. 68.

58. The method of claim 4, wherein said gene corresponds to SEQ ID NO. 68.

59. The method of claim 5, wherein said gene corresponds to SEQ ID NO. 68.

60. The method of claim 6, wherein said gene corresponds to SEQ ID NO. 68.

61. The method of claim 1, wherein said gene corresponds to SEQ ID NO. 71.

62. The method of claim 2, wherein said gene corresponds to SEQ ID NO. 71.

63. The method of claim 3, wherein said gene corresponds to SEQ ID NO. 71.

64. The method of claim 4, wherein said gene corresponds to SEQ ID NO. 71.

65. The method of claim 5, wherein said gene corresponds to SEQ ID NO. 71.

66. The method of claim 6, wherein said gene corresponds to SEQ ID NO. 71.

* * * * *

SEQUENCE LISTING (1) GENERAL INFORMATION:

(iii) NUMBER OF SEQUENCES: 111

(2) INFORMATION FOR SEQ ID NO: 1:

(i) SEQUENCE CHARACTERISTICS:
      (A) LENGTH: 1739 base pairs
      (B) TYPE: nucleic acid
      (C) STRANDEDNESS: single
      (D) TOPOLOGY: linear (xi) SEQUENCE DESCRIPTION: SEQ ID NO: 1:

```
CTCGCAGCCG NYAKYCGWAA ATGGTCCAAT GTACTCCATC CATCACTGCA TCAACCTTAC    60
CTGTTTCTTC GTTCGTACGA TGATCTTTCA CCATTGAGTA TGGATGGAAA ACATATGATC   120
TAATTTGGCT TCCCCAGCCG ATTTCTTTTT GTTCGCCACG AATTTCAGCC ATTTCACGTG   180
CCTGCTCTTC CAATTTTAAT TGATATAATT TAGACTTTAA CATTTTCATA GCTGCTTCAC   240
GGTTTTTAAT TTGAGAACGT TCATTTTGGT TATTAACAAC TATACCTGAG GGTGGTGGG    300
TAATTCGTAT TGCCGATTCA GTTTTGTTAA TATGCTGACC ACCTGCACCA GAAGCTCTGA   360
ATGTATCAAC TGTAATATCA TCCGGATTGA TTTCAATCTC TATTTCATCA TTATTAAAAT   420
CTGGAATAAC GTCGCATGAT GCAAATGATG TATGACGACG TCCTGATGAA TCAAATGGAG   480
AAATTCGTAC TAGTCGGTGT ACACCTTTTT CAGCTTTTAA ATAACCATAA GCATTATGCC   540
CTTTGATGAG CAATGTTACA CTTTTAATCC CCGCTTCATC CCCAGGTAGA TAATCAACAG   600
TTTCAACTTT AAAGCCTTTC TTCTCAACAA TAACGTTGAT ACATTCTAAA TAGCATATTA   660
GCCCAATCTT GAGACTCCGT GCCACCTGCA CCAGGATGTA ACTCTAGAAT TGCGTTATTG   720
GCATCGTGAG GCCCATCTAA TAATAATTGC AATTCGTATT CATCCACTTT AGCCTTAAAA   780
TTAATGACCT CTTGCTCTAA GTCTTCTTTC ATTTCCTTCA TCAAATTCTT CTTGTAATAA   840
ATCCCAAGTA GCATCCATGT CATCTACTTC TGCTTGTAGT GTTTTATAAC CATTAACTAT   900
TGCTTTTAAC GCATTATTTT TATCTATAAT ATCTTGCGCT TTCGTTTGGT TATCCCAAAA   960
ATTAGGTTCT GCCATCATTT CTTCATATTC TTGAATATTA GTTTCTTTGT TCTCTAAGTC  1020
AAAGAGACCC CCTAATTTGT GTTAAATCTT GATTATACTT ATCTATATTT CGTTTGATTT  1080
CTGATAATTC CATAGCATTC GCTCCTATTT ATATTTCAAT TCAAGTCATT GATTTGCATC  1140
TTTTATAATG CTAAATTTTA ACATAATTTT GTTAAATAAC AATGTTAAGA AATATAAGCA  1200
CACTGACAAT TAGTTTATGC ATTTATTGTT TAAAAAWGCA GTACATTTAT GCATCGACAT  1260
ATGCCTAAAC CGATTTTTTA AAACTAAGTA CATAACAACG TTAACAACT TCTTCACATT   1320
TTTTAAAGTA TTTAACGCTT GTAAAATAAA AAGACTCCTC CCATAACACA AACTATAGGT  1380
GTTTAATTGG AAGGAGTTAT TTTATATCAT TTATTTTCCA TGGCAATTTT TGAATTTTTT  1440
ACCACTACCA CATGGACAAT CATCGTTACG ACCAACTTGA TCGCCTTTAA CGATTGGTTT  1500
CGGTTTCACT TTTTCTTTAC CATCTTCAGC TGAAACGTGC TTCGCTTCAC CAAACTCTGT  1560
TGTTTTTTCA CGTTCAATAT TATCTTCAAC TTGTACTACA GATTTTAAAA TGAATTTACA  1620
AGTATCTTCT TCAATATTTT GCATCATGAT ATCAAATAAT TCATGACCTT CATTTTGATA  1680
GTCACGTAAT GGATTTTGTT GTGCATAAGA ACGTAAGTGA ATACCTTGAC GTAATTGAT   1739
```

(2) INFORMATION FOR SEQ ID NO: 2:

(i) SEQUENCE CHARACTERISTICS:
    (A) LENGTH: 2368 base pairs
    (B) TYPE: nucleic acid
    (C) STRANDEDNESS: single
    (D) TOPOLOGY: linear (xi) SEQUENCE DESCRIPTION: SEQ ID NO: 2:

```
CTGCAGGTCG ATCTGCATCT TGATGTTTAT GAAATTCGAG TTGATCTAGT AATTAAATAA     60
CCAGCTAATA ATGACACTAC ATCAGKAAGA ATAATCCACT CGTTATGGAA ATACTCTTTA    120
TAGATTGAGG CACCAATTAA AATTAATGTC AGAATAGTAC CGACCCATTT ACTTCTTGTT    180
ATTACACTAA ATAATACTAC CAAGACACAT GGAAAGAATG CTGCGCTAAA ATACCATATC    240
ATTCATTTTC CTCTTTTCTT TTATTTAAAA TGTTCATGGT TGTTTCTCTT AATTCTGTTC    300
TAGGTATAAA GTTTTCAGTC AACATTTCTG GAATGATATT ATTAATAAAA TCTTGTACAG    360
ATGCTAAATG GTCAAATTGA ATAATTGTTT CTAGACTCAT TTCATAAATT TCGAAAAATA    420
ATTCTTCGGG ATTACGKTTT TGTATTTCTC CAAATGTTTC ATAAAGCAAA TCAATTTTAT    480
CAGCAACTGA AAGTATTTGG CCTTCTAATG AATCATCTTT ACCTTCTTGC AGTCGTTGCT    540
TATAAACATC TCTATATTGT AATGGAATTT CTTCTTCAAT AAAGGTCTCT ACCATTTCTT    600
CTTCAACTTG CGAAAATAAT TTTTTTAATT CACTACTCGC ATATTTAACA GGTGTTTTTA    660
TATCACCAGT AAACACTTCG GSGAAATCAT GATTTAATGC TTTTTCATAT AAGCTTTTCC    720
AATTAAYCTT TCTCCATGAT ATTCTTCAAC TGTTGCTAGA TATTGTGCAA TTTTAGTTAC    780
TTTAAAGGAG TGTGCTGCAA CATTGTGTTC AAAATATTTA AATTTTCCAG GTAATCTTAT    840
AAGTCTTTCC ATATCTGATA ATCTTTTAAA ATATTGATGT ACACCCATTT CAATTACCTC    900
CTCCATTAAT TAATCATAAA TTATACTTTC TTTTTACATA TCAATCAATT AAATATCATT    960
TAAATATCTT CTTTATATAA CTCTGATTAA ATGATACCAA AAAATCCTCT CAACCTGTTA   1020
CTTAAACAGG CTAAGAGGGT AGTCTTGTCT TGATATATTA CTTAGTGGAT GTAATTATAT   1080
TTTCCTGGAT TTAAAATTGT TCTTGAAGAT TTAACATTAA ATCCAGCATA GTTCATTTTC   1140
AGAAACAGTA ATTGTTCCMT TTAGGGTTTA CAGATTCAAC AACACCAACA TGTCCATATG   1200
GACCAGCAGC TGTTTGGAAA ATAGCGCCAA CTTCTGGKGT TTTATCTACT TTTAAATCCT   1260
GCAACTTTTG CTGCGTAATT CCAGTTATTT GCATTGCCCC ATAAACTTCC TATACTTCTA   1320
CCTAATTGTG CACGACGATC GAAAGCATAA TATGTGCAGT TTCCATAAGC ATATAAGTTT   1380
CCTCTGTTAG CAACTGATTT ATTGTAGTTA TGTGCAACAG GTACAGTTGG TACTGATTTT   1440
TGTACTTGAG CAGGTTTGTA TGCTACATTA ACTGTCTTAG TTACTGCTTG CTTAGGTGCT   1500
TGCTTAACTA CTACTTTTTT AGATGCTTGT TGTACAGGTT GTTTTACTAC CTTTTTAGCT   1560
TGGCTTGCTT TTCTTACTGG TGATTTAACC GCTTTAGTTT GTTTCACTTT ATTTTGAGGC   1620
ACAAGTGAAA TCACGTCACC AGGAAAAATT AAAGGTGTTA CACCAGGATT GTATTGAATA   1680
TAATTGATTC AACGTTAAGT GATGCTCTTA AAGCAATCTT ATATTAATGA ATCGCCAGCA   1740
ACTACTGTWT AAGTTGTCGG TGATTGCGTT TGTGCTTGAA CATTTGATAC ATAATTATGT   1800
TGAACAGGTG TTTTTACTTG TGTGCCATGT TGTTGTGCAT GTGCKGCATT ATTTAAAGCK   1860
AAAAAGCTA ACACTGACGA AACCGTCACT GWAAGARART TTTTCATCTK GCTGTCATTC   1920
CTTTGCTGTW AGTATTTTAA GTTATGCAAA TACTATAGCA CAATACATTT TGTCCAAAAG   1980
CTAATTGTTA TAACGANGTA ATCAAATGGT TAACAANATN AANAGAAGAC AACCGTNTAT   2040
CATAGNGGNA AANGTAGNCA TACCATGNAA TTGAGAACGT TNTCAANAAN TAANTCAATA   2100
CCNTGAAAAT CGCCATAGGN AATATTACNA AATGCACACT GCATATGNTG NTTAACAAA   2160
```

```
CACNACTTTT NANAAATATA NTCTAACTCT ATCTACCGAA TTGNACTTAA ATATTCATAA    2220

ANAAATNATA TTCNAAAATC TAATTTACAA TTTATTTAGC TACCTTTAAA AAANCNNAAA    2280

ACCGACGNCC TTTTAGAGCC TCGGTTTTTA NATATATNTT AATCGTGCGA CATTGTCTGT    2340

TTTNAATNTG ATTCGACTCT AGNGGATC                                      2368

(2) INFORMATION FOR SEQ ID NO: 3:

(i) SEQUENCE CHARACTERISTICS:
        (A) LENGTH:         2494 base pairs
        (B) TYPE:           nucleic acid
        (C) STRANDEDNESS:   single
        (D) TOPOLOGY:       linear (xi) SEQUENCE DESCRIPTION: SEQ ID NO: 3:

AATCATTTTA AATGATTGAT CAAGATGGTA TGGCGAAAGA CCAACGTAAT CACTTAATTC      60

TTGCAAATTG AAAGGCTCTA ATAAACGATC TTCAATATAA ACAATTGCCT GTTGTATTTG     120

CTTGATAACG TCCAAAACTT TCACTCCAAT TAATTCAATC ATTTATTTTT ATTCTACATT     180

ATTTCTATAA ATTATACACC CATTTGTTCA ATGATTATTA AAATAGTTTT GGGCATTGTA     240

AAATATAATT TCATAATATA GTCTAGAAAA AAAGCGAATG ATAGAACAAT TGATTTACTT     300

GATTCGTAAT CAATCCTTGT CATTCGCTCA TTTATTTTTG TTTAACATGT GCGTTTTAAT     360

TCAATTATTG AATATCGTCC CACCAATGGT TACCATCACG AGCAAGTAGT AAATCACTTT     420

CTAATGGACC ATTAGTACCT GATTCATAGT TAGGGAATTC TGGATCAACC ATATTCCATT     480

CATCTTGGAA TTGCATCAAC AAATTTCCAT GTTGATTTTA ATTCTTCCCA GTGCGTGAAG     540

TTAGTGGCAT CACCTTTAAG ACAATCAAAT AATAGATTTT CATATGCATC TACAGTATTC     600

ATTTTATCTT GAGCGCTCAT TGAGTAAGAC AATTGGACAG GTTCTGTTTC GATACCTTGT     660

GTWTTTTTCT TAGCATTTAR ATGTAAAGAT ACACCTTCAT TAGGTTGGAT ATTGATTANT     720

AATAGGTTTG AATCTAACAG TTTATCAGTT TCATAGTATA AGTTCATTGG TACTTCTTTA     780

AATTCAACGA CAACTTGAAT TGTTTTAGAT TTCATACGTT TACCAGTACG GATATAGAAT     840

GGTACACCAG CCCATCTAAA GTTATCAATT GTTAATTTAC CTGAAACAAA GGTAGGTGTG     900

TTAGAGTCAT CTGCAACGCG ATCTTCATCA CGGTATGCTT TAACTTGTTT ACCATCGATA     960

TAGCCTTCGC CATATTGACC ACGAACAAAG TTCTTTTTAA CATCTTCAGA TTGGAAATGA    1020

CGCAGTGATT TAAGTACTTT TAACTTTCTC AGCACGGATA TCTTCACTAT TTAAACTAAT    1080

AGGTGCTTCC ATAGCTAATA ATGCAACCAT TTGTAACATG TGGTTTTGCA CCATATCTTT    1140

TAGCGCGCCA CTTGATTCAT AATAACCACC ACGATCTTCA ACACCTAGTA TTTCAGAAGA    1200

TGTAACYYGG ATGTTTGAAA TATATTTGTT ATTCCATAAT GGTTCAAACA TCGCATTCGC    1260

AAAACGTAAT ACCTCGATAT TTTGAACCAT GTCTTTTCCT AAATAGTGGT CMATACGRTA    1320

AATTTCTTCT TCTTTAAATG ATTTACGAAT TTGATTGTTT AATGCTTCGG CTGATTTTAA    1380

ATCACTACCG AATGGTTTTT CGATAACAAG GCGTTTAAAT CCTTTTGTAT CAGTAAGACC    1440

AGAAGATTTT AGATAATCAG AAATAACGCC AAAGAATTGT GGTGCCATTG CTAAATAGAA    1500

TAGTCGATTA CCTTYTAATT CAAATTGGCT ATCTAATTCA TTACTAAAAT CTAGTAATTT    1560

CTTGATAGCT TTCTTCATTA CTAACATCAT GTCTATGATA GAAGACATGT TCCATAAACG    1620

CGTCAATTTT GTTTGTATCT TTWACGTGCT TTTGAATTGA TGATTTTAAC TTGATTACGG    1680

AAATCATCAT TAGTAATGTC ACGACGTCCA ATACCGATGA TGGCAATATG TTCATCTAAA    1740

TTGTCTTGTT GGTAGAGATG GAATATTGAT GGAAACAACT TACGATGGCT TAAGTCACCA    1800
```

-continued

```
GTTGCACCAA AGATTGTGAT TAAACATGGG ATGTGTTTGT TTTTAGTACT CAAGATTAAA      1860

ACCTCAATTC WYMCATTAGA TATATSATTT ATTATKAYMM GATAATCCAT TTCAGTAGGT      1920

CATACMATAT GYTCGACTGT ATGCAGTKTC TTAAATGAAA TATCGATTCA TGTATCATGT      1980

TTAATGTGAT AATTATTAAT GATAAGTATA ACGTAATTAT CAAAATTTAT ATAGTTATGT      2040

CTAACGTTAA AGTTAGAAAA ATTAACTAGC AAAGACGAAT TTTTAACAGA TTTTGATTCA      2100

AGTATAAATT AAAACTAAAT TGATACAAAT TTTATGATAA AATGAATTGA AGAAAAGGAG      2160

GGGCATATAT GGAAGTTACA TTTTTTGGAA CGAGTGCAGG TTTGCCTACA AAAGAGAGAA      2220

ATACACAAGC AATCGCCTTA AATTTAGAAC CATATTCCAA TTCCATATGG CTTTTCGACG      2280

TTGGTGAAGG TACACAGCAC CAAATTTTAC ATCATGCAAT TAAATTAGGA AAAGTGACAC      2340

ATATATTTAT TACTCATATG CATGGCGATC ATATTTTTGG TTTGCCAGGA TTACTTTCTA      2400

GTCGTTCTTT TCAGGGCGGT GAACAGAAGC CGCTTACATT GGTTGGACCA AAAGGAATTA      2460

AAGCATATGT GGAAATGTCT ATGAATTTAT CAGA                                  2494
```

(2) INFORMATION FOR SEQ ID NO: 4:

(i) SEQUENCE CHARACTERISTICS:
        (A) LENGTH:        400 base pairs
        (B) TYPE:          nucleic acid
        (C) STRANDEDNESS:  single
        (D) TOPOLOGY:     linear (xi) SEQUENCE DESCRIPTION: SEQ ID NO: 4:

```
AAATAATCTA AAAATTGGTA GTNCTCCTTC AGATAAAAAT CTTACTTTAA CACCATTCTT       60

TTNAACTNNT TCCGTGTTTC TTTTTCTAAG TCCATCCATA TTTTNAATGA TGTCATCTGC      120

TGTTTTATCT TTTAAATCTA ACACTGAGTG ATAACGGATT TGTAGCACAG GATCAAATCC      180

TTTATGGAAT CCAGTATGTT CAAATCCTAA GTTACTCATT TTATCAAAGA ACCAATCATT      240

ACCAGCATTA CCTGTAATCT CGCCATCATG ATTCAAGTAT TGATATGGTA AATATGGATC      300

GNTATGTAGG TATAGNCAAC GATGTTTTTT AACATATTTT GGATAATTCA TTAAAGNAAA      360

AGTGTACGAG TNCTTGATTT TCATANTCAA TCACTGGACC                            400
```

(2) INFORMATION FOR SEQ ID NO: 5:

(i) SEQUENCE CHARACTERISTICS:
        (A) LENGTH:        398 base pairs
        (B) TYPE:          nucleic acid
        (C) STRANDEDNESS:  single
        (D) TOPOLOGY:     linear (xi) SEQUENCE DESCRIPTION: SEQ ID NO: 5:

```
TGCGTGAAAT NACTGTATGG CNTGCNATCT GTAAAGGCAC CAAACTCTTT AGCTGTTAAA       60

TTTGTAAACT TCATTATCAT TACTCCTATT TGTCTCTCGT TAATTAATTT CATTTCCGTA      120

TTTGCAGTTT TCCTATTTCC CCTCTGCAAA TGTCAAAAAT AATAAATCTA ATCTAAATAA      180

GTATACAATA GTTAATGTTA AAACTAAAAC ATAAACGCTT TAATTGCGTA TACTTTTATA      240

GTAATATTTA GATTTTNGAN TACAATTTCA AAAAAGTAA TATGANCGTT TGGGTTTGCN       300

CATATTACTT TTTTNGAAAT TGTATTCAAT NTTATAATTC ACCGTTTTC ACTTTTTNCA       360

AACAGTATTC GCCTANTTTT TTTAAATCAA GTAAACTT                              398
```

(2) INFORMATION FOR SEQ ID NO: 6:

(i) SEQUENCE CHARACTERISTICS:

```
       (A) LENGTH:              410 base pairs
       (B) TYPE:                nucleic acid
       (C) STRANDEDNESS:        single
       (D) TOPOLOGY:            linear (xi) SEQUENCE DESCRIPTION: SEQ ID NO: 6:

GTAATGACAA ATNTAACTAC AATCGCTTAA AATATTACAA AGACCGTGTG TNAGTACCTT     60

TAGCGTATAT CAACTTTAAT GAATATATTA AAGAACTAAA CGAAGAGCGT GATATTTTAA    120

ATAAAGATTT AAATAAAGCG TTAAAGGATA TTGAAAAACG TCCTGAAAAT AAAAAAGCAC    180

ATAACAAGCG AGATAACTTA CAACAACAAC TTGATGCAAA TGAGCAAAAG ATTGAAGAAG    240

GTAAACGTCT ACAAGANGAA CATGGTAATG AATTACCTAT CTCTNCTGGT TTCTNCTTTA    300

TCAATCCATT TGANGTTGTT TATTATGCTG GTGGTACATC AAATGCATTC CGTCATTTTN    360

CCGGAAGTTA TGCAGTGCAA TGGGAAATGA TTAATTATGC ATTAAATCAT               410

(2) INFORMATION FOR SEQ ID NO: 7:

(i) SEQUENCE CHARACTERISTICS:
           (A) LENGTH:              3479 base pairs
           (B) TYPE:                nucleic acid
           (C) STRANDEDNESS:        single
           (D) TOPOLOGY:            linear (xi) SEQUENCE DESCRIPTION: SEQ ID NO: 7:

AAGCTTCATT AAAAACTTTC TTCAATTTAT CAACATATTC AATGACGTTA GCATGTGCGA     60

CACCAACGGA YTKSAKKTCA TGATCTCCTA TAAATTCAGC AATTTCCTTT TTCAAGTATT    120

GGATACTAGA ATTTTGAGTT CTCGCATTGT GCACAAGCTC TAAGCGACCA TCATCTAGTG    180

TACCAATTGG TTTAATTTTC ATAAGATTAC CAATCAAACC TTTTGTTTTA CTAATTCTGC    240

CACCTTTAAT TAATTGATTC AATTGCCCTA TAACTACAAA TAATTTAATG TTTTCTCTTA    300

AATGATTTAA CTTTTTAACT ATTTCAGAAG TTGAGACACC TTCTTTTACA AGCTCTACTA    360

GGTGTTGTAT TTGATACCCT AAACCAAAAG AAATAGATTT TGAATCAATA ACAGTTACAT    420

TAGCATCTAC CATTTGACTT GCTTGGTAAG CAGTGTTATA TGTACCACTT AATCCTGAAG    480

AAAGATGAAT ACTTATGATT TCAGAGCCAT CTTTTCCTAG TTCTTCATAA GCAGATATAA    540

ATTCACCTAT GGCTGGCTGA CTTGTCTTTA CATCTTCATC ATTTTCAATA TGATTAATAA    600

ATTCTTCTGA TGTAATATCT ACTTGGTCAA CGTATGAAGC TCCTTCAATA GTTAAACTTA    660

AAGGAATTAC ATGWATGTTG TTTGCTTCTA ARTATTCTTT AGATAAATCG ATGTTGAGT     720

CTGTTACTAT AATCTGTTTT GTCATGGTCG TTTTCCCCCT TATTTTTTAC GAATTAAATG    780

TAGAAAGGTA TGTGGAATTG TATTTTTCTC ATCTAGTTTA CCTTCAACTG AAGAGGCAAC    840

TTCCCAGTCT TCAAATGTAT AAGGTGGAAA GAACGTATCA CCACGGAATT TACCTTCAAT    900

AACAGTAATA TACATGTCGT CCACTTTATC AATCATTTCT TCAAATAATG TTTGCCCTCC    960

AAATATGAAA ACATGGCCCG GTAGTTGGTA ATATCTTCA ATAGARTGAA TTACATCAAC    1020

GCCCTCTACG TTGAAACTTG TATCTGAAGT AAGTACAACA TTTCGACGAT TCGGTAGTGG   1080

TTTACCAATC GATTCAAATG TCTTACGACC CATTACTAAA GTATGACCTG TTGATAATTT   1140

TTTAACATGC TTCAAATCAT TTGGTAGGTG CCAAGGTAAT TGATTTTCAA AACCAATTAC   1200

TCGTTGCAAG TCATGTGCAA CTAGAATGGA TAAAGTCATA ATTATCCTCC TTCTTCTATC   1260

ATTTCATTTT TTATTACTAA GTTATCTTTA ATTAACACA ATTTTTATCA TAAAGTGTGA   1320

TAGAAATAAT GATTTTGCAT AATTTATGAA AACGTTAAC ACAAAAAAGT ACTTTTTTGC   1380

ACTTGAAAAT ACTATGATGT CATTTKGATG TCTATATGGT TAGCTAAYTA TGCAATGACT   1440
```

```
ACAMTGCTAT KGGAGCTTTT ATKGCTGGAT GTGATTCATA GTCAACAATT TCCAMAATCT    1500

TCATAATTTA TGTCGAAAAT AGACTTGTCA CTGTTAATTT TTAATGTTGG AGGATTGAAG    1560

CTTTCACGTG CTAATGGTGT TKCGMATCGC ATCAATATGA TTTGAATAAA TATGTGCATC    1620

TCCAAATGTA TGCACAAATT CACCCACTTC AAGTCCACAT TTCTTTGGCA ATAAGGTGTG    1680

TCAATAAAGC GTAGCYTGCG ATATTAAATG GCACACCTAA AAAGATATCT GCGCTACGTT    1740

GGTATAACTG GCAACTTAAC TTACCATCTT GGACATAAAA CTGGAACATG GTATGACAAG    1800

GCGGAAGTGC CATTGTATCA ATTTCTGTTG GATTCCATGC AGATACGATG TGTCGCCTTG    1860

AATCTGGATT ATGCTTAATT TGTTCAATTA CTGTTTTAAG TTGATCAAAA TGATTACCAT    1920

CTTTATCAAC CCAATCTCGC CMATTGTTTA CCATAAACAT TTCCTAAATC CCCGAATTGC    1980

TTCGCAAATG TATCATCTTC AAGAATACGT TGCTTAAATT GTTTCATTTG TTCTTTATAT    2040

TGTTCGTTAA ATTCAGGATC ACTCAATGCA CGATGCCCGA AATCTGTCAT ATCTGGACCT    2100

TTATACTCGT CTGATTTGAT ATAATTTTCA AAAGCCCATT CGTTCCATAT ATTATTATTA    2160

TATTTTAATA AGTATTGGAT GTTTGTATCT CCTTTAATGA ACCATAATAA TTCGGTTGCT    2220

ACTAATTTAA AAGAAACTTT CTTTGTCGTT AATAGTGGAA ATCCTTTAGA TAAGTCAAAG    2280

CGAAGTTGAT GACCAAATTT CGAAATCGTA CCTGTATTTG TGCGATCATT TCGTGTATTT    2340

CCTATTTCTA AAACTTCTTC ACAAAGACTG TGATATGCTG CATCAAATGA ATTTCAACAT    2400

ATGCGATAAC ACCTCATTTT CATTATTTAT AGTATGTATA TTTAGTTTGA TATAACTTAA    2460

CTTTATGTAG CATTTTGTTA TCACTCATTT TAGGAATATG ATATTAATAT CATGAATTCC    2520

GTTACTTTAT TTATAAAATG CTGATTAAGT ACCTACCCCA TCGTAACGTG ATATATGTTT    2580

CCAATTGGTA ATTGTTTACC CAAATCTATA ACTTTAATGC TAAAAATTT TAAAAAGAG     2640

GTTAACACAT GATTTGAATA TTATGTTTGA TGTCCTATTA AAACAGTTAA ATTTCTAGAA    2700

AATATAGTTG GTAAAAACGG ACTTTATTTA ACAAATAGAA TACAACTATA TTCTCTATTT    2760

TCAATGACAG ACACCATTTT TAATATTATA AAATGTGTTA ACCTTTATAT TTATTTATGT    2820

GTACTATTTA CAATTTTCGT CAAAGGCATC CTTTAAGTCC ATTGCAATGT CATTAATATC    2880

TCTACCTTCG ATAAATTCTC TAGGCATAAA ATAAACTAAA TCTTGACCTT TGAATAAAGC    2940

ATACGAAGGA CTAGATGGTG CTTGCTGAAT GAATTCTCGC ATTGTAGCAG TTGCTTCTTT    3000

ATCTTGCCCA GCAAAAACTG TAACTGTATT TGTAGGTCTA TGTTCATTTT GTGTTGCAAC    3060

TGCTACTGCA GCTGGTCTTG CTAATCCAGC TGCACAGCCG CATGTAGAGT TAATAACTAC    3120

AAAAGTAGTG TCATCAGCAT TTACTTGGTT CATATACTCC GATACTGCTT CGCTCGTTTC    3180

TAAACTTGTA AAACCATTTT GAGTTAATTC GCCACGCATT TGTTGCGCAA TTTCTTTCAT    3240

ATAAGCATCA TAYGCATTCA TATTTAATTC CTCCAATTAA ATTGTTCTGT TTGCCATTTG    3300

TYTCCATACT GAACCAAGYG CTTCAYCTCC GTTTTCAATA TCGAGATATG GCCATTTCAA    3360

TTTGTAATTT AACWTCAAAC GCMTKGTCAK KAATATGGGS WTTTAGKGCG GGAAGMTGMT    3420

YWGCATWACS WTCATSAWAG ATAWACAYAG CARCAYSCCA CYTWAYGAKT TTMWKTGGA    3479
```

(2) INFORMATION FOR SEQ ID NO: 8:

(i) SEQUENCE CHARACTERISTICS:
        (A) LENGTH:        2875 base pairs
        (B) TYPE:          nucleic acid
        (C) STRANDEDNESS:  single
        (D) TOPOLOGY:     linear (xi) SEQUENCE DESCRIPTION: SEQ ID NO: 8:

```
GTGGTTCCCT GTCATTYTRA TATCCATCAA ACCTTTATTA ATACACGTRG CTATCGAAGC      60

ATTTTGTAAT TGTATTAATG AAATATGCTT GAGTYCTCTT TGTAACCGTT CAATCATAGG     120

AATTGTTTGA TCAGTAGAAC CACCATCAAT ACAAAGGATT CTATAGTGTT CTTTACTCTC     180

AATAGATATT AACAATTGTC GAATTGTTGC CTCATTATTA CATGTAGGTA TGATTATCGT     240

AAACCTCATT TTGTCACCAT CTTATCTATA TATTCTGTGA GCTGATGTAA ACTTTTATCA     300

GTATTATACT TATGCCAATC TTTAAATAAC GGACTTAATA GATGTTCTTT TTCTTGTATC     360

GTCATTATTA AATCTTCTTC AGTATACACT TTGTAGCTAT CCGGTATTGC TTTGTAAAAT     420

TGATTCAGGC CTCTCACCTG ATCATATGTT CCTTCATCAT ACACATAAAA TATAGTTGGA     480

ATATCTAACA AGCTAGCTTC TATTGGCAGC GAACTATAGT CGCTAATAAT TATATCTGAC     540

ATTAGCATTA ATGTAGACGT GTCGATTGAA GATACGTCAT CAATGTCTGA ATCTTCAATT     600

GATGGATGTA ATTTATTAAT CAGTGTATAT CCTGGTAAAC ATTTTTCAAA ATAAGCTTTA     660

TCAATAGCCC TATTATCTGC TTTATCTTCT CTATATGTTG GTACATATAA TACCAACTTA     720

TTTGTAATTC CATATTTATC CTTTAACTCT GCCTTAACCG TTGCTCTATC AGCTGTGTAA     780

TATTTATTAA TTCTCGGAAG CCCAAAATAC AGCATTTGCT CTTCTGTTGC ACCTAAAGAC     840

TGTTTAAAAC ATTGTGACAT TTGTTCACAA CCCACTAAGT TAAAAATCCG TCGCTTGATA     900

AACTTTACGG TACTGCTGAA CCATTGCCTT GTCAGACACA TCGACTTGAT GATCTGTTAA     960

GCCAAAGTTT TTAATGCAC CACTTGCATG CCACGTTTGA ACAATGTGTT TGATTAGAAK    1020

TCTTATTATA TCCACCTAGC MATAGGTAAT AATTATCGAT AATAATCATC TGCGCGCTTT    1080

TCAAAGCCTT AATTTGTTTT ACCAATGTTC GATTAGTCAT TTCTATCACA TCAACATCGT    1140

CGCTAAGTTC AGATAAATAA GGCGCTTGTT TTGGTGTTGT TAAAACAGTT TTCTGATACG    1200

ACGAATTATT TAATGCTTTG ATGATAGGCT TAATATCTTC TGGAAAAGTC ATCATAAATA    1260

CGATATGCGG TTTATCAATC ACTTGAGGSG TAWTCATTTW AGRAAGTATT CGAACTACCA    1320

AATGATAAAA TTTCTTTATT AAAAACGTTC ATAATAACAC CAACTTAATA TGTTATTTAA    1380

CTTAAATTAT AAACAAAAAT GAACCCCACT TCCATTTATT AATGGTTAGC GGGGTTTCGT    1440

CATATAAATA TATTACAAGA AGTCTGCAAA TTGATCTCTA TATTTCATGT GTWAGTACGC    1500

MCCMATTGCA AAGAAAATGG CAACAATACC GAAATTGTAT AACATTAATT TCCAATGATC    1560

CATGAAATAC CATTCGTGAT ATAAAATTGC TGCACKKTWT KATTMAKCWR TAMRGTMAAC    1620

TRGMTKATAT TTCATCATTK SATGAATTAA ACCACTGATA CCATGGTTCT TTGGTAGCCA    1680

CAAAATTGGT GAAAAGTAAA ATAATATTCT TAATATTGGC TTGCATTAAC ATTTGTGTAT    1740

CTCTAACTAA CAACACCGAG TGTTGATGTT AATAACGTCA CCGAGGCAGT TAAGAAAAAA    1800

CAAAACGGTA CATATATCAA TAATTGAATG ATATGTATTG ATGGATAAAT ACCAGTAAAC    1860

ATACATGCAA TTATCACAAG TAAAAGTAAG CCTAAATGTC CATAAAATCT ACTTGTCACA    1920

ATATATGTCG GTATTATCGA TAACGGGAAG TTCATTTTCG ATACTTGATT AAACTTTTGT    1980

GTAATTGCTT TAGTACCTTC TAAAATACCT TGGTTGATGA AGAACCACAT ACTGATACCA    2040

ACCAATAACC AATAAACAAA AGGTACACCA TGAATTGGTG CATTACTTCT TATTCCTAAT    2100

CCAAAAACCA TCCAGTAAAC CATAATTTGC ATAACAGGGT TAATTAATTC CCAAGCCACA    2160

CCTAAATAGT TACTATGATT GATAATTTTA ACTTGAAACT GAGCCAGTCT TTGAATTAAA    2220

TAAAAGTTCT WTASATGTTC TTTAAAAACT GTTCCTATTG CTGACATTCC ATTAAACCAC    2280

ACTTTCAAAT GTTTAACTAT TTCTCTAACT TAACTAAATA GTATTATAAT AATTGTTGTA    2340
```

-continued

| AATACTATCA CTAWACATGG ATGCTATCAA AATTATTGTC TAGTTCTTTA AAATATTAGT | 2400 |
| AATACTATCA CTAWACATGG ATGCTATCAA AATTATTGTC TAGTTCTTTA AAATATTAGT | 2400 |

```
AATACTATCA CTAWACATGG ATGCTATCAA AATTATTGTC TAGTTCTTTA AAATATTAGT    2400

TTATTACAAA TACATTATAG TATACAATCA TGTAAGTTGA ATAAGTTTA GTTTTTAAAT     2460

ATCATTGTTA TCATTGATGA TTAACATTTT GTGTCAAAAC ACCCACTCTG ATAATAACAA    2520

AATCTTCTAT ACACTTTACA ACAGGTTTTA AAATTTAACA ACTGTTGAGT AGTATATTAT    2580

AATCTAGATA AATGTGAATA AGGAAGGTCT ACAAATGAAC GTTTCGGTAA ACATTAAAAA    2640

TGTAACAAAA GAATATCGTA TTTATCGTAC AAATAAAGAA CGTATGAAAG ATGCGCTCAT    2700

TCCCAAACAT AAAAACAAAA CATTTTTCGC TTTAGATGAC ATTAGTTTAA AAGCATATGA    2760

AGGTGACGTC ATAGGGCTTG TTGGCATCAA TGGTTCCGGC AAATCAACGT TGAGCAATAT    2820

CATTGGCGGT TCTTTGTCGC CTACTGTTGG CAAAGTGGAT CGACCTGCAG TCATA         2875
```

(2) INFORMATION FOR SEQ ID NO: 9:

(i) SEQUENCE CHARACTERISTICS:
        (A) LENGTH:            453 base pairs
        (B) TYPE:              nucleic acid
        (C) STRANDEDNESS:     single
        (D) TOPOLOGY:         linear (xi) SEQUENCE DESCRIPTION: SEQ ID NO: 9:

```
CTTAAAATAT TACAAAGACC GTGTGTNAGT ACCTTNAGCG TATATCAACT TTAATGAATA     60

TATTAAAGAA CTAAACGAAG AGCGTGATAT TTTAAATAAA GATTTAAATA AAGCGTTAAA    120

GGATATTGAA AAACGTCCTG AAAATAAAAA AGCACATAAC AAGCGAGATA ACTTACAACA    180

ACAACTTGAT GCAAATGAGC AAAAGATTGA NGACGGTAAA CGTCTACAAG ANGANCATGG    240

TAATGNTTTA CCTATCTCTC CTGGTTTCTC CTTTATCAAT CCNTTTGANG TTGTTTATTA    300

TGCTGGTGGT ACATCAAATG CNTTCCGTCA TTTTNCCGGA NGTTATGCNG TGCAATGGGA    360

AATGNTTAAT TTTGCATTAA ATCATGGCAT TGNCCGTTAT AATTNCTATG GTGTTAGTGG    420

TNAATTTNCA GNAGGTGCTG AAGATGCTGG TGT                                  453
```

(2) INFORMATION FOR SEQ ID NO: 10:

(i) SEQUENCE CHARACTERISTICS:
        (A) LENGTH:            445 base pairs
        (B) TYPE:              nucleic acid
        (C) STRANDEDNESS:     single
        (D) TOPOLOGY:         linear (xi) SEQUENCE DESCRIPTION: SEQ ID NO: 10:

```
ATGCTCAGGT CGATCATACA TCTATCATCA TTTTAATTTC TAAAATACAA ACTGAATACT     60

TTCCTAGAAT NTNANACAGC AATCATTGCT CATGCATTTA ATAAATTACA ATTAGACAAA    120

TATGACATTT GATATCACAC ACTTGCAAAC ACACACATAT ATAATCAGAC ATAAATTGTT    180

ATGCTAAGGT TTATTCACCA AAANTATAAT ACATATTGGC TTGTTTTGAG TCATATTGNN    240

TGANTTANAA NGTATACTCA ACTCANTCAT TTNCAAATNG GTTGTGCAAT TCNTATTTNT    300

NTTTCTTGCA ATCCCTTGTT AAACTTGTCA TTTNATATAT CATTNTTCGG GGCTTTATTA    360

AAANNCATNT NNNACNGNGC CTATNGNNTC NNTNACTATN NGCCCTAACA TCATTTTCNT    420

CTNTTTCTTA TTTTTTACGG GATTT                                           445
```

(2) INFORMATION FOR SEQ ID NO: 11:

(i) SEQUENCE CHARACTERISTICS:
        (A) LENGTH:            719 base pairs
        (B) TYPE:              nucleic acid
        (C) STRANDEDNESS:     single (D) TOPOLOGY:           linear (xi) SEQUENCE DESCRIPTION: SEQ ID NO: 11:

GATCRAGGAG ATCAAGAAGT GTTTGTTGCC GAATTACAAG AAATGCAAGA AACACAAGTT      60

GATAATGACG CTTACGATGA TAACGAGATA GAAATTATTC GTTCAAAAGA ATTCAGCTTA     120

AAACCAATGG ATTCAGAAGA AGCGGTATTA CAAATGAATC TATTAGGTCA TGACTTCTTT     180

GTATTCACAG ACAGAGAAAC TGATGGAACA AGTATCGTTT ACCGCCGTAA AGACGGTAAA     240

TATGGCTTGA TTCAAACTAG TGAACAATAA ATTAAGTTTA AAGCACTTGT GTTTTTGCAC     300

AAGTGCTTTT TTATACTCCA AAAGCAAATT ATGACTATTT CATAGTTCGA TAATGTAATT     360

TGTTGAATGA AACATAGTGA CTATGCTAAT GTTAATGGAT GTATATATTT GAATGTTAAG     420

TTAATAAATAG TATGTCAGTC TATTGTATAG TCCGAGTTCG AAAATCGTAA AATATTTATA    480

ATATAATTTA TTAGGAAGTT ATAATTGCGT ATTGAGAATA TATTTATTAG TGATAAACTT     540

GTTTGACACA GAATGTTGAA TGAATTATGT CATAAATATA TTTATATTGA TCTACCAATG     600

AGTAAATAAN TATAATTTCC TAACTATAAA TGATAAGANA TATGTTGTNG GCCCAACAGT     660

TTTTTGCTAA AGGANCGAAC GAATGGGATT TTATCCAAAA TCCTGATGGC ATAATAAGA     719

(2) INFORMATION FOR SEQ ID NO: 12:

(i) SEQUENCE CHARACTERISTICS:
        (A) LENGTH:            949 base pairs
        (B) TYPE:              nucleic acid
        (C) STRANDEDNESS:      single
        (D) TOPOLOGY:          linear (xi) SEQUENCE DESCRIPTION: SEQ ID NO: 12:

CTTTACCATC TTCAGCTGAA ACGTGCTTCG CTTCACCAAA CTCTGTTGTT TTTTCACGTT      60

CAATATTATC TTCAACTTGT ACTACAGATT TTAAAATGAA TTTACAAGTA TCTTCTTCAA     120

TATTTTGCAT CATGATATCA AATAATTCAT GACCTTCATT TTGATAGTCA CGTAATGGAT     180

TTTGTTGTGC ATAAGAACGT AAGTGAATAC CTTGACGTAA TTGATCCATT GTGTCGATAT     240

GATCAGTCCA ATGGCTATCA ATAGAACGAA GTAAAATCAT ACGCTCAAAC TCATTCATTT     300

GTTCTTCTAA GATATCTTTT TGACTTTGAT ATGCTGCTTC AATCTTAGCC CAAACGACTT     360

CGAAAATATC TTCAGCATCT TTACCTTTGA TATCATCCTC TGTAATGTCA CCTTCTTGTA     420

AGAAGATGTC ATTAATGTAG TCGATGAATG GTTGATATTC AGGCTCGTCA TCTGCTGTAT     480

TAATATAGTA ATTGATACTA CGTTGTAACG TTGAACGTAG CATTGCATCT ACAACTTGAG     540

AGCTGTCTTC TTCATCAATA ATACTATTTC TTTCGTTATA GATAATTTCA CGTTGTTTAC     600

GTAATACTTC ATCGTATTCT AAGATACGTT TACGCGCGTC GAAGTTATTA CCTTCTACAC     660

GTTTTTGTGC TGATTCTACA GCTCTTGATA CCATTTTTGA TTCAATTGGT GTAGAGTCAT     720

CTAAACCTAG TCGGCTCATC ATTTTCTGTA AACGTTCAGA ACCAAAACGA AATCATTAAT     780

TCATCTTGTA ATGATAAATA GAAGCGACTA TCCCCTTTAT CACCTTGACG TCCAGAACGA     840

CCACGTAACT GGTCATCAAT ACGACGAAGA TTCATGTCGC TCTGTACCTA TTACTGCTAA     900

ACCGCCTAAT TCCTCTACGC CTTCACCTAA TTTGATATCT GTACCACGA                 949

(2) INFORMATION FOR SEQ ID NO: 13:

(i) SEQUENCE CHARACTERISTICS:
        (A) LENGTH:            594 base pairs
        (B) TYPE:              nucleic acid
        (C) STRANDEDNESS:      single
        (D) TOPOLOGY:          linear (xi) SEQUENCE DESCRIPTION: SEQ ID NO: 13:

```
GGGGATCAAT TTANAGGACG TACAATGCCA GGCCGTCGTT NCTCGGAAGG TTTACACCAA      60

GCTATTGAAG CGAGGAAAGG CGTTCAAATT CAAAATGAAA TCTAAAACTA TGGCGTCTAT     120

TACATTCCAA AACTATTTCA GAATGTACAA TAAACTTGCG GGTATGACAG GTACAGCTAA     180

AACTGAAGAA GAAGAATTTA GAAATATTTA TAACATGACA GTAACTCAAA TTCCGACAAA     240

TAAACCTGTG CAACGTAACG ATAAGTCTGA TTTAATTTAC ATTAGCCAAA AAGGTAAATT     300

TGATGCAGTA GTAGAAGATG TTGTTGAAAA ACACAAGGCA GGGCAACCMG TGCTATTAGG     360

TACTGTTGCA GTTGAGACTT CTGTATATAT TTCAAATTTA CTTAAAAAAC GTGGTATCCG     420

TCATGATGTG TTAAATGCGA RAAATCATGA MCGTGAAGCT GAAATTGTTG CAGGCGCTGG     480

RCAAAAAGGT GCCGTTACTA TTGCCACTAM CATGGCTGGT CGTGGTACAG ATATCAAATT     540

AGGTGAAGGC GTTANAANGA AATTAGGCGG TTTANCCAGT AATANGTTCA GAAG           594
```

(2) INFORMATION FOR SEQ ID NO: 14:

(i) SEQUENCE CHARACTERISTICS:
        (A) LENGTH: 2192 base pairs
        (B) TYPE: nucleic acid
        (C) STRANDEDNESS: single
        (D) TOPOLOGY: linear (xi) SEQUENCE DESCRIPTION: SEQ ID NO: 14:

```
GCATGMCTGC AGGTCGATCY SYTGAACAGT CATCAACTAC AACCACTTCA AATTCAGTTT      60

TCGGAAAATC TTGTTTCGCA AGGCTATTAA GTAATTCTGT TATATACTTT TCTGAATTGT     120

ATGTTGGAAC TATTACTGAA AATTTCATCA TTATACCTCT CCCACTTTGA CTACTATATA     180

AACTTAGCTA CCAAATAAAT TTCTGACTAA ACGCTCACTT GATCGGCCAT CTTGATATTT     240

AAAATGTTTA TCTAAGAATG GAATGACTTT TTCTCCTTCA TAATCTTCAT TGTCCAAGGC     300

GTCCATTAAT GCGTCAAATG ATTGCACAAT TTTACCTGGA ACAAATGATT CATATGGTTC     360

ATAAAAATCA CGCGTCGTAA TATAATCTTC TAAATCAAAT GCATAGAAAA TCATTGGCTT     420

TTTAAATACT GCATATTCAT ATATTAAAGA TGAATAGTCA CTAATTAATA AATCTGTTAT     480

GAACAGTATA TCATTAACTT CTCTAAAGTC AGAAACGTCA ACAAAATATT GTTTATGTTT     540

GTCTGCAATA TTAAGTCTAT TTTTCACAAA TGGATGCATT TTAAATAATA CAACCGCGTT     600

ATTTTTTTCG CAATATCTTG CTAAACGTTC AAAATCAATT TTGAAAAATG GGTAATGTGC     660

TGTACCATGA CCACTACCTC TAAATGTTGG TGCGAAAAGA ATGACTTTCT TACCTTTAAT     720

AATTGGTAAT TCATCTTCCA TCTCTTGTTT GATCTGTGTC GCATAAGCTT CATCAAATAG     780

TACATCAGTA CGTTGGGAAC ACCTGTAGGC ACTACATTTT TCTCTTTAAT ACCAAATGCT     840

TCAGCGTAGA ATGGAATATC GGTTTCAAGA TGATACATAA GCTTTTGTAT AAGCTACGGA     900

TGATTTAATG AATCAATAAA TGGTCCACCC TTTTTACCAG TACGACTAAA GCCAACTGTT     960

TTAAAGGCAC CAACGGCATG CCATACTTGA ATAACTTCTT GAGAACGTCT AAAACGCACT    1020

GTATAAATCA ATGGGTGAAA GTCATCAACA AAGATGTAGT CTGCCTTCCC AAGTAAATAT    1080

GGCAATCTAA ACTTGTCGAT GATGCCACGT CTATCTGTAA TATTCGCTTT AAAAACAGTG    1140

TGAATATCAT ACTTTTTATC TAAATTTTGA CGTAACATTT CGTTATAGAT GTATTCAAAG    1200

TTTCCAGACA TCGTTGGTCT AGAGTCTGAT GTGAACAACA CCGTATTCCC TTTTTTCAAG    1260

TGGAAAAATT TCGTCGTATT AAATATCGCT TTAAAAATAA ATTGTCTTGT ATTAAATGAT    1320

TGTTTGCGGA AATACTTACG TAATTCTTTA TATTTACGRA CGATATAAAT ACTTTTAAMT    1380
```

```
TCCCGGAGTC GTTACAACAA CATCAAGGAC AAATTCATTA ACATCGCTAG AAATTTCAGG   1440

TGTAACAGTA TAAACCGTTT TCTTTCGAAA TGCCGCCTTT TCTAAATTCT TTTAGGTAAG   1500

TCTGCAATAA GAAATTGATT TTACCATTTT GTGTTTCTAA TTCGYTGTAT TCTTCTTCTT   1560

GTTCTGGCTT TAGATTTTGA TATGCATCAT TAATCAACAT CTGGGTTTAA CTGTGCAATA   1620

TAATCAAGTT CTTGCTCATT CACTAATAAG TACTTATCTT CAGGTAAGTA ATAACCATTA   1680

TCTAAGATAG CTACATTGAA ACGACAAACG AATTGATTCC CATCTATTTT GACATCATTC   1740

GCCTTCATTG TACGTGTCTC AGTTAAATTT CTTAATACAA AATTACTATC TTCTAAATCT   1800

AGGTTTTCAC TATGTCCTTC AACGAATAAC TGAACACGTT CCCAATAGAT TTTAYCTATA   1860

TATATCTTAC TTTTAACCAA CGTTAATTCA TCCTTTTCTA TTTACATAAT CCATTTTAAT   1920

ACTGTTTTAC CCCAAGATGT AGACAGGTCT GCTTCAAAAG CTTCTGTAAG ATCATTAATT   1980

GTTGCAATTT CAAATTCTTG ACCTTTTAAA CAACGGCTAA TTTATCTAAC AATATCTGGG   2040

TATTGAATGT ATAAGTCTAA CAACATCTTG GAAATCTTTT GAACCACTTC GACTACTACC   2100

AATCAACGTT AGTCCTTTTT CCAATACTAG AACGTGTATT AACTTCTACT GGGAACTCAC   2160

TTACACCTAA CAGTGCAATG CTTCCTTCTG GT                                2192

(2) INFORMATION FOR SEQ ID NO: 15:

(i) SEQUENCE CHARACTERISTICS:
          (A) LENGTH:          2431 base pairs
          (B) TYPE:            nucleic acid
          (C) STRANDEDNESS:    single
          (D) TOPOLOGY:        linear (xi) SEQUENCE DESCRIPTION: SEQ ID NO: 15:

ATGCAGGTCG ATCNCCTNGT TTATTCNGNT TCATCATTTT CCGATAAATA CTGTAAATAT     60

GNNTAGGTCT ACCATTTATA TCGCCTTCGA TATTCATTCG GTCCATTTCA GTACGTATTC    120

TATCAATAGC CGTTTCGATA TACGCTTCAC GTTCACTACG TTTCTTCTTC ATTAAATTGA    180

CTATTCTAAA ATATTGCACA TTATCAATAT AACGAAGAGC CGKATCTTCT AGTTCCCATT    240

TGATTGTATT AATACCAAGA CGATGTGCTA ATGGTGCATA AATTTCTAAT GTTTCTCGAG    300

AAATTCTAAT TTGKTTTTCG CGCGGSATGG STTTCAAGGT ACGCATATTA TGTAATCTGT    360

CTGCTAATTT CAMCAAAATT ACGCGTACAT CTTTGGCAAT CGCAATAAAT AACTTGSGAT    420

GATTTTCAGC TTGTTGTTCT TCTTTTGAGC GGTATTTTAC TTTTTTAAGC TTCGTCACAC    480

CATCAACAAT TCGAGCAACT TCTTCATTGA ACATTTCTTT TACATCTTCA AATGTATACG    540

GTGTATCTTC AATTACATCA TGCAAAAAAC CTGCGACAAT CGTCGGTCCG TCTAATCGCA    600

TTTCTGTTAA AATACCTGCA ACTTGTATAG GATGCATAAT GTATGGTAAT CCGTTTTTTC    660

GGAACTGACC TTTATGTGCT TCATAAGCAA TATGATAGCT TTTTAAAACA TACTCATATT    720

CATCTGCTGA CAAATATGAT TTTGCTTTGT GAAGAACTTC GTCTGCACTA TATGGATATT    780

CGTTGTTCAT TATATGATAC ACCCCATTCA TATTTATTAC TTCGCCTTTA AACAATGGAT    840

TTAGGTACTC TTGTTGAATA GTATTTGTCC CACACCAATC ATACGTCCGT CGACGATAAA    900

TATTTATCCT GTCGTGCATT AATCGTAATA TTAATTTTAC TTGAGCGAGT TTAATTTGTA    960

TACTATTCCT ACTTTTAAAA CTTTTACAAA AATTCGACCT AAATCTACTG TTTCATTTTT   1020

TAAATATTAG TTCTATGATA CTACAATTTA TGARATAAAT AAACGAWGTT ATTAAGGTAT   1080

AATGCTCMAT CATCTATCAT TTTCAGTAAA TAAAAAATCC AACATCTCAT GTTAAGAAAA   1140

CTTAAACAAC TTTTTTAATT AAATCATTGG TYCTTGWACA TTTGATRGAA GGATTTCATT   1200
```

```
TGATAAAATT ATATTATTTA TTATTCGTCG TATGAGATTA AACTMATGGA CATYGTAATY    1260

TTTAAWAKTT TTCMAATACC AWTTAAAWKA TTTCAATTCA AATTATAAAW GCCAATACCT    1320

AAYTACGATA CCCGCCTTAA TTTTTCAACT AATTKTATKG CTGYTCAATC GTACCACCAG    1380

TAGCTAATAA ATCATCTGTA ATTRRSACAG TTGACCTGGK TTAATTGCAT CTTKGTGCAT    1440

TGTYAAAACA TTTGTACCAT ATTCTAGGTC ATAACTCATA ACGAATGACT TCACGAGGTA    1500

ATTTCCCTTC TTTTCTAACA GGTGCAAAGC CAATCCCCAT KGAATAAGCT ACAGGACAGC    1560

CAATGATAAA GCCAACGSGC TTCAGGTCCW ACAACGATAT CAAACATCTC TGTCTTTTGC    1620

GTATTCWACA ATTTTATCTG TTGCATAGCC ATATGCTTCA CCATTATCCA TAATTGTAGT    1680

AATATCCTTG AAACTAACAC CTGGTTTCGG CCAATCTTGA ACTTCTGATA CGTATTGCTT    1740

TAAATCCATT AATATTTCCT CCTAAATTGC TCACGACAAT TGTGACTTTA TCCAATTTTT    1800

TATTTCTGAA AAATCTTGAT ATAATAATTG CTTTTCAACA TCCATACGTT GTTGTCTTAA    1860

TTGATATACT TTGCTGGAAT CAATCGATCT TTTATCAGGT TGTTGATTGA TTCGAATTAA    1920

ACCATCTTCT TGTGTTACAA ATTTTAAGTC TAAGAAAACT TTCAACATGA ATTTAAGTGT    1980

ATCTGGTTTC ACACTTAAAT GTTGACACAA TAACATACCC TCTTTCTGGA TATTTGTTTC    2040

TTGTTTAGTT ATTAATGCTT TATAACACTT TTTAAAAATA TCCATATTAG GTATACCATC    2100

GAAGTAAATC GAATGATTAT GTTGCAAAAC TATAKAAAGW TGAGAAAATT GCAGTTGTTG    2160

CAAGGAATTA GACAAGTCTT CCATTGACGT TGGTAAATCT CTTAATACTA CTTTATCAGT    2220

TTGTTGTTTA ATTCTTCAC CATAATAATA TTCATTCGCA TTTACTTTAT CACTTTTAGG     2280

ATGAATAAGC ACGACAATAT TTTCATCATT TTCTGTAAAA GGTAAACTTT TTCGCTTACT    2340

TCTATAATCT AATATTTGCT GTTCATTCAT CGCAATATCT TGAATAATTA TTTGCGGTGA    2400

TTGATTACCA TTCCATTCGT TGATTTGAAC A                                    2431

(2) INFORMATION FOR SEQ ID NO: 16:

(i) SEQUENCE CHARACTERISTICS:
        (A) LENGTH:         2018 base pairs
        (B) TYPE:           nucleic acid
        (C) STRANDEDNESS:   single
        (D) TOPOLOGY:       linear (xi) SEQUENCE DESCRIPTION: SEQ ID NO: 16:

GCATCAGTTG GTACTTTAAA TAAATGTGCA GTACCAGTCT TAGCAACATT TACAGTTGCT      60

AATTCAGTAT TTTTCTTAGC ATCTTTAATA ACTAAATTTG TTGCACCTTG CTTACTATTC     120

GTTTGCATAG TAGTAAAGTT AATAATTAAT TCTGAATCTG GTTTTACATT TACAGTTTTT     180

GAAATACCGT TAAAGTTACC ATGATCTGTA GAATCATTTG CATTCACACG ACCTAATGCA     240

GCCACGTTTC CTTTAGCTTG ATAGTTTTGA GGGTTATTCT TATCAAACAT ATCGCTTCGT     300

CTTAATTCTG AGTTAACGAA ACCAATCTTA CCGTTGTTAA TTAATGAATA ACCATTTACT     360

TTATCTGTAA CAGTTACAGT TGGATCCTGT CTATTCTCAT CTGTTGATAT GGCAGGATCA     420

TCAAATGTTA ATGTCGTATT AATACTGCCT TCACCAGTAT TGCTAGCATT TGGATCTTGA     480

GTTTGTGCGT TTGCTGCTAC AGGTGCTGCT GGTTGCGCTG CTGCTGGANC ATTCGCTGGC     540

TGTGTTTGAT TTGCCGGTGT TGCATTATTA TWAGGTGTTG CTTGGTTATT TCCTTGACCT     600

GCTTGGTWTG CCGGTGTTGC TTGATTTCCA GGTTGTGCAT GTGCAACGTT ATTCGGATCA     660

GCTTGATCAC CTTGTCCAGC TGGTTGTGTA TTTGGTTGTG CTGCTCCTCC TGCTGGATTA     720

GCCTGTCCAC CTTGGTTTGC TGGTTGTACT GCTGGTTGTC CTTGGTTGGC AGGTGCAGCT     780
```

```
GGCTGTGCTG TAGGATTAGC TTGAGCACCA GCATTTGCGT TAGGCTGTGT ATTGGCATCA    840

GCTGGTTGTG CTGGTTGATT TTGTGCAGGC TGATTTTGCT CTGCTGCAKA CGCTGTTGTC    900

GGGTTAGTAG ATATAAAAGT AACAGTGGCA ATTAAAGCTG AAAAAATACC GACATTAAAT    960

TTTCTGATAC TAAATTTTTG TTGTCTGAAT AAATTCATTA AGTCATCCTC CTGGTTGATT   1020

ATTCTCGCTG TTAAATGATT TCACTTAATC AACTGTTAAG ATAAGTAGTA GCATCTGCGT   1080

TAAAAACACA AAGCAACTCT ATCTAATTAA AATTAATTTT ATCATCATTA TATATTGAGT   1140

ACCAGTGTAT TTTATATTAC ATATTGATTA CTTTGTTTTT ATTTGTTTA TATCATTTTA    1200

CGTTTGTACT ATAAATTATT TCTACAAACA CAAAAAACCG ATGCATACGC ATCGGCTCAT   1260

TTGTAATACA GTATTTATTT ATCTAATCCC ATTTTATCTT GAACCACATC AGCTATTTGT   1320

TGTGCAAATC TTTCAGCATC TTCATCAGTT GCTGCTTCAA CCATGACACG AACTAATGGT   1380

TCTGTTCCAG AAGGTCTTAC TAAAATTCGA CCTTCTCCAT TCATTTCTAC TTCTACTTTA   1440

GTCATAACTT CTTTAACGTC AACATTTTCT TCAACACGAT ATTTATCTGT TACGCGTACG   1500

TTAATTAATG ATTGTGGATA TTTTTTCATT TGTCCAGCTA ATTCACTTAG TGATTTACCA   1560

GTCATTTTTA TTACAGAAGC TAATTGAATA CCAGTTAATA AACCATCACC AGTTGTATTG   1620

TAATCCAYCA TAACGATATG TCCARATKGT TCTCCACCTA AGTTATAATT ACCGCGAMGC   1680

ATTTCTTCTA CTACATATCT GTCGCCAACT TTAGTTTTAT TAGATTTAAT TCCTTCTTGT   1740

TCAAGCGCTT TGTAAAAACC TAAATTACTC ATAACAGTAG AAAACGAATC ATGTCATTAT   1800

TCAATTCTTG ATTTTTATGC ATTTCTTGAC CAATAATAAA CATAATTTGG TCACCGTCAA   1860

CGATTTGACC ATTCTCATCT ACTGCTATGA TTCTGTCTCC ATCGCCGTCA AATGCTAACC   1920

CAAAATCACT TTCAGTTTCA ACTACTTTTT CAGCTAATTT TCAGGATGTG TAAAGCCACA   1980

TTTCTCATTG ATATTATATC CATCAGGGAC TACATCCA                            2018

(2) INFORMATION FOR SEQ ID NO: 17:

(i) SEQUENCE CHARACTERISTICS:
        (A) LENGTH:           2573 base pairs
        (B) TYPE:             nucleic acid
        (C) STRANDEDNESS:     single
        (D) TOPOLOGY:         linear (xi) SEQUENCE DESCRIPTION: SEQ ID NO: 17:

ATTCGAGCTC GGTACCCGKG GATCCTSYAG AGTCGATCCG CTTGAAACGC CAGGCACTGG     60

TACTAGAGTT TTGGGTGGTC TTAGTTATAG AGAAAGCCAT TTTGCATTGG AATTACTGCA    120

TCAATCACAT TTAATTTCCT CAATGGATTT AGTTGAAGTA AATCCATTGA TTGACAGTAA    180

TAATCATACT GCTGAACAAG CGGTTTCATT AGTTGGAACA TTTTTTGGTG AAACTTTATT    240

ATAAATAAAT GATTTGTAGT GTATAAAGTA TATTTTGCTT TTTGCACTAC TTTTTTTAAT    300

TCACTAAAAT GATTAAGAGT AGTTATAATC TTTAAAATAA TTTTTTTCTA TTTAAATATA    360

TGTTCGTATG ACAGTGATGT AAATGATTGG TATAATGGGT ATTATGGAAA ATATTACCC     420

GGAGGAGATG TTATGGATTT TTCCAACTTT TTTCAAAACC TCAGTACGTT AAAAATTGTA    480

ACGAGTATCC TTGATTTACT GATAGTTTGG TATGTACTTT ATCTTCTCAT CACGGTCTTT    540

AAGGGAACTA AAGCGATACA ATTACTTAAA GGGATATTAG TAATTGTTAT TGGTCAGCAG    600

ATAATTWTGA TATTGAACTT GACTGCMACA TCTAAATTAT YCRAWWYCGT TATTCMATGG    660

GGGGTATTAG CTTTAANAGT AATATTCCAA CCAGAAATTA GACGTGCGTT AGAACAACTT    720

GGTANAGGTA GCTTTTTAAA ACGCNATACT TCTAATACGT ATAGTAAAGA TGAAGAGAAA    780
```

```
TTGATTCAAT CGGTTTCAAA GGCTGTGCAA TATATGGCTA AAAGACGTAT AGGTGCATTA      840

ATTGTCTTTG AAAAAGAAAC AGGTCTTCAA GATTATATTG AAACAGGTAT TGCCAATGGA      900

TTCAAATATT TCGCAAGAAC TTTTAATTAA TGTCTTTATA CCTAACACAC CTTTACATGA      960

TGGTGCAAKG ATTATTCAAG CACGAARAT TGCAGCAGCA GCAAGTTATT TGCCATTGTC      1020

TGRWAGTCCT AAGATATCTA AAAGTTGGGT ACAAGACATA GAGCTGCGGT TGGTATTTCA     1080

GAAGTTATCT GATGCATTTA CCGTTATTGT ATCTGAAGAA ACTGGTGATA TTTCGGTAAC     1140

ATTTGATGGA AAATTACGAC GAGACATTTC AAACCGAAAT TTTTGAAGAA TTGCTTGCTG     1200

AACATTGGTT TGGCACACGC TTTCAAAAGA AAGKKKTGAA ATAATATGCT AGAAAKTAAA     1260

TGGGGCTTGA GATTTATTGC CTTTCTTTTT GGCATTGTTT TTCTTTTTAT CTGTTAACAA     1320

TGTTTTTGGA ATATTCTTT AAACACTGGT AATTCTTGGT CAAAAGTCTA GTAAACGGA       1380

TTCAAGATGT ACCCGTTGAA ATTCTTTATA CAACTAAAG ATTTGCATTT AACAAAAGCG      1440

CCTGAAACAG TTAATGTGAC TATTTCAGGA CCACAATCAA AGATAATAAA AATTGAAAAT     1500

CCAGAAGATT TAAGAGTAGT GATTGATTTA TCAAATGCTA AAGCTGGAAA ATATCAAGAA     1560

GAAGTATCAA GTTAAAGGGT TAGCTGATGA CATTCATTAT TCTGTAAAAC CTAAATTAGC     1620

AAATATTACG CTTGAAAACA AAGTAACTAA AAAGATGACA GTTCAACCTG ATGTAAGTCA     1680

GAGTGATATT GATCCACTTT ATAAAATTAC AAAGCAAGAA GTTTCACCAC AAACAGTTAA     1740

AGTAACAGGT GGAGAAGAAC AATTGAATGA TATCGCTTAT TTAAAAGCCA CTTTTAAAAC     1800

TAATAAAAAG ATTAATGGTG ACACAAAAGA TGTCGCAGAA GTAACGGCTT TTGATAAAAA     1860

ACTGAATAAA TTAATGTAT CGATTCAACC TAATGAAGTG AATTTACAAG TTAAAGTAGA      1920

GCCTTTTAGC AAAAAGGTTA AAGTAAATGT TAAACAGAAA GGTAGTTTRS CAGATGATAA     1980

AGAGTTAAGT TCGATTGATT TAGAAGATAA AGAAATTGAA TCTTCGGTAG TCGAGATGAC     2040

TTMCAAAATA TAAGCGAAGT TGATGCAGAA GTAGATTTAG ATGGTATTTC AGAATCAACT    2100

GAAAAGACTG TAAAAATCAA TTTACCAGAA CATGTCACTA AAGCACAACC AAGTGAAACG     2160

AAGGCTTATA TAAATGTAAA ATAAATAGCT AAATTAAAGG AGAGTAAACA ATGGGAAAAT    2220

ATTTTGGTAC AGACGGAGTA AGAGGTGTCG CAAACCAAGA ACTAACACCT GAATTGGCAT    2280

TTAAATTAGG AAGATACGGT GGCTATGTTC TAGCACATAA TAAAGGTGAA AAACACCCAC    2340

GTGTACTTGT AGGTCGCGAT ACTAGAGTTT CAGGTGAAAT GTTAGAATCA GCATTAATAG    2400

CTGGTTTGAT TTCAATTGGT GCAGAAGTGA TGCGATTAGG TATTATTTCA ACACCAGGTG    2460

TTGCATATTT AACACGCGAT ATGGGTGCAG AGTTAGGTGT AATGATTTCA GCCTCTCATA    2520

ATCCAGTTGC AGATAATGGT ATTAAATTCT TTGSCTCGAC CNCCNNGCTN GCA            2573
```

(2) INFORMATION FOR SEQ ID NO: 18:

(i) SEQUENCE CHARACTERISTICS:
        (A) LENGTH: 1962 base pairs
        (B) TYPE: nucleic acid
        (C) STRANDEDNESS: single
        (D) TOPOLOGY: linear (xi) SEQUENCE DESCRIPTION: SEQ ID NO: 18:

```
GTGCTTCCAC CAATACGTTC CACCATATGG AGGATTTCCA ATTAACGCCA CCGGTTCTTC       60

TGTATCAATT GTTAATGTAT TGACATCTTT TACACTAAAT TTAATAATAT CAGACAACCC      120

AACTTCTTCA GCGTTACGCT TAGCAATCTC TACCATTTCT GGATCGATAT CAGAAGCATA      180

TACTTCGATT TCTTTATCAT AATCAGCCAT CTTATCCGCT TCATCACGGT AATCATCATA      240
```

```
AATATTTGCT GGCATGATGT TCCATTGCTC TGATACGAAC TCGCGATTAA AACCAGGTGC      300

GATATTTTGA GCAATTAAAC AAGCTTCTAT AGCTATTGTA CCCGAACCGC AAAATGGATC      360

AATTAAAGGT GTATCACCTT TCCAGTTTGC AAGACGGATT AAACTTGCTG CCAACGTTTC      420

TTTAATTGGT GCTTCACCTT GTGCTAATCT ATAACCACGT CTGTTCAAAC CAGAACCTGA      480

TGTGTCGATA GTCAATAATA CATTATCTTT TAAAATGGCA ACTTCAACAG GGTATTTGGC      540

ACCTGATTCA TTTAACCAAC CTTTTTCGTT ATATGCGCGA CGTAATCGTT CAACAATAGC      600

TTTCTTAGTT ATCGCCTGAC AATCTGGCAC ACTATGTAGT GTTGATTTAA CGCTTCTACC      660

TTGAACTGGG AAGTTACCCT CTTTATCAAT TATAGATTCC CAAGGGAGCG CTTTGGTTTG      720

TTCGAATAAT TCGTCAAACG TTGTTGCGTW AAAACGTCCA ACAACAATTT TGATTCGGTC      780

TGCTGTGCGC AACCATAAAT TTGCCTTTAC AATTGCACTT GCGTCTCCTT CAAAAAATAT      840

ACGACCATTT TCAACATTTG TTTCATAGCC TAATTCTTGA ATTTCCCTAG CAACAACAGC      900

TTCTAATCCC ATCGGACAAA CTGCAAGTAA TTGAAACATA TATGATTCTC CTTTTATACA      960

GGTATTTTAT TCTTAGCTTG TGTTTTTTAT ACATTTCCAA CAAATTTAAT CGCTGATACA     1020

TTAACGCATC CGCTTACTAT TTTAAAACAA GGCAGTGTCA TTATATCAAG ACAAGGCGTT     1080

AATTTTAAGT GTCTTCTTTY CATGAAAAAA GCTCTCCMTC ATCTAGGAGA GCTAAACTAG     1140

TAGTGATATT TCTATAAGCC ATGTTCTGTT CCATCGTACT CATCACGTGC ACTAGTCACA     1200

CTGGTACTCA GGTGATAACC ATCTGTCTAC ACCACTTCAT TTCGCGAAGT GTGTYTCGTT     1260

TATACGTTGA ATTCCGTTAA ACAAGTGCTC CTACCAAATT TGGATTGCTC AACTCGAGGG     1320

GTTTACCGCG TTCCACCTTT TATATTTCTA TAAAAGCTAA CGTCACTGTG GCACTTTCAA     1380

ATTACTCTAT CCATATCGAA AGACTTAGGA TATTTCATTG CCGTCAAATT AATGCCTTGA     1440

TTTATTGTTT CAYCAAGCRC GAACACTACA ATCATCTCAG ACTGTGTGAG CATGGACTTT     1500

CCTCTATATA ATATAGCGAT TACCCAAAAT ATCACTTTTA AAATTATAAC ATAGTCATTA     1560

TTAGTAAGAC AGTTAAACTT TTGTATTTAG TAATTATTTA CCAAATACAG CTTTTTCTAA     1620

GTTTGAAATA CGTTTTAAAA TATCTACATT ATTTGAAGAT GTATTTGTTG TTGTATTATT     1680

CGAAGAAAAA CTTTTATTGT CCTGAGGTCT TGATGTTGCT ACACGTAGTC TTAATTCTTC     1740

TAATTCTTTT TTAAGTTTAT GATTCTCTTC TGATAATTTT ACAACTTCAT TATTCATATC     1800

GGCCATTTTT TGATAATCAG CAATAATGTC ATCTAAAAAT GCATCTACTT CTTCTCTTCT     1860

ATAGCCACGA GCCATCGTTT TTTCAAAATC TTTTTCATAA ATATCTTTTG CTGATAATTT     1920

CAATGAAACA TCTGACATTT TTTCCACCTC ATTAGAAACT TT                         1962

(2) INFORMATION FOR SEQ ID NO: 19:

(i) SEQUENCE CHARACTERISTICS:
         (A) LENGTH:          5253 base pairs
         (B) TYPE:            nucleic acid
         (C) STRANDEDNESS:    single
         (D) TOPOLOGY:        linear (xi) SEQUENCE DESCRIPTION: SEQ ID NO: 19:

TAACTGGACT ACWACCGCCA ACTRAGTATT GAATTGTTTT AACATGCTTT TCCTGTTTTA       60

AATATTTTTA AACATCTTTC GCATGATTCA ACACTGCTTG CTCCGTTTCA CCAGGCTTCG      120

GTGTATAAGT AATAGCTAAA AATTTATCGT CACCTGCTGA AATAAAGCTA GTGCCTAGTC      180

TCGGTCCTCC AAATACAATA GTTGCAACCA AAATTAATGT ACTTAATATA ATTWCAATCC      240

ACTTATGATT TAATGACCAA TGTAATACTT TTTTATAAGT TGTACTAACA ACACCTAATC      300
```

```
CTTCTTGATG TTGTTTATTA CGACGTTTAA CGCCTTTTTT AAATAGTGTA GCTGCCAACG    360
CTGGAACGAG TGTAATTGAC ACTAATAACG ATGCTAATAA ACTAAATGCA ATAGCCAATG    420
CAAAAGGTCT AAACATTTCG CCTACTGAAC CTGATACAAA CACAAGTGGT AAGAAGACGA    480
TAATAGKAAC TAGTGTCGAT GRCATTATTG GTTAAATAC TTCAGTTGTC GCACTGATAA     540
TTAAATTTTC ACCTTTTAGT TGGTTCTTCT GAATCTGTTA AGCGTCGATA AATATTTTCA    600
MCAACTACAA TCGAATCGTC TATCACACGT CCAATCGCTA CTGTTAATGC ACCTAACGTT    660
AGTATATTCA ATGAMACATC ACTCAATTTC AGAGCAATAA GCGSCATAAG AAGTGATAAC    720
GGMATCGATA TMATAGAAAT TGCCGTCGTA CGAATGTTTC TTAAAAACAG CAAAATAACT    780
ATAATTGCCA CGRATTGTAC CTAATGATGC TTTTTCAACC ATCGTATAAA GTGATTTCTC    840
AACAGGCTTT GCAGTATCCA TTGTTTTTGT GACATTAAAA TCTTTATTTT CATCAACGAA    900
TGTATCAATT TTACGTTGTA CATCTTTGGC TACTTGAACT GTATTGGCAT CTTGAGCTTT    960
AGTTATTTGT AGATTAACCG CATCCTTTCC ATTCGTTTTA GAAATAGAAG TACGCACATC    1020
ACCAACTGTA ATATCAGCTA AATCTCCTAG TTTCGCTGTC GGCATACCAC TTATATTATT    1080
TGGTGCTGAC GCTTTTGAAT TTTGCTGTGG TGATGCCTGA TTAACGTCTG ACATGGCTGA    1140
AATTTTGTTT ATTGTCACTT TGGGATTGAG ATTGCCCTTG TCCTCCTGCC AACGTTAATG    1200
GAATATTTAT GTTTTTAAAA GCATCAACAG ATTGATATTG ACCATCAACA ACAATTGATT    1260
TATCTTTATC ACCAAATTGG AACAATCCAA GTGGCGTTGT TCTTGTTGCC GTTTTTAGAT    1320
AGTTTTCTAC ATCATCAGCA GTCAACCCAT ATTTTCAAGT TCATTTTGCT TAAATTTAAG    1380
GGTGATTTCA CGGTTCGTCT GCCCATTTAA TTGCGCATTT TGNACACCAT CTACCGTTTG    1440
CAATTTTGGT ATNAATTGTT CATTCAGTAC TTTCGTTACT TTTTTCAAGT CATTCNCTTT    1500
ATTTGAAAAT GAATATGCTA AAACCGGAAA AGCATCCATC GAATTACGTC NTANTTCTGG    1560
TTGACCAACT TCATCTTTAA ATTTAATTTT NTNTATTTCT NTTNTAAGCT GTTCTTCTGC    1620
TTTATCCAAA TCTGTATTMT TTTCATATTC AACTGTTACA ATTGAAGCAT TTTGTATGGA    1680
TTGCGTTTTA ACATTTTTCA CATATGCCAA TGATCTTACY TGAWTGTCAA TTTTACTACT    1740
TATTTCATCT TGGGTACTTT GTGGCGTTGC ACCCGGCATT GTTGTTGTAA CTGAAATAAC    1800
TGGATKTTGT ACATTTGGTA KTAATTCTMA TTTCAATTTA GCACTCGCAT ATACACCGCC    1860
CAAGACAACT WAAACAACCA TTAMAAAGAT AGCAAACYTA TTCCCTAAAA RGAAAATTGT    1920
AATAGCTTTT TTAWCAACAG TMCTYCCCCC TCTTTCACTA WAATTCAAAA AATTATTTTA    1980
CTCAACCATY CTAWWWTGTG TAAAAAAAAT CTGAACGCAA ATGACAGYCT TATGAGCGTT    2040
CAGATTTCAG YCGTTAATCT ATTTYCGTTT TAATTTACGA GATATTTAA TTTTAGCTTT     2100
TGTTAAACGC GGTTTAACTT GCTCAATTAA TTGGYACAAT GGCTGATTCA ATACATAATC    2160
AAATTCACCA ATCTTTTCAC TTAAGTATGT TCCCCACACT TTTTTAAATG CCCATAATCC    2220
ATAATGTTCT GAGTCTTTAT CTGGATCATT ATCTGTACCA CCGAAATCGT AAGTTGTTGC    2280
ACCATGTTCA CGTGCATACT TCATCATCGT ATACTGCATA TGATGATTTG GTAAAAAATC    2340
TCTAAATTCA TTAGAAGACG CACCATATAA GTAATATGAT TTTGAGCCAG CAAACATTAA    2400
TAGTGCACCA GAAAGATAAA TACCTTCAGG ATGTTCCTTT TCTAAAGCTT CTAGGTCTCG    2460
TTTTAAATCT TCATTTTTAG CAATTTATT TTGCGCATCA TTAATCATAT TTTGCGCTTT     2520
TTTAGCTTGC TTTTCAGATG TTTTCATCTT CTGCTGCCAT TTAGCAATTT CGGCATGAAG    2580
TTCATTCAAT TCTTGATTTA CTTTCGCTAT ATTTTCTTTT GGATCCAACT TTACTAAAAA    2640
```

```
TAGTTCAGCA TCTCCATCTT CATGCAACGC ATCATAAATA TTTTCAAAGT AACTAATATC    2700

ACGCGTTAAG AAGCCATCGC GTTCCCCAGT GATTTTCATT AACTCAGCAA ATGTTTTTAA    2760

ACCTTCTCTA TCAGATCGTT CTACTGTCGT ACCTCGCTTT AAAGCCAAGC GCACTTTTGA    2820

ACGATTTCGG CGTTCAAAAC TATTTAATAA CTCATCATCA TTTTTATCAA TTGGTGTAAT    2880

CATAGTCATA CGTGGTTGGA TGTAGTCTTT TGATAAACCT TCTTTAAATC CTTTATGTTT    2940

AAAACCAAGC GCTTTCAAAT TTTGCAAAGC ATCTGTRCCT TTATCAACTT CAACATCAGG    3000

ATCGRTTTTA ATTGCATACG CTTTCTCAGC TTTAGCAATT TCTTTTGCAC TGTCTAACMA    3060

TGSMTTTAAC GYTTCTTTAT TACTATTAAT CAACAACCAA AACCMCGCGR RAWTATWACM    3120

TAGSGTATAA GGTAATTTAG GTACTTTTTT AAAAAGTAAC TGCGCAACAC CCTGGAACTT    3180

SMCCGTCACG ACCTACAGCG ATTCTTCGCG CGTACCATCC AGTTAATTTC TTTGTTTCTG    3240

CCCATTTCGT TAATTGTAAT AAATCTCCAT TTGGGTGGGR WTTWACAAAT GCGTCATGTT    3300

CCTGATTAGG KGATATGCAT CTTTTCCATG ATTTATGATA TCTCCTTCTA TTTAACAATA    3360

CCTTTAATTA TACAGTTTGT ATCTTATAGT GTCGATTCAG AGCTTGTGTA AGATTTGAAC    3420

TCTTATTTTT GGAAATGTCC ATGCTCCAAT TAATAGTTTA GCAAGTTCAA ATTTACCCAT    3480

TTTAATTGTG AATCATTTTA TATCTATGTT TCGTGTTAAA TTTAATGTTA TCGTACARTT    3540

AATACTTTTC AACTAGTTAC CTATACTTCA ATATACTTTC ATCATCTAAC ACGATATTCA    3600

TTTCTAARAA TGAACCAACT TGACTTCAAT GAATAAATTT TTCCTCAAGC AACCACATTA    3660

ATGTTCATAT ACAATTACCC CTGTTATAAT GTCAATAATC TAACAATGAG GTGTTTGATA    3720

TGAGAACAAT TATTTTAAGT CTATTTATAA TTATGRACAT CGTTGCAATC ATTATGACAT    3780

TGAGTCAACC TCTCCACCGT GAATTACTTT AGTTTACGGG TTATACTTAT CTTTTTCACA    3840

TTTATATTAT CAATCTTTTT CATTTTAATT AAGTCATCAC GATTAAATAA TATATTAACG    3900

ATTMWWTCCA TTGTGCTTGT CATTATTCAT ATGGGCATTC TCGCTCATAG CACTTACGTA    3960

TATTTATACT AATGGTTCAA AGCGATAAAT AGCACCTCTG ATAAAAATTG AATATGGTGA    4020

AGTTGCTTGT GCGTCTTTTA TGATAACCGA ATGATATTTT GAAACTTTAC CATCTTCAAT    4080

TCTAAAATAA ATATCATCAT TTTTTAAAAT CAAATCTGTG TAATGGTCAT TTYKTCHACA    4140

ATGTCCATAT CAARCCATTT CAACCAATTC GATACTGTWK GTGATCGGTT TTTACTTTTC    4200

ACAATAACAG TTTCAAWTGA AAATTGTTTT TGAAAATATT TTTGCAATTT TTTAGTACGC    4260

ATGGAATCAC TTTCTTCCCA TTGAATAAAA AATGGTGGCT TAATTTCATC ATCATCCTGA    4320

TTCATTATAT AAAGCAATTG CCACTTTACC TWCACCATCT TTATGTGTAT CTCTTTCCAT    4380

TTGAATCGGC CCTACTACTT CAACCTGCTC ACTNTGTAGT TTATTTTTAA CTGCCTCTAT    4440

ATCATTTGTA CGCAAACAAA TATTTATTAA AGCCTTGCTC ATACTTCTCT TGAACAATTT    4500

GAGTAGCAAA AGCGACTCCG CCTTCTATCG TTTTTGCCAT CTTTTTCAAC TTTTCATTAT    4560

TTTACTACAT CTAGTAGCTC AAGATAATTT CATTGATATW ACCTAAKKTA TTGAATGTTC    4620

CATATTTATG ATGATACCCA CCTGAATGTA ATTTTATAAC ATCCTCCTGG AAAACTAAAC    4680

CGATCTAACT GATCTATATA ATGAATGATG TGATCANATT TCAATATCAT TAGTATCCCC    4740

CTATTTACAT GTAATTACGC TTATTTTAAA CAAAGTAWAA TTATTTTTGC YCTTAATAAT    4800

TATATAKTGA YYYCWAATTG CTCCCGTTTT ATAATTACTA TTGTTGTAAA ARGGTTAGCT    4860

AAGCTAACTA TTTTGCCTTA GGAGATGTCA CTATGCTATC ACAAGAATTT TCAATAGTT    4920

TTATAACAAT ATAYCGCCCC TATTTAAAAT TAGCCGAGCC GATTTTAGRA AAACACAATA    4980

TATATTATGG CCAATGGTTA ATCTTACGCG ATATCGCTAA ACATCAGCCC ACTACTCTCA    5040
```

```
TTGNAATTTC ACATAGACGG GCAATTGAAA AGCCTACTGC AAGAAAAACT TTAAAAGCTC      5100

TAATAGGAAA TGACCTTATW ACAGTAGAAA ACAGNTTAGA GGATAAACNA CAAAAGNTTT      5160

TAACTTTAAC ACCTAAAGGG CATKAATTAT ATGAGATTGT TTGTCTTGAT GNACAAAAGC      5220

TCCNACAAGC AGNNAGTTGC CAAAACAAAG ATT                                   5253
```

(2) INFORMATION FOR SEQ ID NO: 20:

(i) SEQUENCE CHARACTERISTICS:
        (A) LENGTH:         3263 base pairs
        (B) TYPE:           nucleic acid
        (C) STRANDEDNESS:  single
        (D) TOPOLOGY:      linear (xi) SEQUENCE DESCRIPTION: SEQ ID NO: 20:

```
ACATTGAMAA AGATCACCCA TTACAACCAC ATACAGATGC AGTAGAAGTT TAAAACACAT        60

TTTTCTAATT ATCAAAGCTT AGGATAAATA TGATGTCCTA AGCTTTTCCT TTTACAACTT       120

TTTCGAATAA ACAACAGTTA AATATATTCA CCTTTCTACC AAACTTTTTA TCCCCTCATT       180

TAAATTTTAC CGGKYTCATA TAAAATCCTT TAATTCTTTC TTAACATTAW TTTWTWATCT       240

CTACATYTAT TTTAATAAAT AGAACTGCAC ATTTATTCGA ATACTTAGA TTTCTAGTGA        300

GATAAACTGC TTTATTTATT ATCATTCATC ATGTAAAATA AGATTTAACT GAAATTTTAG      360

TGTTATTTCA CTAATTTTTT AAAATGAACG ACATGATGAA CCTAGTTATT AACCAAATCG      420

TTATTAAGTT ACATTATAGA GATGATTGGA ATGAATTTAT CGATATATAC TCCAATACGA      480

TTTTACTAGG GTTAACAATA AATTAAACAA ACATTCTTAG GAGGRATTTT TAACATGGCA      540

GTATTTAAAG TTTTTTATCA ACATAACAGA GTACGAGGTR RTTGTGCGTG AAAATACACA      600

ATCACTTTAT GTTGAAGCTC ARACAGAAGA ACAAGTAGCG TCGTTACTTG AAAGATCGTA      660

ATTTTAATAT CGAATTTATC ACTAAATTAG AGGGCGCACA TTTAGATTAC GAAAAGAAA       720

ACTCAGCAAC ACTTTAATGT GGAGATTGCT AAATAATGAA ACAATTACAT CCAAATGAAG      780

TAGGTGTATA TGCACTTGGA GGTCTAGGTG AAATCGGTAA AAATACTTAT GCAGTTGAGT      840

ATAAAGACGA AATTGTCATT ATCGATGCCG GTATCAAATT CCCTGATGAT AACTTATTAG      900

GGATTGATTA TGTTATACCT GACTACACAT ATCTAGTTCA AAACCAAGAT AAAATTGTTG      960

GCCTATTTAT AACACATGGT CACGAAGACC ATATAGGCGG TGTGCCCTTC CTATTAAAAC     1020

AACTTAATAT ACCTATTTAT GGTGGTCCTT TAGCATTAGG TTTAATCCGT AATAAACTTG     1080

AAGAAACATC ATTTATTACG TACTGCTAAA CTAAATGAAA TCAATGAGGA CAGTGTGATT     1140

AAATCTAAGC ACTTTACGAT TTCTTTCTAC TTAACTACAC ATAGTATTCC TGAAACTTAT     1200

GGCGTCATCG TAGATACACC TGAAGGAAAA KTAGTTCATA CCGGTGACTT TAAATTTGAT     1260

TTTACACCTG TAGGCAAACC AGCAAACATT GCTAAAATGG CTCAATTAGG CGAAGAAGGC     1320

GTTCTATGTT TACTTTCAGA CTCAACAAAT TCACTTGTGC CTGATTTTAC TTTAAGCGAA     1380

CGTTGAAGTT GGTCAAAACG TTAGATAAGA TCTTCCGTAA TTGTAAAGGT CCGTATTATA     1440

TTTGCTACCT TCGCTTCTAA TATTTACCGA GTTCAACAAG CAGTTGAAGC TGCTATCAAA     1500

AATAACCGTA AAATTGTTAC KTTCGGTCCG TTCGATGGAA AACAATATTA AAATAGKTAT     1560

GGAACTTGGT TATATTAAAG CACCACCTGA ACATTTATT GAACCTAATA AAATTAATAC      1620

CGTACCGAAG CATGAGTTAT TGATACTATG TACTGGTTCA CAAGGTGAAC CAATGGCAGC     1680

ATTATCTAGA ATTGCTAATG GTACTCATAA GCAAATTAAA ATTATACCTG AAGATACCGT     1740

TGTATTTAGT TCATCACCTA TCCCAGGTAA TACAAAAAGT TATTAACAGA ACTATTAATT     1800
```

```
CCTTGTATAA AGCTGGTGCA GATGTTATCC ATAGCAAGAT TTCTAACATC CATACTTCAG    1860

GGCATGGTTC TCAAGGGTGA TCAACAATTA ATGCTTCCGA TTAATCAAGC CGAAATATTT    1920

CTTACCTATT CATGGTGAAT ACCGTATGTT AAAAGCACAT GGTGAGACTG GTGTTGAATG    1980

CGSSKTTGAA GAAGATAATG TCTTCATCTT TGATATTGGA GATGTCTTAG CTTTAACACM    2040

CGATTCAGCA CGTAAAGCTG KTCGCATTCC ATCTGGTAAT GWACTTGTTG ATGGTAGTGG    2100

TATCGGTGAT ATCGGTAATG TTGTAATAAG AGACCGTAAG CTATTATCTG AAGAAGGTTT    2160

AGTTATCGTT GTTGTTAGTA TTGATTTTAA TACAAATAAA TTACTTTCTG GTCCAGACAT    2220

TATTTCTCGA GGATTTGTAT ATATGAGGGA ATCAGGTCAA TTAATTTATG ATGCACAACG    2280

CMAAAWCMAA ACTGATGTTT ATTAGTWAGT TWAATCCAAA ATAAAGAWAT TCAATGGCAT    2340

CAGATTAAAT CTTCTATCAT TGAAACATTA CAACCTTATT TATTKGAAAA AACAGCTAGR    2400

AAACCAATGA TTTTACCAGT CATTATGGAA GGTAAACGAA CAAAARGAAT CAAACAATAA    2460

ATAATCAAAA AGCTACTAAC TTTGAAGTGA AGTTTTAATT AAACTCACCC ACCCATTGTT    2520

AGTAGCTTTT TCTTTATATA TGATGAGCTT GAGACATAAA TCAATGTTCA ATGCTCTACA    2580

AAGTTATATT GGCAGTAGTT GACTGAACGA AAATGCGCTT GTWACAWGCT TTTTTCAATT    2640

STASTCAGGG GCCCCWACAT AGAGAATTTC GAAAAGAAAT TCTACAGGCA ATGCGAGTTG    2700

GGGTGTGGGC CCCAACAAAG AGAAATTGGA TTCCCCAATT TCTACAGACA ATGTAAGTTG    2760

GGGTGGGACG ACGGAAATAA ATTTTGAGAA AATATCATTT CTGTCCCCAC TCCCGATTAT    2820

CTCGTCGCAA TATTTTTTC AAAGCGATTT AAATCATTAT CCATGTCCCA ATCATGATTA    2880

AAATATCACC TATTTCTAAA TTAATATTTG GATTTGGTGA AATGATGAAC TCTTTGCCTC    2940

GTTTAATTGC AATAATGTTA ATTCCATATT GTGCTCTTAT ATCTAAATCA ATGATAGACT    3000

GCCCCGCCAT CTTTTCAGTT GCTTTCAATT CTACAATAGA ATGCTCGTCT GCCAACTCAA    3060

GATAATCAAG TACACTTGCA CTCGCAACAT TATGCGCNAT ACGTCTACCC ATATCACGCT    3120

CAGGGTGCAC AACCGTATCT GCTCCAATTT TATTTAAAAT CTTTGCNTGA TAATCATTTT    3180

GTGCTCTTAG CAGTTACTTT TTTTACACCT AACTCTTTTA AAATTAAAGT CGTCAACGTA    3240

CTTGNTTGAA TATTTTCACC AAT                                            3263

(2) INFORMATION FOR SEQ ID NO: 21:

(i) SEQUENCE CHARACTERISTICS:
         (A) LENGTH:         510 base pairs
         (B) TYPE:           nucleic acid
         (C) STRANDEDNESS:   single
         (D) TOPOLOGY:       linear (xi) SEQUENCE DESCRIPTION: SEQ ID NO: 21:

GGGTACCGAG CTCGAATTCG AGGTGTACGG TAGAAATACT TCACCAATGA TGCACTTACA     60

ATTTTAAATA GATTTTNAAG ACCTTGTTGG TTTTGTACAA TTAATGTGAC ATGACTAGGT    120

CTTGCACGTT TATATGCATC TNCATTACTG AGTTTTTTGT TGATTTCGTT ATGATTTAAT    180

ACGCCTAATT CTTTCATTTG TTGAACCATT TTNATGAAAA TGTAAGCTGT TGCTTCTGTA    240

TCATAAATGG CACGGTGATG TTGCGTTAAT TCTACGCCAT ATTTTTTAGC CAAGAAATTC    300

AAACCATGTT TACCATATTC AGTATTAATC GTACGNGATA ATTCTAAAGT ATCGNTAACA    360

CCATTCGTTG ATGGTCCAAA CCCAAGACGT TCATATCCCG TATCGATGNN GCCCATATCA    420

AACGGAGCAT TATGCGTTAC GGTTTTCGNA TCGGCAACCC TTCTTAAACT CTGTAAGNAC    480

TTCTTCATTT CAGGGGATCT NCTANCATAT                                    510
```

(2) INFORMATION FOR SEQ ID NO: 22:

(i) SEQUENCE CHARACTERISTICS:
        (A) LENGTH:         278 base pairs
        (B) TYPE:           nucleic acid
        (C) STRANDEDNESS:   single
        (D) TOPOLOGY:      linear (xi) SEQUENCE DESCRIPTION: SEQ ID NO: 22:

```
GGGTACCGAG CTCGAATTCT ACACGCTTTT CTTCAGCCTT ATCTTTTTTT GTCGCTTTTT      60

TAATCTCTTC AATATCAGAC ATCATCATAA CTAAATCTCT AATAAATGTA TCTCCTTCAA     120

TACGNCCTTG AGCCCTAACC CATTTACCAA CANTTAGNGC TTTAAAATGT TCTAAATCAT     180

CTTTGTTTTT ACGAGTAAAC ATTTTTAAAA CTAAAGNGTC CGTATAGTCA GTCACTTTAA     240

TTTCTACGGT ATGGNGGCCA CTTTTAAGTT CTTTTAAG                             278
```

(2) INFORMATION FOR SEQ ID NO: 23:

(i) SEQUENCE CHARACTERISTICS:
        (A) LENGTH:         400 base pairs
        (B) TYPE:           nucleic acid
        (C) STRANDEDNESS:   single
        (D) TOPOLOGY:      linear (xi) SEQUENCE DESCRIPTION: SEQ ID NO: 23:

```
GGGTACCGAG CTCGAATTCT GGTACCCCAA ATGTACCTGT TTTACATAAA ATTTCATCTT      60

CAGTAACACC CAAACTTTCA GGTGTACTAA ATATCTGCAT AACTNCTTTA TCATCTACAG     120

GTATTGTTTT TGGNTCAATT CCTGATAAAT CTTGAAGCAT ACGAATCATT GTTGGNTCAT     180

CGTGTCCAAG TATATCANGT TTTAATACAT TATCATGAAT AGAATGGAAA TCAAAATGTG     240

TCGTCATCCA TGCTGAATTT TGATCATCGG CAGGATATTG TATCGGCGTA AAATCATAAA     300

TATCCATGTA ATCAGGTACT ACAATAATAC CCCCTGGNTG CTGTCCAGTT GTACGTTTAA     360

CACCTGTACA TCCTTTAACG NGTCGATCTA TTTCAGCACC                           400
```

(2) INFORMATION FOR SEQ ID NO: 24:

(i) SEQUENCE CHARACTERISTICS:
        (A) LENGTH:         528 base pairs
        (B) TYPE:           nucleic acid
        (C) STRANDEDNESS:   single
        (D) TOPOLOGY:      linear (xi) SEQUENCE DESCRIPTION: SEQ ID NO: 24:

```
GATCATTTGC ATCCATAGCT TCACTTATTT NTCCAGAAGC TAGCGTACAA TCATTTAAAT      60

CTACGCCACC TTCTTTATCA ATAGAGATTC TAAGAAAATN ATCTCTACCC TCTTTGACAT     120

ATTCAACGTC TACAAGTTCA AAATTCAAGT CTTCCATAAT TGGTTTAACA ATCACTTCTA     180

CTTGTCCTGT AATTTTNCTC ATACAGGCCT CCCTTTTTGG CAAATAGAAA AGAGCGGGAA     240

TCTCCCACTC TTCTGCCTGA GTTCACTAAT TTTTAAGCAA CTTAATTATA GCATAAGTTT     300

ATGCTTGAAA CAAATGACTT CACTATTAAT CAGAGATTCT TGTAAAAGTT TGTCCCTTTA     360

TTTCACCATT ACATTTGAAT NGNCTCGTNA GNCATTGTAA AGAGATNCGG GCATAATTTT     420

GTGTCCAGCA TCAATTTTGG TATTTCTTGT CTTACGGCTT ACGGTTNATT AAATACCTNG     480

GNTTTTTNTC TTTTACCTNT NATATNTCGN ANGNTGGGNT TTTTCNNG                  528
```

(2) INFORMATION FOR SEQ ID NO: 25:

(i) SEQUENCE CHARACTERISTICS:
    (A) LENGTH:        557 base pairs
    (B) TYPE:          nucleic acid
    (C) STRANDEDNESS:  single
    (D) TOPOLOGY:      linear (xi) SEQUENCE DESCRIPTION: SEQ ID NO: 25:

```
CAGCCGACAG TTNACAACCA GCNTCACCGT NAGACAGCAA ACGCCACAAA CTACAAGGNT    60
CCAAATGNCT AGACAATACT GGTGNAAGGC ANGTAATAAT ACGACATTAA CATTTGATGA   120
TCCTGCCATA TCAACAGNTC AGAATAGACA GGATCCAACT GTAACTGTTA CAGATAAAGT   180
AAATGGTTAT TCATTAATTA ACAACGGTAA GATTGGTTTC GTTAACTCAG AATTAAGACG   240
AAGCGATATG TTTGATAAGA ATAACCCTCA AAACTATCAA GCTAAAGGAA ACGTGGCTGC   300
ATTAGGTCGT GTGAATGCAA ATGATTCTAC AGATCATGGT AACTTTAACG GTATTTCAAA   360
AACTGTAAAT GTAAAACCAG NTTCAGAATT AATTATTAAC TTTACTACTA TGCAAACCGG   420
ATAGTNAGCA AGGTGCAACA AATTTAGTTA TTAAAGGATG CTAAGGAANN TACTGNNTTA   480
GCACCTGTAA AATGTTGCTT AGGCTGGTCC TGCACATTTA TTTTAAGGTC CNNCTTGTNC   540
TGNTNGGCTC TNGGGGG                                                 557
```

(2) INFORMATION FOR SEQ ID NO: 26:

(i) SEQUENCE CHARACTERISTICS:
        (A) LENGTH:        527 base pairs
        (B) TYPE:          nucleic acid
        (C) STRANDEDNESS:  single
        (D) TOPOLOGY:      linear (xi) SEQUENCE DESCRIPTION: SEQ ID NO: 26:

```
GTCGATCAGC ATCATTGGTA CTTTAAATAA ATGTGCAGTA CCAGTCTTAG CAACATTTAC    60
AGTTGCTAAT TCAGTATTTT CNTTAGCATC TTTAATAACT AANTTTNTNG CACCTTGCNT   120
ACTATTCGTT TGCATAGTAG TAAAGTTAAT AATTAATTCT GANTCTGGTT TTACATTTAC   180
AGTTTTTGAA ATACCGTTAA AGTTACCATG ANCTGTAGNA TCATTTGCNT TCACACGGCC   240
TAATGCAGCC NCGGTTCCTT TAGCTTGATA GTTTTGAGGG GTATTCTTAT CAAACATATC   300
GNTTCGGCTT AATTCTGAGG TAACTGGNAC CNATCTTTAC CNTTGTTAAT TAATGGNTTC   360
CCCTTTACNT TAATCTGTAA CAGTTACAGT TGGGTCCCCG TCTATTCTCA TCTGTTGGTA   420
TGGCAGGGTC ACCACAATGN TAATGTCGGT TTATACTGGN NTCNCCCGNA TTGCTTAGGT   480
TTGGNGCTTG NGGTGTGCGN TTNCTNGCTT CAGGGGNCTG CTGGGTT                 527
```

(2) INFORMATION FOR SEQ ID NO: 27:

(i) SEQUENCE CHARACTERISTICS:
        (A) LENGTH:        578 base pairs
        (B) TYPE:          nucleic acid
        (C) STRANDEDNESS:  single
        (D) TOPOLOGY:      linear (xi) SEQUENCE DESCRIPTION: SEQ ID NO: 27:

```
TGTGAGCTCC CATNACCACC AGTGCGNNCA TTGCCTGGGC TACCGATTGT CAATTTAAAG    60
TCTTCATCTT TAAAGAAAAT TTCAGTACCA TGTTTTTTAA GTACAACAGT TGCACCTAAA   120
CGATCAACTG CTTCACGATT ACGCTCATAT GTCTGTTCCT CAATAGGAAT ACCACTTAAT   180
CGTTCCCATT CTTTGAGGTG TGGTGTAAAG ATCACACGAC ATGTAGGTAA TTGCGGTTTC   240
AGTTTACTAA AGATTGTAAT CGCATCGCCG TCTACGATTA AATTTTGATG CGGTTGTATA   300
TTTTGTAGTA GGAATGTAAT GGCATTATTT CCTTTGAAAT CAACGCCAAG ACCTGGACCA   360
```

| ATTAGTATAC | TGTCAGTCAT | TTCAATCATT | TTCGTCAACA | TTTTCGTATC | ATTAATATCA | 420 |
| ATAACCATCG | CTTCTGGGCA | ACGAGAATGT | AATGCTGAAT | GATTTGTTGG | ATGTGTAGTA | 480 |
| CAGTGATTAA | ACCACTACCG | CTAAATACAC | ATGCACCGAG | CCGCTAACAT | AATGGCACCA | 540 |
| CCTAAGTTAG | CAGATCGGCC | CTCAGGATGA | AGTTGCAT | | | 578 |

(2) INFORMATION FOR SEQ ID NO: 28:

(i) SEQUENCE CHARACTERISTICS:
        (A) LENGTH:         534 base pairs
        (B) TYPE:           nucleic acid
        (C) STRANDEDNESS:   single
        (D) TOPOLOGY:      linear (xi) SEQUENCE DESCRIPTION: SEQ ID NO: 28:

| CGAGCCAGCA | GNTTGCAGCG | GCGTGTCCCA | TAACTAAGGT | GGTGCCATTA | TGTNAGCGGC | 60 |
| TCGTCCATGT | NTATTTGGCG | GTAGTGGTTT | AATCACTGTA | GCTACACATC | CAACAAATCA | 120 |
| TTCAGCATTA | CATTCTCGTN | GCCCAGAAGC | GATGGTTATT | GATATTAATG | ATACGAAAAT | 180 |
| NTTGACGAAA | ATNATTGAAA | TGACTGACAG | TATACTAATN | GGNCCAGGTC | TTGGCGTTGA | 240 |
| TTTCAAGGA | AATAATGCCA | TTNCATTCCT | ACTACAAAAT | ATACAACCGC | ATCAAAATTT | 300 |
| AANCGTAGAC | GGCGNTGCGA | TTNCAATCTT | TNGTAAACTG | NAACCGCAAT | TACCTACATG | 360 |
| TNGTGTGNNC | TTNACACCAC | ACCTCAAAGG | NNTGGGNCGG | TTANGTGGTA | TTCCNNTTGN | 420 |
| GGACAGGCAT | ATGGNGCGTA | ATCGTGNAGC | AGTTGNTCGT | TTAGGNGCAC | TNTNGTCCTT | 480 |
| AAAAAACATG | GTCTGNATNT | CCTTTAANGN | NGNNGCTTTA | AATTGGCAAT | CGGT | 534 |

(2) INFORMATION FOR SEQ ID NO: 29:

(i) SEQUENCE CHARACTERISTICS:
        (A) LENGTH:         565 base pairs
        (B) TYPE:           nucleic acid
        (C) STRANDEDNESS:   single
        (D) TOPOLOGY:      linear (xi) SEQUENCE DESCRIPTION: SEQ ID NO: 29:

| ACCATTCACA | GTGNCATGCA | TCATTGCACA | CCAAATGNTG | TTTGAAGAGG | TGTTTGTTTG | 60 |
| TATAAGTTAT | TTAAAATGAC | ACTAGNCATT | TGCATCCTTA | CGCACATCAA | TAACGACACG | 120 |
| CACACCAGTA | CGTAAACTTG | TTTCATCACG | TAAATCAGTG | ATACCGTCAA | TTTTCTTGTC | 180 |
| ACGAACGAGC | TCTGCAATTT | TTTCAATCAT | ACGAGCCTTA | TTCACTTGGA | AAGGAATTTC | 240 |
| AGTGACAACA | ATACGTTGAC | GTCCGCCTCC | ACGTTCTTCA | ATAACTGCAC | GAGAACGCAT | 300 |
| TTGAATTGAA | CCACGNCCTG | TTTCATATGC | ACGTCTAATA | CCACTCTTAC | CTAAAATAAG | 360 |
| TCCNGCAGTT | GGGGAATCAG | GACCTTCAAT | ATCCTCCATT | AACTCAGCAA | ATTGNAATNT | 420 |
| CAAGGGGTCT | TTACTTTAAG | GCTNAGNNCA | CCCTTGGTTA | ATTCTGTTAA | GTTATTGTGG | 480 |
| TGGGATATTT | CGGTTGCCAT | NCCTNCCNCG | GGTACCCNNA | TGCACCCNTT | GGGTAATNAG | 540 |
| GNTTGGGGGT | TTGTGCCCGG | TAAGC | | | | 565 |

(2) INFORMATION FOR SEQ ID NO: 30:

(i) SEQUENCE CHARACTERISTICS:
        (A) LENGTH:         558 base pairs
        (B) TYPE:           nucleic acid
        (C) STRANDEDNESS:   single
        (D) TOPOLOGY:      linear (xi) SEQUENCE DESCRIPTION: SEQ ID NO: 30:

-continued

| | |
|---|---|
| CGCAAAACGT CANCAGAAGG NACTNCCTAA TGCACTAATG AAGGGCGGTA TTAAATCGTA | 60 |
| CGTTGAGTTA TTGANCGNAA AATAAAGGAA CCTATTCATG AATGAGCCAA TTTATATTCA | 120 |
| TCAATCTAAA GATGATATTG ANGTAGAAAT TGCNATTCAN TATAACTCAG GATATGCCAC | 180 |
| AAATCTTTTA ACTTACGCAA ATAACATTCA TACGTATGAN GGTGGTACGC ATGANGACGG | 240 |
| ATTCAAACGT GCATTTACGC GTGTCTTAAA TAGTTATGGT TTAAGTAGCA AGATTNTGTA | 300 |
| AGANGGAAAA GNTAGNCTTT CTGGTGAAGN TACACGTGAA GGTATNNCNG CNNTTNTATC | 360 |
| TNTCAAACNT GGGGNTCCNC AATTNGGAGG TCAAACGGGG CAAAAATTTG GGNNTTCTGT | 420 |
| AGTGCGTCAN GTTGTNGGTN AATTATTCNN NGNGNCTTTT TACNGTTTTN CTTTGNAAAT | 480 |
| CCNCNAGTCG GNCGTNCNGT GGTTTNNAAA AGGGTTTTTT GNGGCACGTG NACGTGTTNT | 540 |
| TCGGAAAAAA AGCGGGTT | 558 |

(2) INFORMATION FOR SEQ ID NO: 31:

(i) SEQUENCE CHARACTERISTICS:
        (A) LENGTH:         1508 base pairs
        (B) TYPE:           nucleic acid
        (C) STRANDEDNESS:  single
        (D) TOPOLOGY:      linear (xi) SEQUENCE DESCRIPTION: SEQ ID NO: 31:

| | |
|---|---|
| AGTSGWTCCG TGTGCATAGG TRTGAACTTT GAACCACCAC GTTTAATTTC ATCGTCACAA | 60 |
| ATATCTCCAA AACCAAGCTC GTCGATAATC ATCTGTATCA TTGTTAATCT GTGCTGAACG | 120 |
| TCTATAAAAT CATGGTGCTT TTTCAATGGA GACATAAAAC TAGGTAAAAA ATAAAATTCA | 180 |
| TCTGGCTGTA ATTCATGAAA TACTTCGCTA GCTACTATCA TATGTGCAGT ATGGATAGGG | 240 |
| TTAAACTGAC CGCCGTAAAG TACTATCTTT TTCATTATTA TGGCAATTCA ATTTCTTTAT | 300 |
| TATCTTTAGA TTCTCTATAA ATCACTATCA TAGATCCAAT CACTTGCACT AATTCACTAT | 360 |
| GAGTAGCTTC GCTTAATGTT TCAGCTAATT CTTTTTTATC ATCAAAGTTA TTTTGTAGTA | 420 |
| CATGTACTTT AATCAATTCT CTGTTTTCTA ACGTATCATC TATTTGTTTA ATCATATTTT | 480 |
| CGTTGATACC GCCTTTTCCA ATTTGAAAAA TCGGATCAAT ATTGTGTGCT AAACTTCTTA | 540 |
| AGTATCTTTT TTGTTTGCCA GTAAGCATAT GTTATTCTCC TTTTAATTGT TGTAAAACTG | 600 |
| CTGTTTTCAT AGAATTAATA TCAGCATCTT TATTAGTCCA AATTTTAAAG CTTTCCGCAC | 660 |
| CCCTGGTAAA CAAACATATC TAAGCCATTA TAAATATGGT TTCCCTTGCG CTCTGCTTCC | 720 |
| TCTAAAATAG GTGTTTTATA CGGTATATAA ACAATATCAC TCATTAAAGT ATTGGGAGAA | 780 |
| AGATGCTTTA AATTAATAAT ACTTTCGTTA TTTCCAGCCA TACCCGCTGG TGTTGTATTA | 840 |
| ATAACGATAT CGAATTCAGC TAAATAACTT TTCAGCATCT GCTAATGAAA TTTGGTTTAT | 900 |
| ATTTAAATTC CAAGATTCAA AACGAGCCAT CGTTCTATTC GCAACAGTTA ATTTGGGCTT | 960 |
| TACAAATTTT GCTAATTCAT AAGCAATACC TTTACTTGCA CCACCTGCGC CCAAAATTAA | 1020 |
| AATGTATGCA TTTTCTAAAT CTGGATAAAC GCTGTGCAAT CCTTTAACAT AACCAATACC | 1080 |
| ATCTGTATTA TACCCTATCC ACTTGCCATC TTTTATCAAA ACAGTGTTAA CTGCACCTGC | 1140 |
| ATTAATCGCT TGTTCATCAA CATAATCTAA ATACGGTATG ATACGTTCTT TATGAGGAAT | 1200 |
| TGTGATATTA AAGCCTTCTA ATTCTTTTTT CGAAATAATT TCTTTAATTA AATGAAAATC | 1260 |
| TTCAATTGGA ATATTTAAAG CTTCATAAGT ATCATCTAAT CCTAAAGAAT TAAAATTTGC | 1320 |
| TCTATGCATA ACGGGCGACA AGGAATGTGA AATAGGATTT CCTATAACTG CAAATTTCAT | 1380 |
| TTTTTTAATC ACCTTATAAA ATAGAATTTC TTAATACAAC ATCAACATTT TTAGGAACAC | 1440 |

GAACGATTAC TTTAGCCCCT GGTCCTATAG TTATAAAGCC TAGACCAGAG ATCGACCTGC    1500

AGGCAGCA    1508

(2) INFORMATION FOR SEQ ID NO: 32:

(i) SEQUENCE CHARACTERISTICS:
        (A) LENGTH:             1810 base pairs
        (B) TYPE:               nucleic acid
        (C) STRANDEDNESS:     single
        (D) TOPOLOGY:           linear (xi) SEQUENCE DESCRIPTION: SEQ ID NO: 32:

CGCGTCTTCC AAATTTCNAA AGCTGTAAAA AGTTATTAAA TCAAATCTTG CGAATTTGGA    60

TNTAGAGGCA CAATCTGANG TTTATAAAAN TAATGCAGAT AGAGCTTTAA AAGCNTTGTC    120

AAAACGTGAT ATTCAATTTG ATNTCATTTT CTTAGATCCA CCTTATAATA AAGGTCTCAT    180

TGATAAAGCT TTAAAACTAA TTTCAGAGTT TAATTTATTG AAAGAAAATG GTATCATCGT    240

TTGTGAATTT AGCAATCATG AAGAAATAGA TTATCAACCG TTTAATATGA TTAAACGTTA    300

CCATTATGGG TTGACAGACA CATTGTTATT AGAAAAGGGA GAATAGCATG GAACATACAA    360

TAGCGGTCAT TCCGGGTAGT TTTGACCCCA TTACTTATGG TCATTTAGAC ATTATTGAGA    420

GAAGTACAGA TAGATTTGAT GAAATTCATG TCTGTGTTCT TAAAAATAGT AAAAAAGAAG    480

GTACGTTTAG TTTAGAAGAG CGTATGGATT TAATTGAACA ATCTGTTAAA CATTTACCTA    540

ATGTCAAGGT TCATCAATTT AGTGGTTTAC TAGTCGATTA TTGTGAACAA GTAGGAGCTA    600

AAACAATCAT ACGTGGTTTA AGAGCAGTCA GTGATTTTGA ATATGAATTA CGCTTAACTT    660

CMATGAATAA AAAGTTGAAC AATGAAATTG AAACGTTATA TATGATGTCT AGTACTAATT    720

ATTCATTTAT AAGTTCAAGT ATTGTTAAAG AAGTTGCAGC TTATCGAGCA GATATTTCTG    780

AATTCGTTCC ACCTTATGTT GAAAAGGCAT TGAAGAAGAA ATTTAAGTAA TAAAAATAAC    840

AGTATTTTAG GTTTATCATG GTTTACAATC CTAAAATACT GTTTTCATTT GTTAACGATA    900

TTGCTGTATG ACAGGCGTGT TGAAATCTGT TTGTTGTTGC CCGCTTATTG CATTGTATAT    960

GTGTGTTGCT TTGATTTCAT TTGTGAAGTA ATGTGCATTG CTTTTGTTAA TATTGGTTAT    1020

ATATTGTCTT TCTGGGAACG CTGTTTTTAA ATGCTTTAAA TATTGTCTGC CACGGTCGTT    1080

CATCGCTAAT ACTTTAACTG CGTGAATGTT ACTCGTAACA TCTGTAGGTT TAATGTTTAA    1140

TAATACATTC ATTAACAGTC TTTGGATATG CGTATATGTA TAACGCTTTG TTTTTAGTAA    1200

TTTTACAAAA TGATGAAAAT CAGTTGCTTC ATAAATGTTA GATTTCAAAC GATTTTCAAA    1260

ACCTTCAGTA ACAGTATAAA TATTTTTTAA TGAATCTGTA GTCATAGCTA TGATTTGATA    1320

TTTCAAATAT GGAAATATTT GATTTAATGT WATATGAGGT GTTACGTACA AGTGTTGAAT    1380

ATCTTTAGGT ACCACATGAT GCCAATGATC ATCTTGACTA ATGATTGATG TTCTAATAGA    1440

TGTACCACTT SCAAACTGAT GGTGTTGAAT TAATGAATCA TGATGTTGAG CATTTCTCG     1500

TTTGATAGAA ATTGCATTGA TGTTTTTAGC ATTTTTAGCA ATTGCTTTCA GGTAACTAAT    1560

ACCAAGTATG TTGTTAGGAC TTGCTAGTGC TTCATGATGC TCTAATAATT CGCTAATGAT    1620

ACGAGGGTAG CTTTTACCTT CTTTTACTTT TNGTGAAAAG GATTCAGATN GTTCAATTTC    1680

ATTAATNCTG NGTGCTAATT GCTTTAANGT TTNGATATCA TTATTTTCAC TACCAAATGC    1740

AATGGTATCG ACACTCATAT AATCNGCGAC TTNAACGGCT AGTTCGGCCA AGGGATCGAC    1800

CGGCAGGCAG    1810

(2) INFORMATION FOR SEQ ID NO: 33:

(i) SEQUENCE CHARACTERISTICS:
  (A) LENGTH: 1876 base pairs
  (B) TYPE: nucleic acid
  (C) STRANDEDNESS: single
  (D) TOPOLOGY: linear (xi) SEQUENCE DESCRIPTION: SEQ ID NO: 33:

```
TCTGAATGAT CTARACGGAT TAAATTATTT AGCTGGTAAA ACAATCGACG AAGTTAACAC     60
AAAAGCATTC GAAGGTACAT TATTAGCGCA TACTGATGGT GGTGTTCCTA ACATGGTAGT    120
GAACATTCCA CAATTAGATG AAGAAACTTT CGGTTACGTC GTATACTTCT TCGAACTTGC    180
TTGTGCAATG AGTGGATACC AATTAGGCGT AAATCCATTT AACCAACCTG GTGTAGAAGC    240
ATATAAACAA AACATGTTCG CATTATTAGG TAAACCTGGT TTTGAAGACT TGAAAAAAGA    300
ATTAGAAGAA CGTTTATAAA ATACATTACT TCAAAGATTA GTGAAGTTTG AAAAGATAGA    360
ACTAGACGTT AACTATTTAA AGCATATTTT CGAGGTTGTC ATTACAAATG TAAAAATGTA    420
ATGACAACCT CGTTTTTATT TATATGCAAG AACTAGGTTA CTAGCTAATG TGACAAGATG    480
TTWAGAGAAA ATTAAAGATA AAATAATATC TGCCTTACAA TAATATTGTT ATACTACTAG    540
AGACTGATTT ATTAGCATGA TTACATGTTA ATGTTTCTTT ACTTAGTAAT TAACTTTRTA    600
ATGTAARAHT AATTATCTTC ADCCAHAGAA AGGGATTGAT GATTTGTCGT WTCMTCAATT    660
AGAAGAATGG TTTGAGATAT KTCGACAGTT TGGTTWTTTA CCTGGATTTA TATTGTTATA    720
TATTAGAGCT NTAATTCCAG TATTTCCTTT ARCACTCTAT ATTTTAATTA ACATTCAAGC    780
TTATGGACCT ATTTTAGGTA TATTGATTAG TTGGCTTGGA TTAATTTCTG GAACATTTAC    840
AGTCTATTTG ATCTGTAAAC GATTGGTGAA CACTGAGAGG ATGCAGCGAA TTAAACAACG    900
TACTGCTGTT CAACGCTTGA TTAGTTTTAT TGATCGCCAA GGATTAATCC CATTGTTTAT    960
TTTACTTTGT TTTCCTTTTA CGCCAAATAC ATTAATAAAT TTTGTAGCGA GTCTATCTCA   1020
TATTAGACCT AAATATTATT TCATTGTTTT GGCATCATCA AAGTTAGTTT CAACAATTAT   1080
TTTAGGTTAT TTAGGTAAGG AAATTACTAC AATTTTAACG CATCCTTTAA GARGGATATT   1140
AATGTTAGTT GGTGTTGGTT GTATTTGGA TTGTTGGAAA AAAGTTAGAA CAGCATTTTA    1200
TGGGATCGAA AAAGGAGTGA CATCGTGAAA AAAGTTGTAA AATATTTGAT TTCATTGATA   1260
CTTGCTATTA TCATTGTACT GTTCGTACAA ACTTTTGTAA TAGTTGGTCA TGTCATTCCG   1320
AATAATGATA TGYMCCCAAC CCTTAACAAA GGGGATCGTG TTATTGTWAA TAAAATTAAA   1380
GTAACATTTA ATCAATTGAA TAATGGTGAT ATCATAACAT ATAGGCGTGG TAACGGAGAT   1440
ATATACTAGT CGAATTATTG CCAAACCTGG TCAATCAATG GCGTTTCGTC AGGGACAATT   1500
ATACCGTGAT GACCGACCGG TTGACGCATC TTATGCCAAG AACAGAAAAA TTAAAGATTT   1560
TAGTTTGCGC AATTTTAAAG AATTAGGATG GTGATATTAT TCCGCCAAAC AATTTTGTTG   1620
TGCTAAATGA TCAAGATAAT AACAAGCACG ATTCAAGACA ATTTGGTTTA ATCGATAAAA   1680
AGGATATTAT TGGTAATGTT AGTTTACGAT ACTATCCTTT TTCAAAATGG ACTGTTCAGT   1740
TCAAATCTTA AAAAGAGGTG TCAAAATTGA AAAAAGAAAT ATTGGAATGG ATTATTTCAA   1800
TTGCAGTCGC TTTTGTCATT TTATTTATAG TAGGTAAATT TATTGTTACG CCATATACAA   1860
TTAAAGGTGA ATCAAT                                                  1876
```

(2) INFORMATION FOR SEQ ID NO: 34:

(i) SEQUENCE CHARACTERISTICS:
  (A) LENGTH: 2687 base pairs

```
      (B) TYPE:            nucleic acid
      (C) STRANDEDNESS:    single
      (D) TOPOLOGY:        linear (xi) SEQUENCE DESCRIPTION: SEQ ID NO: 34:

TATGATGATG GTAAAGATCC TAAAGGATTA CCTAAAGCTG ATATTGTTTT ACTTGGTATT      60

TCGAGAACTT CAAAGACACC ATTATCTCAG TATTTAGCGC ATAAGAGTTA CAAAGTTATG     120

AATGTACCGA TTGTACCAGA AGTGACACCG CCAGATGGCT TATATGATAT TAATCCAAAG     180

AAATGTATCG CACTTAAAAT AAGTGAAGAA AAATTAAATC GCATTAGAAA AGAGCGACTA     240

AAACAATTAG GACTAGGTGA CACAGCTCGA TATGCAACAG AAGCACGAAT TCAAGAAGAA     300

TTGAATTACT TTGAAGAAAT CGTAAGTGAA ATTGGATGTC CTGTCATTGA TGTTTCTCAA     360

AAAGCAATCG AAGAAACAGC AAACGATATA ATCCATTATA TTGAACAAAA TAAATCGAAA     420

TGATTTCATT TTTGTCGAAA ATTAGGTATA ATAGTATAAC TAATGCTTAA TAGGTGATTT     480

AATTTGCGAA TAGATCAATC GATCATTAAT GAAATAAAAG ATAAAACCGA CATTTTAGAC     540

TTGGTAAGTG AATATGTWAA ATTAGAAAAG AGAGGACGCA ATTATATAGG TTTGTGTCCT     600

TTTCATGATG AAAAGACACC TTCATTTACA GTTTCTGAAG ATAAACAAAT TTGTCATTGT     660

TTTGGTTGTA AAAAAGGTGG CAATGTTTTC CAATTTACTC AAGAAATTAA AGACATATTC     720

ATTTGTTGAM GCGGTTAAAG AATTAGGTGG WTAGRGTTAA TGTTTGCTGT AGRTATTGAG     780

GCAMCACAAT CTTWACTCAA ATGTYCAAAT TSCTTCTSRY GRTTTACAAA TGATTGACAW     840

TGCATGGRGT TAWTACAAGR ATTTTATTAT TACGCTTTAA CAAAGACAGT CGAAGGCGAA     900

CAAGCATTAA CGTACTTACA AGAACGTGGT TTTACAGATG CGCTTATTAA AGAGCGAGGC     960

ATTGGCTTTG CACCCGATAG CTCACATTTT TGTCATGATT TTCTTCAAAA AAAGGGTTAC    1020

GATATTGAAT TAGCATATGA AGCCGGATTA TWATCACGTA ACGAAGAAAA TTTCAGTTAT    1080

TTACGATAGA TTYCGAAAYC GTATTATGTT YCCTTTGAAA AATGCGCAAG GAAGAATTGT    1140

TGGATATTCA GGTCGAACAT ATACCGGTCA AGAACCAAAA TACTTAAATA GTCCTGAAAC    1200

ACCTATCTTT CAAAAAAGAA AGTTGTTATA CAACTTAGAT AAAGCGCGTA ATCAATTAG    1260

AAAATTAGAT GAAATCGTAT TACTAGAAGG TTTTATGGAT GTTATAAAAT CTGATACTGC    1320

TGGCTTGAAA AACGTTGTTG CAACAATGGG TACACAGTTG TCAGATGAAC ATATTACTTT    1380

TATACGAAAG TTAACATCAA ATATAACATT AATGTTTGAT GGGGATTTTG CGGGTAGTGA    1440

AGCAACACTT AAAACAGGTY CAAAATTTGT TACAGCAAGG CTAAATGTR TTTKTTATAC    1500

AATTGCCATC AGGCATGGAT CCGGATGAAT ACATTGGTAA GTATGGCAAC GATGCATTTM    1560

CTGCTTTTST AAAAAATGAC AAAAAGTCAT TTSCACATTA TAAAGTGAGT ATATTAAAAG    1620

ATGAAATTGC ACATAATGAC CTTTCATATG AACGTTATTT GAAAGAMCTA AGTCATGATA    1680

TTTCGCTTAT GAAATCATCG ATTTTGCAAC AAAAGGCTTT AAATGATGTT GCACCATTTT    1740

TCAATGTTAG TCCTGAGCAA TTAGCTAACG AAATACAATT CAATCAAGCA CCAGCCAATT    1800

ATTATCCAGA AGATGAGTAT GGCGGTTACA TTGAACCTGA GCCAATTGGT ATGGCACAAT    1860

TTGACAATTT GAGCCGTCAA GAAAAAGCGG AGCGAGCATT TTTAAAACAT TTAATGAGAG    1920

ATAAAGATAC ATTTTTAAAT TATTATGAAA GTGTTGATAA GGATAACTTC ACAAATCAGC    1980

ATTTTAAATA TGTATTCGAA GTCTTACATG ATTTTTATGC GGAAAATGAT CAATATAATA    2040

TCAGTGATGC TGTGCAGTAT GTTAATTCAA ATGAGTTGAG AGAAACACTA ATTAGCTTAG    2100

AACAATATAA TTTGAATGAC GAACCATATG AAAATGAAAT TGATGATTAT GTCAATGTTA    2160

TTAATGAAAA AGGACAAGAA ACAATTGAGT CATTGAATCA TAAATTAAGG GAAGCTACAA    2220
```

```
GGATTGGCGA TGTAGAATTA CAAAAATACT ATTTACAGCA AATTGTTGCT AAGAATAAAG    2280

AACGCATGTA GCATGTGATT TTAAAGAATA ATACGAATAA TGATTATGTC AAAATGTATA    2340

AGGGTAAATG ATAGTTACCG CATTTAAACA ACACTATTGA AAAATAAATA TTGGGATTAG    2400

TTCCAATTTG TAAAATAAAA TTAAAAATAT GGATGAATTA ATTAAGAATT TAGTTTAAAA    2460

TAGCAATATT GAATAAATTT CGAATGTTCA TATTTAAAAT CGGGAGGCCG TTTCATGTCT    2520

GATAACACAG TTAAAATTAA AAAACAAACA ATTGATCCGA CATTAACATT AGAAGATGTT    2580

AAGAAGCAAT TAATTGAAAA AGGTAAAAAA GAGGGTCATT TAAGTCATGA AGAAATTGCT    2640

GAAAAACTTC AGAATTTTGA TATCGACTCT GATCAAATGG ATGATTT                 2687

(2) INFORMATION FOR SEQ ID NO: 35:

(i) SEQUENCE CHARACTERISTICS:
           (A) LENGTH:         2800 base pairs
           (B) TYPE:           nucleic acid
           (C) STRANDEDNESS:   single
           (D) TOPOLOGY:       linear (xi) SEQUENCE DESCRIPTION: SEQ ID NO: 35:

NTNAATTAAC ATGCGAGGNC ACCCCTTTAT TGCTACTCCA TACTTCTCAT AAAATCATAT      60

TAACATAACA CCCTTAATTG TCAGACTATT NAAATAAATA AAACACTTCA TTTTTACGCA     120

TTTCTGCCAA ATTAAGATGA AGTAAAAGCT AAGTCGACCT AAAAAAGCAC CCTTCTAGTC     180

GATTAATCTA AAAGGGGTGC CATATACTTT AATTTTAATA CATGATTGAT TCTAAAAAAG     240

TGAATTATTC CACAGTAACT GATTTAGCAA GGTTACGTGG TTTATCAACA TCTAAATCTC     300

TGTGTAATGC TGCATAGTAT GAAATTAATT GTAATGCAAC CACTGATACT AATGGCGTTA     360

ACAATTCATG TACATGAGGA ATGACATAAG TGTCGCCTTC TTTTTCAAGA CCCTCCATAG     420

AAATAATACA TGGATGTGCA CCACGTGCTA CTACCTCTTT AACGTTACCA CGAATTGATA     480

AATTAACTTT CTCTTGTGTT GCTAAACCTA CAACTGGTGT ACCTTCTTCG ATTAAGGCAA     540

TTGTACCATG TTTAAGTTCT CCACCAGCAA AACCTTCTGC TTGAATGTAA GAAATTTCTT     600

TAAGTTTTAA CGCACCTTCT AAACTTACGT TATAGTCAAT AGTACGTCCG ATAAANAATG     660

CATTGCGTGT TGTTTCTAAG AAATCTGTAG CAATTTGTTC CATAATTGGT GCATCGTCAA     720

CAATTGCTTC TATTGCTGTT GTTACTTTTG CTAATTCTCT CAATAAATCA ATATCTGCTT     780

CACGACCATG CTCTTTTGCA ACGATTTGAG ACAAGAWTGA TAATACTGCA ATTTGTGCAG     840

WATAWGCTTT TGTAGATGCA ACTGCGAWTT CAGGGACCCG CGTGTAATAA CAATGTGTGG     900

TCTGCTTCAC GTTGATAAAG TTGAACCTGC AACATTAGTG ATTGTTAATG AWTTATGAMC     960

TAATTTATTA GTTWCAACTA AATACGGCGC GGCTATCTGG CAGTTTCACC TGATTGAGAA    1020

ATATAAACGA ACAATGGTTT TTAAGATAAT AATGGCATGT TGTAGACAAA CTCTGATGCA    1080

ACGTGTACTT CAGTTGGTAC GCCAGCCCAT TTTTCTAAAA ATTCTTTACC TACTAAACCT    1140

GCATGGTAGC TTGTACCTGC TGCAATAACG TAAATGCGGT CTGCTTCTTT AACATCATTG    1200

ATGATGTCTT GATCAATTTT CAAGTTACCT TCTGCATCTT GATATTCTTG AATAATACGA    1260

CGCATTACTG CTGGTTGTTC ATGAATTTCT TTAACATGT AGTGTGCATA AACACCTTTT    1320

TCAGCATCTG ATGCATCAAT TTCAGCAATA TATGAATCAC GTTCTACAAC GTTTCCATCT    1380

GCATCTTTAA TAATAACTTC ATCTTTTTTA ACAATAACGA TTTCATGGTC ATGGRTTTCT    1440

TTATATTCGC TTGTCACTTG TAACATTGCA AGTGCGTCTG ATGCGATAAC ATTGAAACCT    1500

TCACCAACAC CTAATAATAA TGGTGATTTA TTTTTAGCAA CATAGATTGT GCCTTTGHCT    1560
```

```
TCAGCATCTA ATAAACCTAA TGCATATGAA CCATGTAATA ATGACACAAC TTTTGTAAAT    1620

GCTTCTTCAG TTGAAAGTCC TTGATTTGAA AAGTATTCAA CTAATTGAAC GATAACTTCT    1680

GTATCTGTTT CTGAAATGAA TGATACACCT TGTAAGTATT CACCTTTTAA CTCTTCATAG    1740

TTTTCAATAA CACCGTTATG AACTAGAGTA AAACGGCCAT TTGATGATTG ATGTGGATGA    1800

GAGTTTTCAT GATTCGGTAC ACCGTGTGTT GCCCAACGTG TGTGACCGAT TCCAACAGGT    1860

CCATTCAAAA TCGCTACTAT CAGCAACTTT ACGTAATTCT GCAATACGAC CTTTTTCTTT    1920

AAATACAGTT GTATTATCAT YATTTACTAC TGCGATACCT GCAGAGTCAT AACCTCTGTA    1980

TTCTAATTTT TCTACAACCT TTTAATAATA ATTTCTTTGG CATTATCATA GCCAATATAA    2040

CCAACAATTC CACACATAAC GACATTTTCC TCCATATTGG AATAGTACGS GTAAATTATG    2100

ATTTATTGCC GATAATTTAG ATTGACAATC TGCTTTCATA ATATAAATAG GAACATGCTA    2160

TCATCGCATT CATCCATAAC AAATTAAGCA TAGTTATTTT TACAACTATA CAAATTGCTC    2220

ACACTGTACT TTCCATATTA ATATTTTTA TATTCAATTT CTGGCGATCT TATTAACTTT     2280

GTCCATTAAG TCACCCTAAT GTTTTACTTA ATAAGCTAAC GAATGAGCCA CATCCGGGAT    2340

AGCATCCGCC GATCTATTCG ATCACTATCC TCTTCGTCTA CAAATACATA TATTGCACTC    2400

TATAAAGGCC ACTCATATAT TAACCTTTAA TCTTCAAATA CAAATATTTA TTTGCACAGG    2460

CGCTTTAACT GTACTGCCGA ACTTTCCCCC TTTCCATTAA TCATTATTGT ACAACGGTGT    2520

TGTTTTGTTT TGCAAATATT TTCACAATAA AATTTTAAAA ATCCTAAAAC AATTTTTTG     2580

TTTTACTTTT TCAAAATATC TATACTGTCA CATTGATGAC ACTTTATTTA ATTTTGTCAC    2640

ATTTATTTTG ACAAGTTGA TTTTTGTTTA TATTGAGTAA CAAGTAACCT CTCTATACAC     2700

TATATATAGT CACATATATT AAAAAAGAGG TGTAAACATG TCACAAACTG AAGAGAAAAA    2760

AGGAATTGGT CGTCGTGTTC AAGCATTTGG ATCGACCGCA                          2800

(2) INFORMATION FOR SEQ ID NO: 36:

(i) SEQUENCE CHARACTERISTICS:
        (A) LENGTH:         2934 base pairs
        (B) TYPE:           nucleic acid
        (C) STRANDEDNESS:   single
        (D) TOPOLOGY:       linear (xi) SEQUENCE DESCRIPTION: SEQ ID NO: 36:

CATGAAATGC AAGAAGAACG TCGTATTTGT TATGTAGCAA TTACAAGGGC TGAAGAGGTG    60

TTATATATCA CTCATGCGAC ATCAAGAATG TTATTTGGTC GCCCTCAGTC AAATATGCCA    120

TCCAGATTTT TAAAGGAAAT TCCAGAATCA CTATTAGAAA ATCATTCAAG TGGCAAACGA    180

CAAACGATAC AACCTAAGGC AAAACCTTTT GCTAAACGCG GATTTAGTCA ACGAACAACG    240

TCAACGAAAA AACAAGTATT GTCATCTGAT TGGAATGTAG GTGACAAAGT GATGCATAAA    300

GCCTGGGGAG AAGGCATGGT GAGTAATGTA AACGAGAAAA ATGGCTCAAT CGAACTAGAT    360

ATTATCTTTA AATCACAAGG GCCAAAACGT TTGTTAGCGC AATTTGCACC AATTGAAAAA    420

AAGGAGGATT AAGGGATGGC TGATTTATCG TCTCGTGTGA ACGRDTTACA TGATTTATTA    480

AATCAATACA GTTATGAATA CTATGTAGAG GATAATCCAT CTGTACCAGA TAGTGAATAT    540

GACAAATTAC TTCATGAACT GATTAAAATA GAAGAGGAGC ATCCTGAGTA TAAGACTGTA    600

GATTCTCCAA CAGTTAGAGT TGGCGGTGAA GCCCAAGCCT CTTTCAATAA AGTCAACCAT    660

GACACGCCAA TGTTAAGTTT AGGGAATGCA TTTAATGAGG ATGATTTGAG AAAATTCGAC    720

CAACGCATAC GTGAACAAAT TGGCAACGTT GAATATATGT GCGAATTAAA AATTGATGGC    780
```

-continued

```
TTAGCAGTAT CATTGAAATA TGTTGATGGA TACTTCGTTC AAGGTTTAAC ACGTGGTGAT    840

GGAACAACAG GTTGAAGATA TTACCGRAAA TTTAAAAACA ATTCATGCGA TACCTTTGAA    900

AATGAAAGAA CCATTAAATG TAGAAKTYCG TGGTGAAGCA TATATGCCGA GACGTTCATT    960

TTTACGATTA AATGAAGAAA AAGAAAAAAA TGATGAGCAG TTATTTGCAA ATCCAAGAAA   1020

CGCTGCTGCG GGATCATTAA GACAGTTAGA TTCTAAATTA ACGGCAAAAC GAAAGCTAAG   1080

CGTATTTATA TATAGTGTCA ATGATTTCAC TGATTTCAAT GCGCGTTCGC AAAGTGAAGC   1140

ATTAGATGAG TTAGATAAAT TAGGTTTTAC AACGAATAAA AATAGAGCGC GTGTAAATAA   1200

TATCGATGGT GTTTTAGAGT ATATTGAAAA ATGGACAAGC CAAAGAAGAG TTCATTACCT   1260

TATGATATTG ATGGGATTGT TATTAAGGTT AATGATTTAG ATCAACAGGA TGAGATGGGA   1320

TTCACACAAA AATCTCCTAG ATGGGCCATT GCTTATAAAT TTCCAGCTGA GGAAGTAGTA   1380

ACTAAATTAT TAGATATTGA ATTAAGTATT GGACGAACAG GTGTAGTCAC ACCTACTGCT   1440

ATTTTAGAAC CAGTAAAAGT AGCTGGTACA ACTGTATCAA GAGCATCTTT GCACAATGAG   1500

GATTTAATTC ATGACAGAGA TATTCGAATT GGTGATAGTG TTGTAGTGAA AAAAGCAGGT   1560

GACATCATAC CTGAAGTTGT ACGTAGTATT CCAGAACGTA GACCTGAGGA TGCTGTCACA   1620

TATCATATGC CAACCCATTG TCCAAGTTGT GGACATGAAT TAGTACGTAT TGAAGGCGAA   1680

GTTAGCACTT CGTTGCATTA ATCCAAAATG CCAAGCACAA CTTGTTGAAG GATTGATTCA   1740

CTTTGTATCA AGACAAGCCA TGAATATTGA TGGTTTAGGC ACTAAAATTA TTCAACAGCT   1800

TTATCAAAGC GAATTAATTA AGATGTTGC TGATATTTTC TATTTAACAG AAGAAGATTT   1860

ATTACCTTTA GACAGAATGG GGCAGAAAAA AGTTGATAAT TTATTAGCTG CCATTCAACA   1920

AGCTAAGGAC AACTCTTTAG AAAATTTATT ATTTGGTCTA GGTATTAGGC ATTTAGGTGT   1980

TAAAGCGAGC CAAGTGTKAG CAGAAAAATA TGAAACGATA GATCGATTAC TAACGGTAAC   2040

TGAAGCGGAA TTAGTAGAAT TCATGATATA GGTGATAAAG TAGCGCAATC TGTAGTTACT   2100

TATTTAGCAA ATGAAGATAT TCGTGCTTTA ATTCCATAGG ATTAAAAGAT AAACATGTTA   2160

ATATGATTTA TGAAGGTATC CAAAACATCA GATATTGAAG GACATCCTGA ATTTAGTGGT   2220

AAAACGATAG TACTGACTGG TAAGCTACAT CCAAATGACA CGCAATGAAG CATCTAAATG   2280

GCTTGCATCA CCAAGGTGCT AAAGTTACAA GTAGCGTTAC TAAAAATACA GATGTCGTTA   2340

TTGCTGGTGA AGATGCAGGT TCAAAATTAA CAAAAGCACA AAGTTTAGGT ATTGAAATTT   2400

GGACAGAGCA ACAATTTGTA GATAAGCAAA ATGAATTAAA TAGTTAGAGG GGTATGTCGA   2460

TGAAGCGTAC ATTAGTATTA TTGATTACAG CTATCTTTAT ACTCGCTGCT TGTGGTAACC   2520

ATAAGGATGA CCAGGCTGGA AAAGATAATC AAAAACATAA CAATAGTTCA AATCAAGTAA   2580

AAGAAATTGC AACGGATAAA AATGTACAAG GTGATAACTA TCGTACATTG TTACCATTTA   2640

AAGAAAGCCA GGCAAGAGGA CTTTTACAAG ATAACATGGC AAATAGTTAT AATGGCGGCG   2700

ACTTTGAAGA TGGTTTATTG AACTTAAGTA AAGAAGTATT TCCAACAGAT AAATATTTGT   2760

ATCAAGATGG TCAATTTTTG GACAAGAAAA CAATTAATGC CTATTTAAAT CCTAAGTATA   2820

CAAAACGTGA AATCGATAAA ATGTCTGAAA AAGATAAAAA AGACAAGAAA GCGAATGAAA   2880

ATTTAGGACT TAATCCATCA CACGAAGGTG AAACAGATCG ACCTGCAGKC ATGC         2934
```

(2) INFORMATION FOR SEQ ID NO: 37:

(i) SEQUENCE CHARACTERISTICS:
    (A) LENGTH:    2515 base pairs
    (B) TYPE:     nucleic acid

| (C) STRANDEDNESS: | single |
| (D) TOPOLOGY: | linear |

(xi) SEQUENCE DESCRIPTION: SEQ ID NO: 37:

| | | | | | |
|---|---|---|---|---|---|
| CSYCGGWACC | CGGGGATCCT | CTAGAGTCGA | TCGTTCCAGA | ACGTATTCGA | ACTTATAATT | 60 |
| ATCCACAAAG | CCGTGTAACA | GACCATCGTA | TAGGTCTAAC | GCTTCAAAAA | TTAGGGCAAA | 120 |
| TTATGGAAGG | CCATTTAGAA | GAAATTATAG | ATGCACTGAC | TTTATCAGAG | CAGACAGATA | 180 |
| AATTGAAAGA | ACTTAATAAT | GGTGAATTAT | AAAGAAAAGT | TAGATGAAGC | AATTCATTTA | 240 |
| ACACAACAAA | AAGGGTTTGA | ACAAACACGA | GCTGAATGGT | TAATGTTAGA | TGTATTTCAA | 300 |
| TGGACGCGTA | CGGACTTTGT | AGTCCACATG | CATGATGATA | TGCCGAAAGC | GATGATTATG | 360 |
| AAGTTCGACT | TAGCATTACA | ACGTATGTTA | TTAGGGAGAG | CCTATACAGT | ATATAGTTGG | 420 |
| CTTTGCCTCA | TTTTATGGTA | GAACGTTTGA | TGTAAACTCA | AATTGTTTGA | TACCAAGACC | 480 |
| TGAAACTGAA | GAAGTAATGT | TGCATTTCTT | ACAACAGTTA | GAAGATGATG | CAACAATCGT | 540 |
| AGATATCGGA | ACGGGTAGTG | GTGTACTTGC | AATTACTTTG | AAATGTTGAA | AAGCCGGATT | 600 |
| TAAATGTTAT | TGCTACTGAT | ATTTCACTTG | AAGCAATGAA | TATGGCTCCG | TAATAATGCT | 660 |
| GAGAAGCATC | AATCACAAAT | ACAATTTTTA | ACAGGGGATG | CATTAAAGCC | CTTAATTAAT | 720 |
| GAAGGTATCA | AKTTGAACGG | CTTTGATATC | TAATCCMCCA | TATATAGATG | AAAAAGATAT | 780 |
| GGTTACGATG | TCTCCMACGG | TTACGARATT | CGAACCACAT | CAGGCATTGT | TTGCAGATAA | 840 |
| CCATGGATAT | GCTATTTATG | AATCAATCAT | GGAAGATTTA | CCTCACGTTA | TGGAAAAAGG | 900 |
| CAGCCCAGTT | GTTTTTGAAA | TTGGTTACAA | TCAAGGTGAG | GCACTTAAAT | CAATAATTTT | 960 |
| AAATAAATTT | CCTGACAAAA | AAATCGACAT | TATTAAAGAT | ATAAATGGCC | ACGATCGAAT | 1020 |
| CGTCTCATTT | AAATGGTAAT | TAGAAGTTAT | GCCTTTGCTA | TGATTAGTTA | AGTGCATAGC | 1080 |
| TTTTTGCTTT | ATATTATGAT | AAATAAGAAA | GGCGTGATTA | AGTTGGATAC | TAAAATTTGG | 1140 |
| GATGTTAGAG | AATATAATGA | AGATTTACAG | CAATATCCTA | AAATTAATGA | AATAAAAGAC | 1200 |
| ATTGTTTTAA | ACGGTGGTTT | AATAGGTTTA | CCAACTGAAA | CAGTTTATGG | ACTTGCAGCA | 1260 |
| AATGCGACAG | ATGAAGAAGC | TGTAGCTAAA | ATATATGAAG | CTAAAGGCCG | TCCATCTGAC | 1320 |
| AATCCGCTTA | TTGTTCATAT | ACACAGTAAA | GGTCAATTAA | AAGATTTTAC | ATATACTTTG | 1380 |
| GATCCACGCG | TAGAAAAGTT | AATGCAGGCA | TTCTGGCCGG | GCCCTATTTC | GTTTATATTG | 1440 |
| CCGTTAAAGC | TAGGCTATCT | ATGTCGAAAA | GTTTCTGGAG | GTTTATCATC | AGTTGCTGTT | 1500 |
| AGAATGCCAA | GCCATTCTGT | AGGTAGACAA | TTATTACAAA | TCATAAATGA | ACCTCTAGCT | 1560 |
| GCTCCAAGTG | CTAATTTAAG | TGGTAGACCT | TCACCAACAA | CTTTCAATCA | TGTATATCAA | 1620 |
| GATTTGAATG | GCCGTATCGA | TGGTATTGTT | CAAGCTGAAC | AAAGTGAAGA | AGGATTAGAA | 1680 |
| AGTACGGTTT | TAGATTGCAC | ATCTTTTCCT | TATAAAATTG | CAAGACCTGG | TTCTATAACA | 1740 |
| GCAGCAATGA | TTACAGAAAT | AMTTCCGAAT | AGTATCGCCC | ATGCTGATTA | TAATGATACT | 1800 |
| GAACAGCCAA | TTGCACCAGG | TATGAAGTAT | AAGCATTACT | CAACCCAATA | CACCACTTAC | 1860 |
| AATTATTACA | GATATTGAGA | GCAAAATTGG | AAATGACGGT | AAAGATTRKW | MTTCTATAGC | 1920 |
| TTTTATTGTG | CCGAGTAATA | AGGTGGCGTT | TATACCAAGT | GARSCGCAAT | TCATTCAATT | 1980 |
| ATGTCAGGAT | GMCAATGATG | TTAAACAAGC | AAGTCATAAT | CTTTATGATG | TGTTACATTC | 2040 |
| ACTTGATGAA | AATGAAAATA | TTTCAGCGGC | GTATATATAC | GGCTTTGAGC | TGAATGATAA | 2100 |
| TACAGAAGCA | ATTATGAATC | GCATGTTAAA | AGCTGCAGGT | AATCACATTA | TTAAAGGATG | 2160 |
| TGAACTATGA | AGATTTTATT | CGTTTGTACA | GGTAACACAT | GTCGTAGCCC | ATTAGCGGGA | 2220 |

```
AGTATTGCAA AAGAGGTTAT GCCAAATCAT CAATTTGAAT CAAGAGGTAT ATTCGCTGTG    2280

AACAATCAAG GTGTTTCGAA TTATGTTGAA GACTTAGTTG AAGAACATCA TTTAGCTGAA    2340

ACGACCTTAT CGCAACAATT TACTGAAGCA GATTTGAAAG CAGATATTAT TTTGACGATG    2400

TCGTATTCGC ACAAAGAATT AATAGAGGCA CACTTTGGTT TGCAAAATCA TGTTTTCACA    2460

TTGCATGAAT ATGTAAAAGA AGCAGGAGAA GTTATAGATC GACCTGCAGG CATGC         2515

(2) INFORMATION FOR SEQ ID NO: 38:

(i) SEQUENCE CHARACTERISTICS:
        (A) LENGTH:           2635 base pairs
        (B) TYPE:             nucleic acid
        (C) STRANDEDNESS:     single
        (D) TOPOLOGY:         linear (xi) SEQUENCE DESCRIPTION: SEQ ID NO: 38:

ATTCTCTGTG TTGGGGCCCC TGACTAGAGT TGAAAAAAGC TTGTTGCAAG CGCATTTTCA      60

TTCAGTCAAC TACTAGCAAT ATAATATTAT AGACCCTAGG ACATTGATTT ATGTCCCAAG     120

CTCCTTTTAA ATGATGTATA TTTTTAGAAA TTTAATCTAG ACATAGTTGG AAATAAATAT     180

AAAACATCGT TGCTTAATTT TGTCATAGAA CATTTAAATT AACATCATGA AATTCGTTTT     240

GGCGGTGAAA AAATAATGGA TAATAATGAA AAAGAAAAAA GTAAAAGTGA ACTATTAGTT     300

GTAACAGGTT TATCTGGCGC AGGTAAATCT TTGGTTATTC AATGTTTAGA AGACATGGGA     360

TATTTTGTG TAGATAATCT ACCACCAGTG TTATTGCCTA AATTTGTAGA GTTGATGGAA      420

CAAGGGAAAT CCATCCTTAA GAAAAAGTGG CAATTGCAAT TGATTTAAGA RGTAAGGAAC     480

TATTTAATTC ATTAGTTGCA GTAGTGGATA AAGTTCAAAA GTTGAAAGTG ACGTCATCAT     540

TGATGTTATG TTTTTAGAAG CAAGTACTGA AAAATTAATT TCAAGATATA AGGAAACGCG     600

TCCKTGCACA TCCTTTGATG GAACAAGGTT AAAAGATCGT TAATCAATGC MATTAATGAT     660

GAGCGAGAGC ATTTGTCTCA AATTAGAAGT ATAGCTAATT TTGTTATAGA TAACTACAAA     720

GTTATCACCT AAAGAATTAA AAGAACGCAT TCGTCGATAC TATGAAGATG AAGAGTTTGA     780

AACTTTTACA ATTAATGTCA CAAGTTTCGG TTTTAAACAT GGGATTCAGA TGGATGCAGA     840

TTTAGTATTT GATGTACGAT TTTTACCAAA TCCATATTAT GTAGTAGATT TAAGACCTTT     900

AACAGGATTA GATAAGACG TTTATAATTA TGTTATGAAA TGGAAAGAGA CGGAGATTTT      960

TCTTTGAAAA ATTAACTGAT TTGTTAGATT TTATGATACC CGGGTWTAAA AAAGAAGGGA    1020

AATCTCAATT AGTAATTGCC ATCGGTTGTA CGGGTGGGAC AACATCGATC TGTAGCATTA    1080

GCAGAACGAC TAGGTWATTA TCTAAATGAA GTWTTTGAAT ATAATGTTTA TGTGCATCAT    1140

AGGGACGCAC ATATTGAAAG TGGCGAGAAA AAATGAGACA AATAAAAGTT GTACTTATCG    1200

GGTGGTGGCA CTGGCTTATC AGTTATGGCT AGGGGATTAA GAGAATTCCC AATTGATATT    1260

ACGGCGATTG TAACAGTTGC TGATAATGGT GGGAGTACAG GGAAAATCAG AGATGAAATG    1320

GATATACCAG CACCAGGAGA CATCAGAAAT GTGATTGCAG CTTTAAGTGA TTCTGAGTCA    1380

GTTTTAAGCC AACTTTTTCA GTATCGCTTT GAAGAAAATC AAATTAGCGG TCACTCATTA    1440

GGTAATTTAT TAATCGCAGG TATGACTAAT ATTACGAATG ATTTCGGACA TGCCATTAAA    1500

GCATTAAGTA AAATTTTAAA TATTAAAGGT AGAGTCATTC CATCTACAAA TACAAGTGTG    1560

CAATTAAATG CTGTTATGGA AGATGGAGAA ATTGTTTTTG GAGAAACAAA TATTCCTAAA    1620

AAACATAAAA AAATTGATCG TGTGTTTTA GAACCTAACG ATGTGCAACC AATGGAAGAA     1680

GCAATCGATG CTTTAAGGGA AGCAGATTTA ATCGTTCTTG GACCAGGGTC ATTATATACG    1740
```

```
AGCGTTATTT CTAACTTATG TTKTGAATGG TATTTCAGAT GCGTTWATTC ATTCTGATGC    1800

GCCTAAGCTA TATGTTTCTA ATGTGATGAC GCAACCTGGG GAAACAGATG GTTATAGCGT    1860

GAAAGATCAT ATCGATGCGA TTCATAGACA AGCTGGACAA CCGTTTATTG ATTATGTCAT    1920

TTGTAGTACA CAAACTTTCA ATGCTCAAGT TTTGAAAAAA TATGAAGAAA AACATTCTAA    1980

ACCAGTTGAA GTTAATAAGG CTGAACTKGA AAAAGAAAGC ATAAATGTAA AAACATCTTC    2040

AAATTTAGTT GAAATTTCTG AAAATCATTT AGTAAGACAT AATACTAAAG TGTTATCGAC    2100

AATGATTTAT GACATAGCTT TAGAATTAAT TAGTACTATT CCTTTCGTAC CAAGTGATAA    2160

ACGTAAATAA TATAGAACGT AATCATATTA TGATATGATA ATAGAGCTGT GAAAAAAATG    2220

AAAATAGACA GTGGTTCTAA GGTGAATCAT GTTTTAAATA AGAAAGGAAT GACTGTACGA    2280

TGAGCTTTGC ATCAGAAATG AAAAATGAAT TAACTAGAAT AGACGTCGAT GAAATGAATG    2340

CAAAAGCAGA GCTCAGTGCA CTGATTCGAA TGAATGGTGC ACTTAGTCTT TCAAATCAAC    2400

AATTTGTTAT AAATGTTCAA ACGGAAAATG CAACAACGGC AAGACGTATT TATTCGTTGA    2460

TTAAACGTGT CTTTAATGTG GAAGTTGAAA TATTAGTCCG TAAAAAAATG AAACTTAAAA    2520

AAAATAATAT TTATATTTGT CGTACAAAGA TGAAAGCGAA AGAAATTCTT GATGAATTAG    2580

GAATTTTAAA AGACGGCATT TTTACGCATG AAATTGATCG ACCTGCAGGC ATGCA         2635

(2) INFORMATION FOR SEQ ID NO: 39:

(i) SEQUENCE CHARACTERISTICS:
        (A) LENGTH:          1952 base pairs
        (B) TYPE:            nucleic acid
        (C) STRANDEDNESS:    single
        (D) TOPOLOGY:        linear (xi) SEQUENCE DESCRIPTION: SEQ ID NO: 39:

TGCATGTACA GCAGGCTCTA CACAACCGTC GCATGTTTTA GATGCAATGT TCGAAGATGA      60

GGAGCGATCA AATCATTCGA TTCGATTTAG TTTTAACGAA TTGACTACTG AAAATGAAAT     120

TAATGCAATT GTAGCTGAAA TTCATAAAAT ATATTTTAAA TTTAAGGAGG AGTCATAATT     180

GTCAAATAAA GATATAACGT GTTGTCGTTG GTATGTCAGG CGGTGTAGAT AGTTCTGTAA     240

CAGCCCACGT CTTAAAAGAA CAAGGTTATG ATGTCATTGG CATATTTATG AAAAACTGGG     300

ATGACACTGA CGAAAATGGC GTATGTACTG CAACTGAAGA TTACAACGAT GTTATTGAAG     360

TGTGTAATCA AATTGGCATT CCGTATTACG CTGTTAATTT TGAAAAAGAA TATTGGGATA     420

AAGTCTTTAC GTATTTCTTA GATGAATACA AAAAAGGTCG TACTCCAAAT CCAGACGTTA     480

TGTGTAATAA AGAAATTAAG TTTAAAGCCT TTTTAGATCA TGCGATGAAT TTAGGTGCAG     540

ATTATGTAGC AACAGGACAT TACGCACGCA TACATCGTCA TGAASRTGGT CATGTTGAAA     600

TGTTACGTGG TGTAGATAAT AATAAAGATC ARACATACTK CWKGMATGCA AKTATCTCAA     660

CAACAACTTT CAAAAGTGAT GTTCCCAATT GGCGACATCG AAAAGAGTGA AGTGCGTCGA     720

ATTGCTGAAG AACAAGGACT TGTTACTGCT AAGAAAAAAG ATTCTACAGG CATTTGTTTT     780

ATCGGCGAAA AAAACTTTAA AACATTTTTA TCACAATATT TACCTGCACA ACCGGGTGAT     840

ATGATAACAC TTGATGGTAA GAAAATGGGT AAACATAGTG GTTTGATGTA TTACACAATA     900

GGACAAAGAC ATGGATTAGG TATAGGTGGG AGATGGCGAT CCTTGGTTTG TTGTCGGTAA     960

AAACCTAAAA GATAATGTTT TATATGTWGA ACAAGGATCC ATCACGATGC ATTATACAGT    1020

GATTACTTAA TTGCTTCAGA CTATTCATTT GTAAATCCCA GAAGATAATG ACTTAGATCA    1080

AGGTTTTGAA TGTACAGCTA AATTTAGATA TCGCCAAAAA GATACGAAAG TTTTTGTGAA    1140
```

-continued

```
ACGTGAAAAA CGACCATGCA CTACGTGTTA CTTTTGCTGA GCCAGTAAGA GCAATCACAC    1200

CTGGACAAGC AGTTGTTTTT TATCAAGGTG ATGTGTTGTC TTGGTGGTGC AACAATTGAC    1260

GATGTKTTCA AAAATGAAGG TCAATTAAAT TATGTTGTAT ANACAATGGC AACAATAAAT    1320

TACTTATTTG AAGTTTCNAC GTTGAAAATG ACGAAAGACA GTTTTTGATG AGAATAATTC    1380

ATGAGGATAG AGTCTGGGAC ATCACAATGT CCTAGGCTCT ACAATGTTAT ATKGGCGGGA    1440

CCACAACATA GAGAATTTCG TAAAGAAATT CWACAGGCAA TGCCAGTTGG GGATAACGAA    1500

TTTAATTTTG TTAAAATATC ATTTCTGTCC CACTCCCTAT GCATGAATCT AATTATGTAT    1560

TCTTATTTTT AAGTACATAA TAGTGGTGGC TAATGTGGAA GAACCATTAC ATAATAAACC    1620

GTTAATGGTT CTTAAGCATT TYTATTCCAT TCCCGCTTTT TCATGAATGA AGATGATATT    1680

AGATTATATT TTATTCGTTG TTAAGTGATT CGAGACATAC AATTTATCAA GATGTTTATA    1740

ATTGATGAGA AATGAGGTTC GTAAATGATA GATCAACAAA CAATTTATCA ATACATACAA    1800

AATGGAAAAA TAGAAGAAGC GTTACAAGCA TTGTTCGGAA ATATCGAAGA AAATCCTACA    1860

ATTATTGAAA ATTATATTAA TGCTGGTATC GTACTTGCTG ATGCGAATGA GATTGAAAAG    1920

GCAGAGCGTT TTTTCCAAAA AGCTTTAACA AT                                 1952
```

(2) INFORMATION FOR SEQ ID NO: 40:

(i) SEQUENCE CHARACTERISTICS:
        (A) LENGTH: 2273 base pairs
        (B) TYPE: nucleic acid
        (C) STRANDEDNESS: single
        (D) TOPOLOGY: linear (xi) SEQUENCE DESCRIPTION: SEQ ID NO: 40:

```
TAACCAATAT TGATAAAACC TTGATGTGTT TCGTGTCAAT GACATACCAT ATCGACTAGG      60

TACCTTTTTA GAATGTTGAT TAATCACAAC AAATATCATG GCAAGGTCAT CTTCAAAATG     120

ATTCGATTCA AGTGGAACGG CATATGACGT CTCATCACTA TACCCTTTTT CCCATTCTGC     180

AAATCCACCA TAAATACTAC GCGACGCAGA ACCCGAACCA ATTCGCGCCA ATCTCGATAA     240

ATCCTTATCT GACAGCTGCA TGTCTAGCGC TTGATTACAA GCTGCTGCTA AAGCTGCATA     300

TGCGCTTGCC GATGAAGCCA ACCCTGCTGC TGTTGGTACA AAATTGTCGC TTTCAATTTC     360

TGCATACCAA TCGATGCCAG CTCTATTTCT GACAATATCC ATATATTTTG AAATTTTCTC     420

TAATTCTTTG CCACTAACCT TTTCACCATT CAACCAAAAT TGATCCTGTG TTAACTGGTC     480

GTTAAAAGTG ACTTTCGTTT CAGTGTWAAA TTTTTCTAAT GTWACAGATA TGCTATTATT     540

CATTGGAATG ATTAGTGCTT CATCTTTTTT ACCCCAATAT TTTATAAGTG CAATATTCGT     600

ATGTGCACGT GCTTTGCCAC TTTTAATCAA CGCATTAACC TCCTAAATTC TCAATCCAAG     660

TATGTGCTGC ACCAGCTTTT TCTACAGCTT TTACAATATT TTTCGCTGTT GGTAAATCTT     720

TGGCAAGCAA TAACATACTT CCACCACGAC CAGCGCCAGT AAGTTTTCCA GCAATCGCAC     780

CATTTTCTTT ACCAATTTTC ATTAATTGTT CTATTTTATC ATGACTAACT GTCAACGCCT     840

TTAAATCCGC ATGACATTCA TTAAAAATAT CCGCTAAGGS TTCAAAGTTA TGATGTTCAA     900

TCACATCACT CGCACGTAAA ACTAACTTAC CGATATGTTT TACATGTGAC ATGTACTGAG     960

GGTCCTCACA AAGTTTATGA ACATCTTCTA CTGCTTGTCT TGTTGAACCT TTCACACCAG    1020

TATCTATAAC AACCATATAG CCGTCTAAAC TTAACGTTTT CAACGTTTCA GCATGACCTT    1080

TTTGGAACCA AACTGGTTTG CCTGATACAA TCGTTTGCGT ATCAATACCA CTTGGTTTAC    1140

CATGTGCAAT TTGCTCTGCC CAATTAGCCT TTTCAATGAG TTCTTCTTTC GTTAATGATT    1200
```

-continued

```
TCCCTAAAAA ATCATAACTT GCACGAACAA AAGCAACCGC GACAGCTGCA CTCGATCCTA      1260

ATCCACGTGA TGGTGGTAAA TTCGTTTGGA TCGTTACTGC TAGCGGCTCT GTAATATTAT      1320

TTAATTCTAC AAAACGGTTC ACCAAAGAMT TAAGATGGTC AGGCGCATCA TATAAACATA      1380

CCATCGTAAA ACATCGCTTT TAATAGAGGA ATAGTTCCCG CTCTCTAAGG TTCTATTAAA      1440

ACTTTGATTT TAACCGGCGT TAAACGGTAC TGCAATAGCA GGCTCTCCAA ATGTAACAGC      1500

ATGTTCTCCT ATTAAAATAA TCTTACCTGT CGATTCCCCA TATCCTTTTC TTGTCATGTC      1560

AATATCACCT TTTATATTTA TCCTAWACTT GATTCATTAT TTTTATTTAT TAGTAAAAGA      1620

CATCATATTC TAAGTKGCAW ACGCATTCGC GTTAAATTTC ATTGCAGTCT TTATCTCACA      1680

TTATTCATAT TATGTATAAT CTTTATTTTG AATTTATATT TGACTTAACT TGATTAGTAT      1740

AAAACTAACT TTCGTTTACT TCAAAGTTTA AATCTTATCG AGTGATATTT CAGATTCTTT      1800

ATCTTTTTAT AAAATAGCCC TACAATTTAT AATTTTCCAC CCTAACTATA ATACTACAAA      1860

TAATAATTGG AATATATAGA TTTACTACTA AAGTATTAGA ACATTTCAAT AGAAGGTCGT      1920

TTCTTTCATA GTCATACGCA TTATATATAC CCTATTCTCA ATCTATTTAA TACGTAAAAC      1980

ATGAAATTTT CTTATTAAAT TTATTATTTC CATCATATCA TTACTTTTAA TTTAATGATG      2040

TTCAATTTAA ATATTAGGTC AATAACATAT TTATGCTTTT TATGGATACT TTCAAAAATA      2100

ACAGCCCCAA ACGATAACTT GAAAGGGGCT GTTAAATATT TAACTATTGC ATTTGATCKA      2160

TCATTYTMKW GKWTCYYYSR RTMMYKWKMT CRAAATACGT ATCGTATCTT TGCCATTCTT      2220

CTTGAGTAAT TGGCGTCATA TTTAATACAC CGCCAAGATC GACCTGCAGG CAT            2273
```

(2) INFORMATION FOR SEQ ID NO: 41:

(i) SEQUENCE CHARACTERISTICS:
        (A) LENGTH:         928 base pairs
        (B) TYPE:           nucleic acid
        (C) STRANDEDNESS:  single
        (D) TOPOLOGY:     linear (xi) SEQUENCE DESCRIPTION: SEQ ID NO: 41:

```
TCCTCTAGAG TCGATCAATA TGAGTATTAT TATCAAAAAA TGCTAAATNA GCATAACAAA       60

AGTAAAGGCG AGTAATAATA TGGATAAATC ATTATTTGAA YAGGCAAGGC CTATATTAGA      120

ACAAATTCAA GACAATGGTT TTNAAGCATA TTATGTAGGT GGCTCTGTAA GAGATTATGT      180

CATGGGAAGA AATATTCATG ATATAGATAT CACAACAAGT GCAACGNCGG ATGAAATAGA      240

ATCTATCTTT AGTCATACGA TACCTGTAGG TAAAGAACAT GGCACGATAA ATGTAGTTTT      300

TAATGATGAA AATTATGAAG TGACAACATT CCGGGCTGAA GAAGATTATG TCGATCACCG      360

TAGACCAAGT GGTGTTACAT TTGTYCGTGA TTTATACGAR GATTTGCAAC GACGAGATTT      420

CACGATGAAT GCGATAGAAT GGATACAGCA TACAAATTGT ATGATTATTT TGATGGTCAA      480

CAAGATATTA ATAATCGAWT AATAAGAACT GTAGGTATAG CTGAGGAACG TTCCAAGAAG      540

ATGCTTTACG TATGATTCGA TGTTTAAGGT TCCAGTCACA ATTATCATTT GATATTGCAA      600

CGGAAACATT CGAAGCGATG CGTATACAAA TGGCAGATAT TAAATTTTTA TCAATTGAGC      660

GTATAGTGAT TGAACTAACT AAATTAATGC GAGGTATTAA TGTTGAAAAG AGTTTTAATC      720

ATTTAAAATC GCTGAAAGCA TTTAATTATA TGCCGTATTT CGAACATCTT GATATGAATC      780

AAATTAATGT AACTGAAGCA ATTGATTTAG AATTGTTGAT TGCTATAGTA TCAGTTAAAT      840

TTGATATTAA TTACTCATTG AAGCCTTTAA AGCTAAGTTA ACCGACAAGT TAAAAGATAT      900

CAATCAATAT ATTCAAATTA TGAATGCA                                         928
```

(2) INFORMATION FOR SEQ ID NO: 42:

(i) SEQUENCE CHARACTERISTICS:
        (A) LENGTH: 2119 base pairs
        (B) TYPE: nucleic acid
        (C) STRANDEDNESS: single
        (D) TOPOLOGY: linear (xi) SEQUENCE DESCRIPTION: SEQ ID NO: 42:

```
TGCATGCCTG CAGGTCGATC TAATATAGTT TCCGCTAAAT ATAATTGTTG CGGTCGATAT      60
GTTAAGCCAR GTYGATCTAC AGCTTTGCTA TATAAAGACT TCAAGCTGCC ATTATAATTT     120
GTTGTCGGCT TTTTAAAATC AACTTGCTTA CGATAGATAA TCTGTTCGAA CTTTTCGTAC     180
GATTTATCCA ATGGCTTTGC ATCATATTGC CTAACCATCT CAAAGAAAAT ATCATACAAA     240
TCGTATTTCA ACTGTTTACT TAAATAATAT AATTGCTTCA AGTATCTAA  CGGTAACTTT     300
TCAAATTTTT CAAAAGCTAA TATCATCAAT TTAGCAGTAG TAGCGGCATC TTCGTCAGCT     360
CGATGGGCAT TTGCTAAGGT AATACCATGT GCCTCTGCTA ATTCACTTAA TTGATAGCTT     420
TTATCTGTAG GAAAAGCTAT TTTAAAGATT TCTAGTGTAT CTATAACTTT TTTGGGACGA     480
TATTGAATAT TACAATCTTT AAATGCCTTT TTAATAAAAT TCAAATCAAA ATCTACATTA     540
TGAGCTACAA AAATGCAATC TTTWATCTTA TCGTAGATTT CTTGTGCAAC TTGATTAAAA     600
TATGGCGCTT GTTGTAGCAT ATTTKCTTCA ATGGATGTTA ACGCWTGAAT GAACGGCGGA     660
AWCTCTAAAT TTGTTCTAAT CATAGAATGA TATGTATCAA TAATTTGGTT ATTGCGSACA     720
AACGTTATAC CAATTTGAAT GATATCGTCA AAATCTAATT GGTTGCCTGT TGTTTCCAAA     780
TCCACAACGG CATAGGTTGC CATACCCATA GCTATCTCTC CTTGCTTTAG TGTTAAAAAT     840
CTATATCTGC ACTAATTAAA CGGTGTGATT CACCCGCTTC ATCTCTAACA ATTAGATAGC     900
CATCGTAATC TAAATCAATT GCTTGTCCTT TAAACTGTTT ATCATTTTCT GTAAATAGCA     960
ACGTTCTATT CCAAATATTA GAAGCTGCAG TATATTCTTC ACGAATTTCA GAAAAAGGTA    1020
ACGTTAAAAA TTGATTATAT CTTTTTYCAA TTTCTTGAAG TAATATCTCT AAAAATTGAT    1080
ATCTATCTAA TTWATTTTTA TCATGTAATT GTATACTTGT TGCTCTATGT CTAATACTTY    1140
CATCAAAGTT TTCTAGTTGT TTGCGTTCAA ATTAATACCT ATACCACATA TTATTGCTTC    1200
TATACCATCC ATTATTAGCA ACCATTTCAG TTAAGAAACC ACACACTTTA CCATTATCAA    1260
TAAATATATC ATTCGGCCAT TTCACTTTGA CTTCATCTTG ACTAAAATGT TGAATCGCAT    1320
CTCTTATCCC TAATGCAATA AATAAATTAA ATTTAGATAT CATTGAGAAT GCAACGTTAG    1380
GTCTTAACAC GACAGACATC CAAAGTCCTT GCCCTTTTGA AGAACTCCAA TGTCTATTAA    1440
ATCGCCCACG ACCTTTCGTT TGTTCATCAC TCAAGATAAA AAATGAAGAT TGATTTCCAA    1500
CAAGTGACTT TTTCGCAGCA AGTTGTGTAG AATCTATTGA ATCGTATACT TCACTAAAAT    1560
CAAACAAAGC AGAACTTTTT GTATATTGGT CTATTATACC TTGATACCAA ATATCTGGGA    1620
GCTGTTGTAA TAAATGCCCT TTATGATTTA CTGAATCTAT TTTACATCCC TCTAACTTTA    1680
ATTGGTCAAT CACTTTTTTT ACTGCAGTGC GTGGAAATAT TAAGTTGATT CCGCAATGCT    1740
TTGTCCAGAA TATATAATTC GGTTTATTTT TATAGAGTAA TTGAAGTTAC ATCTTGACTA    1800
TATTTTNACA TGATTATCCA CCCATTTCAA AATTNCAGTT TCTNCGTTGC TTACTTTACC    1860
TGTNACAATC GCTATCTCAA TTTGTCTTAG CACATCTTTT AACCACGGAC CACTTTTGGC    1920
ATTTAAATGT GCCATAAGTA CACCGCCATT AACCATCATG TCTTTNCTAT TATGCATAGG    1980
TAAACGATGT AATGTTTCAT CAATCGTTTG AAGGTTAACG CTTAATGGTT CATGTCCTTG    2040
```

```
GTATCATAAC GCCTGTNTCA AGCGTTCTNC AANCATGTAC AGTTNTTCAA TGTGGNGTGT    2100

CCGNATTAAC GCTATTCAA                                                 2119
```

(2) INFORMATION FOR SEQ ID NO: 43:

(i) SEQUENCE CHARACTERISTICS:
        (A) LENGTH:         1407 base pairs
        (B) TYPE:           nucleic acid
        (C) STRANDEDNESS:   single
        (D) TOPOLOGY:      linear (xi) SEQUENCE DESCRIPTION: SEQ ID NO: 43:

```
TTCACAGTGT TGTCGGGATA CGATATAGTA CACTGTACAG TACGNTGGAG ATTTATTAGA      60

TTTTCACAGA ATTNTGAAAA TAAGACNACG GGTCATGGAA ATGTTACTAT TACCTGAACA     120

AAGGCTATTA TATAGTGATA TGGTTGNTCG TATTTTATTC AATAATTCAT TAAAATATTA     180

TATGAACGAA CACCCAGCAG TAACGCACAC GACAATTCAA CTCGTAAAAG ACTATATTAT     240

GTCTATGCAG CATTCTGATT ATGTATCGCA AAACATGTTT GACATTATAA ATACAGTTGA     300

ATTTATTGGT GAGAATTGGG ATAGAGAAAT ATACGAATTG TGGCGACCAA CATTAATTCA     360

AGTGGGCATT AATAGGCCGA CTTATAAAAA ATTCTTGATA CAACTTAAAG GGAGAAAGTT     420

TGCACATCGA ACAAAATCAA TGTTAAAACG ATAACGTGTA CATTGATGAC CATAAACTGC     480

AATCCTATGA TGTGACAATA TGAGGAGGAT AACTTAATGA AACGTGTAAT AACATATGGC     540

ACATATGACT TACTTCACTA TGGTCATATC GAATTGCTTC GTCGTGCAAG AGAGATGGGC     600

GATTATTTAA TAGTAGCATT ATCAACAGAT GAATTTAATC AAATTAAACA TAAAAAATCT     660

TATTATGATT ATGAACAACG AAAAATGATG CTTGAATCAA TACGCTATGT CRTATTTAGT     720

CATTCCAGAA AAGGGCTGGG GACAAAAAGA AGACGATGTC GAAAAATTTG ATGTAGATGT     780

TTTTGTTATG GGACATGACT GGGAAGGTGA ATTCGACTTC TTAAAGGATA AATGTGAAGT     840

CATTTATTTA AAACGTACAG AAGGCATTTC GACGACTAAA ATCAAACAAG AATTATATGG     900

TAAAGATGCT AAATAAATTA TATAGAACTA TCGATACTAA ACGATAAATT AACTTAGGTT     960

ATTATAAAAT AAATATAAAA CGGACAAGTT TCGCAGCTTT ATAATGTGCA ACTTGTCCGT    1020

TTTTAGTATG TTTTATTTTC TTTTTCTAAA TAAACGATTG ATTATCATAT GAACAATAAG    1080

TGCTAATCCA GCGACAAGGC ATGTACCACC AATGATAGTG AATAATGGAT GTTCTTCCCA    1140

CATACTTTTA GCAACAGTAT TTGCCTTTTG AATAATTGGC TGATGAACTT CTACAGTTGG    1200

AGGTCCATAA TCTTTATTAA TAAATTCTCT TGGATAGTCC GCGTGTACTT TACCATCTTC    1260

GACTACAAGT TTATAATCTT TTTTACTAAA ATCACTTGGT AAAACATCGT AAAGATCATT    1320

TTCAACATAA TATTTCTTAC CATTTATCCT TTGCTCACCT TTAGACAATA TTTTTACATA    1380

TTTATACTGA TCAAATGAVC GTTCCAT                                       1407
```

(2) INFORMATION FOR SEQ ID NO: 44:

(i) SEQUENCE CHARACTERISTICS:
        (A) LENGTH:         1996 base pairs
        (B) TYPE:           nucleic acid
        (C) STRANDEDNESS:   single
        (D) TOPOLOGY:      linear (xi) SEQUENCE DESCRIPTION: SEQ ID NO: 44:

```
TCCTCTAGAG TCGATCGTAT TAAATTATCA AATAACGCTG AAAAGGTTAC GACGCCAGGT      60

AAGAAAAATG TATATCGCAT TATAAACAAG AAAACAGGTA AGGCAGAAGG CGATTATATT     120

ACTTTGGAAA ATGAAAATCC ATACGATGAA CAACCTTTAA AATTATTCCA TCCAGTGCAT     180
```

```
ACTTATAAAA TGAAATTTAT AAAATCTTTC GAAGCCATTG ATTTGCATCA TAATATTTAT      240

GAAAATGGTA AATTAGTATA TCAAATGCCA ACAGAAGATG AATCACGTGA ATATTTAGCA      300

CTAGGATTAC AATCTATTTG GGATGAAAAT AAGCGTTTCC TGAATCCACA AGAATATCCA      360

GTCGATTTAA GCAAGGCATG TTGGGATAAT AAACATAAAC GTATTTTGA AGTTGCGGAA       420

CACGTTAAGG AGATGGAAGA AGATAATGAG TAAATTACAA GACGTTATTG TACAAGAAAT      480

GAAAGTGAAA AAGCGTATCG ATAGTGCTGA AGAAATTATG GAATTAAAGC AATTTATAAA      540

AAATTATGTA CAATCACATT CATTTATAAA ATCTTTAGTG TTAGGTATTT CAGGAGGACA      600

GGATTCTACA TTAGTTGGAA AACTAGTACA AATGTCTGTT AACGAATTAC GTGAAGAAGG      660

CATTGATTGT ACGTTTATTG CAGTTAAATT ACCTTATGGA GTTCAAAAAG ATGCTGATGA      720

AGTTGAGCAA GCTTTGCGAT TCATTGAACC AGATGAAATA GTAACAGTCA ATATTAAGCC      780

TGCAGTTGAT CAAAGTGTGC AATCATTAAA AGAAGCCGGT ATTGTTCTTA CAGATTTCCA      840

AAAAGGAAAT GAAAAAGCGC GTGAACGTAT GAAAGTACAA TTTTCAATTG CTTCAAACCG      900

ACAAGGTATT GTAGTAGGAA CAGATCATTC AGCTGAAAAT ATAACTGGGT TTTATACGAA      960

GTACGGTGAT GGTGCTGCAG ATATCGCACC TATATTTGGT TTGAATAAAC GACAAGGTCG     1020

TCAATTATTA GCGTATCTTG GTGCGCCAAA GGAATTATAT GAAAAAACGC CAACTGCTGA     1080

TTTAGAAGAT GATAAACCAC AGCTTCCAGA TGAAGATGCA TTAGGTGTAA CTTATGAGGC     1140

GATTGATAAT TATTTAGAAG GTAAGCCAGT TACGCCAGAA GAACAAAAAG TAATTGAAAA     1200

TCATTATATA CGAAATGCAC ACAAACGTGA ACTTGCATAT ACAAGATACA CGTGGCCAAA     1260

ATCCTAATTT AATTTTTTCT TCTAACGTGT GACTTAAATT AAATATGAGT TAGAATTAAT     1320

AACATTAAAC CACATTCAGC TAGACTACTT CAGTGTATAA ATTGAAAGTG TATGAACTAA     1380

AGTAAGTATG TTCATTTGAG AATAAATTTT TATTTATGAC AAATTCGCTA TTTATTTATG     1440

AGAGTTTTCG TACTATATTA TATTAATATG CATTCATTAA GGTTAGGTTG AAGCAGTTTG     1500

GTATTTAAAG TGTAATTGAA AGAGAGTGGG GCGCCTTATG TCATTCGTAA CAGAAAATCC     1560

ATGGTTAATG GTACTAACTA TATTTATCAT TAACGTTTGT TATGTAACGT TTTTAACGAT     1620

GCGAACAATT TTAACGTTGA AAGGTTATCG TTATATTGCT GCATCAGTTA GTTTTTTAGA     1680

AGTATTAGTT TATATCGTTG GTTTAGGTTT GGTTATGTCT AATTTAGACC ATATTCAAAA     1740

TATTATTGCC TACGCATTTG GTTTTTCAAT AGGTATCATT GTTGGTATGA AAATAGAAGA     1800

AAAACTGGCA TTAGGTTATA CAGTTGTAAA TGTAACTTCA GCAGAATATG AGTTAGATTT     1860

ACCGAATGAA CTTCGAAATT TAGGATATGG CGTTACGCAC TATGCTGCGT TTGGTAGAGA     1920

TGGTAGTCGT ATGGTGATGC AAATTTTAAC ACCAAGAAAA TATGAACGTA AATTGATGGA     1980

TACGATAAAA AATTTA                                                     1996
```

(2) INFORMATION FOR SEQ ID NO: 45:

(i) SEQUENCE CHARACTERISTICS:
        (A) LENGTH:        1017 base pairs
        (B) TYPE:          nucleic acid
        (C) STRANDEDNESS:  single
        (D) TOPOLOGY:     linear (xi) SEQUENCE DESCRIPTION: SEQ ID NO: 45:

```
CTTYGARCTC GGTACCCGGG GMTCCTCTAR AGTCGATCTT TATACTCTTG TAACACATTT       60

AAGTCTTCAT CAATCATAGC ATTCGTTAAT TCAGCTCGAT GCGCTTCCAA AAATTGCTTA      120

ACATCTGGGT CATWGATGTC TCCTGATTTT ATCTTTTCTA TTCTTTTTTC AAAGTCCTGC      180
```

```
GACGTGTTAA TTATACTTTT AAATTGCTTC ATTATTGACT GTCCTCCTCC CATTTTTTAG        240

ATAATTTATC TAGAAATGCT TGTCGATCTT GCTCTAATTG TTGATCATCT ACGCTATTAT        300

CTTTAGCCGA ATCTTCTTCA CTAGGTTTAT CTCTATTTTC TAACCATTTA GGTGTTTTTT        360

CTTTTGAAAT ACGATTACGC TGCCCATAGT ATGAACCACG CTTTTGGTAA TTTCCGCTAG        420

AACCCTCATT TTTAGGTTGA TTAACTTTTT TAGCGTAATT ATATGCTTCT TTAGCTGTCT        480

TAATACCTTT TTTCTTCCAA TTTGATGCTA TTTCCAAAAT ATACGCTTTA GGAAGTTTCA        540

TATCTTCTTT TAACATGACA AATTGCAACA AAATATTAAT GACGCCAAAA GACATTTTTT        600

CACGTTTCAA TTAATTCTTC AACCATTGTC TTTTGCGATA TAGTTGGTYC TGATTCAGAM        660

CAAGAAGCTA ACATATCAAT TGGACTCGTT TGTTCAAGTA ACTCAAACCA TTCATCACTT        720

TGTGGCTTTG GATTCACTTC TGAAGATTTG CCCGCCGAAG ATGATGTAGC AGGAGATTTC        780

ACCTGTAATT TAGGCATTTG ATTTTCGTGT TCCATTAAGT AATACGAGCG TGCTTGTTTA        840

CGCATTTCTT CAAAGGATAA CTGTTGTCCA CTTGTAATTG AATTTAAAAT AACATGCTTC        900

ATGCCATCTG CTGTTAAACC ATATAAATCN CGAATTGTGT TATTAAACCC TTGCATCTTG        960

GTAACAATGT CTTGACTAAT AAATGTTTAC CTAACATTGT CTCCACATTT CNANTCC         1017
```

(2) INFORMATION FOR SEQ ID NO: 46:

(i) SEQUENCE CHARACTERISTICS:
        (A) LENGTH:         1035 base pairs
        (B) TYPE:           nucleic acid
        (C) STRANDEDNESS:  single
        (D) TOPOLOGY:      linear (xi) SEQUENCE DESCRIPTION: SEQ ID NO: 46:

```
TGCATGCCTG CAGGTCGATC AAGGGGTGCT TTTAATGTCA AMGAATATTG CAATTRATGG         60

TATGGGTAGA ATTGGAAGAA TGGTATTACG TATTGCATTA CAAAATAAAA ATTTAAATGT        120

AGTAGCGATA AATGCTAGTT ATCCACCCGA AACAATTGCA CATTTAATCA ATTACGATAC        180

GACACATGGA AAATATAATC TAAAAGTTGA ACCGATTGAA AATGGATTGC AAGTTGGAGA        240

TCATAAAATT AAATTGGTTG CTGATCGCAA TCCTGAAAAC TTGCCATGGA AAGAATTAGA        300

TATCGATATT GCTATAGATG CAACTGGTAA ATTTAATCAT GGTGATAAAG CCATCGCACA        360

TATTAAAGCA GGTGCCAAAA AAGTTTTGTT AACTGGTCCT TCAAAAGGTG GACATGTTCA        420

AATGGTAGTT AAAGGCGTAA ATGATAACCA ATTAGATATA GAAGCATTTG ACATTTTTAG        480

TAATGCTTCA TGTACTACTA ATTGCATTGG TCCAGTTGCA AAAGTTTTAA ATAATCAGTT        540

TGGGAATAGT TAATGGTTTA ATGACTACTG TTCACGCTAT TACAAATGAC CAAAAAAATA        600

TTGATAATCC MCATAAAGAT TTAAGACGTG CACGTTCATG TWATGAAAGC ATTATTCCTA        660

CTTCTACTGG TGCGGCGAAA GCTTTAAAAG AAGTATTACC AGAATTAGAA GGTAAATTAC        720

ACGGCATGGC ATTACGTTGT ACCAACAAAG AATGTATCGC TCGTTGATTT AGTTGTTGAT        780

TTAGAAAAAG AAGTAACTGC AGAAGAANTA AACCAAGCTT TTGAAAATGC AGGTTTAGAA        840

GGTATCATAG AANTCGAACA TCACCACTAG TGTCTGTTGA TTTTAATACT AATCCCAATT        900

CAGCTATTAT TGATGCCAAA CCACNATGTC ATGTTCCGGG AAATAAGTAA ANTTATTGCT        960

TGGTATGAAN ATGAATGGGG TTATTCCAAT AAATTGTTAA NNTTGCNGAA CAAATTGGAC       1020

NCTTTGGANT CCAAA                                                        1035
```

(2) INFORMATION FOR SEQ ID NO: 47:

```
    (i) SEQUENCE CHARACTERISTICS:
        (A) LENGTH:           483 base pairs
        (B) TYPE:             nucleic acid
        (C) STRANDEDNESS:     single
        (D) TOPOLOGY:         linear (xi) SEQUENCE DESCRIPTION: SEQ ID NO: 47:

CTCCGTTTGT TTTCGCTTAA AATCCCTTGC ATCGATGCTA ACAATTGATC AACATCTTTA    60

AATTCTTTAT AGACTGATGC AAATCTAACA TATGAAACTT GATCAACATG CATTAACAAG   120

TTCATAACGT GTTCACCTAT ATCTCGTGAA GACACTTCCG TATGACCTTC ATCTCGTAAT   180

TGCCATTCAA CCTTGTTAGT TATGACTTCA AGTTGTTGAT ATCTAACTGG TCGTTTCTCA   240

CAAGAACGCA CAAGTCCATT AAGTTATCTT TTCTCTTGAA AACTGCTCTC TTGTGCCATC   300

TTTTTTCACA ACTATAAGCT GACTAACTTC GATATGNTTC AAATGTTAGT GGAAACGTTG   360

TTTCCACAAT TTTCACATTC TCTTCGTCTT CCGAAATGGC ATTTAATTCA TCGGGCATGC   420

CTTGAATCTA CAACTTTAGA ATTGTGTTAG AATTACATTT CGGGCATTTC ATTACATCAC   480

CTC                                                                 483

(2) INFORMATION FOR SEQ ID NO: 48:

(i) SEQUENCE CHARACTERISTICS:
        (A) LENGTH:           5718 base pairs
        (B) TYPE:             nucleic acid
        (C) STRANDEDNESS:     single
        (D) TOPOLOGY:         linear (xi) SEQUENCE DESCRIPTION: SEQ ID NO: 48:

CTCGGTACCC GGGGATCGTC ATGGAATACC GGAATATTAG TTTCTTTTTT CAATCGTTCT    60

TCAATTTCAA AACAACGTGG TGCCGAAATA TCCTCTAAAT TAATACCACC ATAATTAGGT   120

TCTAACAACT TAACTGTTTT AATGATTTCT TCGGTATCAG TTGTATTTAA CGCAATAGGC   180

ACCCCATTGA TACCAGCGAA GCTTTTGAAT AATACTGCTT TACCTTCCAT TACAGGAATA   240

CTTGCTTCAG GTCCAATGTT ACCTAAACCT AATACCGCTG TTCCATCAGT AATAACTGCA   300

ACTGTATTTC CTTTAATTGT GTAATCATAT ACTTTTCTTT TATCTTCATA AATATCTTTA   360

CACGGTTCAG CAACGCCAGG TGAGTATGCT AAACTTAATT CCTCTTTATT AGTAACTTTT   420

ACATTGGTT TAACTTCTAA TTTACCTTGA TTACGTTTGT GCATTTCCAA TGCTTCATCT   480

CTTAATGACA TGAAATCAGC CCCTAATTCA ATATTTATTT TTAAAAAATA ACTTGGATAA   540

AACGCATTAC ATTATAAAAG TAAAAATATT GGGTAATCTG AATGARTAAG AATTTATGGT   600

TTTGATTATG TAACACAAAT AGCGATAAAC GATAATAAAA TAATATTTAT AAAGATACAT   660

TAAACCATAC TATCTAAAGA TATACCTTTA ATTATTATAA TGGATAGCAA AAACCAATAT   720

ATCAAAAAGT TATTATTTTT CCGCACGATA TATCGACAAA ATTCTTTACT CAATTTATGT   780

ATACTGCTTT TTGTGCTAAT TATTCTTATG GATTAATCAA TAATGTAAAG TGAAACTCAT   840

AAAAATAATA AGCATAAAAA ACTAATATAA ACGCAAACTG ATGGTTAAAA AATATCTAAC   900

CATCAGTTTA CTATATCATA ATTTATTAGT TGATAAAAGT TATATAAGCC TAATATCACT   960

AGGGTTAAAG GGATTGTATA AAATTATTAA ACATACTATC TTTTTGATTA ATATAGCCTA  1020

AAGTAGTCAT TTGTTTAATC GTTTCATCAT AAAAGGATAA CACAACATCA TTAGCATTCT  1080

CTTTCGTAGC TTTAATCATC TCTTCAAACA TATCTATTTG TGATTTATTT CTAATTATAA  1140

TTTGTTTGGC AAATGCTAAT TTTTGTTCTT CAAAAGTGGC TAATGTCTGA ATCTCATTTA  1200

TAATTAGTTG ACGTTGTTGC TTTCTATGGT CAAATTTCCC GCTAACTATA AACAAGTCAT  1260
```

-continued

```
TATGTGATAA CAACTCTTCG TACTTTTTAA ACTGATTAGG GAAAATCACA CCATCTAAAG      1320
TTTCAATGCC ATCATTTAAT GTTGACGAAT GCCATATTTT GACCATTTTT AGTTCGAATT      1380
TGTTTAACTT TATCAAACTG TACTAATATA GGTTTATATA TCTGCGCGTT ACTCAATTTA      1440
AATATCGTTA AATATTGTTT GGCAACAAAC TTTTTATCTA CTGGGTGTTG CGAAACATAA      1500
AATCCTAAAT ATTCTTTTTC GTACTGACTA ATAAGTGCAT CAGGCAATTC TTCTTTATCT      1560
TCATACATCT GTTTTGGCGT TAAAATATCA ATAAAAAAC CATCTTGTTC AATGTTTAAA       1620
TCGCCATCCA ACACTTGATC AATAGCTTGC AACAACGTTG AACGTGTTTT ACCAAAAGCA      1680
TCAAACGCTC CCACTAAAAT CAGTGCTTCA AGTAACTTTC TCGTTWTGAM YCTCTTCGGT      1740
ATACGTCTAG CAWAATCAAA GAAATCTTTA AATTTGCCGT TCTGATAACG TTCATCAACA      1800
ATCACTTTCA CACTTTGATA ACCAACACCT TAATTGTAC CAATTGATAA ATAAATGCCT       1860
TCTTGGGAAG GTTTATAAAA CCAATGACTT TCGTTAATGT TCGGTGGCAA TATAGTGATA      1920
CCTTGTTTTT TTGCTTCTTC TATCATTTGA GCAGTTTTCT TCTCACTTCC AATAACATTA      1980
CTTAAAATAT TTGCGTAAAA ATAATTTGGA TAATGGACTT TTAAAAAGCT CATAATGTAT      2040
GCAATTTTAG AATAGCTGAC AGCATGTGCT CTAGGAAAAC CATAATCAGC AAATTTCAGA      2100
ATCAAATCAA ATATTTGCTT ACTAATGTCT TCGTGATAAC CATTTTGCTT TGSMCCTTCT      2160
ATAAAATGTT GACGCTCACT TTCAAGAACA GCTCTATTTT TTTTACTCAT TGCTCTTCTT     2220
AAAAATATCCG CTTCACCATA ACTGAAGTTT GCAAATGTGC TCGCTATTTG CATAATTTGC    2280
TCTTGATAAA TAATAACACC GTAAGTATTT TTTAATATAG GTTCTAAATG CGGATGTAAA     2340
TATTGAACTT TGCTTGGATC ATGTCTTCTT GTAATGTAAG TTGGAATTTC TTCCATTGGA     2400
CCTGGTCTAT ACAAGAAGT TACAGCAACA ATATCTTCAA AGTGTTCCGG CTTTAATTTT      2460
TTTAATACAC TTCTTACACC GTCAGACTCT AATTGGAATA TGCCAGTCGT ATCTCCTTGC     2520
GACAACAATT CAAACACTTT TTGATCATCA AACGGAATCT TTTCGATATC AATATTAATA     2580
CCTAAATCTT TTTTGACTTG TGTTAAGATT TGATGAATAA TCGATAAGTT TCTCAACCCT     2640
AGAAAATCTA TTTTTAATAA CCCAATACGT YCGGCTTCAG TCATTGTCCA TTGCGTTAAT     2700
AATCCTGTAT CCCCTTTCGT TAAAGGGGCA TATTCATATA ATGGATGGTC ATTAATAATA     2760
ATYCCTGCCG CATGTGTAGA TGTATGTCTT GGTAAACCTT CTAACTTTTT ACAAATACTG     2820
AACCAGCGTT CATGTCGATG GTTTCGATGT ACAAACTCTT TAAAATCGTC AATTTGATAT     2880
GCTTCATCAA GTGTAATTCC TAATTTATGT GGGATTAAAC TTGAAAATTT CATTTAATGT     2940
AACTTCATCA AACCCCATAA TTCTTCCAAC ATCTCTAGCA ACTGCTCTTG CAAGCAGATG     3000
AMCGAAAGTC ACAATTCCAG ATACATGTAG CTCGCCATAT TTTTCTTGGA CGTACTGAAT     3060
GACCCTTTCT CGGCGTGTAT CTTCAAAGTC AATATCAATA TCAGGCATTG TTACACKTTC    3120
TGGGTTTAAA AAACGTTCAA ATAATAGATT GAATTTAATA GGATCAATCG TTGTAATTCC     3180
CAATAAATAA CTGACCAGTG AGCCAGCTGA AGAACCACGA CCAGGACCTA CCATCACATC     3240
ATTCGTTTTC GCATAATGGA TTAAATCACT WACTATTAAG AAATAATCTT CAAAACCCAT     3300
ATTAGTAATA ACTTATACT CATATTTCAA TCGCTCTAAA TAGACGTCAT AATTAAGTTC      3360
TAATTTTTTC AATTGTGTAA CTAAGACACG CCACAAATAT TTTTTAGCTG ATTCATCATT     3420
AGGTGTCTCA TATTGAGGAA GTAGAGATTG ATGATATTTT AATTCTGCAT CACACTTTTG     3480
AGCTATAACA TCAACCTGCG TTAAATATTT CTTGGTTAAT ATCTAATTGA TTAATTTCCT    3540
TTTTCAGTTA AAAAATGTGC ACCAAAATCT TTCTTGATCA TGAATTAAGT CTAATTTTGT    3600
ATTGTCTCTA ATAGCTGCTA ATGCAGAAAT CGTATCGGCA TCTTGACGTG TTTGGTAACA    3660
```

```
AACATTTTGA ATCCAAACAT GTTTTCTACC TTGAATCGAA ATACTAAGGT GGTCCATATA    3720

TGTGTCATTA TGGGTTTCAA ACACTTGTAC AATATCACGA TGTTGATCAC CGACTTTTTT    3780

AAAAATGATA ATCATATTGT TAGAAAATCG TTTTAATAAT TCAAACGACA CATGTTCTAA    3840

TGCATTCATT TTTATTTCCG ATGATAGTTG ATACAAATCT TTTAATCCAT CATTATTTTT    3900

AGCTAGAACA ACTGTTTCGA CTGTATTTAA TCCATTTGTC ACATATATTG TCATACCAAA    3960

AATCGGTTTA ATGTTATTTG CTATACATGC ATCATAAAAT TTAGGAAAAC CATACAATAC    4020

ATTGGTGTCA GTTATGGCAA GTGCATCAAC ATTTTCAGAC ACAGCAAGTC TTACGGCATC    4080

TTCTATTTTT AAGCTTGAAT TTAACAAATC ATAAGCCGTA TGAATATTTA AATATGCCAC    4140

CATGATTGAA TGGCCCCTTT CTATTAGTTA AGTTTTGTGC GTAAAGCTGT AGCAAGTTGC    4200

TCAAATTCAT CCCAGCTGTC CAACTGAAAY TCCTGACGCA TTCGGATGAC CACCGCCACC    4260

AAAATCTTGC GCAATATCAT TAATAATCAA TTGCCCTTTA GAACGTAATC GACATCTGAT    4320

TTCATTACCT TCATCGACTG CAAATACCCA TATTTTCAAG CCTTTGATGT CAGCAATTGT    4380

ATTAACAAAC TGAGATGCTT CATTTGGCTG AATACCGAAT TGCTCCAATA CATCTTCAGT    4440

TATTTTAACT KGGCAGAATC CATCATCCAT AAGTTCGAAA TGTTGYAAAA CATAACCTTG    4500

AAACGGCAAC ATTKYTGGGT CCTTCTCCAT CATTTTATTT AAAAGCGCAT TATGATCAAT    4560

ATCATGCCCA ATTAACTTTC CAGCAATTTC CATAGTATGT TCWGAGGTAT TGTTAAAAAG    4620

GRGATCGCCC AGTATCACCG ACGATACCAA GATATAAAAC GCTCGCGATA TCTTTATTAA    4680

CAATTGCTTC ATCATTAAAA TGTGAGATTA AATCGTAAAT GATTTCACTT GTAGATGACG    4740

CGTTCGTATT AACTAAATTA ATATCACCAT ACTGATCAAC TGCAGGATGA TGATCTATTT    4800

TAATAAGTYT ACGACCTGTA CTATAACGTT CATCGTCAAT TCGTGGAGCA TTGGCAGTAT    4860

CACATACAAT TACAAGCGCA TCTTGATATG TTTTATCATC AATGTTATCT AACTCTCCAA    4920

TAAAACTTAA TGATGATTCC GCTTCACCCA CTGCAAATAC TTGCTTTTGC GGAAATTTCT    4980

GCTGAATATA GTATTTTAAA CCAAGTTGTG AACCATATGC ATCAGGATCK RSTYTARMRK    5040

RTCYSYGKMT AMYRATTGYA TCGTTGTCTT CGATACATTT CATAATTTCA TTCAAAGTAC    5100

TAATCATTTT CAWACTCCCT TTTTTAGAAA AGTGGCTTAA TTTAAGCATT AGTCTATATC    5160

AAAATATCTA AATTATAAAA ATTGTTACTA CCATATTAAA CTATTTGCCC GTTTTAATTA    5220

TTTAGATATA TATATTTTCA TACTATTTAG TTCAGGGGCC CCAACACAGA GAAATTGGAC    5280

CCCTAATTTC TACAAACAAT GCAAGTTGGG GTGGGGCCCC AACGTTTGTG CGAAATCTAT    5340

CTTATGCCTA TTTTCTCTGC TAAGTTCCTA TACTTCGTCA AACATTTGGC ATATCACGAG    5400

AGCGCTCGCT ACTTTGTCGT TTTGACTATG CATGTTCACT TCTATTTTGG CGAAGTTTCT    5460

TCCGACGTCT AGTATGCCAA AGCGCACTGT TATATGTGAT TCAATAGGTA CTGTTTTAAT    5520

ATACACGATA TTTAAGTTCT CTATCATGAC ATTACCTTTT TTAAATTTAC GCATTTCATA    5580

TTGTATTGTT TCTTCTATAA TACTTACAAA TGCCGCTTTA CTTACTGTTC CGTAATGATT    5640

GATTAAAAGT GGTGAAACTT CTACTGTAAT TCCATCTTGA TTCATTGTTA TATATTTGGC    5700

GATTTGATCC TCTAGAGT                                                 5718
```

(2) INFORMATION FOR SEQ ID NO: 49:

(i) SEQUENCE CHARACTERISTICS:
        (A) LENGTH: 513 base pairs
        (B) TYPE: nucleic acid
        (C) STRANDEDNESS: single
        (D) TOPOLOGY: linear (xi) SEQUENCE DESCRIPTION: SEQ ID NO: 49:

```
TTCTTGCCTC CCAATCGCCT AATAGCCCTN AAAACTACTT TTTTTAATCT ATAGGCGATG     60

TAAAAATACC ATATATTGAN GGTGCTATAC CTCCTAAAAT AGCAGTTCCC AAAGTTGTCA    120

TTACTGAAAT TACTGCGAAA GTATCATCCG AAAGCAATAA ATTCAAACTA ATGCATTGTT    180

TATTACCCAT CGAATTTATT GACCAAATAG CTAGAGAAAT AAACAACCCA AAATTTAAAA    240

TAAATGATAT AGTAATAGCA ATTGTTTACA AAACACGGAA TTTTTCATTT TTATTTATAT    300

TATCCATTTT NCTCCCTTTT NCTTAAATCA TTTTATTATA TATTNCAATA ATCAATCTGA    360

AATGTTGATG TAATTTGNNA AAAATATCAT ACTTTTNCTC CTGAAAACCT CCCTAAATCA    420

TCAATATGGN AATCNGTNTT NGGGTATTGC GNTTNCAACT CTTTTAAANC TCACTCNTTC    480

TTCTCATCGN CTTAACCGTA CTATCANTAA AAT                                 513
```

(2) INFORMATION FOR SEQ ID NO: 50:

(i) SEQUENCE CHARACTERISTICS:
        (A) LENGTH: 533 base pairs
        (B) TYPE: nucleic acid
        (C) STRANDEDNESS: single
        (D) TOPOLOGY: linear (xi) SEQUENCE DESCRIPTION: SEQ ID NO: 50:

```
CTGAGCTGCT TNCANNNCCA NTNTGAAAAA GCCCCCAGNN CAGCCCGNTT NCAAAACAAC     60

GNCTNCATTT GAANCCCCAT GAAAAGAAC GAATTTTGAC AATGGNTTAA AAAACANGNA     120

AGATAATAAG AAAAAGTGCC GTCAACTGCA TATAGTAAAA GTTGGCTAGC AATTGTATGT    180

NCTATGATGG TGGTATTTTC AATCATGCTA TTCTTATTTG TAAAGCGAAA TAAAAAGAAA    240

AATAAAAACG AATCACAGCG ACGNTAATCC GTGTGTGAAT TCGTTTTTTT TATTATGGAA    300

TAAAAATGTG ATATATAAAA TTCGCTTGTC CCGTGGCTTT TTTCAAAGCC TCAGGNTTAA    360

GTAATTGGAA TATAACGNCA AATCCGTTTT GTAACATATG GGTAATAATT GGGAACAGCA    420

AGCCGTTTTG TCCAAACCAT ATGCTAATGN AAAAATGNCA CCCATACCAA AATAAACTGG    480

GATAAATTTG GNATCCATTA TGTGCCTAAT GCAAATNCCT NATGACCTTC CTT           533
```

(2) INFORMATION FOR SEQ ID NO: 51:

(i) SEQUENCE CHARACTERISTICS:
        (A) LENGTH: 568 base pairs
        (B) TYPE: nucleic acid
        (C) STRANDEDNESS: single
        (D) TOPOLOGY: linear (xi) SEQUENCE DESCRIPTION: SEQ ID NO: 51:

```
CCGACAGTCG TTCCCNTCAT GCAAAATATG GGGGCTAAAC TCAGTTCAAG AAGTCGGCAA     60

ATAAGACAAA TGAAATTGCC TGGTGACGGT AGNACAACTG CAACAGTATT AGCTCAAGCA    120

ATGATTCAAG AAGGCTTGAA AAATGTTACA AGTGGTGCGA ACCCAGTTGG TTTACGACAA    180

GGTATCGACA AAGCAGTTAA AGTTGCTGTT GAAGCGTTAC ATGAAAATTC TCAAAAAGTT    240

GAAAATAAAA ATGAAATTNC GCAAGTAGGT GCGNTTTCAG CAGCAGATGN AGNAATTNGA    300

CGTTATATTT CTGAAGCTAT NGGNAAAGTA GGTAACGNTG GTGTCATTAC ANTTNTNGGG    360

TCAAATGGGC TNTNCACTNN NCTNGANGTG GTTGNNGGTG TNCNATTTGA TCNNNGTTAT    420

CANTCACCNN CTATNGTTAC TGCTTCNGCT AAAATGGTTG CTGCNTTTGG NCGCCCCTAC    480

ATTTTTGTNA CNGCTTNGGG ANTCTCGTCT TTNCNCGATT CTTTCCCCTT TTTGGCCCNT    540
```

```
GGGNAATCTT TTNGGNCNCC CTTTATTT                                              568
```

(2) INFORMATION FOR SEQ ID NO: 52:

(i) SEQUENCE CHARACTERISTICS:
        (A) LENGTH:         437 base pairs
        (B) TYPE:           nucleic acid
        (C) STRANDEDNESS:   single
        (D) TOPOLOGY:      linear (xi) SEQUENCE DESCRIPTION: SEQ ID NO: 52:

```
CAAYTTAGYC AACTACTACC AATATAGCAC TAGAACTGGA AATGATAATT TAATATTGKG            60

CACTTTTTSA TTGKTTAAAC ATGTACATAT TTNAAAAAAT AGGAGAGCAA AGKAAATAAT           120

TGATATAGTT ATTTTSAGAG TAATCCTAGG AACTATTGTA TTTATATTTS TCTCCCCTAC           180

TTTTAAATGT CATTCATTAT ACATAAGCAT TTTGATATAG AATTTATCAC ATATGCAAAT           240

TGAAAACAGG TTAAGACCAT TTTTTGTCTC AACCTGTTTT ATTTATTATC TATTTMTAAT           300

TTCATCAATT TCTTTGTATA TTTTTYCTAA TGCAACTTTA GCATCAGCCA TTGATACGAA           360

ATCATTTTYC TTAAGTGCCG CTTTAGCTCT ATATTCATTC ATYATAATCG TACGTTTATA           420

ATATGGATTT ACGTTGA                                                         437
```

(2) INFORMATION FOR SEQ ID NO: 53:

(i) SEQUENCE CHARACTERISTICS:
        (A) LENGTH:         659 base pairs
        (B) TYPE:           nucleic acid
        (C) STRANDEDNESS:   single
        (D) TOPOLOGY:      linear (xi) SEQUENCE DESCRIPTION: SEQ ID NO: 53:

```
CCCGATTCGA GCTCGGTACC GGNGATCCTC TAGAGTCGAT CTATCAAGCA GTAAATGAAA            60

AAATGGACAT TAATGATATT AATATCGACA ATTTCCAATC TGTCTTTTTT GACGTGTCTA           120

ATTTGAATTT AGTAATTCTA CCAACGTTAA TCATTAGCTG GGTCACAATA TTTAACTATA           180

GAATGAGAAG TTACAAATAA AATCTATGAG ATTATACCTN CAGACACCAA CATTCAAATG           240

GTGTCTTTTN TGTTGTGTGG TTTTATTTNT GAAATNCGAA AAAGTAGAGG CATGAATTTT           300

GTGACTAGTG TATAAGTGCT GATGAGTCAC AAGATAGATA GCTATATTTT GTCTATATTA           360

TAAAGTGTTT ATAGNTAATT AATAATTAGT TAATTTCAAA AGTTGTATAA ATAGGATAAC           420

TTAATAAATG TAAGATAATA ATTTGGAGGA TAATTAACAT GAAAAATAAA TTGATAGCAA           480

AATCTTNATT AACATTAGGG GCAATAGGTA TTACTACAAC TACAATTGCG TCAACAGCAG           540

ATGCGAGCGA AGGATACGGT CCAAGAGAAA AGAAACCAGT GAGTATTAAT CACAATATCG           600

NAGAGTACAA TGATGGTACT TTTAATATCA ATCTTGANCA AAATTACTCA ACAACCTAA           659
```

(2) INFORMATION FOR SEQ ID NO: 54:

(i) SEQUENCE CHARACTERISTICS:
        (A) LENGTH:         298 base pairs
        (B) TYPE:           nucleic acid
        (C) STRANDEDNESS:   single
        (D) TOPOLOGY:      linear (xi) SEQUENCE DESCRIPTION: SEQ ID NO: 54:

```
AATNCTCCTC CNATGNTTTA TNATGAAACT AACTTTAAGT NAAATATTTN TCCAGACTAC            60

TTGCATCTCC NTTATNCCCT TCTATAGTTN CTATCCCAGT TNATGATAAA AGTAATGCTA           120

ATGTNCCTGT NAATATATAT TTNTAAAAAT NNATTATAAG CNCTCCTTAA AATTNATACT           180
```

```
TACTGAGTAT ATAGTCAATT TNNGGACAAT TACATTAACC TGTCATTAAA TNGATTACTT        240

TTTNNATTAA CAAAAATTAA CATAACATTT AATTAATTNT TTCCNGATAN CAGCAACG         298
```

(2) INFORMATION FOR SEQ ID NO: 55:

(i) SEQUENCE CHARACTERISTICS:
        (A) LENGTH:         535 base pairs
        (B) TYPE:           nucleic acid
        (C) STRANDEDNESS:   single
        (D) TOPOLOGY:      linear (xi) SEQUENCE DESCRIPTION: SEQ ID NO: 55:

```
TCCAAATATT CACCAAGCTG TAGTTCAAGA TGATAACCCT NATTTTAANT CTGGCGAAAT        60

CACTCAAGAN CTACAAAAAG GATACAAGCT TAAAGATAGA GTATTAAGAC CATCANTGGT       120

CAAAGTAAAC CAATAACTTA AATTTGGCGA AAAGACATTG TTTAAAATTA ANTTAATTTA       180

ATGATTAATT GGAGGNATTT TNTTATGAGT AAAATTNTTG GTATAGACTT AGGTACAACA       240

NATTCATGTG TAACAGTATT AGANGGCGAT GAGCCAAAAG TAATTCAAAA CCCTGANGGT       300

TCACGTACAA CACCATCTGT NGTAGCTTTC AAAAATGGAG AAACTCAAGT TGGTGAAGTA       360

GCAAAACGTC AAGCTATTAC AAACCCAAAC ACTGTTCANT CTATTAGNCG TCATATGGGT       420

ACTGNTTATA ANGTAGATAT TGAGGGTAAA TCATACACAC CACAAGNNNT CTCAGCTNTG       480

NTTTTNCAAA ACTTANNANT TNCAGCTGNA GTNATTTAGG TGNGNNNGTT GNCAA            535
```

(2) INFORMATION FOR SEQ ID NO: 56:

(i) SEQUENCE CHARACTERISTICS:
        (A) LENGTH:         540 base pairs
        (B) TYPE:           nucleic acid
        (C) STRANDEDNESS:   single
        (D) TOPOLOGY:      linear (xi) SEQUENCE DESCRIPTION: SEQ ID NO: 56:

```
ATGACTGCAG GTCGATCCAT GATTTACAAG TATATTGGTA GCCAATTCTA CTGCTTCATG        60

ATTAATAATA ATTGAAAGCT CTGTCCAGTT CATACTTTAT TCTCCCTTAA AGAATCTTTT       120

TGNTCTATCT TTAAAATTCG AAGGTTGTTC ATTAATTTCT TCACCATTTA ATTGGGCAAA       180

TTCTTTCATT AGTTCTTTNT GTCTATCTGT TAATTTAGTA GGCGTTACTA CTTTAATATC       240

AACATATAAA TCTCCGTATC CATAGCCATG AACATTTTTT ATACCCTTTT CTTTTAAGCG       300

GAATTGCTTA CCTGTTTGTG TACCAGCAGG GGATTGTTAA CATAACTTCA TTATTTAATG       360

TTGGTATTTT TATTTCATCG CCTAAAGCTG CTTGTGGGAA GCTAACATTT AATTTGNAAT       420

AAATATCATC ACCATCACGT TTAAATGTTT CAGATGGTTT AACTCTAAAT ACTACGTATT       480

AATCANCAGG AGGTCCTCCA TTCACGGCTG GAGAGGCTTC AACAGCTAAT CTTATTTGGT       540
```

(2) INFORMATION FOR SEQ ID NO: 57:

(i) SEQUENCE CHARACTERISTICS:
        (A) LENGTH:         536 base pairs
        (B) TYPE:           nucleic acid
        (C) STRANDEDNESS:   single
        (D) TOPOLOGY:      linear (xi) SEQUENCE DESCRIPTION: SEQ ID NO: 57:

```
TTTATAATTT CATCTNTTGA AGCATCCTTA CTAATGCCTA AAACTTCATA ATAATCTCTT        60

TTGGCCACAG CTATCTCTCC TTTNCTNAAT TAACTCATAT AGTTTAACGT AATATGTCAT       120

ACTATCCAAA TAAAAAGCCA AAGCCAATGT NCTATTGACT TTNACTTTTC ANATCATGAC       180
```

```
AACATTCTAA TTGTATTGTT TAATTATTTT NTGTCGTCGT CTTTNACTTC TTTAAATTCA      240

GCATCTTCTA CAGTACTATC ATTGTTTTNA CCAGCATTAG CACCTTGTNT TGTTGTTGCT      300

GTTGAGCCGC TTGCTCATAT ACTTTTNCTG NTAATTCTTG ANTCACTTTT TCAAGTTCTT      360

CTTTTTTAGA TTTANTATCT TCTATATNCT TGACCTTTCT AANGCAGTTT TAAGAGCGTC      420

TTTTTTCCTC TTTCTGCAGT TTTNTTATAC TTCCTTTCAC CGTNATTTTT CGGCTTATTT      480

CAGTTAAANG TTTTTCCANC TTGGGTNTAN CTATGGCTAG NAAAGNTTCG NTTCCT         536
```

(2) INFORMATION FOR SEQ ID NO: 58:

(i) SEQUENCE CHARACTERISTICS:
        (A) LENGTH:       536 base pairs
        (B) TYPE:         nucleic acid
        (C) STRANDEDNESS:  single
        (D) TOPOLOGY:     linear (xi) SEQUENCE DESCRIPTION: SEQ ID NO: 58:

```
AAGATAAAAT GGCATTACAA CGTTTNAAAG ATGCTGCTGA AAAANCTAAA AAAGACTTAT       60

CAGGTGTATC ACAAACTCAA ATCTCATTAC CATTTATCTC AGCTGGTGAA AACGGTCCAT      120

TACACTTAGA AGTAAACTTA ACTCGTNCTA AATTTGAAGA ATTATCAGAT TCATTAATTA      180

GAAGANCAAT GGAACCTACA CGCCAAGCAA TGAAAGACGC TGGCTTAACA AACTCAGATA      240

TCGATGAAGT TATCTTAGTT GGTGGNTCAA CTCGTATTCC AGCAGTACAA GANGCTGTCA      300

AAAAAGAAAT CGGTAAAGAG CCTAACAAAG GAGTAAACCC GGNCGAAGTA GGTGGCAATG      360

GGNGCTGCAA TCCAAGGTGG CGTTATTCAC AGGTGACGTT TAAAGACGTG TATTATTAGG      420

NCGTAACACC ACTATCTTTA GGTATTGAAA TTTTAGGTGG NCGTATGNAT TACGGTAATT      480

GAACGTAACA CTACGGTTCC TNCATTCTAA NTCTCAAAAT CTNTTCAACA GCAGTT         536
```

(2) INFORMATION FOR SEQ ID NO: 59:

(i) SEQUENCE CHARACTERISTICS:
        (A) LENGTH:       925 base pairs
        (B) TYPE:         nucleic acid
        (C) STRANDEDNESS:  single
        (D) TOPOLOGY:     linear (xi) SEQUENCE DESCRIPTION: SEQ ID NO: 59:

```
CTAGAGTCGA TCTAAAGAAT ATNTAANTCC TNATATKSCT GATGTTGTAA AAGAAGTGGA       60

TGTTGAAAAT AAAAAAATTA TCATCACGCC AATGGAAGGA TTGTTGGATT AATGAAAATT      120

GATTATTTAA CTTTATTTCC TGAAATGTTT GATGGTGTTT TAAATCATTC AATTATGAAA      180

CGTGCCCANG AAAACAATAA ATTACAAATC AATACGGTTA ATTTTAGAGA TTATGCAATT      240

AACAAGCACA ACCAAGTAGA TGATTATCCG TATGGTGGCG GWCAAGGTAT GGTGTTAAAG      300

CCTGACCCTG TTTTTAATGC GATGGAAGAC TTAGATGTCA CAGAMCAAAC ACGCGTTATT      360

TTAATGTGTC CACAAGGCGA GCCATTTTCA CATCAGAAAG CTGTTGATTT AAGCAAGGCC      420

GACCACATCG TTTTCATATG CGGACATTAT GAAGGTTACG ATGAACGTAT CCGAACACAT      480

CTTGTCACAG RTGAAATATC AATGGGTGAC TATGTTTTAA CTGGTGGAGA ATTGCCAGCG      540

ATGACCATGA CTGATGCTAT TGTTAGACTA ATTCCAGGTG TTTTAGGTAA TGNACAGTCA      600

CATCAAGACG ATTCATTTTC AGATGGGTTA TTAGAGTTTC GCAATATAC ACGTCCGCGT       660

GAATTTAAGG GTCTAACAGT TCCAGATGTT TTATTGTCTG GAAATCATGC CAATATTGAT      720

GCATGGGAC ATGAGCAAAA GTTGAACCGC ACATATAATN AAAGACCTGA CTTAATTNNA       780

AAATACCCAT TAANCCAATG GCAGCATAAG GCAAATCATT CAGNAAANAT CATTAAAATC      840
```

AGGTATTNGT AAAAAGGTTN AGTGATTGTG NNNAACNNAN TNGNATGTGG CAAACATNCN    900

AANTACATCC TGGAAGGACC TCACG    925

(2) INFORMATION FOR SEQ ID NO: 60:

(i) SEQUENCE CHARACTERISTICS:
      (A) LENGTH: 2531 base pairs
      (B) TYPE: nucleic acid
      (C) STRANDEDNESS: single
      (D) TOPOLOGY: linear (xi) SEQUENCE DESCRIPTION: SEQ ID NO: 60:

TGGYTTRTTT CAACATAATA TAGACATTTY CAATGTTATT CTATTAATTC TCCACGAAAC    60

TGTTATCTTA TCGTTTTCTG GTTCTAATAT GTGTTTTTTG GGTGATTTAA TTACTTGTTC    120

CGTTGAACAT TTACAAGGCC TTTTTTAAGT TAACTGTTTG ACCTCATTAC GTGTACCGAC    180

GCCCATATTT GCTAAAAATT TATCTATTCT CATCGTAAAA ACCTAACTCT ACGTCTTAAT    240

TTTTCAGGAA TTTCACCTAA GAATTCGTCC GCAAGACGCG TTTTAATTGT GAWTGTACCG    300

TAAATTAGAA TACCTACTGT AACACCTAAA ATAATAATGA TTAAGTWACC AAGTTTTAGT    360

AGGTYCTAAR AATARATTTG CAAGGNAAAA TACTAATTCT ACACCTAGCA TCATAATNNT    420

GNATACAAGG ATATWTWTGC AAAATGGATC CCAACTATAG CTGAATTTAA ACTTCGCATA    480

TWTTTTAAGR ATWTAGRAAT TACATCCMAT TGCAAATAAT TAATGCGATA CTAGTACGTA    540

AAATTGCACC AGGTGTATGG AATAACATAA TTAATGGATA GTTTAACGCT AACTTGATAA    600

CTACAGAAGC TAAAATAACA TAAACTGTTA ATTTCTGTTT ATCTATACCT TGTAANATNG    660

ATGCCGTTAC ACTTAATAGT GAAATYAGTA TTGCTACAGG CGCATAATAK AATAATAAGC    720

GACTACCATC ATGGTTAGGG TCATGACCTA WAACAATTGG ATCGTAACCA TAGATAAACT    780

GTGAAATTAA TGGTTGTGCC AAGGCCATAA TCYCCAATAC TAGCTGGGAA CAGTTATAAA    840

CATTWAGTTA CACCAATTAG ATGTTCCTAA TTTGATGATG CATTTCATGT AAGCGACCTT    900

CTGCAAATGT TTTTGTAATA TAAGGAATTA AACTCACTGC AAAACCAGCA CTTAATGATG    960

TCGGAATCAT TACAATTTTA TTAGTTGACA TATTTAGCAT ATTAAAGAAT ATATCTTGTA    1020

ACTGTGAAGG TATACCAACT AAAGATAAAG CACCGTTATG TGTAAATTGA TCTACTAAGT    1080

TAAATAATGG ATAATTCAAA CTTACAATAA CGAACGGTGA TACTATAAGC AATAATTTCT    1140

TTATACATCT TGCCATATGA CACATCTATA TCTGTGTAAT CAGATTCGAC CATACGATCA    1200

ATATTATGCT TACGCTTTCT CCAGTAATAC CAGAGTGTGR ATATRCCAAT AATCGCACCA    1260

ACTGCTGCTG CAAAAGTAGC AATACCATTG GCTAATAAAA TAGAGCCATC AAAGACATTT    1320

AGTACTAAAT AACTTCCGAT TAATATGAAA ATCACGCGTG CAATTTGCTC AGTTACTTCT    1380

GACACTGCTG TTGGCCCCAT AGATTTATAA CCTTGGAATA TCCCTCTCCA TGTCGCTAAT    1440

ACAGGAATAA AGATAACAAC CATACTAATG ATTCTTATAA TCCAAGTTAA TATCATCCGA    1500

CTGACCAACC GTTTTATCA TGAATGTTTC TAGCTAATGT TAATTCAGAA ATATAAGGTG    1560

YTAAGAAATA CAGTACCAAG AAACCTAAAA CACCGGTAAT ACTCATTACA ATAAAAYTCG    1620

ATTTATAAAA WTTCTGACTT WACTTTAWAT GCCCCAATAG CATTATATTT CGCAACATAT    1680

TTCGAAGCTG CTAATGGTAC ACCTGCTGTC GCCAACTGCA ATTGCAATAT TATATGGTGC    1740

ATAAGCGTWT GTTGAACGGS GCCATATTTT CTTGTCCCNC CAATTAAATA GTTGAATGGA    1800

ATGATAAAAA GTACGCCCAA TACCTTGGTA ATTAATATAC TAATGGTAAT TAAAAAGGTT    1860

CCACGCACCA TTTCTTTACT TTCACTCATT ACGAATCTCC CTATCTCATG TTTATTAAAG    1920

```
TTTTGTAAAC TAAAAGCTGT TTCTCTGTAA AATCATTTTT CATTATTATG AAATATCAC     1980

AAAACTTTAT TTCATYGTCG TATATTTCAA TGGAATTATC CATAACAAAA TTATCAACAC    2040

ATTGTCATTG AATACTAGAT TTTGATTAGA ATATTACGAA ATTTCATATA AACATTATAC    2100

TACTATTTGA GATGAACATC GCATAACAGT AGAAAAATCA TTCTTATCAT ACACATACAT   2160

CTTCATTTTT TATGAAGTTC ACATTATAAA TATATTCAAC ATAATTGTCA TCTCATAACA   2220

CAAGAGATAT AGCAAAGTTT AAAAAAGTAC TATAAAATAG CAATTGAATG TCCAGTAACA   2280

AATTTGGAGG AAGCGTATAT GTATCAAACA ATTATTATCG GAGGCGGACC TAGCGGCTTA   2340

ATGGCGGCAG TAGCWGCAAG CGAACAAAGT AGCAGTGTGT TACTCATTGA AAAAAAGAAA   2400

GGTCTAGGTC GTAAACTCAA AATATCTGGT GGCGGTAGAT GTAACGTAAC TAATCGAYTA   2460

CCATATGCTG AAATTATTCA AGGAACATTC CCTGGAAATG GGAAATTTTY ATCATAGTTC   2520

CCTTTTCAAT T                                                        2531
```

(2) INFORMATION FOR SEQ ID NO: 61:

(i) SEQUENCE CHARACTERISTICS:
        (A) LENGTH:         888 base pairs
        (B) TYPE:           nucleic acid
        (C) STRANDEDNESS:  single
        (D) TOPOLOGY:     linear (xi) SEQUENCE DESCRIPTION: SEQ ID NO: 61:

```
TCGAGCTCGG TACCCGGGGA TCCTCTAGAG TCGATCTACA GAGCTGTTTA ACGTTTGTAC     60

TGAGTCACCG ATACCTTTAA CAGCATCTAC AACTGAGTTT AAACGATCTA CTTTACCTTG    120

GATATCCTCA GTTAAACGGT TTACTTTATG AAGTAAATCT GTTGTTTCAC GAGTAATACC    180

TTGAACTTGA CCTTCTACAC CGTCAAGTGT TTTTGCAACA TAATCTAAGT TTTTCTTAAC    240

AGAATTTAAT ACAGCTACGA TACCGATACA TAAAATTAAG AATGCAATCG CAGCGATAAT    300

TCCAGCAATT GGTAAAATCC AATCCATTAA AAACGCCTCC TAATTAACAT GTAATAATGT    360

CATTAATAAT AAATACCCAT ACTACTCTAT TATAAACATA TTAAAACGCA TTTTTCATGC    420

CTAATTTATC TAAATATGCA TTTTGTAATT TTTGAATATC ACCTGCACCC ATAAATGAAA    480

ATAACAGCAT TATCAAATTG TTCTAATACA TTAATAGAAT CTTCATTAAT TAACGATGCA    540

CCTTCAATTT TATCAATTAA ATCTTGTWTC GTTAATGCGC CAGTATTTTC TCTAATTGAT    600

CCAAAAATTT CACAATAAGA AATACACGAT CTGCTTTACT TAAACTTTCT GCAAATTCAT    660

TTAAAAATGC CTGTGTTCTA GAGAAAGTGT GTGGTTTGAN ATACTGCAAC AACTTCTTTA    720

TGTGGATATT TCTTTCGTGC GGTTTCAATT GNNGCACTAA NTTCTCTTGG ATGGTGTNCA    780

TAATCAGCTA CATTAACTTG ATTTGCGATT GTAGTNTCAT NGANNGACGT TTAACNCCAC    840

CAACGTTTCT AATGCTTCTT TAANATTGGG ACATCTAACT TCTCTAAA                 888
```

(2) INFORMATION FOR SEQ ID NO: 62:

(i) SEQUENCE CHARACTERISTICS:
        (A) LENGTH:         902 base pairs
        (B) TYPE:           nucleic acid
        (C) STRANDEDNESS:  single
        (D) TOPOLOGY:     linear (xi) SEQUENCE DESCRIPTION: SEQ ID NO: 62:

```
GCATGCCTGC AGGTCGATCC AAAAATGGTT GAATTAGCTC CTTATAATGG TTTGCCMMMT     60

TTRGTTGCCA CCGKTAATTA CAGATGTCMA AGCCAGCTAC ACAGAGTTTG AAAAKGGSCC    120
```

|                                                                      |      |
|----------------------------------------------------------------------|------|
| STWGAAAGGA AATGGAACGA ACGTKATAAG TTATTTGCCA CATTACCATG TACGTAATAT     | 180  |
| AACAGCCATT TAACAAAAAA GCCACCATAT GATGAAAGAW TGCCAAAAAT TGTCATTGTA     | 240  |
| ATTGATGAGT TGGCTGATTT AATGATGATG GCTCCGCAAG AAGTTGAACA GTCTATTGCT     | 300  |
| AGAATTGCTC AAAAAGCGAG AGCATGTGGT ATTCATATGT TAGTAGCTAC GCAAAGACCA     | 360  |
| TCTGTCAATG TAATTACAGG TTTAATTAAA GCCAACATAC CAACAAGAAT TGCATTTATG     | 420  |
| GTATCATCAA GTGTAGATTC GAGAACGATA TTAGACAGTG GTGGAGCAGA ACGCTTGTTA     | 480  |
| GGATATGGCG ATATGTTATA TCTTGGTAGC GGTATGAATA AACCGATTAG AGTTCAAGGT     | 540  |
| ACATTTGTTT CTGATGACGA AATTGATGAT GTTGTTGATT TTATCAAACA ACAAAGAGAA     | 600  |
| CCGGACTATC TATTTGAAGA AAAAAGAAAT TGTTGAAAAA AACACAAACA CMATCMCMAG     | 660  |
| ATGAATTATT TGATGATGTT TGTGCATTTA TGGTTAATGA AGGACATATT TCAACATCAT     | 720  |
| TAATCCAAAG ACATTTCCAA ATTGGCTATA ATAGAGCAGC AAGAATTATC GATCAATTAG     | 780  |
| AAGCAACTCG GTTATGTTTC GAGTGCTAAT NGGTTCAAAA ACCNAGGGAT GTTTATGTTA     | 840  |
| CGGAAGCCGA TTTTAAATAA AGAATAATTT ATGATTAAGG ATTTTTATAT AATGGACACC     | 900  |
| CC                                                                   | 902  |

(2) INFORMATION FOR SEQ ID NO: 63:

(i) SEQUENCE CHARACTERISTICS:
        (A) LENGTH:        3592 base pairs
        (B) TYPE:          nucleic acid
        (C) STRANDEDNESS:  single
        (D) TOPOLOGY:      linear (xi) SEQUENCE DESCRIPTION: SEQ ID NO: 63:

|                                                                      |      |
|----------------------------------------------------------------------|------|
| GATCCTTATT CTGAATATTT AACAAAWGCA ACAAACGAAA TCCCTTTGAA TGAAAGGTGT     | 60   |
| TTCAGGTGCA TTTTKTAGGT ATTGGTGCAG AAAATGCAAA AGAAAAATGA ATCAAATTAT     | 120  |
| GGTTACTAGT CCTATGAAGG GWTCTCCAGC AGAACGTGCT GGCATTCGTC CTAAAGATGT     | 180  |
| CATTACTAAA GTAAATGGAA AATCAATTAA AGGTAAAGCA TTAGATGAAG TTGTCAAAGA     | 240  |
| TGTTCGTGGT AAAGAAAACA CTGAAGTCAC TTTAACTGTT CAACGAGGTA GTGAAGAAAA     | 300  |
| AGACGTTAAG ATTAAACGTG RAAAAATTCA TGTTAAAAGT GTTGAGTATW AGRAAAAAGG     | 360  |
| TAAAGTTGGA GTTATTACTA TTAATAAATT CCAGAMTGAT ACATCCAGGT GRATTGAAAG     | 420  |
| ATGCAGTTCT AAAAGCTCAC CAAAGATGGT TTGWAAAAGA TTGTTTTAGA TTTAAGAAAT     | 480  |
| AATCCAGGTG GACTACTAGA TGAAGCTGTT AAAATGGCAA ATATTTTTAT CGATAAAGGA     | 540  |
| AAAACTGTTG TTAAACTARA AAAAGGTAAA GATACTGAAG CAATTCNNAC TTCTAATGAT     | 600  |
| GCGTTAAAAG AAGCGAAAGA CATGGATATA TCCATCTTAG TGAATGAAGG TTCNGCTNGC     | 660  |
| GCTTCTGAAG TGTTTACTGG TGCGCTAAAA GACTNTAATA AAGCTAAAGT TTATGGGTCA     | 720  |
| AAAACATTCG GCAAAGGTGT CGTACAAACT ACAAGAGAGT TTAAGGGATG GTTCATTGTT     | 780  |
| AAAATATACT GAAATGGAAA TGGTTAACGC CAGATGGTCA TTATATTCAC NGTACAAGGC     | 840  |
| ATNAAACCAG ACGTTACTNT TTGACACACC TGAAATANCA ATCTTTTAAA TGTCATTCCT     | 900  |
| AATACGANAA CATTTAAAGT TNGGAGACGA TGAATCTAAA ATATTAAAAC TATTAAAAWT     | 960  |
| GGTTTATCAG CTTTAGGTTA TAAAGTTGAT AAATGGAATC AACGCCAATT TGGATAAAGC     | 1020 |
| TTTAGAAAAT CAAGTTAAAG CTTYCCAMCA AGCGAATAAA CTTGAGGTAM YKGGKGAWTT     | 1080 |
| TAATAAAGAA ACGAATAATA AATTTACTGA GTTATTAGTT GAAAAGCTA ATAAACATGA      | 1140 |
| TGATGTTCTC GATAAGTTGA TTAATATTTT AAAATAAGCG ATACACACTA CTAAAATTGT     | 1200 |

-continued

| | | | | | |
|---|---|---|---|---|---|
| ATTATTATTA | TGTTAATGAC | ACGCCTCCTA | AATTTGCAAA | GATAGCAATT | TAGGAGGCGT | 1260 |
| GTTTATTTTT | ATTGACGTCT | AACTCTAAAA | GATATAAATT | AGACATTTAC | AAATGATGTA | 1320 |
| AATAACGCAA | TTTCTATCAT | CGCTGATAAC | AATTCATGGT | TTAATATGCA | ATGAGCATAT | 1380 |
| ACTTTTTAAA | TAGTATTATT | CACTAGTTTT | AACAATCAAT | TAATTGGTAT | ATGATACTTT | 1440 |
| TATTGGTTAT | TTTTATCCCA | TAGTGTGATA | AWTACTATTT | TTCATTCAYA | ATAAAGGTTT | 1500 |
| AAAGCATGTT | AATAGTGTGT | TAAGATTAAC | ATGTACTGAA | AAACATGTTT | WACAATAATG | 1560 |
| AATATAAGGA | KTGACGTTAC | ATGAWCCGTC | CTAGGTAAAA | TGTCMGAWTT | AGATCAAATC | 1620 |
| TTAAATCTAG | TAGAAGAAGC | AAAAGAATTA | ATGAAAGAAC | ACGACAACGA | GCAATGGGAC | 1680 |
| GATCAGTACC | CACTTTTAGA | ACATTTTGAA | GAAGATATTG | CTAAAGATTA | TTTGTACGTA | 1740 |
| TTAGAGGAAA | ATGACAAAAT | TTATGGCTTT | ATTGTTGTCG | ACCAAGACCA | AGCAGAATGG | 1800 |
| TATGATGACA | TTGACTGGCC | AGTAAATAGA | GAAGGCGCCT | TTGTTATTCA | TCGATTAACT | 1860 |
| GGTTCGAAAG | AATATAAAGG | AGCTGCTACA | GAATTATTCA | ATTATGTTAT | TGATGTAGTT | 1920 |
| AAAGCACGTG | GTGCAGAAGT | TATTTTAACG | GACACCTTTG | CGTTAAACAA | ACCTGCACAA | 1980 |
| GGTTTATTTG | CCAAATTTGG | ATTTCATAAG | GTCGGTGAAC | AATTAATGGA | ATATCCGCCM | 2040 |
| TATGATAAAG | GTGAACCATT | TTATGCATAT | TATAAAAATT | TAAAAGAATA | GAGGTAATAT | 2100 |
| TAATGACGAA | AATCGCATTT | ACCGGAGGGG | GAACAGTTGG | ACACGTATCA | GTAAATTTWA | 2160 |
| RTTTAATTCC | AACTGCATTA | TCACAAGGTT | ATGGARGCGC | TTTATATTGG | TTCTAAAAAT | 2220 |
| GGTATTGAAA | GAGAGAATGA | TTGAWTCACC | AACTACCCRG | AAATTAAGTA | TTATCCTATT | 2280 |
| TCGGAGTGKT | AAATTAAGAA | GATATATTTC | TTTAGAAAAT | GCCAAAGACG | TATTTAAAGT | 2340 |
| ATTGAAAGGT | ATTCTTGATG | CTCGTAAAGT | TTTGAAAAAA | GAAAAACCTG | ATCTATTATT | 2400 |
| TTCAAAAGGT | GGATTTGTAT | CTGTGCCTGT | TGTTATTGCA | GCCAAATCAT | TAAATATACC | 2460 |
| AACTATTATT | CATGAATCTG | ACTTAACACC | AGGATTAGCG | AATAAGATAG | CACTTAAATT | 2520 |
| TGCCAAGAAA | ATATATACAA | CATTTGAAGA | AACGCTAAAC | TACTTACCTA | AAGAGAAAGC | 2580 |
| TGATTTTATT | GGAGCAACAA | TTCGAGAAGA | TTTAAAAAAT | GGTAATGCAC | ATAATGGTTA | 2640 |
| TCAATTAACA | GGCTTTWATG | RAAATAAAAA | AGTTTTACTC | GTYATGGGTG | GAAGCTTWGG | 2700 |
| AAGTAAAAAA | TTAAATAGCA | TTATTCGCGA | AAACTTAGAT | GCATTATTA | CAACAATATC | 2760 |
| AAGTGATACA | TTTAACTGGT | AAAGGATTAA | AAGATGCTCA | AGTTAAAAAA | TCAGGATATA | 2820 |
| TACAATATGA | ATTTGTTAAA | GNGGATTTAA | CAGATTTATT | AGCAATTACG | GATACAGTAA | 2880 |
| TAAGTAGAGC | TGGATCAAAT | GCGATTTATG | GAGTTCTTAA | CATTACGTNT | ACCAATGTTA | 2940 |
| TTAGTACCAT | TAGGTTTAGA | TCAATCCCGA | GGCGACCAAA | TTGACANTGC | AAATCATTTT | 3000 |
| GCTGATAAAG | GATATGCTAA | AGCGATTGAT | GAAGAACAAT | TAACAGCACA | AATTTTATTA | 3060 |
| CAAGAACTAA | ATGAAATGGA | ACAGGAAAGA | ACTCGAATTA | TCAATAATAT | GAAATCGTAT | 3120 |
| GAACAAAGTT | ATACGAAAGA | AGCTTTATTT | GATAAGATGA | TTAAAGACGC | ATTGAATTAA | 3180 |
| TGGGGGGTAA | TGCTTTATGA | GTCAATGGAA | ACGTATCTCT | TTGCTCATCG | TTTTTACATT | 3240 |
| GGTTTTTGGA | ATTATCGCGT | TTTTCCACGA | ATCAAGACTT | GGGAAATGGA | TTGATAATGA | 3300 |
| AGTTTATGAG | TTTGTATATT | CATCAGAGAG | CTTTATTACG | ACATCTATCA | TGCTTGGGGC | 3360 |
| TACTAAAGTA | GGTGAAGTCT | GGGCAATGTT | ATGTATTTCA | TTACTTCTTG | TGGCATATCT | 3420 |
| CATGTTAAAG | CGCCACAAAA | TTGAAGCATT | ATTTTTTGCA | TTAACAATGG | CATTATCTGG | 3480 |
| AATTTTGAAT | CCAGCATTAA | AAAATATATT | CGATAGAGAA | AGGACCTGAC | ATTGCTGGCG | 3540 |
| TTTGAATTGG | ATGATTAACA | GGRTTTAGTT | TTCCTGAGCG | GTCATGCTAT | GG | 3592 |

(2) INFORMATION FOR SEQ ID NO: 64:

(i) SEQUENCE CHARACTERISTICS:
        (A) LENGTH:            2573 base pairs
        (B) TYPE:              nucleic acid
        (C) STRANDEDNESS:     single
        (D) TOPOLOGY:         linear (xi) SEQUENCE DESCRIPTION: SEQ ID NO: 64:

```
ATTCGAGCTC GGTACCCGKG GATCCTSYAG AGTCGATCCG CTTGAAACGC CAGGCACTGG     60

TACTAGAGTT TTGGGTGGTC TTAGTTATAG AGAAAGCCAT TTTGCATTGG AATTACTGCA    120

TCAATCACAT TTAATTTCCT CAATGGATTT AGTTGAAGTA ATCCATTGA TTGACAGTAA    180

TAATCATACT GCTGAACAAG CGGTTTCATT AGTTGGAACA TTTTTTGGTG AAACTTTATT    240

ATAAATAAAT GATTTGTAGT GTATAAAGTA TATTTTGCTT TTTGCACTAC TTTTTTTAAT    300

TCACTAAAAT GATTAAGAGT AGTTATAATC TTTAAAATAA TTTTTTTCTA TTTAAATATA    360

TGTTCGTATG ACAGTGATGT AAATGATTGG TATAATGGGT ATTATGGAAA AATATTACCC    420

GGAGGAGATG TTATGGATTT TTCCAACTTT TTTCAAAACC TCAGTACGTT AAAAATTGTA    480

ACGAGTATCC TTGATTTACT GATAGTTTGG TATGTACTTT ATCTTCTCAT CACGGTCTTT    540

AAGGGAACTA AAGCGATACA ATTACTTAAA GGGATATTAG TAATTGTTAT TGGTCAGCAG    600

ATAATTWTGA TATTGAACTT GACTGCMACA TCTAAATTAT YCRAWWYCGT TATTCMATGG    660

GGGGTATTAG CTTTAANAGT AATATTCCAA CCAGAAATTA GACGTGCGTT AGAACAACTT    720

GGTANAGGTA GCTTTTTAAA ACGCNATACT TCTAATACGT ATAGTAAAGA TGAAGAGAAA    780

TTGATTCAAT CGGTTTCAAA GGCTGTGCAA TATATGGCTA AAAGACGTAT AGGTGCATTA    840

ATTGTCTTTG AAAAAGAAAC AGGTCTTCAA GATTATATTG AAACAGGTAT TGCCAATGGA    900

TTCAAATATT TCGCAAGAAC TTTTAATTAA TGTCTTTATA CCTAACACAC CTTTACATGA    960

TGGTGCAAKG ATTATTCAAG GCACGAAARAT TGCAGCAGCA GCAAGTTATT TGCCATTGTC   1020

TGRWAGTCCT AAGATATCTA AAAGTTGGGT ACAAGACATA GAGCTGCGGT TGGTATTTCA   1080

GAAGTTATCT GATGCATTTA CCGTTATTGT ATCTGAAGAA ACTGGTGATA TTTCGGTAAC   1140

ATTTGATGGA AAATTACGAC GAGACATTTC AAACCGAAAT TTTTGAAGAA TTGCTTGCTG   1200

AACATTGGTT TGGCACACGC TTTCAAAAGA AAGKKKTGAA ATAATATGCT AGAAAKTAAA   1260

TGGGGCTTGA GATTTATTGC CTTTCTTTTT GGCATTGTTT TTCTTTTTAT CTGTTAACAA   1320

TGTTTTTGGA ATATTCTTT AAACACTGGT AATTCTTGGT CAAAAGTCTA GTAAAACGGA   1380

TTCAAGATGT ACCCGTTGAA ATTCTTTATA ACAACTAAAG ATTTGCATTT AACAAAAGCG   1440

CCTGAAACAG TTAATGTGAC TATTTCAGGA CCACAATCAA AGATAATAAA AATTGAAAAT   1500

CCAGAAGATT TAAGAGTAGT GATTGATTTA TCAAATGCTA AAGCTGGAAA ATATCAAGAA   1560

GAAGTATCAA GTTAAAGGGT TAGCTGATGA CATTCATTAT TCTGTAAAAC CTAAATTAGC   1620

AAATATTACG CTTGAAAACA AAGTAACTAA AAAGATGACA GTTCAACCTG ATGTAAGTCA   1680

GAGTGATATT GATCCACTTT ATAAAATTAC AAAGCAAGAA GTTTCACCAC AAACAGTTAA   1740

AGTAACAGGT GGAGAAGAAC AATTGAATGA TATCGCTTAT TTAAAAGCCA CTTTTAAAAC   1800

TAATAAAAAG ATTAATGGTG ACACAAAAGA TGTCGCAGAA GTAACGGCTT TTGATAAAAA   1860

ACTGAATAAA TTAATGTGTAT CGATTCAACC TAATGAAGTG AATTTACAAG TTAAAGTAGA   1920

GCCTTTTAGC AAAAAGGTTA AAGTAAATGT TAAACAGAAA GGTAGTTTRS CAGATGATAA   1980

AGAGTTAAGT TCGATTGATT TAGAAGATAA AGAAATTGAA TCTTCGGTAG TCGAGATGAC   2040
```

-continued

```
TTMCAAAATA TAAGCGAAGT TGATGCAGAA GTAGATTTAG ATGGTATTTC AGAATCAACT      2100

GAAAAGACTG TAAAAATCAA TTTACCAGAA CATGTCACTA AAGCACAACC AAGTGAAACG      2160

AAGGCTTATA TAAATGTAAA ATAAATAGCT AAATTAAAGG AGAGTAAACA ATGGGAAAAT      2220

ATTTTGGTAC AGACGGAGTA AGAGGTGTCG CAAACCAAGA ACTAACACCT GAATTGGCAT      2280

TTAAATTAGG AAGATACGGT GGCTATGTTC TAGCACATAA TAAAGGTGAA AAACACCCAC      2340

GTGTACTTGT AGGTCGCGAT ACTAGAGTTT CAGGTGAAAT GTTAGAATCA GCATTAATAG      2400

CTGGTTTGAT TTCAATTGGT GCAGAAGTGA TGCGATTAGG TATTATTTCA ACACCAGGTG      2460

TTGCATATTT AACACGCGAT ATGGGTGCAG AGTTAGGTGT AATGATTTCA GCCTCTCATA      2520

ATCCAGTTGC AGATAATGGT ATTAAATTCT TTGSCTCGAC CNCCNNGCTN GCA            2573
```

(2) INFORMATION FOR SEQ ID NO: 65:

(i) SEQUENCE CHARACTERISTICS:
        (A) LENGTH: 2976 base pairs
        (B) TYPE: nucleic acid
        (C) STRANDEDNESS: single
        (D) TOPOLOGY: linear (xi) SEQUENCE DESCRIPTION: SEQ ID NO: 65:

```
GRTCGACTCT AGAGTCGATC TTTAAATGGG TCTCTTTCAA CAACCGCGTC ATATTTTTMA        60

ACATAACCTT TTTTRATAAG TCCATCTAAA CTGGATTTTR AAAAGCCCAT ATCCTCAATA       120

TCAGTTAAAA ATATTGTTTT ATGTTGTTCT TCAGACAAGT AAGCATACAA ATCGTATTGT       180

TTAATAACTT TCTCCAACTT AGCTAATACT TCATCAGGAT GATACCCTTC AATGACACGA       240

ACAGCACGCT TGGTTTTTTT AGTTATATTT TGTGTGAGAA TCGTTTTTTC TTCAACGATA       300

TCATCTTTTA ACAACTTCAT AAGCAATTGA ATATCATTAT TTTTTTGCGC ATCTTTATAA       360

TAATAGTAAC CATGCTTATC AAATTTTTGT AATAAAGCTG AAGGTAGCTC TATGTCATCT       420

TTCATCTTAA ATGCTTTTTT ATACTTCGCT TTAATAGCAC TCGGAAGCAT CACTTCTAGC       480

ATAGAAATAC GTTAATGAC ATGAGTTGAA CCCATCCACT CACTTAAAGC TATTAATTCT       540

GATGTTAATT CTGGTTGTAT ATCTTTCACT TCTATGATTT TTTTTAACTT CGAAACGTCA       600

AGTTGTGCAT CAGGTTCTGC TGTTACTTCC ATTACATAAC CTTGAATCGT TCTTGGTCCA       660

AAAGGTACAA TTACACGCAC ACCAGGTTGG ATGACAGATT CGAGTTGTTC GGGAATTATA       720

TAATCAAATT TATAGTCAAC GCTCTTCGAC GCGACATCGA CTATGACTTT CGCTATCATT       780

ATKGCCACCT AGTTTCTAGT TCATCTAAAA TTTGTGCAGC WAATACTACK TTTTKNCCTT       840

YCTTGATATT TACKTTTTCA TTAKTTTTAA AATGCATTGT CAATTCATTA TCATCAGAAC       900

TAAATCCGAT AGACATATCC CCAACATTAT TTGAAATAAT CACATCTGCA TTTTTCTTGC       960

GTAATTTTTG TTGTGCATAA TTTTCAATAT CTTCAGTCTC TGCTGCAAAG CCTATTAAAT      1020

ACTGTGATGT TTTATGTTCA CCTAAATATT TAAGAATGTC TTTAGTACGT TTAAAAGATA      1080

CTGACAAATC ACCATCCTGC TTTTTCATCT TATGTTCCTA ATACATCAAC CGGTGTATAG      1140

TCAGATACGG CTGCTGCTTT TACAACAATA TYTTGTTCCG TYAAATCGGC TTGTCACTT G     1200

GTTCAAACAT TTCTTCAGGC ACTTTGRACA TGAATAACTT CAATATCTTT TGGATCCT CT     1260

AGTGTTGTAG GACCAGCAAC TAACGTCACG ATAGCTCCTC GATTTCGCAA TGCTTCA GCT     1320

ATTGCATAGC CCATTTTTCC AGAAGAACGA TTGGATACAA ATCTGACTGG ATCGAT AACT     1380

TCAATAGTTG GTCCTGCTGT AACCAATGCG CGTTTATCTT GAAATGAACT ATTAG CTAAA     1440

CGATTACTAT TTTGAAAATG AGCATCAATT ACAGAAACGA TTTGAAGCGG TTCT TCCATA     1500
```

```
CGTCCTTTAG CAACATAACC ACATGCTAGA AATCCGCTTC CTGGTTCGAT AAA ATGATAC      1560

CCATCTTCTT TTAAAATATT AATATTTTGC TGCGTTACGT TTATTTTCAT AC ATATGCAC      1620

ATTCATAGCA GGCGCAATAA ATTTCGGTGT CTCTGTTGCT AGCAACGTTG A TGTCACCAA     1680

ATCATCAGCA ATACCTACAC TCAATTTTGC AATTGTATTT GCCGTTGCAG  GTGCAACAAT    1740

GATTGCATCK GCCCAATCCA CCTAATGCAA TATGCTGTAT TTCTGGAAGG  ATTTTYTTCT    1800

ATAAAAGTAT CTGTATAAAC AGCATTTCGA MTTATTGCTT GAAATGCTA A TGGTGTCACA    1860

AATTTTTGTG CGTGATTCGT TAAACATAAC GCGAACTTCA TAACCCAG AT TGTGTTAACT    1920

TACTTGTCAA ATCAATTGCT TTATATGCCG CAATGCCACC TGTAACG GCT AATAATATTT    1980

TCTTCATATT CAATCTCCCT TAAATATCAC TATGACATTT ACGCTT TACA TCATCATATG    2040

CGCACAAATG CTCATTACTT TTTTATAGAT ACAAATTTAG TATTA TTATA ACATCAATCA    2100

TTGGATAAAC TAAAAAAACA CACCTACATA GGTGCGTTTG ATTT GGATAT GCCTTGACGT    2160

ATTTGATGTA ACGTCTAGCT TCACATATTT TTAATGGTCG AAA CTATTCT TTACCATAAT    2220

AATCACTTGA AATAACAGGG CGAATTTTAC CGTCAGCAAT TT CTTCTAAC GCTCTACCAA    2280

CTGGTTTAAA TGAATGATAT TCACTTAATA ATTCAGTTTC A GGTTGTTCA TCAATTTCAC    2340

GCGCTCTTTT CGCTGCAGTT GTTGCAATTA AATACTTTGA  TTTAATTTGT GACGTTAATT   2400

GGTTTAAAGG TGGATTTAAC ATTATTTTTT AGCCTCCAAA  ATCATTTTTC TATACTTAGC   2460

TTCTACGCGC TCTCTTTTTA AGTGCTCAGC TTCTACAAT A CATTGAATTC TATTCTTCGC    2520

AAGTTCTACT TCATCATTAA CTACAACGTA ATCGTATA AA TTCATCATTT CAACTTCTTT    2580

ACGCGCTTCG TTAATACGAC TTTGTATTTT CTCATCA GAT TCTGTTCCTC TACCTACTAA    2640

TCGCTCTCTC AAGTGTTCTA AACTTGGAGG TGCTAA GAAA ATAAATAGCG CATCTGGAAA    2700

TTTCTTTCTA ACTTGCTTTG CACCTTCTAC TTCAA TTTCT AAAAATACAT CATGACCTTC    2760

GTCCATTGTA TCTTTAACAT ATTGAACTGG TGTA CCATAA TAGTTGCCTA CATATTCAGC    2820

ATATTCTATA AATTGGTCAT CTTTGATTAA AGC TTCAAAC GCATCCCTAG TTTTAAAAAA    2880

GTAATCTACG CCATTCAACW TCACCTTCAC GC ATTTGACG TGTTGTCATT GGAATAGRAG    2940

AGCTTRANNG ATGTATNGNG ATCGACCTGC A GTCAT                              2976

(2) INFORMATION FOR SEQ ID NO: 66:

(i) SEQUENCE CHARACTERISTICS:
        (A) LENGTH:       540 base pairs
        (B) TYPE:         nucleic acid
        (C) STRANDEDNESS: single
        (D) TOPOLOGY:     linear (xi) SEQUENCE DESCRIPTION: SEQ ID NO:  66:

TACCCGGGGA CCTTGAAAAA TACCTGGTGT ATCATACATA AATGANGTGT CATCTANAGG        60

AATATCTATC ATATCTNAAG TTGTTCCAGG GANTCTTGAA GTTGTTACTA CATCTTTTTC      120

ACCAACACTA GCTTCAATCA GTTTATTAAT CAATGTAGAT TTCCCAACAT TCGTTGTCCC      180

TACAATATAC ACATCTTCAT TTTCTCGAAT ATTCGCAATT GATGATAATA AGTCNTNTNT      240

GCCCCAGCCT TTTTCAGCTG AAATTAATAC GACATCGTCA GCTTCCAAAC CATATTTTCT      300

TGCTGTTCGT TTTAACCATT CTTTAACTCG ACGTTTATTA ATTTGTTTCG GCAATAAATC      360

CAATTTATTT GCTGCTAAAA TGATTTTTTT GTTTCCGACA ATACGTTTAA CTGCATTAAT      420

AAATGATCCT TCAAAGTCAA ATACATCCAC GACATTGACG ACAATACCCT TTTTATCCGC      480

AAGTCCTGAT AATAATTTTA AAAAGTCTTC ACTTTCTAAT CCTACATCTT GAACTTCGTT      540
```

(2) INFORMATION FOR SEQ ID NO: 67:

(i) SEQUENCE CHARACTERISTICS:
    (A) LENGTH:        519 base pairs
    (B) TYPE:          nucleic acid
    (C) STRANDEDNESS:  single
    (D) TOPOLOGY:      linear (xi) SEQUENCE DESCRIPTION: SEQ ID NO: 67:

```
GACGCGTAAT TGCTTCATTG AAAAAATATA TTTGTNGAAA GTGGTGCATG ACAAATGTAC      60
TGCTCTTTTT GTAGTGTATC AGTATTGTGA TGTTTTAATG AGAATATTAT ATGAATCATT     120
ATGAAATTTA ATAAAAATAA AAGAAATGAT TATCATTTTT TCTTATATAC TGTTAAACGG     180
TTTGGAATTT TTAGGTATAC ACTGTATTGG TTGATATAAC TCAACTAATA ATTGCGAACA     240
GAGTATTTCA AATTGAAAAG TATTATGAGC GTGATACATA ATCAAAATTG TAGGCTCAAG     300
AACCACTACA TAATAAACCA TAAGCGGTTC TTTATCATTT ATGTCTCGCT CTCAAATGTA     360
AATTAATAAT TGTTTTGGGG GAGTTTGAAG TTAAATATTT AACAGGATTT ATTTTAATAT     420
TATTGTTAGA AGGAATTTTT ACAAATTCAG CGAGTGCAAT CGAATATTCA GACTTACATC     480
ATAAAAGTAA GTTTGATTCA AAGCGTCCTA AGTTAATGC                            519
```

(2) INFORMATION FOR SEQ ID NO: 68:

(i) SEQUENCE CHARACTERISTICS:
    (A) LENGTH:        3308 base pairs
    (B) TYPE:          nucleic acid
    (C) STRANDEDNESS:  single
    (D) TOPOLOGY:      linear (xi) SEQUENCE DESCRIPTION: SEQ ID NO: 68:

```
ACCAATATAT GCATCTGAAC GACTTAATAT CTTTTCGCCT GTGTTTAACA CTTTACCTGC      60
AGCGTTAATA CCTGCCATCA ATCCTTGTCC TGCTGCTTCT TCATAACCAG ATGTACCATT     120
AATTTGACCT GCAGTATATA AGTTTTTAAT CATTTTCGTT TCAAGTGTAG GCCATAACTG     180
CGTTGGCACA ATCGCATCAT ATTCAATTGC GTAGCCGGCA CGCATCATAT CTGCTTTTTC     240
AAGACCTGGT ATCGTCTCTA ACATTTGACG TTGCACATGT TCAGGAAGAC TTGTNGACAA     300
TCCTTGCACA TATACTTCAT TTGTATTAAC GACCTTCAGG CTCTAAGAAA AAGTTGATGT     360
CGCGGCTTAT CATTAAATCG AACAAATTTA TCTTCAATTG AAGGGCAATA ACGTGGCCCG     420
GTTCCTTTAA TCATCCCTGA ATACATTGCA GATAGATGTA AATTATCATC GATAACTTTG     480
TGTGTTTCAN CATTAGTATA CGTTAGCCAA CATGGCAATT GATCKAMYAT ATATTCTGTT     540
GTTTCAAAGC TGAATGCACG ACCTACATCG TCACCTGGTT GTATTTCAGT CTTCGAATAR     600
TCAATTGTTT TTGAATTGTA CACGGCGGWG GTGTACCTGT TTTAAAACGA ACAATATCAA     660
AACCAAGTTC TCTTARATGK GKSTGATAAT GTGATTGATG GTAATTGGTG GATTTGGTCC     720
ACTTGAATAC TTCATATTAC CTAAAATGAT TTCACCACGT ATRAAATGTT GCCCGTWGTA     780
ATAATTACTG CTTTAGATAA ATACTCTGTA CCAATATTTG TACGTACACC TTKAACTGTC     840
ATTAWCTTCT ATAAKAAGTT CGTCTACCAT ACCTTGCATT AATATGCAAA TTTTCTTCAT     900
CTTCAATCAM GCGTTTCATT TCTTGTTGAT AAAGTACTWT AKCTGCTTGC GCCKCTWAGT     960
GCTCTTACAR CAGGTCCTTT AACTGTATTT AACATTCTCA TTTGAATGTG TGTTTTATCG    1020
ATTGTTTTTG CCATTTGTCC ACCTAAAGCA TCAATTTCAC GAACAACGAT ACCTTTAGCT    1080
GGTCCACCTA CAGATGGGTT ACATGGCATA AATGCAATAT TATCTAAATT TATTGTTAGC    1140
```

-continued

```
ATTAATGTTT TAGCACCACG TCTTGCAGAT GCTAAACCTG CTTCTACACC TGCATGTCC C       1200

GCACCTATAA CGATTACATC ATATTCTTGA ACCACAATAT AAACCTCCTT ATTTGATA TC       1260

TTACTAGCCK TCTTAAGACG GTATTCCGTC TATTTCAATT ACTATTTACC TAAGCAG AAT       1320

TGACTGAATA ACTGATCGAT GAGTTCATCA CTTGCAGTCT CACCAATAAT TTCTCC TAAT      1380

ATTTCCCAAG TTCTAGTTAA ATCAATTTGT ACCATATCCA TAGGCACACC AGATT CTGCT      1440

GCATCAATCG CMTCTWGTAT CGTTTGTCTT GCTTGTTTTA ATAATGAAAT ATGT CTTGAA      1500

TTAGAAACAT AAGTCATATC TTGATTTTTG TACTTCTCCA CCAAAGAACA AAT CTCGAAT     1560

TTGTATTTCT AATTCATCAA TACCTCCTTG TTTTAACATT GAAGTTTGAA TT AATGGCGT     1620

ATCACCTATC ATATCTTTAA CTTCATTAAT ATCTATGTTT TGCTCTAAAT C CATTTTATT    1680

AACAATTACG ATTACATCTT CATTTTTAAC CACTTCATAT AATGTGTAAT   CTTCTTGAGT    1740

CAATGCTTCG TTATTGTTTA ATACAAATAA AATTAAGTCT GCTTGGCTAA    GAGCCTTTCT   1800

AGAGCGTTCA ACACCAATCT TCTCTACTAT ATCTTCTGTC TCACGTATA C CAGCAGTATC    1860

AACTAATCTT AATGGCACGC CACGAACATT GACGTAMTCT TCTAAGAC AT CTCTAGTAGT    1920

ACCTGCTACY TCAGTTACAA TCGCTTTATT ATCTTGTATT AAATTAT TTA ACATCGATGA   1980

TTTACCTACG TTTGGTTTAC CAACAATAAC TGTAGATAAA CCTTCA CGCC ATAATTTTAC    2040

CCTGCGCACC GGTATCTAAT AAACGATTAA TTTCCTGTTT GATTT CTTTA GACTGCTCTA    2100

AAAGAAATTC AGTAGTCGCA TCTTCAACAT CATCGTATTC AGGA TAATCA ATATTCACTT    2160

CCACTTGAGC GAGTATCTCT AATATAGATT GACGTTGTTT TTT GATTAAG TCACTTAGAC   2220

GACCTTCAAT TTGATTCATC GCAACTTTAG AAGCTCTATC TG TCTTCGAG CGAWWAAAGT   2280

CCATAACTGY TTCAGCTTGA GATAAATCAA TACGACCATT T AAAAAGGCA MGTTTGTAA    2340

ATTCAACCTG GCTCAGCCAT TCTAGCGCCA TATGTCATAG  TAAGTTCCAG CACTCTATTA   2400

ATCGTTAAAA TACCACCATG ACAATTAATT TCTATAATAT  CTTCGCGTGT AAATGTTTTT   2460

GGCGCTCTTA ACACAGACAC CATAACTTNT TCAACCATT C TTTAGACTCT GGATCAATAA   2520

TATGACCGTA ATTAATCGTA TGTGATGGAA CATCATTT AA AAGATGTTTT CCTTTATATA   2580

ATTTGTCAGC AATTTCAACG GCTTGCGGTC CAGACAA TCG AACAATTCCA ATTGCCCCTT   2640

CACCCATTGG TGTTGAAATA CTCGTAATTG TATCTA AATC CATATTGCTA CTCGCCTCCT   2700

TCAACGATGT GAATACATTT TAAAGTAAGT TATTA AACC CTAAGGTCAG TCTTAACGTT    2760

TGTCTGAGGT AAGACTTCGG GATGTGTTGA GTGG TTAATG TTTTCCTTCC CCTACCCTAT   2820

CCTTACTTAA TCTTTTTATT AAAAACTTTG GCA ATTTTAA GTACGTGCTC AAGACTATTC  2880

TGTATTTGTA AAGTCGTCAT ATCTTTAGCT GG CTGTCTTG CTATTACAAT AATATCTTTG  2940

GCCAATATAT GCGACTTATG TACTTTGAAA T TTTCACGTA TTGCTCTTTT AATCTTGTTT   3000

CTTAACACTG CATTACCTAG TTTTTTAGAA  ACACTAATAC CTAAGCGAAA ATGGTCTATT  3060

TCTTTATTAT TACAAGTGTA TACAACAAAT  TGTCTGTTGG CTACAGAATG ACCTTTTTA   3120

TATATTCTCT GAAAATCTGC ATTCTTTTT A ATTCGGTAAG CTTTTTCCAA TAACATCACT   3180

CGCTTATTTA TCGTTTTTAT TTGAAGCT AT ATTTAAACTT CTATTGAGCT TATAACATAA   3240

ATTTCTATTT ATTCTTAATT TAAACGA AAA AAAAGATCGA CTCTAGAGGA TCCCCGGGTA   3300

CCGAGCTC                                                             3308
```

(2) INFORMATION FOR SEQ ID NO: 69:

(i) SEQUENCE CHARACTERISTICS:
        (A) LENGTH:            1004 base pairs

-continued

```
            (B) TYPE:              nucleic acid
            (C) STRANDEDNESS:      single
            (D) TOPOLOGY:          linear (xi) SEQUENCE DESCRIPTION: SEQ ID NO: 69:

AGTTACGGCT TAATACTTGA ACCNAAAACC CAATTTTATA ATATGTATAG AAAAGGCTTG      60

CTCAAACTTG CTAATGAGGA TTTAGGTGCT GACATGTATC AGTTGCTGAT GTCTAANATA     120

GAACAATCTC CTTTCCATCA ATACGAAATA TCTAATTTTG CATTAGATGG CCATGANTCN     180

NAACATAATA AGGTTTACTG GTTTAATGAG GAATATTATG GATTTGGAGC AGGTGCAAGT     240

GGTTATGTAN ATGGTGTGCG TTATACGAAT ATCAATCCAG TGAATCATTA TATCAAAGCT     300

ATNAATAAAG AAAGTAAAGC AATTTTAGTA TCAAATAAAC CTTCTTTGAC TGAGAGAATG     360

GAAGAAGAAA TGTTTCTTGG GTTGCGTTTA AATGAAAGTG TGAGTAGTAG TAGGTTCAAA     420

AAGAAGTTTG ACCAATCTAT TGAAAGTGTC TTTGGTCAAA CAATAAATAA TTTAAAAGAG     480

AAGGAATTAA TTGTAGAAAA AGAACGATGT GATTGCACTT ACAAATAGAG GGAAAGTCAT     540

ANGTAATGAG GTTTTTGAAG CTTTCCTAAT CAATGATTAA GAAAAATTGA AATTTCGAGT     600

CTTTAACATT GACTTANTTT GACCAATTTG ATAAATTATA ATTAGCACTT GAGATAAGTG     660

AGTGCTAATG AGGTGAAAAC ATGANTACAG ATAGGCAATT GAGTATATTA AACGCAATTG     720

TTGAGGATTA TGTTGATTTT GGACAACCCG TTGGTTCTAA AACACTAATT GAGCGACATA     780

ACTTGAATGT TAGTCCTGCT ACAATTAGAA ATGAGATGAA ACAGCTTGAA GATTTAAACT     840

ATATCGAGAA GACACATAGT TCTTCAGGGC GTTCGCCATC ACAATTAGGT TTTAGGTATT     900

ATGTCAATCG TTTACTTGAA CAAACATCTC ATCAAAAAAC AAATAAATTA AGACGATTAA     960

ATCAATTGTT AGTTGAGAAC AATATGATGT TTCATCAGCA TTGA                    1004

(2) INFORMATION FOR SEQ ID NO: 70:

(i) SEQUENCE CHARACTERISTICS:
           (A) LENGTH:             1021 base pairs
           (B) TYPE:               nucleic acid
           (C) STRANDEDNESS:       single
           (D) TOPOLOGY:           linear (xi) SEQUENCE DESCRIPTION: SEQ ID NO: 70:

CCTGCAGGTC GATCCTGACA ACATTCTAAT TGTATTGTTT AATTATTTTT TGTCGTCGTC      60

TTTTACTTCT TTAAATTCAG CATCTTCTAC AGTACTATCA TTGTTTTGAC CAGCATTAGC     120

ACCTTGTGCT TGTTGTTGCT GTTGAGCCGC TTGCTCATAT ACTTTTGCTG ATAATTCTTG     180

AATCACTTTT TCAAGTTCTT CTTTTTTAGA TTTAATATCT TCTATATCTT GACCTTCTAA     240

AGCAGTTTTA AGAGCGTCTT TTTTCTCTTC AGCAGATTTT TTATCTTCTT CACCGATATT     300

TTCGCCTAAA TCAGTTAAAG TTTTTTCAAC TTGGAATACT AGACTGTCAG CTTCGTTTCT     360

TAAGTCTACT TCTTCACGAC GTTTTTTATC TGCTTCAGCG TTAACTTCAG CATCTTTTAC     420

CATACGGTCR ATTTCTTCGT CTGATAATGA AGAACTTGAT TGAATTGTAA TTCTTTGTTC     480

TTTATTTGTA CCTAAGTCTT TTGGCAGTTA CATTTACAAT ACCGTTTTTA TCGATATCAA     540

ACGTTACTTC AATTTGGAGG TTTACCACCG TTTCARMWGG TGGAATATCA GTCAATTGGA     600

ATCTACCAAG TGTTTTATTA TCCGCAGCCA TTGGACGTTC ACCTTGTAAT ACGTGTACAT     660

CTACTGATGG TTGATTATCT ACTGCTGTTG AATAGATTTG AGATTTAGAT GTAGGAATCG     720

TAGTGTTACG TTCAATTAAC GTATTCATAC GTCCACCTAA AATTTCAATA CCTAAAGATA     780

GTGGTGTTAC GTCTAATAAT ACTACGTCTT TAACGTCACC TGTGATAACG CCACCTTGGA     840
```

-continued

| | | |
|---|---|---|
| TTGCAGCTCC CATTGCCACT ACTTCGTCCG GGTTTACTCC TTTGTTAGGC TCTTTACCGA | 900 | |
| TTTCTTTTTT GACAGCTTCT TGTACTGCTG GAATACGAAT TGATCCACCA ACTAAGATAA | 960 | |
| CTTCATCGAT ATCTGANTTT GTTAAGCCAG CGTCTTTCAT TGCTTGGCGT GTAGGTCCAT | 1020 | |
| C | 1021 | |

(2) INFORMATION FOR SEQ ID NO: 71:

(i) SEQUENCE CHARACTERISTICS:
        (A) LENGTH:          3010 base pairs
        (B) TYPE:            nucleic acid
        (C) STRANDEDNESS:    single
        (D) TOPOLOGY:        linear (xi) SEQUENCE DESCRIPTION: SEQ ID NO: 71:

| | |
|---|---|
| ATGCCTGCAG GTCGATCACG ATGNAAGTCA TTCAATAAGA ATGATTATGA AAATAGAAAC | 60 |
| AGCAGTAAGA TATTTTCTAA TTGAAAATCA TCTCACTGCT GTTTTTTAAA GGTTTATACC | 120 |
| TCATCCTCTA AATTATTTAA AAATAATTAA TGGTATTTGA GCACGTTTAG CGACTTTATG | 180 |
| ACTGACATTA CCAATTTCCA TTTCTTGCCA GATATTCAAA CCACGTGTAC TCAAAATGAT | 240 |
| AGCTTGGTAT GTACCTCCAA TAGTAATTTC AATAACTTTG TCTGTTGAAC ACTAAGAGCA | 300 |
| ATTTTAATTT CATAATGTGT TGTAAACATT TTTTTTGATT GGAGTTTTTT TCTGAGTTAA | 360 |
| ACGATATCCT GATGTATTTT TAATTTTGCA CCATTTCCAA AAGGATAAGT GACATAAGTA | 420 |
| AAAAGGCATC ATCGGGAGTT ATCCTATCAG GAAAACCAAG ATAATACCTA AGTAGAAAAG | 480 |
| TGTTCAATCC GTGTTAAATT GGGAAATATC ATCCATAAAC TTTATTACTC ATACTATAAT | 540 |
| TCAATTTTAA CGTCTTCGTC CATTTGGGCT TCAAATTCAT CGAGTARTGC TCGTGCTTCT | 600 |
| GCAATTGATT GTGTGTTCAT CAATTGATGT CGAAGTTCGC TAGCGCCTCT TATGCCACGC | 660 |
| ACATAGATTT TAAAGAATCT ACGCAAGCTC TTGAATTGTC GTATTTCATC TTTTTCATAT | 720 |
| TTGTTAAACA ATGATAAATG CAATCTCAAT AGATCTAATA GTTCCTTGCT TGTGTGTTCG | 780 |
| CGTGGTTCTT TTTCAAAAGC GAATGGATTG TGGAAAATGC CTCTACCAAT CATGACGCCA | 840 |
| TCAATGCCAT ATTTTCTGC CAGTTCAAGT CCTGTTTTTC TATCGGGAAT ATCACCGTTA | 900 |
| ATTGTTAACA ATGTATTTGG TGCAATTTCG TCACGTAAAT TTTTAATAGC TTCGATTAAT | 960 |
| TCCCAATGTG CATCTACTTT ACTCATTTCT TTACGTTGTA CGAAGATGAA TAGATAAATT | 1020 |
| GGCAATGTCT TGTTCGAAGA CAKTGCTTCA ACCAATCTTT CCATTCATCG ATTTCATAKT | 1080 |
| AGCCAAGGCG TGTTTTTAAC ACTTTACCGG AASCCCACCT GCTTTAGTCG CTTGAATAAT | 1140 |
| TTCGGCAGCA ACGTCAGGTC TTAAGATTAA GCCGGANCCC TTACCCTTTT TAGCAACATT | 1200 |
| TGCTACAGGA CATCCCATAT TTAAGTCTAT GCCTTTAAAG CCCATTTTAG CTAATTGAAT | 1260 |
| ACTCGTTTCA CGGAACTGTT CTGGCTTATC TCCCCATATA TGAGCGACCA TCGGCTGTTC | 1320 |
| ATCTTCACTA AAAGTTAAGC GTCCGCGCAC ACTATGTATG CCTTCAGGGT GGCAAAAGCT | 1380 |
| TTCAGTATTT GTAAATTCAG TGAAAAACAC ATCCRGTCTA GNTGCTTCAN TTACAACGTG | 1440 |
| TCGAAAGACG ATATCTGTAA CGTCTTCCAT TGGCGCCAAA ATAAAAAATG GACGTGGTAA | 1500 |
| TTCACTCCAA AAATTTTCTT TCATAATATA TTTATACCCT CTTTATAATT AGTATCTCGA | 1560 |
| TTTTTTATGC ATGATGATAT TACCACAAAA GCNTAACTTA TACAAAGGA ATTTCAATAG | 1620 |
| ATGCAACCAT TKGAAAAGGG AAGTCTAAGA GTAGTCTAAA ATAAATGTTG TGGTAAGTTG | 1680 |
| ATCAATACAA AGATCAAGGA TTATAGTATT AAATTGTTCA TTATTAATGA TACACTACTT | 1740 |
| ATGAATATGA TTCAGAATTT TCTTTGGCTA CTNCTTACAG TAAAGCGACC TTTTAGTTAT | 1800 |

-continued

```
CTTATAACAA AGACAAATTT CTAAAGGTGA TATTATGGAA GGTTTAAAGC ATTCTTTAAA      1860

AAGTTTAGGT TGGTGGGATT NATTTTTTGC GATACCTATT TTTCTGCTAT TCGCATACCT      1920

TCCAAACTNT AATTTTATAA NCATATTTCT TAACATTGTT ATCATTATTT TCTTTTCCNT      1980

AGGTTTGATT TTAACTACGC ATATAATTAT AGATAAAAYT AAGAGCAACA CGAAATGAAT      2040

CATTAATACG GAATGTGATT AAAACATAAA ACTGAAGGAG CGATTACAAT GGCGACTAAG      2100

AAAGATGTAC ATGATTTATT TTTAAATCAT GTGAATTCAA ACGCGGTTAA GACAAGAAAG      2160

ATGATGGGAG AATATATTAT TTATTATGAT GGCGTGGTTA TAGGTGGTTT GTATGATAAT      2220

AGATTATTGG TCAAGGCGAC TAAAAGTGCC CAGCAGAAAT TGCAAGATAA TACATTAGTT      2280

TCGCCATATC CAGGTTTCTA AAGAAATGAT ATTAATTTTA GACTTTACCG AAGCAACAAA      2340

TCTCACTGAT TTATTTAAGA CCATAAAAAA TGATTTGAAA AAGTGAAGTA GTGAAGTGTG      2400

GGTGCAGAGA GAACTAAGCC CATCGWTAAA TGGTCGCTTG TTAAAGAAGA GTGACGGTCA      2460

CTCTTCTTTA TGTGCATATT TTATTTTGTC TGTTTBGTTA ACAAGCAGCA GTGTAACAAA      2520

TATGAGTAAG GATAAAATGA GTATAATATA GAAACCGAAT TTATCATTAA TTTCATTAAT      2580

CCATCTTCCT AAAAATGGAG CAATTAAACT TTGCAGTAAC AATGAAATTG ACGTCCATAT      2640

CGTAAATGAG CGACCGACAT ATTTATCTGA AACAGTGTTC ATTATAGCWG TATTCATATA      2700

AATTCTGATT GATGAAATTG AGTAGCCTAG TATAAAKGAT CCTATGAATA AGTAAAATGC      2760

TGAGTTTATC CAAATAAATA GTGCKGAATT TATGACTRRC TATGAAATAT AACAAAAATA      2820

TCACATACTT TAGKTGAGAT TTTCTTSGAA AGAATAGCTG AAATTAAACC TGCACATAAT      2880

CCTCCAATGC CATATAACAT ATCTGAAMAA CCAAAKTGTA CAGACCGAAA GTTTTAAAAC      2940

ATTATAAACA TATCCTGGTA ATGATATGTT AAAGATCGAC TCTAGAGGAT CCCCGGNTAC      3000

CGAGCTCGAA                                                            3010
```

(2) INFORMATION FOR SEQ ID NO: 72:

(i) SEQUENCE CHARACTERISTICS:
        (A) LENGTH:          548 base pairs
        (B) TYPE:            nucleic acid
        (C) STRANDEDNESS:   single
        (D) TOPOLOGY:      linear (xi) SEQUENCE DESCRIPTION: SEQ ID NO: 72:

```
ATCGGTACCC GGGGACCAAT ANACAGAAAG TATATTAAGT TTNGTAAATA ATGTACGTAC       60

TNAAGATGGT GGTACACATG AAGTTGGTTT TAAAACAGCA ATGACACGTG TATTTAATGA      120

TTATGCACGT CGTATTAATG AACTTAAAAC AAAAGATAAA AACTTAGATG GTAATGATAT      180

TCGTGAAGGT TTAACAGCTG TTGTGTCTGT TCGTATTCCA GAAGAATTAT TGCAATTTGA      240

ANGACAAACG AAATCTAAAT TGGGTACTTC TGAAGCTAGA AGTGCTGTTG ATTCAGTTGT      300

TGCAGACAAA TTGCCATTCT ATTTAGAAGA AAAAGGACAA TTGTCTAAAT CACTTGTGGA      360

AAAAAGCGAT TAAAGCACAA CAAGCAAGGG AAGCTGCACG TAAAGCTCGT GAAGATGCTC      420

GTTCAGGTAA GAAAAACAAG CGTAAAGACA CTTTGCTATC TGGTAAATTA ACACCTGCAC      480

AAAGTTAAAA ACACTGGAAA AAAATGAATT GTATTTAGTC GAAGGTGATT CTGCGGGAAG      540

TTCAGCAA                                                              548
```

(2) INFORMATION FOR SEQ ID NO: 73:

(i) SEQUENCE CHARACTERISTICS:
        (A) LENGTH:          541 base pairs
        (B) TYPE:            nucleic acid

```
        (C) STRANDEDNESS:         single
        (D) TOPOLOGY:             linear (xi) SEQUENCE DESCRIPTION: SEQ ID NO: 73:

ACTGCAGGTC GAGTCCAGAG GWCTAAATTA AATAGCAATA TTACTAAAAC CATACCAATG        60

TAAATGATAG CCATAATCGG TACAATTAAC GAAGATGACG TAGCAATACT ACGTACACCA       120

CCAAATATAA TAATAGCTGT TACGATTGCT AAAATAATAC CTGTGATTAC TGGACTAATA       180

TTATATTGCG TATTTAACGA CTCCGCAATT GTATTAGATT GCACTGTGTT AAATACAAAT       240

GCAAATGTAA TTGTAATTAA AATCGCAAAT ACGATACCTA GCCATTTTTG ATTTAAACCT       300

TTAGTAATAT AGTAAGCTGG ACCACCACGG GAATCCACCA TCTTTATCAT GTACTTTATA       360

AACCTGAGCC AAAGTCGCTT CTATAAATGC ACTCGCTGCA CCTATAAATG CAATAACCCA       420

CATCCAAAAT ACTGCACCTG GACCGCCTAA AACAATCGCA GTCGCAACAC CAGCAATATT       480

ACCAGTACCA ACTCTCGAAC CAGCACTAAT CGCAAATGCT TGGAATGGCG AAATACCCTT       540

C                                                                      541

(2) INFORMATION FOR SEQ ID NO: 74:

(i) SEQUENCE CHARACTERISTICS:
        (A) LENGTH:               558 base pairs
        (B) TYPE:                 nucleic acid
        (C) STRANDEDNESS:         single
        (D) TOPOLOGY:             linear (xi) SEQUENCE DESCRIPTION: SEQ ID NO: 74:

AGGGTCTNNC ACGGTACCCG GGGNCCAATT WGATGAGGAG GAAATCTAGT GAGTGAAATA        60

ATKCAAGATT TATCACTTGA AGATGTTTTA GGTGATCGCT TTGGAAGATA TAGTAAATAT       120

ATTATTCAAG AGCGTGCATT GCCAGATGTT CGTGATGGTT TAAAACCAGT ACAACGTCGT       180

ATTTTATATG CAATGTATTC AAGTGGTAAT ACACACGATA AAAATTTCCG TAAAAGTGCG       240

AAAACAGTCG GTGATGTTAT TGGTCAATAT CATCCACATG GGAGACTCCT CAGTGTACGA       300

AGCAATGGTC CGTTTAAGTC AAGACTGGAA GTTACGACAT GTCTTAATAG AAATGCATGG       360

TAATAATGGT AGTATCGATA ATGATCCGCC AGCGGCAATG CGTTACACTG AAGCTAAGTT       420

AAGCTTACTA GCTGAAGAGT TATTACGTGA TATTAATAAA GAGACAGTTT CTTTCATTCC       480

AAACTATGAT GATACGACAC TCCGAACCAA TGGTATTGCC ATCAAGAATT TCCTAACTTA       540

CTAAKTGAAT GGTTCTAC                                                    558

(2) INFORMATION FOR SEQ ID NO: 75:

(i) SEQUENCE CHARACTERISTICS:
        (A) LENGTH:               2234 base pairs
        (B) TYPE:                 nucleic acid
        (C) STRANDEDNESS:         single
        (D) TOPOLOGY:             linear (xi) SEQUENCE DESCRIPTION: SEQ ID NO: 75:

AGTCGATCTT TATTCTACAT GTCTCGTAAA AAATTATTGA AGAGTCAATT TGCAATGTCT        60

AACGTGGCAT TCTTAATCAA CTTCTTCATA ATGGGAATTT GGCATGGTAT CGAAGTGTAT       120

TACATTGTTT ATGGTTTATA CCATGCAGCA TTGTTTATAG GTTATGGCTA TTATGAACGT       180

TGGCGTAAGA AACATCCGCC ACGTTGGCAA AATGGTTTCA CAACAGCACT TAGCATTGTG       240

ATTACATTCC ACTTTGTAAC ATTTGGCTTT TTAATCTTCT CAGGTAAACT TATATAATAA       300

AGGAGAATTT AATTATGGAA TTTAGAGAAC AAGTATTAAA TTTATTAGCA GAAGTAGCAG       360
```

```
AAAAATGATA TTGTAAAAGA AAATCCAGAC GTAGAAATTT TTGAAGAAGG TATTATTGAT      420

TCTTTCCAAA CAGTTGGATT ATTATTAGAG ATTCAAAATA AACTTGATAT CGAAGTATCT      480

ATTATGGACT TTGATAGAAG ATGAGTGGGC MACACCAAAT AAAATCGTTG AAGCATTAGA      540

AGAGTTACGA TGAAATTAAA ACCTTTTTTA CCCATTTTAA TTAGTGGAGC GGTATTCATT      600

GTCTTTCTAT TATTACCTGC TAGTTGGTTT ACAGGATTAG TAAATGAAAA GACTGTAGAA      660

GATAATAGAA CTTCATTGAC AGATCAAGTA CTAAAAGGCA CACTCAWTCA AGATAAGTTA      720

TACGAATCAA ACAAGTATTA TCCTATATAC GGCTCTAGTG AATTAGGTAA AGATGACCCA      780

TTTAATCCTG CAATTGCATT AAATAAGCAT AACGCCAACA AAAAAGCATT CTTATTAGGT      840

GCTGGTGGTT CTACAGACTT AATTAACGCA GTTGAACTTG CATCACAGTT ATGATAAATT      900

AAAAGGTTAA GAAATTAACA TTTATTATTT CACCACAATG GTTACAAAAC CCATGGTTTA      960

ACGAATCCAA AACTTTGATG CTCSTATGTC TCAAACTCMA ATTAATCAAA TGTTCCCASC     1020

AGAAAAACAT GTCTACTGAA TTAAAACGTC GTTATGCACA ACGTTATTA CAGTTTCCAC     1080

ATGTACACAA TAAAGAATAC TTGAAATCTT ATGCTAAAAA CCCTAAAGAA ACTAAAGRTA     1140

GTTATATTTC TGGKTTTWAA RAGAGATCAA TTGATTAAAA TAGAAGCGAT TAAATCATTG     1200

TTTGCAATGG ATAAATCTCC ATTAGAACAT GTTAAACCCT GCTACAAAAC CAGACGCTTC     1260

TTGGGATGAG ATGAAACAAA AAGCAGTTGA AATTGGTAAA GCTGATACTA CATCGAATAA     1320

ATTTGGTATT AGAGATCAAT ACTGGAAATT AATTCCAAGA AAGTAAGCCG TTAAAGTTAG     1380

ACGTTGACTA CGAATTCMAT GTTWATTCTC CCAGAATTCC MAGATTTAGA ATTACTTGTW     1440

AAAAMMATGC KTGCTGCTGG TGCAGATGTT CAATATGTAA GTATTCCATC AAACGGTGTA     1500

TGGTATGACC ACATTGGTAT CGATAAAGAA CGTCGTCAAG CAGTTTATAA AAAAATCCAT     1560

TCTACTGTTG TAGATAATGG TGGTAAAATT TACGATATGA CTGATAAAGA TTATGAAAAA     1620

TATGTTATCA GTGATGCCGT ACACATCGGT TGGAAAGGTT GGGTTTATAT GGATGAGCAA     1680

ATTGCGAAAC ATATGAAAGG TGAACCACAA CCTGAAGTAG ATAAACCTAA AAATTAAAAT     1740

ACAAATAGCA CATAACTCAA CGATTTTGAT TGAGCGTATG TGCTATTTTT ATATTTTAAA     1800

TTTCATAGAA TAGAATAGTA ATATGTGCTT GGATATGTGG CAATAATAAA ATAATTAATC     1860

AGATAAATAG TATAAAATAA CTTTCCCATC AGTCCAATTT GACAGCGAAA AAAGACAGGT     1920

AATAACTGAT TATAAATAAT TCAGTATTCC TGTCTTTGTT GTTATTCATA ATATGTTCTG     1980

TTAACTTAAT ATCTTTATAT TAGAATACTT GTTCTACTTC TATTACACCA GGCACTTCTT     2040

CGTGTAATGC ACGCTCAATA CCAGCTTTAA GAGTGATTGT AGAACTTGGG CATGTACCAC     2100

ATGCACCATG TAATTGTAAT TTAACAATAC CGTCTTCCAC GTCAATCAAT GAGCAGTCGC     2160

CACCATCACG TAATAAAAAT GGACGAAGAC GTTCAATAAC TTCTGCTACT TGATCGACCT     2220

GCAGGCATGC AAGC                                                      2234
```

(2) INFORMATION FOR SEQ ID NO: 76:

(i) SEQUENCE CHARACTERISTICS:
        (A) LENGTH:        3305 base pairs
        (B) TYPE:          nucleic acid
        (C) STRANDEDNESS:  single
        (D) TOPOLOGY:      linear (xi) SEQUENCE DESCRIPTION: SEQ ID NO: 76:

```
GAGCTCGGTA CCCGGGGATC CTCTAGAGTC GATCCAATGA AAATAATATA TTTTTCATTT       60

ACTGGAAATG TCCGTCGTTT TATTAAGAGA ACAGAACTTG AAAATACGCT TGAGATTACA      120
```

-continued

```
GCAGAAAATT GTATGGAACC AGTTCATGAA CCGTTTATTA TCGTTACTGG CACTATTGGA        180
TTTGGAGAAG TACCAGAACC CGTTCAATCT TTTTTAGAAG TTAATCATCA ATACATCAGA        240
GGTGTGGCAG CTAGCGGTAA TCGAAATTGG GGACTAAATT TCGCAAAAGC GGGTCGCACG        300
ATATCAGAAG AGTATAATGT CCCTTTATTA ATGAAGTTTG AGTTACATGG GAAAAAACAA        360
AGACGTTATT GAATTTAAGA ACAAGGTGGG TAATTTTAAT GAAACCATG  GAAGAGAAAA        420
AGTACAATCA TATTGAATTA AATAATGAGG TCACTAAACG AAGAGAAGAT GGATTCTTTA        480
GTTTAGAAAA AGACCAAGAA GCTTTAGTAG CTTATTTAGA AGAAGTAAAA GACAAAACAA        540
TCTTCTTCGA CACTGAAATC GAGCGTWTAC GTTMTTTAGT AGACMACGAT TTTTATTTCA        600
ATGTGTTTGA TATWTATAGT GAAGCGGATC TAATTGAAAT CACTGATTAT GCAAAATCAA        660
TCCCGTTTAA TTTTGCAAGT TATATGTCAG CTAGTAAATT TTTCAAAGAT TACGCTTTGA        720
AAACAAATGA TAAAAGTCAA TACTTAGAAG ACTATAATCA ACACGTTGCC ATTGTTGCTT        780
TATACCTAGC AAATGGTAAT AAAGCACAAG CTAAACAATT TATTTCTGCT ATGGTTGAAC        840
AAAGATATCA ACCAGCGACA CCAACATTTT TAAACGCAGG CCGTGCGCGT TCGTGGTGGA        900
GCTAGTGTTC ATTGTTTCCT TATTAGAAGT TGGATGGACA GCTTAAATTC AATTTAACTT        960
TATTGGATTC AACTGCAAAA CAATTAAGTW AAATTGGGGG CGGSGTTTGC MATTAACTTA       1020
TCTAAATTGC GTGCACGTGG TGAAGCAATT AAAGGAATTA AAGGCGTAGC GAAAGGCGTT       1080
TTACCTATTG CTAAGTCACT TGAAGGTGGC TTTAGCTATG CAGATCAACT TGGTCAACGC       1140
CCTGGTGCTG GTGCTGTGTA CTTAAATATC TTCCATTATG ATGTAGAAGA ATTTTTAGAT       1200
ACTAAAAAAG TAAATGCGGA TGAAGATTTA CGTTTATCTA CAATATCAAC TGGTTTAATT       1260
GTTCCATCTA AATTCTTCGA TTTAGCTAAA GAAGGTAAGG ACTTTTATAT GTTTGCACCT       1320
CATACAGTTA AAGAAGAATA TGGTGTGACA TTAGCGATA  TCGATTTAGA AAAATATTAT       1380
GATGACATGG TTGCAAACCC AAATGTTGAG AAAAAGAAAA AGAATGCGCG TGAAATGTTG       1440
AATTTAATTG CGCMAACACA ATTACAATCA GGTTATCCAT ATTTAATGTT TAAAGATAAT       1500
GCTAACAGAG TGCATCCGAA TTCAAACATT GGACAAATTA AATGAGTAA  CTTATGTACG       1560
GAAATTTTCC AACTACAAGA AACTTCAATT ATTAATGACT ATGGTATTGA AGACGAAATT       1620
AAACGTGATA TTTCTTGTAA CTTGGGCTCA TTAAATATTG TTAATGTAAT GGAAAGCGGA       1680
AAATTCAGAG ATTCAGTTCA CTCTGGTATG GACGCATTAA CTGTTGTGAG TGATGTAGCA       1740
AATATTCAAA ATGCACCAGG AGTTAGAAAA GCTAACAGTG AATTACATTC AGTTGKTCTT       1800
GGGTGTGATG AATTWACACG GTTACCTAGC AAAAAATAAA ATTGGTTATG AGTCAGAAGA       1860
AGCAAAAGAT TTTGCAAATA TCTTCTTTAT GATGATGAAT TTCTACTCAA TCGAACGTTC       1920
AATGGAAATC GCTAAAGAGC GTGGTATCAA ATATCAAGAC TTTGAAAAGT CTGATTATGC       1980
TAATGGCAAA TATTTCGAGT TCTATACAAC TCAAGAATTT GAACCTCAAT TCGAAAAAGT       2040
ACGTGAATTA TTCGATGGTA TGGCTATTCC TACTTCTGAG GATTGGAAGA AACTACAACA       2100
AGATGTTGAA CAATATGGTT TATATCATGC ATATAGATTA GCAATTGCTC CAACACAAAG       2160
TATTTCTTAT GTTCAAAATG CAACAAGTTC TGTAATGCCA ATCGTTGACC AAATTGAACG       2220
TCGTACTTAT GGTAAATGCG GAAACATTTT ACCCTATGCC ATTCTTATCA CCACAAACAA       2280
TGTGGTACTA CAAATCAGCA TTCAATACTG ATCAGATGAA ATTAATCGAT TTAATTGCGA       2340
CAATTCAAAC GCATATTGAC CAAGGTATCT CAACGATCCT TTATGTTAAT TCTGAAATTT       2400
CTACACGTGA GTTAGCAAGA TTATATGTAT ATGCGCACTA TAAAGGATTA AAATCACTTT       2460
ACTATACTAG AAATAAATTA TTAAGTGTAG AAGAATGTAC AAGTTGTTCT ATCTAACAAT       2520
```

| | |
|---|---:|
| TAAATGTTGA AAATGACAAA CAGCTAATCA TCTGGTCTGA ATTAGCAGAT GATTAGACTG | 2580 |
| CTATGTCTGT ATTTGTCAAT TATTGAGTAA CATTACAGGA GGAAATTATA TTCATGATAG | 2640 |
| CTGTTAATTG GAACACACAA GAAGATATGA CGAATATGTT TTGGAGACAA AATATATCTC | 2700 |
| AAATGTGGGT TGAAACAGAA TTTAAAGTAT CAAAAGACAT TGCAAGTTGG AAGACTTTAT | 2760 |
| CTGAAGCTGA ACAAGACACA TTTAAAAAAG CATTAGCTGG TTTAACAGGC TTAGATACAC | 2820 |
| ATCAAGCAGA TGATGGCATG CCTTTAGTTA TGCTACATAC GACTGACTTA AGGAAAAAAG | 2880 |
| CAGTTTATTC ATTTATGGCG ATGATGGAGC AAATACACGC GAAAAGCTAT TCACATATTT | 2940 |
| TCACAACACT ATTACCATCT AGTGAAACAA ACTACCTATT AGATGAATGG GTTTTAGAGG | 3000 |
| AACCCCATTT AAAATATAAA TCTGATAAAA TTGTTGCTAA TTATCACAAA CTTTGGGGTA | 3060 |
| AAGAAGCTTC GATATACGAC CAATATATGG CCAGAGTTAC GAGTGTATTT TTAGAAACAT | 3120 |
| TCTTATTCTT CTCAGGTTTC TATTATCCAC TATATCTTGC TGGTCAAGGG AAAATGACGA | 3180 |
| CATCAGGTGA AATCATTCGT AAAATTCTTT TAGATGAATC TATTCATGGT GTATTTACCG | 3240 |
| GTTTAGATGC ACAGCATTTA CGAAATGAAC TATCTGAAAG TGAGAAACAA AAAGCAGATC | 3300 |
| GACCT | 3305 |

(2) INFORMATION FOR SEQ ID NO: 77:

(i) SEQUENCE CHARACTERISTICS:
        (A) LENGTH:        1945 base pairs
        (B) TYPE:          nucleic acid
        (C) STRANDEDNESS:  single
        (D) TOPOLOGY:      linear (xi) SEQUENCE DESCRIPTION: SEQ ID NO: 77:

| | |
|---|---:|
| TTGATAGTTT ATTGGAGAGA AAGAAGTATT AATCAAGTCG AAATCGTTGG TGTATGTACC | 60 |
| GATATTTGCG TGTTACATAC AGCAATTTCT GCATACAACT TAGGTTATAA AATTTCAGTA | 120 |
| CCTGCTGAGG GAGTGGCTTC ATTTAATCAA AAAGGGCATG AATGGGCACT TGCACATTTC | 180 |
| AAAAACTCAT TAGGTGCAGA GGTAGAACAA CACGTTTAAA TCGTGCTAAA ATAATTATAA | 240 |
| AGAATACAAT TTACAAGGGA GATATTTGAC AATGGCTAAA ACATATATTT TCGGACATAA | 300 |
| GAATCCAGAC ACTGATGCAA TTTCATCTGC GATTATTATG GCAGAATTTG AACAACTTCG | 360 |
| AGGTAATTCA GGAGCCAAAG CATACCGTTT AGGTGATGTG AGTGCARAAA CTCAATTCGC | 420 |
| GTTAGATACA TTTAATGTAC CTGCTCCGGA ATTATTAACA GATGATTTAG ATGGTCAAGA | 480 |
| TGTTATCTTA GTTGATCATA ACGAATTCCA ACAAGTTCT GATACGATTG CCTCTGCTAC | 540 |
| AATTAAGCAT GTAATTGATC ATCACAGAAT TGCAAATTTC GAAACTGCTG GTCCTTTATG | 600 |
| TTATCGTGCT GAACCAGTTG GTTGTACAGC TACAATTTTA TACAAAATGT TTAGAGAACG | 660 |
| TGGCTTTGAA ATTAAACCTG AAATTGCCGG TTTAATGTTA TCAGCAATTA TCTCAGATAG | 720 |
| CTTACTTTTC AAATCACAAC ATGTACACAA CAAGATGTTA AAGCAGCTGA AGAATTAAAA | 780 |
| GATATTGCTA AAGTTGATAT TCAAAAGTAC GGCTTAGATA TGTTAAAAGC AGGTGCTTCA | 840 |
| ACAACTGATA AATCAGTTGA ATTCTTATTA AACATGGATG CTAAATCATT TACTATGGGT | 900 |
| GACTATGKGA YTCGTATTGC AACAAGTTAA TGCTGTTGAC CTTGACGAAG TGTTAAWTCG | 960 |
| TAAAGAAGAT TTAGAAAAAG AAATGTTAGC TGTAAGTGCA CAAGAAAAAT ATGACTTATT | 1020 |
| TGTACTTGTT GTTACKGACA TCATTAATAG TGATTCTAAA ATTTTAGTTG TAGGTGCTGA | 1080 |
| AAAAGATAAA GTTGGCGAAG CATTCAATGT TCAATTAGAA GATGACATGG CCYTCTTATC | 1140 |
| TGGTGTCGTW TCTCGAAAAA AACAAATCGT ACCTCAAATC ACTGAAGCAT TAACAAAATA | 1200 |

```
ATACTATATT ACTGTCTAAT TATAGACATG TTGTATTTAA CTAACAGTTC ATTAAAGTAG    1260

AATTTATTTC ACTTTCCAAT GAACTGTTTT TTATTTACGT TTGACTAATT TACAACCCTT    1320

TTTCAATAGT AGTTTTTATT CCTTTAGCTA CCCTAACCCA CAGATTAGTG ATTTCTATAC    1380

AATTCCCCTT TTGTCTTAAC ATTTTCTTAA AATATTTGCG ATGTTGAGTA TAAATTTTTG    1440

TTTTCTTCCT ACCTTTTTCG TTATGATTAA AGTTATAAAT ATTATTATGT ACACGATTCA    1500

TCGCTCTATT TTCAACTTTC AACATATATA ATTCGAAAGA CCATTTAAAA TTAACGGCCA    1560

CAACATTCAA ATCAATTAAT CGCTTTTTCC AAAATAATCA TATAAGGAGG TTCTTTTCAT    1620

TATGAATATC ATTGAGCAAA AATTTTATGA CAGTAAAGCT TTTTTCAATA CACAACAAAC    1680

TAAAGATATT AGTTTTAGAA AAGAGCAATT AAAGAAGTTA AGCAAAGCTA TTAAATCATA    1740

CGAGAGCGAT ATTTTAGAAG CACTATATAC AGATTAGGA AAAAATAAAG TCGAAGCTTA    1800

TGCTACTGAA ATTGGCATAA CTTTGAAAAG TATCAAAATT GCCCGTAAGG AACTTAAAAA    1860

CTGGACTAAA ACAAAAAATG TAGACACACC TTTATATTTA TTTCCAACAA AAAGCTATAT    1920

CAAAAAAGAA CCTTATGGAA CAGTT                                         1945
```

(2) INFORMATION FOR SEQ ID NO: 78:

(i) SEQUENCE CHARACTERISTICS:
        (A) LENGTH:        2590 base pairs
        (B) TYPE:          nucleic acid
        (C) STRANDEDNESS:   single
        (D) TOPOLOGY:      linear (xi) SEQUENCE DESCRIPTION: SEQ ID NO: 78:

```
TCGAACTCGG TACCCGGGGA TCCTCTAGAG TCGATCAACT ACAACTACAA TTAAACAAAT      60

TGAGGAACTT GATAAAGTTG TAAAATAATT TTAAAAGAGG GGAACAATGG TTAAAGGTCT     120

TAATCATTGC TCCCCTCTTT TCTTTAAAAA AGGAAATCTG GACGTCAAT CAATGTCCTA      180

GACTCTAAAA TGTTCTGTTG TCAGTCGTTG GTTGAATGAA CATGTACTTG TAACAAGTTC     240

ATTTCAATAC TAGTGGGCTC CAAACATAGA GAAATTTGAT TTTCAATTTC TACTGACAAT     300

GCAAGTTGGC GGGGCCCAAA CATAGAGAAT TCAAAAAGG AATTCTACAG AAGTGGTGCT      360

TTATCATGTC TGACCCACTC CCTATAATGT TTTGACTATG TTGTTTAAAT TTCAAAATAA     420

ATATGATAGT GATATTTACA GCGATTGTTA AACCGAGATT GGCAATTTGG ACAACGCTCT     480

ACCATCATAT ATTCATTGAT TGTTAATTCG TGTTTGCATA CACCGCATAA GATTGCTTTT     540

TCGTTAAATG AAGGCTCAGA CCAACGCTTA ATGGCGTGCT TTTCAAACTC ATTATGGCAC     600

TTATAGCATG GATAGTATTT ATTACAACAT TTAAATTTAA TAGCAATAAT ATCTTCTTCG     660

GTAAAATAAT GGCGACAGCG TGTTTCAGTA TCGATTAATG AACCATAAAC TTTAGGCATA     720

GACAAAGCTC CTTAACTTAC GATTCCTTTG GATGTTCACC AATAATGCGA ACTTCACGAT     780

TTAATTCAAT GCCAAWTTTT TCTTTGACGG TCTTTTGTAC ATAATGAATA AGGTTTTCAT     840

AATCTGTAGC AGTTCCATTG TCTACATTTA CCATAAAACC AGCGTGTTTG GTTGAAACTT     900

CAACGCCGCC AATACGGTGA CCTTGCAAAT TAGAATCTTG TATCAATTTA CCTGCAAAAT     960

GACCAGGCGG TCTTTGGAAT ACACTACCAC ATGAAGGATA CTCTAAAGGT TGTTTAAATT    1020

CTCTACGTTC TGTTAAATCA TCCATTTTAG CTTGTATTTC AGTCATTTTA CCAGGAGCTA    1080

AAGTAAATGC AGCTTCTAAT ACAACTAANT GTTCTTTTTG AATAATGCTA TTACNATAAT    1140

CTAACTCTAA TTCTTTTGTT GTAAGTTTAA TTAACGAGCC TTGTTCGTTT ACGCAAAGCG    1200

CATRGTCTAT ACAATCTTTA ACTTCGCCAC CATAAGCGCC AGCATTCATA TACACTGCAC    1260
```

-continued

```
CACCAATTGA ACCTGGAATA CCACATGCAA ATTCAAGGCC AGTAAGTGCG TAATCACGAG    1320

CAACACGTGA GACATCAATA ATTGCAGCGC CGCTACCGGC TATTATCGCA TCATCAGATA    1380

CTTCCGATAT GATCTAGTGA TAATAAACTA ATTACAATAC CGCGAATACC ACCTTCACGG    1440

ATAATAATAT TTGAGCCATT TCCTAAATAT GTAACAGGAA TCTCATTTTG ATAGGCATAT    1500

TTAACAACTG CTTGTACTTC TTCATTTTTA GTAGGGTAA TGTAAAAGTC GGCATTACCA    1560

CCTGTTTTAG TATAAGTGTA TCGTTTTAAA GGTTCATCAA CTTTAATTTT TTCAKTYGRS    1620

MTRARKKSWT GYAAAGCTTG ATAGATGTCT TTATTTATCA CTTCTCAGTA CATCCTTTCT    1680

CATGTCTTTA ATATCATATA GTATTATACC AATTTTAAAA TTCATTTGCG AAAATTGAAA    1740

AGRAAGTATT AGAATTAGTA TAATTATAAA ATACGGCATT ATTGTCGTTA TAAGTATTTT    1800

TTACATAGTT TTTCAAAGTA TTGTTGCTTT TGCATCTCAT ATTGTCTAAT TGTTAAGCTA    1860

TGTTGCAATA TTTGGTGTTT TTTTGTATTG AATTGCAAAG CAATATCATC ATTAGTTGAT    1920

AAGAGGTAAT CAAGTGCAAG ATAAGATTCA AATGTTTGGG TATTCATTTG AATGATATGT    1980

AGACGCACCT GTTGTTTTAG TTCATGAAAA TTGTTAAACT TCGCCATCAT AACTTTCTTA    2040

GTATATTTAT GATGCAAACG ATAAAACCCT ACATAATTTA AGCGTTTTTC ATCTAAGGAT    2100

GTAATATCAT GCAAATTTTC TACACCTACT AAAATATCTA AAATTGGCTC TGTTGAATAT    2160

TTAAAATGAT GCGTACCGCC AATATGTTTT GTATATTTTA CTGGGCTGTC TAAGAGGTTG    2220

AATAATAATG ATTCAATTTC AGTGTATTGT GATTGAAAAC AATTAGTTAA ATCACTATTA    2280

ATGAATGGTT GAACATTTGA ATACATGATA AACTCCTTTG ATATTGAAAA TTAATTTAAT    2340

CACGATAAAG TCTGGAATAC TATAACATAAA TTCATTTTCA TAATAAACAT GTTTTTGTAT    2400

AATGAATCTG TTAAGGAGTG CAATCATGAA AAAAATTGTT ATTATCGCTG TTTTAGCGAT    2460

TTTATTTGTA GTAATAAGTG CTTGTGGTAA TAAAGAAAAA GAGGCACAAC ATCMATTTAC    2520

TAAGCAATTT AAAGATGTTG AGCAAACACA WAAAGAATTA CAACATGTCA TGGATAATAT    2580

ACATTTGAAA                                                          2590
```

(2) INFORMATION FOR SEQ ID NO: 79:

(i) SEQUENCE CHARACTERISTICS:
        (A) LENGTH:        1019 base pairs
        (B) TYPE:          nucleic acid
        (C) STRANDEDNESS:  single
        (D) TOPOLOGY:      linear (xi) SEQUENCE DESCRIPTION: SEQ ID NO: 79:

```
ATTCGAGCTC GGTACCCGGG GATCCTCTAG AGTCGCTCGA TAACTTCTAT ATGAACATCA      60

TGTTTATAAT ATGCTTTTTT CAATAATAAC TGAATTGCCC CAAAAAAGTG ATCTAATCGT     120

CCGCCTGTTG CACCATAAAT TGTAATACTA TCAAATCCAA GTGCAACAGC TTTATCAACC     180

GCTAAAGCTA AATCCGTATC AGCTTTTTCA GCTTGAACTG GTTTGATTTG TAACTGTTCT     240

GTTAGAAGTT GGCGTTCTTC TTTACTGACT GAATCAAAGT CTCCCACTGA GAAAAAGGG     300

ATAATTTGAT GCTTCAATAA AATCAAAGCA CCTCTATCAA CGCCGCCCCA TTTACCTTCA     360

TTACTTTTGG CCCAAATATC TTGCGGCAAG TGTCGATCAG AACATAATAA ATTTATATGC     420

ATATACACTC AACCTTTCAA TGCTTGTGTT GACTTTTTTA TAATCCTCTT GTTTAAAGAA     480

AAATGAACCT GTTACTAGCA TTGTTAGCAC CATTTTCAAC ACAAACTTTC GCTGTTATCG     540

GTATTTACGC CTCCATCAAC TTCAATATCA AAGTTTAATT GACGTTCCAT TTAATAGCA     600

TTAAGACCCG CTATTTTTTC TACGCATTGA TCAATAAATG ATTGACCACC AAACCCTGGG     660
```

```
TTAACTGTCA TCACTAGTAC ATAATCAACA ATGTCTAAAA TAGGTTCAAT TTGTGATATT    720

GGTGTACCAG GATTAATTAC TACACCAGCT TTTTTATCTA AATGTTTAAT CATTTGAATA    780

GCACGATGAA ATATGAGGCG TTGATTCGAC ATGAATTGNA ATCATATCG GCACCATGTT     840

CTGCAAATGA TGCAATATAC TTTTCTGGAA TTTTCAATCA TCAAATGTAC GTCTATANGT    900

AATGTTGTGC CTTTTCTTAC TGCATCTAAT ATTGGTAAAC CAATAGATAT ATTAGGGACA    960

AATTGACCAT CCATAACATC AAAATGAACT CCGTCGAANC CCGGCTTCTC CAGTCGTTT    1019
```

(2) INFORMATION FOR SEQ ID NO: 80:

(i) SEQUENCE CHARACTERISTICS:
        (A) LENGTH:        1105 base pairs
        (B) TYPE:          nucleic acid
        (C) STRANDEDNESS:  single
        (D) TOPOLOGY:      linear (xi) SEQUENCE DESCRIPTION: SEQ ID NO: 80:

```
CNTGCATGCC TGCAGGTCGA TCTANCAAAG CATATTAGTG AACATAAGTC GAATCAACCT     60

AAACGTGAAA CGACGCAAGT ACCTATTGTA AATGGGCCTG CTCATCATCA GCAATTCCAA    120

AAGCCAGAAG GTACGGTGTA CGAACCAAAA CCTAAAAAGA AATCAACACG AAAGATTGTG    180

CTCTTATCAC TAATCTTTTC GTTGTTAATG ATTGCACTTG TTTCTTTTGT GGCAATGGCA    240

ATGTTTGGTA ATAAATACGA AGAGACACCT GATGTAATCG GGAAATCTGT AAAAGAAGCA    300

GAGCAAATAT TCAATAAAAA CAACCTGAAA TTGGGTAAAA TTTCTAGAAG TTATAGTGAT    360

AAATATCCTG AAAATGAAAT TATTAAGACA ACTCCTAATA CTGGTGAACG TGTTGAACGT    420

GGTGACAGTG TTGATGTTGT TATATCAAAG GGSCCTGAAA AGGTTAAAAT GCCAAATGTC    480

ATTGGTTTAC CTAAGGAGGA AGCCTTGCAG AAATTAAAAT CCGTTAGGTC TTAAAGATGT    540

TACGATTGAA AAAGTWTATA ATAATCCAAG CGCCMAAAGG ATACATTGCA AATCAAAKTG    600

TTAMCCGCAA ATACTGAAAT CGCTATTCAT GATTCTAATA TTAAACTATA TGAATCTTTA    660

GGCATTAAGC AAGTTTATGT AGAAGACTTT GAACATAAAT CCTTTAGCAA AGCTAAAAAA    720

GCCTTAGAAG AAAAAGGGTT TAAAGTTGAA AGTAAGGAAG AGTATAGTGA CGATATTGAT    780

GAGGGTGATG TGATTTCTCA ATCTCCTAAA GGAAAATCAG TAGATGAGGG GTCAACGATT    840

TCATTTGTTG TTTCTAAAGG TAAAAAAAGT GACTCATCAG ATGTCNAAAC GACAACTGAA    900

TCGGTAGATG TTCCATACAC TGGTNAAAAT GATAAGTCAC AAAAAGTTCT GGTTTATCTT    960

NAAGATAANG ATAATGACGG TTCCACTGAA AAAGGTAGTT TCGATATTAC TAATGATCAC   1020

GTTATAGACA TCCTTTAAGA ATTGAAAAAG GGAAAACGCA GTTTTATTGT TAAATTGACG   1080

GTAAACTGTA CTGAAAAAAA NTCGC                                         1105
```

(2) INFORMATION FOR SEQ ID NO: 81:

(i) SEQUENCE CHARACTERISTICS:
        (A) LENGTH:        2375 base pairs
        (B) TYPE:          nucleic acid
        (C) STRANDEDNESS:  single
        (D) TOPOLOGY:      linear (xi) SEQUENCE DESCRIPTION: SEQ ID NO: 81:

```
AATATGACAG AACCGATAAA GCCAAGTTCC TCTCCAATCA CTGAAAAGAT AAAGTCAGTA     60

TGATTTTCAG GTATATAAAC TTCACCGTGA TTGTATCCTT TACCTAGTAA CTGTCCAGAA    120

CCGATAGCTT TAAGTGATTC AGTTAAATGA TAGCCATCAC CACTACTATA TGTATAGGGG    180

TCAAGCCATG AATTGATTCG TCCCATTTGA TACAGTTGGA CACCTAATAA ATTTTCAATT    240
```

-continued

```
AATGCGGGTG CATATAGAAT ACCTAAAATG ACTGTCATTG CACCAACAAT ACCTGTAATA    300

AAGATAGGTG CTAAGATACG CCATGTTATA CCACTTACTA ACATCACACC TGCAATAATA    360

GCAGCTAATA CTAATGTAGT TCCTAGGTCA TTTTGCAGTA ATATTAAAAT ACTTGGTACT    420

AACGAGACAC CAATAATTTT GAAAAATAAT AACAAATCAC TTTGGAATGA TTTATTGAAT    480

GTGAATTGAT TATGTCTAGA AACGACACGC GCTAATGCTA AAATTAAAAT AATTTTCATG    540

AATTCAGATG GCTGAATACT GATAGGGCCA AACGTGTTYC AACTTTTGGC ACCATTGATA    600

ATAGGTGTTA TAGGTGACTC AGGAATAACG AACCAGCCTA TTWATAWTAG ACAGATTAAG    660

AAATACAATA AATATGTATA ATGTTTAATC TTTTTAGGTG AAATAAACAT GATGATACCT    720

GCAAAAATTG CACCTAAAAT GTAATAAAAA ATTTGTCTGA TACCGAAATT AGCACTGTAT    780

TGACCACCGC CCATTGCCGA GTTAATAAGC AGAACACTGA AAATTGCTAA AACAGCTATA    840

GTGGCTACTA ATACCCAGTC TACTTTGCGA AGCCAATGCT TATCCGGCTG TTGACGAGAT    900

GAATAATTCA TTGCAAACTC CTTTTATACT CACTAATGTT TATATCAATT TTACATGACT    960

TTTTAAAAAT TAGCTAGAAT ATCACAGTGA TATCAGCYAT AGATTTCAAT TTGAATTAGG   1020

AATAAAATAG AAGGGAATAT TGTTCTGATT ATAAATGAAT CAACATAGAT ACAGACACAT   1080

AAGTCCTCGT TTTTAAAATG CAAAATAGCA TTAAAATGTG ATACTATTAA GATTCAAAGA   1140

TGCGAATAAA TCAATTAACA ATAGGACTAA ATCAATATTA ATTTATATTA AGGTAGCAAA   1200

CCCTGATATA TCATTGGAGG GAAAACGAAA TGACAAAAGA AAATATTTGT ATCGTTTTTG   1260

GAGGGAAAAG TGCAGAACAC GAAGTATCGA TTCTGACAGC AYWAAATGTA TTAAATGCAR   1320

TAGATAAAGA CAAATATCAT GTTGATATCA TTTATATTAC CAATGATGGT GATTGGAGAA   1380

AGCAAAATAA TATTACAGCT GAAATTAAAT CTACTGATGA GCTTCATTTA GAAAAATGGA   1440

GAGGCGCTTG AGATTTCACA GCTATTGAAA GAAAGTAGTT CAGGACAACC ATACGATGCA   1500

GTATTCCCAT TATTACATGG TCCTAATGGT GAAGATGGCA CGATTCAAGG GCTTTTTGAA   1560

GTTTTGGATG TACCATATGT AGGAAATGGT GTATTGTCAG CTGCAAGTTT CTATGGACAA   1620

ACTTGTAATG AAACAATTAT TTGAACATCG AGGGTTACCA CAGTTACCTT ATATTAGTTT   1680

CTTACGTTCT GAATATGAAA AATATGAACA TAACATTTTA AAATTAGTAA ATGATAAATT   1740

AAATTACCCA GTCTTTGTTA AACCTGCTAA CTTAGGGTCA AGTGTAGGTA TCAGTAAATG   1800

TAATAATGAA GCGGAACTTA AAGGAGGTAT TAAAGAAGCA TTCCAATTTG ACCGTAAGCT   1860

TGTTATAGAA CAAGGCGTTA ACGCAACGTG AAATTGAAGT AGCAGTTTTA GGAAATGACT   1920

ATCCTGAAGC GACATGGCCA GGTGAAGTCG TAAAAGATGT CGCGTTTTAC GATTACAAAT   1980

CAAAATATAA AGGATGGTAA GGTTCAATTA CAAATTCCAG CTGACTTAGA CGGAAGATGT   2040

TCAATTAACG GCTTAGAAAT ATGGCATTAG AGGCATTCAA AGCGACAGAT TGTTCTGGTT   2100

TAGTCCGTGC TGATTTCTTT GTAACAGAAG ACAACCAAAT ATATATTAAT GAAACAAATG   2160

CAATGCCTGG ATTTACGGCT TTCAGTATGT ATCCAAAGTT ATGGGAAAAT ATGGGCTTAT   2220

CTTATCCAGA ATTGATTACA AAACTTATCG AGCTTGCTAA AGAACGTCAC CAGGATAAAC   2280

AGAAAAATAA ATACAAAATT SMCTWAMTGA GGTTGTTATK RTGATTAAYG TKACMYTAWA   2340

GYAAAWTCAA TCATGGATTN CCTTGTGAAA TTGAA                              2375
```

(2) INFORMATION FOR SEQ ID NO: 82:

(i) SEQUENCE CHARACTERISTICS:
        (A) LENGTH:        1543 base pairs
        (B) TYPE:          nucleic acid

```
            (C) STRANDEDNESS:         single
            (D) TOPOLOGY:             linear (xi) SEQUENCE DESCRIPTION: SEQ ID NO: 82:

AATCATTTTC AGTTTATCAT TAAACAAATA TATTGAACYM MYMAAAATGT CATACTGATA      60

AAGATGAATG TCACTTAATA AGTAACTTAG ATTTAACAAA TGATGATTTT TAATTGTAGA     120

AAACTTGAAA TAATCACTTA TACCTAAATC TAAAGCATTG TTAAGAAGTG TGACAATGTT     180

AAAATAAATA TAGTTGAATT AATGAATTTG TTCTAYAATT AACAKGTTWT WGAWTTTAAT     240

AATGAGAAAA GAATTGACGA AAGTAAGGTG AATTGAATGG TTATTCMATG GTATCCAGGA     300

CMTATGGCGA AAAGCCAAAA GAGAAGTAAG TGAACAATTA AMAAAAGTAG ATGTAGTGTT     360

TGAACTAGTA GATGCAAGAA TTCCATATAG TTCAAGAAAC CCTATGATAG ATGAAGTTAT     420

TAACCAAAAA CCACGTGTTG TTATATTAAA TAAAAAAGAT ATGTCTAATT TAAATGAGAT     480

GTCAAAATGG GAACAATTTT TTATTGATAA AGGATACTAT CCTGTATCAG TGGATGCTAA     540

GCACGGTAAA AATTTAAAGA AAGTGGAAGC TGCAGCAATT AAGGCGACTG CTGAAAAATT     600

TGAACGCGAA AAAGCGAAAG GACTTAAACC TAGAGCGATA AGAGCAATGA TCGTTGGAAT     660

TCCAAATGTT GGTAAATCCA CATTAATAAA TAAACTGGCA AAGCGTAGTA TTGCGCAGAC     720

TGGTAATAAA CCAGGTGTGA CCAAACAACA ACAATGGATT AAAGTTGGTA ATGCATTACA     780

ACTATTAGAC ACACCAGGGA TACTTTGGCC TAAATTTGAA GATGAAGAAG TCGGTAAGAA     840

GTTGAGTTTA ACTGGTGCGA TAAAAGATAG TATTGTGCAC TTAGATGAAG TTGCCATCTA     900

TGGATTAAAC TTTTTAATTC AAAATGATTT AGCGCGATTA AAGTCACATT ATAATATTGA     960

AGTTCCTGAA GATGCMGAAA TCATAGCGTG GTTTGATGCG ATAGGGAAAA AACGTGGCTT    1020

AATTCGACGT GGTAATGAAA TTGATTACGA AGCAGTCATT GAACTGATTA TTTATGATAT    1080

TCGAAATGCT AAAATAGGAA ATTATTGTTT TGATATTTTT AAAGATATGA CTGAGGAATT    1140

AGCAAATGAC GCTAACAATT AAAGAAGTTA CGCAGTTGAT TAATGCGGTT AATACAATAG    1200

AAGAATTAGA AAATCATGAA TGCTTTTTAG ATGAGCGAAA AGGTGTTCAA AATGCCATAG    1260

CTAGGCGCAG AAAAGCGTTA GAAAAGAAC AAGCTTTAAA AGAAAGTAT GTTGAAATGA    1320

CTTACTTTGA AAATGAAATA TTAAAAGAGC ATCCTAATGC TATTATTTGT GGGATTGATG    1380

AAGTTGGAAG AGGACCTTTA GCAGGTCCAG TCGTTGCATG CGCAACAATT TTAAATTCAA    1440

ATCACAATTA TTTGGGCCTT GATGACTCGA AAAAGTACC TGTTACGAAA CGTCTAGAAT    1500

TAAATGAAGC ACTAAAAAAT GAAGTTACTG YTTTTGCATA TGG                      1543

(2) INFORMATION FOR SEQ ID NO: 83:

(i) SEQUENCE CHARACTERISTICS:
            (A) LENGTH:               2185 base pairs
            (B) TYPE:                 nucleic acid
            (C) STRANDEDNESS:         single
            (D) TOPOLOGY:             linear (xi) SEQUENCE DESCRIPTION: SEQ ID NO: 83:

TTAAACAATT AAGAAAATCT GGTAAAGTAC CAGCASYAGT ATACGGTTAC GGTACTAAAA      60

ACGTGTCAGT TAAAGTTGAT GAAGTAGAAT TCATCAAAGT TATCCGTGAA GTAGGTCGTA     120

ACGGTGTTAT CGAATTAGGC GTTGGTTCTA AAACTATCAA AGTTATGGTT GCAGACTACC     180

AATTCGATCC ACTTAAAAAC CAAATTACTC ACATTGACTT CTTWKCAATC AATATGAGTG     240

AAGAACGTAC TGTTGAAGTA CCAGTTCAAT TAGTTGGTGA AGCAGTAGGC GCTAAAGAAA     300

GGCGGCGTTA GTTGAACAAC CATTATTCAA CTTAGAAAGT AACTGCTACT CCAGACAATA     360
```

```
TTCCAGAAGC AATCGAAGTA GACATTACTG AATTAAACAT TAACGACAGC TTAACTGTTG      420

CTGATGTTAA AGTAACTGGC GACTTCAAAA TCGAAAACGA TTCAGCTGAA TCAGTAGTAA      480

CAGTAGTTGC TCCAACTGAA GAACCAACTG AAGAAGAAAT CGAAGCCTAT GGAAGGCGAA      540

CAMCAAACTG AAGAACCAGA AGTTGTTGGC GAAAGCAAAG AAGACGAAGA AAAAACTGAA      600

GAGTAATTTT AATCTGTTAC ATTAAAGTTT TTATACTTTG TTTAACAAGC ACTGTGCTTA      660

TTTTAATATA AGCATGGTGC TTTTKGTGTT ATTATAAAGC TTAATTAAAC TTTATWACTT      720

TGTACTAAAG TTTAATTAAT TTTAGTGAGT AAAAGACATT AAACTCAACA ATGATACATC      780

ATAAAAATTT TAATGTACTC GATTTTAAAA TACATACTTA CTAAGCTAAA GAATAATGAT      840

AATTGATGGC AATGGCGGAA AATGGATGTT GTCATTATAA TAATAAATGA AACAATTATG      900

TTGGAGGTAA ACACGCATGA AATGTATTGT AGGTCTAGGT AATATAGGTA AACGTTTTGA      960

ACTTACAAGA CATAATATCG GCTTTGAAGT CGTTGATTAT ATTTTAGAGA AAAATAATTT     1020

TTCATTAGAT AAACAAAAGT TTAAAGGTGC ATATACAATT GAACGAATGA ACGGCGATAA     1080

AGTGTTATTT ATCGAACCAA TGACAATGAT GAATTTGTCA GGTGAAGCAG TTGCACCGAT     1140

TATGGATTAT TACAATGTTA ATCCAGAAGA TTTAATTGTC TTATATGATG ATTTAGATTT     1200

AGAACAAGGA CAAGTTCGCT TAAGACAAAA AGGAAGTGCG GGCGGTCACA ATGGTATGAA     1260

ATCAATTATT AAAATGCTTG GTACAGACCA ATTTAAACGT ATTCGTATTG GTGTGGGAAG     1320

ACCAACGAAT GGTATGACGG TACCTGATTA TGTTTTACAA CGCTTTTCAA ATGATGAAAT     1380

GGTAACGATG GGAAAAAGTT ATCGAACACG CAGCACGCGC AATTGAAAAG TTTGTTGAAA     1440

CATCACRATT TGACCATGTT ATGAATGAAT TTAATGGTGA AKTGAAATAA TGACAATATT     1500

GACAMCSCTT ATAAAAGAAG ATAATCATTT TCAAGACCTT AATCAGGTAT TTGGACAAGC     1560

AAACACACTA GTAACTGGTC TTTCCCCGTC AGCTAAAGTG ACGATGATTG CTGAAAAATA     1620

TGCACAAAGT AATCAACAGT TATTATTAAT TACCAATAAT TTATACCAAG CAGATAAATT     1680

AGAAACAGAT TTACTTCAAT TTATAGATGC TGAAGAATTG TATAAGTATC CTGTGCAAGA     1740

TATTATGACC GAAGAGTTTT CAACACAAAG CCCTCAACTG ATGAGTGAAC GTATTAGAAC     1800

TTTAACTGCG TTAGCTCCAA GGTAAGAAAG GGTTATTTAT CGTTCCTTTA AATGGTTTGA     1860

AAAAGTGGTT AACTCCTGTT GAAATGTGGC AAAATCACCA AATGACATTG CGTGTTGGTG     1920

AGGATATCGA TGTGGACCAA TTTMWWAACA AATTAGTTAA TATGGGGTAC AAACGGGAAT     1980

CCGTGGTATC GCATATTGGT GAATTCTCAT TGCGAGGAGG TATTATCGAT ATCTTTCCGC     2040

TAATTGGGGA ACCAATCAGA ATTGAGCTAT TTGATACCGA AATTGATTCT ATTCGGGATT     2100

TTGATGTTGA AACGCAGCGT TCCAAAGATA ATGTTGAAGA AGTCGATATC ACAACTGCAA     2160

GTGATTATAT CATTACTGAA GAAGT                                          2185
```

(2) INFORMATION FOR SEQ ID NO: 84:

(i) SEQUENCE CHARACTERISTICS:
        (A) LENGTH:        2525 base pairs
        (B) TYPE:          nucleic acid
        (C) STRANDEDNESS:  single
        (D) TOPOLOGY:     linear (xi) SEQUENCE DESCRIPTION: SEQ ID NO: 84:

```
AATCTGTTCC TACTACAATA CCTTGTCGGT TTGAAGCACC NGAAAATNGT ACTTTCATAC       60

GTTCACGCGC TTTTTCATTT CCTTTTTGGA AATCTGTAAG AACAATACCG GCTTCTTTTA      120

ATGATTGCAC ACTTTGATCA ACTGCAGGCT TAATATTGAC TGTTACTATT TCATCTGGTT      180
```

```
CAATGAATCG CAAAGCTTGC TCAACTTCAT CAGCATCTTT TTGAACTCCA TAAGGTAATT      240

TAACTGCAAT AAACGTACAA TCAATGCCTT CTTCACGTAA TTCGTTAACA GACATTTGTA      300

CTAGTTTTCC AACTAATGTA GAATCCTGTC CTCCTGAAAT ACCTAACACT AAAGATTTTA      360

TAAATGAATG TGATTGTACA TAATTTTTTA TAAATTGCTT TAATTCCATA ATTTCTTCAG      420

CACTATCGAT ACGCTTTTTC ACTTTCATTT CTTGTACAAT AACGTCTTGT AATTTACTCA      480

TTATCTTCTT CCATCTCCTT AACGTGTTCC GCAACTTCAA AAATACGTTT ATGTTTATTA      540

TCCCAACATG CCTTGCTTAA ATCGACTGGA TATTCTTGTG GATTCAGGAA ACGCTTATTT      600

TCATCCCAAA TAGATTGTAA TCCTAGTGCT AAATATTCAC GTGATTCATC TTCTGTTGGC      660

ATTTGATATA CTAATTTACC ATTTTCATAA ATATTATGAT GCAAATCAAT GGCTTCGAAA      720

GATTTTATAA ATTTCATTTT ATAAGTATGC ACTGGATGGA ATAATTTTAA AGGTTGTTCA      780

TCGTATGGAT TTTCATTTTC CAAAGTAATA TAATCGCCTT CTGCCTTACC TGTTTTCTTG      840

TTTATAATGC GATATACATT TTTCTTACCT GGCGTCGTAA CCTTTTCAGC GTTATTTGAT      900

AATTTAATAC GATCACTATA TGAACCATCT TCATTTTCAA TAGCTACAAG TTTATATACT      960

GCACCTAATG CTGGTTGATC GTATCCTGTA ATCAGCTTTG TACCAACGCC CCAAGAATCT     1020

ACTTTTGCAC CTTGTGCTTT CAAACTCGTA TTCGTTTCTT CATCCAAATC ATTAGAYGCG     1080

ATAATTTTAG TTTCAGTAAA TCCTGYTTCA TCAAGCATAC GTCTTGCYTC TTTAGATAAA     1140

TAAGCGATAT CTCCAGAATC TAATCGAATA CCTAACAAAG TTAATTTTGT CACCTAATTC     1200

TTTTGCAACT TTTATTGCAT TTGGCACGCC AGATTTTAAA GTATGGAATG TATCTACTAG     1260

GAACACACAA TTTTTATGTC TTTCAGCATA TTTTTTGAAG GCAACATATT CGTCTCCATA     1320

AGTTTGGACA AATGCATGTG CATGTGTACC AGACACAGGT ATACCAAATA ATTTTCCCCG     1380

CCCTAACATT ACTTGTAGAA TCAAAGCCCC CGATGTAAGC AGCTCTAGCG CCCCACAATG     1440

CTGCATCAAT TTCTTGCGCA CGACGTGTTA CCAAACTCCA TTAATTTATC ATTTGATGCA     1500

ATTTGACGAA ATTCTGCTAG CCTTTGTTGT AATTAATGTA TGGAAATTTA CAATGTTTAA     1560

TAAAATTGTT CTATTAATTG CGCTTGAATC AATGGTGCTT CTACGCGTAA CAATGGTTCG     1620

TTACCAAAGC ATAATTCGCC TTCTTGCATC GAACGGATGC TGCCTGTGAA TTTTAAATCT     1680

TTTAAATATG ATAAGAAATC ATCCTTGTAG CCAATAGACT TTAAATATTC CAAATCAGAT     1740

TCTGAAAATC CAAAATGTTC TATAAAATCA ATGACGCGTT TTAAACCATT AAAAACAGCA     1800

TAGCCACTAT TAAATGGCAT TTTTCTAAAA TACAAATCAA ATACAGCCAT TTTTTCATGA     1860

ATATTATCAT TCCAATAACT TTCAGCCATA TTTATTTGAT ATAAGTCATT ATGTAACATT     1920

AAACTGTCGT CTTCTAATTG GTACACTTGT ATCTCTCCAA TCGACCTAAA TATTTTCTTA     1980

CATTTTATCA TAATTCATTT TTTTATATAC ATAAGAGCCC CTTAATTTCC ATACTTTTAA     2040

TTAAAATCAA CCAACAATTT AATGACATAT ACATAATTTT TAAGAGTATT TTAATAATGT     2100

AGACTATAAT ATAAAGCGAG GTGTTGTTAA TGTTATTTAA AGAGGCTCAA GCTTTCATAG     2160

AAAACATGTA TAAAGAGTGT CATTATGAAA CGCAAATTAT CAATAAACGT TTACATGACA     2220

TTGAACTAGA AATAAAAGAA ACTGGGACAT ATACACATAC AGAAGAAGAA CTTATTTATG     2280

GTGCTAAAAT GGCTTGGCGT AATTCAAATC GTTGCATTGG TCGTTTATTT TGGGATTCGT     2340

TAAATGTCAT TGATGCAAGA GATGTTACTG ACGAAGCATC GTTCTTATCA TCAATTACTT     2400

ATCATATTAC ACAGGCTACA AATGAAGGTA AATTAAAGCC GTATATTACT ATATATGCTC     2460

CAAAGGATGG ACCTAAAATT TTCAACAATC AATTAATTCG CTATGCTGGC TATGACAATT     2520
```

-continued

```
GTGGT                                                                  2525
```

(2) INFORMATION FOR SEQ ID NO: 85:

(i) SEQUENCE CHARACTERISTICS:
        (A) LENGTH:         2181 base pairs
        (B) TYPE:           nucleic acid
        (C) STRANDEDNESS:   single
        (D) TOPOLOGY:       linear (xi) SEQUENCE DESCRIPTION: SEQ ID NO: 85:

```
ATCGATAGGA AGAAGTACAA CGACTGAAGA TCAAACGGGT GATACATTGG AAACAAAAGG       60

TGTACACTCA GCAGATTTTA ATAAGGACGA TATTGACCGA TTGTTAGAAA GTTTTAAAGG      120

TATCATTGAA CAAATTCCGC CGATGTACTC ATCCGTCAAA GTAAATGGTA AAAAATTATA      180

TGAATATGCG CGTAATAATG AAACAGTTGA AAGACCAAAG CGTAAAGTTA ATATTAAAGA      240

CATTGGGCGT ATATCTGAAT TAGATTTTAA AGAAAATGAG TGTCATTTTA AAATACGCGT      300

CATCTGTGGT AAAGGTACAT ATATTAGAAC GCTAGCAACT GATATTGGTG TGAAATTAGG      360

CTTTCCGGCA CATATGTCGA AATTAACACG AATCGAGTCT GGTGGATTTG TGTTGAAAGA      420

TAGCCTTACA TTAGAACAAA TAAAAGAACT TCATGAGCAG GATTCATTGC AAAATAAATT      480

GTTTCCTTTA GAATATGGAT TAAAGGGTTT GCCAAGCATT AAAATTAAAG ATTCGCACAT      540

AAAAAAACGT ATTTTAAATG GGCAGAAATT TAATAAAAAT GAATTTGATA ACAAAATTAA      600

AGACCAAATT GTATTTATTG ATGATGATTC AGAAAAAGTA TTAGCAATTT ATATGGTACA      660

CCCTACGAAA AGAATCAGAA ATTAAACCTA AAAAAGTCTT TAATTAAAGG AGATAGAATT      720

TATGAAAGTT CATAGAAAGT GACACATCCT ATACAATCCT AAACAGTTAT ATTACAGGAG      780

GATGTTGCAA TGGGCATTCC GGATTTTTCG ATGGCATGCA TAAAGGTCAT GACAAAGTCT      840

TTGATATATT AAACGAAATA GCTGAGGCAC GCAGTTTAAA AAAAGCGGTG ATGACATTTG      900

ATCCGCATCC GTCTGTCGTG TTTGAATCCT AAAAGAAAAC GAACACGTTT TTACGCCCCT      960

TTCAGATAAA ATCCGAAAAA TTACCCACAT GATATTGATT ATTGTATAGT GGTTAATTTT     1020

TCATCTAGGT TTGCTAAAGT GAGCGTAGAA GATTTTGTTG AAAATTATAT AATTAAAAAT     1080

AATGTAAAAG AAGTCATTGC TGGTTTTGAT TTTAACTTTT GGTAAATTTG GAAAAGGTAA     1140

TATGACTGTA ACTTCAAGAA TATGATGCGT TTAATACGAC AATTGTGAGT AAACAAGAAA     1200

TTGAAAATGA AAAATTTCT ACAACTTCTA TTCGTCAAGG ATTTAATCAA TGGTGAGTTG      1260

CCAAAAAGGC GAATGGATGG CTTTTAGGCT ATATATATTT CTTATTAAAA GGCACTGTAG     1320

TGCAAGGTGA AAAAAGGGGA AGAACTATTG GCTTCCCCAA CAGCTAACAT TCAACCTAGT     1380

GATGATTATT TGTTACCTCG TAAAGGTGTT TATGCTGTTA GTATTGAAAT CGGCACTGAA     1440

AATAAATTAT ATCGAGGGGT AGCTAACATA GGTGTAAAGC CAACATTTCA TGATCCTAAC     1500

AAAGCAGAAG TTGTCATCGA AGTGAATATC TTTGACTTTG AGGATAATAT TTATGGTGAA     1560

CGAGTGACCG TGAATTGGCA TCATTTCTTA CGTCCTGAGA TTAAATTTGA TGGTATCGAC     1620

CCATTAGTTA AACAAATGAA CGATGATAAA TCGCGTGCTA AATATTTATT AGCAGTTGAT     1680

TTTGGTGATG AAGTAGCTTA TAATATCTAG AGTTGCGTAT AGTTATATAA ACAATCTATA     1740

CCACACCTTT TTTCTTAGTA GGTCGAATCT CCAACGCCTA ACTCGGATTA AGGAGTATTC     1800

AAACATTTTA AGGAGGAAAT TGATTATGGC AATTTCACAA GAACGTAAAA ACGAAATCAT     1860

TAAAGAATAC CGTGTACACG AAACTGATAC TGGTTCACCA GAAGTACAAA TCGCTGTACT     1920

TACTGCAGAA ATCAACGCAG TAAACGAACA CTTACGTACA CACAAAAAAG ACCACCATTC     1980
```

| | |
|---|---|
| ACGTCGTGGA TTATTAAAAA TGGTAGGTCG TCGTAGACAT TTATTAAACT ACTTACGTAG | 2040 |
| TAAAGATATT CAACGTTACC GTGAATTAAT TAAATCACTT GGTATCCGTC GTTAATCTTA | 2100 |
| ATATAACGTC TTTGAGGTTG GGGCATATTT ATGTTCCAAC CCTTAATTTA TATTAAAAAA | 2160 |
| GCTTTTTRCA WRYMTKMASR T | 2181 |

(2) INFORMATION FOR SEQ ID NO: 86:

(i) SEQUENCE CHARACTERISTICS:
        (A) LENGTH:        2423 base pairs
        (B) TYPE:          nucleic acid
        (C) STRANDEDNESS:  single
        (D) TOPOLOGY:      linear (xi) SEQUENCE DESCRIPTION: SEQ ID NO: 86:

| | |
|---|---|
| ACATTAAAAA GGATGAAATT TGGTCAAAGT ATTCGAGAAG AAGGTCCACA AAGCCATATG | 60 |
| AAGAAGACTG GTACACCAAC GATGGGTGGA CTAACATTTC TATTAAGTAT TGTGATAACG | 120 |
| TCTTTGGTGG CTATTATATT TGTAGATCAA GCWAATCCAA TCATACTGTT ATTATTTGTG | 180 |
| ACGATTGGTT TTGGGTTAAT TGGTTCTTAT ACGATGATTA TATTATTGTT GTTAAAAGA | 240 |
| ATAACCAAGG TTTAACAAGT AAACAGAAGT TTTTGGCGCA AATTGGTATT GCGATTATAT | 300 |
| TCTTTGTTTT AAGTAATGTG TTTCATTTGG TGAATTTTTC TACGAGCATA CATATTCCAT | 360 |
| TTACGAATGT AGCAATCCCA CTATCATTTG CATATGTTAT TTTCATTGTT TTTTGGCAAG | 420 |
| TAGGTTTTTC TAATGCAGTA AATTTAACAG ATGGTTTAGA TGGATTAGCA ACTGGACTGT | 480 |
| CAATTATCGG ATTTACAATG TATGCCATCA TGAGCTTTGT GTTAGGAGAA ACGGCAATTG | 540 |
| GTATTTTCTG TATCATTATG TTGTTTGCAC TTTTAGGATT TTTACCATAT AACATTAACC | 600 |
| CTGCTAAAGT GTTTATGGGA GATACAGGTA GCTTAGCTTT AGGTGGTATA TTTGCTACCA | 660 |
| TTTCAATCAT GCTTAATCAG GAATTATCAT TAATTTTTAT AGGTTTAGTA TTCGTAATTG | 720 |
| AAACATTATC TGTTATGTTA CAAGTCGCTA GCTTTAAATT GACTGGAAAG CGTATATTTA | 780 |
| AAATGAGTCC GATTCATCAT CATTTTGAAT TGATAGGATG GAGCGAATGG AAAGTAGTTA | 840 |
| CAGTATTTTG GGCTGTTGGT CTGATTTCAG GTTTAATCGG TTTATGGATT GGAGTTGCAT | 900 |
| TAAGATGCTT AATTATACAG GGTTAGAAAA TAAAAATGTW TTAGTTGTCG GTTTGGCAAA | 960 |
| AAGTGGTTAT GAAGCAGCTA AATTATTAAG TAAATTAGGT GCGAATGTAA CTGTCAATGA | 1020 |
| TGGAAAAGAC TTATCACAAG ATGCTCATGC AAAAGATTTA GAWTCTATGG GCATTTCTGT | 1080 |
| TGTAAGTGGA AGTCATCCAT TAACGTTGCT TGATAATAAT CCAATAATTG TTAAAAATCC | 1140 |
| TGGAATACCC TTATACAGTA TCTATTATTG ATGAAGCAGT GAAACGAGGT TTGAAAATTT | 1200 |
| TAACAGAAGT TGAGTTAAGT TATCTAATCT CTGAAGCACC AATCATAGCT GTAACGGGTA | 1260 |
| CAAATGGTAA AACGACAGTT ACTTCTCTAA TTGGAGATAT GTTTAAAAAA AGTCGCTTAA | 1320 |
| CTGGAAGATT ATCCGGCAAT ATTGGTTATG TTTGCATCTA AAGTWGCACA AGAAGTWAAG | 1380 |
| CCTACAGATT ATTTAGTTAC AGAGTTGTCG TCATTCCAGT TACTTGGAAT CGAAAAGTAT | 1440 |
| AAACCACACA TTGCTATAAT TACTAACATT TATTCGGCGC ATCTAGATTA CCATGRAAAT | 1500 |
| TTAGAAAACT ATCAAAATGC TAAAAAGCAA ATATATAAAA ATCAAACGGA AGAGGATTAT | 1560 |
| TTGATTTGTA ATTATCATCA AAGACAAGTG ATAGAGTCGG AAGAATTAAA AGCTAAGACA | 1620 |
| TTGTATTTCT CAAACTCAAC AAGAAGTTGA TGGTATTTAT ATTAAAGATG RTTTTATCGT | 1680 |
| TTATAAAGGT GTTCGTATTA TTAACACTGA AGATCTAGTA TTGCCTGGTG AACATAATTT | 1740 |
| AGAAAATATA TTAGCCAGCT GKGCTKGCTT GTATTTWAGY TGGTGTACCT ATTAAAGCAA | 1800 |

-continued

```
TTATTGATAG TTWAAYWACA TTTTCAGGAA TAGAGCATAG ATTGCAATAT GTTGGTACTA      1860

ATAGAACTTA ATAAATATTA TAATGATTCC AAAGCAACAA ACACGCTAGC AACACAGTTT      1920

GCCTTAAATT CATTTAATCA ACCAATCATT TGGTTATGTG GTGGTTTGGA TCGGAGGGAA      1980

TGAATTTGAC GAACTCATTC CTTATATGGA AAATGTTCGC GCGATGGTTG TATTCGGACA      2040

AACGAAAGCT AAGTTTGCTA AACTAGGTAA TAGTCAAGGG AAATCGGTCA TTGAAGCGAA      2100

CAATGTCGAA GACGCTGTTG ATAAAGTACA AGATATTATA GAACCAAATG ATGTTGTATT      2160

ATTGTCACCT GCTTGTGCGA GTTGGGATCA ATATAGTACT TTTGAAGAGC GTGGAGAGAA      2220

ATTTATTGAA AGATTCCGTG CCCATTTACC ATCTTATTAA AGGGTGTGAG TATTGATGGA      2280

TGATAAAACG AAGAACGATC AACAAGAATC AAATGAAGAT AAAGATGAAT TAGAATTATT      2340

TACGAGGAAT ACATCTAAGA AAAGACGGCA AAGAAAAAGW TCCTCTAGAG TCGACCCTGC      2400

AGGCATGCAA GCTTGGCGTA NCC                                              2423
```

(2) INFORMATION FOR SEQ ID NO: 87:

(i) SEQUENCE CHARACTERISTICS:
        (A) LENGTH:        2094 base pairs
        (B) TYPE:          nucleic acid
        (C) STRANDEDNESS:  single
        (D) TOPOLOGY:     linear (xi) SEQUENCE DESCRIPTION: SEQ ID NO: 87:

```
CACATAAACC AGTTGTTGCT ATTTTAGGTG GAGCAAAAGT ATCTGACAAA ATTAATGTCA      60

TCAAAAACTT AGTTAACATA GCTGATAAAA TTATCATCGG CGGAGGTATG GCTTATACTT      120

TCTTAAAAGC GCAAGGTAAA GAAATTGGTA TTTCATTATT AGAAGAAGAT AAAATCGACT      180

TCGCAAAAGA TTTATTAGAA AAACATGGTG ATAAAATTGT ATTACCAGTA GACACTAAAG      240

TTGCTAAAGA ATTTTCTAAT GATGCCAAAA TCACTGTAGT ACCATCTGAT TCAATTCCAG      300

CAGACCAAGA AGGTATGGAT ATTGGACCAA ACACTGTAAA ATTATTTGCA GATGAATTAG      360

AAGGTGCGCA CACTGTTGTT ATGGAATGGA CCTATGGGTT GTTATTCGAG TTCAGTAACT      420

TTGCACAAGG TACAATTGGT GTTTGTTAAA GCAATTGCCA ACCTTAAAGA TGCCATTACG      480

ATTATCGGTG GCGGTGATTC AGCCTGCAGC AGCCATCTCT TTAGGTTTTT GAAAATGACT      540

TCACTCMTAT TTCCACTGGT GGCGGCSCKC CATTAGAKTA CCTAGAAGGT WAAGAATGCC      600

TGGTWTCMAA GCAAYCAWTA WTAAWTAATA AAGTGATAGT TTAAAGTGAT GTGGCATGTT      660

TGTTTAACAT TGTTACGGGA AAACAGTCAA CAAGATGAAC ATCGTGTTTC ATCAACTTTT      720

CAAAAATATT TACAAAAACA AGGAGTTGTC TTTAATGAGA ACACCAATTA TAGCTGGTAA      780

CTGGAAAATG AACAAAACAG TACAAGAAGC AAAAGACTTC GTCAATACAT TACCAACACT      840

ACCAGATTCA AAAGAAKTWR AATCAGTWAT TTGTTGCMCC AGCMATTCAA TTAGATGCAT      900

TAACTACTGC AGTTWAAGAA GGAAAAGCAC AAGGTTTAGA AATCGGTGCT CAAAATNCGT      960

ATTTCGAAGA AATGGGGCTT MACAGTGAAA KTTTCCAGTT GCATAGCAGA TTAGGCTTAA      1020

AAAGTTGTAT TCGGTCATTC TGAACTTCGT GAATATTCCA CGGAACCAGA TGAAGAAATT      1080

AACAAAAAAG CGCACGTATT TTCAAACATG GAATGAMTCC AATTATATGT GTTGGTGAAA      1140

CAGACGAAGA GCGTGAAAGT GGTAAAGCTA ACGATGTTGT AGGTGAGCAA GTTAAAGAAA      1200

GCTGTTGCAG GTTTATCTGA AGATCAAACT TAAATCAGTT GTAATTGCTT ATGAACCAAT      1260

CTGGGCAATC GGAACTGGTA AATCATCAAC ATCTGAAGAT GCAAATGAAA TGTGTGCATT      1320

TGTACGTCAA ACTATTGCTG ACTTATCAAG CAAAGAAGTA TCAGAAGCAA CTCGTATTCA      1380
```

| | |
|---|---|
| ATATGGTGGT AGTGTTAAAC CTAACAACAT TAAAGAATAC ATGGCACAAA CTGATATTGA | 1440 |
| TGGGGCATTA GTAGGTGGCG CATCACTTAA AGTTGAAGAT TTCGTACAAT TGTTAGAAGG | 1500 |
| TGCAAAATAA TCATGGCTAA GAAACCAACT GCGTTAATTA TTTTAGATGG TTTTGCGAAC | 1560 |
| CGCGAAAGCG AACATGGTAA TGCGGTAAAA TTAGCAAACA AGCCTAATTT TTNGATCGGT | 1620 |
| TNATTACCAA CCAAATATCC CAACCGAACT TCAAAATTCG AAGGCGAGTG GCTTAAGATG | 1680 |
| TTGGACTACC CTGAAGGACA AATGGGTAAC TCAGAAGTTG GTCATATGAA TATCGGTGCA | 1740 |
| GGACGTATCG TTTATCAAAG TTTAACTCGA ATCAATAAAT CAATTGAAGA CGGTGATTTC | 1800 |
| TTTGAAAATG ATGTTTTAAA TAATGCAATT GCACACGTGA ATTCACATGA TTCAGCGTTA | 1860 |
| CACATCTTTG GTTTATTGTC TGACGGTGGT GTACACAGTC ATTACAAACA TTTATTTGCT | 1920 |
| TTGTTAGAAC TTGCTAAAAA ACAAGGTGTT GAAAAAGTTT ACGTACACGC ATTTTTAGAT | 1980 |
| GGCCGTGACG TAGATCAAAA ATCCGCTTTG AAATACATCG AAGAGACTGA AGCTAAATTC | 2040 |
| AATGAATTAG GCATTGGTCA ATTTGCATCT GTGTCTGGTC GTTATTATGC ANTG | 2094 |

(2) INFORMATION FOR SEQ ID NO: 88:

(i) SEQUENCE CHARACTERISTICS:
        (A) LENGTH:        954 base pairs
        (B) TYPE:          nucleic acid
        (C) STRANDEDNESS:  single
        (D) TOPOLOGY:     linear (xi) SEQUENCE DESCRIPTION: SEQ ID NO: 88:

| | |
|---|---|
| GGGGWYYCTC TAGAGYCGAC CTRCAGGCAT SCAAGCTTBA CCAGGWTCAA TTAGAGGTRA | 60 |
| TTWAGGTTTA RCTKTTSGTV GAADTATCAT BMTCGGTTCA GATTCCTGAG AGTCTGCTGA | 120 |
| ACGTGAAATT AATCTATGGT TTAATGAAAA TGAAATTACT AGCTATGCTT CACCACGTGA | 180 |
| TGCATGGTTA TATGAATAAA ATATAAACTG TAAACCTTTA CGATTTATTT ATAAAGGTAG | 240 |
| AAAGGGTTTT GTTATGTGGT TAGTCATTAT GATTATACAT AACAAGGCCC GTTTTTTATG | 300 |
| TTGTAGTAAA TTACTTGAAA AATTTTATAG TTTTTTGGTA ACACGTATTA AAAAGAGAGG | 360 |
| AATATTCTTT ATCAAATGAA ACTAAACAGA GAGAAGGGGT TGTTAAAATG AAGAATATTA | 420 |
| TTTCGATTAT TTTGGGGATT TTAATGTTCT TAAAATTAAT GGAATTACTA TATGGTGCTA | 480 |
| TATTTTTAGA TAAACCACTT AATCCTATAA CAAAAATTAT TTTTATACTG ACTCTCATTT | 540 |
| ATATTTTTTA TGTATTAGTA AAAGAATTGA TTATATTTTT GAAGTCAAAG TATAACAAAA | 600 |
| GCGCTTAACA TATGTTTATT TTAATATCAT AATTTTTTTA AACGGGACTG ATTAACYTTT | 660 |
| ATTAATAATT AACAGTTCGT TCTTTTGTAT TAAGAAATGT AGTCAGTATA TTATTTGCTA | 720 |
| AAGTTGCGAT ACGATTATAT TAAAACGGCT AATCATTTTT AATTAATGAT TATATGATGC | 780 |
| AACTGTTTAG AAATTCATGA TACTTTTCTA CAGACGAATA TATTATAATT AATTTTAGTT | 840 |
| CGTTTAATAT TAAGATAATT CTGACATTTA AAATGAGATG TCATCCATTT TCTTAATTGA | 900 |
| GCTTGAAAAC AAACATTTAT GAATGCACAA TGAATATGAT AAGATTAACA ACAT | 954 |

(2) INFORMATION FOR SEQ ID NO: 89:

(i) SEQUENCE CHARACTERISTICS:
        (A) LENGTH:        841 base pairs
        (B) TYPE:          nucleic acid
        (C) STRANDEDNESS:  single
        (D) TOPOLOGY:     linear (xi) SEQUENCE DESCRIPTION: SEQ ID NO: 89:

| | |
|---|---|
| CTTTMAWKRC CTRAACCACT TAACAAACCT GCCAATAATC GTGTTGTCGT ACCAGAATTA | 60 |

```
CCTGTATACA ATACTTGATG TGGCGTGTTA AAAGATTGAT ATCCTGGGGA AGTCACAACT    120

AATTTTTCAT CATCTTCTTT GATTTCTACA CCTAACAGTC GGAAAATGTC CATCGTACGA    180

CGACAATCTT CGCCAAGTAG TGGCTTATAT ATAGTAGATA CACCTTCAGC TAGCGACGCC    240

AACATGATTG CACGGTGTGT CATTGACTTA TCGCCCGGCA CTTCTATTTC GCCCTTTAAC    300

GGACCTGAAA TATCAATGAT TTGTTCATTT ACCATTTCAT TCACCTACTT AAAATATGTT    360

TTTAATTGTT CACATGCATG TTGTAATGTT AGTTGATCAA CATGTTGTAC AACGATATCT    420

CCAAATTGTC TAATCAAGAC CATTTGTACA CCTTGCTTAT CATTCTTTTT ATCACTTAGC    480

ATATATTGGT ATAACGTTTC AAAATCCAAG TCAGTTATCA TGTCTAAAGG ATAGCCGAGT    540

TGTATTAAAT ATTGAATATA ATGATTAATA TCATGCTTAG RATCAAACAA AGCATTCGCA    600

ACTATAAATT GATAGATAAT GCCAACCATC ACTGACATGA CCATGAGGTA TTTTATGATA    660

GTATTCAACA GCATGACCAA ATGTATGACC TAAATTTAAR AATTTACGTA CACCTTGTTC    720

TTTTTSATCT GGCGAATAAC AATATCCAGC TTSGTTTCAA TACCTTTRGS AATWTATTTR    780

TCCATACCAT TTAATGACTG TAATATCTCT CTATCTTTAA AGTGCTGTTC GATATCTTGC    840

G                                                                   841
```

(2) INFORMATION FOR SEQ ID NO: 90:

(i) SEQUENCE CHARACTERISTICS:
        (A) LENGTH:        568 base pairs
        (B) TYPE:          nucleic acid
        (C) STRANDEDNESS:  single
        (D) TOPOLOGY:      linear (xi) SEQUENCE DESCRIPTION: SEQ ID NO: 90:

```
CCGGGGATCC TCTAGAGTCG ATCTTTGCAT TCTTTAAGCT TAAATTTTCT ATTCTTCTTT     60

CTCTACGGCG CATAGCATTA ATATTACCGT AACTTATCCC AGTATCTTTA TTAATTTGAT    120

AACTCGATAT CTCTTTGTTT TCTATCAATT CTTTGATTGT ATTGAATATT TCATCATAGC    180

AATTCATAAA TTAGATGAGG CGAAATTTTT AATTTTTTAG AATATCAATA GTANTATAAC    240

TAAAATGAAA ATACCGATCG ATAAACAAAA AGATATTTTT TGTTTTGTTT CTCTTTTCAT    300

ATAGTATTAC CCCCTTAATA ATGCGTAGTA AGGTCCCTCT TTTCGGGGTC TTACCTTANA    360

AACGTTCTGC AAATGAATTC GATGAGAAGT AATATGAATA TGGCTATTTT CAAGTAATAC    420

TCAACGTTTT CGCGACGTTC TTTTATCGCC TCATCTCATC ACCTCAAAT ATATTAAAAT    480

TCATGTGAAC TAAAATATAA AATGGTCTTC CCCAGCTTTA AAAAAATAAA TACATAAAAC    540

ATTTTACTTG GACCAAAACT TGGACCCC                                      568
```

(2) INFORMATION FOR SEQ ID NO: 91:

(i) SEQUENCE CHARACTERISTICS:
        (A) LENGTH:        581 base pairs
        (B) TYPE:          nucleic acid
        (C) STRANDEDNESS:  single
        (D) TOPOLOGY:      linear (xi) SEQUENCE DESCRIPTION: SEQ ID NO: 91:

```
ATGCCTGCAG GTCGATCATT AATTAAAAAC CCTGGCGGTG GTTTAGCTAA GATTGGTGGA     60

TACATTGCTG GTAGAAAAGA TTTAATTGAA CGATGTGGTT ATAGATTGAC AGCACCTGGT    120

ATTGGTAAAG AAGCGGGTGC ATCATTAAAT GCATTGCTTG AAATGTATCA AGGTTTCTTT    180

TTAGCACCAC ACGTTGTCAG TCAGAGTCTT AAAGGTGCAT TGTTTACTAG TTTATTTTTA    240
```

```
GAAAAAATGA ATATGAACAC AACGCCGAAG TACTACGAAA AACGAACTGA TTTAATTCAA    300

ACAGTTAAAT TGAAACGAA AGAACAAATG ATTTCATTTT GTCAAAGTAT TCAACACGCA     360

TCCCCAATTA ATGCACATTT TAGTCCANAA CCTAGTTATA TGCCTGGTTA CGAAGATGAT    420

GTTATTATGG CAGCTGGTAC GTTTATTCAA GGTTCATCCG ATTGAATTAT CTGCAGATGG    480

ACCTATTCGT CCTCCTTATG AAGCATATGT TCAAGGANGA TTAACATATG AACACGTTAA    540

AATTGCTGTT GACAAGANCT GTTTAATCAG TTTGAAAAAA C                        581
```

(2) INFORMATION FOR SEQ ID NO: 92:

(i) SEQUENCE CHARACTERISTICS:
        (A) LENGTH:        2001 base pairs
        (B) TYPE:          nucleic acid
        (C) STRANDEDNESS:  single
        (D) TOPOLOGY:      linear (xi) SEQUENCE DESCRIPTION: SEQ ID NO: 92:

```
CGGGGATCCT CTAAAGTCGA TCAAATTGGG CGAATGAAGC AAGGAAAAAC AATTTTAAAA    60

AAGATTTCTT GGCAAATTGC TAAAGGTGAT AAATGGATAT TATATGGGTT GAATGGTGCT    120

GGCAAGACAA CACTTCTAAA TATTTTAAAT GCGTATGAGC CTGCAACATC TGGAACTGTT    180

AACCTTTTCG GTAAAATGCC AGGCAAGGTA GGGTATTCTG CAGAGACTGT ACGACAACAT    240

ATAGGTTTTG TATCTCATAG TTTACTGGAA AAGTTTCAAG AGGGTGAAAG AGTAATCGAT    300

GTGGTGATAA GCCGTGCCTT TAAATCAATT GGTGTTTATC AAGATATTGA TGATGAGATA    360

CGTAATGAAG CACATCAATT ACTTAAATTA GTTGGAATGT CTGCTAAAGC GCAACAATAT    420

ATTGGTTATT TATCTACCGG TGAAAAACAA CGAGTGATGA TTGCACGAGC TTTAATGGGG    480

CAACCCCAGG TTTTAATTTT AGATGAGCCA GCAGCTGGTT TAGACTTTAT TGCACGAGAA    540

TCGTTGTTAA GTATACTTGA CTCATTGTCA GATTCATATC CAACGCTTGC GATGATTTAT    600

GTGACGCACT TTATTGAAGA ATAACTGCT AACTTTTCCA AAATTTTACT GCTAAAAGAT     660

GGCCAAAGTA TTCAACAAGG CGCTGTAGAA GACATATTAA CTTCTGAAAA CATGTCACGA    720

TTTTTCCAGA AAAATGTAGC AGTTCAAAGA TGGAATAATC GATTTTCTAT GGCAATGTTA    780

GAGTAAATAT TTTGCAAATA ATAAGTAATA ATGACAAAAT TTAATTAAGA TAAAATGGAC    840

AGTGGAGGGC AATATGGATA ACGTTAAAAG CAATATTTTT GGACATGGAT GGAACAATTT    900

TACATTGAAA ATAATCCAAG CATCCAACGT WTACGAAAGA TGTTCATTAA TCAATTGGAG    960

AGAGAAAGGA TATWAAGTAT TTTTGGSCAA CAGGACGTTC GCATTCTGAA ATACATCMAA    1020

YTTGTACCTC AAGATTTTGC GGTTAATGGC ATCATTAGTT CAAATGGAAC AATTGGAGAA    1080

GTAGATGGAG AAATTATCTT CAAGCATGGT TTATCATTGG CTCAAGTGCA ACAAATTACT    1140

AATTTAGCTA AGCGCCAACA AATTTATTAT GAGGTATTTC CTTTTGAAGG TAATAGAGTT    1200

TCTTTAAAAG AAGATGAAAC ATGGATGCGA GATATGATTC GTAGTCAAGA TCCTATTAAT    1260

GGCGTAAGTC ATAGTGAATG GTCTTCAAGA CAAGATGCGC TTGCTGGTAA GATAGATTGG    1320

GTAACTAAGT TTCCTGAAGG TGAATATTCA AAAATTTATC TATTCAGTTC TAATTTAGAA    1380

AAAATAACAG CATTTAGAGA TGAATTAAAG CAAAATCATG TGCAACTACA GATTAGTGTT    1440

TCAAATTCAT CAAGATTTAA TGCGGAAACA ATGGCTTATC AAACTGATAA AGGTACAGGC    1500

ATTAAAGAAA TGATTGCACA TTTTGGTATT CATCAAGAAG AAACGTTAGT TATTGGAGAT    1560

AGCGACAATG ATAGAGCAAT GTTTGAATTT GGTCATTATA CAGTTGCTAT GAAAAATGCA    1620

CGCCCTGAAA TCCAAGCATT AACTTCAGAT GTAACGGCAT ACACGAATGA AGAGGATGGC    1680
```

-continued

```
GCAGCAAAAT ATTTAGCAGA GCATTTTTA GCTGAATAAT AAAATAGGTA GTTATTTATT     1740

ATTTAATTTA CAATAGTTGA TGAGTAATGT ACAAAGAGCA GTAAAGTTAT TTTCTATTAG     1800

AAAATGTCTT ACTGCTCTTT TGTATGCTTA TAAATATTTG AATCATCTAT ATTTAATTGG     1860

ACAAACTCTA TGAGAATAAA TATTGTTAAA ACTAATAAGA TAGGAAATTC ATTGATTTTG     1920

AATAATATTT CTTGTTTTAA GGTTTAACTA TTGAATTGTA TACTTCTTTT TTTAGTAGCA     1980

ACAGATCGAC CTGCAGGCAT A                                               2001
```

(2) INFORMATION FOR SEQ ID NO: 93:

(i) SEQUENCE CHARACTERISTICS:
        (A) LENGTH:          2522 base pairs
        (B) TYPE:            nucleic acid
        (C) STRANDEDNESS:    single
        (D) TOPOLOGY:        linear (xi) SEQUENCE DESCRIPTION: SEQ ID NO: 93:

```
GANCTCGGTA CCCGGGGATG CCTSYAGAGT CGATCGCTAC CACCTTGAAT GACTTCAATT       60

CTTTCATCAG AAATTTTGAA TTTTCTAAGT GTATCTTTCG TATGCGTCAT CCATTGTTGT      120

GGCGTCGCGA TAATAATTTT TTCAAAATCA TTAATTAAAA TAAATTTTTC TAATGTATGG      180

ATTAAAATCG GTTTGTTGTC TAAATCTAAA AATTGTTTAG GTAAAGGTAC GTTACCCATT      240

CTTGAGCCTA TACCTCCAGC TAGAATACCA GCGTATTTCA TAAATACTT CCTCCATTCA       300

ACTATATCTA TATTTAATTA TTTAAATTTC GTTGCATTTT CCAATTGAAA ACTCATTTTA      360

AAATCAAAAC TCTAAATGTC TGTGTATTAC TTAAAATTAT ACATATTTTG CTTATATTTT      420

AGCATATTTT GTTAAACCT ATATTACATT ATATCAGACG TTTTCATACA CAAATAATAA       480

CATACAAGCA AACATTTCGT TTATTATTTA TATCACTTAA CTAATTAATT TATAATTTTT      540

TATTGTTTTT AAGTTATCAC TTAAAAATCG TTTGGCAAAT TCGTTGTGAC GCTTGTCCAT      600

CTTCTAATGA ACAGAATTTT TGATAAAATA CCGTTCGTGC TTCAATATAC TCATTTGCAG      660

TCTCATCGAT TTGTTTTAAT GCATCAATGA GTGCTGTTTG ATTTTCAACA ATTGGAMCTG      720

GCAACTCTTT TTTATAATCC ATGTAAAAAC CTCTAAGCTC ATCGCCATAT TTATCTAAGT      780

CATATGCATA GAAAATTTGC GGACGCTTTA ATACACCGAA GTCGAACATG ACAGATGAGT      840

AGTCGGTAAC TAACGCATCG CTGATTAAGT TATAAATCCG AAATGCCTTC ATAATCTGGA      900

AAMGTCTTTC AACAAAATCA TCAATGTTCA TCAATAACGY GTCAACAACT AAATAATGCA      960

KGCGTAATAA AATAACATAA TCATCATCCA GCGCTTGACG CAAAGCTTCT ATATCAAAGT     1020

TAACATTAAA TTGATATGAA CCCTTCTCGG AATCGCTTCA TCGTCAACGC CAAGTTGGCG     1080

CGTACATAAT CAACTTTTTT ATCTAATGGA ATATTTAATC TTGTCTTAAT ACCATTAATA     1140

TATTCAGTAT CATTGCGTTT ATGTGATAAT TTATCATTTC TTGGATAACC TGTTTCCAAA     1200

ATCTTATCTC GACTAACATG AAATGCATTT TGAAATATCG ATGTCGAATA TGGATTAGGT     1260

GACACTAGAT AATCCCACCG TTGGCTTTCT TTTTTAAAGC CATCTTGGTA ATTTTGAGTA     1320

TTTGTTCCTA GCATTTTAAC GTTACTAATA TCCAAACCAA TCTTTTTTAA TGGCGTGCCA     1380

TGCCATGTTT GTAAGTACGT CGTTCGCGGT GATTTATATA ACCAATCTGG TGTACGTGTG     1440

TTAATCATCC ACGCTTTCGC TCTTGGCATC GCTAAAAACC ATTTCATTGA AAACTTTGTA     1500

ACATATGGTA CATTGTGCTG TTGGAATATG TGTTCATATC CTTTTTTCAC ACCCCATATT     1560

AATTGGGCAT CGCTATGTTC AGTTAAGTAT TCATATAATG CTTTGGGGTT GTCGCTGTAT     1620

TGTTTACCAT GAAAGCTTTC AAAATAAATT AGATTCTTGT TTGGCAATTT TGGATAGTAA     1680
```

```
TTTAAAAGTC GTATATATAC TATGTTCTAT CAATTTTTTA ATTGTATTTT TAATCATGTC    1740

GTACCTCCGA CGTGTTTTTG TAATTATATT AATATGTATG AGCAAGCTCA TTGTAACCAT    1800

GCCTATTATA GCATTTCATC ATAAAATACA TTTAACCATT ACACTTGTCG TTAATTATCA    1860

TACGAAATAC ATGATTAATG TACCACTTTA ACATAACAAA AAATCGTTAT CCATTCATAA    1920

CGTATGTGTT TACACATTTA TGAATTAGAT AACGATTGGA TCGATTATTT TATTTWACAA    1980

AATGACAATT CAGTTGGAAG GTGATTGCTT TTGATTGAAT CGCCTTATGC ATGAAAAATC    2040

AAAAGGTTAT TCTCATTGTA TAGTCCTGCT TCTCATCATG ACATGTTGCT CACTTCATTG    2100

TCAGAACCCT TCTTGAAAAC TATGCCTTAT GACTCATTTG CATGGCAAGT AATATATGCC    2160

AACATTAGCG TCTAAACAAA TCTTTGACTA AACGTTCACT TGAGCGACCA TCTTGATATT    2220

TAAAATGTTT ATCTAAGAAT GGCACAACTT TTTCAACCTC ATAATCTTCA TTGTCCAAAG    2280

CATCCATTAA TGCATCAAAG GACTGTACAA TTTTACCTGG AACAAATGAT TCAAATGGTT    2340

CATAGAAATC ACGCGTCGTA ATGTAATCTT CTAAGTCAAA TGCATAGAAA ATCATCGGCT    2400

TTTTAAATAC TGCATATTCA TATATTAAAG ATGAATAATC ACTAATCAAC AAGTCTGTAA    2460

CAAAGAGAAT ATCGTTWACT TCASGRTCGA TCGACTCTAG AGGATCCCCG GGTACCGAGC    2520

TC                                                                   2522

(2) INFORMATION FOR SEQ ID NO: 94:

(i) SEQUENCE CHARACTERISTICS:
             (A) LENGTH:        1335 base pairs
             (B) TYPE:          nucleic acid
             (C) STRANDEDNESS:  single
             (D) TOPOLOGY:      linear (xi) SEQUENCE DESCRIPTION: SEQ ID NO: 94:

CAGAGTTGTT AATTCGTACT TCAGGAGAAC AAAGAATAAG TAATTTCTTG ATTTGGCAAG      60

TTTCGTATAG TGAATTTATC TTTAATCAAA AATTATGGCC TGACTTTGAC GAAGATGAAT    120

TAATTAAATG TATAAAAATT TATCAGTCAC GTCAAAGACG CTTTGGCGGA TTGARTGAKG    180

AGKATRTATA GTATGAAAGT TAGAACGCTG ACAGCTATTA TTGCCTTAAT CGTATTCTTG    240

CCTATCTTGT TAAAAGGCGG CCTTGTGTTA ATGATATTTG CTAATATATT AGCATTGATT    300

GCATTAAAAG AAATTGTTGA ATATGAATAT GATTAAATTT GTTTCAGTTC CTGGTTTAAT    360

TAGTGCAGTT GGTCTTATCA TCATTATGTT GCCACAACAT GCAGGGCCAT GGGTACAAGT    420

AATTCAATTA AAAAGTTTAA TTGCAATGAG CTTTATTGTA TTAAGTTATA CTGTCTTATC    480

TAAAAACAGA TTTAGTTTTA TGGATGCTGC ATTTTGCTTA ATGTCTGTGG CTTATGTAGG    540

CATTGGTTTT ATGTTCTTTT ATGAAACGAG ATCAGAAGGA TTACATTACA TATTATATGC    600

CTTTTTAATT GTTTGGCTTA CAGATACAGG GGCTTACTTG TTTGGTAAAA TGATGGGTTA    660

AACATAAGCT TTGGCCAGTA ATAAKTCCGA ATAAAACAAT CCGAAGGATY CATAGGTGGC    720

TTGTTCTGTA GTTTGATAGT ACCACTTGCA ATGTTATATT TTGTAGATTT CAATATGAAT    780

GTATGGATAT TACTTGGAGT GACATTGATT TTAAGTTTAT TTGGTCAATT AGGTGATTTA    840

GTGGAATCAG GATTTAAGCG TCATTTNGGC GTTAAAGACT CAGGTCGAAT ACTACCTGGA    900

CACGGTGGTA TTTTAGACCG ATTTGACAGC TTTATGTTTG TGTTACCATT ATTAAATATT    960

TTATTAATAC AATCTTAATG CTGAGAACAA ATCAATAAAC GTAAAGAGGA GTTGCTGAGA   1020

TAATTTAATG AATCCTCAGA ACTCCCTTTT GAAAATTATA CGCAATATTA ACTTTGAAAA   1080

TTATACGCAA TATTAACTTT GAAAATTAGA CGTTATATTT TGTGATTTGT CAGTATCATA   1140
```

-continued

```
TTATAATGAC TTATGTTACG TATACAGCAA TCATTTTTAA AATAAAAGAA ATTTATAAAC      1200

AATCGAGGTG TAGCGAGTGA GCTATTTAGT TACAATAATT GCATTTATTA TTGTTTTTGG      1260

TGTACTAGTA ACTGTTCATG AATATGGCCA TATGTTTTTT GCGAAAAGAG CAGGCATTAT      1320

GTGTCCAGAA TTTGC                                                      1335
```

(2) INFORMATION FOR SEQ ID NO: 95:

(i) SEQUENCE CHARACTERISTICS:
        (A) LENGTH: 2902 base pairs
        (B) TYPE: nucleic acid
        (C) STRANDEDNESS: single
        (D) TOPOLOGY: linear (xi) SEQUENCE DESCRIPTION: SEQ ID NO: 95:

```
GAGCTCGGTA CCCGGGGATC CTCTAGAGTC GATCATTACC TAATTCGTAT TGTCGAACAA        60

TTTGATACAT TTTACCTAAA TCATCATATT TACAGAAATC ATGTAATACA CCTGCTAATT       120

CTACTTTACT AGTGTCTCCA TCATAAATTT CTGCCRATTT AATCGCTGTT TCTGCAACTC       180

TTAAAGAATG ATTGATRACG TTTCTCTGGA CAGTTTCTCT TTTGCAAGCC GTTTTGCTTT       240

TTCAATGTWC ATATAATCCT TCCCCCTTAA TATAGTTTTC AACGGATTTA GGAACAAGAA       300

CTTGGATAGA TTTCCCTTCA CTAACTCTTT GTCGAATCAT TGTCGAACTT ATATCTACCC       360

TAGGTATCTG AATTGCAATC ATAGCATTTT CAACATTTTG ACTATTTTTG TCTCGATTTA       420

CAACTACAAA AGTAACCATT TCTTTTAAGT ATTCAATTTG ATACCATTTC TCTAGTTGGT       480

TATACTGATC CGTCCCAATA ACAAAGTACA ACTCACTGTC TTTGTGTTGC TCCTTGAATG       540

CCTTGATCGT GTCATAGGTA TAACTTTGAC CACCACGTTT AATTTCATCG TCACAAATAT       600

CTCCAAAACC AAGCTCGTCG ATAATCATCT GTATCATTGT TAATCTGTGC TGAACGTCTA       660

TAAAATCATG GTGCTTTTTC AATGGAGAMA WAAAAMWARR WAAAAAATAA AATTCATCTG       720

GCTGTAATTC ATGAAATACT TCGCTAGCTA CTATCATATG TTGCAGTATG GATAGGGTTA       780

AACTGACCGC CGTAAAGTAC TATCTTTTTC ATTATTATGG CAATTCAATT TCTTTATTAT       840

CTTTAGATTC TCTATAAATC ACTATCATAG ATCCAATCAC TTGCACTAAT TCACTATGAA       900

KTAGCTTCCG CTTAATGTTT CCAGCTAATY CTTTTTTATC ATCAAAGTTT ATTTTGTTAK       960

TACATGTTAC TTTAATCAAT YCTCTGTTTT CYAACGTTAT CATCTATTTG TTTAATCATA      1020

TTTTCGTTGA TACCGCCTTT TCCAATTTGA AAAATCGGAT CAATATTGTG TGCTAAACTT      1080

CTTAAGTATC TTTTTTGTTT GCCAGTAAGC ATATGTTATT CTCCTTTTAA TTGTTGTAAA      1140

ACTGCTGTTT TCATAGAATT AATATCAGCA TCTTTATTAG TCCAAATTTT AAAGCTTTCC      1200

GCACCCTGGT AAACAAACAT ATCTAAGCCA TTATAAATAT GGTTTCCCTT GCGCTCTGCT      1260

TCCTCTAAAA TAGGTGTTTT ATACGGTATA TAAACAATAT CACTCATTAA AGTATTGGGA      1320

GAAAGAGCTT TAAATTAATA ATACTTTCGT TATTTCCAGC CATACCCGCT GGTGTTGTAT      1380

TAATAACGAT ATCGAATTCA GCTAAATACT TTTCAGCATC TGCTAATGAA ATTTGGTTTA      1440

TATTTAAATT CCAAGATTCA AAACGAGCCA TCGTTCTATT CGCAACAGTT AATTTGGGCT      1500

TTACAAATTT TGCTAATTCA TAAGCAATAC CTTTACTTGC ACCACCTGCG CCCAAAATTA      1560

AAATGTATGC ATTTTCTAAA TCTGGATAAA CGCTGTGCAA TCCTTTAACA TAACCAATAC      1620

CATCTGTATT ATACCCTATC CACTTGCCAT CTTTTATCAA AACAGTGTTA ACTGCACCTG      1680

CATTAATCGC TTGTTCATCA ACATAATCTA AATCGGTAT GATACGTTCT TTATGAGGAA      1740

TTGTGATATT AAASCCTTCT AATTYTTTTT TSGAATAAT TTCTTTAATT AAATGAAAAA      1800
```

-continued

```
TTYTTCAATT GGGAATATTT AAAGCTTCAT AAGTATCATC TTAATCCTAA AGAATTAAAA    1860

TTTGCTCTAT GCATAACGGG CGACAAGGAA TGTGAAATAG GATTTCCTAT AACTGCAAAT    1920

TTCATTTTTT TAATCACCTT ATAAAATAGA ATTYTTTAAT ACAACATCAA CATTTTTAGG    1980

AACACGAACG ATTACTTTAG CCCCTGGTCC TATAGTTATA AAGCCTAGAC CAGAGATCAT    2040

AACATCGCGT TTCTCTTTGC CTGTTTCAAG TCTAACAGCC TTTACCTCAT TAAGATCAAA    2100

ATTTTGTGGA TTTCCAGGTG GCGTTAATAA ATCGCCAAGT TGATTACGCC ATAAATCATT    2160

AGCCTTCTCC GTTTTAGTAC GATGTATATT CAAGTCATTA GAAAAGAAAC AAACTAACGG    2220

ACGTTTACCA CCTGAWACAT AATCTATGCG CGCTAGACCG CCGAAGAATA ATGTCKGCGC    2280

CTCATTTAAT TGATATACGC GTTGTTTTAT TTCTTTCTTA GGCATAATAA TTTTCAATYC    2340

TTTTTCACTA ACTAAATGCG TCATTTGGTG ATCTTGAATA ATACCTGGTG TATCATACAT    2400

AAATGATGTT TCATCTAAAG GAATATCTAT CATATCTAAA GTTGYTTCCA GGGAATCTTG    2460

AAGTTGTTAC TACATCTTTT TCACCAACAC TAGCTTCAAT CAGTTTATTA ATCAATGTAG    2520

ATTTCCCAAC ATTCGTTGTC CCTACAATAT ACACATCTTC ATTTTCTCGA ATATTCGCAA    2580

TTGATGATAA TAAGTCGTCT ATGCCCCAGC CTTTTTCAGC TGAAATTAAT ACGACATCGT    2640

CAGCTTCCAA ACCATATTTT CTTGCTGTTC GTTTTAACCA TTCTTTAACT CGACGTTTAT    2700

TAATTTGTTT CGGCAATAAA TCCAATTTAT TTGCTGCTAA AATGATTTTT TTGTTTCCGA    2760

CAATACGTTT AACTGCATTA ATAAATGATC CTTCAAAGTC AAATACATCC ACGACATTGA    2820

CGACAATACC CTTTTTATCC GCAAGTCCTG ATAATAATTT TAAAAAGTCT TCACTTTCTA    2880

ATCCTACATC TTGAACTTCG TT    2902
```

(2) INFORMATION FOR SEQ ID NO: 96:

(i) SEQUENCE CHARACTERISTICS:
        (A) LENGTH: 1916 base pairs
        (B) TYPE: nucleic acid
        (C) STRANDEDNESS: single
        (D) TOPOLOGY: linear (xi) SEQUENCE DESCRIPTION: SEQ ID NO: 96:

```
AGTCGATCAA AGCCAATGTT CCAGTTGTTC CTGGTAGTGA CGGTTTAATG AAAGACGTCT      60

CAGAAGCTAA GAAAATCGCC AAAAAAATTG GCTATCCGGT CATCATTAAA GCTACTGCTG     120

GCGGTGGCGG AAAAGGTATC CGTGTTGCTC GTGATGAAAA AGAACTTGAA ACTGGCTTCC     180

GAATGACAGA ACAAGAAGCT CAAACTGCAT TTGGTAATGG TGGACTTTAT ATGGAGAAAT     240

TCATCGAAAA CTTCCGCCAT ATTGAAATCC AAATTGTTGG GGACAGCTAT GGTAATGTAA     300

TTCATTTAGG AGAACGTGAT TGTACAATTC AAAGACGTNT GCAGAAATTA GTGGAAGAAG     360

CACCTTCCCC NATTTTAGAT GATGAAACAC GTCGTGAAAT GGGAAATGCC GCAGTTCGTG     420

CAGCGAAAGC TGTAAATTAT GAAAATGCGG GAACAATTGA GTTTATATAT GATTTAAATG     480

ATAATAAATT TTATTTTATG GAAATGAATA CACGTATTCA AGTAGAACAT CCTGTAACTG     540

AAATGGTAAC AGGAATTGAT TTAGTTAAAT TACAATTACA AGTTGCTATG GGTGACGTGT     600

TACCGTATAA ACAAGAAGAT ATTAAATTAA CAGGACACGC AATTGAATTT AGAATTAATG     660

CTGAAAATCC TTACAAGAAC TTTATGCCAT CACCAGGTAA AATTGAGCAA TATCTTGCAC     720

CAGGTGGATA TGGTGTTCGA ATAGAGTCAG CATGTTATAC TAATTATACG ATACCGCCAT     780

ATTATGATTC GATGGTAGCG AAATTAATCA TACATGAACC GACACGAGAT GARGCGATTA     840

TGGSTGGCAT TCGTGCACTA ARKGRAWTTG TGGTTYTTGG GTATTGATAC AACTATTCCA     900
```

-continued

```
TTTCCATATT AAATTATTGA ATAACGGATA TATTTAGGAA GCGGTAAATT TAATACAAAC      960

TTTTTAGAAG CAAAATAGCA TTATTGAATG ATGAAAGGTT AATAGGAGGT CMATCCCMTG     1020

GTCAAAGTAA CTGATTATTC MAATTCMAAA TTAGGTAAAG TAGAAATAGC GCCAGAAGTG     1080

CTATCTGTTA TTGCAAGTAT AGCTACTTCG GAAGTCGAAG GCATCACTGG CCATTTTGCT     1140

GAATTAAAAG AAACAAATTT AGAAAAAGTT AGTCGTAAAA ATTTAAGCCG TGATTTAAAA     1200

ATCGAGAGTA AAGAAGATGG CATATATATA GATGTATATT GTGCATTAAA ACATGGTGTT     1260

AATATTTCAA AAACTGCAAA CAAAATTCAA ACGTCAATTT TTAATTCAAT TTCTAATATG     1320

ACAGCGATAG AACCTAAGCA AATTAATATT CACATTACAC AAATCGTTAT TGAAAAGTAA     1380

TGTCATACCT AATTCAGTAA TTAAATAAAG AAAAATACAA ACGTTTGAAG GAGTTAAAAA     1440

TGAGTCGTAA AGAATCCCGA GTGCAAGCTT TTCAAACTTT ATTTCAATTA GAAATGAAGG     1500

ACAGTGATTT AACGATAAAT GAAGCGATAA GCTTTATTAA AGACGATAAT CCAGATTTAG     1560

ACTTCGAATT TATTCATTGG CTAGTTTCTG GCGTTAAAGA TCACGAACCT GTATTAGACG     1620

AGACAATTAG TCCTTATTTA AAAGATTGGA CTATTGCACG TTTATTAAAA ACGGATCGTA     1680

TTATTTTAAG AATGGCAACA TATGAAATAT TACACAGTGA TACACCTGCT AAAGTCGTAA     1740

TGAATGAAGC AGTTGAATTA ACAAAACAAT TCAGTGATGA TGATCATTAT AAATTTATAA     1800

ATGGTGTATT GAGTAATATA AAAAAATAAA ATTGAGTGAT GTTATATGTC AGATTATTTA     1860

AGTGTTTCAG CTTTAACGAA ATATATTAAA TATAAATTTG ATCGACCTGC AGGCAT        1916
```

(2) INFORMATION FOR SEQ ID NO: 97:

(i) SEQUENCE CHARACTERISTICS:
        (A) LENGTH:         1932 base pairs
        (B) TYPE:           nucleic acid
        (C) STRANDEDNESS:   single
        (D) TOPOLOGY:      linear (xi) SEQUENCE DESCRIPTION: SEQ ID NO: 97:

```
CGGGGATCCT CTAGAGTCGA TCCGTTTGGT GGTGGTTTTG GTTTCTTCGA GTAAGTGTAA       60

GGAGGCTATG AATTGARRAC GGTCGGTGAA GCGCTAAAAG GTANACGTGA AAGGTTAGGA      120

ATGACTTYAA CAGAATTAGA GCAACGTACT GGAATTAANC GTGAAATGCT AGTGCATATT      180

GAAAATAATG AATTCGATCA ACTACCGAAT AAAAATTACA GCGAAGGATT TATTAGAAAA      240

TATGCAAGCG TAGTAAATAT TGAACCTAAC CAATTAATTC AAGCTCATCA AGATGAAATT      300

CCATCGAACC AGAGCCGAAT GGGACGAAGT AATTACAGTT TCAATAGAT AATAAAGACT       360

TACGATTATA AGAGTAAATC AAAGANAGCC AATACAATTA TTAGTAATCA TGGGTTATTA      420

CAGTTTTAAT AACTTTATTG TTATGGATCA TGTTAGTTTT AATATTTTAA CAGAAATAAA      480

TTAGTGAGAA ATGAGGATGT TATAATGAAT ATTCCGAACC AGATTACGGT TTTTAGAGTT      540

AGTGTTAATA CCAGTTTTTA TATTGTTTGC GTTAGTTGAT TTTGGATTTG GCAATGTGTC      600

ATTTCTAGGA GGATATGAAA TAAGAATTGA GTTATTAATC AGTGGTTTTA TTTTTATATT      660

GGCTTCCCTT AGCGATTTTG TTGATGGTTA TTTAGCTAGA AAATGGAATT TAGTTACAAA      720

TATGGGGAAA TTTTTGGATC CATTAGCGGA TAAATTATTA GTTGCAAGTG CTTTAATTGT      780

ACTTGTGCAA CTAGGACTAA CAAATTCTGT AGTAGCAATC ATTATTATTG CCAGAGAATT      840

TGCCGTAACT GGTTTACGTT TACTACAAAT TGAACAAGGA TTCCGTAAGT TGCAGCTGGT      900

CCAATTTAGG TWAAAWTWAA AACAGCCAGT TACTATGGTT AGCMAWTWAC TTGGTTGTTW      960

ATTAAGKTGA TCCCATTGGG CAACATTGAT TGGTTTGTCC ATTARGACAA ATTTTAATTA     1020
```

-continued

```
TAACATTGGC GTTATWTTTW ACTATCYTAT CTGGTATTGA ATAACTTTTA TAAAGGTAGA    1080

GATGTTTTTA AACAAAAATA AATATTTGTT TATACTAGAT TTCATTTTCA TATGGAATCT    1140

AGTTTTTTTA ATCCCAATTT TAGAAATTAG CCACGCAATT GTTTATAATG ATATATTGTA    1200

AAACAATATT TGTTCATTTT TTTAGGGAAA ATCTGTAGTA GCATCTGATA CATTGAATCT    1260

AAAATTGATG TGAATTTTTA AATGAAATAC ATGAAAAAAT GAATTAAACG ATACAAGGGG    1320

GATATAAATG TCAATTGCCA TTATTGCTGT AGGCTCAGAA CTATTGCTAG GTCAAATCGC    1380

TAATACCAAC GGACAATTTC TATCTAAAGT ATTTAATGAA ATTGGACAAA ATGTATTAGA    1440

ACATAAAGTT ATTGGAGATA ATAAAAAACG TTTAGAATCA AGTGTAACGT CATGCGCTAG    1500

AAAAATATGA TACTGTTATT TTAACAGGTG GCTTAGGTCC TACGAAAGAT GACTTAACGA    1560

AGCATACAGT GGCCCAGATT GTTGGTAAAG ATTTAGTTAT TGATGAGCCT TCTTTAAAAT    1620

ATATTGAAAG CTATTTTGAG GAACAAGGAC AAGAAATGAC ACCTAATAAT AAACAACAGG    1680

CTTTAGTAAT TGAAGGTTCA ACTGTATTAA CAAATCATCA TGGCATGGCT CCAGGAATGA    1740

TGGTGAATTT TGAAAACAAA CAATTATTT TATTACCAGG TCCACCGAAA GAAATGCAAC    1800

CAATGGTGAA AAATGAATTG TTGTCACATT TTATAAACCA TAATCGAATT ATACATTCTG    1860

AACTATTAAG ATTTGCGGGA ATAGGTGAAT CTAAAGTAGA AACAATATTA ATAGATCGAC    1920

CTGCAGGCAT GC                                                      1932
```

(2) INFORMATION FOR SEQ ID NO: 98:

(i) SEQUENCE CHARACTERISTICS:
        (A) LENGTH: 619 base pairs
        (B) TYPE: nucleic acid
        (C) STRANDEDNESS: single
        (D) TOPOLOGY: linear (xi) SEQUENCE DESCRIPTION: SEQ ID NO: 98:

```
ATTCGAGCTC GGTACCCGGG GATCCTCTAN AGTCGATCTT ACGGATGAAC AATTAGTGGA     60

ATTAATGGAA AGAATGGTAT GGACTCGTAT CCTTGATCAA CGTTCTATCT CATTAAACAG    120

ACAAGGACGT TTAGGTTTCT ATGCACCAAC TGCTGGTCAA GAAGCATCAC AATTAGCGTC    180

ACAATACGCT TTAGAAAAAG AAGATTACAT TTTACCGGGA TACAGAGATG NTCCTCAAAT    240

TATTTGGCAT GGTTTACCAT TAACTGAAGC TTTCTTATTC TCAAGAGGTC ACTTCAAAGG    300

AAATCAATTC CCTGAAGGCG TTAATGCATT AAGCCCACAA ATTATTATCG GTGCACAATA    360

CATTCAAGCT GCTGGTGTTT GCATTTGCAC TTAAAAAACG TTGGTAAAAA TGCAGTTGCA    420

ATCACTTACA CTGGTTGACG GTGGTTCTTC ACAAGGTTGA TTTCTACGAA GGTATTAACT    480

TTGCAGCCAG CTTTATAAAG CACCTGGCAA TTTTCCGTTA TTCAAAACAA TAACTATGCA    540

ATTTCAACAC CCAAGAANCA AGCNAACTGC TGCTGAAACA TTACTCAAAA ACCATTGCTG    600

TAGTTTTCCT GGTATCCAT                                                619
```

(2) INFORMATION FOR SEQ ID NO: 99:

(i) SEQUENCE CHARACTERISTICS:
        (A) LENGTH: 616 base pairs
        (B) TYPE: nucleic acid
        (C) STRANDEDNESS: single
        (D) TOPOLOGY: linear (xi) SEQUENCE DESCRIPTION: SEQ ID NO: 99:

```
CTTGCATGCC TGCAGGTCGA TCANCATGTT TAACAACAGG TACTAATAAT CCTCTATCAG     60

TGTCTGCTGC AATACCGATA TTCCAGTAAT GTTTATGAAC GATTTCACCA GCTTCTTCAT    120
```

```
TGAATGAAGT GTTAAGTGCT GGGTATTTTT TCAATGCAGA ACAAGTGCT TTAACAACAT    180

AAGGTAAGAA TGTTAACTTA GTACCTTGTT CAGCTGCGAT TTCTTTAAAT TTCTTACGGT    240

GATCCCATAA TGCTTGAACA TCAATTTCAT CCATTAATGT TACATGAGGT GCAGTATGCT    300

TAGAGTTAAC CATTGCTTTC GCAATTGCTC TACGCATAGC AGGGATTTTT TCAGTTGTTT    360

CTGGGAAGTC GCCTTCTAAT GTTACTGCTG CAGGTGCTGC AGGAGTTTCA GCAACTTCTT    420

CACTTGTAGC TGAAGCAGCT GATTCATTTG AAGCTGTTGG TGCACCACCA TTTAAGTATG    480

CATCTACATC TTCTTTTGTA ATACGACCAT TTTTTACCAG ATCCAGAAAC TGCTTTAATG    540

TTTAACACCT TTTTCACGTG CGTTATTTAC TTACTGAAGG CATTGCTTTA AACAGTCTGT    600

TTTCATCTAC TTCCTC                                                    616
```

(2) INFORMATION FOR SEQ ID NO: 100:

(i) SEQUENCE CHARACTERISTICS:
        (A) LENGTH:         655 base pairs
        (B) TYPE:           nucleic acid
        (C) STRANDEDNESS:  single
        (D) TOPOLOGY:     linear (xi) SEQUENCE DESCRIPTION: SEQ ID NO: 100:

```
GTACCGGGGA TCGTCACTTA NCCTCTCTAT TTCAATTTCA ACTTATTTCG TCATCAAGTA    60

TATGTGTTAT GCTTTTATAA CTTTGATTTC AATTCTATCA ATATCTGTGA CATTGATAAC    120

ATCGGACATA CGGTCTTCTT GTAACTTTTT ATCCAATTCA AATGTATACT TTCCATAGTA    180

TTTCTTTTTG ACTGTAATTT TTCCTGTACT CATTTCACCG TAAAGACCAT AATTATCAAT    240

AAGGTATTTT CTTAATTTAA AATCAATCTC TTTCAATGAC ATCGCTTCTT TATCTATTTT    300

AAATGGGAAA AAGTCATAAT CATATTCACC AGTATGATCT TCTTTAATAA CTCTTGCTTC    360

TGCTATTAGG TCGACAGCTT TATCGTTTGC ACTCGTGATA CCCCCAATAG AGTACTTTGC    420

ACCTTCAAAT CTCTTATCCT CATTAACGTA AAATATATTA AGAWTACGAW KKTACACCCG    480

TATGATAATG TTTGCTTATC TTTGCCAATT AAAGCAATAT TATTAACAGA ATTACCATCT    540

ATGATATTCA TAAATTTAAT ACTTGGTTGA ATGAAACTGG ATATAACCTG TCMCATTTTT    600

AATATTCMAT ACTAGGTTGA ATWATAATAA GCTTTTAATT TTTKGCTATT TTCCC         655
```

(2) INFORMATION FOR SEQ ID NO: 101:

(i) SEQUENCE CHARACTERISTICS:
        (A) LENGTH:         650 base pairs
        (B) TYPE:           nucleic acid
        (C) STRANDEDNESS:  single
        (D) TOPOLOGY:     linear (xi) SEQUENCE DESCRIPTION: SEQ ID NO: 101:

```
GTCGACTCTA GAGGACTGCG TAATAACCTA TGAAAAATGA TATGAGCAAC GCCGCTCTGC    60

TTTGCCGCAT ATACTAAATT TTCCACTTCA GGAATACGTT TGAATGATGG ATGGATAATA    120

CTTGGAATAA ACACAACGGT ATCCATTCCT TTAAATGCTT CTACCATGCT TTCTTGATTA    180

AAATAATCTA ATTGTCGAAC AGGAACTTTT CCGCGCCAAT CTTCTGGAAC TTTCTCAACA    240

TTTCTAACAC CAATGTGAAA ATGATCTATG TGATTTGCAA TGGCTTGATT TGTAATATGT    300

GTGCCTAAAT GACCTGTAGC ACCTGTTAAC ATAATATTCA TTCACTTCAT CTCCTAATCT    360

TTATATACAT AACATAATAC TTATTTGATG GTTTTCAAAA CATTTGATTT TATAAAAAAT    420

TCTAATCTGT ATTTATTGTC GACGTGTATA GTAAATACGT AAATATTANT AATGTTGAAA    480
```

-continued

```
ATGCCGTAAT GACGCGTTTT AGTTGATGTG TTTCACTAAT ATCATTGAAA ATTTTAATCA      540

GGTACTACGA CAATATGAAG TCTGTTTTGT GTCTGAAAAT TTTACAGTTT TTAAAATAAA      600

AATGGTATAA GTTGTGATTT GGTTTAAAAA ANAATCTCGA CGGATAANAA                 650
```

(2) INFORMATION FOR SEQ ID NO: 102:

(i) SEQUENCE CHARACTERISTICS:
        (A) LENGTH:        2341 base pairs
        (B) TYPE:          nucleic acid
        (C) STRANDEDNESS:  single
        (D) TOPOLOGY:     linear (xi) SEQUENCE DESCRIPTION: SEQ ID NO: 102:

```
CTTGCATGCC TGCAGGTCGA TCTTTATTAT NATCTACACC ACGTANCATT TCAACATGAC       60

CACGNTCATG ACGATGTATG CGTGCGTAAW GTCCTGTKGY WACATAATCK GCACCTAAAT      120

TCATCGCATG ATCTAAAAAG GCTTTAAACT TAATTTCTTT ATWAMACATA ACGTCTGGAT      180

TTGGAGTACG ACCTTTTTTG TATTCATCTA AGAAATACGT AAAGACTTTA TCCCAATATT      240

CTTTTTCAAA ATTAACAGCG TAATACGGAA TGCCAATTTG ATTACACACT TCAATAACAT      300

CGTTGTAATC TTCAGTTGCA GTACATACGC CATTTTCGTC AGTGTCATCC CAGTTTTTCA      360

TAAATATGCC AATGACATCA TAACCTTGTT CTTTTAAGAC GTGGGCTGTT ACAGAACTAT      420

CTACACCGCC TGACATACCA ACGACAACAC GTTATATCTT TATTTGACAA TTATGACTCC      480

TCCTTAAATT TAAATATAT TTTATGAATT TCAGCTACAA TTGCATTAAT TTCATTTTCA       540

GTAGTCAATT CGTTAAAACT AAATCGAATC GAATGATTTG ATCGCTCCTC ATCTTCGAAC      600

ATTGCATCTA AAACATGCGA CGGTTGTGTA GAGCCTGCTG TACATGCAGA TCCAGACGAC      660

ACATAGATTT GTGCCATATC CAACAATGTT AACATCGTTT CAACTTCAAC AAACGGAAAA      720

TATAGATTTA CAATATGGCC TGTAGCATCC GTCATTGAAC CATTTAATTC AAATGGAATC      780

GCTCTTTCTT GTAATTTAAC TAAAAATTGT TCTTTTAAAT TCATTAAATG AATATTGTTA      840

TCGTCTCGAT TCTTTTCTGC TAATTGTAAT GCTTTAGCCA TCCCAACAAT TTGCGCAAGA      900

TTTTCAKTGC CTAGCACGGC GTTTCAATTC TTGTTCACCG CCAAGTTGAG GATAATCTAG      960

TGTAACATGG TCTTTAACTA GTAATGCACC GACACCTTTT GGTCCGCCAA ACTTATGAGC     1020

AGTAATACTC ATTGCGTCGA TCTCAAATTC GTCAAWCTTA ACATCAAGAT GTCCAATTGC     1080

TTGAACCGCA TCAACATGGA AATATGCATT TGTCTCAGCA ATAATATCTT GAATATCATA     1140

AATTTGTTGC ACTGTGCCAA CTTCATTATT TACAAACATA ATAGATACTA AAATCGTCTT     1200

ATCTGTAATT GTTTCTTCAA GTTTGATCTA AATCAATAGC ACCTGTATCA TCARCATCTA     1260

GATATGTTTA CATCAAAACC TYCTCGCTCT AATTGTTCAA AAACATGTAA CACAGAATGA     1320

TGTTCAATCT TCGATGTGAT AATGTGATTA CCCAATTGTT CATTTGCTTT TACTATGCCT     1380

TTAATTGCCG TATTATTCGA TTCTGTTGCG CCACTCGTAA ATATAATTTC ATGTGTATCT     1440

GCACCAAGTA ATTGTGCAAT TTGACGTCTT GACTCATCTA AATATTTACG CGCATCTCTT     1500

CCCTTAGCAT GTATTGATGA TGGATTACCA TAATGCGAAT TGTAAATCGT CATCATCGCA     1560

TCTACTAACT TCAGGTTTTA CTGGTGTGGT CGCAGCATAA TCTGCATAAA TTTCCCATGT     1620

TTGGACAACT CCTCACAATT TTATCAATGT TCCAATAATA GCACCTTAAC ATACTATTTT     1680

TCTAACTTTT CTGTTTAACT TTATTTATAA TGTTTTTAAT TATATTTTAC CATTTTCTAC     1740

ACATGCTTTT CGATAGGCTT TTTTAAGTTT ATCGCTTTAT TCTTGTCTTT TTTATAAATT     1800

TTAGTATTTG CAGATATTTT TTTATTTGTA AAATGTAACG TACTATTATT TTGGTTATGA     1860
```

```
GCAATTTAAT ATTTATCTGG TTATTCGGAT TGGTATACTT CTTATATCAT AAAAAAGGAA      1920

GGACGATATA AAAATGGCGG ATTAAATATT CAGCAKKRAA CCTTGTCCCT ATTCGAGAAG      1980

GTGAAGATGA ACAAACAGCA ATTAATAATA TGGTTAATCT CGCACAACAT TTAGACGAAT     2040

TATCATATGA AGATATTGG ATTGCTGAAC ACCATAACGC TCCCAACCTA GTAAGTTCAG      2100

CAACTGCTTT ATTAATTCAA CATACGTTAG AACATACGAA ACACATACGT GTAGGTTCTG     2160

GAGGCATCAT GTTACCTAAT CATGCTCCAT TAATCGTTGC GGAACAATTT GGCACGATGG     2220

CAACATTATT TCCAAATCGT GTCGATTTAG GATTAGGACG TGCACCTGGA ACAGATATGA     2280

TGACCGCAAG TGCATTAAGA CGAGATCGAC TNTAGAGGAT CCCCGGGTAC CGAGCTCGAA     2340

T                                                                    2341
```

(2) INFORMATION FOR SEQ ID NO: 103:

(i) SEQUENCE CHARACTERISTICS:
        (A) LENGTH:        2026 base pairs
        (B) TYPE:          nucleic acid
        (C) STRANDEDNESS:  single
        (D) TOPOLOGY:     linear (xi) SEQUENCE DESCRIPTION: SEQ ID NO: 103:

```
AAGGAAACCA CCAACACCTG CGCCAACTAA ACCKCCTGTT AGTGCAGAAA TAACGCTAAT       60

AGCCCCCGCA CCTAAAGCAG CTRKNGTTTT TGTATATGCA GAAGAAAGAT ATAATGTTGC      120

AGTATCTTTA CCTGTTTCTA CATATTGAGT TTTACCCGCT CTCAATTGGT CTTCAGCTTT     180

ATATTTNTWT ATTTCTTCTW TAGTAAATAT ATCTTCCRGT TTATAACCTT TTTTCTCAAG     240

TTCATCAAAT AAATTTWGGT TACTCAAATA TATTACCTTT GCTTGAGAAT GGTCTAACTT     300

ATCTTCAGCA TGAGCTACAT CTGAATTATA GAGATAATGA AATTGGACTA ACAAATAATA     360

CACCAGCAGC TRRTAATAAG AGATTTTTAA TTCGTTTTTC ATTAGTTTCT TTTAGATGAT     420

TTTTGTATTT AGATTTCGTA TAAACAGAAA CTAGATTTTT TCATGATCGA CCTATCTTTT     480

GTCCAGATAC AGTGAGACCT TGTCATTTAA ATGATTTTTA ATTCGTCTTG TACCAGAGAC     540

TTTTCTATTA GAATTAAAAA TATTTATGAC GGCTGTTCTA TGTTTGAATC ATCTTTAGTG     600

ATTTTATTAT CTTTTCTTTT TATAGAATCA TAATAGGTAC TTCTTAGTAT TATCAGGACT     660

TTACACATTG NTGATACTGA ATANTGATGT GCATTCTTTT GAATGACTTC TATTTTTGCC     720

CCATAATCAG CGCTACTTGC TTTAAAATAT CGTGCTCCAT TTTAAAATGT TGAACTTCTT     780

TGCGTAATTT AATCAGGTCT TTTTCTTCAT CCGATAAGTT ATCTTGGTGA TTGAATGTAC     840

CCGTGTTTTG ATGTTGCTTT ATCCATTTTC CTACATTTTA TAACCGCCAT TTACAAACGT     900

CGAAKGTGTG AAATCATACT CGCGTWTAAT TTCATTCCTA GGCTTACCAT TTTTATATAA     960

TCTAACCATT TGTAACTTAA ACTCTGAACT AAATGATCTT CTTTCTCTTG TCATAATAAA    1020

ATCGCCTACT TTCTTAAATT AACAATATCT ATTCTCATAG AATTTGTCCA ATTAAGTGTA    1080

GACGATTCAA TCTATCAGCT AGAATCATAT AACTTATCAG AAGCAAGTGA CTGTGCWTGT    1140

ATATTTGCCG MTGATATAAT AGTAGAGTCG CCTATCTCTC AGGCGTCAAT TTAGACGCAG    1200

AGAGGAGGTG TATAAGGTGA TGCTYMTTTT CGTTCAACAT CATAGCACCA GTCATCAGTG    1260

GCTGTGCCAT TGCGTTTTTY TCCTTATTGG CTAAGTTAGA CGCAATACAA AATAGGTGAC    1320

ATATAGCCGC ACCAATAAAA ATCCCCTCAC TACCGCAAAT AGTGAGGGGA TTGGTGTATA    1380

AGTAAATACT TATTTTCGTT GTCTTAATTA TACTGCTAAT TTTTCTTTTT GTAAAATATG    1440

CAAGGTTTTA AAGAGAAACA TCAAGAACTA AAAAAGGCTY TATGTCAAAT TGGACTGATG    1500
```

-continued

```
CGTTCAATAT CCGAAGTTAA GCAACTAAAC ATTGCTTAAC TTCCTTTTTA CTTTTTGGAG    1560

CGTAAAGTTT TGAACATAAT AATATTCGAT TGCGCAAATG ATTGTAACTT CCATAACCAA    1620

AAGATGTACG TTTAATTAAT TTTATTTTGT TATTTATACC TTCTAAAGGA CCATTTGATA    1680

AATTGTAATA ATCAATGGTT ACACTATTAA AAGTGTCACA AATTCTTATG AATCTGGCAT    1740

AAACTTTGAA TTAACTAAAT AAGTAAGAAA ACCTCGGCAC TTTATCATTT TAATAGTGTC    1800

GAGATTTTTA TAGATACTAC AAATATTTAT AACATAGTTA AACTCATCTA ATGACTTATA    1860

TTTTTGTTTC ATCACAATAT GAACAATTAT TTATTGGACG TATTTTGCTC TTTTTTTATT    1920

TCAGAAACTG ACTTAGGATT TTTATTAAAT TTTCTACCCA ATTCATCTGT ATAAGAAATA    1980

TCGGTATCAA ATTGAAAATC ATCAACAGAT CGACCTGCAG GCATGC                  2026
```

(2) INFORMATION FOR SEQ ID NO: 104:

(i) SEQUENCE CHARACTERISTICS:
        (A) LENGTH:          2736 base pairs
        (B) TYPE:            nucleic acid
        (C) STRANDEDNESS:    single
        (D) TOPOLOGY:        linear (xi) SEQUENCE DESCRIPTION: SEQ ID NO: 104:

```
TGCCTGCAGG TCGATCTTCT ATGTAAATAA TCAAATGACG TTTCTTCTAT AGATATAAAT      60

TGATATASAA AACTAAAAAT ACAACTGCAA CTATAAGATA ACAATACTAC CAAATGACAA     120

CCTCCTTATG TAAATTATAG TTAGTTATTA CCAAAATGTA AATATACACT ATTTTTCAAG     180

AATTGAACCG CTTTTTCATT TAAATTTTTC AATATTGCTA AGCATAATTG ATGGATACTT     240

TAACAACCCA TTACTGCTCG GCAAAATTAA TAATGGCAAG AAATTGAACC TTATAAACAC     300

ATACGATTTA GAGCATAAAA AATAACCATG AAGCTCTACC TATTGATTAA ATARATTCTT     360

CATGGCTATT TTAGTTTTAG TTTTATAATG CTTCAAAGTC TAATTTTGAT TTAACTTCAC     420

TTATGAAATA CAGACTACCG GTAATTACTA ATGTATCACC TTGATAATTT TTTATAAATT     480

CAACGTAGTC ATCTACTAAT TGTATTTCAT CATTTTCAAT ACTACCTACA ATTTCTTCTT     540

TGCGTAACGC TTTCGGAAAA TCAAATTCAG TTGCATAAAA CGTATGCGCA ATTAAACTTA     600

AATGTTTGAC CATCTCGTTA ATCGGTTTTC CGTTTATTGC TGASAACAAA ATATCTACTT     660

TTTCTTTATC ATGGTACTGT TTAATTGTAT CAATTAGAGC ATCTATACTC TCTGAATTAT     720

GYGCGCCATC CAAAATGATT AAAGGYTTGT CATGCACCTG CTCAATACGT CCAGTCCAAC     780

GAACTGATTC AATACCGTCT ATCATCTTAT TGAAATCTAA TTCAATTAAT CCTTGTTCAT     840

TTAATTCAAT AAGAGCTGTT ATGGCTAATG CAGCAAWTTT GTTTCTGATG TTTCACCTAA     900

CATGCTTAAA ATGATTGTTT CTAATTCATA ATCTTTATAA CGGTAAGTTA AATTCATCAT     960

TTTGCGATAC AACAACAATT TCTCTATCTA ATTCAATGGC TTTGCATGTT GTTCAATTGC    1020

GCGTTCACGA ACATATTTTA ATGCATCTTC ATTTTTTACA GCATATATCA CTGGAACKTT    1080

AGGSTTTATA ATCGCGCCYT TATCCCTAGC AATATCTAGA TAAGTACCAC TAAAATATC    1140

TGTATGGTCT AGACCGATAC TAGTTAAGAT TGATAAAACC GGTGTAAAGA CATTTGTCGA    1200

ATCGTTCTTT ATACCCAATC CAGCCTCAAC AATGACAAAA TCAACAGGAT GTATTTCACC    1260

AAAATATAAA AACATCATCG CTGTGATTAT TTCGAATTCA GTTGCAAMMM CTAAATCTGT    1320

TTCAMSTTCC ATCATTTCAA TTAACTGGTT TAATACGTGA TACTAATTCT AACAATAGCG    1380

TCATTTGATA TTGGCAACAC CATTTAGRAT AATTCGTTCA TTAAATGTTT CAATAAACGG    1440

CGACGTAAAT GTACCTACTT CATAACCATT TTCAACTAAA GCTGTTCTAA GGTAAGCAAC    1500
```

-continued

| | |
|---|---|
| TGTAGAGCCT TTACCATTTG TGCCACSKAC ATGAATACCC TTAATGWTAT TTTGAGGATT | 1560 |
| ATTAAATTGT GCTAGCATCC ATTCCATACG TTTAACACCT GGTTTGATGC CAAATTTAGT | 1620 |
| TCTTTCGTGT ATCCAATACA AGCTCTCTAG GTAATTCATT GTTACTAACT CCTATGCTTT | 1680 |
| TAATTGTTCA ATTCTTGCCT TCACACCATC ATATTTTTCT TGATAATCTT GTTTTTTACG | 1740 |
| TTTTTCTTCA TTTATAACCT TTTCAGGTGC TTTACTTACA AAGTTTTCAT TAGAGAGCTT | 1800 |
| TTTATCTACT CTATCTAATT CGCTTTGAAG TTTAGCTAAT TCTTTTTCCA AACGGCTGAT | 1860 |
| TTCCTTATCC ATATCAATTA GCCCTTCTTA ATGGTAATAC CCACTTTACC TGCAATTACA | 1920 |
| ACTGATGTCA TTGCTTTCTC AGGAATTTCC AACGTCAGTG CTAATATTTA AGGTACTAGG | 1980 |
| ATTACAGAAT TTGATTAAAT AATCTTTGTT TTGTGATAAA GTTGTTTCAA TTTCTTTATC | 2040 |
| TTTAGCTTGA ATTAAAATAG GTATTTCTTT AGACAATGGC GTATTTACTT CTACACGTGA | 2100 |
| TTGTCTTACA GATTAATGA TTTCAACAAG TGGTKGCATT GTTTGTTAAC TTTCTTCAAA | 2160 |
| AATCAATGAT TCACGCACTT CTGGCCATGA AGCTTTAACA ATTGTGTCAC CTTCATGTGG | 2220 |
| TAAACTTTGC CATATTTTCT CTGTTACAAA TGGCATGAAT GGATGTAGCA TTCTCATAAT | 2280 |
| ATTGTCTAAA GTATAACTCA ATACTGAACG TGTAACTTGT TTTTGTTCTT CATCATTACT | 2340 |
| ATTCATTGGA ATTTTACTCA TTTCAATGTA CCAATCACAG AAATCATCCC AAATGAAATT | 2400 |
| ATATAATGCA CGTCCAACTT CGCCGAATTC ATATTTGTCA CTTAAATCAG TAACTGTTGC | 2460 |
| AATCGTTTCA TTTAAACGTG TTAGAATCCA TTTATCTGCT AATGATAAGT TACCACTTAA | 2520 |
| ATCGATATCT TCAACTTTAA AGTCTTCACC GATATTCATT AAACTGAAAC GTGCCCCATT | 2580 |
| CCAGATTTTA TTGATAAAGT TCCACACTGA CTCAACTTTT TCAGTTGAGT ATCTTAAATC | 2640 |
| ATGTCCTGGA GATGAACCTG TTGCTAAGAA GTAACGCAAG CTATCAGCAC CGTATTCGTC | 2700 |
| AATAACATCC ATTGGATCGA CCTGCAGGCA TGCAAG | 2736 |

(2) INFORMATION FOR SEQ ID NO: 105:

(i) SEQUENCE CHARACTERISTICS:
        (A) LENGTH:        2255 base pairs
        (B) TYPE:          nucleic acid
        (C) STRANDEDNESS:  single
        (D) TOPOLOGY:     linear (xi) SEQUENCE DESCRIPTION: SEQ ID NO: 105:

| | |
|---|---|
| CNCGNNAGCG ANGTNGCCGA GGATCCTCTA GAGTCNATCG GTTATCGGTG AAAAGATATG | 60 |
| TCGCATCATT GATTACTGCA CTGAGAACCG TTTACCATTT ATTCTTTTCT CTGCAAGTGG | 120 |
| TGGTGCACGT ATGCAAGAAG GTATTATTTC CTTGATGCAA ATGGGTAAAA CCAGTGTATC | 180 |
| TTTAAAACGT CATTCTGACG CTGGACTATT ATATATATCA TATTTAACAC ATCCAACTAC | 240 |
| TGGTGGTGTA TCTGCAAGTT TTGCATCAGT TGGTGATATA AATTTAAGTG AGCCAAAAGC | 300 |
| GTTGATAGGT TTTGCAGGTC GTCGAGTTAT TGAACAGACA ATAAACGAAA AATTGCCAGA | 360 |
| TGATTTCCAA ACTGCAGAAT TTTTATTAGA GCATGGACAA TTGGATAAAG TTGTACATCG | 420 |
| TAATGATATG CGTCAAACAT TGTCTGAAAT TCTAAAAATC CATCAAGAGG TGACTAAATA | 480 |
| ATGTTAGATT TTGAAAAACC ACTTTTTGAA ATTCGAAATA AAATTGAATC TTTAAAAGAA | 540 |
| TCTCAAGATA AAAATGATGT GGATTTACCA AAGAAGAATT TGCATGCCT TGAARCGTCM | 600 |
| TTGGRACGAG AAACTAAAAA AATATATACA AATCTAAAAC CATGGGATCG TGTGCAAATT | 660 |
| GCGCGTTTGC AAGAAAGACC TACGACCCTA GATTATATTC CATATATCTT TGATTCGTTT | 720 |
| ATGGAACTAC ATGGTGATCG TAATTTTAGA GATGATCCAG CAATGATTGG TGGTATTGGC | 780 |

```
TTTTTAAATG GTCGTGCTGT TACAGTYRTK GGACAACAAC GTGGAAAAGA TACWAAAGAT        840

RATATTTATC GAAATTTTKG GTATGGCGCA TCCAGAAGGT TATCGAAAAG CATTACGTTT        900

AATGAAACAA GCTGAAAAAT TCAATCGTCC TATCTTTACA TTTATAGATA CAAAAGGTGC        960

ATATCCTGGT AAAGCTGCTG AAGAACGTGG ACAAAGTGAA TCTATCGCAA CAAATTTGAT       1020

TGAGATGGCT TCATTAAAAG TACCAGTTAT TGCGATTGTC ATTGKYGAAG GTGGCAGTGG       1080

AGGTGCTCTA GGTATTGGTA TTGCCAATAA AGYATTGATG TTAGAGAATA GTACTTACTC       1140

TGWTATATCT CCTGAAGGTG CAGCGGCATT ATTATGGAAA GACAGTAATT TGGCTAAAAT       1200

YGCAGCTGAA ACAATGAAWA TTACTGCCCA TGATATTAAG CAATTAGGTA TTATAGATGA       1260

TGYCATTTCT GAACCACTTG GCGGTGCACA TAAAGATATT GAACAGCAAG CTTTAGCTAT       1320

TAAATCAGCG TTTGTTGCAC AGTTAGATTC ACTTGAGTCA TTATCAACGT GATGAAATTG       1380

CTAATGATCG CTTTGAAAAA TTCAGAAATA TCGGTTCTTA TATAGAATAA TCAACTTGAG       1440

CATTTTTATG TTAAATCGAT ACTGGGTTTT ACCATAAATT GAAGTACATT AAAACAATAA       1500

TTTAATATTT AGATACTGAA TTTTTAACTA AGATTAGTAG TCAAAATTGT GGCTACTAAT       1560

CTTTTTTTAA TTAAGTTAAA ATAAAATTCA ATATTTAAAA CGTTTACATC AATTCAATAC       1620

ATTAGTTTTG ATGGAATGAC ATATCAATTT GTGGTAATTT AGAGTTAAAG ATAAATCAGT       1680

TATAGAAAGG TATGTCGTCA TGAAGAAAAT TGCAGTTTTA ACTAGTGGTG GAGATTCACC       1740

TGGAATGAAT GCTGCCGTAA GAGCAGTTGT TCGTACAGCA ATTTACAATG AAATTGAAGT       1800

TTATGGTGTG TATCATGGTT ACCAAGGATT GTTAAATGAT GATATTCATA AACTTGAATT       1860

AGGATCRAGT TGGGGATACG ATTCAGCGTG GAGGTACATT CTTGTATTCA GCAAGATGTC       1920

CAGAGTTTAA GGAGCAAGAA GTACGTAAAG TTGCAATCGA AAACTTACGT AAAAGAGGGA       1980

TTGAGGGCCT TGTAGTTATT GGTGGTGACG GTAGTTATCG CGGTGCACAA CGCATCAGTG       2040

AGGAATGTAA AGAAATTCAA ACTATCGGTA TTCCTGGTAC GATTGACAAT GATATCAATG       2100

GTACTGATTT TACAATTGGA TTTGACACAG CATTAAATAC GATTATTGGC TTAGTCGACA       2160

AAATTAGAGA TACTGCGTCA AGTCACGCAC GAACATTTAT CATTGAAGCA ATGGGCCGTG       2220

ATTGTGGAGT CATCTGGAGT CGACCTGCTA GTCTT                                  2255
```

(2) INFORMATION FOR SEQ ID NO: 106:

(i) SEQUENCE CHARACTERISTICS:
        (A) LENGTH:        417 base pairs
        (B) TYPE:          nucleic acid
        (C) STRANDEDNESS:  single
        (D) TOPOLOGY:      linear (xi) SEQUENCE DESCRIPTION: SEQ ID NO: 106:

```
GTGATGGATT AAGTCCTAAA TTTNNATTCG CTTTCTTGTC TTTTTAATCT TTTTCAGACA         60

TTTTATCGAT TTCACGTTTT GTATACTTAG GATTTAAATA GGCATTAATT GTTTTCTTGT        120

CCAAAAATTG ACCATCTTGA TACAAATATT TATCTGTTGG AAATACTTCT TTACTTAAGT        180

NCAATAAACC ATCTTCAAAG TCGCCGCCAT TATAACTATT TGCCATGTTA TCTTGTAAAA        240

GTCCTCTTGC CTGGNTTTCT TTAAATGGTA ACAATGTACG NTAGTTATCA CCTTGTACAT        300

TTTTATCCGT TGCAATTTCT TNTACTTGAT TTGAACTATT GTTATGTTTT NAATTATCTT        360

TTCCCAGCCT GGGTCATCCT TATGGTTANC ACAAGCAGCG AGTATAAAGG TAGCTGT          417
```

(2) INFORMATION FOR SEQ ID NO: 107:

(i) SEQUENCE CHARACTERISTICS:

-continued

```
        (A) LENGTH:              497 base pairs
        (B) TYPE:                nucleic acid
        (C) STRANDEDNESS:        single
        (D) TOPOLOGY:            linear (xi) SEQUENCE DESCRIPTION: SEQ ID NO: 107:

TAATGTAGCA ATTACAAGGC CTGAAGAGGT GTTATATATC ACTCATGCGA CATCAAGAAT    60

GTNATTTGGN CGCCCTCAGT CAAATATGCC ATCCAGNTTT TNAAAGGAAA TTCCAGAATC   120

ACTATTAGAA AATCATTCAA GTGGCAAACG ACAAACGGTA CAACCTNNGG CAAAACCTTT   180

TNCTAAACGC GGNTTTTGTC AACGGNCAAC GTCAACGGNN AANCAAGTAT TNTNATCTGN   240

TTGGAATNTT GGTGGCAANG TGGTGCNTAA NGNCNCCGGG GGGAGGCATT GTNNGTAATT   300

TTAACGNGGA NAATGGCTCN NTCGGNCTNG GTNTTATNTT TTATTCACAC AGGGNCGCGN   360

CANGTTTTTT TTGTNGGATT TTTTTCCCCC NTTTTTNAAA AGGNGGGGTN TTNNGGGTGG   420

CTGNTTTANT NGTCTCNGNG TGGNCGTGNN TCATTNNTTT TTTTNTTNNA TCCAAGCCTT   480

NTATGACTTT NNTTGGG                                                  497

(2) INFORMATION FOR SEQ ID NO: 108:

(i) SEQUENCE CHARACTERISTICS:
        (A) LENGTH:              22 base pairs
        (B) TYPE:                nucleic acid
        (C) STRANDEDNESS:        single
        (D) TOPOLOGY:            linear (xi) SEQUENCE DESCRIPTION: SEQ ID NO: 108:

CTGAAGAGGT GTTATATATC AC                                             22

(2) INFORMATION FOR SEQ ID NO: 109:

(i) SEQUENCE CHARACTERISTICS:
        (A) LENGTH:              22 base pairs
        (B) TYPE:                nucleic acid
        (C) STRANDEDNESS:        single
        (D) TOPOLOGY:            linear (xi) SEQUENCE DESCRIPTION: SEQ ID NO: 109:

GTGATGGATT AAGTCCTAAA TT                                             22

(2) INFORMATION FOR SEQ ID NO: 110:

(i) SEQUENCE CHARACTERISTICS:
        (A) LENGTH:              22 base pairs
        (B) TYPE:                nucleic acid
        (C) STRANDEDNESS:        single
        (D) TOPOLOGY:            linear (xi) SEQUENCE DESCRIPTION: SEQ ID NO: 110:

CTCAGTCAAA TATGCCATCC AG                                             22
```

(2) INFORMATION FOR SEQ ID NO: 111:

(i) SEQUENCE CHARACTERISTICS:
        (A) LENGTH:          22 base pairs
        (B) TYPE:            nucleic acid
        (C) STRANDEDNESS:    single
        (D) TOPOLOGY:        linear (xi) SEQUENCE DESCRIPTION: SEQ ID NO: 111:

CTTTAAATGG TAACAATGTA CG                    22